(12) United States Patent
Bartberger et al.

(10) Patent No.: US 11,407,721 B2
(45) Date of Patent: *Aug. 9, 2022

(54) CIS-MORPHOLINONE AND OTHER COMPOUNDS AS MDM2 INHIBITORS FOR THE TREATMENT OF CANCER

(71) Applicant: AMGEN INC., Thousand Oaks, CA (US)

(72) Inventors: Michael D. Bartberger, Sherman Oaks, CA (US); Hilary Plake Beck, Emerald Hills, CA (US); Michael R. Degraffenreid, San Francisco, CA (US); Brian M. Fox, Brisbane, CA (US); Felix Gonzalez Lopez De Turiso, Cambridge, MA (US); Lisa D. Julian, Frisco, CO (US); Frank Kayser, San Francisco, CA (US); Julio C. Medina, San Carlos, CA (US); Steven H. Olson, Millbrae, CA (US); Yosup Rew, Foster City, CA (US); Philip M. Roveto, Albuquerque, NM (US); Daqing Sun, Foster City, CA (US); Xuelei Yan, Foster City, CA (US)

(73) Assignee: AMGEN INC., Thousand Oaks, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/048,677

(22) Filed: Jul. 30, 2018

(65) Prior Publication Data

US 2018/0354918 A1   Dec. 13, 2018

Related U.S. Application Data

(63) Continuation-in-part of application No. 14/768,529, filed as application No. PCT/US2014/016971 on Feb. 18, 2014, now abandoned.

(60) Provisional application No. 61/766,625, filed on Feb. 19, 2013.

(51) Int. Cl.
| | |
|---|---|
| *C07D 265/32* | (2006.01) |
| *C07D 413/06* | (2006.01) |
| *C07D 487/04* | (2006.01) |
| *C07D 279/12* | (2006.01) |
| *C07D 413/04* | (2006.01) |

(52) U.S. Cl.
CPC ......... *C07D 265/32* (2013.01); *C07D 279/12* (2013.01); *C07D 413/04* (2013.01); *C07D 413/06* (2013.01); *C07D 487/04* (2013.01)

(58) Field of Classification Search
CPC .. C07D 263/32; C07D 279/12; C07D 413/04; C07D 413/06; C07D 487/04
See application file for complete search history.

(56) References Cited

U.S. PATENT DOCUMENTS

| | | |
|---|---|---|
| 3,308,121 A | 3/1967 | Gannon et al. |
| 3,518,236 A | 6/1970 | Hunter |
| 5,334,720 A | 8/1994 | Schmiesing et al. |
| 6,620,815 B1 | 9/2003 | Lagu et al. |
| 6,860,940 B2 | 3/2005 | Segelke et al. |
| 7,015,041 B2 | 3/2006 | Santarsiero et al. |
| 7,052,545 B2 | 5/2006 | Quake et al. |
| 7,195,670 B2 | 3/2007 | Hansen et al. |
| 7,214,540 B2 | 5/2007 | DeLucas et al. |
| 7,229,500 B2 | 6/2007 | Haushalter et al. |
| 7,425,638 B2 | 9/2008 | Haley et al. |
| 7,776,875 B2 | 8/2010 | Chen et al. |
| 8,003,790 B2 | 8/2011 | Yoshida et al. |
| 8,569,341 B2 | 10/2013 | Gribble, Jr. et al. |
| 8,952,036 B2 | 2/2015 | Rew |
| 9,296,736 B2 | 3/2016 | Bartberger et al. |
| 9,376,386 B2 | 6/2016 | Bio et al. |
| 9,376,425 B2 | 6/2016 | Bartberger et al. |
| 9,593,129 B2 | 3/2017 | Bartberger et al. |

(Continued)

FOREIGN PATENT DOCUMENTS

| | | |
|---|---|---|
| CN | 102153557 A | 8/2011 |
| DE | 3246148 A1 | 6/1984 |

(Continued)

OTHER PUBLICATIONS

Voskoglou-Nomikos et al., Clinical Cancer Research, vol. 9, 4227-4239.*
Ptcl.chem.ox.ac.uk/MSDS structure activity relationship; Jaworska, 1-8, 2004.*
Cancer and Metastasis Reviews (1998), 17(1), 91-106.*
Science (1999), vol. 286, 531-537.*
Caira, MR, Crystalline Polymorphism of Organic Compounds. In: Weber E. et al. (eds) Design of Organic Solids. Topics in Current Chemistry, vol. 198. Springer, Berlin, Heidelberg; pp. 163-208 (1998).
U.S. Appl. No. 15/927,426, filed Mar. 21, 2018, Amgen Inc.

(Continued)

*Primary Examiner* — Rebecca L Anderson
(74) *Attorney, Agent, or Firm* — Markus Bergauer

(57) ABSTRACT

The present invention provides MDM2 inhibitor compounds of Formula I, or the pharmaceutically acceptable salts thereof,

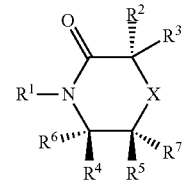

I wherein the variables are defined above, which compounds are useful as therapeutic agents, particularly for the treatment of cancers. The present invention also relates to pharmaceutical compositions that contain an MDM2 inhibitor.

46 Claims, No Drawings

(56) References Cited

U.S. PATENT DOCUMENTS

| | | | |
|---|---|---|---|
| 9,623,018 | B2 | 4/2017 | Bio et al. |
| 9,757,367 | B2 | 9/2017 | Caille et al. |
| 9,758,495 | B2 * | 9/2017 | Gonzalez Buenrostro ............... A61P 35/00 |
| 9,801,867 | B2 | 10/2017 | Bio et al. |
| 9,855,259 | B2 | 1/2018 | Bio et al. |
| 2004/0186134 | A1 | 9/2004 | O'Connor et al. |
| 2007/0129416 | A1 | 6/2007 | Ding et al. |
| 2008/0280769 | A1 | 11/2008 | Doemling |
| 2009/0143364 | A1 | 6/2009 | Fotouhi et al. |
| 2009/0163512 | A1 | 6/2009 | Chen et al. |
| 2009/0258904 | A1 | 10/2009 | Tillekeratne et al. |
| 2010/0075949 | A1 | 3/2010 | Burdack et al. |
| 2011/0275586 | A1 | 11/2011 | Aggen et al. |
| 2011/0319378 | A1 | 12/2011 | Gribble, Jr. et al. |
| 2014/0011796 | A1 | 1/2014 | Bartberger et al. |
| 2014/0235629 | A1 | 8/2014 | Bartberger et al. |
| 2014/0315895 | A1 | 10/2014 | Bartberger et al. |
| 2014/0364455 | A1 | 12/2014 | Bio et al. |
| 2016/0002185 | A1 | 1/2016 | Bartberger et al. |
| 2016/0039774 | A1 | 2/2016 | Gonzalez Buenrostro et al. |
| 2016/0137667 | A1 | 5/2016 | Bartberger et al. |
| 2016/0264526 | A1 | 9/2016 | Bio et al. |
| 2016/0287570 | A1 | 10/2016 | Bio et al. |
| 2016/0289178 | A1 | 10/2016 | Caille et al. |
| 2016/0289190 | A1 | 10/2016 | Bio et al. |
| 2016/0289243 | A1 | 10/2016 | Bio et al. |
| 2017/0144971 | A1 | 5/2017 | Bartberger et al. |
| 2018/0092898 | A1 | 4/2018 | Bio et al. |
| 2019/0062276 | A1 | 2/2019 | Bartberger et al. |
| 2020/0281912 | A1 | 9/2020 | Bio et al. |
| 2021/0179560 | A1 | 6/2021 | Bartberger et al. |

FOREIGN PATENT DOCUMENTS

| | | |
|---|---|---|
| EP | 0408357 A2 | 1/1991 |
| EP | 2386552 A1 | 11/2001 |
| JP | H10291982 A | 11/1998 |
| TW | 200801000 A | 1/2008 |
| TW | 200808781 A | 2/2008 |
| WO | WO95/23135 A1 | 2/1996 |
| WO | WO96/06095 A1 | 2/1996 |
| WO | WO97/30045 A1 | 8/1997 |
| WO | WO99/06397 A2 | 2/1999 |
| WO | WO99/31507 A1 | 6/1999 |
| WO | WO02/017912 A1 | 3/2002 |
| WO | WO02/089738 A2 | 11/2002 |
| WO | WO02/094787 A1 | 11/2002 |
| WO | WO03/051359 A1 | 6/2003 |
| WO | WO04/031149 A1 | 4/2004 |
| WO | WO05/110996 A1 | 11/2005 |
| WO | WO05/123691 A1 | 12/2005 |
| WO | WO06/011669 A1 | 2/2006 |
| WO | WO06/097261 A1 | 9/2006 |
| WO | WO06/107859 A2 | 10/2006 |
| WO | WO06/107860 A2 | 10/2006 |
| WO | WO06/131923 A2 | 12/2006 |
| WO | WO07/063013 A1 | 6/2007 |
| WO | WO07/104664 A1 | 9/2007 |
| WO | WO08/005268 A1 | 1/2008 |
| WO | WO08/010953 A2 | 1/2008 |
| WO | WO08/021338 A2 | 2/2008 |
| WO | WO08/021339 A2 | 2/2008 |
| WO | WO08/076754 A2 | 6/2008 |
| WO | WO08/110793 A1 | 9/2008 |
| WO | WO08/125487 A1 | 10/2008 |
| WO | WO08/141975 A1 | 11/2008 |
| WO | WO09/004430 A1 | 1/2009 |
| WO | WO09/007750 A1 | 1/2009 |
| WO | WO09/047161 A1 | 4/2009 |
| WO | WO09/082038 A2 | 7/2009 |
| WO | WO09/114950 A1 | 9/2009 |
| WO | WO09/156735 A2 | 12/2009 |
| WO | WO10/028862 A1 | 3/2010 |
| WO | WO10/031713 A1 | 3/2010 |
| WO | WO10/121995 A1 | 10/2010 |
| WO | WO11/023677 A1 | 3/2011 |
| WO | WO11/035159 A1 | 3/2011 |
| WO | WO11/44501 A2 | 4/2011 |
| WO | WO11/067185 A1 | 6/2011 |
| WO | WO11/076786 A1 | 6/2011 |
| WO | WO11/153509 A1 | 12/2011 |
| WO | WO12/097000 A1 | 7/2012 |
| WO | WO13/002420 A1 | 3/2013 |
| WO | WO13/049250 A1 | 4/2013 |
| WO | WO14/130470 A1 | 8/2014 |
| WO | WO14/134201 A1 | 9/2014 |
| WO | WO14/151863 A1 | 9/2014 |
| WO | WO14/200937 A1 | 12/2014 |
| WO | WO15/070224 A2 | 5/2015 |

OTHER PUBLICATIONS

"Guidance for Industry ANDAs: Pharmaceutical Solid Polymorphism Chemistry Manufacturing, and Controls Information," U.S. Department of Health and Human Services, Food and Drug Administration, Center for Drug Evaluation and Research (CDER), Jul. 2007, pp. 1-13.

Alexakis, A. et al., "Monoaminals of Glyoxal: Versatile Chirons," J. Am. Chem. Soc. 117, 10767-10768 (1995).

Allen, J. G. et al., "Discovery and Optimization of Chromenotriazolopyrimidines as Potent Inhibitors of the Mouse Double Minute 2-Tumor Protein 53 Protein-Protein Interaction," Journal of Medicinal Chemistry 52(22), 7044-7053 (2009).

Allen, P., "Aliphatic Sulfinic Acids. I. Analysis and Identification," J. Org. Chem. 7, 23-30 (1942).

Anthony, N. J. et al., "Pseudo-Allylic A1,3 Strain as a Conformational Control Element: Stereoselective Syntheses of ψ[CH2O] Pseudodipeptides," Tetrahedron Letters 36(22), 3821-3824 (1995).

Braverman, M. et al., "Product Class 3: Alkanesulfinic Acids and Acyclic Derivatives," Science of Synthesis 39, 187-243 (2007).

Damia, G. et al., "Contemporary pre-clinical development of anticancer agents—What are the optimal preclinical models?," European Journal of Cancer 45, 2768-2781 (2009).

Fenton et al., "CCVI.—Influence of Poles and Polar Linkings on the Course pursued by Elimination Reactions. Part IV. Further Experiments on the Olefinic Degradation of Sulphones," J. Chem. Soc., 2338-2341 (1929).

Garcia Ruano, J. L. et al., "Synthesis of 2-phenyl-, 3-phenyl-, cis-2,3-diphenyl-, and trans-2,3-diphenyl-1,4-thiazanes and derivatives (N-methyl, N-alkoxycarbonyl, S-oxides, and S,S-dioxides)," Journal of Organic Chemistry 57(15), 4215-4224 (1992).

Gattermann, L. "The Practical Methods of Organic Chemistry," 1896, MacMillan: New York, pp. 1-14.

Golub, T.R. et al., "Molecular Classification of Cancer: Class Discovery and Class Prediction by Gene Expression Monitoring," Science 286, 531-537 (1999).

Gonzalez, A. Z. et al., "Novel Inhibitors of the MDM2-p53 Interaction Featuring Hydrogen Bond Acceptors as Carboxylic Acid Isosteres," Journal of Medicinal Chemistry 57(7), 2963-2988 (2014).

He, Q. et al., "Novel morpholin-3-one derivatives induced apoptosis and elevated the level of P53 and Fas in A549 lung cancer cells," Bioorganic & Medicinal Chemistry 15(11), 3889-3895 (2007).

International Search Report, PCT/US2011/039184, dated Sep. 9, 2011, pp. 1-3.

International Search Report, PCT/US2012/057389, dated Jan. 18, 2013, pp. 1-4.

International Search Report, PCT/US2014/016971, dated May 15, 2014, pp. 1-5.

International Search Report, PCT/US2014/018759, dated Jun. 12, 2014, pp. 1-5.

International Search Report, PCT/US2014/026584, dated Jun. 26, 2014, pp. 1-5.

International Search Report, PCT/US2014/041594, dated Aug. 18 2014, pp. 1-7.

Jaworska, et al., "Review of Methods for Assessing the Applicability Domains of SARS and QSARS. Paper 4: SARS Applicability Domain" ptcl.chem.ox.ac.uk/MSDS structure activity relationship; 2004; pp. 1-8.

(56) References Cited

OTHER PUBLICATIONS

Johnson, J. et al., "Relationships between drug activity in NCI preclinical in vitro and in vivo models and early clinical trials," British Journal of Cancer 84, 1424-1431 (2001).
Lala, P. K. et al., "Role of nitric oxide in tumor progression: Lessons from experimental tumors," Cancer Metastasis Rev. 17(1), 91-106 (1998).
Lawrence, H. R. et al., "Identification of a disruptor of the MDM2-p53 protein-protein interaction facilitated by high-throughput in silico docking," Bioorganic & Medicinal Chemistry Letters 19, 3756-3759 (2009).
Ledford, H., "US cancer institute overhauls cell lines," Nature 530, 391 (2016).
Lucas, B. S. et al., "An Expeditious Synthesis of the MDM2-p53 Inhibitor Am-8553," J. Am. Chem. Soc. 134:12855-12860 (2012).
Michelsen, K. et al., "Ordering of the N-Terminus of Human MDM2 by Small Molecule Inhibitors," Journal American Chemical Society 134(41), 17059-17067 (2012).
Morissette, S. L. et. al. "High-throughput crystallization: polymorphs, salts, co-crystals and solvates of pharmaceutical solids," Advanced Drug Delivery Reviews 56, 275-300 (2004).
Nakayama, H. et al., "Hydrates of Organic Compounds. X. The Formation of Clathrate Hydrates of Tetrabutylammonium Alkanesulfonates," Bulletin of the Chemical Society of Japan, 833-837 (1986).
Ocana, A. et al., "Preclinical development of molecular-targeted agents for cancer," Nat. Rev. Clin. Oncol. 8, 200-209 (2011).
Office Action dated Aug. 10, 2015 for U.S. Appl. No. 14/347,628, filed Mar. 26, 2014, pp. 1-4.
Office Action dated Dec. 24, 2014 for U.S. Appl. No. 14/347,628, filed Mar. 26, 2014, pp. 1-21.
Office Action dated Feb. 9, 2017 for U.S. Appl. No. 14/774,645, filed Sep. 10, 2015, pp. 1-15.
Office Action dated Mar. 15, 2017 for U.S. Appl. No. 15/175,798, filed Jun. 7, 2016, pp. 1-10.
Office Action dated Mar. 21, 2017 for U.S. Appl. No. 15/175,824, filed Jun. 7, 2016, pp. 1-6.
Office Action dated Mar. 22, 2017 for U.S. Appl. No. 15/175,798, filed Jun. 7, 2016, pp. 1-11.
Office Action dated Mar. 28, 2017 for U.S. Appl. No. 14/768,529, filed Aug. 18, 2015, pp. 1-23.
Office Action dated Mar. 6, 2017 for U.S. Appl. No. 15/163,186, filed May 24, 2016, pp. 1-10.
Office Action dated Mar. 7, 2018 for U.S. Appl. No. 14/768,529, filed Aug. 18, 2015, pp. 1-18.
Office Action dated May 13, 2015 for U.S. Appl. No. 14/347,628, filed Mar. 26, 2014, pp. 1-7.
Office Action dated Sep. 21, 2017 for U.S. Appl. No. 15/412,804, filed Jan. 23, 2017, pp. 1-9.
Okaku, N. et al., "Synthesis of Chelating Agents. IV.*1 Synthesis and Chelating Behavior of 1-Phenyl-ethylenedinitrilo-N, N, N', N'-tetraacetic Acid and 1, 2-Diphenyl-ethylenedinitrilo-N, N, N', N'-tetraacetic Acid*2," Bulletin of the Chemical Society of Japan 40, 2326-2332 (1967).
Patani, G. A. et al., "Bioisosterism: A Rational Approach in Drug Design," Chemical Reviews 96(8), 3147-3176 (1996).
Patel, S. et al., "Small-molecule inhibitors of the p53-HDM2 interaction for the treatment of cancer," Expert Opin. Investig. Drugs 17, 1865-1882 (2008).
Rew, Y. et al., "Structure-Based Design of Novel Inhibitors of the MDM2-p53 Interaction," Journal of Medicinal Chemistry 55(11), 4936-4954 (2012).
Rothweiler, U. et al., "Isoquinolin-1-one Inhibitors of the MDM2-p53 Interaction," Chem. Med. Chem. 3(7), 1118-1128 (2008).
Sharma, S. V. et al., "Cell line-based platforms to evaluate the therapeutic efficacy of candidate anticancer agents," Nature Reviews 10, 241-253 (2010).
Stefanovsky, J. N. et al., "Ueber die Verhaeltnisse bei Ringschlussreaktionen epimerer 2-Amino-1,2-diphenyl-aethanole," Chem. Ber. 102, 717-727 (1969), cited on p. 19 of in Office Action dated Dec. 24, 2014 for U.S. Appl. No. 14/347,628, pp. 1-21 (attached).
Sun, D. et al., "Discovery of AMG 232, a Potent, Selective, and Orally Bioavailable MDM2-p53 Inhibitor in Clinical Development," Journal of Medicinal Chemistry 57(4), 1454-1472 (2014).
Voskoglou-Nomikos, T. et al., "Clinical Predictive Value of the in Vitro Cell Line, Human Xenograft, and Mouse Allograft Preclinical Cancer Models," Clin Cancer Res. 9(11), 4227-39 (2003).
Written Opinion of the International Searching Authority, PCT/US2014/041594, dated Aug. 18, 2014, pp. 1-12.
Written Opinion of the International Searching Authority, PCT/US2011/039184, dated Sep. 9, 2011, pp. 1-5.
Written Opinion of the International Searching Authority, PCT/US2014/016971, dated May 15, 2014, pp. 1-3.
Written Opinion of the International Searching Authority, PCT/US2014/026584, dated Jun. 26, 2014, pp. 1-6.
Written Opinion of the International Searching Authority, PCT/US2014/018759, dated Jun. 12, 2014, pp. 1-7.
Written Opinion of the International Searching Authority, PCT/US2012/057389, dated Jan. 18, 2013, pp. 1-6.
Zeitler, J. A. et al. "Characterization of Temperature-Induced Phase Transistions in Five Polymorphic Forms of Sulfathiazole by Terahertz Pulsed Spectroscopy and Differential Scanning Calorimerty," Journal of Pharmaceutical Sciences 95(11), 2486-2498 (2006).
STN Registry 92616-13-2, Dec. 17, 1984.
Braga, D et al., "Crystal Polymorphism and Multiple Crystal Forms", in: Molecular Networks, Berlin, Springer, pp. 25-50 (Structure and Bonding) (2009).
U.S. Appl. No. 16/535,279, filed Aug. 8, 2019, Bartberger et al.
U.S. Appl. No. 17/500,039, filed Oct. 13, 2021, Bio et al.

* cited by examiner

CIS-MORPHOLINONE AND OTHER COMPOUNDS AS MDM2 INHIBITORS FOR THE TREATMENT OF CANCER

This application is a continuation-in-part of U.S. patent application Ser. No. 14/768,529, which is a national stage application under 35 U.S.C. § 371 of International Application No. PCT/US2014/016971, having an international filing date of Feb. 18, 2014, which claims the benefit of U.S. Provisional Patent Application No. 61/766,625, filed Feb. 19, 2013. U.S. patent application Ser. No. 14/768,529 is incorporated herein by reference in its entirety.

FIELD OF THE INVENTION

The present invention relates to compounds that are MDM2 inhibitors that are useful as therapeutic agents, particularly for the treatment of cancers. The invention also relates to pharmaceutical compositions that contain a MDM2 inhibitor.

BACKGROUND OF THE INVENTION p53 is a tumor suppressor and transcription factor that responds to cellular stress by activating the transcription of numerous genes involved in cell cycle arrest, apoptosis, senescence, and DNA repair. Unlike normal cells, which have infrequent cause for p53 activation, tumor cells are under constant cellular stress from various insults including hypoxia and pro-apoptotic oncogene activation. Thus, there is a strong selective advantage for inactivation of the p53 pathway in tumors, and it has been proposed that eliminating p53 function may be a prerequisite for tumor survival. In support of this notion, three groups of investigators have used mouse models to demonstrate that absence of p53 function is a continuous requirement for the maintenance of established tumors. When the investigators restored p53 function to tumors with inactivated p53, the tumors regressed.

p53 is inactivated by mutation and/or loss in 50% of solid tumors and 10% of liquid tumors. Other key members of the p53 pathway are also genetically or epigenetically altered in cancer. MDM2, an oncoprotein, inhibits p53 function, and it is activated by gene amplification at incidence rates that are reported to be as high as 10%. MDM2, in turn, is inhibited by another tumor suppressor, p14ARF. It has been suggested that alterations downstream of p53 may be responsible for at least partially inactivating the p53 pathway in $p53^{WT}$ tumors (p53 wildtype). In support of this concept, some $p53^{WT}$ tumors appear to exhibit reduced apoptotic capacity, although their capacity to undergo cell cycle arrest remains intact. One cancer treatment strategy involves the use of small molecules that bind MDM2 and neutralize its interaction with p53. MDM2 inhibits p53 activity by three mechanisms: 1) acting as an E3 ubiquitin ligase to promote p53 degradation; 2) binding to and blocking the p53 transcriptional activation domain; and 3) exporting p53 from the nucleus to the cytoplasm. All three of these mechanisms would be blocked by neutralizing the MDM2-p53 interaction. In particular, this therapeutic strategy could be applied to tumors that are $p_{53}^{WT}$, and studies with small molecule MDM2 inhibitors have yielded promising reductions in tumor growth both in vitro and in vivo. Further, in patients with p53-inactivated tumors, stabilization of wildtype p53 in normal tissues by MDM2 inhibition might allow selective protection of normal tissues from mitotic poisons.

The present invention relates to compounds capable of inhibiting the interaction between p53 and MDM2 and activating p53 downstream effector genes. As such, compounds of the present invention would be useful in the treatment of cancers, bacterial infections, viral infections, ulcers and inflammation. In particular, the compounds of the present invention are useful to treat solid tumors such as: breast, colon, lung and prostate tumors; and liquid tumors such as lymphomas and leukemias. As used herein, MDM2 means a human MDM2 protein and p53 means a human p53 protein. It is noted that human MDM2 can also be referred to as HDM2 or hMDM2.

SUMMARY OF THE INVENTION

In embodiment 1, the present invention provides compounds of Formula I, or pharmaceutically acceptable salts thereof,

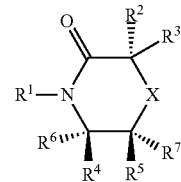

I wherein,
X is O or —S(=O)$_2$—;
R$^1$ is hydrogen, C$_{1-6}$alkyl, —(CR$^e$R$^e$)$_n$C$_{6-8}$aryl, —(CR$^e$R$^e$)$_n$C$_{3-8}$cycloalkyl, —(CR$^e$R$^e$)$_n$3-8 membered heterocycloalkyl,
—S(=O)$_2$C$_{3-8}$cycloalkyl, —C(=O)C$_{3-8}$cycloalkyl, or

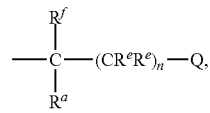

wherein any heteroaryl or heterocycloalkyl group has one or more heteroatoms independently selected from O, N or S, and wherein any cycloalkyl, heterocycloalkyl, heteroaryl or aryl group can be unsubstituted or substituted with from 1 to 3 substituents independently selected from C$_{1-6}$alkyl, halo, —CN, —CF$_3$, —SR$^e$, —S(=O)$_2$R$^e$, —CHF$_2$, —CH$_2$F, —NR$^e$R$^e$, —OCF$_3$, —OCHF$_2$, —OCH$_2$F, or —OR$^e$;
Q is —(CR$^e$R$^e$)$_n$C$_{6-8}$aryl, —(CR$^e$R$^e$)$_n$3-8 membered heterocycloalkyl, —(CR$^e$R$^e$)$_n$5-8 membered heteroaryl, —(CR$^e$R$^e$)$_n$C$_{3-8}$cycloalkyl, —CN, —(CR$^e$R$^e$)$_n$OH, —C(=O)OH, —NR$^e$R$^e$, —(CR$^e$R$^e$)$_n$OR$^e$, —C(=O)N(R$^e$) S(=O)$_2$R$^e$, —C(=O)NR$^e$R$^e$, —C(=O)NR$^e$(CR$^e$R$^e$)$_n$C(=O)OR$^e$, —C(=O)NR$^e$(CR$^e$R$^e$)$_n$C(=O)NR$^e$R$^e$, —N(R$^e$) (CR$^e$R$^e$)$_n$C(=O)OR$^e$, —OC(=O)NR$^e$R$^e$, —S(=O)$_2$C$_{3-8}$ cycloalkyl, —C(=O)N(R$^e$)(CR$^e$R$^e$)$_n$OH, —C(=O)N(R$^e$) (CR$^e$R$^e$)$_n$3-8 membered heterocycloalkyl, —N(R$^e$)C(=O) (CR$^e$R$^e$)$_n$OH, —N(R$^e$)S(=O)$_2$R$^e$, —N(R$^e$)C(=O) (CR$^e$R$^e$)$_n$ C(=O)OR$^e$, —C(=O)3-8 membered heterocycloalkyl, —S(=O)$_2$3-8 membered heterocycloalkyl, —C(=O)N(R$^e$)S(=O)$_2$C$_{3-8}$cycloalkyl, —O(CR$^e$R$^e$)$_n$C (=O)R$^e$, —C(=O)N(R$^e$)(CR$^e$R$^e$)5-8 membered heteroaryl, —N(R$^e$)C(=O)(CR$^e$R$^e$)5-8 membered heteroaryl, —C(=O)3-8 membered heterocycloalkyl(CR$^e$R$^e$)$_n$ C(=O) OR$^e$, or —C(=O)(CR$^e$R$^e$)$_n$C(=O)OR$^e$, wherein any heteroaryl or heterocycloalkyl group has one or more heteroatoms independently selected from O, N or S, and wherein any cycloalkyl, heterocycloalkyl, heteroaryl or aryl group can be unsubstituted or substituted with from 1 to 3 substituents independently selected from $C_{1-6}$alkyl, halo, —CN, —$SR^e$, —C(=O)$OR^e$, —$CF_3$, —S(=O)$_2R^e$, —$CHF_2$, —$CH_2F$, —$NR^eR^e$, —$OCF_3$, —$OCHF_2$, —$OCH_2F$, or —$OR^e$;

$R^2$ is hydrogen, $C_{1-6}$alkyl, —$(CR^eR^e)_nC(=O)OR^e$, —$(CR^eR^e)_nNR^eR^e$, —$(CR^eR^e)_nC(=O)NR^eR^e$, —$(CR^eR^e)_n$OH, —$(CR^eR^e)_nC(=O)H$, —$(CR^eR^e)_nC_{6-8}$aryl, —$(CR^eR^e)_n$ 3-8 membered heterocycloalkyl, —$(CR^eR^e)_n$ 5-8 membered heteroaryl, —$(CR^eR^e)_nCN$, —$(CR^eR^e)_nC(=O)$5-8 membered heterocycloalkyl, —$(CR^eR^e)_nC(=O)N(R^e)(CR^eR^e)_n$3-8 membered heterocycloalkyl, —$(CR^eR^e)_n$—CH(OH)$CH_2$OH, —CH=CH5-8 membered heteroaryl, —$(CR^eR^e)_n$CH=$CR^eR^e$, —$(CR^eR^e)_nOS(=O)_2C_{1-6}$alkyl, —$(CR^eR^e)_nOS(=O)OR^e$, or —$(CR^eR^e)_nOC(=O)NR^eR^e$, wherein any heteroaryl or heterocycloalkyl group has one or two heteroatoms independently selected from O, N or S, and wherein any cycloalkyl, heterocycloalkyl, heteroaryl or aryl group can be unsubstituted or substituted with from 1 to 3 substituents independently selected from $C_{1-6}$alkyl, halo, —$(CR^eR^e)_n$halo, —$OC_{1-6}$alkyl, —$OCF_3$, —$OCF_2H$, —$OCFH_2$, —CN, —S(=O)$_2CF_3$, —C(=O)$NR^eR^e$, -5-8 membered heteroaryl, —C(=O)$OR^e$, $C_{6-8}$aryl, 5-8 membered heteroaryl, —$CF_3$, —$SR^e$, —S(=O)$_2R^e$, —$CHF_2$, —$CH_2F$, —$NR^eR^e$, or —$OR^e$;

$R^3$ is hydrogen or $C_{1-6}$alkyl;

$R^4$ is $C_{6-8}$aryl or 5-9 membered heteroaryl, wherein any heteroaryl group has one or more heteroatom independently selected from O, N or S, and wherein the aryl or heteroaryl group is substituted with from 1 to 3 substituents independently selected from $C_{1-6}$alkyl, halo, —$CF_3$, —CN, $C_{3-8}$cycloalkyl, —$SR^e$, —S(=O)$_2R^e$, —$CHF_2$, —$CH_2F$, —$NR^eR^e$, —$OCF_3$, —$OCHF_2$, —$OCH_2F$, or —$OR^e$;

$R^5$ is $C_{6-8}$aryl or 5-9 membered heteroaryl, wherein any heteroaryl group has one or more heteroatom independently selected from O, N or S, and wherein the aryl or heteroaryl group is substituted with from 1 to 3 substituents independently selected from $C_{1-6}$alkyl, halo, —$CF_3$, —CN, $C_{3-8}$cycloalkyl, —$SR^e$, —S(=O)$_2R^e$, —$CHF_2$, —$CH_2F$, —$NR^eR^e$, —$OCF_3$, —$OCHF_2$, —$OCH_2F$, or —$OR^e$;

$R^6$ is hydrogen or $C_{1-6}$alkyl;
$R^7$ is hydrogen or $C_{1-6}$alkyl;
each $R^a$ is independently hydrogen, $C_{1-6}$alkyl, $C_{2-6}$alkenyl, —$(CR^eR^e)_nC_{3-8}$cycloalkyl, or —$(CR^eR^e)_nC_{6-8}$aryl, wherein any cycloalkyl or aryl group can be unsubstituted or substituted with from 1 to 3 substituents independently selected from $C_{1-6}$alkyl, halo, —CN, —$SR^e$, —C(=O)$OR^e$—$CF_3$, —S(=O)$_2R^e$, —$CHF_2$, —$CH_2F$, —$NR^eR^e$, —$OCF_3$, —$OCHF_2$, —$OCH_2F$, or —$OR^e$;
each $R^e$ is independently hydrogen, $C_{1-6}$alkyl, or —OH;
each $R^f$ is independently hydrogen, $C_{1-6}$alkyl, or —OH;
each n is independently 0, 1, 2, 3 or 4; and
each m is independently 0, 1, 2, 3 or 4,
provided that $R^2$ and $R^3$ are not both hydrogen.

In embodiment 2, the present invention provides compounds in accordance with embodiment 1 wherein X is O.

In embodiment 3, the present invention provides compounds in accordance with embodiment 1 wherein X is —S(=O)$_2$—.

In embodiment 4, the present invention provides compounds in accordance with any one of embodiments 1 to 3 wherein $R^3$ is hydrogen.

In embodiment 5, the present invention provides compound in accordance with any one of embodiments 1 to 3 wherein $R^3$ is $C_{1-6}$alkyl.

In embodiment 6, the present invention provides compounds in accordance with any one of embodiments 1 to 3 wherein $R^3$ is methyl.

In embodiment 7, the present invention provides compounds in accordance with any one of embodiments 1 to 6 wherein $R^6$ is hydrogen.

In embodiment 8, the present invention provides compounds in accordance with any one of embodiments 1 to 6 wherein $R^6$ is methyl.

In embodiment 9, the present invention provides compounds in accordance with any one of embodiments 1 to 8 wherein $R^7$ is hydrogen.

In embodiment 10, the present invention provides compounds in accordance with any one of embodiments 1 to 8 wherein $R^7$ is methyl.

In embodiment 11, the present invention provides compounds in accordance with any one of embodiments 1 to 10 wherein $R^4$ is substituted $C_{6-8}$aryl.

In embodiment 12, the present invention provides compounds in accordance with any one of embodiments 1 to 10 wherein $R^4$ is substituted phenyl.

In embodiment 13, the present invention provides compounds in accordance with any one of embodiments 1 to 10 wherein $R^4$ is phenyl substituted with from 1 to 3 halo groups.

In embodiment 14, the present invention provides compounds in accordance with any one of embodiments 1 to 10 wherein $R^4$ is phenyl substituted with a fluorine.

In embodiment 15, the present invention provides compounds in accordance with any one of embodiments 1 to 10 wherein $R^4$ is phenyl substituted with a bromine.

In embodiment 16, the present invention provides compounds in accordance with any one of embodiments 1 to 10 wherein $R^4$ is 4-chlorophenyl or 4-bromophenyl.

In embodiment 17, the present invention provides compounds in accordance with any one of embodiments 1 to 16 wherein $R^5$ is substituted $C_{6-8}$aryl.

In embodiment 18, the present invention provides compounds in accordance with any one of embodiments 1 to 16 wherein $R^5$ is substituted phenyl.

In embodiment 19, the present invention provides compounds in accordance with any one of embodiments 1 to 16 wherein $R^5$ is phenyl substituted with from 1 to 3 halo groups.

In embodiment 20, the present invention provides compounds in accordance with any one of embodiments 1 to 16 wherein $R^5$ is phenyl substituted with a fluorine.

In embodiment 21, the present invention provides compounds in accordance with any one of embodiments 1 to 16 wherein $R^5$ is phenyl substituted with a bromine.

In embodiment 22, the present invention provides compounds in accordance with any one of embodiments 1 to 16 wherein $R^5$ is 4-chlorophenyl or 4-bromophenyl.

In embodiment 23, the present invention provides compounds in accordance with any one of embodiments 1 to 16 wherein $R^5$ is 3-chlorophenyl or 3-bromophenyl.

In embodiment 24, the present invention provides compounds in accordance with any one of embodiments 1 to 23 wherein $R^2$ is hydrogen.

In embodiment 25, the present invention provides compounds in accordance with any one of embodiments 1 to 23 wherein $R^2$ is $C_{1-6}$alkyl.

In embodiment 26, the present invention provides compounds in accordance with any one of embodiments 1 to 23 wherein $R^2$ is —$CH_2C(=O)OH$.

In embodiment 27, the present invention provides compounds in accordance with any one of embodiments 1 to 23 wherein $R^2$ is —$CH_2$phenyl.

In embodiment 28, the present invention provides compounds in accordance with any one of embodiments 1 to 23 wherein $R^2$ is —$CH_2$phenyl substituted with from 1 to 3 substituents independently selected from $C_{1-6}$alkyl, halo, —$(CR^eR^e)_n$halo, —$OC_{1-6}$alkyl, —$OCF_3$, —$OCF_2H$, —$OCFH_2$, —CN, —$S(=O)_2CF_3$, —$C(=O)NR^eR^e$, —$C(=O)OR^e$, $C_{6-8}$aryl, —$CF_3$, —$SR^e$, —$S(=O)_2R^e$, —$CHF_2$, —$CH_2F$, —$NR^eR^e$, or —$OR^e$.

In embodiment 29, the present invention provides compounds in accordance with any one of embodiments 1 to 23 wherein $R^2$ is —$CH_2$phenyl substituted with from 1 to 3 substituents independently selected from $C_{1-6}$alkyl, halo, —$OC_{1-6}$alkyl, —$OCF_3$, —$OCF_2H$, —$OCFH_2$, —CN, —$CF_3$, —$SR^e$, —$S(=O)_2R^e$, —$CHF_2$, —$CH_2F$, —$NR^eR^e$, or —$OR^e$.

In embodiment 30, the present invention provides compounds in accordance with any one of embodiments 1 to 23 wherein $R^2$ is —$CH_2$pyridyl.

In embodiment 31, the present invention provides compounds in accordance with any one of embodiments 1 to 23 wherein $R^2$ is —$CH_2$pyridyl substituted with from 1 to 3 substituents independently selected from $C_{1-6}$alkyl, halo, —$OC_{1-6}$alkyl, —$OCF_3$, —$OCF_2H$, —$OCFH_2$, —CN, —$CF_3$, —$SR^e$, —$S(=O)_2R^e$, —$CHF_2$, —$CH_2F$, —$NR^eR^e$, or —$OR^e$.

In embodiment 32, the present invention provides compounds in accordance with any one of embodiments 1 to 31 wherein $R^1$ is $C_{1-6}$alkyl.

In embodiment 33, the present invention provides compounds in accordance with any one of embodiments 1 to 31 wherein $R^1$ is methyl.

In embodiment 34, the present invention provides compounds in accordance with any one of embodiments 1 to 31 wherein $R^1$ is —$(CR^eR^e)_nC_{3-8}$cycloalkyl.

In embodiment 35, the present invention provides compounds in accordance with any one of embodiments 1 to 31 wherein $R^1$ is —$CH_2$cyclopropyl, —$CH_2$cyclobutyl or —$CH_2$cyclohexyl.

In embodiment 36, the present invention provides compounds in accordance with any one of embodiments 1 to 31 wherein $R^1$ is

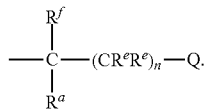

In embodiment 37, the present invention provides compounds in accordance with any one of embodiments 1 to 31 wherein $R^1$ is

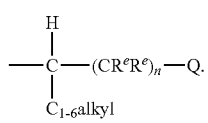

In embodiment 38, the present invention provides compounds in accordance with any one of embodiments 1 to 31 wherein $R^1$ is

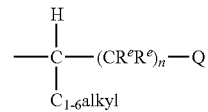

Q is —$C(=O)OR^e$, —$C(=O)NR^e(CR^eR^e)_nC(=O)OR^e$, or 5-8 membered heteroaryl.

In embodiment 39, the present invention provides compounds in accordance with any one of embodiments 1 to 31 wherein $R^1$ is 5-8 membered heteroaryl.

In embodiment 40, the present invention provides compounds in accordance with embodiment 1 wherein:
X is O;
$R^3$ is hydrogen or methyl;
$R^4$ is phenyl substituted with from 1 to 3 halo groups;
$R^5$ is phenyl substituted with from 1 to 3 halo groups;
$R^6$ is hydrogen or methyl; and
$R^7$ is hydrogen or methyl.

In embodiment 41, the present invention provides compounds in accordance with embodiment 40 wherein: $R^2$ is —$CH_2C(=O)OH$.

In embodiment 42, the present invention provides compounds in accordance with embodiment 40 wherein: $R^2$ is —$CH_2$phenyl substituted with from 1 to 3 substituents independently selected from $C_{1-6}$alkyl, halo, —$OC_{1-6}$alkyl, —$OCF_3$, —$OCF_2H$, —$OCFH_2$, —CN, —$CF_3$, —$SR^e$, —$S(=O)_2R^e$, —$CHF_2$, —$CH_2F$, —$NR^eR^e$, or —$OR^e$.

In embodiment 43, the present invention provides the compounds, or a pharmaceutically acceptable salts, selected from:
(2S,5R,6S)-2-benzyl-5,6-bis(4-bromophenyl)-4-methylmorpholin-3-one;
(2R,5S,6R)-2-benzyl-5,6-bis(4-bromophenyl)-4-methylmorpholin-3-one;
(2S,5R,6S)-2-benzyl-5,6-bis(4-chlorophenyl)-4-methylmorpholin-3-one;
(2R,5S,6R)-2-benzyl-5,6-bis(4-chlorophenyl)-4-methylmorpholin-3-one;
(2S,5R,6S)-2-(4-bromobenzyl)-5,6-bis(4-bromophenyl)-4-methylmorpholin-3-one;
(2R,5S,6R)-2-(4-bromobenzyl)-5,6-bis(4-bromophenyl)-4-methylmorpholin-3-one;
(2S,5R,6S)-5,6-bis(4-bromophenyl)-2-(4-fluorobenzyl)-4-methylmorpholin-3-one;
(2R,5S,6R)-5,6-bis(4-bromophenyl)-2-(4-fluorobenzyl)-4-methylmorpholin-3-one;
(2S,5R,6S)-5,6-bis(4-bromophenyl)-2-(4-methoxybenzyl)-4-methylmorpholin-3-one;
(2R,5S,6R)-5,6-bis(4-bromophenyl)-2-(4-methoxybenzyl)-4-methylmorpholin-3-one;
(2S,5R,6S)-5,6-bis(4-bromophenyl)-4-methyl-2-(4-(trifluoromethoxy)benzyl)morpholin-3-one;
(2R,5S,6R)-5,6-bis(4-bromophenyl)-4-methyl-2-(4-(trifluoromethoxy)benzyl)morpholin-3-one;
(2S,5R,6S)-5,6-bis(4-bromophenyl)-2-(3-methoxybenzyl)-4-methylmorpholin-3-one;
(2R,5S,6R)-5,6-bis(4-bromophenyl)-2-(3-methoxybenzyl)-4-methylmorpholin-3-one;
(R)-2-((2S,5R,6S)-2-(4-fluorobenzyl)-5,6-bis(4-chlorophenyl)-3-oxomorpholino)pentanoic acid;

(5R,6S)-6-(3-chlorophenyl)-5-(4-chlorophenyl)-4-methylmorpholin-3-one;

(5S,6R)-6-(3-chlorophenyl)-5-(4-chlorophenyl)-4-methylmorpholin-3-one;

(5R,6S)-6-(3-chlorophenyl)-5-(4-chlorophenyl)-4-(cyclopropylmethyl)morpholin-3-one;

(5S,6R)-6-(3-chlorophenyl)-5-(4-chlorophenyl)-4-(cyclopropylmethyl)morpholin-3-one;

(2S,5R,6S)-2-benzyl-6-(3-chlorophenyl)-5-(4-chlorophenyl)-4-methylmorpholin-3-one;

(2R,5S,6R)-2-benzyl-6-(3-chlorophenyl)-5-(4-chlorophenyl)-4-methylmorpholin-3-one;

(2S,5R,6S)-6-(3-chlorophenyl)-5-(4-chlorophenyl)-4-(cyclopropylmethyl)-2-((S)-2,3-dihydroxypropyl)morpholin-3-one;

(2S,5R,6S)-6-(3-chlorophenyl)-5-(4-chlorophenyl)-4-(cyclopropylmethyl)-2-((R)-2,3-dihydroxypropyl)morpholin-3-one;

(2S,5S,6R)-6-(3-chlorophenyl)-5-(4-chlorophenyl)-4-(cyclopropylmethyl)-2-((S)-2,3-dihydroxypropyl)morpholin-3-one;

(2S,5S,6R)-6-(3-chlorophenyl)-5-(4-chlorophenyl)-4-(cyclopropylmethyl)-2-((R)-2,3-dihydroxypropyl)morpholin-3-one;

(2-((2S,5R,6S)-6-(3-chlorophenyl)-5-(4-chlorophenyl)-4-(cyclopropylmethyl)-3-oxomorpholin-2-yl)acetaldehydeacetaldehyde;

(2-((2R,5S,6R)-6-(3-chlorophenyl)-5-(4-chlorophenyl)-4-(cyclopropylmethyl)-3-oxomorpholin-2-yl)acetaldehydeacetaldehyde;

(2S,5R,6S)-6-(3-chlorophenyl)-5-(4-chlorophenyl)-4-(cyclopropylmethyl)-2-(2-hydroxyethyl)morpholin-3-one;

(2R,5S,6R)-6-(3-chlorophenyl)-5-(4-chlorophenyl)-4-(cyclopropylmethyl)-2-(2-hydroxyethyl)morpholin-3-one;

(2-((2S,5R,6S)-6-(3-chlorophenyl)-5-(4-chlorophenyl)-4-(cyclopropylmethyl)-3-oxomorpholin-2-yl)acetic acid;

(2-((2R,5S,6R)-6-(3-chlorophenyl)-5-(4-chlorophenyl)-4-(cyclopropylmethyl)-3-oxomorpholin-2-yl)acetic acid;

(2S,5R,6S)-6-(3-chlorophenyl)-5-(4-chlorophenyl)-4-(cyclopropylmethyl)-2-(2-(methylamino)ethyl)morpholin-3-one;

(2R,5S,6R)-6-(3-chlorophenyl)-5-(4-chlorophenyl)-4-(cyclopropylmethyl)-2-(2-(methylamino)ethyl)morpholin-3-one;

(2S,5R,6S)-6-(3-chlorophenyl)-5-(4-chlorophenyl)-4-(cyclopropylmethyl)-2-(3-hydroxypropyl)morpholin-3-one;

(2R,5S,6R)-6-(3-chlorophenyl)-5-(4-chlorophenyl)-4-(cyclopropylmethyl)-2-(3-hydroxypropyl)morpholin-3-one;

3-((2S,5R,6S)-6-(3-chlorophenyl)-5-(4-chlorophenyl)-4-(cyclopropylmethyl)-3-oxomorpholin-2-yl)propanoic acid;

3-((2R,5S,6R)-6-(3-chlorophenyl)-5-(4-chlorophenyl)-4-(cyclopropylmethyl)-3-oxomorpholin-2-yl)propanoic acid;

2-((2S,5R,6S)-6-(3-chlorophenyl)-5-(4-chlorophenyl)-4-(cyclopropylmethyl)-3-oxomorpholin-2-yl)acetic acid;

2-((2R,5S,6R)-6-(3-chlorphenyl)-5-(4-chlorophenyl)-4-(cyclopropylmethyl)-3-oxomorpholin-2-yl)acetic acid;

2-((2S,5R,6S)-6-(3-chlorophenyl)-5-(4-chlorophenyl)-4-(cyclobutylmethyl)-3-oxomorpholin-2-yl)acetic acid;

2-((2R,5S,6R)-6-(3-chlorophenyl)-5-(4-chlorophenyl)-4-(cyclobutylmethyl)-3-oxomorpholin-2-yl)acetic acid;

(2S,5R,6S)-6-(3-chlorophenyl)-5-(4-chlorophenyl)-4-isobutyl-3-oxomorpholin-2-yl)acetic acid;

(2R,5S,6R)-6-(3-chlorophenyl)-5-(4-chlorophenyl)-4-isobutyl-3-oxomorpholin-2-yl)acetic acid;

2-((2S,5R,6S)-6-(3-chlorophenyl)-5-(4-chlorophenyl)-4-(cyclohexylmethyl)-3-oxomorpholin-2-yl)acetic acid;

2-((2R,5S,6R)-6-(3-chlorophenyl)-5-(4-chlorophenyl)-4-(cyclohexylmethyl)-3-oxomorpholin-2-yl)acetic acid;

2-((2S,5R,6S)-4-benzyl-6-(3-chlorophenyl)-5-(4-chlorophenyl)-3-oxomorpholin-2-yl)acetic acid;

2-((2R,5S,6R)-4-benzyl-6-(3-chlorophenyl)-5-(4-chlorophenyl)-3-oxomorpholin-2-yl)acetic acid;

(R)-2-((2S,3R,6S)-2,3-bis(4-chlorophenyl)-6-(4-fluorobenzyl)-5-oxomorpholino)-N-(methylsulfonyl)pentanamide;

(S)-2-((2R,3S,6R)-2,3-bis(4-chlorophenyl)-6-(4-fluorobenzyl)-5-oxomorpholino)-N-(methylsulfonyl)pentanamide;

1-((R)-2-((2S,3R,6S)-2,3-bis(4-chlorophenyl)-6-(4-fluorobenzyl)-5-oxomorpholino)pentanoyl)azetidine-3-carboxylic acid;

1-((S)-2-((2R,3S,6R)-2,3-bis(4-chlorophenyl)-6-(4-fluorobenzyl)-5-oxomorpholino)pentanoyl)azetidine-3-carboxylic acid;

(R)-2-((2S,3R,6S)-2-(4-chloro-3-fluorophenyl)-3-(4-chlorophenyl)-6-(4-fluorobenzyl)-5-oxomorpholino)pentanoic acid;

(S)-2-((2R,3S,6R)-2-(4-chloro-3-fluorophenyl)-3-(4-chlorophenyl)-6-(4-fluorobenzyl)-5-oxomorpholino)pentanoic acid;

(S)-2-((2S,3R,6S)-2-(4-chloro-3-fluorophenyl)-3-(4-chlorophenyl)-6-(4-fluorobenzyl)-5-oxomorpholino)pentanoic acid;

(R)-2-((2R,3S,6R)-2-(4-chloro-3-fluorophenyl)-3-(4-chlorophenyl)-6-(4-fluorobenzyl)-5-oxomorpholino)pentanoic acid;

(R)-2-((2S,3R,6S)-2-(4-chloro-2-methylphenyl)-3-(4-chlorophenyl)-6-(4-fluorobenzyl)-5-oxomorpholino)pentanoic acid;

(S)-2-((2R,3S,6R)-2-(4-chloro-2-methylphenyl)-3-(4-chlorophenyl)-6-(4-fluorobenzyl)-5-oxomorpholino)pentanoic acid;

(S)-2-((2S,3R,6S)-2-(4-chloro-2-methylphenyl)-3-(4-chlorophenyl)-6-(4-fluorobenzyl)-5-oxomorpholino)pentanoic acid;

(R)-2-((2R,3S,6R)-2-(4-chloro-2-methylphenyl)-3-(4-chlorophenyl)-6-(4-fluorobenzyl)-5-oxomorpholino)pentanoic acid;

(R)-4-((2R,3S,6S)-2,3-bis(4-chlorophenyl)-6-(4-fluorobenzyl)-5-oxomorpholino)heptanoic acid;

(S)-4-((2R,3S,6S)-2,3-bis(4-chlorophenyl)-6-(4-fluorobenzyl)-5-oxomorpholino)heptanoic acid;

4-((R)-2-((2S,3R,6S)-2,3-bis(4-chlorophenyl)-6-(4-cyanobenzyl)-5-oxomorpholino)pentanamido)butanoic acid;

3-((R)-2-((2S,3R,6S)-2,3-Bis(4-chlorophenyl)-6-(4-cyanobenzyl)-5-oxomorpholino)pentanamido)propanoic acid;

(R)—N-(2-amino-2-oxoethyl)-2-((2S,3R,6S)-2,3-bis(4-chlorophenyl)-6-(4-cyanobenzyl)-5-oxomorpholino)pentanamide;

(S)—N-(2-amino-2-oxoethyl)-2-((2R,3S,6R)-2,3-bis(4-chlorophenyl)-6-(4-cyanobenzyl)-5-oxomorpholino)pentanamide;

4-(((2S,5R,6S)-4-((R)-1-(1H-tetrazol-5-yl)butyl)-5,6-bis(4-chlorophenyl)-3-oxomorpholin-2-yl)methyl)-2-fluorobenzonitrile;

(2S,5R,6S)-4-((R)-1-(1H-tetrazol-5-yl)butyl)-5,6-bis(4-chlorophenyl)-2-(4-iodobenzyl)morpholin-3-one;

(2R,5S,6R)-4-((S)-1-(1H-tetrazol-5-yl)butyl)-5,6-bis(4-chlorophenyl)-2-(4-iodobenzyl)morpholin-3-one;

(R)-2-((2S,3R)-2,3-bis(4-chlorophenyl)-5-oxomorpholino) pentanoic acid;

(S)-2-((2R,3S,6R)-2,3-bis(4-chlorophenyl)-6-(4-fluorobenzyl)-5-oxomorpholino)pentanoic acid;

(2R,5S,6R)-5,6-bis(4-chlorophenyl)-4-methyl-2-(2-morpholinoethyl)morpholin-3-one;
(2S,5R,6S)-5,6-bis(4-chlorophenyl)-4-methyl-2-(2-morpholinoethyl)morpholin-3-one;
(2R,5S,6R)-5,6-bis(4-chlorophenyl)-4-methyl-2-(pyridin-4-ylmethyl)morpholin-3-one;
(2S,5R,6S)-5,6-bis(4-chlorophenyl)-4-methyl-2-(pyridin-4-ylmethyl)morpholin-3-one;
(S)-2-((2R,3S,6R)-2,3-bis(4-chlorophenyl)-5-oxo-6-(pyridin-4-ylmethyl)morpholino)pentanoic acid;
(R)-2-((2S,3R,6S)-2,3-bis(4-chlorophenyl)-5-oxo-6-(pyridin-4-ylmethyl)morpholino)pentanoic acid;
(R)-2-((2S,3R)-2-(4-chlorophenyl)-3-(1H-indol-2-yl)-5-oxomorpholino)pentanoic acid;
(S)-2-((2R,3S)-2-(4-Chlorophenyl)-3-(1H-indol-2-yl)-5-oxomorpholino)pentanoic acid;
(R)-2-((2S,5R,6S)-2-benzyl-5,6-bis(4-chlorophenyl)-3-oxomorpholino)pentanoic acid;
(R)-2-((2S,3R,6S)-2,3-bis(4-chlorophenyl)-6-(2-cyano-4-fluorobenzyl)-5-oxomorpholino)pentanoic acid;
(R)-2-((2S,3R,6S)-2,3-bis(4-chlorophenyl)-6-(2-cyanobenzyl)-5-oxomorpholino)pentanoic acid;
(R)-2-((2S,3R,6S)-2,3-bis(4-chlorophenyl)-6-(2-fluorobenzyl)-5-oxomorpholino)pentanoic acid;
(R)-2-((2S,3R,6S)-2,3-bis(4-chlorophenyl)-6-(3-fluorobenzyl)-5-oxomorpholino)pentanoic acid;
(R)-2-((2S,3R,6S)-2,3-bis(4-chlorophenyl)-6-(3-cyanobenzyl)-5-oxomorpholino)pentanoic acid;
(R)-2-((2S,3R,6S)-2,3-bis(4-chlorophenyl)-6-(3-(methylsulfonyl)benzyl)-5-oxomorpholino)pentanoic acid;
(R)-2-((2S,3R,6S)-2,3-bis(4-chlorophenyl)-6-(2-(methylsulfonyl)benzyl)-5-oxomorpholino)pentanoic acid;
(R)-2-((2S,3R,6S)-2,3-bis(4-chlorophenyl)-6-(4-fluoro-2-(methylsulfonyl)benzyl)-5-oxomorpholino)pentanoic acid;
(R)-2-((2S,3R,6S)-2,3-bis(4-chlorophenyl)-6-(3-fluoro-4-(methylsulfonyl)benzyl)-5-oxomorpholino)pentanoic acid;
(R)-2-((2S,3R,6S)-2,3-bis(4-chlorophenyl)-6-(4-(methylsulfonyl)benzyl)-5-oxomorpholino)pentanoic acid;
(R)-2-((2S,3R,6S)-2,3-bis(4-chlorophenyl)-5-oxo-6-(4-((trifluoromethyl)sulfonyl)benzyl)morpholino)pentanoic acid;
(R)-2-((2S,3R,6S)-2,3-bis(4-chlorophenyl)-5-oxo-6-(4-((trifluoromethyl)sulfonyl)benzyl)morpholino)pentanoic acid;
(R)-2-((2S,3R,6S)-2,3-bis(4-chlorophenyl)-6-(3-morpholinopropyl)-5-oxomorpholino)pentanoic acid;
(2S,5R,6S)-5,6-bis(4-chlorophenyl)-4-(2-chloropyridin-4-yl)-2-(4-fluorobenzyl)morpholin-3-one;
(2R,5S,6R)-5,6-bis(4-chlorophenyl)-4-(2-chloropyridin-4-yl)-2-(4-fluorobenzyl)morpholin-3-one;
(2S,5R,6S)-5,6-bis(4-chlorophenyl)-2-(4-fluorobenzyl)-4-phenylmorpholin-3-one;
(2R,5S,6R)-5,6-bis(4-chlorophenyl)-2-(4-fluorobenzyl)-4-phenylmorpholin-3-one;
(2S,5R,6S)-5,6-bis(4-chlorophenyl)-2-(4-fluorobenzyl)-4-(1H-pyrazol-4-yl)morpholin-3-one;
(2R,5S,6R)-5,6-bis(4-chlorophenyl)-2-(4-fluorobenzyl)-4-(1H-pyrazol-4-yl)morpholin-3-one;
(2S,5R,6S)-5,6-bis(4-chlorophenyl)-2-(4-fluorobenzyl)-4-(pyridin-4-yl)morpholin-3-one;
(2R,5S,6R)-5,6-bis(4-chlorophenyl)-2-(4-fluorobenzyl)-4-(pyridin-4-yl)morpholin-3-one;
(2S,5R,6S)-5,6-bis(4-chlorophenyl)-2-(4-(methylsulfonyl)benzyl)-4-(pyridin-3-yl)morpholin-3-one;
(2R,5S,6R)-5,6-bis(4-chlorophenyl)-2-(4-(methylsulfonyl)benzyl)-4-(pyridin-3-yl)morpholin-3-one;
(2S,5R,6S)-5,6-bis(4-chlorophenyl)-2-(2-fluoro-4-(methylsulfonyl)benzyl)-4-(pyridin-3-yl)morpholin-3-one;
(2R,5S,6R)-5,6-bis(4-chlorophenyl)-2-(2-fluoro-4-(methylsulfonyl)benzyl)-4-(pyridin-3-yl)morpholin-3-one;
(2S,5R,6S)-6-(3-chlorophenyl)-5-(4-chlorophenyl)-4-(cyclopropylmethyl)-2-(2-(4-methylpiperazin-1-yl)-2-oxoethyl)morpholin-3-one;
(2R,5S,6R)-6-(3-chlorophenyl)-5-(4-chlorophenyl)-4-(cyclopropylmethyl)-2-(2-(4-methylpiperazin-1-yl)-2-oxoethyl)morpholin-3-one;
2-((2S,5R,6S)-4-((R)-1-amino-1-oxopentan-2-yl)-6-(3-chlorophenyl)-5-(4-chlorophenyl)-3-oxomorpholin-2-yl)acetic acid;
2-((2R,5S,6R)-4-((S)-1-amino-1-oxopentan-2-yl)-6-(3-chlorophenyl)-5-(4-chlorophenyl)-3-oxomorpholin-2-yl)acetic acid;
2-((2S,5R,6S)-4-((S)-1-amino-1-oxopentan-2-yl)-6-(3-chlorophenyl)-5-(4-chlorophenyl)-3-oxomorpholin-2-yl)acetic acid;
2-((2R,5S,6R)-4-((R)-1-amino-1-oxopentan-2-yl)-6-(3-chlorophenyl)-5-(4-chlorophenyl)-3-oxomorpholin-2-yl)acetic acid;
2-((2S,5R,6S)-6-(3-chlorophenyl)-5-(4-chlorophenyl)-4-((R)-1-cyanobutyl)-3-oxomorpholin-2-yl)acetic acid;
2-((2R,5S,6R)-6-(3-chlorophenyl)-5-(4-chlorophenyl)-4-((S)-1-cyanobutyl)-3-oxomorpholin-2-yl)acetic acid;
2-((2S,5R,6S)-6-(3-chlorophenyl)-5-(4-chlorophenyl)-4-((S)-1-cyanobutyl)-3-oxomorpholin-2-yl)acetic acid;
2-((2R,5S,6R)-6-(3-chlorophenyl)-5-(4-chlorophenyl)-4-((R)-1-cyanobutyl)-3-oxomorpholin-2-yl)acetic acid;
2-((2S,5R,6S)-4-((R)-1-(1H-tetrazol-5-yl)butyl)-6-(3-chlorophenyl)-5-(4-chlorophenyl)-3-oxomorpholin-2-yl)acetic acid;
2-((2R,5S,6R)-4-((S)-1-(1H-tetrazol-5-yl)butyl)-6-(3-chlorophenyl)-5-(4-chlorophenyl)-3-oxomorpholin-2-yl)acetic acid;
2-((2S,5R,6S)-4-((S)-1-(1H-tetrazol-5-yl)butyl)-6-(3-chlorophenyl)-5-(4-chlorophenyl)-3-oxomorpholin-2-yl)acetic acid;
2-((2R,5S,6R)-4-((R)-1-(1H-tetrazol-5-yl)butyl)-6-(3-chlorophenyl)-5-(4-chlorophenyl)-3-oxomorpholin-2-yl)acetic acid;
2-((2S,5R,6S)-6-(3-chlorophenyl)-5-(4-chlorophenyl)-4-((R)-1-(5-methyl-1,3,4-oxadiazol-2-yl)butyl)-3-oxomorpholin-2-yl)acetic acid;
2-((2R,5S,6R)-6-(3-chlorophenyl)-5-(4-chlorophenyl)-4-((S)-1-(5-methyl-1,3,4-oxadiazol-2-yl)butyl)-3-oxomorpholin-2-yl)acetic acid;
2-((2S,5R,6S)-6-(3-chlorophenyl)-5-(4-chlorophenyl)-4-((S)-1-(5-methyl-1,3,4-oxadiazol-2-yl)butyl)-3-oxomorpholin-2-yl)acetic acid;
2-((2R,5S,6R)-6-(3-chlorophenyl)-5-(4-chlorophenyl)-4-((R)-1-(5-methyl-1,3,4-oxadiazol-2-yl)butyl)-3-oxomorpholin-2-yl)acetic acid;
2-((2S,5R,6S)-6-(3-chlorophenyl)-5-(4-chlorophenyl)-4-((R)-cyclopropyl(5-methyl-1,3,4-oxadiazol-2-yl)methyl)-3-oxomorpholin-2-yl)acetic acid;
2-((2R,5S,6R)-6-(3-chlorophenyl)-5-(4-chlorophenyl)-4-((S)-cyclopropyl(5-methyl-1,3,4-oxadiazol-2-yl)methyl)-3-oxomorpholin-2-yl)acetic acid;
2-((2S,5R,6S)-6-(3-chlorophenyl)-5-(4-chlorophenyl)-4-((S)-cyclopropyl(5-methyl-1,3,4-oxadiazol-2-yl)methyl)-3-oxomorpholin-2-yl)acetic acid;

2-((2R,5S,6R)-6-(3-chlorophenyl)-5-(4-chlorophenyl)-4-((R)-cyclopropyl(5-methyl-1,3,4-oxadiazol-2-yl)methyl)-3-oxomorpholin-2-yl)acetic acid;
(S)-2-((2S,3R,6S)-2,3-bis(4-chlorophenyl)-6-(4-cyanobenzyl)-5-oxomorpholino)-2-cyclopropylacetic acid;
(R)-2-((2R,3S,6R)-2,3-bis(4-chlorophenyl)-6-(4-cyanobenzyl)-5-oxomorpholino)-2-cyclopropylacetic acid;
(R)-2-((2S,3R,6S)-2,3-bis(4-chlorophenyl)-6-(4-cyanobenzyl)-5-oxomorpholino)-2-cyclopropylacetic acid;
(S)-2-((2R,3S,6R)-2,3-bis(4-chlorophenyl)-6-(4-cyanobenzyl)-5-oxomorpholino)-2-cyclopropylacetic acid;
(S)-2-((2S,3R,6S)-2,3-bis(4-chlorophenyl)-6-(4-cyanobenzyl)-5-oxomorpholino)-2-cyclopropylacetic acid;
(R)-2-((2R,3S,6R)-2,3-bis(4-chlorophenyl)-6-(4-cyanobenzyl)-5-oxomorpholino)-2-cyclopropylacetic acid;
(R)-2-((2S,3R,6S)-2,3-bis(4-chlorophenyl)-6-(4-cyanobenzyl)-5-oxomorpholino)-2-cyclopropylacetic acid;
(S)-2-((2R,3S,6R)-2,3-bis(4-chlorophenyl)-6-(4-cyanobenzyl)-5-oxomorpholino)-2-cyclopropylacetic acid;
(5R,6S)-6-(3-chlorophenyl)-5-(4-chlorophenyl)-4-(cyclopropylmethyl)thiomorpholin-3-one;
(5R,6S)-6-(3-chlorophenyl)-5-(4-chlorophenyl)-4-(cyclopropylmethyl)-2,2-dimethylthiomorpholin-3-one 1,1-dioxide;
(5R,6S)-6-(3-chlorophenyl)-5-(4-chlorophenyl)-4-isopropylthiomorpholin-3-one;
2-((2R,5S,6S)-6-(3-chlorophenyl)-5-(4-chlorophenyl)-4-isopropyl-1,1-dioxido-3-oxothiomorpholin-2-yl)acetic acid;
2-((2S,5R,6S)-6-(3-chlorophenyl)-5-(4-chlorophenyl)-4-isopropyl-1,1-dioxido-3-oxothiomorpholin-2-yl)acetic acid;
2-((2S,5R,6S)-6-(3-chlorophenyl)-5-(4-chlorophenyl)-4-((S)-1-hydroxybutan-2-yl)-3-oxomorpholin-2-yl)acetic acid;
2-((2R,5R,6S)-6-(3-chlorophenyl)-5-(4-chlorophenyl)-4-((S)-1-hydroxybutan-2-yl)-3-oxomorpholin-2-yl)acetic acid;
2-((2R,5R,6S)-6-(3-chlorophenyl)-5-(4-chlorophenyl)-4-((S)-1-hydroxybutan-2-yl)-3-oxomorpholin-2-yl)acetic acid;
2-((2S,5R,6S)-6-(3-chlorophenyl)-5-(4-chlorophenyl)-4-((S)-1-hydroxybutan-2-yl)-3-oxomorpholin-2-yl)acetic acid;
(2S,5R,6S)-5,6-bis(4-chlorophenyl)-2-(4-fluorobenzyl)morpholin-3-one;
(2R,5S,6R)-5,6-bis(4-chlorophenyl)-2-(4-fluorobenzyl)morpholin-3-one; or
2-((2S,5R,6S)-6-(3-chlorophenyl)-5-(4-chlorophenyl)-4-(cyclopropylmethyl)-5-methyl-3-oxomorpholin-2-yl)acetic acid.

In embodiment 44, the present invention provides the compounds, or a pharmaceutically acceptable salts, selected from:

1,1-dimethylethyl (2R,3S)-2,3-bis(4-bromophenyl)-5-oxo-1-piperazinecarboxylate;
1,1-dimethylethyl (2S,3R)-2,3-bis(4-bromophenyl)-5-oxo-1-piperazinecarboxylate;
(2R,5S,6R)-5,6-bis(4-bromophenyl)-4-methyl-2-(2-propen-1-yl)-3-morpholinone;
(2S,5R,6S)-5,6-bis(4-bromophenyl)-4-methyl-2-(2-propen-1-yl)-3-morpholinone;
(5R,6S)-5,6-bis(4-bromophenyl)-4-cyclopropyl-3-morpholinone;
(5S,6R)-5,6-bis(4-bromophenyl)-4-cyclopropyl-3-morpholinone
(2S,5R,6S)-5,6-bis(4-bromophenyl)-2,4-dimethyl-3-morpholinone;
(2R,5R,6S)-5,6-bis(4-bromophenyl)-2,4-dimethyl-3-morpholinone;
(2R,5S,6R)-5,6-bis(4-bromophenyl)-4-cyclopropyl-2-(phenylmethyl)-3-morpholinone;
(2S,5R,6S)-5,6-bis(4-bromophenyl)-4-cyclopropyl-2-(phenylmethyl)-3-morpholinone;
(2R)-2-((2S,3R,6S)-2,3-bis(4-chlorophenyl)-6-(4-(methylsulfonyl)benzyl)-5-oxo-4-morpholinyl)pentanoic acid;
(2S)-2-((2R,3S,6R)-2,3-bis(4-chlorophenyl)-6-(4-(methylsulfonyl)benzyl)-5-oxo-4-morpholinyl)pentanoic acid;
(2R,5S,6R)-5,6-bis(4-bromophenyl)-4-methyl-2-phenyl-3-morpholinone;
(2S,5R,6S)-5,6-bis(4-bromophenyl)-4-methyl-2-phenyl-3-morpholinone;
N-((2R)-2-((2S,3R,6S)-2,3-bis(4-chlorophenyl)-6-(4-cyano-3-fluorobenzyl)-5-oxo-4-morpholinyl)pentanoyl)glycine;
(5R,6S)-5,6-bis(4-bromophenyl)-1-methyl-4-(phenylmethyl)-2-piperazinone;
(5S,6R)-5,6-bis(4-bromophenyl)-1-methyl-4-(phenylmethyl)-2-piperazinone;
(2R)-2-((2S,3R,6S)-2,3-bis(4-chlorophenyl)-6-(3-fluorobenzyl)-5-oxo-4-morpholinyl)pentanoic acid;
(2R,5S,6R)-5,6-bis(4-bromophenyl)-4-methyl-2-(3-methyl-2-buten-1-yl)-3-morpholinone;
(2S,5R,6S)-5,6-bis(4-bromophenyl)-4-methyl-2-(3-methyl-2-buten-1-yl)-3-morpholinone;
(2R)-2-((2S,3R,6S)-2,3-bis(4-chlorophenyl)-6-(4-cyano-3-fluorobenzyl)-5-oxo-4-morpholinyl)pentanoic acid;
(5R,6S)-5,6-bis(4-bromophenyl)-4-(phenylmethyl)-2-piperazinone;
(5S,6R)-5,6-bis(4-bromophenyl)-4-(phenylmethyl)-2-piperazinone;
(2R)-2-((2S,3R,6S)-2,3-bis(4-chlorophenyl)-6-(4-cyanobenzyl)-5-oxo-4-morpholinyl)pentanoic acid;
(2S)-2-((2R,3S,6R)-2,3-bis(4-chlorophenyl)-6-(4-cyanobenzyl)-5-oxo-4-morpholinyl)pentanoic acid;
(5R,6S)-5,6-bis(4-chlorophenyl)-4-((1R)-2-hydroxy-1-phenylethyl)-3-morpholinone;
(5R,6S)-5,6-bis(4-chlorophenyl)-4-((1S)-2-hydroxy-1-phenylethyl)-3-morpholinone;
(5S,6R)-5,6-bis(4-chlorophenyl)-4-((1R)-2-hydroxy-1-phenylethyl)-3-morpholinone;
(5S,6R)-5,6-bis(4-chlorophenyl)-4-((1S)-2-hydroxy-1-phenylethyl)-3-morpholinone;
(2R)-2-((2S,3R)-2,3-bis(4-chlorophenyl)-5-oxo-4-morpholinyl)-3-phenylpropanoic acid;
(2S)-2-((2R,3S)-2,3-bis(4-chlorophenyl)-5-oxo-4-morpholinyl)-3-phenylpropanoic acid;
(2S)-2-((2S,3R)-2,3-bis(4-chlorophenyl)-5-oxo-4-morpholinyl)-3-phenylpropanoic acid;
(2R)-2-((2R,3S)-2,3-bis(4-chlorophenyl)-5-oxo-4-morpholinyl)-3-phenylpropanoic acid;
(5R,6S)-5,6-bis(4-chlorophenyl)-4-((1R)-1-(hydroxymethyl)butyl)-3-morpholinone;
(5S,6R)-5,6-bis(4-chlorophenyl)-4-((1S)-1-(hydroxymethyl)butyl)-3-morpholinone;
(5R,6S)-5,6-bis(4-chlorophenyl)-4-((1S)-1-(hydroxymethyl)butyl)-3-morpholinone;
(5S,6R)-5,6-bis(4-chlorophenyl)-4-((1R)-1-(hydroxymethyl)butyl)-3-morpholinone;
(2R)-2-((2S,3R,6S)-2,3-bis(4-chlorophenyl)-6-(2-methoxybenzyl)-5-oxo-4-morpholinyl)pentanoic acid;
(2R)-((2S,3R)-2,3-bis(4-chlorophenyl)-5-oxo-4-morpholinyl)(4-chlorophenyl)ethanoic acid;

(2S)-((2R,3S)-2,3-bis(4-chlorophenyl)-5-oxo-4-morpholinyl)(4-chlorophenyl)ethanoic acid;
(2S)-((2S,3R)-2,3-bis(4-chlorophenyl)-5-oxo-4-morpholinyl)(4-chlorophenyl)ethanoic acid;
(2R)-((2R,3S)-2,3-bis(4-chlorophenyl)-5-oxo-4-morpholinyl)(4-chlorophenyl)ethanoic acid;
(2R)-2-((2R,3S)-2,3-bis(4-chlorophenyl)-5-oxo-4-morpholinyl)-3-phenylpropanoic acid;
(2S)-2-((2S,3R)-2,3-bis(4-chlorophenyl)-5-oxo-4-morpholinyl)-3-phenylpropanoic acid;
(2S)-2-((2R,3S)-2,3-bis(4-chlorophenyl)-5-oxo-4-morpholinyl)-3-phenylpropanoic acid;
(2R)-2-((2S,3R)-2,3-bis(4-chlorophenyl)-5-oxo-4-morpholinyl)-3-phenylpropanoic acid
(2R,5S,6R)-5,6-bis(4-chlorophenyl)-2-(4-fluorobenzyl)-4-((1S)-1-(hydroxymethyl)butyl)-3-morpholinone;
(2S,5R,6S)-5,6-bis(4-chlorophenyl)-2-(4-fluorobenzyl)-4-((1R)-1-(hydroxymethyl)butyl)-3-morpholinone;
(2R,5S,6R)-5,6-bis(4-chlorophenyl)-2-(4-fluorobenzyl)-4-((1R)-1-(hydroxymethyl)butyl)-3-morpholinone;
(2S,5R,6S)-5,6-bis(4-chlorophenyl)-2-(4-fluorobenzyl)-4-((1S)-1-(hydroxymethyl)butyl)-3-morpholinone;
(5R,6S)-5,6-bis(4-chlorophenyl)-4-((1R)-1-(4-chlorophenyl)-2-hydroxyethyl)-3-morpholinone;
(5S,6R)-5,6-bis(4-chlorophenyl)-4-((1S)-1-(4-chlorophenyl)-2-hydroxyethyl)-3-morpholinone;
(5R,6S)-5,6-bis(4-chlorophenyl)-4-((1S)-1-(4-chlorophenyl)-2-hydroxyethyl)-3-morpholinone;
(5S,6R)-5,6-bis(4-chlorophenyl)-4-((1R)-1-(4-chlorophenyl)-2-hydroxyethyl)-3-morpholinone;
(5R,6S)-5,6-bis(4-chlorophenyl)-4-((1R)-1-(1-hydroxy-1-methylethyl)butyl)-3-morpholinone;
(5S,6R)-5,6-bis(4-chlorophenyl)-4-((1S)-1-(1-hydroxy-1-methylethyl)butyl)-3-morpholinone;
(5R,6S)-5,6-bis(4-chlorophenyl)-4-((1S)-1-(1-hydroxy-1-methylethyl)butyl)-3-morpholinone;
(5S,6R)-5,6-bis(4-chlorophenyl)-4-((1R)-1-(1-hydroxy-1-methylethyl)butyl)-3-morpholinone;
(2R)-2-((2S,3R,6S)-2,3-bis(4-chlorophenyl)-6-(4-fluorobenzyl)-5-oxo-4-morpholinyl)pentanamide;
(2S)-2-((2R,3S,6R)-2,3-bis(4-chlorophenyl)-6-(4-fluorobenzyl)-5-oxo-4-morpholinyl)pentanamide;
(2S)-2-((2S,3R,6S)-2,3-bis(4-chlorophenyl)-6-(4-fluorobenzyl)-5-oxo-4-morpholinyl)pentanamide;
(2R)-2-((2R,3S,6R)-2,3-bis(4-chlorophenyl)-6-(4-fluorobenzyl)-5-oxo-4-morpholinyl)pentanamide;
(2R)-2-((2S,3R)-2,3-bis(4-chlorophenyl)-5-oxo-4-morpholinyl)pentanamide;
(2S)-2-((2R,3S)-2,3-bis(4-chlorophenyl)-5-oxo-4-morpholinyl)pentanamide;
(2S)-2-((2S,3R)-2,3-bis(4-chlorophenyl)-5-oxo-4-morpholinyl)pentanamide;
(2R)-2-((2R,3S)-2,3-bis(4-chlorophenyl)-5-oxo-4-morpholinyl)pentanamide;
(2S,5R,6S)-5,6-bis(4-chlorophenyl)-2-(4-fluorobenzyl)-4-((1R)-1-(hydroxymethyl)butyl)-3-morpholinone;
(2S,5R,6S)-5,6-bis(4-chlorophenyl)-2-(4-fluorobenzyl)-4-((1S)-1-(hydroxymethyl)butyl)-3-morpholinone;
(2R)-2-((2S,3R,6S)-2,3-bis(4-chlorophenyl)-6-(4-fluorobenzyl)-5-oxo-4-morpholinyl)pentanamide;
(2S)-2-((2S,3R,6S)-2,3-bis(4-chlorophenyl)-6-(4-fluorobenzyl)-5-oxo-4-morpholinyl)pentanamide;
(2R)-2-((2S,3R)-2,3-bis(4-chlorophenyl)-5-oxo-4-morpholinyl)pentyl carbamate;
(2S)-2-((2S,3R)-2,3-bis(4-chlorophenyl)-5-oxo-4-morpholinyl)pentyl carbamate;
(2S)-2-((2S,3R)-2,3-bis(4-chlorophenyl)-5-oxo-4-morpholinyl)pentyl carbamate;
(2R)-2-((2R,3S)-2,3-bis(4-chlorophenyl)-5-oxo-4-morpholinyl)pentyl carbamate;
(2R)-2-((2S,3R,6S)-3-(4-chlorophenyl)-2-(3,4-dichlorophenyl)-6-(4-fluorobenzyl)-5-oxo-4-morpholinyl)pentanoic acid;
(2S)-2-((2R,3S,6R)-3-(4-chlorophenyl)-2-(3,4-dichlorophenyl)-6-(4-fluorobenzyl)-5-oxo-4-morpholinyl)pentanoic acid;
(2S)-2-((2S,3R,6S)-3-(4-chlorophenyl)-2-(3,4-dichlorophenyl)-6-(4-fluorobenzyl)-5-oxo-4-morpholinyl)pentanoic acid;
(2R)-2-((2R,3S,6R)-3-(4-chlorophenyl)-2-(3,4-dichlorophenyl)-6-(4-fluorobenzyl)-5-oxo-4-morpholinyl)pentanoic acid;
((2R,5S,6R)-6-(3-chlorophenyl)-5-(4-chlorophenyl)-4-(cyclopropylmethyl)-3-oxo-2-morpholinyl)acetic acid;
((2S,5S,6R)-6-(3-chlorophenyl)-5-(4-chlorophenyl)-4-(cyclopropylmethyl)-3-oxo-2-morpholinyl)acetic acid;
((2S,5R,6S)-6-(3-chlorophenyl)-5-(4-chlorophenyl)-4-(cyclopropylmethyl)-3-oxo-2-morpholinyl)acetic acid;
((2R,5R,6S)-6-(3-chlorophenyl)-5-(4-chlorophenyl)-4-(cyclopropylmethyl)-3-oxo-2-morpholinyl)acetic acid;
((2R,5S,6R)-6-(3-chlorophenyl)-5-(4-chlorophenyl)-4-((1R)-1-methylbutyl)-3-oxo-2-morpholinyl)acetic acid;
((2S,5R,6S)-6-(3-chlorophenyl)-5-(4-chlorophenyl)-4-((1S)-1-methylbutyl)-3-oxo-2-morpholinyl)acetic acid;
((2R,5S,6R)-6-(3-chlorophenyl)-5-(4-chlorophenyl)-4-((1S)-1-methylbutyl)-3-oxo-2-morpholinyl)acetic acid;
((2S,5R,6S)-6-(3-chlorophenyl)-5-(4-chlorophenyl)-4-((1R)-1-methylbutyl)-3-oxo-2-morpholinyl)acetic acid;
(2R)-2-((2S,3R)-3-(4-chlorophenyl)-2-(3,4-dichlorophenyl)-5-oxo-4-morpholinyl)pentanamide;
(2S)-2-((2R,3S)-3-(4-chlorophenyl)-2-(3,4-dichlorophenyl)-5-oxo-4-morpholinyl)pentanamide;
(2S)-2-((2S,3R)-3-(4-chlorophenyl)-2-(3,4-dichlorophenyl)-5-oxo-4-morpholinyl)pentanamide;
(2R)-2-((2R,3S)-3-(4-chlorophenyl)-2-(3,4-dichlorophenyl)-5-oxo-4-morpholinyl)pentanamide;
(2R)-((2S,3R,6S)-2,3-bis(4-chlorophenyl)-6-(4-fluorobenzyl)-5-oxo-4-morpholinyl)(4-chlorophenyl)ethanoic acid;
(2S)-((2R,3S,6R)-2,3-bis(4-chlorophenyl)-6-(4-fluorobenzyl)-5-oxo-4-morpholinyl)(4-chlorophenyl)ethanoic acid;
(2S)-((2S,3R,6S)-2,3-bis(4-chlorophenyl)-6-(4-fluorobenzyl)-5-oxo-4-morpholinyl)(4-chlorophenyl)ethanoic acid;
(2R)-((2R,3S,6R)-2,3-bis(4-chlorophenyl)-6-(4-fluorobenzyl)-5-oxo-4-morpholinyl)(4-chlorophenyl)ethanoic acid;
(2R)-2-((2S,3R,6S)-2,3-bis(4-chlorophenyl)-6-(4-fluorobenzyl)-5-oxo-4-morpholinyl)-2-(4-chlorophenyl)ethanamide;
(2S)-2-((2R,3S,6R)-2,3-bis(4-chlorophenyl)-6-(4-fluorobenzyl)-5-oxo-4-morpholinyl)-2-(4-chlorophenyl)ethanamide;
(2S)-2-((2S,3R,6S)-2,3-bis(4-chlorophenyl)-6-(4-fluorobenzyl)-5-oxo-4-morpholinyl)-2-(4-chlorophenyl)ethanamide;
(2R)-2-((2R,3S,6R)-2,3-bis(4-chlorophenyl)-6-(4-fluorobenzyl)-5-oxo-4-morpholinyl)-2-(4-chlorophenyl)ethanamide;
methyl 4-(((2R)-2-((2S,3R,6S)-2,3-bis(4-chlorophenyl)-6-(4-(methylsulfonyl)benzyl)-5-oxo-4-morpholinyl)pentanoyl)amino)butanoate;
(2R)-2-((2S,3R,6S)-2-(3-chlorophenyl)-3-(4-chlorophenyl)-6-((2R)-2,3-dihydroxypropyl)-5-oxo-4-morpholinyl)pentanamide;

(2S)-2-((2R,3S,6R)-2-(3-chlorophenyl)-3-(4-chlorophenyl)-6-((2S)-2,3-dihydroxypropyl)-5-oxo-4-morpholinyl)pentanamide;
(2S)-2-((2S,3R,6S)-2-(3-chlorophenyl)-3-(4-chlorophenyl)-6-((2R)-2,3-dihydroxypropyl)-5-oxo-4-morpholinyl)pentanamide;
(2R)-2-((2R,3S,6R)-2-(3-chlorophenyl)-3-(4-chlorophenyl)-6-((2S)-2,3-dihydroxypropyl)-5-oxo-4-morpholinyl)pentanamide;
(2R)-2-((2S,3R,6S)-2-(3-chlorophenyl)-3-(4-chlorophenyl)-6-((2S)-2,3-dihydroxypropyl)-5-oxo-4-morpholinyl)pentanamide;
(2S)-2-((2R,3S,6R)-2-(3-chlorophenyl)-3-(4-chlorophenyl)-6-((2R)-2,3-dihydroxypropyl)-5-oxo-4-morpholinyl)pentanamide;
(2S)-2-((2S,3R,6S)-2-(3-chlorophenyl)-3-(4-chlorophenyl)-6-((2S)-2,3-dihydroxypropyl)-5-oxo-4-morpholinyl)pentanamide;
(2R)-2-((2R,3S,6R)-2-(3-chlorophenyl)-3-(4-chlorophenyl)-6-((2R)-2,3-dihydroxypropyl)-5-oxo-4-morpholinyl)pentanamide;
(2R)-2-((2S,3R)-2,3-bis(4-chlorophenyl)-5-oxo-4-morpholinyl)-2-(4-chlorophenyl)ethanamide;
(2S)-2-((2S,3R)-2,3-bis(4-chlorophenyl)-5-oxo-4-morpholinyl)-2-(4-chlorophenyl)ethanamide;
(2S)-2-((2S,3R)-2,3-bis(4-chlorophenyl)-5-oxo-4-morpholinyl)-2-(4-chlorophenyl)ethanamide;
(2R)-2-((2R,3S)-2,3-bis(4-chlorophenyl)-5-oxo-4-morpholinyl)-2-(4-chlorophenyl)ethanamide;
(2R)-2-((2S,3R,6S)-3-(4-chlorophenyl)-2-(3,4-dichlorophenyl)-6-(4-fluorobenzyl)-5-oxo-4-morpholinyl)pentanamide;
(2S)-2-((2R,3S,6S)-3-(4-chlorophenyl)-2-(3,4-dichlorophenyl)-6-(4-fluorobenzyl)-5-oxo-4-morpholinyl)pentanamide;
(2S)-2-((2S,3R,6S)-3-(4-chlorophenyl)-2-(3,4-dichlorophenyl)-6-(4-fluorobenzyl)-5-oxo-4-morpholinyl)pentanamide;
(2R)-2-((2R,3S,6S)-3-(4-chlorophenyl)-2-(3,4-dichlorophenyl)-6-(4-fluorobenzyl)-5-oxo-4-morpholinyl)pentanamide;
(2R)-2-((2S,3R,6S)-2,3-bis(4-chlorophenyl)-6-(2-(4-methyl-1-piperazinyl)ethyl)-5-oxo-4-morpholinyl)pentanoic acid;
(2R)-2-((2S,3R)-2,3-bis(4-chlorophenyl)-5-oxo-4-morpholinyl)-N-methylpentanamide;
(2S)-2-((2R,3S)-2,3-bis(4-chlorophenyl)-5-oxo-4-morpholinyl)-N-methylpentanamide;
(2S)-2-((2S,3R)-2,3-bis(4-chlorophenyl)-5-oxo-4-morpholinyl)-N-methylpentanamide;
(2R)-2-((2R,3S)-2,3-bis(4-chlorophenyl)-5-oxo-4-morpholinyl)-N-methylpentanamide;
(2R)-2-((2S,3R)-2,3-bis(4-chlorophenyl)-5-oxo-4-morpholinyl)-N-(2-hydroxyethyl)pentanamide;
(2S)-2-((2R,3S)-2,3-bis(4-chlorophenyl)-5-oxo-4-morpholinyl)-N-(2-hydroxyethyl)pentanamide;
(2S)-2-((2S,3R)-2,3-bis(4-chlorophenyl)-5-oxo-4-morpholinyl)-N-(2-hydroxyethyl)pentanamide;
(2R)-2-((2R,3S)-2,3-bis(4-chlorophenyl)-5-oxo-4-morpholinyl)-N-(2-hydroxyethyl)pentanamide;
(2R)-2-((2S,3R)-2,3-bis(4-chlorophenyl)-5-oxo-4-morpholinyl)-N,N-dimethylpentanamide;
(2S)-2-((2R,3S)-2,3-bis(4-chlorophenyl)-5-oxo-4-morpholinyl)-N,N-dimethylpentanamide;
(2S)-2-((2S,3R)-2,3-bis(4-chlorophenyl)-5-oxo-4-morpholinyl)-N,N-dimethylpentanamide;
(2R)-2-((2R,3S)-2,3-bis(4-chlorophenyl)-5-oxo-4-morpholinyl)-N,N-dimethylpentanamide;
(2R)-2-((2S,3R)-2,3-bis(4-chlorophenyl)-5-oxo-4-morpholinyl)-N-(2-(4-morpholinyl)ethyl)pentanamide;
(2S)-2-((2R,3S)-2,3-bis(4-chlorophenyl)-5-oxo-4-morpholinyl)-N-(2-(4-morpholinyl)ethyl)pentanamide;
(2S)-2-((2S,3R)-2,3-bis(4-chlorophenyl)-5-oxo-4-morpholinyl)-N-(2-(4-morpholinyl)ethyl)pentanamide;
(2R)-2-((2R,3S)-2,3-bis(4-chlorophenyl)-5-oxo-4-morpholinyl)-N-(2-(4-morpholinyl)ethyl)pentanamide;
(2R)-2-((2S,3R,6S)-2,3-bis(4-chlorophenyl)-6-(3-(1H-imidazol-1-yl)propyl)-5-oxo-4-morpholinyl)pentanoic acid;
(2R)-2-((2S,3R)-2,3-bis(4-chlorophenyl)-5-oxo-4-morpholinyl)-N-propylpentanamide;
(2S)-2-((2R,3S)-2,3-bis(4-chlorophenyl)-5-oxo-4-morpholinyl)-N-propylpentanamide;
(2S)-2-((2S,3R)-2,3-bis(4-chlorophenyl)-5-oxo-4-morpholinyl)-N-propylpentanamide;
(2R)-2-((2R,3S)-2,3-bis(4-chlorophenyl)-5-oxo-4-morpholinyl)-N-propylpentanamide;
(5R,6S)-4-((1R)-1-(aminomethyl)butyl)-5,6-bis(4-chlorophenyl)-3-morpholinone;
(5S,6R)-4-((1S)-1-(aminomethyl)butyl)-5,6-bis(4-chlorophenyl)-3-morpholinone;
(5R,6S)-4-((1S)-1-(aminomethyl)butyl)-5,6-bis(4-chlorophenyl)-3-morpholinone;
(5S,6R)-4-((1R)-1-(aminomethyl)butyl)-5,6-bis(4-chlorophenyl)-3-morpholinone;
(2R)-2-((2S,3R,6S)-2-(4-chloro-3-fluorophenyl)-3-(4-chlorophenyl)-6-(4-fluorobenzyl)-5-oxo-4-morpholinyl)pentanamide;
(2S)-2-((2R,3S,6R)-2-(4-chloro-3-fluorophenyl)-3-(4-chlorophenyl)-6-(4-fluorobenzyl)-5-oxo-4-morpholinyl)pentanamide;
(2S)-2-((2S,3R,6S)-2-(4-chloro-3-fluorophenyl)-3-(4-chlorophenyl)-6-(4-fluorobenzyl)-5-oxo-4-morpholinyl)pentanamide;
(2R)-2-((2R,3S,6R)-2-(4-chloro-3-fluorophenyl)-3-(4-chlorophenyl)-6-(4-fluorobenzyl)-5-oxo-4-morpholinyl)pentanamide;
(2R)-2-((2S,3R,6S)-2,3-bis(4-chlorophenyl)-5-oxo-6-(2-propen-1-yl)-4-morpholinyl)pentanamide;
(2S)-2-((2R,3S,6R)-2,3-bis(4-chlorophenyl)-5-oxo-6-(2-propen-1-yl)-4-morpholinyl)pentanamide;
(2S)-2-((2S,3R,6S)-2,3-bis(4-chlorophenyl)-5-oxo-6-(2-propen-1-yl)-4-morpholinyl)pentanamide;
(2R)-2-((2R,3S,6R)-2,3-bis(4-chlorophenyl)-5-oxo-6-(2-propen-1-yl)-4-morpholinyl)pentanamide;
(2R)-2-((2R,3S,6R)-2,3-bis(4-chlorophenyl)-6-(4-fluorobenzyl)-5-oxo-4-morpholinyl)pentanoic acid;
(2R)-2-((2S,3R,6S)-2,3-bis(4-chlorophenyl)-6-(4-fluorobenzyl)-5-oxo-4-morpholinyl)pentanoic acid;
(2S)-2-((2R,3S,6R)-2,3-bis(4-chlorophenyl)-6-(4-fluorobenzyl)-5-oxo-4-morpholinyl)pentanoic acid;
(2S)-2-((2S,3R,6S)-2,3-bis(4-chlorophenyl)-6-(4-fluorobenzyl)-5-oxo-4-morpholinyl)pentanoic acid;
N-((2R)-2-((2S,3R)-2,3-bis(4-chlorophenyl)-5-oxo-4-morpholinyl)pentyl)-2-hydroxyacetamide;
N-((2S)-2-((2R,3S)-2,3-bis(4-chlorophenyl)-5-oxo-4-morpholinyl)pentyl)-2-hydroxyacetamide;
N-((2S)-2-((2S,3R)-2,3-bis(4-chlorophenyl)-5-oxo-4-morpholinyl)pentyl)-2-hydroxyacetamide;
N-((2R)-2-((2R,3S)-2,3-bis(4-chlorophenyl)-5-oxo-4-morpholinyl)pentyl)-2-hydroxyacetamide;
(2R)-2-((2S,3R,6S)-2,3-bis(4-chlorophenyl)-6-(3-methoxybenzyl)-5-oxo-4-morpholinyl)pentanoic acid;

(2R)-2-((2S,3R)-2-(4-chloro-2-methylphenyl)-3-(4-chlorophenyl)-5-oxo-4-morpholinyl)pentanoic acid;
(2S)-2-((2R,3S)-2-(4-chloro-2-methylphenyl)-3-(4-chlorophenyl)-5-oxo-4-morpholinyl)pentanoic acid;
(2S)-2-((2S,3R)-2-(4-chloro-2-methylphenyl)-3-(4-chlorophenyl)-5-oxo-4-morpholinyl)pentanoic acid;
(2R)-2-((2R,3S)-2-(4-chloro-2-methylphenyl)-3-(4-chlorophenyl)-5-oxo-4-morpholinyl)pentanoic acid;
(3R)-3-((2R,3S,6R)-2-(3-chlorophenyl)-3-(4-chlorophenyl)-6-(4-fluorobenzyl)-5-oxo-4-morpholinyl)hexanoic acid;
(2R)-2-((2S,3R,6S)-2,3-bis(4-chlorophenyl)-5-oxo-6-(2-propen-1-yl)-4-morpholinyl)pentanoic acid;
(2S)-2-((2R,3S,6R)-2,3-bis(4-chlorophenyl)-5-oxo-6-(2-propen-1-yl)-4-morpholinyl)pentanoic acid;
(2R)-2-((2S,3R,6S)-2,3-bis(4-chlorophenyl)-6-((2S)-2,3-dihydroxypropyl)-5-oxo-4-morpholinyl)pentanamide;
(2S)-2-((2R,3S,6R)-2,3-bis(4-chlorophenyl)-6-((2R)-2,3-dihydroxypropyl)-5-oxo-4-morpholinyl)pentanamide;
(2R)-2-((2S,3R,6S)-2,3-bis(4-chlorophenyl)-6-((2R)-2,3-dihydroxypropyl)-5-oxo-4-morpholinyl)pentanamide;
(2S)-2-((2R,3S,6R)-2,3-bis(4-chlorophenyl)-6-((2S)-2,3-dihydroxypropyl)-5-oxo-4-morpholinyl)pentanamide;
(2R)-2-((2S,3R,6S)-2,3-bis(4-chlorophenyl)-6-((2R)-2,3-dihydroxypropyl)-5-oxo-4-morpholinyl)pentanamide;
(2S)-2-((2R,3S,6R)-2,3-bis(4-chlorophenyl)-6-((2S)-2,3-dihydroxypropyl)-5-oxo-4-morpholinyl)pentanamide;
(2R)-2-((2S,3R,6S)-2,3-bis(4-chlorophenyl)-6-((2S)-2,3-dihydroxypropyl)-5-oxo-4-morpholinyl)pentanamide;
(2S)-2-((2R,3S,6R)-2,3-bis(4-chlorophenyl)-6-((2R)-2,3-dihydroxypropyl)-5-oxo-4-morpholinyl)pentanamide;
(2R)-2-((2S,3R,6S)-2,3-bis(4-chlorophenyl)-6-((2R)-2,3-dihydroxypropyl)-5-oxo-4-morpholinyl)pentanoic acid;
(2R)-2-((2S,3R,6S)-2,3-bis(4-chlorophenyl)-6-((2S)-2,3-dihydroxypropyl)-5-oxo-4-morpholinyl)pentanoic acid;
(2S)-2-((2R,3S,6R)-2,3-bis(4-chlorophenyl)-6-((2R)-2,3-dihydroxypropyl)-5-oxo-4-morpholinyl)pentanoic acid;
(2S)-2-((2R,3S,6R)-2,3-bis(4-chlorophenyl)-6-((2S)-2,3-dihydroxypropyl)-5-oxo-4-morpholinyl)pentanoic acid;
(2R)-2-((2S,5R,6S)-2-(2-amino-2-oxoethyl)-5,6-bis(4-chlorophenyl)-3-oxo-4-morpholinyl)pentanoic acid;
(2S)-2-((2R,5S,6R)-2-(2-amino-2-oxoethyl)-5,6-bis(4-chlorophenyl)-3-oxo-4-morpholinyl)pentanoic acid;
((2R,5S,6R)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid;
((2S,5R,6S)-6-(3-chlorophenyl)-5-(4-chlorophenyl)-4-((1R)-1-(((cyclopropylsulfonyl)(phenyl)amino)methyl)propyl)-3-oxo-2-morpholinyl)acetic acid;
((2S,5S,6R)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid;
((2R,5R,6S)-6-(3-chlorophenyl)-5-(4-chlorophenyl)-4-((1R)-1-(((cyclopropylsulfonyl)(phenyl)amino)methyl)propyl)-3-oxo-2-morpholinyl)acetic acid;
((2R,5S,6R)-6-(3-chlorophenyl)-5-(4-chlorophenyl)-4-((1R)-1-(((cyclopropylsulfonyl)(phenyl)amino)methyl)propyl)-3-oxo-2-morpholinyl)acetic acid;
((2S,5R,6S)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid;
((2S,5S,6R)-6-(3-chlorophenyl)-5-(4-chlorophenyl)-4-((1R)-1-(((cyclopropylsulfonyl)(phenyl)amino)methyl)propyl)-3-oxo-2-morpholinyl)acetic acid;
((2R,5R,6S)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid;
((2R,5S,6R)-4-((1S)-1-carbamoylbutyl)-5,6-bis(4-chlorophenyl)-3-oxo-2-morpholinyl)acetic acid;
((2S,5R,6S)-4-((1R)-1-carbamoylbutyl)-5,6-bis(4-chlorophenyl)-3-oxo-2-morpholinyl)acetic acid;
((2R,5S,6R)-6-(3-chlorophenyl)-5-(4-chlorophenyl)-4-((1S)-1-(ethoxycarbonyl)butyl)-3-oxo-2-morpholinyl)acetic acid;
((2S,5R,6S)-6-(3-chlorophenyl)-5-(4-chlorophenyl)-4-((1R)-1-(ethoxycarbonyl)butyl)-3-oxo-2-morpholinyl)acetic acid;
((2R,5S,6R)-6-(3-chlorophenyl)-5-(4-chlorophenyl)-4-((1R)-1-(ethoxycarbonyl)butyl)-3-oxo-2-morpholinyl)acetic acid;
((2S,5R,6S)-6-(3-chlorophenyl)-5-(4-chlorophenyl)-4-((1S)-1-(ethoxycarbonyl)butyl)-3-oxo-2-morpholinyl)acetic acid;
(2R)-2-((2S,3R,6S)-2,3-bis(4-chlorophenyl)-6-(4-fluorobenzyl)-5-oxo-4-morpholinyl)-N-(2-(4-morpholinyl)ethyl)pentanamide;
(2S)-2-((2R,3S,6R)-2,3-bis(4-chlorophenyl)-6-(4-fluorobenzyl)-5-oxo-4-morpholinyl)-N-(2-(4-morpholinyl)ethyl)pentanamide;
(5R,6S)-5,6-bis(4-chlorophenyl)-4-((1R)-1-(4-morpholinylmethyl)butyl)-3-morpholinone;
(5S,6R)-5,6-bis(4-chlorophenyl)-4-((1S)-1-(4-morpholinylmethyl)butyl)-3-morpholinone;
((2R,5R,6S)-6-(3-chlorophenyl)-5-(4-chlorophenyl)-4-(cyclopropylmethyl)-3-oxo-2-morpholinyl)acetic acid;
((2S,5S,6R)-6-(3-chlorophenyl)-5-(4-chlorophenyl)-4-(cyclopropylmethyl)-3-oxo-2-morpholinyl)acetic acid;
((2R,5S,6R)-6-(3-chlorophenyl)-5-(4-chlorophenyl)-4-(cyclopropylmethyl)-3-oxo-2-morpholinyl)acetic acid;
((2S,5S,6R)-6-(3-chlorophenyl)-5-(4-chlorophenyl)-4-(cyclopropylmethyl)-3-oxo-2-morpholinyl)acetic acid;
N-((2R)-2-((2S,3R)-2,3-bis(4-chlorophenyl)-5-oxo-4-morpholinyl)pentyl)methanesulfonamide;
N-((2S)-2-((2R,3S)-2,3-bis(4-chlorophenyl)-5-oxo-4-morpholinyl)pentyl)methanesulfonamide;
(2R,5S,6R)-5,6-bis(4-chlorophenyl)-2-(4-fluorobenzyl)-4-((1S)-1-((4-methyl-1-piperazinyl)carbonyl)butyl)-3-morpholinone;
(2S,5R,6S)-5,6-bis(4-chlorophenyl)-2-(4-fluorobenzyl)-4-((1R)-1-((4-methyl-1-piperazinyl)carbonyl)butyl)-3-morpholinone;
(2R,5S,6R)-5,6-bis(4-chlorophenyl)-2-(4-fluorobenzyl)-4-((1S)-1-(4-morpholinylcarbonyl)butyl)-3-morpholinone;
(2S,5R,6S)-5,6-bis(4-chlorophenyl)-2-(4-fluorobenzyl)-4-((1R)-1-(4-morpholinylcarbonyl)butyl)-3-morpholinone;
(2R,5S,6R)-4-((1S)-1-(aminomethyl)butyl)-5,6-bis(4-chlorophenyl)-2-(4-fluorobenzyl)-3-morpholinone;
(2S,5R,6S)-4-((1R)-1-(aminomethyl)butyl)-5,6-bis(4-chlorophenyl)-2-(4-fluorobenzyl)-3-morpholinone;
(5R,6S)-2-benzyl-5,6-bis(4-chlorophenyl)-4-methyl-3-morpholinone;
(5S,6R)-2-benzyl-5,6-bis(4-chlorophenyl)-4-methyl-3-morpholinone;
((2R,5S,6R)-6-(3-chlorophenyl)-5-(4-chlorophenyl)-4-(cyclopropylsulfonyl)-3-oxo-2-morpholinyl)acetic acid;
((2S,5R,6S)-6-(3-chlorophenyl)-5-(4-chlorophenyl)-4-(cyclopropylsulfonyl)-3-oxo-2-morpholinyl)acetic acid;
(2R,5S,6R)-5,6-bis(4-chlorophenyl)-2-(4-fluorobenzyl)-4-((1S)-1-(4-morpholinylmethyl)butyl)-3-morpholinone;
(2S,5R,6S)-5,6-bis(4-chlorophenyl)-2-(4-fluorobenzyl)-4-((1R)-1-(4-morpholinylmethyl)butyl)-3-morpholinone;
(2R)-2-((2S,3R,6S)-3-(4-chlorophenyl)-6-(4-fluorobenzyl)-5-oxo-2-phenyl-4-morpholinyl)pentanoic acid;

(2S)-2-((2R,3S,6R)-3-(4-chlorophenyl)-6-(4-fluorobenzyl)-5-oxo-2-phenyl-4-morpholinyl)pentanoic acid;
(2S)-2-((2S,3R,6S)-3-(4-chlorophenyl)-6-(4-fluorobenzyl)-5-oxo-2-phenyl-4-morpholinyl)pentanoic acid;
(2R)-2-((2R,3S,6R)-3-(4-chlorophenyl)-6-(4-fluorobenzyl)-5-oxo-2-phenyl-4-morpholinyl)pentanoic acid;
(2R)-2-((2S,3R,6S)-2,3-bis(4-chlorophenyl)-6-(2-(4-morpholinyl)ethyl)-5-oxo-4-morpholinyl)pentanoic acid;
(2R)-((2S,3R,6S)-2,3-bis(4-chlorophenyl)-6-(4-fluorobenzyl)-5-oxo-4-morpholinyl)(phenyl)ethanoic acid;
(2S)-((2R,3S,6R)-2,3-bis(4-chlorophenyl)-6-(4-fluorobenzyl)-5-oxo-4-morpholinyl)(phenyl)ethanoic acid;
(2S)-((2S,3R,6S)-2,3-bis(4-chlorophenyl)-6-(4-fluorobenzyl)-5-oxo-4-morpholinyl)(phenyl)ethanoic acid;
(2R)-((2R,3S,6R)-2,3-bis(4-chlorophenyl)-6-(4-fluorobenzyl)-5-oxo-4-morpholinyl)(phenyl)ethanoic acid;
(2R)-2-((2S,3R)-2-(4-chlorophenyl)-3-(3,4-dichlorophenyl)-5-oxo-4-morpholinyl)pentanoic acid;
(2S)-2-((2R,3S)-2-(4-chlorophenyl)-3-(3,4-dichlorophenyl)-5-oxo-4-morpholinyl)pentanoic acid;
(2S)-2-((2S,3R)-2-(4-chlorophenyl)-3-(3,4-dichlorophenyl)-5-oxo-4-morpholinyl)pentanoic acid;
(2R)-2-((2R,3S)-2-(4-chlorophenyl)-3-(3,4-dichlorophenyl)-5-oxo-4-morpholinyl)pentanoic acid;
(5R,6S)-6-(3-chlorophenyl)-5-(4-chlorophenyl)-4-(1-methylethyl)-3-thiomorpholinone 1,1-dioxide;
(2R)-2-((2S,3R,6S)-2-(3-chlorophenyl)-3-(4-chlorophenyl)-6-(2-(4-morpholinyl)-2-oxoethyl)-5-oxo-4-morpholinyl)pentanoic acid;
(2S)-2-((2R,3S,6R)-2-(3-chlorophenyl)-3-(4-chlorophenyl)-6-(2-(4-morpholinyl)-2-oxoethyl)-5-oxo-4-morpholinyl)pentanoic acid;
(2S)-2-((2S,3R,6S)-2-(3-chlorophenyl)-3-(4-chlorophenyl)-6-(2-(4-morpholinyl)-2-oxoethyl)-5-oxo-4-morpholinyl)pentanoic acid;
(2R)-2-((2R,3S,6R)-2-(3-chlorophenyl)-3-(4-chlorophenyl)-6-(2-(4-morpholinyl)-2-oxoethyl)-5-oxo-4-morpholinyl)pentanoic acid;
(2R)-2-((2S,3R)-3-(4-bromophenyl)-2-(4-chlorophenyl)-5-oxo-4-morpholinyl)pentanoic acid;
(2S)-2-((2R,3S)-3-(4-bromophenyl)-2-(4-chlorophenyl)-5-oxo-4-morpholinyl)pentanoic acid;
(2S)-2-((2S,3R)-3-(4-bromophenyl)-2-(4-chlorophenyl)-5-oxo-4-morpholinyl)pentanoic acid;
(2R)-2-((2R,3S)-3-(4-bromophenyl)-2-(4-chlorophenyl)-5-oxo-4-morpholinyl)pentanoic acid;
(2R)-2-((2S,3R,6S)-2,3-bis(4-chlorophenyl)-5-oxo-6-(2-(1-piperidinyl)ethyl)-4-morpholinyl)pentanoic acid;
(2R)-2-((2S,3R)-2-(4-chlorophenyl)-3-(4-cyclopropylphenyl)-5-oxo-4-morpholinyl)pentanoic acid;
(2S)-2-((2R,3S)-2-(4-chlorophenyl)-3-(4-cyclopropylphenyl)-5-oxo-4-morpholinyl)pentanoic acid;
(2S)-2-((2S,3R)-2-(4-chlorophenyl)-3-(4-cyclopropylphenyl)-5-oxo-4-morpholinyl)pentanoic acid;
(2R)-2-((2R,3S)-2-(4-chlorophenyl)-3-(4-cyclopropylphenyl)-5-oxo-4-morpholinyl)pentanoic acid;
(2R)-2-((2S,3R,6S)-3-(4-bromophenyl)-2-(4-chlorophenyl)-6-(4-fluorobenzyl)-5-oxo-4-morpholinyl)pentanoic acid;
(2S)-2-((2R,3S,6R)-3-(4-bromophenyl)-2-(4-chlorophenyl)-6-(4-fluorobenzyl)-5-oxo-4-morpholinyl)pentanoic acid;
(2S)-2-((2S,3R,6S)-3-(4-bromophenyl)-2-(4-chlorophenyl)-6-(4-fluorobenzyl)-5-oxo-4-morpholinyl)pentanoic acid;
(2R)-2-((2R,3S,6R)-3-(4-bromophenyl)-2-(4-chlorophenyl)-6-(4-fluorobenzyl)-5-oxo-4-morpholinyl)pentanoic acid;
2-(((2R,5S,6R)-5,6-bis(4-chlorophenyl)-4-methyl-3-oxo-2-morpholinyl)methyl)benzonitrile;
2-(((2S,5R,6S)-5,6-bis(4-chlorophenyl)-4-methyl-3-oxo-2-morpholinyl)methyl)benzonitrile;
(2R)-2-((2S,3R,6S)-2-(3-chlorophenyl)-3-(4-chlorophenyl)-6-(4-fluorobenzyl)-5-oxo-4-morpholinyl)pentanamide;
(2S)-2-((2R,3S,6R)-2-(3-chlorophenyl)-3-(4-chlorophenyl)-6-(4-fluorobenzyl)-5-oxo-4-morpholinyl)pentanamide;
(2S)-2-((2S,3R,6S)-2-(3-chlorophenyl)-3-(4-chlorophenyl)-6-(4-fluorobenzyl)-5-oxo-4-morpholinyl)pentanamide;
(2R)-2-((2R,3S,6R)-2-(3-chlorophenyl)-3-(4-chlorophenyl)-6-(4-fluorobenzyl)-5-oxo-4-morpholinyl)pentanamide;
(2R)-2-((2S,3R,6S)-2,3-bis(4-chlorophenyl)-6-(2-fluoro-4-(methylsulfonyl)benzyl)-5-oxo-4-morpholinyl)pentanoic acid
(2S)-2-((2R,3S,6R)-2,3-bis(4-chlorophenyl)-6-(2-fluoro-4-(methylsulfonyl)benzyl)-5-oxo-4-morpholinyl)pentanoic acid;
(2R)-2-((2S,3R,6S)-2,3-bis(4-chlorophenyl)-6-(4-fluorobenzyl)-5-oxo-4-morpholinyl)hexanoic acid;
(2S)-2-((2R,3S,6R)-2,3-bis(4-chlorophenyl)-6-(4-fluorobenzyl)-5-oxo-4-morpholinyl)hexanoic acid;
(2S)-2-((2S,3R,6S)-2,3-bis(4-chlorophenyl)-6-(4-fluorobenzyl)-5-oxo-4-morpholinyl)hexanoic acid;
(2R)-2-((2R,3S,6R)-2,3-bis(4-chlorophenyl)-6-(4-fluorobenzyl)-5-oxo-4-morpholinyl)hexanoic acid;
(2R,5S,6R)-5,6-bis(4-chlorophenyl)-2-(4-fluorobenzyl)-4-((1S)-1-(1H-tetrazol-5-yl)butyl)-3-morpholinone;
(2S,5R,6S)-5,6-bis(4-chlorophenyl)-2-(4-fluorobenzyl)-4-((1R)-1-(1H-tetrazol-5-yl)butyl)-3-morpholinone;
N-((2R)-2-((2S,3R,6S)-2,3-bis(4-chlorophenyl)-6-(4-fluorobenzyl)-5-oxo-4-morpholinyl)pentanoyl)glycine;
N-((2S)-2-((2R,3S,6R)-2,3-bis(4-chlorophenyl)-6-(4-fluorobenzyl)-5-oxo-4-morpholinyl)pentanoyl)glycine;
(2R)-2-((2S,3R,6S)-3-(4-bromophenyl)-2-(4-chlorophenyl)-6-(4-cyanobenzyl)-5-oxo-4-morpholinyl)pentanoic acid;
(2S)-2-((2R,3S,6R)-3-(4-bromophenyl)-2-(4-chlorophenyl)-6-(4-cyanobenzyl)-5-oxo-4-morpholinyl)pentanoic acid;
3-((2R,5S,6R)-6-(3-chlorophenyl)-5-(4-chlorophenyl)-4-(cyclopropylmethyl)-3-oxo-2-morpholinyl)propanenitrile;
3-((2S,5R,6S)-6-(3-chlorophenyl)-5-(4-chlorophenyl)-4-(cyclopropylmethyl)-3-oxo-2-morpholinyl)propanenitrile;
((2S,5S,6R)-6-(3-chlorophenyl)-5-(4-chlorophenyl)-4-(cyclopropylmethyl)-3-oxo-2-morpholinyl)acetic acid;
((2R,5R,6S)-6-(3-chlorophenyl)-5-(4-chlorophenyl)-4-(cyclopropylmethyl)-3-oxo-2-morpholinyl)acetic acid;
((2R,5S,6R)-6-(3-chlorophenyl)-5-(4-chlorophenyl)-4-(cyclopropylmethyl)-3-oxo-2-morpholinyl)acetic acid;
((2S,5R,6S)-6-(3-chlorophenyl)-5-(4-chlorophenyl)-4-(cyclopropylmethyl)-3-oxo-2-morpholinyl)acetic acid;
2-((2R,5S,6R)-6-(3-chlorophenyl)-5-(4-chlorophenyl)-4-(cyclopropylmethyl)-3-oxo-2-morpholinyl)-N-(2-(4-morpholinyl)ethyl)acetamide;
2-((2S,5R,6S)-6-(3-chlorophenyl)-5-(4-chlorophenyl)-4-(cyclopropylmethyl)-3-oxo-2-morpholinyl)-N-(2-(4-morpholinyl)ethyl)acetamide;
(2R)-2-((2S,3R)-2-(3-chlorophenyl)-3-(4-chlorophenyl)-6-(4-fluorobenzyl)-5-oxo-4-morpholinyl)pentanoic acid;
(2S)-2-((2R,3S)-2-(3-chlorophenyl)-3-(4-chlorophenyl)-6-(4-fluorobenzyl)-5-oxo-4-morpholinyl)pentanoic acid;
(2S)-2-((2S,3R)-2-(3-chlorophenyl)-3-(4-chlorophenyl)-6-(4-fluorobenzyl)-5-oxo-4-morpholinyl)pentanoic acid;

(2R)-2-((2R,3S)-2-(3-chlorophenyl)-3-(4-chlorophenyl)-6-(4-fluorobenzyl)-5-oxo-4-morpholinyl)pentanoic acid;

(S)-2-((2R,5S,6R)-6-(3-chlorophenyl)-5-(4-chlorophenyl)-4-(cyclopropylmethyl)-3-oxomorpholin-2-yl)-2-hydroxyacetic acid;

(R)-2-((2S,5R,6S)-6-(3-chlorophenyl)-5-(4-chlorophenyl)-4-(cyclopropylmethyl)-3-oxomorpholin-2-yl)-2-hydroxyacetic acid;

(R)-2-((2R,5S,6R)-6-(3-chlorophenyl)-5-(4-chlorophenyl)-4-(cyclopropylmethyl)-3-oxomorpholin-2-yl)-2-hydroxyacetic acid;

(S)-2-((2S,5R,6S)-6-(3-chlorophenyl)-5-(4-chlorophenyl)-4-(cyclopropylmethyl)-3-oxomorpholin-2-yl)-2-hydroxyacetic acid;

(2R)-2-((2S,3R,6S)-2-(3-chlorophenyl)-3-(4-chlorophenyl)-6-((2S)-2,3-dihydroxypropyl)-5-oxo-4-morpholinyl)pentanamide;

(2S)-2-((2S,3S,6R)-2-(3-chlorophenyl)-3-(4-chlorophenyl)-6-((2R)-2,3-dihydroxypropyl)-5-oxo-4-morpholinyl)pentanamide;

(2S)-2-((2S,3R,6S)-2-(3-chlorophenyl)-3-(4-chlorophenyl)-6-((2S)-2,3-dihydroxypropyl)-5-oxo-4-morpholinyl)pentanamide;

(2R)-2-((2R,3S,6R)-2-(3-chlorophenyl)-3-(4-chlorophenyl)-6-((2R)-2,3-dihydroxypropyl)-5-oxo-4-morpholinyl)pentanamide;

(2R)-2-((2S,3R,6S)-2-(3-chlorophenyl)-3-(4-chlorophenyl)-6-((2R)-2,3-dihydroxypropyl)-5-oxo-4-morpholinyl)pentanamide;

(2S)-2-((2R,3S,6R)-2-(3-chlorophenyl)-3-(4-chlorophenyl)-6-((2S)-2,3-dihydroxypropyl)-5-oxo-4-morpholinyl)pentanamide;

(2S)-2-((2S,3R,6S)-2-(3-chlorophenyl)-3-(4-chlorophenyl)-6-((2R)-2,3-dihydroxypropyl)-5-oxo-4-morpholinyl)pentanamide;

(2R)-2-((2R,3S,6R)-2-(3-chlorophenyl)-3-(4-chlorophenyl)-6-((2S)-2,3-dihydroxypropyl)-5-oxo-4-morpholinyl)pentanamide;

((2R,5S,6R)-6-(3-chloro-2-fluorophenyl)-5-(4-chlorophenyl)-4-(cyclopropylmethyl)-3-oxo-2-morpholinyl)acetic acid;

((2S,5R,6S)-6-(3-chloro-2-fluorophenyl)-5-(4-chlorophenyl)-4-(cyclopropylmethyl)-3-oxo-2-morpholinyl)acetic acid;

((2R,5S,6R)-4-butyl-6-(3-chlorophenyl)-5-(4-chlorophenyl)-3-oxo-2-morpholinyl)acetic acid; ((2S,5R,6S)-4-butyl-6-(3-chlorophenyl)-5-(4-chlorophenyl)-3-oxo-2-morpholinyl)acetic acid;

(2R)-2-((2S,3R)-3-(4-chlorophenyl)-2-(2,4-dichlorophenyl)-5-oxo-4-morpholinyl)pentanoic acid;

(2S)-2-((2R,3S)-3-(4-chlorophenyl)-2-(2,4-dichlorophenyl)-5-oxo-4-morpholinyl)pentanoic acid;

(2S)-2-((2S,3R)-3-(4-chlorophenyl)-2-(2,4-dichlorophenyl)-5-oxo-4-morpholinyl)pentanoic acid;

(2R)-2-((2R,3S)-3-(4-chlorophenyl)-2-(2,4-dichlorophenyl)-5-oxo-4-morpholinyl)pentanoic acid;

N'-acetyl-2-((2R,5S,6R)-6-(3-chlorophenyl)-5-(4-chlorophenyl)-4-(cyclopropylmethyl)-3-oxo-2-morpholinyl)acetohydrazide;

N'-acetyl-2-((2S,5R,6S)-6-(3-chlorophenyl)-5-(4-chlorophenyl)-4-(cyclopropylmethyl)-3-oxo-2-morpholinyl)acetohydrazide;

(2R,5S,6R)-6-(3-chlorophenyl)-5-(4-chlorophenyl)-4-(cyclopropylmethyl)-2-(2-(4-morpholinyl)-2-oxoethyl)-3-morpholinone;

(2S,5R,6S)-6-(3-chlorophenyl)-5-(4-chlorophenyl)-4-(cyclopropylmethyl)-2-(2-(4-morpholinyl)-2-oxoethyl)-3-morpholinone;

(2R)-2-((2S,3R)-2-(3-chlorophenyl)-3-(4-chlorophenyl)-5-oxo-4-morpholinyl)pentanamide;

(2S)-2-((2R,3S)-2-(3-chlorophenyl)-3-(4-chlorophenyl)-5-oxo-4-morpholinyl)pentanamide;

(2S)-2-((2S,3R)-2-(3-chlorophenyl)-3-(4-chlorophenyl)-5-oxo-4-morpholinyl)pentanamide;

(2R)-2-((2R,3S)-2-(3-chlorophenyl)-3-(4-chlorophenyl)-5-oxo-4-morpholinyl)pentanamide;

2-((2R,5S,6R)-6-(3-chlorophenyl)-5-(4-chlorophenyl)-4-(cyclopropylmethyl)-3-oxo-2-morpholinyl)ethyl carbamate;

2-((2S,5R,6S)-6-(3-chlorophenyl)-5-(4-chlorophenyl)-4-(cyclopropylmethyl)-3-oxo-2-morpholinyl)ethyl carbamate;

(2R)-((2S,3R,6S)-2,3-bis(4-chlorophenyl)-6-(4-fluorobenzyl)-5-oxo-4-morpholinyl)(3-chlorophenyl)ethanoic acid;

(2S)-((2R,3S,6R)-2,3-bis(4-chlorophenyl)-6-(4-fluorobenzyl)-5-oxo-4-morpholinyl)(3-chlorophenyl)ethanoic acid;

(2S)-((2S,3R,6S)-2,3-bis(4-chlorophenyl)-6-(4-fluorobenzyl)-5-oxo-4-morpholinyl)(3-chlorophenyl)ethanoic acid;

(2R)-((2R,3S,6R)-2,3-bis(4-chlorophenyl)-6-(4-fluorobenzyl)-5-oxo-4-morpholinyl)(3-chlorophenyl)ethanoic acid;

((2S,5S,6R)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid;

((2R,5R,6S)-6-(3-chlorophenyl)-5-(4-chlorophenyl)-4-((1R)-1-(((cyclopropylsulfonyl)(phenyl)amino)methyl)propyl)-3-oxo-2-morpholinyl)acetic acid;

((2S,5S,6R)-6-(3-chlorophenyl)-5-(4-chlorophenyl)-4-((1R)-1-(((cyclopropylsulfonyl)(phenyl)amino)methyl)propyl)-3-oxo-2-morpholinyl)acetic acid;

((2R,5R,6S)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid;

((2R,5S,6R)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid;

((2S,5R,6S)-6-(3-chlorophenyl)-5-(4-chlorophenyl)-4-((1R)-1-(((cyclopropylsulfonyl)(phenyl)amino)methyl)propyl)-3-oxo-2-morpholinyl)acetic acid;

((2R,5S,6R)-6-(3-chlorophenyl)-5-(4-chlorophenyl)-4-((1R)-1-(((cyclopropylsulfonyl)(phenyl)amino)methyl)propyl)-3-oxo-2-morpholinyl)acetic acid;

((2S,5R,6S)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid;

(2R)-2-((2S,3R,6S)-3-(4-chlorophenyl)-2-(2,4-dichlorophenyl)-6-(4-fluorobenzyl)-5-oxo-4-morpholinyl)pentanoic acid;

(2S)-2-((2R,3S,6R)-3-(4-chlorophenyl)-2-(2,4-dichlorophenyl)-6-(4-fluorobenzyl)-5-oxo-4-morpholinyl)pentanoic acid;

(2S)-2-((2S,3R,6S)-3-(4-chlorophenyl)-2-(2,4-dichlorophenyl)-6-(4-fluorobenzyl)-5-oxo-4-morpholinyl)pentanoic acid;

(2R)-2-((2R,3S,6R)-3-(4-chlorophenyl)-2-(2,4-dichlorophenyl)-6-(4-fluorobenzyl)-5-oxo-4-morpholinyl)pentanoic acid;

4-(((2R)-2-((2S,3R,6S)-2,3-bis(4-chlorophenyl)-6-(4-(methylsulfonyl)benzyl)-5-oxo-4-morpholinyl)pentanoyl)amino)butanoic acid;

((2R,5S,6R)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid;

((2S,5S,6R)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid;

((2S,5R,6S)-6-(3-chlorophenyl)-5-(4-chlorophenyl)-4-((1R)-1-(((cyclopropylsulfonyl)(phenyl)amino)methyl)propyl)-3-oxo-2-morpholinyl)acetic acid;

((2R,5R,6S)-6-(3-chlorophenyl)-5-(4-chlorophenyl)-4-((1R)-1-(((cyclopropylsulfonyl)(phenyl)amino)methyl)propyl)-3-oxo-2-morpholinyl)acetic acid;

((2R,5S,6R)-6-(3-chlorophenyl)-5-(4-chlorophenyl)-4-((1R)-1-(((cyclopropylsulfonyl)(phenyl)amino)methyl)propyl)-3-oxo-2-morpholinyl)acetic acid and ((2S,5S,6R)-6-(3-chlorophenyl)-5-(4-chlorophenyl)-4-((1R)-1-(((cyclopropylsulfonyl)(phenyl)amino)methyl)propyl)-3-oxo-2-morpholinyl)acetic acid;

((2S,5R,6S)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid;

((2R,5R,6S)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid;

(S)-2-((2S,5R,6S)-6-(3-chlorophenyl)-5-(4-chlorophenyl)-4-(cyclopropylmethyl)-3-oxomorpholin-2-yl)-2-hydroxyacetic acid;

(R)-2-((2R,5S,6R)-6-(3-chlorophenyl)-5-(4-chlorophenyl)-4-(cyclopropylmethyl)-3-oxomorpholin-2-yl)-2-hydroxyacetic acid;

(R)-2-((2S,5R,6S)-6-(3-chlorophenyl)-5-(4-chlorophenyl)-4-(cyclopropylmethyl)-3-oxomorpholin-2-yl)-2-hydroxyacetic acid;

(S)-2-((2R,5S,6R)-6-(3-chlorophenyl)-5-(4-chlorophenyl)-4-(cyclopropylmethyl)-3-oxomorpholin-2-yl)-2-hydroxyacetic acid;

3-((2R,3S)-3-(4-chlorophenyl)-4-(cyclopropylmethyl)-5-oxo-2-morpholinyl)benzonitrile;

3-((2S,3R)-3-(4-chlorophenyl)-4-(cyclopropylmethyl)-5-oxo-2-morpholinyl)benzonitrile;

(2R)-2-((2R,3S,6R)-2-(3-chlorophenyl)-3-(4-chlorophenyl)-6-(4-fluorobenzyl)-5-oxo-4-morpholinyl)pentanoic acid;

(2S)-2-((2S,3R,6S)-2-(3-chlorophenyl)-3-(4-chlorophenyl)-6-(4-fluorobenzyl)-5-oxo-4-morpholinyl)pentanoic acid;

(2S)-2-((2R,3S,6R)-2-(3-chlorophenyl)-3-(4-chlorophenyl)-6-(4-fluorobenzyl)-5-oxo-4-morpholinyl)pentanoic acid;

(2R)-2-((2S,3R,6S)-2-(3-chlorophenyl)-3-(4-chlorophenyl)-6-(4-fluorobenzyl)-5-oxo-4-morpholinyl)pentanoic acid;

N-((2R)-2-((2S,3R,6S)-2,3-bis(4-chlorophenyl)-6-(4-cyanobenzyl)-5-oxo-4-morpholinyl)pentanoyl)glycine;

N-((2S)-2-((2R,3S,6R)-2,3-bis(4-chlorophenyl)-6-(4-cyanobenzyl)-5-oxo-4-morpholinyl)pentanoyl)glycine;

N-((2R)-2-((2S,3R)-2,3-bis(4-chlorophenyl)-5-oxo-4-morpholinyl)pentanoyl)glycine;

N-((2S)-2-((2R,3S)-2,3-bis(4-chlorophenyl)-5-oxo-4-morpholinyl)pentanoyl)glycine;

2-((2R,5S,6R)-6-(3-chlorophenyl)-5-(4-chlorophenyl)-4-(cyclopropylmethyl)-3-oxo-2-morpholinyl)-N,N-dimethylacetamide;

2-((2S,5R,6S)-6-(3-chlorophenyl)-5-(4-chlorophenyl)-4-(cyclopropylmethyl)-3-oxo-2-morpholinyl)-N,N-dimethylacetamide;

ethyl (2R)-2-((2S,3R,6S)-2,3-bis(4-chlorophenyl)-6-(3-(4-morpholinyl)propyl)-5-oxo-4-morpholinyl)pentanoate;

(2R)-2-((2S,3R)-3-(4-chlorophenyl)-2-(4-cyanophenyl)-5-oxo-4-morpholinyl)pentanoic acid;

(2S)-2-((2R,3S)-3-(4-chlorophenyl)-2-(4-cyanophenyl)-5-oxo-4-morpholinyl)pentanoic acid;

(2S)-2-((2S,3R)-3-(4-chlorophenyl)-2-(4-cyanophenyl)-5-oxo-4-morpholinyl)pentanoic acid;

(2R)-2-((2R,3S)-3-(4-chlorophenyl)-2-(4-cyanophenyl)-5-oxo-4-morpholinyl)pentanoic acid;

(2R)-2-((2S,3R,6S)-2,3-bis(4-chlorophenyl)-6-(3-hydroxypropyl)-5-oxo-4-morpholinyl)pentanoic acid;

(2R)-2-((2S,3R,6S)-2,3-bis(4-chlorophenyl)-6-(4-iodobenzyl)-5-oxo-4-morpholinyl)pentanamide;

(2S)-2-((2R,3S,6R)-2,3-bis(4-chlorophenyl)-6-(4-iodobenzyl)-5-oxo-4-morpholinyl)pentanamide;

(2R)-2-((2S,3R,6S)-2,3-bis(4-chlorophenyl)-6-(4-fluorobenzyl)-5-oxo-4-morpholinyl)-4-pentenoic acid;

(2S)-2-((2R,3S,6R)-2,3-bis(4-chlorophenyl)-6-(4-fluorobenzyl)-5-oxo-4-morpholinyl)-4-pentenoic acid;

(2S)-2-((2S,3R,6S)-2,3-bis(4-chlorophenyl)-6-(4-fluorobenzyl)-5-oxo-4-morpholinyl)-4-pentenoic acid;

(2R)-2-((2R,3S,6R)-2,3-bis(4-chlorophenyl)-6-(4-fluorobenzyl)-5-oxo-4-morpholinyl)-4-pentenoic acid;

(2R)-2-((2S,3R,6S)-2,3-bis(4-chlorophenyl)-6-(4-iodobenzyl)-5-oxo-4-morpholinyl)pentanenitrile;

(2S)-2-((2R,3S,6R)-2,3-bis(4-chlorophenyl)-6-(4-iodobenzyl)-5-oxo-4-morpholinyl)pentanenitrile;

4-(((2R,5S,6R)-5,6-bis(4-chlorophenyl)-3-oxo-4-((1S)-1-(1H-tetrazol-5-yl)butyl)-2-morpholinyl)methyl)benzonitrile;

4-(((2S,5R,6S)-5,6-bis(4-chlorophenyl)-3-oxo-4-((1R)-1-(1H-tetrazol-5-yl)butyl)-2-morpholinyl)methyl)benzonitrile;

(5R,6S)-6-(3-chlorophenyl)-5-(4-chlorophenyl)-4-(cyclopropylmethyl)-3-morpholinone;

(5S,6R)-6-(3-chlorophenyl)-5-(4-chlorophenyl)-4-(cyclopropylmethyl)-3-morpholinone;

(5R,6S)-6-(3-chlorophenyl)-5-(4-chlorophenyl)-4-(((1R,2R)-2-methylcyclopropyl)methyl)-3-morpholinone;

(5R,6S)-6-(3-chlorophenyl)-5-(4-chlorophenyl)-4-(((1S,2S)-2-methylcyclopropyl)methyl)-3-morpholinone;

(5S,6R)-6-(3-chlorophenyl)-5-(4-chlorophenyl)-4-(((1R,2R)-2-methylcyclopropyl)methyl)-3-morpholinone;

(5S,6R)-6-(3-chlorophenyl)-5-(4-chlorophenyl)-4-(((1S,2S)-2-methylcyclopropyl)methyl)-3-morpholinone;

N-((2R)-2-((2S,3R,6S)-2,3-bis(4-chlorophenyl)-6-(4-cyanobenzyl)-5-oxo-4-morpholinyl)pentanoyl)-beta-alanine;

N-((2S)-2-((2R,3S,6R)-2,3-bis(4-chlorophenyl)-6-(4-cyanobenzyl)-5-oxo-4-morpholinyl)pentanoyl)-beta-alanine;

N-((2S)-2-((2S,3R,6S)-2,3-bis(4-chlorophenyl)-6-(4-cyanobenzyl)-5-oxo-4-morpholinyl)pentanoyl)-beta-alanine;

N-((2R)-2-((2R,3S,6R)-2,3-bis(4-chlorophenyl)-6-(4-cyanobenzyl)-5-oxo-4-morpholinyl)pentanoyl)-beta-alanine;

N-((2R)-2-((2R,3S,6R)-2,3-bis(4-chlorophenyl)-6-(4-cyanobenzyl)-5-oxo-4-morpholinyl)pentanoyl)-beta-alanine;

N-((2S)-2-((2S,3R,6S)-2,3-bis(4-chlorophenyl)-6-(4-cyanobenzyl)-5-oxo-4-morpholinyl)pentanoyl)-beta-alanine;

N-((2R)-2-((2R,3S,6R)-2,3-bis(4-chlorophenyl)-6-(4-cyanobenzyl)-5-oxo-4-morpholinyl)pentanoyl)-beta-alanine;

N-((2S)-2-((2S,3R,6S)-2,3-bis(4-chlorophenyl)-6-(4-cyanobenzyl)-5-oxo-4-morpholinyl)pentanoyl)-beta-alanine;

N-((2R)-2-((2S,3R)-2,3-bis(4-chlorophenyl)-5-oxo-4-morpholinyl)pentanoyl)-beta-alanine;

N-((2S)-2-((2R,3S)-2,3-bis(4-chlorophenyl)-5-oxo-4-morpholinyl)pentanoyl)-beta-alanine;

N-((2S)-2-((2S,3R)-2,3-bis(4-chlorophenyl)-5-oxo-4-morpholinyl)pentanoyl)-beta-alanine;

N-((2R)-2-((2R,3S)-2,3-bis(4-chlorophenyl)-5-oxo-4-morpholinyl)pentanoyl)-beta-alanine;

(5R,6S)-6-(3-chlorophenyl)-5-(4-chlorophenyl)-4-(cyclopropylsulfonyl)-3-morpholinone;

(5S,6R)-6-(3-chlorophenyl)-5-(4-chlorophenyl)-4-(cyclopropylsulfonyl)-3-morpholinone;

4-(((2R,5S,6R)-5,6-bis(4-chlorophenyl)-4-methyl-3-oxo-2-morpholinyl)methyl)benzamide;

4-(((2S,5R,6S)-5,6-bis(4-chlorophenyl)-4-methyl-3-oxo-2-morpholinyl)methyl)benzamide;

(3R)-3-((2S,3R,6S)-2-(3-chlorophenyl)-3-(4-chlorophenyl)-6-(4-fluorobenzyl)-5-oxo-4-morpholinyl)hexanoic acid;

(((2R)-2-((2S,3R)-2,3-bis(4-chlorophenyl)-5-oxo-4-morpholinyl)pentyl)oxy)acetic acid;

(((2S)-2-((2R,3S)-2,3-bis(4-chlorophenyl)-5-oxo-4-morpholinyl)pentyl)oxy)acetic acid;

(2R)-2-((2R,3S,6R)-2,3-bis(4-chlorophenyl)-6-(4-(methylsulfonyl)benzyl)-5-oxo-4-morpholinyl)pentanoic acid;

(2S)-2-((2S,3R,6S)-2,3-bis(4-chlorophenyl)-6-(4-(methylsulfonyl)benzyl)-5-oxo-4-morpholinyl)pentanoic acid;

4-(((2R,5S,6R)-5,6-bis(4-chlorophenyl)-4-methyl-3-oxo-2-morpholinyl)methyl)-2-fluorobenzonitrile;

4-(((2S,5R,6S)-5,6-bis(4-chlorophenyl)-4-methyl-3-oxo-2-morpholinyl)methyl)-2-fluorobenzonitrile;

(2R,5S,6R)-5,6-bis(4-chlorophenyl)-2-(4-fluorobenzyl)-4-(4-pyridinyl)-3-morpholinone;

(2S,5R,6S)-5,6-bis(4-chlorophenyl)-2-(4-fluorobenzyl)-4-(4-pyridinyl)-3-morpholinone;

(2R,5S,6R)-6-(3-chlorophenyl)-5-(4-chlorophenyl)-4-(cyclopropylmethyl)-2-((5-methyl-1,3,4-oxadiazol-2-yl)methyl)-3-morpholinone;

(2S,5R,6S)-6-(3-chlorophenyl)-5-(4-chlorophenyl)-4-(cyclopropylmethyl)-2-((5-methyl-1,3,4-oxadiazol-2-yl)methyl)-3-morpholinone;

(2R)-2-((2S,3R,6S)-2,3-bis(4-chlorophenyl)-6-(4-cyano-2-fluorobenzyl)-5-oxo-4-morpholinyl)pentanoic acid;

(2S)-2-((2R,3S,6R)-2,3-bis(4-chlorophenyl)-6-(4-cyano-2-fluorobenzyl)-5-oxo-4-morpholinyl)pentanoic acid;

(5R,6R)-6-(3-chlorophenyl)-5-(4-chlorophenyl)-2,2,6-trimethyl-4-(1-methylethyl)-3-thiomorpholinone 1,1-dioxide;

(5S,6S)-6-(3-chlorophenyl)-5-(4-chlorophenyl)-2,2,6-trimethyl-4-(1-methylethyl)-3-thiomorpholinone 1,1-dioxide;

(5R,6S)-6-(3-chlorophenyl)-5-(4-chlorophenyl)-2,2,6-trimethyl-4-(1-methylethyl)-3-thiomorpholinone 1,1-dioxide;

(5S,6R)-6-(3-chlorophenyl)-5-(4-chlorophenyl)-2,2,6-trimethyl-4-(1-methylethyl)-3-thiomorpholinone 1,1-dioxide;

3-(((2R)-2-((2S,3R)-2,3-bis(4-chlorophenyl)-5-oxo-4-morpholinyl)pentyl)amino)-3-oxopropanoic acid;

3-(((2S)-2-((2R,3S)-2,3-bis(4-chlorophenyl)-5-oxo-4-morpholinyl)pentyl)amino)-3-oxopropanoic acid;

N-((2R)-2-((2S,3R)-2,3-bis(4-chlorophenyl)-5-oxo-4-morpholinyl)pentyl)glycine;

N-((2S)-2-((2R,3S)-2,3-bis(4-chlorophenyl)-5-oxo-4-morpholinyl)pentyl)glycine;

((2R,5S,6R)-6-(3-chloro-4-fluorophenyl)-5-(4-chlorophenyl)-4-(cyclopropylmethyl)-3-oxo-2-morpholinyl)acetic acid;

((2S,5R,6S)-6-(3-chloro-4-fluorophenyl)-5-(4-chlorophenyl)-4-(cyclopropylmethyl)-3-oxo-2-morpholinyl)acetic acid;

(2R,5S,6R)-5,6-bis(4-chlorophenyl)-4-methyl-2-(4-(methylsulfonyl)benzyl)-3-morpholinone;

(2S,5R,6S)-5,6-bis(4-chlorophenyl)-4-methyl-2-(4-(methylsulfonyl)benzyl)-3-morpholinone;

(2R)-2-((2S,3R,6S)-2,3-bis(4-chlorophenyl)-6-(4-cyanobenzyl)-5-oxo-4-morpholinyl)-N-(1H-tetrazol-5-ylmethyl)pentanamide;

(2S)-2-((2R,3S,6R)-2,3-bis(4-chlorophenyl)-6-(4-cyanobenzyl)-5-oxo-4-morpholinyl)-N-(1H-tetrazol-5-ylmethyl)pentanamide;

((2R,5S,6R)-6-(3-chlorophenyl)-5-(4-chlorophenyl)-4-(cyclopropylcarbonyl)-3-oxo-2-morpholinyl)acetic acid;

((2S,5R,6S)-6-(3-chlorophenyl)-5-(4-chlorophenyl)-4-(cyclopropylcarbonyl)-3-oxo-2-morpholinyl)acetic acid;

(5R,6S)-6-(3-chlorophenyl)-5-(4-chlorophenyl)-4-(cyclopropylmethyl)-3-thiomorpholinone 1,1-dioxide;

2-((2R,5S,6R)-6-(3-chlorophenyl)-5-(4-chlorophenyl)-4-(cyclopropylmethyl)-3-oxo-2-morpholinyl)ethyl methanesulfonate;

2-((2S,5R,6S)-6-(3-chlorophenyl)-5-(4-chlorophenyl)-4-(cyclopropylmethyl)-3-oxo-2-morpholinyl)ethyl methanesulfonate;

(2R)-2-((2S,3R,6S)-2,3-bis(4-chlorophenyl)-6-(4-cyanobenzyl)-5-oxo-4-morpholinyl)-N-(2-(1H-tetrazol-5-yl)ethyl)pentanamide;

(2S)-2-((2R,3S,6R)-2,3-bis(4-chlorophenyl)-6-(4-cyanobenzyl)-5-oxo-4-morpholinyl)-N-(2-(1H-tetrazol-5-yl)ethyl)pentanamide;

N-((2R)-2-((2S,3R)-2,3-bis(4-chlorophenyl)-5-oxo-4-morpholinyl)pentyl)-2-(1H-tetrazol-5-yl)acetamide;

N-((2S)-2-((2R,3S)-2,3-bis(4-chlorophenyl)-5-oxo-4-morpholinyl)pentyl)-2-(1H-tetrazol-5-yl)acetamide;

4-(((2R)-2-((2S,3R,6S)-2,3-bis(4-chlorophenyl)-6-(4-cyanobenzyl)-5-oxo-4-morpholinyl)pentanoyl)amino)butanoic acid;

4-(((2S)-2-((2R,3S,6R)-2,3-bis(4-chlorophenyl)-6-(4-cyanobenzyl)-5-oxo-4-morpholinyl)pentanoyl)amino)butanoic acid;

(2R)-2-((2S,3R,6S)-2,3-bis(4-chlorophenyl)-6-(4-cyanobenzyl)-5-oxo-4-morpholinyl)pentanoic acid;

(5R,6S)-5,6-bis(4-chlorophenyl)-4-(2-(methylsulfanyl)-4-pyrimidinyl)-3-morpholinone;

(5S,6R)-5,6-bis(4-chlorophenyl)-4-(2-(methylsulfanyl)-4-pyrimidinyl)-3-morpholinone;

1-((2R)-2-((2S,3R)-2,3-bis(4-chlorophenyl)-5-oxo-4-morpholinyl)pentanoyl)-4-piperidinecarboxylic acid;

1-((2S)-2-((2R,3S)-2,3-bis(4-chlorophenyl)-5-oxo-4-morpholinyl)pentanoyl)-4-piperidinecarboxylic acid;

(4-((2R)-2-((2S,3R)-2,3-bis(4-chlorophenyl)-5-oxo-4-morpholinyl)pentanoyl)-1-piperazinyl)acetic acid;

(4-((2S)-2-((2R,3S)-2,3-bis(4-chlorophenyl)-5-oxo-4-morpholinyl)pentanoyl)-1-piperazinyl)acetic acid;

(2S)-4-(((2R)-2-((2S,3R,6S)-2,3-bis(4-chlorophenyl)-6-(4-cyanobenzyl)-5-oxo-4-morpholinyl)pentanoyl)amino)-2-hydroxybutanoic acid;

(2S)-4-(((2S)-2-((2R,3S,6R)-2,3-bis(4-chlorophenyl)-6-(4-cyanobenzyl)-5-oxo-4-morpholinyl)pentanoyl)amino)-2-hydroxybutanoic acid;

(3R)-4-(((2R)-2-((2S,3R,6S)-2,3-bis(4-chlorophenyl)-6-(4-cyanobenzyl)-5-oxo-4-morpholinyl)pentanoyl)amino)-3-hydroxybutanoic acid;

(3R)-4-(((2S)-2-((2R,3S,6R)-2,3-bis(4-chlorophenyl)-6-(4-cyanobenzyl)-5-oxo-4-morpholinyl)pentanoyl)amino)-3-hydroxybutanoic acid;

(3S)-4-(((2R)-2-((2S,3R,6S)-2,3-bis(4-chlorophenyl)-6-(4-cyanobenzyl)-5-oxo-4-morpholinyl)pentanoyl)amino)-3-hydroxybutanoic acid;

(3S)-4-(((2S)-2-((2R,3S,6R)-2,3-bis(4-chlorophenyl)-6-(4-cyanobenzyl)-5-oxo-4-morpholinyl)pentanoyl)amino)-3-hydroxybutanoic acid;

(2R)-3-(((2R)-2-((2S,3R,6S)-2,3-bis(4-chlorophenyl)-6-(4-cyanobenzyl)-5-oxo-4-morpholinyl)pentanoyl)amino)-2-methylpropanoic acid;

(2R)-3-(((2S)-2-((2R,3S,6R)-2,3-bis(4-chlorophenyl)-6-(4-cyanobenzyl)-5-oxo-4-morpholinyl)pentanoyl)amino)-2-methylpropanoic acid;

(2S)-3-(((2R)-2-((2S,3R,6S)-2,3-bis(4-chlorophenyl)-6-(4-cyanobenzyl)-5-oxo-4-morpholinyl)pentanoyl)amino)-2-methylpropanoic acid;
(2S)-3-(((2S)-2-((2R,3S,6R)-2,3-bis(4-chlorophenyl)-6-(4-cyanobenzyl)-5-oxo-4-morpholinyl)pentanoyl)amino)-2-methylpropanoic acid;
N-((2R)-2-((2S,3R,6S)-2,3-bis(4-chlorophenyl)-6-(4-cyanobenzyl)-5-oxo-4-morpholinyl)pentanoyl)-L-alanine;
N-((2S)-2-((2R,3S,6R)-2,3-bis(4-chlorophenyl)-6-(4-cyanobenzyl)-5-oxo-4-morpholinyl)pentanoyl)-D-alanine;
(2R)-2-((2R,3S)-2-(4-chlorophenyl)-3-(1H-indol-2-yl)-5-oxo-4-morpholinyl)pentanoic acid;
(2S)-2-((2S,3R)-2-(4-chlorophenyl)-3-(1H-indol-2-yl)-5-oxo-4-morpholinyl)pentanoic acid;
N-((2R)-2-((2S,3R,6S)-2,3-bis(4-chlorophenyl)-6-(4-cyanobenzyl)-5-oxo-4-morpholinyl)pentanoyl)-D-alanine;
N-((2S)-2-((2R,3S,6R)-2,3-bis(4-chlorophenyl)-6-(4-cyanobenzyl)-5-oxo-4-morpholinyl)pentanoyl)-L-alanine;
methyl 4-(((2R,5S,6R)-5,6-bis(4-chlorophenyl)-4-methyl-3-oxo-2-morpholinyl)methyl)benzoate;
methyl 4-(((2S,5R,6S)-5,6-bis(4-chlorophenyl)-4-methyl-3-oxo-2-morpholinyl)methyl)benzoate;
3-(((2R)-2-((2S,3R,6S)-2,3-bis(4-chlorophenyl)-6-(4-cyanobenzyl)-5-oxo-4-morpholinyl)pentanoyl)amino)-N-(tert-butoxycarbonyl)-D-alanine;
3-(((2S)-2-((2R,3S,6R)-2,3-bis(4-chlorophenyl)-6-(4-cyanobenzyl)-5-oxo-4-morpholinyl)pentanoyl)amino)-N-(tert-butoxycarbonyl)-D-alanine;
(5R,6S)-6-(3-chlorophenyl)-5-(4-chlorophenyl)-4-(cyclobutylmethyl)-3-morpholinone;
(5S,6R)-6-(3-chlorophenyl)-5-(4-chlorophenyl)-4-(cyclobutylmethyl)-3-morpholinone;
4-(((2R,5S,6R)-5,6-bis(4-chlorophenyl)-4-methyl-3-oxo-2-morpholinyl)methyl)benzonitrile;
4-(((2S,5R,6S)-5,6-bis(4-chlorophenyl)-4-methyl-3-oxo-2-morpholinyl)methyl)benzonitrile;
(4-((2R)-2-((2S,3R,6S)-2,3-bis(4-chlorophenyl)-6-(4-cyanobenzyl)-5-oxo-4-morpholinyl)pentanoyl)-1-piperazinyl)acetic acid;
(4-((2S)-2-((2R,3S,6R)-2,3-bis(4-chlorophenyl)-6-(4-cyanobenzyl)-5-oxo-4-morpholinyl)pentanoyl)-1-piperazinyl)acetic acid;
3-(((2R)-2-((2S,3R,6S)-2,3-bis(4-chlorophenyl)-6-(4-cyanobenzyl)-5-oxo-4-morpholinyl)pentanoyl)amino)-2,2-dimethylpropanoic acid;
3-(((2S)-2-((2R,3S,6R)-2,3-bis(4-chlorophenyl)-6-(4-cyanobenzyl)-5-oxo-4-morpholinyl)pentanoyl)amino)-2,2-dimethylpropanoic acid;
(5R,6S)-5,6-bis(4-chlorophenyl)-4-(2-chloro-4-pyridinyl)-3-morpholinone;
(5S,6R)-5,6-bis(4-chlorophenyl)-4-(2-chloro-4-pyridinyl)-3-morpholinone;
3-(((2R,5S,6R)-5,6-bis(4-chlorophenyl)-4-methyl-3-oxo-2-morpholinyl)methyl)benzamide;
3-(((2S,5R,6S)-5,6-bis(4-chlorophenyl)-4-methyl-3-oxo-2-morpholinyl)methyl)benzamide;
3-(((2R)-2-((2S,3R,6S)-2,3-bis(4-chlorophenyl)-6-(4-cyanobenzyl)-5-oxo-4-morpholinyl)pentanoyl)amino)-D-alanine;
3-(((2S)-2-((2R,3S,6R)-2,3-bis(4-chlorophenyl)-6-(4-cyanobenzyl)-5-oxo-4-morpholinyl)pentanoyl)amino)-D-alanine;
(2R)-2-((2S,3R,6S)-2,3-bis(4-chlorophenyl)-6-(4-methoxybenzyl)-5-oxo-4-morpholinyl)pentanoic acid;
(2S)-2-((2R,3S,6R)-2,3-bis(4-chlorophenyl)-6-(4-methoxybenzyl)-5-oxo-4-morpholinyl)pentanoic acid;
(2R)-2-((2S,3R)-2-(3-chlorophenyl)-3-(4-chlorophenyl)-5-oxo-4-morpholinyl)pentanoic acid;
(2S)-2-((2R,3S)-2-(3-chlorophenyl)-3-(4-chlorophenyl)-5-oxo-4-morpholinyl)pentanoic acid;
3-(4-((2R)-2-((2S,3R)-2,3-bis(4-chlorophenyl)-5-oxo-4-morpholinyl)pentanoyl)-1-piperazinyl)propanoic acid;
3-(4-((2S)-2-((2R,3S)-2,3-bis(4-chlorophenyl)-5-oxo-4-morpholinyl)pentanoyl)-1-piperazinyl)propanoic acid;
(2R)-((2S,3R,6S)-2-(3-chlorophenyl)-3-(4-chlorophenyl)-6-(4-fluorobenzyl)-5-oxo-4-morpholinyl)(cyclopropyl)ethanoic acid;
(2S)-((2R,3S,6R)-2-(3-chlorophenyl)-3-(4-chlorophenyl)-6-(4-fluorobenzyl)-5-oxo-4-morpholinyl)(cyclopropyl)ethanoic acid;
(2S)-((2S,3R,6S)-2-(3-chlorophenyl)-3-(4-chlorophenyl)-6-(4-fluorobenzyl)-5-oxo-4-morpholinyl)(cyclopropyl)ethanoic acid;
(2R)-((2R,3S,6R)-2-(3-chlorophenyl)-3-(4-chlorophenyl)-6-(4-fluorobenzyl)-5-oxo-4-morpholinyl)(cyclopropyl)ethanoic acid;
(2R,5S,6R)-5,6-bis(4-chlorophenyl)-2-(4-fluorobenzyl)-4-(1-methyl-1H-imidazol-4-yl)-3-morpholinone;
(2S,5R,6S)-5,6-bis(4-chlorophenyl)-2-(4-fluorobenzyl)-4-(1-methyl-1H-imidazol-4-yl)-3-morpholinone;
4-(((2R,5S,6R)-5,6-bis(4-chlorophenyl)-4-methyl-3-oxo-2-morpholinyl)methyl)benzoic acid;
4-(((2S,5R,6S)-5,6-bis(4-chlorophenyl)-4-methyl-3-oxo-2-morpholinyl)methyl)benzoic acid;
(5R,6S)-6-(3-chlorophenyl)-5-(4-chlorophenyl)-4-(2-methylpropyl)-3-morpholinone;
(5S,6R)-6-(3-chlorophenyl)-5-(4-chlorophenyl)-4-(2-methylpropyl)-3-morpholinone;
1-((2R)-2-((2S,3R,6S)-2,3-bis(4-chlorophenyl)-6-(4-fluorobenzyl)-5-oxo-4-morpholinyl)pentanoyl)-D-proline;
1-((2S)-2-((2R,3S,6R)-2,3-bis(4-chlorophenyl)-6-(4-fluorobenzyl)-5-oxo-4-morpholinyl)pentanoyl)-D-proline;
(5R,6S)-5,6-bis(4-chlorophenyl)-4-(2-pyrazinyl)-3-morpholinone;
(5S,6R)-5,6-bis(4-chlorophenyl)-4-(2-pyrazinyl)-3-morpholinone;
(2R,5S,6R)-5,6-bis(4-chlorophenyl)-4-(cyclopropylmethyl)-2-((2R)-2,3-dihydroxypropyl)-3-morpholinone;
(2R,5S,6R)-5,6-bis(4-chlorophenyl)-4-(cyclopropylmethyl)-2-((2S)-2,3-dihydroxypropyl)-3-morpholinone;
(2S,5R,6S)-5,6-bis(4-chlorophenyl)-4-(cyclopropylmethyl)-2-((2R)-2,3-dihydroxypropyl)-3-morpholinone;
(2S,5R,6S)-5,6-bis(4-chlorophenyl)-4-(cyclopropylmethyl)-2-((2S)-2,3-dihydroxypropyl)-3-morpholinone;
(5R,6S)-6-(3-chlorophenyl)-5-(4-chlorophenyl)-4-cyclopentyl-3-morpholinone;
(5S,6R)-6-(3-chlorophenyl)-5-(4-chlorophenyl)-4-cyclopentyl-3-morpholinone;
methyl 1-((2R)-2-((2S,3R,6S)-2,3-bis(4-chlorophenyl)-6-(4-fluorobenzyl)-5-oxo-4-morpholinyl)pentanoyl)-L-prolinate;
methyl 1-((2S)-2-((2R,3S,6R)-2,3-bis(4-chlorophenyl)-6-(4-fluorobenzyl)-5-oxo-4-morpholinyl)pentanoyl)-L-prolinate;
(5R,6S)-5,6-bis(4-chlorophenyl)-4-methyl-3-morpholinone;
1-((2R)-2-((2S,3R,6S)-2,3-bis(4-chlorophenyl)-6-(4-iodobenzyl)-5-oxo-4-morpholinyl)pentanoyl)-4-piperidinecarboxylic acid;
1-((2S)-2-((2R,3S,6R)-2,3-bis(4-chlorophenyl)-6-(4-iodobenzyl)-5-oxo-4-morpholinyl)pentanoyl)-4-piperidinecarboxylic acid;
(2R)-2-((2S,5R,6S)-2-(4-chlorobenzyl)-5,6-bis(4-chlorophenyl)-3-oxo-4-morpholinyl)pentanoic acid;

(2S)-2-((2R,5S,6R)-2-(4-chlorobenzyl)-5,6-bis(4-chlorophenyl)-3-oxo-4-morpholinyl)pentanoic acid;
(2R,5S,6R)-2-(4-(aminomethyl)benzyl)-5,6-bis(4-chlorophenyl)-4-methyl-3-morpholinone;
(2S,5R,6S)-2-(4-(aminomethyl)benzyl)-5,6-bis(4-chlorophenyl)-4-methyl-3-morpholinone;
3-(((2R)-2-((2S,3R,6S)-2,3-bis(4-chlorophenyl)-6-(4-iodobenzyl)-5-oxo-4-morpholinyl)pentyl)amino)-3-oxopropanoic acid;
3-(((2S)-2-((2R,3S,6R)-2,3-bis(4-chlorophenyl)-6-(4-iodobenzyl)-5-oxo-4-morpholinyl)pentyl)amino)-3-oxopropanoic acid;
(5R,6S)-6-(3-chlorophenyl)-5-(4-chlorophenyl)-4-(1,3-thiazol-4-ylmethyl)-3-morpholinone;
(5S,6R)-6-(3-chlorophenyl)-5-(4-chlorophenyl)-4-(1,3-thiazol-4-ylmethyl)-3-morpholinone;
(5R,6S)-6-(3-chlorophenyl)-5-(4-chlorophenyl)-4-(2-hydroxy-2-methylpropyl)-3-morpholinone; (5S,6R)-6-(3-chlorophenyl)-5-(4-chlorophenyl)-4-(2-hydroxy-2-methylpropyl)-3-morpholinone;
(5S,6R)-2-benzyl-5,6-bis(4-chlorophenyl)-4-methyl-3-morpholinone;
((2R,5S,6R)-6-(3-chlorophenyl)-5-(4-chlorophenyl)-4-((1-cyanocyclopropyl)methyl)-3-oxo-2-morpholinyl)acetic acid;
((2S,5R,6S)-6-(3-chlorophenyl)-5-(4-chlorophenyl)-4-((1-cyanocyclopropyl)methyl)-3-oxo-2-morpholinyl)acetic acid;
1-((((2R)-2-((2S,3R,6S)-2,3-bis(4-chlorophenyl)-6-(4-cyanobenzyl)-5-oxo-4-morpholinyl)pentanoyl)amino)methyl)cyclopentanecarboxylic acid;
1-((((2S)-2-((2R,3S,6R)-2,3-bis(4-chlorophenyl)-6-(4-cyanobenzyl)-5-oxo-4-morpholinyl)pentanoyl)amino)methyl)cyclopentanecarboxylic acid;
(3S)-3-((2R,3S,6R)-2-(3-chlorophenyl)-3-(4-chlorophenyl)-6-(4-fluorobenzyl)-5-oxo-4-morpholinyl)hexanoic acid;
(3S)-3-((2S,3R,6S)-2-(3-chlorophenyl)-3-(4-chlorophenyl)-6-(4-fluorobenzyl)-5-oxo-4-morpholinyl)hexanoic acid;
(2R)-2-((2R,3S)-2-(3-chlorophenyl)-3-(4-chlorophenyl)-5-oxo-4-morpholinyl)pentanoic acid;
(2R)-2-((2S,3R)-2-(3-chlorophenyl)-3-(4-chlorophenyl)-5-oxo-4-morpholinyl)pentanoic acid;
(2S)-2-((2R,3S)-2-(3-chlorophenyl)-3-(4-chlorophenyl)-5-oxo-4-morpholinyl)pentanoic acid;
(2S)-2-((2S,3R)-2-(3-chlorophenyl)-3-(4-chlorophenyl)-5-oxo-4-morpholinyl)pentanoic acid;
(2R)-2-((2S,3R,6S)-2,3-bis(4-chlorophenyl)-6-(4-iodobenzyl)-5-oxo-4-morpholinyl)pentanoic acid;
(2S)-2-((2R,3S,6R)-2,3-bis(4-chlorophenyl)-6-(4-iodobenzyl)-5-oxo-4-morpholinyl)pentanoic acid;
(5R,6S)-5,6-bis(4-chlorophenyl)-4-(4-pyridinyl)-3-morpholinone;
(5S,6R)-5,6-bis(4-chlorophenyl)-4-(4-pyridinyl)-3-morpholinone;
(2R)-((2R,3S)-2-(3-chlorophenyl)-3-(4-chlorophenyl)-5-oxo-4-morpholinyl)(cyclopropyl)ethanoic acid;
(2R)-((2S,3R)-2-(3-chlorophenyl)-3-(4-chlorophenyl)-5-oxo-4-morpholinyl)(cyclopropyl)ethanoic acid;
(2S)-((2R,3S)-2-(3-chlorophenyl)-3-(4-chlorophenyl)-5-oxo-4-morpholinyl)(cyclopropyl)ethanoic acid;
(2S)-((2S,3R)-2-(3-chlorophenyl)-3-(4-chlorophenyl)-5-oxo-4-morpholinyl)(cyclopropyl)ethanoic acid;
(2R)-2-((2R,3S)-2,3-bis(4-chlorophenyl)-5-oxo-4-morpholinyl)pentanoic acid;
(2R)-2-((2S,3R)-2,3-bis(4-chlorophenyl)-5-oxo-4-morpholinyl)pentanoic acid;
(2S)-2-((2R,3S)-2,3-bis(4-chlorophenyl)-5-oxo-4-morpholinyl)pentanoic acid;
(2S)-2-((2S,3R)-2,3-bis(4-chlorophenyl)-5-oxo-4-morpholinyl)pentanoic acid;
(2R)-2-((2S,5R,6S)-2-(4-biphenylylmethyl)-5,6-bis(4-chlorophenyl)-3-oxo-4-morpholinyl)pentanoic acid;
(2S)-2-((2R,5S,6R)-2-(4-biphenylylmethyl)-5,6-bis(4-chlorophenyl)-3-oxo-4-morpholinyl)pentanoic acid;
ethyl (2R)-2-((2S,3R,6S)-2,3-bis(4-chlorophenyl)-6-(4-cyano-2-fluorobenzyl)-5-oxo-4-morpholinyl)pentanoate;
ethyl (2S)-2-((2R,3S,6R)-2,3-bis(4-chlorophenyl)-6-(4-cyano-2-fluorobenzyl)-5-oxo-4-morpholinyl)pentanoate;
(2R,5S,6R)-5,6-bis(4-chlorophenyl)-2-(4-((dimethylamino)methyl)benzyl)-4-methyl-3-morpholinone;
(2S,5R,6S)-5,6-bis(4-chlorophenyl)-2-(4-((dimethylamino)methyl)benzyl)-4-methyl-3-morpholinone;
(5R,6S)-5,6-bis(4-chlorophenyl)-6-methyl-3-morpholinone and (5S,6R)-5,6-bis(4-chlorophenyl)-6-methyl-3-morpholinone
(2R)-2-((2S,5R,6S)-2-(4-carbamoylbenzyl)-5,6-bis(4-chlorophenyl)-3-oxo-4-morpholinyl)pentanoic acid;
(2S)-2-((2R,5S,6R)-2-(4-carbamoylbenzyl)-5,6-bis(4-chlorophenyl)-3-oxo-4-morpholinyl)pentanoic acid;
(2R)-2-((2S,3R,6S)-2,3-bis(4-chlorophenyl)-5-oxo-6-(4-(1H-pyrazol-1-yl)benzyl)-4-morpholinyl)pentanoic acid;
(2S)-2-((2R,3S,6R)-2,3-bis(4-chlorophenyl)-5-oxo-6-(4-(1H-pyrazol-1-yl)benzyl)-4-morpholinyl)pentanoic acid;
(2R)-2-((2S,3R,6S)-2,3-bis(4-chlorophenyl)-5-oxo-6-(4-(1H-pyrrol-1-yl)benzyl)-4-morpholinyl)pentanoic acid;
(2S)-2-((2R,3S,6R)-2,3-bis(4-chlorophenyl)-5-oxo-6-(4-(1H-pyrrol-1-yl)benzyl)-4-morpholinyl)pentanoic acid;
(2R)-2-((2S,3R)-2,3-bis(4-chlorophenyl)-5-oxo-4-morpholinyl)hexanoic acid;
(2S)-2-((2R,3S)-2,3-bis(4-chlorophenyl)-5-oxo-4-morpholinyl)hexanoic acid;
(2S)-2-((2S,3R)-2,3-bis(4-chlorophenyl)-5-oxo-4-morpholinyl)hexanoic acid;
(2R)-2-((2R,3S)-2,3-bis(4-chlorophenyl)-5-oxo-4-morpholinyl)hexanoic acid;
(2R)-2-((2S,3R)-2,3-bis(4-chlorophenyl)-2-methyl-5-oxo-4-morpholinyl)pentanoic acid;
(2S)-2-((2R,3S)-2,3-bis(4-chlorophenyl)-2-methyl-5-oxo-4-morpholinyl)pentanoic acid;
(2S)-2-((2S,3R)-2,3-bis(4-chlorophenyl)-2-methyl-5-oxo-4-morpholinyl)pentanoic acid;
(2R)-2-((2R,3S)-2,3-bis(4-chlorophenyl)-2-methyl-5-oxo-4-morpholinyl)pentanoic acid;
(5R,6S)-5,6-bis(4-chlorophenyl)-4-(3-pyridinyl)-3-morpholinone;
(5S,6R)-5,6-bis(4-chlorophenyl)-4-(3-pyridinyl)-3-morpholinone;
(5S,6R)-5,6-bis(4-bromophenyl)-4-(1-methylethyl)-3-morpholinone;
(5R,6S)-5,6-bis(4-bromophenyl)-4-(1-methylethyl)-3-morpholinone;
(2R)-2-((2R,3S)-2,3-bis(4-chlorophenyl)-2-methyl-5-oxo-4-morpholinyl)pentanoic acid;
(2S)-2-((2S,3R)-2,3-bis(4-chlorophenyl)-2-methyl-5-oxo-4-morpholinyl)pentanoic acid;
(2S)-2-((2R,3S)-2,3-bis(4-chlorophenyl)-2-methyl-5-oxo-4-morpholinyl)pentanoic acid;
(2R)-2-((2S,3R)-2,3-bis(4-chlorophenyl)-2-methyl-5-oxo-4-morpholinyl)pentanoic acid;
(5R,6S)-6-(3-chlorophenyl)-5-(4-chlorophenyl)-4-(2-methoxyethyl)-3-morpholinone;
(5S,6R)-6-(3-chlorophenyl)-5-(4-chlorophenyl)-4-(2-methoxyethyl)-3-morpholinone;

(2R)-((2S,3R)-2,3-bis(4-chlorophenyl)-5-oxo-4-morpholinyl)(phenyl)ethanoic acid;
(2S)-((2R,3S)-2,3-bis(4-chlorophenyl)-5-oxo-4-morpholinyl)(phenyl)ethanoic acid;
(2S)-((2S,3R)-2,3-bis(4-chlorophenyl)-5-oxo-4-morpholinyl)(phenyl)ethanoic acid;
(2R)-((2R,3S)-2,3-bis(4-chlorophenyl)-5-oxo-4-morpholinyl)(phenyl)ethanoic acid;
(2R)-((2S,3R)-2-(3-chlorophenyl)-3-(4-chlorophenyl)-5-oxo-4-morpholinyl)(cyclopropyl)ethanoic acid;
(2S)-((2R,3S)-2-(3-chlorophenyl)-3-(4-chlorophenyl)-5-oxo-4-morpholinyl)(cyclopropyl)ethanoic acid;
(2S)-((2S,3R)-2-(3-chlorophenyl)-3-(4-chlorophenyl)-5-oxo-4-morpholinyl)(cyclopropyl)ethanoic acid;
(2R)-((2R,3S)-2-(3-chlorophenyl)-3-(4-chlorophenyl)-5-oxo-4-morpholinyl)(cyclopropyl)ethanoic acid;
(2R)-2-((2R,3S,6R)-2,3-bis(4-chlorophenyl)-6-(2-fluoro-4-(methylsulfonyl)benzyl)-5-oxo-4-morpholinyl)pentanoic acid;
(2S)-2-((2S,3R,6S)-2,3-bis(4-chlorophenyl)-6-(2-fluoro-4-(methylsulfonyl)benzyl)-5-oxo-4-morpholinyl)pentanoic acid;
((2R,5S,6R)-5,6-bis(4-chlorophenyl)-4-methyl-3-oxo-2-morpholinyl)acetonitrile;
((2S,5R,6S)-5,6-bis(4-chlorophenyl)-4-methyl-3-oxo-2-morpholinyl)acetonitrile;
(5R,6S)-5,6-bis(4-chlorophenyl)-4-phenyl-3-morpholinone;
(5S,6R)-5,6-bis(4-chlorophenyl)-4-phenyl-3-morpholinone;
(2R)-2-((2S,3R,6S)-2,3-bis(4-chlorophenyl)-5-oxo-6-(4-(1H-1,2,4-triazol-1-yl)benzyl)-4-morpholinyl)pentanoic acid;
(2S)-2-((2R,3S,6R)-2,3-bis(4-chlorophenyl)-5-oxo-6-(4-(1H-1,2,4-triazol-1-yl)benzyl)-4-morpholinyl)pentanoic acid;
(2R)-2-((2S,3R,6S)-2,3-bis(4-chlorophenyl)-6-(4-fluorobenzyl)-2-methyl-5-oxo-4-morpholinyl)pentanoic acid;
(2S)-2-((2R,3S,6R)-2,3-bis(4-chlorophenyl)-6-(4-fluorobenzyl)-2-methyl-5-oxo-4-morpholinyl)pentanoic acid;
(2S)-2-((2S,3R,6S)-2,3-bis(4-chlorophenyl)-6-(4-fluorobenzyl)-2-methyl-5-oxo-4-morpholinyl)pentanoic acid;
(2R)-2-((2R,3S,6R)-2,3-bis(4-chlorophenyl)-6-(4-fluorobenzyl)-2-methyl-5-oxo-4-morpholinyl)pentanoic acid;
(2R,5S,6R)-5,6-bis(4-chlorophenyl)-4-methyl-2-(1H-tetrazol-5-ylmethyl)-3-morpholinone;
(2S,5R,6S)-5,6-bis(4-chlorophenyl)-4-methyl-2-(1H-tetrazol-5-ylmethyl)-3-morpholinone;
(2R)-2-((2R,3S)-2,3-bis(4-chlorophenyl)-5-oxo-4-morpholinyl)hexanoic acid;
(2R)-2-((2S,3R)-2,3-bis(4-chlorophenyl)-5-oxo-4-morpholinyl)hexanoic acid;
(2S)-2-((2R,3S)-2,3-bis(4-chlorophenyl)-5-oxo-4-morpholinyl)hexanoic acid;
(2S)-2-((2S,3R)-2,3-bis(4-chlorophenyl)-5-oxo-4-morpholinyl)hexanoic acid;
(2R)-2-((2S,3R)-2-(3-chlorophenyl)-3-(4-chlorophenyl)-2-methyl-5-oxo-4-morpholinyl)pentanoic acid;
(2S)-2-((2R,3S)-2-(3-chlorophenyl)-3-(4-chlorophenyl)-2-methyl-5-oxo-4-morpholinyl)pentanoic acid;
(2S)-2-((2S,3R)-2-(3-chlorophenyl)-3-(4-chlorophenyl)-2-methyl-5-oxo-4-morpholinyl)pentanoic acid;
(2R)-2-((2R,3S)-2-(3-chlorophenyl)-3-(4-chlorophenyl)-2-methyl-5-oxo-4-morpholinyl)pentanoic acid;
(2R)-2-((2S,3R)-2,3-bis(4-chlorophenyl)-5-oxo-4-morpholinyl)-4-methylpentanoic acid;
(2S)-2-((2R,3S)-2,3-bis(4-chlorophenyl)-5-oxo-4-morpholinyl)-4-methylpentanoic acid;
(2S)-2-((2S,3R)-2,3-bis(4-chlorophenyl)-5-oxo-4-morpholinyl)-4-methylpentanoic acid;
(2R)-2-((2R,3S)-2,3-bis(4-chlorophenyl)-5-oxo-4-morpholinyl)-4-methylpentanoic acid;
4-(((2R)-2-((2S,3R,6S)-2,3-bis(4-chlorophenyl)-6-(4-iodobenzyl)-5-oxo-4-morpholinyl)pentanoyl)amino)butanoic acid;
((2R,5S,6R)-6-(3-chlorophenyl)-5-(4-chlorophenyl)-4-(cyclopropylmethyl)-6-methyl-3-oxo-2-morpholinyl)acetic acid;
((2S,5R,6S)-6-(3-chlorophenyl)-5-(4-chlorophenyl)-4-(cyclopropylmethyl)-6-methyl-3-oxo-2-morpholinyl)acetic acid;
(4R)-4-((2R,3S)-2,3-bis(4-chlorophenyl)-5-oxo-4-morpholinyl)heptanoic acid;
and (4S)-4-((2S,3R)-2,3-bis(4-chlorophenyl)-5-oxo-4-morpholinyl)heptanoic acid;
(4R)-4-((2S,3R)-2,3-bis(4-chlorophenyl)-5-oxo-4-morpholinyl)heptanoic acid;
(4S)-4-((2R,3S)-2,3-bis(4-chlorophenyl)-5-oxo-4-morpholinyl)heptanoic acid;
(2R)-2-((2R,3S)-2,3-bis(4-chlorophenyl)-5-oxo-4-morpholinyl)butanoic acid;
(2R)-2-((2S,3R)-2,3-bis(4-chlorophenyl)-5-oxo-4-morpholinyl)butanoic acid;
(2S)-2-((2R,3S)-2,3-bis(4-chlorophenyl)-5-oxo-4-morpholinyl)butanoic acid;
(2S)-2-((2S,3R)-2,3-bis(4-chlorophenyl)-5-oxo-4-morpholinyl)butanoic acid;
(5R,6S)-5,6-bis(4-chlorophenyl)-4-(cyclopropylmethyl)-3-morpholinone;
(5S,6R)-5,6-bis(4-chlorophenyl)-4-(cyclopropylmethyl)-3-morpholinone;
(5S,6R)-5,6-bis(4-bromophenyl)-4-ethyl-3-morpholinone;
(5R,6S)-5,6-bis(4-bromophenyl)-4-ethyl-3-morpholinone;
2-((2R,5S,6R)-5,6-bis(4-chlorophenyl)-4-methyl-3-oxo-2-morpholinyl)acetamide;
2-((2S,5R,6S)-5,6-bis(4-chlorophenyl)-4-methyl-3-oxo-2-morpholinyl)acetamide;
(2R)-2-((2R,3S,6R)-2-(3-chlorophenyl)-3-(4-chlorophenyl)-6-(4-fluorobenzyl)-5-oxo-4-morpholinyl)-2-(4-fluorobenzyl)pentanoic acid;
(2S)-2-((2S,3R,6S)-2-(3-chlorophenyl)-3-(4-chlorophenyl)-6-(4-fluorobenzyl)-5-oxo-4-morpholinyl)-2-(4-fluorobenzyl)pentanoic acid;
(2S)-2-((2R,3S,6R)-2-(3-chlorophenyl)-3-(4-chlorophenyl)-6-(4-fluorobenzyl)-5-oxo-4-morpholinyl)-2-(4-fluorobenzyl)pentanoic acid;
(2R)-2-((2S,3R,6S)-2-(3-chlorophenyl)-3-(4-chlorophenyl)-6-(4-fluorobenzyl)-5-oxo-4-morpholinyl)-2-(4-fluorobenzyl)pentanoic acid;
(2R,5S,6R)-5,6-bis(4-chlorophenyl)-2-(2-hydroxyethyl)-4-methyl-3-morpholinone;
(2S,5R,6S)-5,6-bis(4-chlorophenyl)-2-(2-hydroxyethyl)-4-methyl-3-morpholinone;
(2R,5S,6R)-5,6-bis(4-chlorophenyl)-2-((2R)-2,3-dihydroxypropyl)-4-methyl-3-morpholinone;
(2R,5S,6R)-5,6-bis(4-chlorophenyl)-2-((2S)-2,3-dihydroxypropyl)-4-methyl-3-morpholinone;
(2S,5R,6S)-5,6-bis(4-chlorophenyl)-2-((2R)-2,3-dihydroxypropyl)-4-methyl-3-morpholinone;
(2S,5R,6S)-5,6-bis(4-chlorophenyl)-2-((2S)-2,3-dihydroxypropyl)-4-methyl-3-morpholinone;
1-((2R)-2-((2S,3R,6S)-2,3-bis(4-chlorophenyl)-6-(4-fluorobenzyl)-5-oxo-4-morpholinyl)pentyl)-4-piperidinecarboxylic acid;

1-((2S)-2-((2R,3S,6R)-2,3-bis(4-chlorophenyl)-6-(4-fluorobenzyl)-5-oxo-4-morpholinyl)pentyl)-4-piperidinecarboxylic acid;
N-((2R)-2-((2S,3R,6S)-2,3-bis(4-chlorophenyl)-6-(4-fluorobenzyl)-5-oxo-4-morpholinyl)pentanoyl)-N-methylglycine;
N-((2S)-2-((2R,3S,6R)-2,3-bis(4-chlorophenyl)-6-(4-fluorobenzyl)-5-oxo-4-morpholinyl)pentanoyl)-N-methylglycine;
(3R,5R,6S)-5,6-bis(4-chlorophenyl)-3-propyl-2,5,6,8-tetrahydro-3H-imidazo[2,1-c][1,4]oxazine;
(3S,5S,6R)-5,6-bis(4-chlorophenyl)-3-propyl-2,5,6,8-tetrahydro-3H-imidazo[2,1-c][1,4]oxazine;
(2R)-2-((2S,3R,6S)-2,3-bis(4-chlorophenyl)-6-(2-(dimethylamino)ethyl)-5-oxo-4-morpholinyl)pentanoic acid;
(2S)-2-((2R,3S,6R)-2,3-bis(4-chlorophenyl)-6-(2-(dimethylamino)ethyl)-5-oxo-4-morpholinyl)pentanoic acid;
N-((2R)-2-((2S,3R,6S)-2,3-bis(4-chlorophenyl)-6-(4-fluorobenzyl)-5-oxo-4-morpholinyl)pentanoyl)-N-methyl-beta-alanine;
N-((2S)-2-((2R,3S,6R)-2,3-bis(4-chlorophenyl)-6-(4-fluorobenzyl)-5-oxo-4-morpholinyl)pentanoyl)-N-methyl-beta-alanine;
4-(((2S,5R,6S)-5-(4-chlorophenyl)-4-methyl-6-(2-methylpropyl)-3-oxo-2-morpholinyl)methyl)-2-fluorobenzonitrile;
4-(((2R,5S,6R)-5-(4-chlorophenyl)-4-methyl-6-(2-methylpropyl)-3-oxo-2-morpholinyl)methyl)-2-fluorobenzonitrile;
(2R)-2-((2R,3S)-2,3-bis(4-chlorophenyl)-5-oxo-4-morpholinyl)propanoic acid;
(2R)-2-((2S,3R)-2,3-bis(4-chlorophenyl)-5-oxo-4-morpholinyl)propanoic acid;
(2S)-2-((2R,3S)-2,3-bis(4-chlorophenyl)-5-oxo-4-morpholinyl)propanoic acid;
(2S)-2-((2S,3R)-2,3-bis(4-chlorophenyl)-5-oxo-4-morpholinyl)propanoic acid;
(5R,6S)-5,6-bis(4-chlorophenyl)-4-(2,6-dichloro-4-pyridinyl)-3-morpholinone;
(5S,6R)-5,6-bis(4-chlorophenyl)-4-(2,6-dichloro-4-pyridinyl)-3-morpholinone;
(2R)-2-((2S,3R,6S)-2,3-bis(4-chlorophenyl)-6-(4-iodobenzyl)-5-oxo-4-morpholinyl)-N-hydroxypentanamide;
(2S)-2-((2R,3S,6R)-2,3-bis(4-chlorophenyl)-6-(4-iodobenzyl)-5-oxo-4-morpholinyl)-N-hydroxypentanamide;
(2R)-2-((2S,3R,6S)-2,3-bis(4-chlorophenyl)-6-(4-fluorobenzyl)-5-oxo-4-morpholinyl)-N-(cyclopropylsulfonyl)pentanamide;
(2S)-2-((2R,3S,6R)-2,3-bis(4-chlorophenyl)-6-(4-fluorobenzyl)-5-oxo-4-morpholinyl)-N-(cyclopropylsulfonyl)pentanamide;
(2R)-2-((2R,3S)-2,3-bis(4-chlorophenyl)-5-oxo-4-morpholinyl)-3-methylbutanoic acid;
(2R)-2-((2S,3R)-2,3-bis(4-chlorophenyl)-5-oxo-4-morpholinyl)-3-methylbutanoic acid;
(2S)-2-((2R,3S)-2,3-bis(4-chlorophenyl)-5-oxo-4-morpholinyl)-3-methylbutanoic acid;
(2S)-2-((2S,3R)-2,3-bis(4-chlorophenyl)-5-oxo-4-morpholinyl)-3-methylbutanoic acid;
(2R,5R,6S)-5,6-bis(4-chlorophenyl)-2-hydroxy-4-methyl-3-morpholinone;
(2S,5S,6R)-5,6-bis(4-chlorophenyl)-2-hydroxy-4-methyl-3-morpholinone;
(2R,5S,6R)-5,6-bis(4-chlorophenyl)-4-((1S)-1-((4-(cyclopropylmethyl)-1-piperazinyl)carbonyl)butyl)-2-(4-iodobenzyl)-3-morpholinone;
(2S,5R,6S)-5,6-bis(4-chlorophenyl)-4-((1R)-1-((4-(cyclopropylmethyl)-1-piperazinyl)carbonyl)butyl)-2-(4-iodobenzyl)-3-morpholinone;
(3R,5S,6R)-5,6-bis(4-chlorophenyl)-3-propyl-2,5,6,8-tetrahydro-3H-imidazo[2,1-c][1,4]oxazine;
(3S,5R,6S)-5,6-bis(4-chlorophenyl)-3-propyl-2,5,6,8-tetrahydro-3H-imidazo[2,1-c][1,4]oxazine;
1-((2R)-2-((2S,3R,6S)-2,3-bis(4-chlorophenyl)-6-(4-cyanobenzyl)-5-oxo-4-morpholinyl)pentanoyl)-3-azetidinecarboxylic acid;
1-((2S)-2-((2R,3S,6R)-2,3-bis(4-chlorophenyl)-6-(4-cyanobenzyl)-5-oxo-4-morpholinyl)pentanoyl)-3-azetidinecarboxylic acid;
3-(((2R,5S,6R)-5,6-bis(4-chlorophenyl)-4-methyl-3-oxo-2-morpholinyl)methyl)benzoic acid;
3-(((2S,5R,6S)-5,6-bis(4-chlorophenyl)-4-methyl-3-oxo-2-morpholinyl)methyl)benzoic acid;
(2R,5R,6S)-5,6-bis(4-chlorophenyl)-2-(4-fluorobenzyl)-4-(3-pyridinyl)-3-morpholinone;
(2S,5S,6R)-5,6-bis(4-chlorophenyl)-2-(4-fluorobenzyl)-4-(3-pyridinyl)-3-morpholinone;
4-(((2R,5S,6R)-5,6-bis(4-chlorophenyl)-4-((1S)-1-((4-(cyclopropylmethyl)-1-piperazinyl)carbonyl)butyl)-3-oxo-2-morpholinyl)methyl)benzonitrile;
4-(((2S,5R,6S)-5,6-bis(4-chlorophenyl)-4-((1R)-1-((4-(cyclopropylmethyl)-1-piperazinyl)carbonyl)butyl)-3-oxo-2-morpholinyl)methyl)benzonitrile;
3-(((2R,5S,6R)-5,6-bis(4-chlorophenyl)-4-methyl-3-oxo-2-morpholinyl)methyl)benzonitrile;
3-(((2S,5R,6S)-5,6-bis(4-chlorophenyl)-4-methyl-3-oxo-2-morpholinyl)methyl)benzonitrile;
(2R)-2-((2S,3R,6S)-2,3-bis(4-chlorophenyl)-6-(4-cyanobenzyl)-5-oxo-4-morpholinyl)-N-(methylsulfonyl)pentanamide; or
(2S)-2-((2R,3S,6R)-2,3-bis(4-chlorophenyl)-6-(4-cyanobenzyl)-5-oxo-4-morpholinyl)-N-(methylsulfonyl)pentanamide.

In embodiment 45, the present invention provides the compounds, or a pharmaceutically acceptable salts, selected from:
(5S,6R,Z)-5,6-bis(4-chlorophenyl)-4-methyl-2-(pyridin-3-ylmethylene)morpholin-3-one;
(5R,6S,Z)-5,6-bis(4-chlorophenyl)-4-methyl-2-(pyridin-3-ylmethylene)morpholin-3-one;
(3R,4S,8R)-4-(3-chlorophenyl)-3-(4-chlorophenyl)-2-isopropyltetrahydropyrrolo[1,2-a]pyrazine-1,6(2H,7H)-dione;
(3R,4S,8S)-4-(3-chlorophenyl)-3-(4-chlorophenyl)-2-isopropyltetrahydropyrrolo[1,2-a]pyrazine-1,6(2H,7H)-dione;
((2R,5S,6R)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid;
((2S,5S,6R)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid;
((2R,5S,6R)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid;
((2S,5S,6R)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid;
(2R)-2-((2R,3S)-2-(4-chlorophenyl)-3-(1H-indol-2-yl)-5-oxo-4-morpholinyl)pentanoic acid;
(2S)-2-((2S,3R)-2-(4-chlorophenyl)-3-(1H-indol-2-yl)-5-oxo-4-morpholinyl)pentanoic acid;

3-(((2R)-2-((2S,3R,6S)-2,3-bis(4-chlorophenyl)-6-(4-cyanobenzyl)-5-oxo-4-morpholinyl)pentanoyl)amino)-N-(tert-butoxycarbonyl)-D-alanine;

3-(((2S)-2-((2R,3S,6R)-2,3-bis(4-chlorophenyl)-6-(4-cyanobenzyl)-5-oxo-4-morpholinyl)pentanoyl)amino)-N-(tert-butoxycarbonyl)-D-alanine;

1-((((2R)-2-((2S,3R,6S)-2,3-bis(4-chlorophenyl)-6-(4-cyanobenzyl)-5-oxo-4-morpholinyl)pentanoyl)amino)methyl)cyclopentanecarboxylic acid;

1-((((2S)-2-((2R,3S,6R)-2,3-bis(4-chlorophenyl)-6-(4-cyanobenzyl)-5-oxo-4-morpholinyl)pentanoyl)amino)methyl)cyclopentanecarboxylic acid;

(2R,3R)-3-(4-chlorophenyl)-4-(cyclopropylmethyl)-N-(2-hydroxyphenyl)-5-oxo-2-morpholinecarboxamide;

(3R,5R,6S)-5,6-bis(4-chlorophenyl)-3-propyl-2,5,6,8-tetrahydro-3H-imidazo[2,1-c][1,4]oxazine;

(3S,5S,6R)-5,6-bis(4-chlorophenyl)-3-propyl-2,5,6,8-tetrahydro-3H-imidazo[2,1-c][1,4]oxazine;

4-(((2S,5R,6S)-5-(4-chlorophenyl)-4-methyl-6-(2-methylpropyl)-3-oxo-2-morpholinyl)methyl)-2-fluorobenzonitrile;

(2R)-2-((2S,3R,6S)-2,3-bis(4-chlorophenyl)-6-(4-iodobenzyl)-5-oxo-4-morpholinyl)-N-hydroxypentanamide;

(2S)-2-((2R,3S,6R)-2,3-bis(4-chlorophenyl)-6-(4-iodobenzyl)-5-oxo-4-morpholinyl)-N-hydroxypentanamide;

(2R,5S,6R)-5,6-bis(4-chlorophenyl)-4-((1S)-1-((4-(cyclopropylmethyl)-1-piperazinyl)carbonyl)butyl)-2-(4-iodobenzyl)-3-morpholinone;

(2S,5R,6S)-5,6-bis(4-chlorophenyl)-4-((1R)-1-((4-(cyclopropylmethyl)-1-piperazinyl)carbonyl)butyl)-2-(4-iodobenzyl)-3-morpholinone;

(3R,5S,6R)-5,6-bis(4-chlorophenyl)-3-propyl-2,5,6,8-tetrahydro-3H-imidazo[2,1-c][1,4]oxazine, (3S,5R,6S)-5,6-bis(4-chlorophenyl)-3-propyl-2,5,6,8-tetrahydro-3H-imidazo[2,1-c][1,4]oxazine;

4-(((2R,5S,6R)-5,6-bis(4-chlorophenyl)-4-((1S)-1-((4-(cyclopropylmethyl)-1-piperazinyl)carbonyl)butyl)-3-oxo-2-morpholinyl)methyl)benzonitrile; or 4-(((2S,5R,6S)-5,6-bis(4-chlorophenyl)-4-((1R)-1-((4-(cyclopropylmethyl)-1-piperazinyl)carbonyl)butyl)-3-oxo-2-morpholinyl)methyl)benzonitrile.

In embodiment 46, the present invention provides pharmaceutical compositions comprising a compound of any one of embodiments 1 to 45, or a pharmaceutically acceptable salt thereof, and a pharmaceutically acceptable excipient.

In embodiment 47, the present invention provides methods of treating cancer in a subject in need thereof, the methods comprising administering to the subject an effective dosage amount of a compound according to any one of embodiments 1 to 45, or a pharmaceutically acceptable salt thereof.

In embodiment 48, the present invention provides the methods of embodiment 47, wherein the cancer is selected from bladder, breast, colon, rectum, kidney, liver, small cell lung cancer, non-small-cell lung cancer, esophagus, gallbladder, ovary, pancreas, stomach, cervix, thyroid, prostate, skin, acute lymphocytic leukemia, chronic myelogenous leukemia, acute lymphoblastic leukemia, B-cell lymphoma, T-cell-lymphoma, Hodgkin's lymphoma, non-Hodgkin's lymphoma, hairy cell lymphoma, Burkett's lymphoma, acute and chronic myelogenous leukemia, melanoma, endometrial cancer, head and neck cancer, glioblastoma, or osteosarcoma.

DETAILED DESCRIPTION OF THE INVENTION

The present invention provides compounds of Formula I, as defined above, or pharmaceutically acceptable salts thereof. The present invention also provides pharmaceutical compositions comprising a compound of Formula I, or pharmaceutically acceptable salts thereof, and methods of treating diseases and/or conditions, such as cancer, using compounds of Formula I, or pharmaceutically acceptable salts thereof.

The term "alkyl" means a straight or branched chain hydrocarbon. Representative examples of alkyl groups include methyl, ethyl, propyl, isopropyl, butyl, isobutyl, tert-butyl, sec-butyl, pentyl and hexyl. Typical alkyl groups are alkyl groups having from 1 to 8 carbon atoms, which groups are commonly represented as $C_{1-8}$alkyl.

The term "alkoxy" means an alkyl group bonded to an oxygen atom. Representative examples of alkoxy groups include methoxy, ethoxy, tert-butoxy, propoxy and isobutoxy. Common alkoxy groups are $C_{1-8}$alkoxy.

The term "halogen" or "halo" means chlorine, fluorine, bromine or iodine.

The term "alkenyl" means a branched or straight chain hydrocarbon having one or more carbon-carbon double bonds. Representative examples of alkenyl groups include ethenyl, propenyl, allyl, butenyl and 4-methylbutenyl. Common alkenyl groups are $C_{2-8}$alkenyl.

The term "alkynyl" means a branched or straight chain hydrocarbon having one or more carbon-carbon triple bonds. Representative examples of alkynyl groups include ethynyl, propynyl (propargyl) and butynyl. Common alkynyl groups are $C_{2-8}$ alkynyl.

The term "cycloalkyl" means a cyclic, nonaromatic hydrocarbon. Examples of cycloalkyl groups include cyclopropyl, cyclobutyl, cyclopentyl, cyclohexyl and cycloheptyl. A cycloalkyl group can contain one or more double bond. Examples of cycloalkyl groups that contain double bonds include cyclopentenyl, cyclohexenyl, cyclohexadienyl and cyclobutadienyl. Common cycloalkyl groups are $C_{3-8}$ cycloalkyl groups. A cycloalkyl group can also be a bicyclic group comprising a cycloalkyl ring fused to an aryl or heteroaryl ring. An example of such a fused bicyclic group is tetrahydronaphthalene.

The term "perfluoroalkyl" means an alkyl group in which all of the hydrogen atoms have been replaced with fluorine atoms. Common perfluoroalkyl groups are $C_{1-8}$perfluoroalkyl. An example of a common perfluoroalkyl group is —$CF_3$.

The term "acyl" means a group derived from an organic acid by removal of the hydroxy group (—OH). For example, the acyl group $CH_3C(=O)$— is formed by the removal of the hydroxy group from $CH_3C(=O)OH$.

The term "aryl" means a cyclic, aromatic hydrocarbon. Examples of aryl groups include phenyl and naphthyl. Common aryl groups are six to thirteen membered rings.

The term "heteroatom" as used herein means an oxygen, nitrogen or sulfur atom.

The term "heteroaryl" means a cyclic, aromatic hydrocarbon in which one or more carbon atoms of an aryl group have been replaced with a heteroatom. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, indolyl, triazolyl, pyridazinyl, indazolyl, purinyl, quinolizinyl, isoquinolyl, quinolyl, naphthyridinyl, quinoxalinyl, isothiazolyl and benzo[b]thienyl. Common heteroaryl groups are five to thirteen membered rings that contain from 1 to 4 heteroatoms. Heteroaryl groups that are five and six membered rings that contain 1 to 3 heterotaoms are particularly common.

The term "heterocycloalkyl" means a cycloalkyl group in which one or more of the carbon atoms has been replaced with a heteroatom. If the heterocycloalkyl group contains more than one heteroatom, the heteroatoms may be the same or different. Examples of heterocycloalkyl groups include tetrahydrofuryl, morpholinyl, piperazinyl, piperidinyl and pyrrolidinyl. It is also possible for the heterocycloalkyl group to have one or more double bonds, but is not aromatic. Examples of heterocycloalkyl groups containing double bonds include dihydrofuran. Common heterocycloalkyl groups are three to ten membered rings containing from 1 to 4 heteroatoms. Heterocycloalkyl groups that are five and six membered rings that contain 1 to 2 heterotaoms are particularly common. A heterocycloalkyl group can also be a bicyclic group comprising a heterocycloalkyl ring fused to an aryl or heteroaryl ring. Examples of such fused bicyclic ring include tetrahydroquinoline or tetrahydroisoquinoline.

It is also noted that the cyclic ring groups, i.e., aryl, heteroaryl, cycloalkyl, and heterocycloalkyl, can comprise more than one ring. For example, the naphthyl group is a fused bicyclic ring system. It is also intended that the present invention include ring groups that have bridging atoms, or ring groups that have a spiro orientation.

Representative examples of five to six membered aromatic rings, optionally having one or two heteroatoms, are phenyl, furyl, thienyl, pyrrolyl, oxazolyl, thiazolyl, imidazolyl, pyrazolyl, isoxazolyl, isothiazolyl, pyridinyl, pyridiazinyl, pyrimidinyl, and pyrazinyl.

Representative examples of partially saturated, fully saturated or fully unsaturated five to eight membered rings, optionally having one to three heteroatoms, are cyclopentyl, cyclohexyl, cycloheptyl, cyclooctyl and phenyl. Further exemplary five membered rings are furyl, thienyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyl, 1,2,5-oxadiazolyl, 1,3,4oxadiazolyl, 1,2,3-triazolyl, 1,2,4-trizaolyl, 1,3,4-thiadiazolyl, 3H-1,2,3-dioxazolyl, 1,2,4-dioxazolyl, 1,3,2-dioxazolyl, 1,3,4-dioxazolyl, 5H-1,2,5-oxathiazolyl, and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyndazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-(3 oxathiazinyl, and 1,4,2-oxadiazinyl.

Further exemplary seven membered rings are azepinyl, oxepinyl, thiepinyl and 1,2,4-triazepinyl.

Further exemplary eight membered rings are cyclooctyl, cyclooctenyl and cyclooctadienyl.

Exemplary bicyclic rings consisting of two fused partially saturated, fully saturated or fully unsaturated five and/or six membered rings, optionally having one to four heteroatoms, are indolizinyl, indolyl, isoindolyl, indolinyl, cyclopenta(b)pyridinyl, pyrano(3,4-b)pyrrolyl, benzofuryl, isobenzofuryl, benzo(b)thienyl, benzo(c)thienyl, 1H-indazolyl, indoxazinyl, benzoxazolyl, anthranilyl, benzimidazolyl, benzthiazolyl, purinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)pyridinyl, pyrido(3,2-b)pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

A cyclic ring group may be bonded to another group in more than one way. If no particular bonding arrangement is specified, then all possible arrangements are intended. For example, the term "pyridyl" includes 2-, 3-, or 4-pyridyl, and the term "thienyl" includes 2-, or 3-thienyl.

The term "substituted" means that a hydrogen atom on a molecule or group is replaced with a group or atom. Typical substitutents include: halogen, $C_{1-8}$alkyl, hydroxyl, $C_{1-8}$alkoxy, —NR$^x$R$^x$, nitro, cyano, halo or perhalo$C_{1-8}$alkyl, $C_{2-8}$alkenyl, $C_{2-8}$alkynyl, —SR$^x$, —S(=O)$_2$R$^x$, —C(=O)OR$^x$, —C(=O)R$^x$, wherein each R$^x$ is independently hydrogen or $C_1$-$C_8$ alkyl. It is noted that when the substituent is —NR$^x$R$^x$, the R$^x$ groups may be joined together with the nitrogen atom to form a ring.

The term "oxo", when used as a substituent, means the =O group, which is typically attached to a carbon atom.

A group or atom that replaces a hydrogen atom is also called a substituent.

Any particular molecule or group can have one or more substituent depending on the number of hydrogen atoms that can be replaced.

The symbol "-" represents a covalent bond and can also be used in a radical group to indicate the point of attachment to another group. In chemical structures, the symbol is commonly used to represent a methyl group in a molecule.

The term "comprising" is meant to be open ended, including the indicated component but not excluding other elements.

The term "therapeutically effective amount" means an amount of a compound that ameliorates, attenuates or eliminates one or more symptom of a particular disease or condition, or prevents or delays the onset of one of more symptom of a particular disease or condition.

The terms "patient" and "subject" may be used interchangeably and mean animals, such as dogs, cats, cows, horses, sheep and humans. Particular patients are mammals. The term patient includes males and females.

The term "pharmaceutically acceptable" means that the referenced substance, such as a compound of Formula I, or a salt of a compound of Formula I, or a formulation containing a compound of Formula I, or a particular excipient, are suitable for administration to a patient.

The terms "treating", "treat" or "treatment" and the like include preventative (e.g., prophylactic) and palliative treatment.

The term "excipient" means any pharmaceutically acceptable additive, carrier, diluent, adjuvant, or other ingredient, other than the active pharmaceutical ingredient (API), which is typically included for formulation and/or administration to a patient.

The compounds of the present invention are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

In addition, the compounds of the present invention can be administered alone, in combination with other compounds of the present invention, or with other pharmaceutically active compounds. The other pharmaceutically active compounds can be intended to treat the same disease or condition as the compounds of the present invention or a different disease or condition. If the patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered via a tablet, while another is administered via injection or orally as a syrup. All combinations, delivery methods and administration sequences are contemplated.

The term "cancer" means a physiological condition in mammals that is characterized by unregulated cell growth. General classes of cancers include carcinomas, lymphomas, sarcomas, and blastomas.

The compounds of the present invention can be used to treat cancer. The methods of treating a cancer comprise administering to a patient in need thereof a therapeutically effective amount of a compound of Formula I, or a pharmaceutically acceptable salt thereof.

The compounds of the present invention can be used to treat tumors. The methods of treating a tumor comprise administering to a patient in need thereof a therapeutically effective amount of a compound of Formula I, or a pharmaceutically acceptable salt thereof.

The invention also concerns the use of a compound of the present invention in the manufacture of a medicament for the treatment of a condition such as a cancer.

Cancers which may be treated with compounds of the present invention include, without limitation, carcinomas such as cancer of the bladder, breast, colon, rectum, kidney, liver, lung (small cell lung cancer, and non-small-cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocytic leukemia, chronic myelogenous leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g., soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma). Other cancers that can be treated with a compound of the present invention include endometrial cancer, head and neck cancer, glioblastoma, malignant ascites, and hematopoietic cancers.

Particular cancers that can be treated by the compounds of the present invention include soft tissue sarcomas, bone cancers such as osteosarcoma, breast tumors, bladder cancer, Li-Fraumeni syndrome, brain tumors, rhabdomyosarcoma, adrenocortical carcinoma, colorectal cancer, non-small cell lung cancer, and acute myeleogenous leukemia (AML).

In a particular embodiment of the invention that relates to the treatment of cancers, the cancer is identified as p53wildtype ($p53^{WT}$). In another particular embodiment, the cancer is identified as $p53^{WT}$ and CDKN2A mutant. In another aspect, the present invention provides a diagnostic for determining which patients should be administered a compound of the present invention. For example, a sample of a patient's cancer cells may be taken and analyzed to determine the status of the cancer cells with respect to p53 and/or CDKN2A. In one aspect, a patient having a cancer that is $p53^{WT}$ will be selected for treatment over patients having a cancer that is mutated with respect to p53. In another aspect, a patient having a cancer that is both $p53^{WT}$ and has a mutant CDNK2A protein is selected over a patient that does not have these characteristics. The taking of a cancer cells for analyses is well known to those skilled in the art. The term "$p53^{WT}$" means a protein encoded by genomic DNA sequence no. NC_000017 version 9 (7512445 . . . 7531642)(GenBank); a protein encoded by cDNA sequence no. NM_000546 (GenBank); or a protein having the GenBank sequence no. NP_000537.3. The term "CDNK2A mutant" means a CDNK2A protein that in not wildtype. The term "CDKN2A wildtype" means a protein encoded by genomic DNA sequence no. 9:21957751-21984490 (Ensembl ID); a protein encoded by cDNA sequence no. NM_000077 (GenBank) or NM_058195 (GenBank) or; or a protein having the GenBank sequence no. NP_000068 or NP_478102.

The compounds of the present invention can also be used to treat hyperproliferative disorders such as thyroid hyperplasia (especially Grave's disease), and cysts (such as hypervascularity of ovarian stroma, characteristic of polycystic ovarian syndrome (Stein-Leventhal syndrome)).

The compounds of the present invention can also be used to treat the following diseases or conditions: asthma, chronic obstructive pulmonary disease (COPD), emphysema, psoriasis, contact dermatitis, conjunctivitis, allergic rhinitis, systemic lupus erythematosus (SLE), ulcerative colitis, Crohn's disease, multiple sclerosis, rheumatoid arthritis, inflammatory bowel disease, Alzheimer's disease, atherosclerosis and Huntington's disease.

The compounds of the present invention can also be used to treat inflammatory diseases, hypoxia, ulcers, viral infections, bacterial infections, and bacterial sepsis.

The compounds of Formula I, or the pharmaceutically acceptable salts thereof, may also be administered in combination with one or more additional pharmaceutically active compounds/agents. In a particular embodiment, the additional pharmaceutically active agent is an agent that can be used to treat a cancer. For example, an additional pharmaceutically active agent can be selected from antineoplastic agents, anti-angiogenic agents, chemotherapeutic agents and peptidal cancer therapy agents. In yet another embodiment, the antineoplastic agents are selected from antibiotic-type agents, alkylating agents, antimetabolite agents, hormonal agents, immunological agents, interferon-type agents, kinase inhibitors, miscellaneous agents and combinations thereof. It is noted that the additional pharmaceutically active compounds/agents may be a traditional small organic chemical molecules or can be macromolecules such as a proteins, antibodies, peptibodies, DNA, RNA or fragments of such macromolecules.

Examples of specific pharmaceutically active agents that can be used in the treatment of cancers and that can be used in combination with one or more compound of the present invention include: methotrexate; tamoxifen; fluorouracil; 5-fluorouracil; hydroxyurea; mercaptopurine; cisplatin; carboplatin; daunorubicin; doxorubicin; etoposide; vinblastine; vincristine; pacitaxel; thioguanine; idarubicin; dactinomycin; imatinib; gemcitabine; altretamine; asparaginase; bleomycin; capecitabine; carmustine; cladisat. aq. NaCl solution; cyclophosphamine; cytarabine; decarazine; docetaxel; idarubicin; ifosfamide; irinotecan; fludarabine; mitosmycin; mitoxane; mitoxantrone; topotecan; vinorelbine; adriamycin; mithram; imiquimod; alemtuzmab; exemestane; bevacizumab; cetuximab; azacitidine; clofarabine; decitabine; desatinib; dexrazoxane; docetaxel; epirubicin; oxaliplatin; erlotinib; raloxifene; fulvestrant; letrozole; gefitinib; gemtuzumab; trastuzumab; gefitinib; ixabepilone; lapatinib; lenalidomide; aminolevulinic acid; temozolomide; nelarabine; sorafenib; nilotinib; pegaspargase; pemetrexed; rituximab; dasatinib; thalidomide; bexarotene; temsirolimus; bortezomib; vorinostat; capecitabine; zoledronic acid; anastrozole; sunitinib; aprepitant and nelarabine, or a pharmaceutically acceptable salt thereof.

Additional pharmaceutically active agents that can be used in the treatment of cancers and that can be used in combination with one or more compound of the present invention include: vascular endothelial growth factor (VEGF) inhibitors, hepatocyte growth factor/scatter factor (HGF/SF) inhibitors, angiopoietin 1 and/or 2 inhibitors, tumor necrosis factor-related apoptosis-inducing ligand (TRAIL) agonists, recombinant human apo2 ligand (TRAIL), insulin-like growth factor 1 receptor (IGFR-1) inhibitors, cFMS inhibitors, HER 2 inhibitors, c-met inhibitors, aurora kinase inhibitors, CDK 4 and/or 6 inhibitors, and B-raf inhibitors.

Further additional pharmaceutically active agents that can be used in the treatment of cancers and that can be used in combination with one or more compound of the present invention include antibody drug conjugates (ADCs) whereby an antibody that binds to a protein, preferably on a cancer cell, is conjugated using a linker with a chemical compound that is detrimental to the cancer cell. Examples of chemical compounds that are detrimental to a cancer cell include maytansinoids derivatives and auristatin derivatives.

Still further additional pharmaceutically active agents that can be used in the treatment of cancers and that can be used in combination with one or more compound of the present invention include: epoetin alfa; darbepoetin alfa; panitumumab; pegfilgrastim; palifermin; filgrastim; denosumab; ancestim; AMG 102; AMG 319; AMG 386; AMG 479 (Ganitumab); AMG 511, AMG 900, AMG 655 (Conatumumab); AMG 745; AMG 951; and AMG 706 (Motesanib), or a pharmaceutically acceptable salt thereof.

In another aspect, the present invention relates to the use of the compounds of the present invention in combination with one or more pharmaceutical agent that is an inhibitor of a protein in the phosphatidylinositol 3-kinase (PI3K) pathway. Combinations of compounds of the present invention along with inhibitors of proteins in the PI3K pathway have shown synergy in cancer cell growth assays, including enhanced apoptosis and cell killing. Examples of proteins in the PI3K pathway include PI3K, mTOR and PKB (also known as Akt). The PI3K protein exists in several isoforms including α, β, δ, or γ. It is contemplated that a PI3K inhibitor that can be used in combination with a compound of the present invention can be selective for one or more isoform. By selective it is meant that the compounds inhibit one or more isoform more that other isoforms. Selectivity is a concept well known to those is the art and can be measured with well known activity in vitro or cell-based assays. Preferred selectivity includes greater than 2 fold, preferably 10 fold, or more preferably 100 fold greater selectivity for one or more isoform over the other isoforms. In one aspect, the PI3K inhibitors that can be used in combination with compounds of the present invention is a PI3K α selective inhibitor. In another aspect the compound is a PI3K δ selective inhibitor.

Examples of PI3K inhibitors that can be used in combination with one or more compounds of the present invention include those disclosed in the following: PCT published application no. WO2010/151791; PCT published application no. WO2010/151737; PCT published application no. WO2010/151735; PCT published application no. WO2010151740; PCT published application no. WO2008/118455; PCT published application no. WO2008/118454; PCT published application no. WO2008/118468; U.S. published application no. US20100331293; U.S. published application no. US20100331306; U.S. published application no. US20090023761; U.S. published application no. US20090030002; U.S. published application no. US20090137581; U.S. published application no. US2009/0054405; U.S. published application no. U.S. 2009/0163489; U.S. published application no. US 2010/0273764; U.S. published application no. U.S. 2011/0092504; or PCT published application no. WO2010/108074.

Preferred PI3K inhibitors for use in combination with compounds of the present invention include:

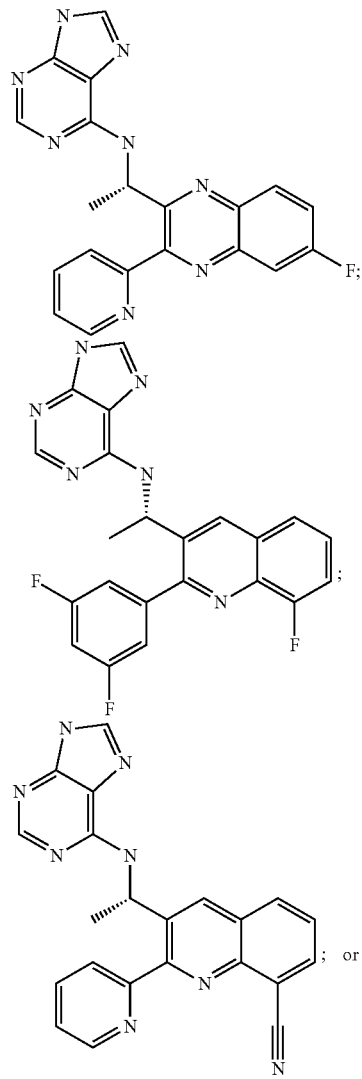

-continued or a pharmaceutically acceptable salt thereof.

Also preferred is a compound of Formula IIa below, or a pharmaceutically acceptable salt thereof,

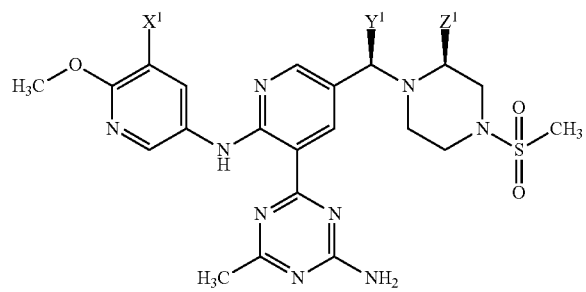

IIa wherein $X^1$ is fluorine or hydrogen; $Y^1$ is hydrogen or methyl; and $Z^1$ is hydrogen or methyl.

Compounds that inhibit both PI3K and mTOR (dual inhibitors) are known. In still another aspect, the present invention provides the use of dual PI3K and mTOR inhibitors for use in combination with a compound of the present invention.

mTOR is a protein in the PI3K pathway. It is another aspect of the present invention to use an mTOR inhibitor in combination with one or more compounds of the present invention. mTOR inhibitors that can be used in combination with compounds of the present invention include those disclosed in the following documents: PCT published application no. WO2010/132598 or PCT published application no. WO2010/096314.

PKB (Akt) is also a protein in the PI3K pathway. It is another aspect of the present invention to use an mTOR inhibitor in combination with one or more compounds of the present invention. PKB inhibitors that can be used in combination with compounds of the present invention include those disclosed in the following documents: U.S. Pat. Nos. 7,354,944; 7,700,636; 7,919,514; 7,514,566; U.S. patent application publication no. US 2009/0270445 A1; U.S. Pat. Nos. 7,919,504; 7,897,619; or PCT published application no. WO 2010/083246 A1.

The compounds of the present invention can be used in combination with CDK4 and/or 6 inhibitors. CDK 4 and/or 6 inhibitors that can be used in combination with compounds of the present invention include those disclosed in the following documents: PCT published application no. WO 2009/085185 or U.S. patent application publication no. US2011/0097305.

The compounds of the present invention can also be used in combination with pharmaceutically active agents that treat nausea. Examples of agents that can be used to treat nausea include: dronabinol; granisetron; metoclopramide; ondansetron; and prochlorperazine; or a pharmaceutically acceptable salt thereof.

In addition, the compounds of the present invention can be used in combination with other agents that can be used to treat cancer such as acemannan; aclarubicin; aldesleukin; alitretinoin; amifostine; amrubicin; amsacrine; anagrelide; arglabin; arsenic trioxide; BAM 002 (Novelos); bicalutamide; broxuridine; celmoleukin; cetrorelix; cladribine; clotrimazole; DA 3030 (Dong-A); daclizumab; denileukin diftitox; deslorelin; dilazep; docosanol; doxercalciferol; doxifluridine; bromocriptine; cytarabine; HIT diclofenac; interferon alfa; tretinoin; edelfosine; edrecolomab; eflornithine; emitefur; epirubicin; epoetin beta; etoposide phosphate; exisulind; fadrozole; finasteride; fludarabine phosphate; formestane; fotemustine; gallium nitrate; gemtuzumab zogamicin; gimeracil/oteracil/tegafur combination; glycopine; goserelin; heptaplatin; human chorionic gonadotropin; human fetal alpha fetoprotein; ibandronic acid; interferon alfa; interferon alfa natural; interferon alfa-2; interferon alfa-2a; interferon alfa-2b; interferon alfa-N1; interferon alfa-n3; interferon alfacon-1; interferon alpha natural; interferon beta; interferon beta-1a; interferon beta-1 b; interferon gamma natural; interferon gamma-1a; interferon gamma-1b; interleukin-1 beta; iobenguane; irsogladine; lanreotide; LC 9018 (Yakult); leflunomide; lenograstim; lentinan sulfate; letrozole; leukocyte alpha interferon; leuprorelin; levamisole+fluorouracil; liarozole; lobaplatin; lonidamine; lovastatin; masoprocol; melarsoprol; metoclopramide; mifepristone; miltefosine; mirimostim; mismatched double stranded RNA; mitoguazone; mitolactol; mitoxantrone; molgramostim; nafarelin; naloxone+pentazocine; nartograstim; nedaplatin; nilutamide; noscapine; novel erythropoiesis stimulating protein; NSC 631570 octreotide; oprelvekin; osaterone; paclitaxel; pamidronic acid; peginterferon alfa-2b; pentosan polysulfate sodium; pentostatin; picibanil; pirarubicin; rabbit antithymocyte polyclonal antibody; polyethylene glycol interferon alfa-2a; porfimer sodium; raltitrexed; rasburicase; rhenium $R^e$ 186 etidronate; RII retinamide; romurtide; samarium (153 Sm) lexidronam; sargramostim; sizofiran; sobuzoxane; sonermin; strontium-89 chloride; suramin; tasonermin; tazarotene; tegafur; temoporfin; teniposide; tetrachlorodecaoxide; thymalfasin; thyrotropin alfa; toremifene; tositumomab-iodine 131; treosulfan; tretinoin; trilostane; trimetrexate; triptorelin; tumor necrosis factor alpha natural; ubenimex; bladder cancer vaccine; Maruyama vaccine; melanoma lysate vaccine; valrubicin; verteporfin; virulizin; zinostatin stimalamer; abarelix; AE 941 (Aetema); ambamustine; antisense oligonucleotide; bcl-2 (Genta); APC 8015 (Dendreon); dexaminoglutethimide; diaziquone; EL 532 (Elan); EM 800 (Endorecherche); eniluracil; etanidazole; fenretinide; filgrastim SDO1 (Amgen); galocitabine; gastrin 17 immunogen; HLA-B7 gene therapy (Vical); granulocyte macrophage colony stimulating factor; histamine dihydrochloride; ibritumomab tiuxetan; ilomastat; IM 862 (Cytran); interleukin-2; iproxifene; LDI 200 (Milkhaus); leridistim; lintuzumab; CA 125 monoclonal antibody(MAb) (Biomira); cancer MAb (Japan Pharmaceutical Development); HER-2 and Fc MAb (Medarex); idiotypic 105AD7 MAb (CRC Technology); idiotypic CEA MAb (Trilex); LYM-1-iodine 131 MAb (Techniclone); polymorphic epithelial mucin-yttrium 90 MAb (Antisoma); marimastat; menogaril; mitumomab; motexafin gadolinium; MX 6 (Galderma); nolatrexed; P 30 protein; pegvisomant; porfiromycin; prinomastat; RL 0903 (Shire); rubitecan; satraplatin; sodium phenylacetate; sparfosic acid; SRL 172 (SR Pharma); SU 5416 (Pfizer); TA 077 (Tanabe); tetrathiomolybdate; thaliblastine; thrombopoietin; tin ethyl etiopurpurin; tirapazamine; cancer vaccine (Biomira); melanoma vaccine (New York University); melanoma vaccine (Sloan Kettering Institute); melanoma oncolysate vaccine (New York Medical College); viral melanoma cell lysates vaccine (Royal Newcastle Hospital); or valspodar. It is noted that the agents recited above may also be administered as pharmaceutically acceptable salts when appropriate.

The compounds of the present invention may also be used in combination with radiation therapy, hormone therapy, surgery and immunotherapy, which therapies are well known to those skilled in the art.

Since one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present invention and other pharmaceutically active compounds, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quatemary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents.

Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. They may also contain opacifying agents, and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferable suppositories, which can be prepared by mixing the compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of a compound of the present invention include ointments, powders, sprays and inhalants. The active compound or fit compounds are admixed under sterile condition with a physiologically acceptable carrier, and any preservatives, buffers, or propellants that may be required. Opthalmic formulations, eye ointments, powders, and solutions are also contemplated as being within the scope of this invention.

The compounds of the present invention can be administered to a patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is within the ordinary skill in the art.

The compounds of the present invention can be administered as pharmaceutically acceptable salts, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

Examples of pharmaceutically acceptable esters of the compounds of the present invention include $C_1$-$C_8$ alkyl esters. Acceptable esters also include $C_5$-$C_7$ cycloalkyl esters, as well as arylalkyl esters such as benzyl. $C_1$-$C_4$ alkyl esters are commonly used. Esters of compounds of the present invention may be prepared according to methods that are well known in the art.

Examples of pharmaceutically acceptable amides of the compounds of the present invention include amides derived from ammonia, primary $C_1$-$C_8$ alkyl amines, and secondary $C_1$-$C_8$ dialkyl amines. In the case of secondary amines, the amine may also be in the form of a 5 or 6 membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compounds of the present invention may be prepared according to methods well known to those skilled in the art.

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, if the compound of the invention contains a carboxylic acid functional group, a prodrug can comprise an ester formed by the replacement of the hydrogen atom of the acid group with a group such as ($C_1$-$C_8$ alkyl, ($C_2$-$C_{12}$) alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_{2-3}$)alkyl.

Similarly, if a compound of the present invention comprises an alcohol functional group, a prodrug can be formed by the replacement of the hydrogen atom of the alcohol group with a group such as $(C_1-C_6)$alkanoyloxymethyl, 1-$((C_1-C_6)$alkanoyloxy)ethyl, 1-methyl-1-$((C_1-C_6)$alkanoyloxy)ethyl, $(C_1-C_6)$alkoxycarbonyloxymethyl, N—$(C_1-C_6)$ alkoxycarbonylaminomethyl, succinoyl, $(C_1-C_6)$alkanoyl, α-amino$(C_1-C_4)$alkanoyl, arylacyl and α-aminoacyl, or α-aminoacyl-α-aminoacyl, where each α-aminoacyl group is independently selected from the naturally occurring L-amino acids, —P(O)(OH)$_2$, —P(O)(O$(C_1-C_6)$alkyl)$_2$ or glycosyl (the radical resulting from the removal of a hydroxyl group of the hemiacetal form of a carbohydrate).

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond, both the cis and trans forms (designated as Z and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can also be separated by converting the enantiomeric mixture into a diastereomeric mixture by reaction with an appropriate optically active compound (e.g., an alcohol), separating the diastereomers and converting (e.g., hydrolyzing) the individual diastereomers to the corresponding pure enantiomers. Also, some compounds may be atropisomers (e.g., substituted biaryls).

The compounds of the present invention may exist in unsolvated as well as solvated forms with pharmaceutically acceptable solvents such as water (hydrate), ethanol, and the like. The present invention contemplates and encompasses both the solvated and unsolvated forms.

It is also possible that compounds of the present invention may exist in different tautomeric forms. All tautomers of compounds of the present invention are contemplated. For example, all of the tautomeric forms of the tetrazole moiety are included in this invention. Also, for example, all keto-enol or imine-enamine forms of the compounds are included in this invention.

Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{16}$O, $^{17}$O, $^{18}$O, $^{31}$P, $^{32}$P, $^{35}$S, $^{18}$F, and $^{36}$Cl. In one aspect, the present invention relates to compounds wherein one or more hydrogen atom is replaced with deuterium ($^2$H) atoms.

Compounds of the present invention that contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detection. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

The compounds of the present invention may exist in various solid states including crystalline states and as an amorphous state. The different crystalline states, also called polymorphs, and the amorphous states of the present compounds are contemplated as part of this invention.

In synthesizing compounds of the present invention, it may be desirable to use certain leaving groups. The term "leaving groups" ("LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., SCH$_3$), N-hydroxysuccinimide, N-hydroxybenzotriazole, and the like. Examples of nucleophiles include, but are not limited to, amines, thiols, alcohols, Grignard reagents, anionic species (e.g., alkoxides, amides, carbanions) and the like.

All patents, published patent applications and other publications recited herein are hereby incorporated by reference.

The examples presented below illustrate specific embodiments of the present invention. These examples are meant to be representative and are not intended to limit the scope of the claims in any manner. Unless otherwise noted, when a percent is used herein with respect to a solid, the percent is by weight with respect to the referenced solid composition. When a percent is used herein with respect to a liquid, the percent is by volume with respect to the referenced solution.

$^1$H-NMR spectra were typically acquired on a Bruker Avance III 500 spectrometer system (Bruker, Bilerica, Mass.) operating at a $^1$H frequency of 500.13 MHz, equipped with a Bruker 5 mm PABBI probe with a z-axis gradient; or on a Bruker Avance II or Avance III 400 spectrometer operating at a $^1$H frequency of 400.23 MHz, equipped with a Bruker 5 mm PABBO probe with a z-axis gradient. Samples were typically dissolved in 500 μL of either DMSO-d$_6$ or CD$_3$OD for NMR analysis. $^1$H chemical shifts are referenced, for example, to the residual solvent signals from DMSO-d$_6$ at δ 2.50 and CD$_3$OD at δ 3.30.

Significant peaks are tabulated and typically include: number of protons, multiplicity (s, singlet; d, doublet; dd, doublet of doublets; t, triplet; q, quartet; m, multiplet; br s, broad singlet) and coupling constant(s) in Hertz.

Electron Ionization (EI) mass spectra were typically recorded on an Agilent Technologies 6140 Quadrupole LC/MS mass spectrometer. Mass spectrometry results are reported as the ratio of mass over charge, sometimes followed by the relative abundance of each ion (in parentheses). Starting materials in the Examples below are typically either available from commercial sources such as Sigma-Aldrich, St. Louis, Mo., or via literature procedures.

The following abbreviations may be used herein:

~ about
+ve or pos. ion positive ion
Δ heat
Ac acetyl
Ac₂O acetic anhydride
aq aqueous
AcOH acetic acid
9-BBN 9-borabicylo[3.3.1] nonane
Bn benzyl
Boc tert-butyloxycarbonyl
BSA bovine serum albumin
Bu butyl
Burgess Reagent Methyl N-(triethylammoniumsulfonyl) carbamate
Bz benzoyl
Calcd or Calc'd calculated
Conc. concentrated
CSA camphor-10-sulfonic acid
d day(s)
DBU 1,8-diazabicyclo[5.4.0]undec-7-ene
DCE dichloroethane
DCM dichloromethane
DDQ 2,3-dichloro-5,6-dicyano-1,4-benzoquinone
DEA diethylamine
Dess-Martin periodinane; 1,1,1-triacetoxy-1,1-dihydro-1,2-benziodoxol-3-(1H)-one Dess-Martin reagent
DIBAL diisobutylaluminum hydride
DIEA or DIPEA diisopropylethylamine
DMAP 4-dimethylaminopyridine
DME 1,2-dimethoxyethane
DMF N,N-dimethylformamide
DMSO dimethyl sulfoxide
DPPA diphenylphosphoryl azide
dr diastereomeric ratio
DTT dithiothreitol
DVB divinylbenzene
EDC N-ethyl-N'-(3-dimethylaminopropyl)carbodiimide
ee or e.e. enantiomeric excess
eq equivalent
ESI or ES electrospray ionization
Et ethyl
Et₂O diethyl ether
Et₃N triethylamine
EtOAc ethyl acetate
EtOH ethyl alcohol
g gram(s)
h hour(s)
HATU O-(7-azabenzotriazol-1-yl)-N,N,N',N'-tetramethyluronium hexafluorophosphate
HBTU O-benzotriazole-N,N,N',N'-tetramethyl-uronium-hexafluorophosphate
Hex hexanes
HMPA hexamethylphosphoramide
HOAt 1-hydroxy-7-azabenzotriazole
HOBt hydroxybenzotriazole
HRMS high resolution mass spectrometry
HPLC high pressure liquid chromatography
IPA or iPrOH isopropyl alcohol
Jones reagent solution of chromium(IV)oxide and sulfuric acid in water
KHMDS potassium hexamethyldisilazide
KOAc potassium acetate
LCMS, LC-MS or LC/MS liquid chromatography mass spectrometry
LDA lithium diisopropylamide
LHMDS or LiHMDS lithium hexamethyldisilazide
L-Selectride® lithium tri-sec-butylborohydride (Sigma-Aldrich, St. Louis)
M molar (mol L$^{-1}$)
mCPBA m-chloroperoxybenzoic acid
Me methyl
MeCN acetonitrile
MeI iodomethane
MeOH methyl alcohol
mg milligram(s)
min minute(s)
mL milliliter(s)
M mole(s)
MS mass spectrometry
MsCl methanesulfonyl chloride
MTBE or MtBE methyl tert-butyl ether
m/z mass-to-charge ratio
NaHMDS sodium hexamethyldisilazide
NaOtBu sodium tert-butoxide
NBS N-bromosuccinimide
nBuLi n-butyl lithium
NMO N-methylmorpholine-N-oxide
NMP 1-methyl-2-pyrrolidinone
NMR nuclear magnetic resonance
N-Selectride® sodium tri-sec-butylborohydride (Sigma-Aldrich, St. Louis)
PBS phosphate buffered saline
PMB paramethoxybenzyl
Pr propyl
ppm parts per million
PTFE polytetrafluoroethylene
p-tol para-toluoyl
rac racemic
RP-HPLC or RPHPLC reversed phase high pressure liquid chromatography
RT or rt or r.t. room temperature
sat. or sat'd or satd saturated
SFC supercritical fluid chromatography
SmI₂ samarium (II) iodide
TBAF tetrabutylammonium fluoride
TBDMS tert-butyldimethylsilyl
TBDMS-Cl tert-butyldimethylsilyl chloride
TBDPS tert-butyldiphenylsilyl
TEMPO (2,2,6,6-tetramethylpiperidin-1-yl)oxidanyl
tert or t tertiary
TFA triflouroacetic acid
TFAA triflouroacetic acid anhydride
THF tetrahydrofuran
TIPS triisopropylsilyl
TLC thin layer chromatography
TMEDA tetramethylethylenediamine
TMS trimethylsilyl or trimethylsilane
TPAP tetrapropylammonium perruthenate
$t_R$ retention time
tBuOH tert-butyl alcohol
v/v volume per volume

EXAMPLES

General Synthetic Schemes

Compounds of the present invention generally can be prepared beginning with commercially available starting materials and using synthetic techniques known to those of skill in the art. Outlined below are some reaction schemes suitable for preparing compounds of the present invention. Further exemplification is found in the specific examples provided.
Examples 1 to 3
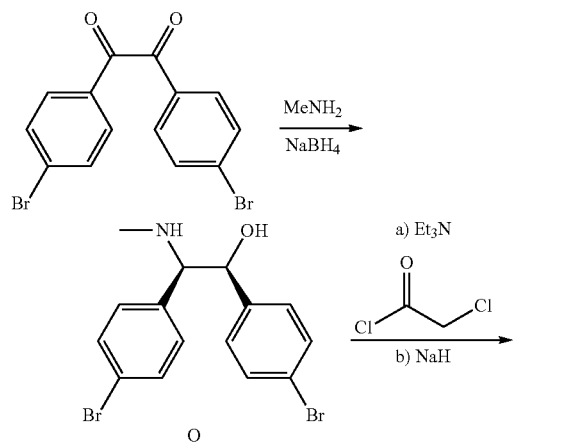
Examples 4 to 9 and 11 to 13
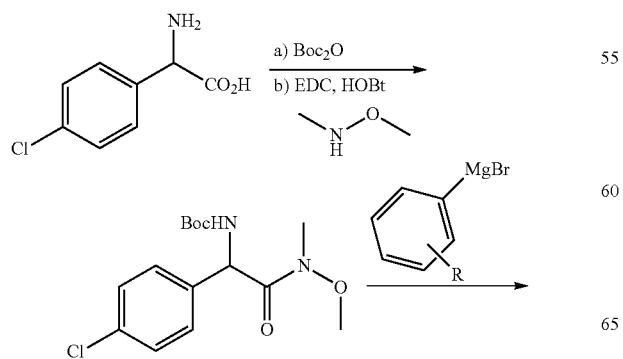
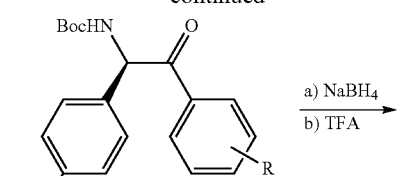
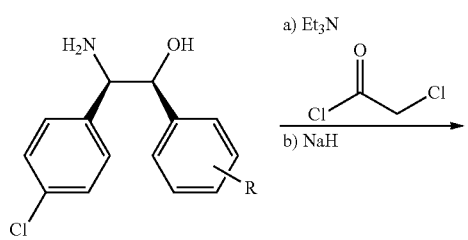
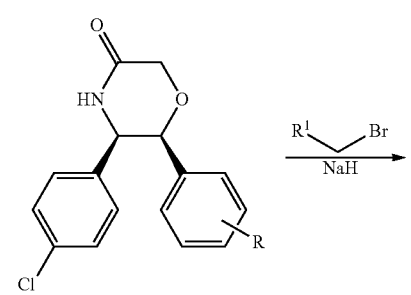
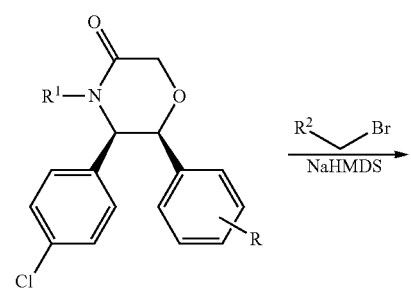
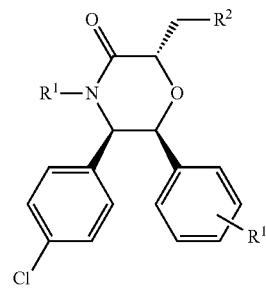

Examples 10, 29 to 30, 38 and 44 to 49
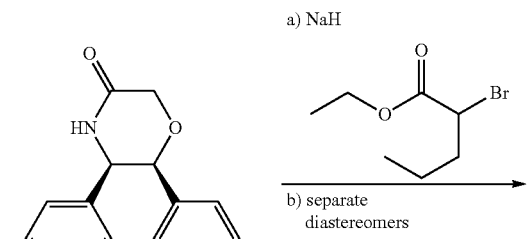
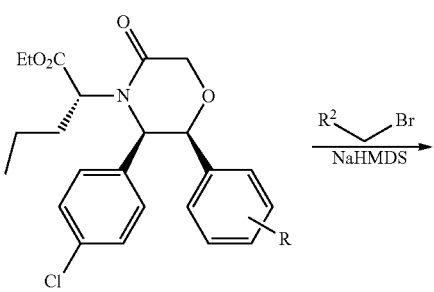
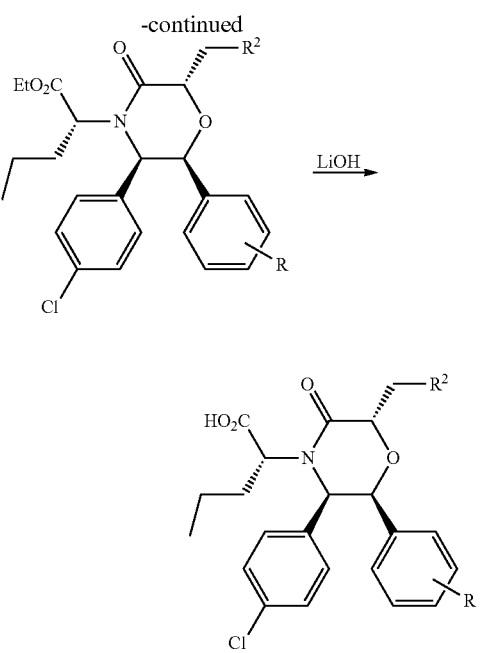
Examples 14 to 22
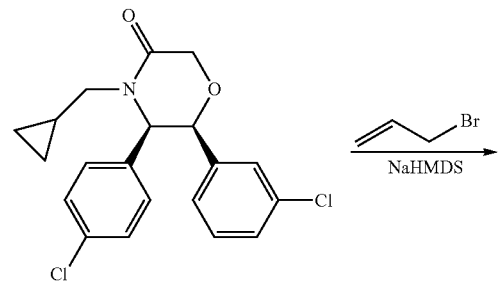
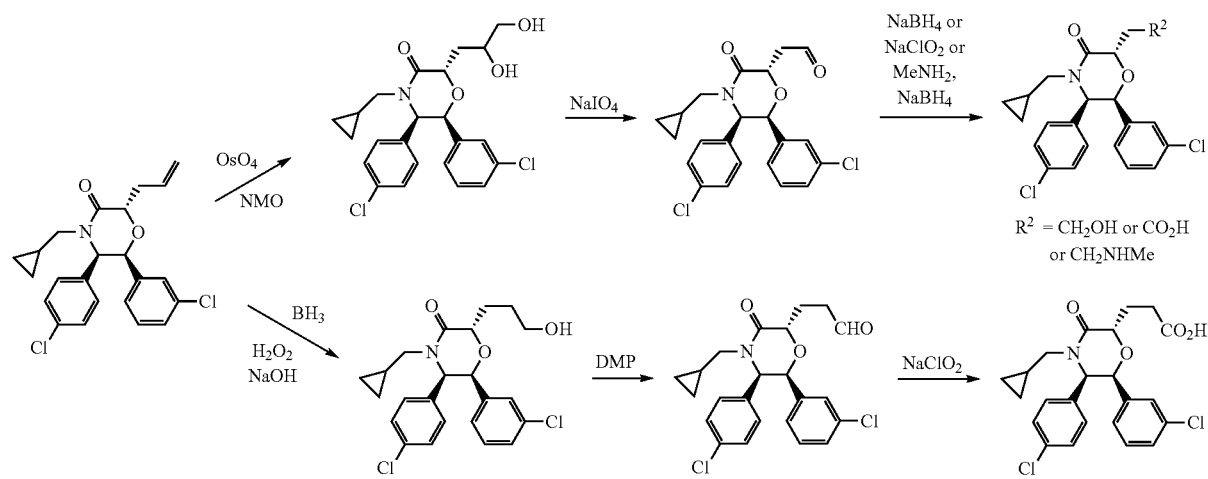

Examples 23 to 26
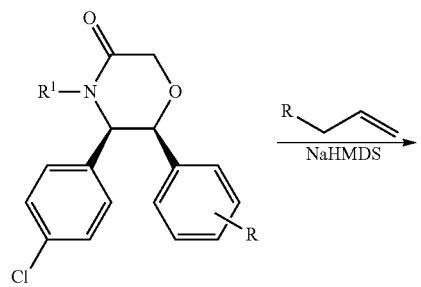
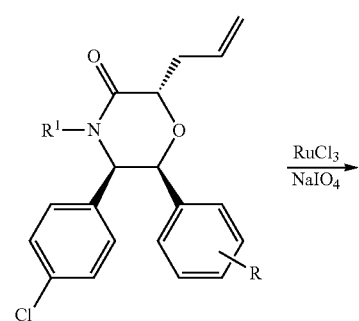
Example 27
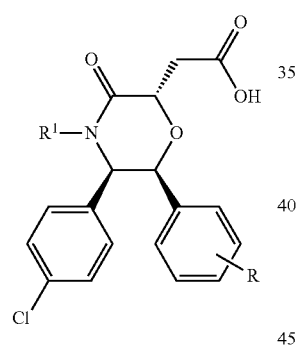
-continued
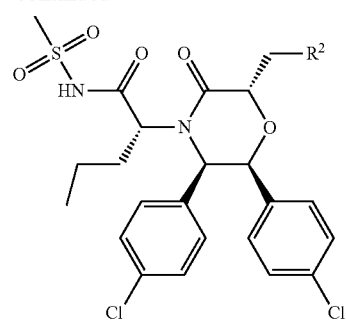
Example 28
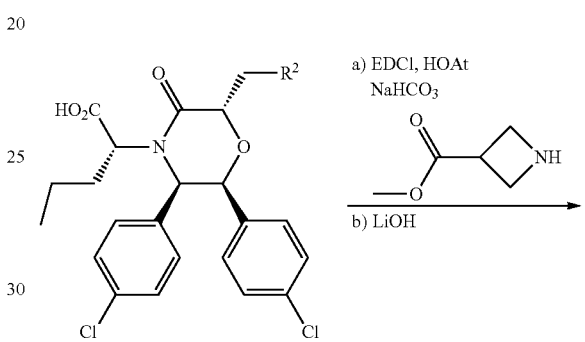
Example 31
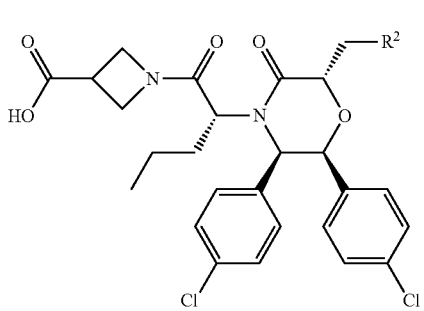
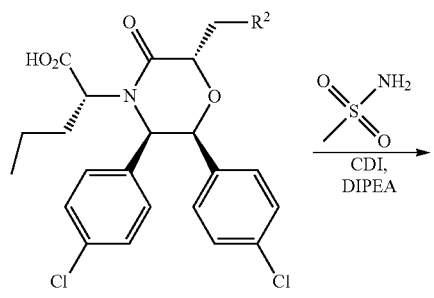

59
-continued
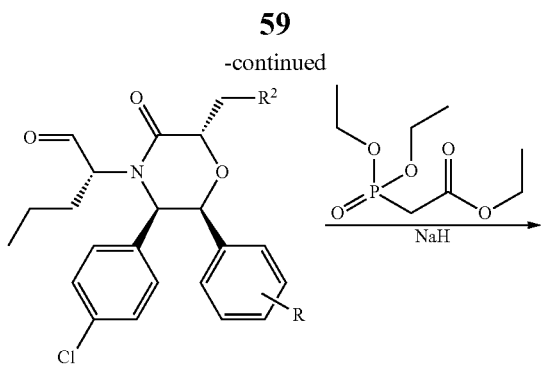
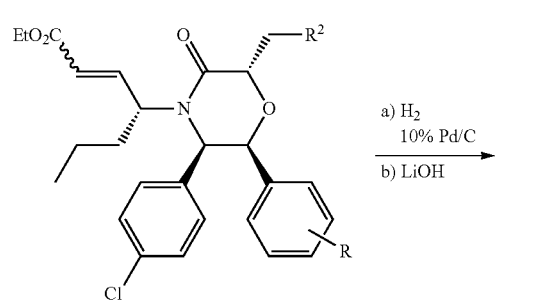
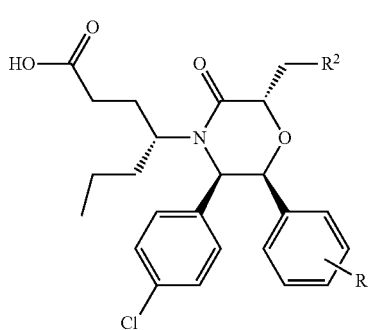
Example 32
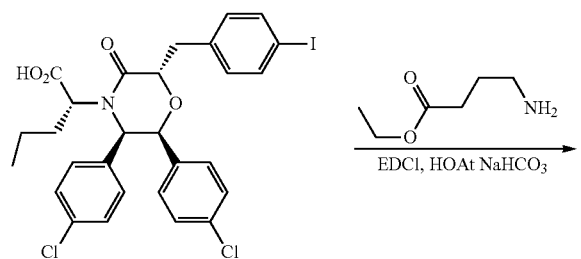
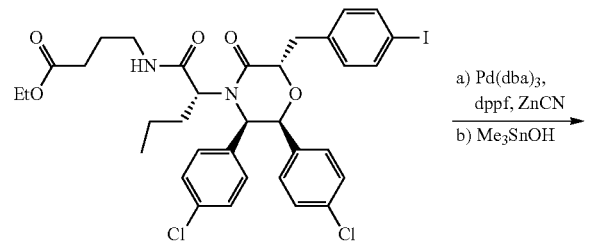
60
-continued
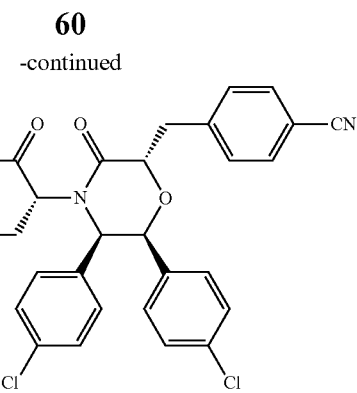
Example 33
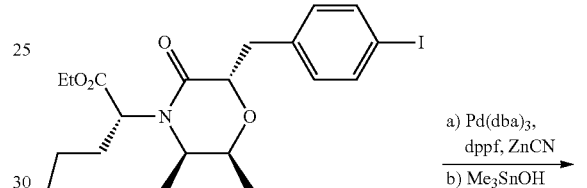
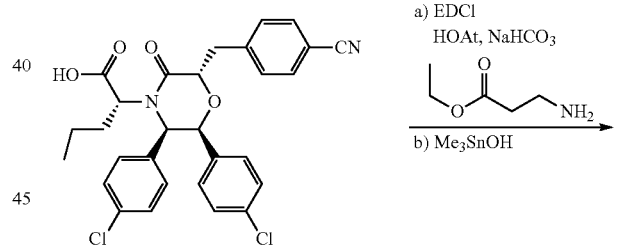

Example 34
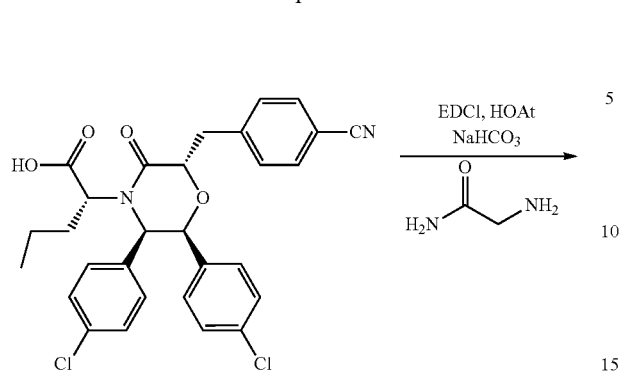
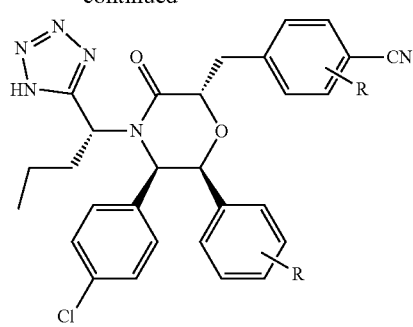
Example 37
Examples 35 to 36
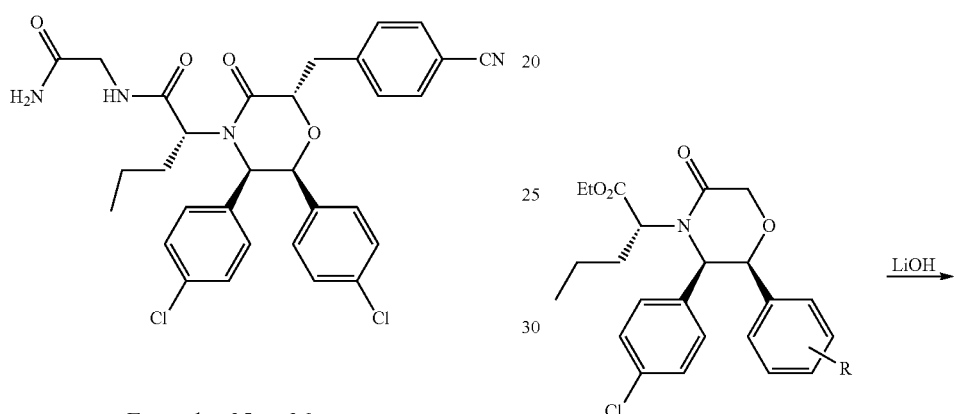
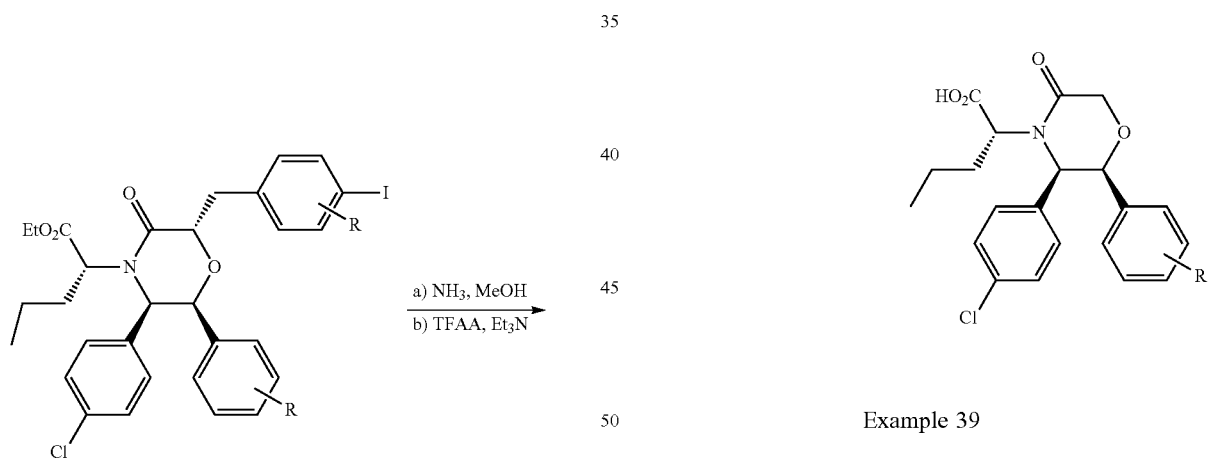
Example 39
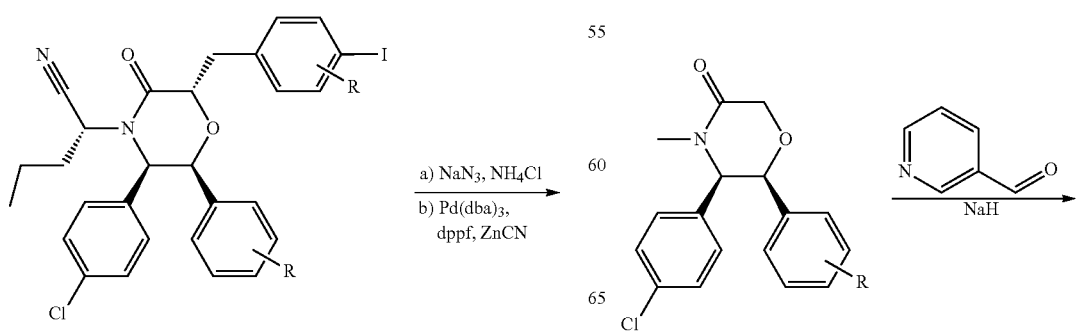

63
-continued
Example 40
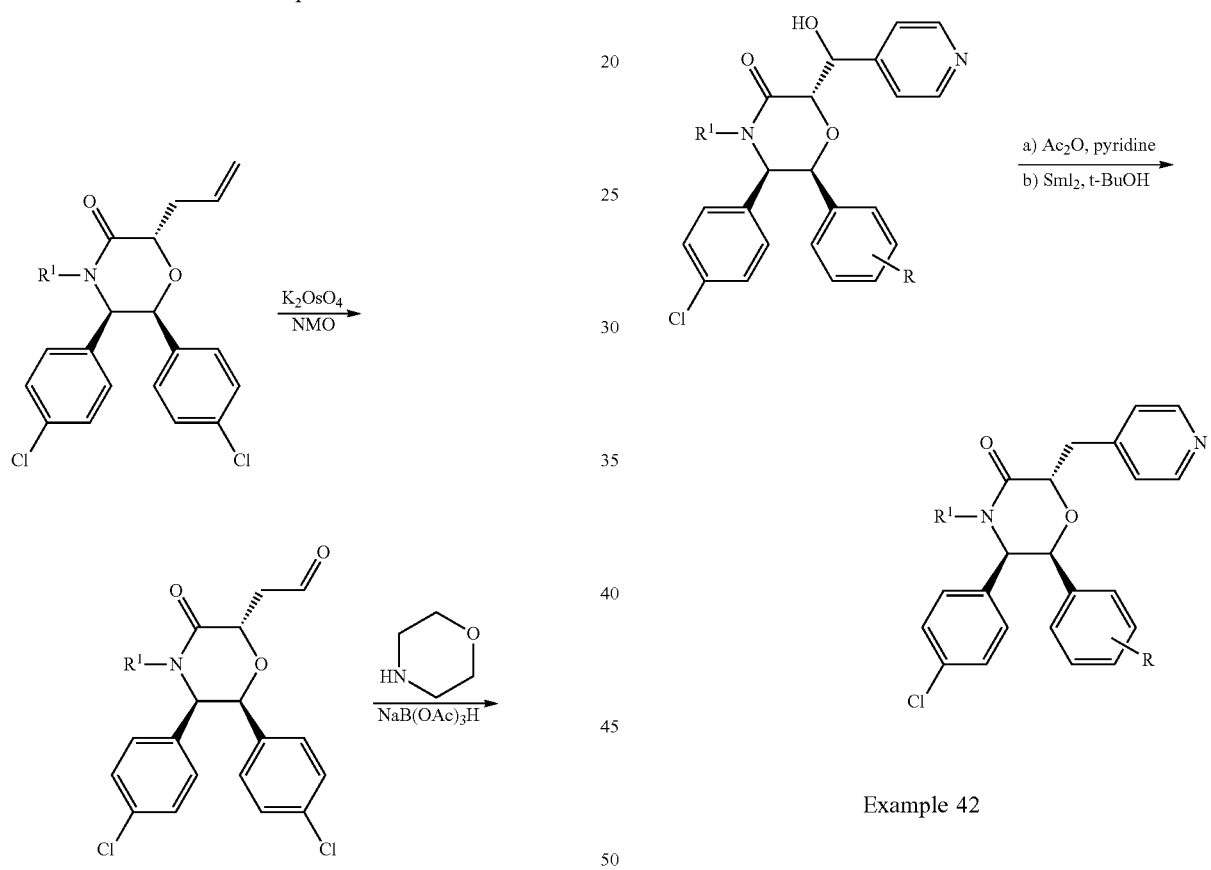
64
Example 41
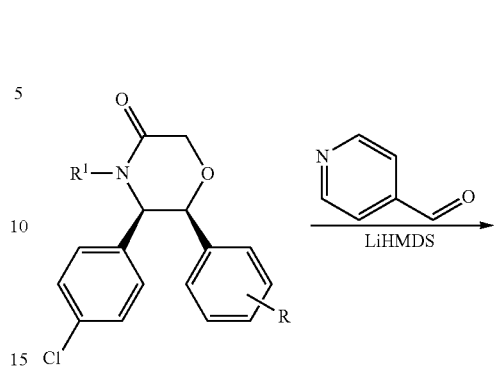
Example 42
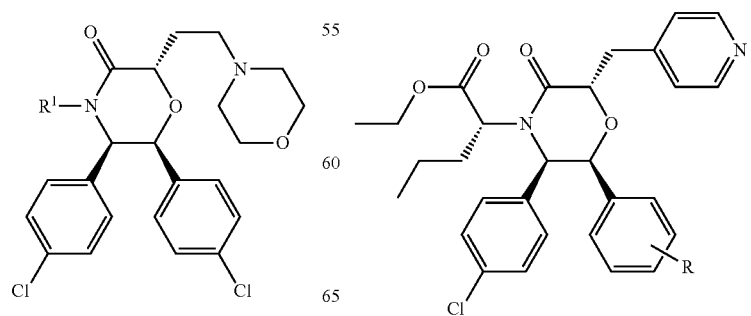

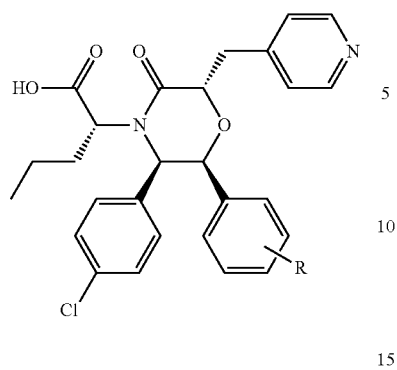
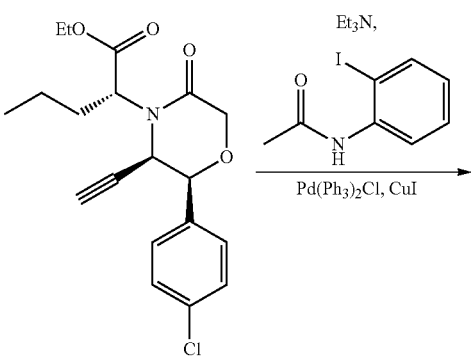
Example 43
Example 50 to 54
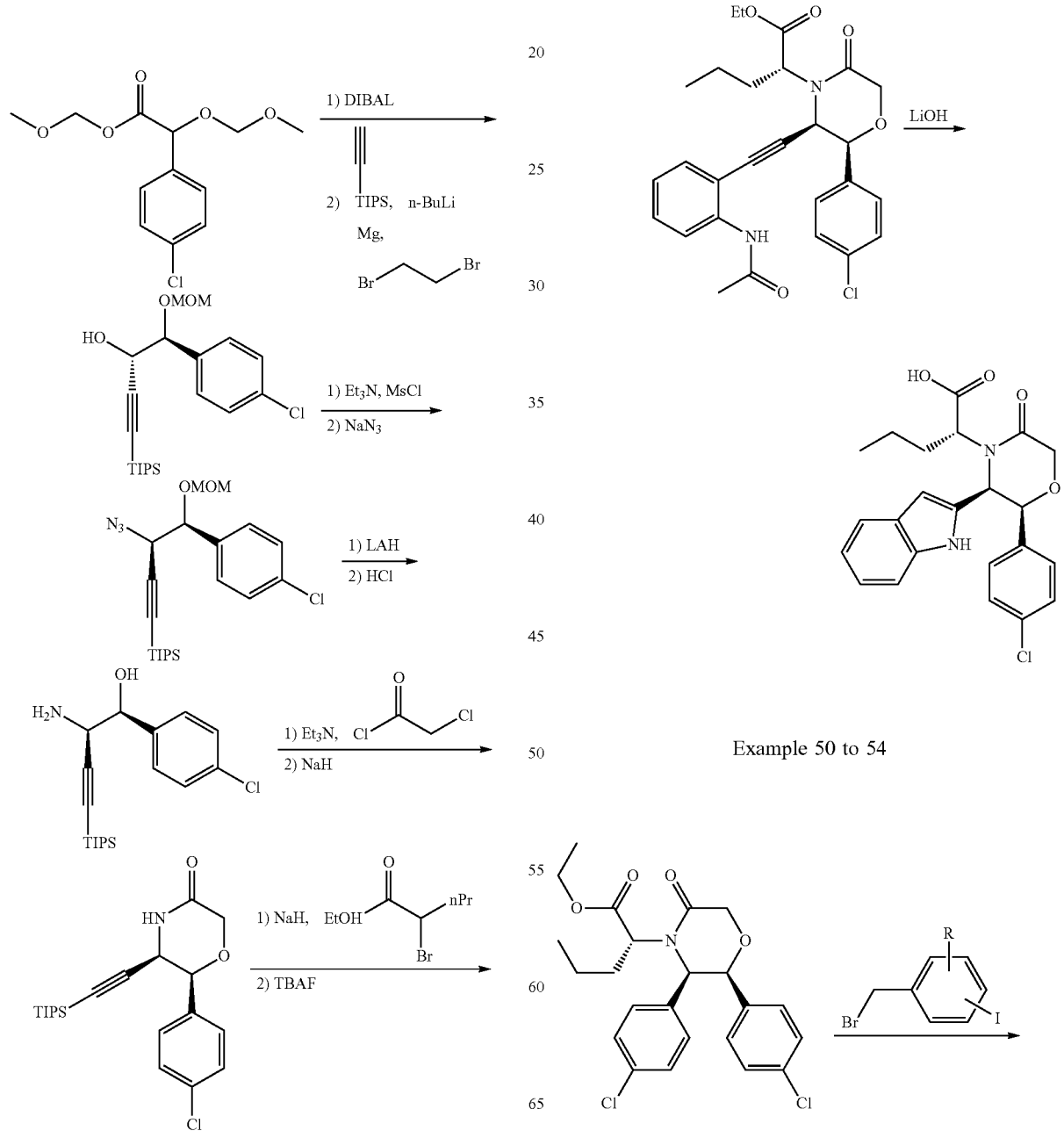

67
-continued
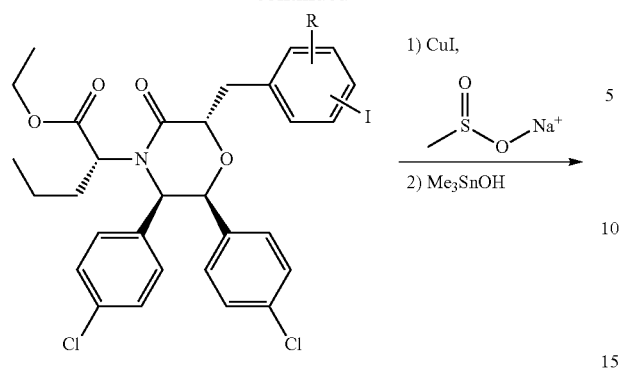
68
-continued
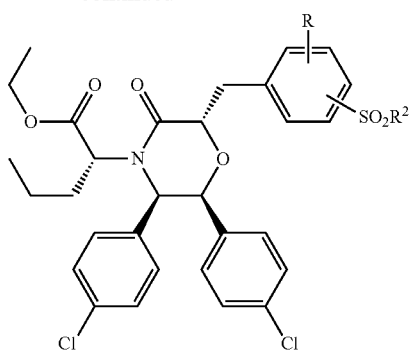
Example 57
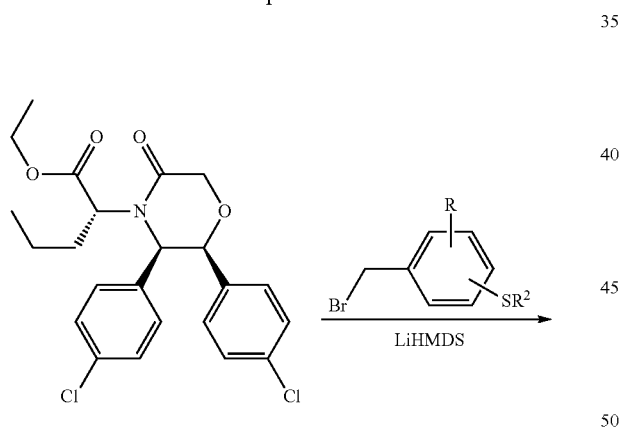
Example 55 to 56
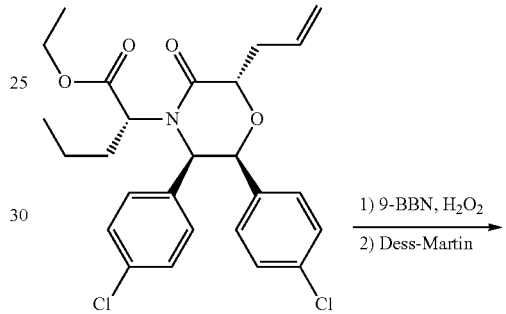
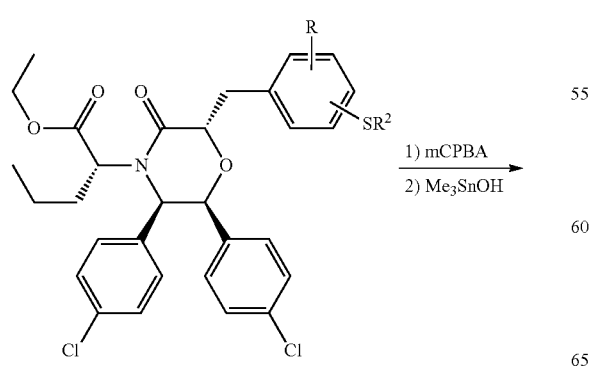
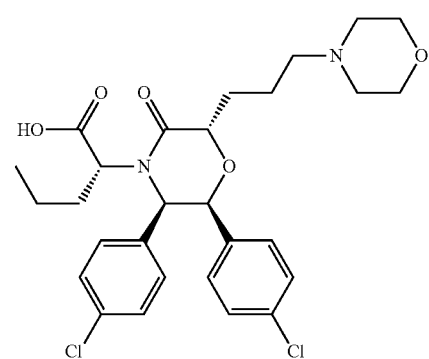

Examples 58 to 63
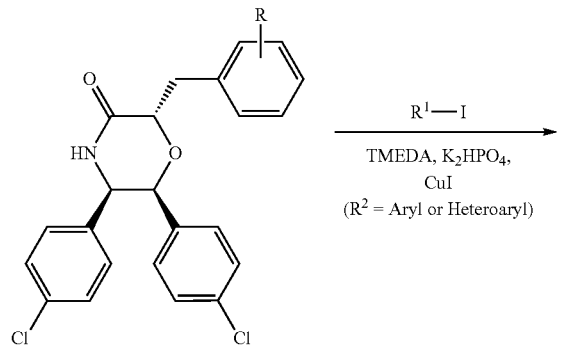
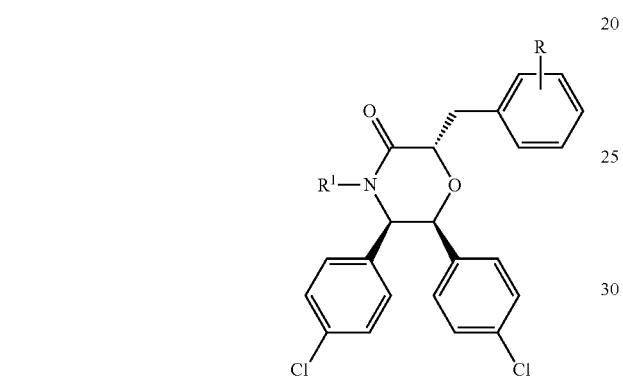
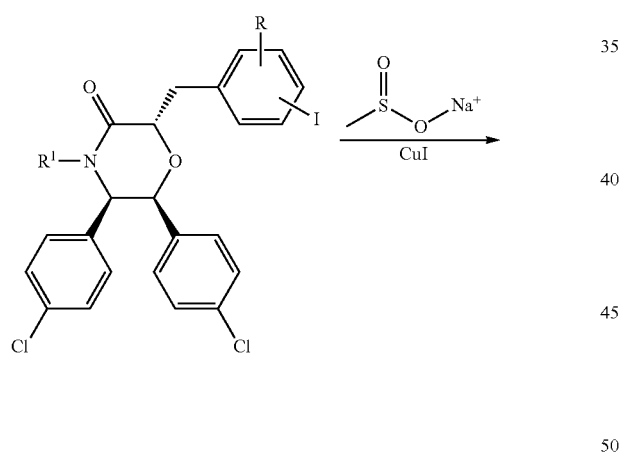
Example 64
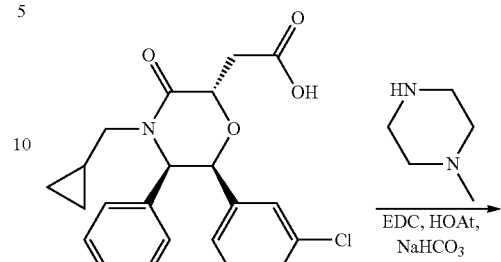
Examples 65 to 66
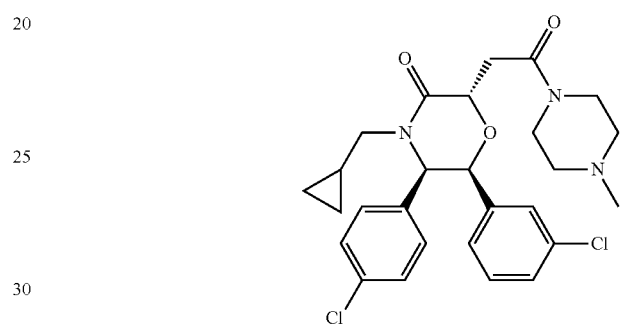
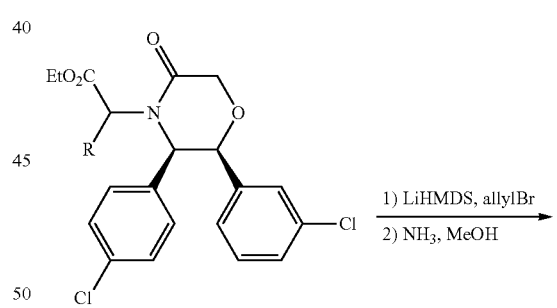
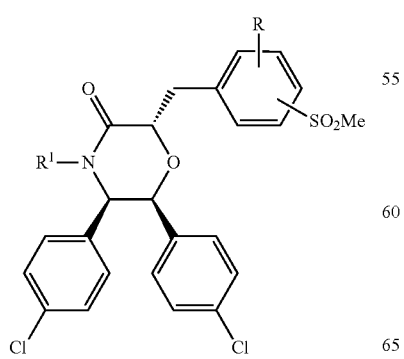
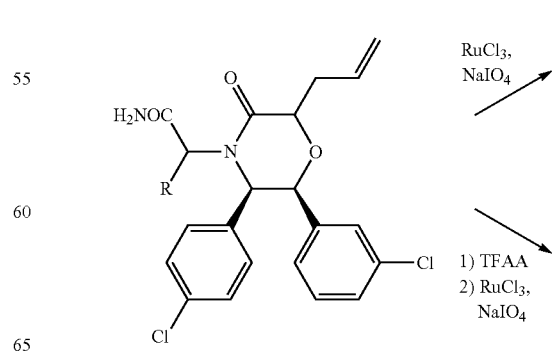

Examples 67 to 69
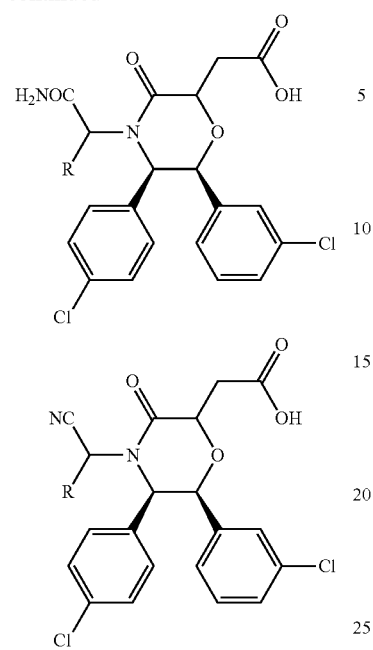
Example 70 to 71
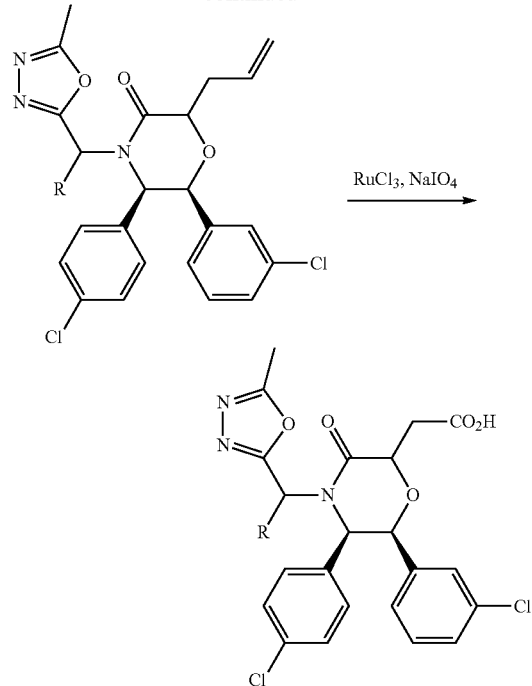
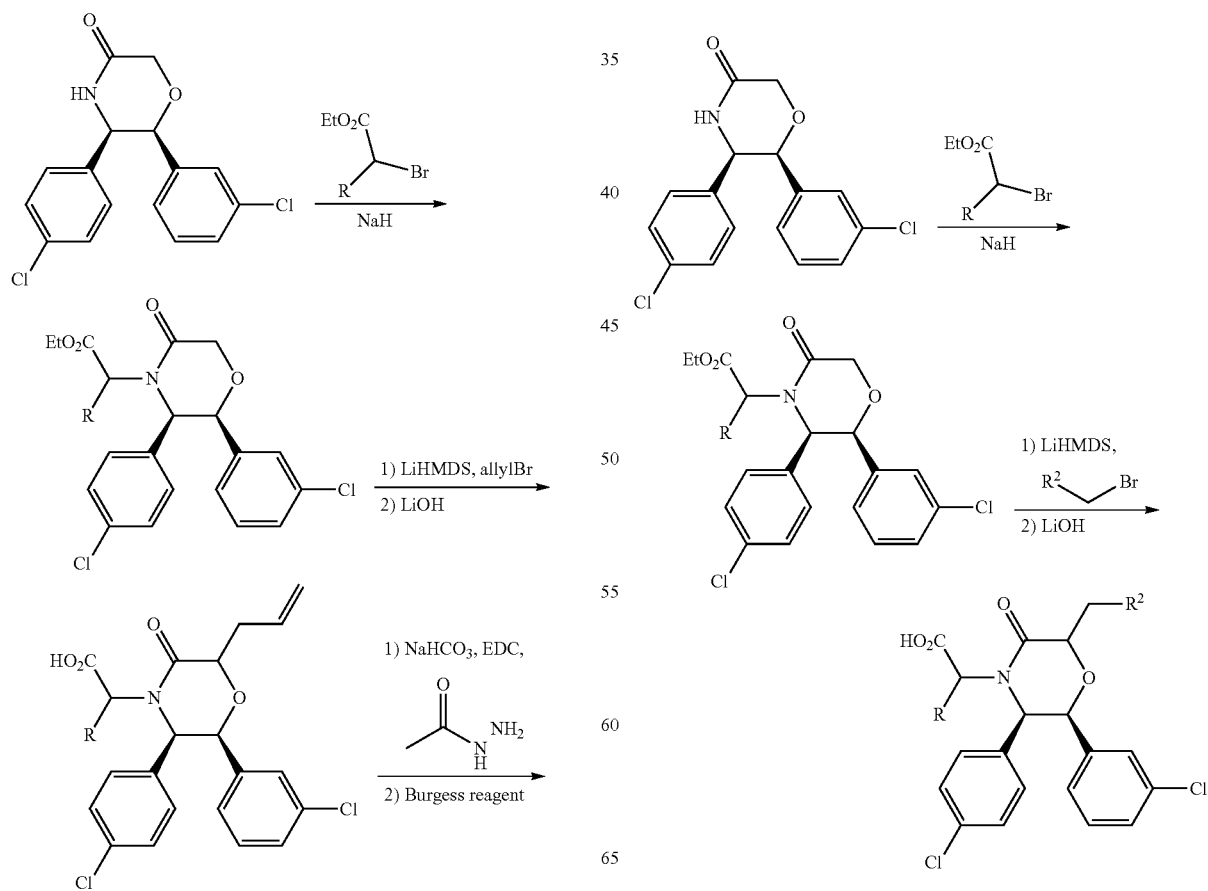

Examples 72 to 75
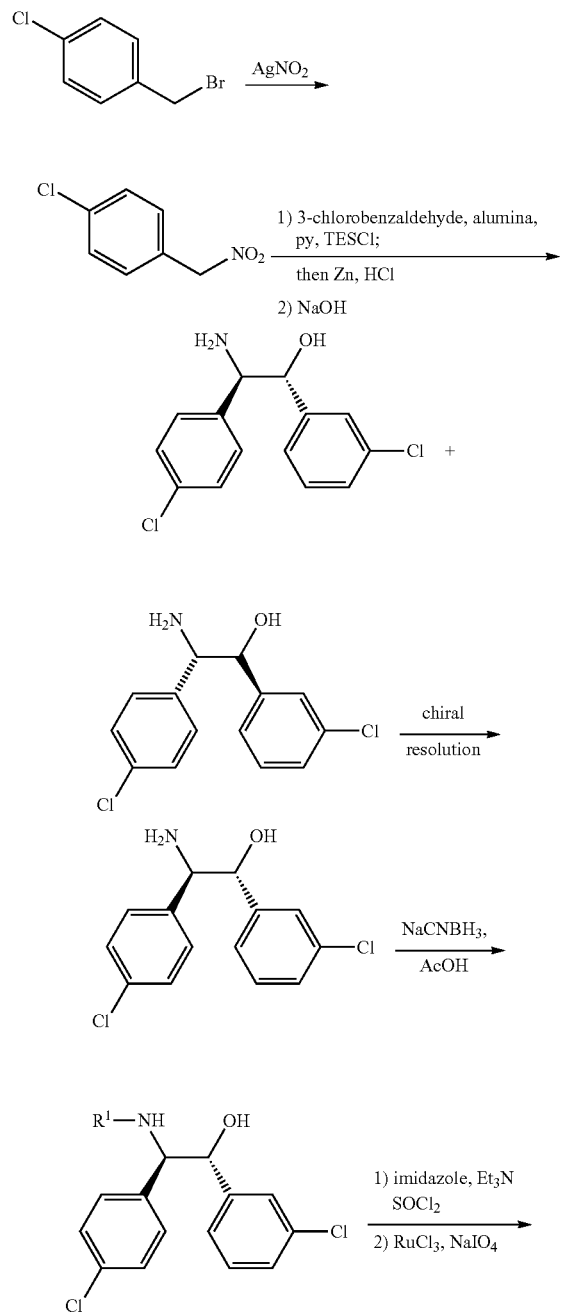
Examples 76 to 77
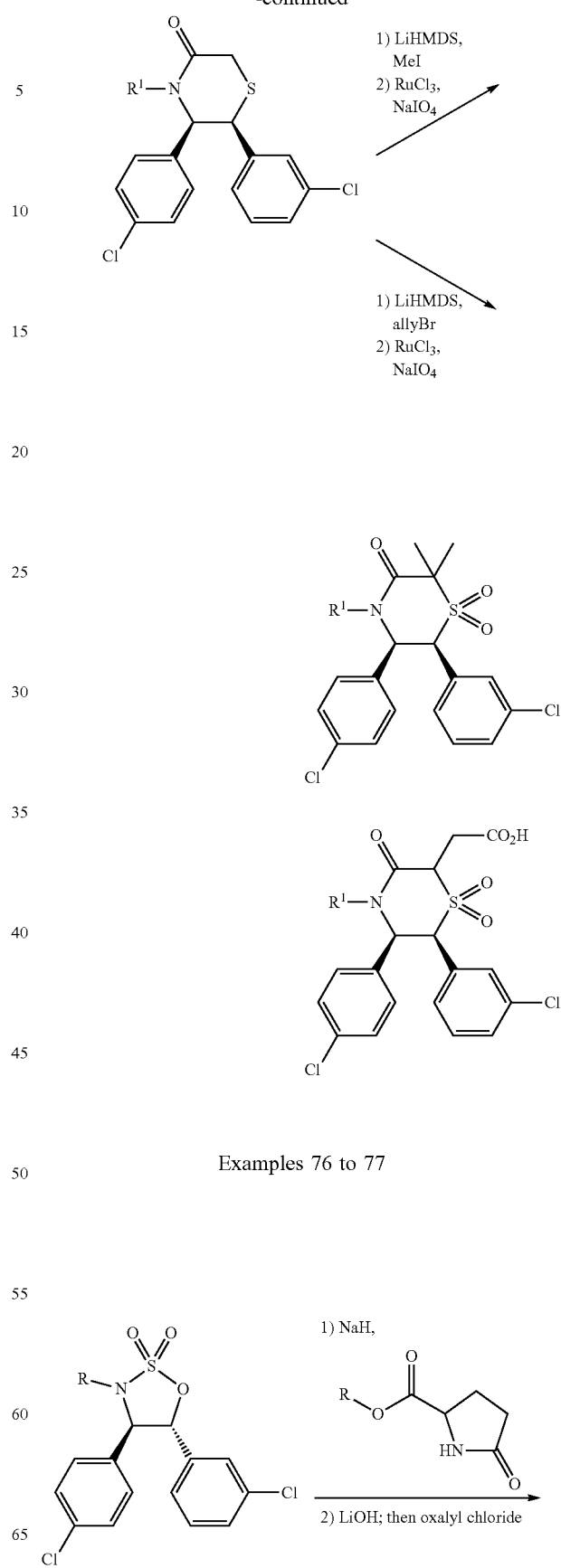

75
-continued
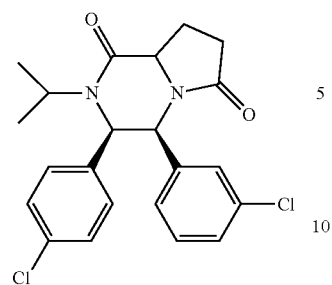
76
-continued
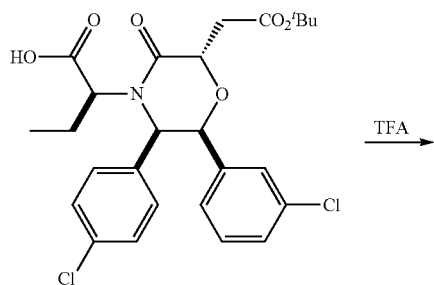
Examples 78 to 79
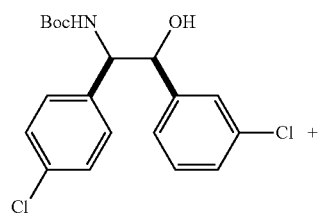
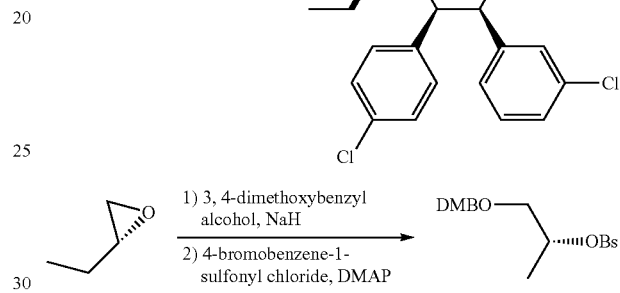
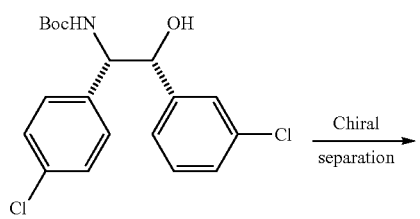
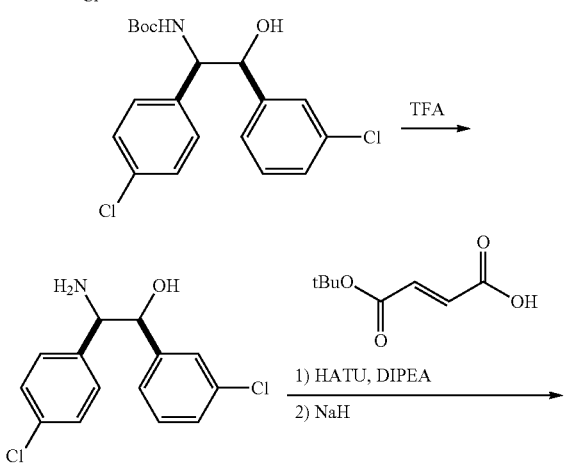
Examples 80 and 81
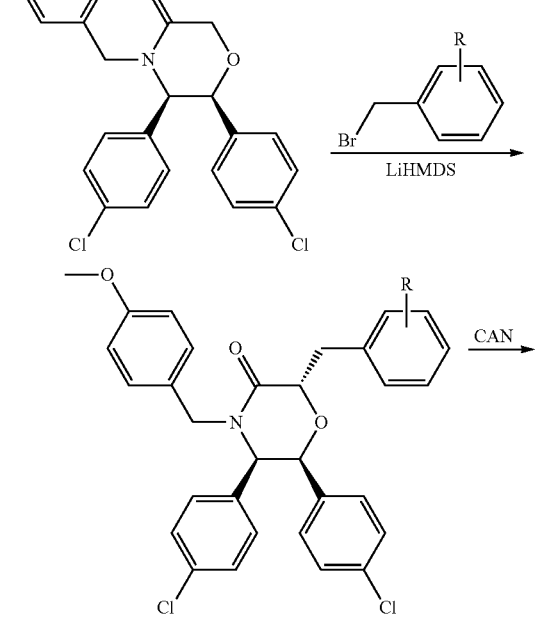

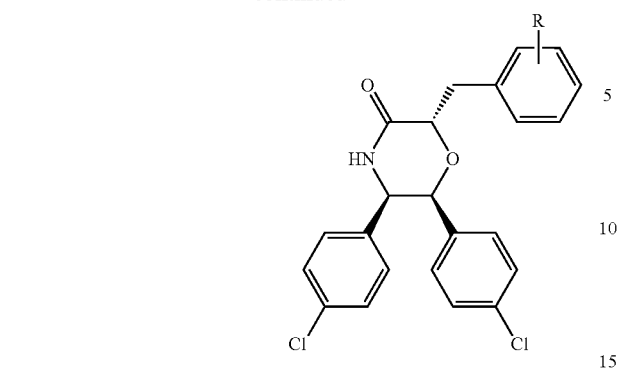
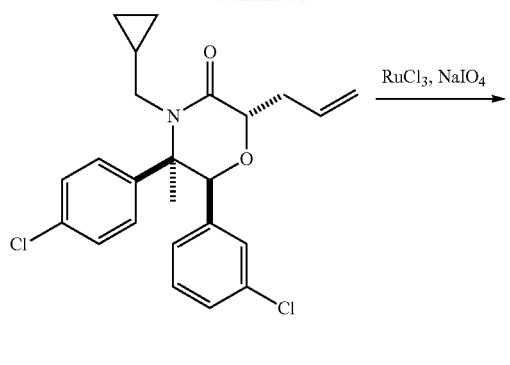
Example 82
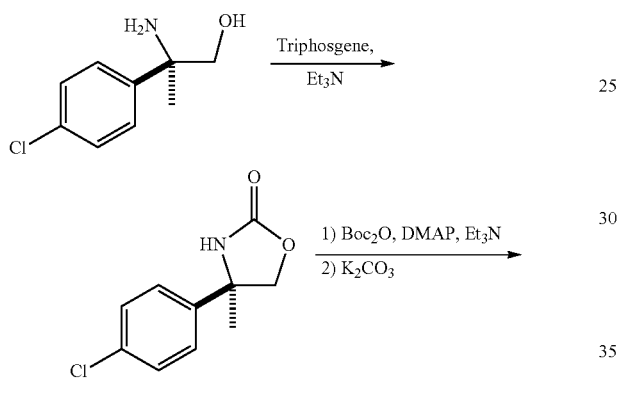
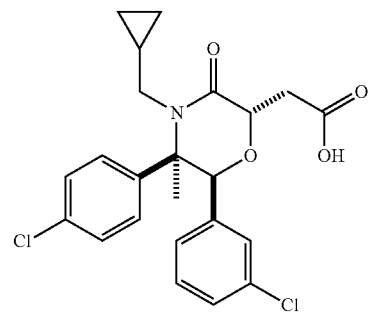
Example 1
(2S, 5R, 6S)-2-Benzyl-5,6-bis(4-bromophenyl)-4-methylmorpholin-3-one and (2R,5S,6R)-2-benzyl-5,6-bis(4-bromophenyl)-4-methylmorpholin-3-one
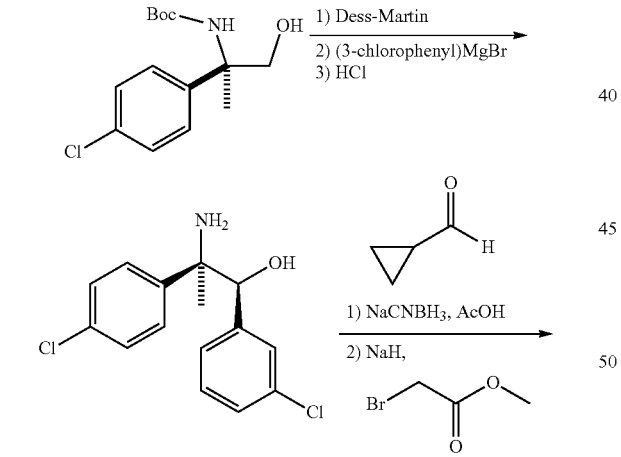
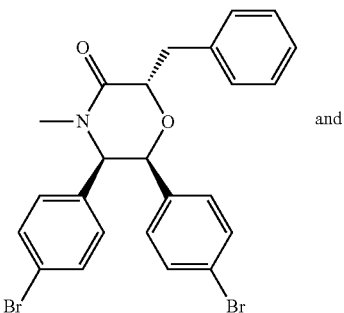
and
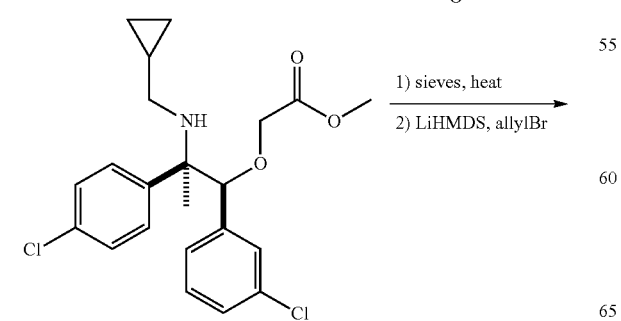
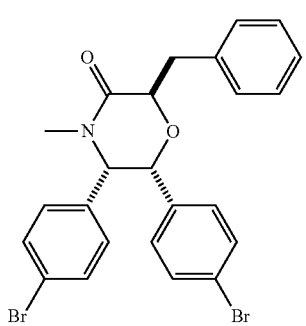

Step A. (1S, 2R)-1,2-Bis(4-bromophenyl)-2-(methylamino)ethanol and (1R,2S)-1,2-bis(4-bromophenyl)-2-(methylamino)ethanol

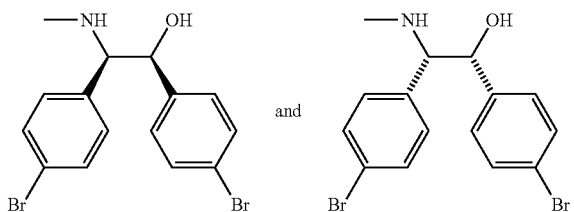 [SMILES: CN[C@H](c1ccc(Br)cc1)[C@@H](O)c1ccc(Br)cc1 ; CN[C@@H](c1ccc(Br)cc1)[C@H](O)c1ccc(Br)cc1]

Methylamine (5.2 mL, 60 mmol) was added to a solution of 1,2-bis(4-bromophenyl)ethane-1,2-dione (7.3 g, 20 mmol) in MeOH (45 mL) at room temperature. The mixture was refluxed for 5 hours, and the solution was cooled to room temperature and concentrated under reduced pressure. The residue was dissolved in MeOH (50 mL) and sodium borohydride (3.8 g, 99 mmol) was added in portions over 10 minutes. After stirring for 1 hour, the mixture was quenched with water and extracted with 10% MeOH/DCM. The combined organic layers were washed with saturated aqueous sodium chloride, dried over $Na_2SO_4$, filtered and the filtrate was concentrated under reduced pressure. The residue was purified by flash chromatography on silica gel (eluent: 10% MeOH in DCM) to afford the title compounds.

1H NMR (500 MHz, $CDCl_3$, δ ppm): 7.32-7.40 (m, 4H), 6.92-6.96 (m, 4H), 4.83 (d, J=5.0 Hz, 1H), 3.66 (s, J=5.0 Hz, 1H), 3.42 (s, 1H), 2.24 (s, 3H); MS (ESI) 383.9 $[M+H]^+$.

Step B. (5R,6S)-5,6-Bis(4-bromophenyl)-4-methylmorpholin-3-one and (5S, 6R)-5,6-bis(4-bromophenyl)-4-methylmorpholin-3-one

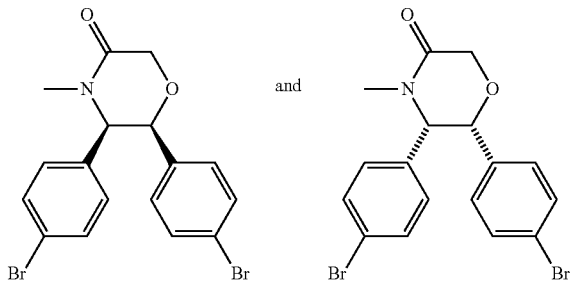 [SMILES: CN1C(=O)CO[C@@H](c2ccc(Br)cc2)[C@H]1c1ccc(Br)cc1 ; CN1C(=O)CO[C@H](c2ccc(Br)cc2)[C@@H]1c1ccc(Br)cc1]

2-Chloroacetyl chloride (0.25 mL, 3.1 mmol) was added to a stirring solution of (1S, 2R)-1,2-bis(4-bromophenyl)-2-(methylamino)ethanol and (1R,2S)-1,2-bis(4-bromophenyl)-2-(methylamino)ethanol (1.2 g, 3.1 mmol, Example 1, Step A) and triethylamine (0.65 mL, —4.65 mmol) in THF (30 mL) at 0° C. under nitrogen. After stirring at 0° C. for 1 hour, the reaction was quenched with saturated aqueous $NH_4Cl$ and extracted with ethyl acetate (2×). The combined organic layers were washed with saturated NaCl solution, dried over $Na_2SO_4$, filtered, and the filtrate was concentrated under reduced pressure. The residue was dissolved in THF (50 mL), and sodium hydride (0.31 g, 7.8 mmol, 60% suspension in oil) was added at room temperature over 5 minutes. After stirring at room temperature overnight, the reaction was quenched with saturated aqueous $NH_4Cl$ solution and extracted with ethyl acetate (2×). The combined organic layers were washed with saturated NaCl solution, dried over $Na_2SO_4$, filtered, and the filtrate was concentrated under reduced pressure. The purification of the residue by silica gel flash chromatography (eluent: 70% ethyl acetate/hexanes) gave the title compounds as a white solid.

1H NMR (500 MHz, $CDCl_3$, δ ppm): 7.25-7.35 (m, 4H), 6.81 (d, J=5.0 Hz, 2H), 6.71 (d, J=5.0 Hz, 2H), 5.15 (d, J=5.0 Hz, 1H), 4.63 (s, J=5.0 Hz, 1H), 4.49 (d, J=12.0 Hz, 1H), 4.35 (d, J=12.0 Hz, 1H), 2.89 (s, 3H); MS (ESI) 426.0 $[M+H]^+$.

Step C. (2S, 5R, 6S)-2-Benzyl-5,6-bis(4-bromophenyl)-4-methylmorpholin-3-one and (2R, 5S, 6R)-2-Benzyl-5,6-bis(4-bromophenyl)-4-methylmorpholin-3-one

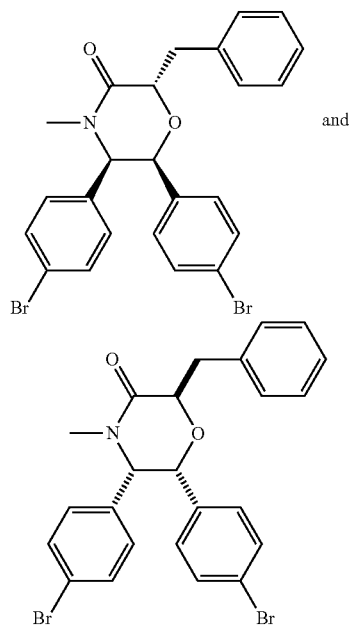

Sodium bis(trimethylsilyl)amide (1.0 M in THF, 1023 µL, 1023 µmol) was added dropwise to a solution of (5R, 6S)-5,6-bis(4-bromophenyl)-4-methylmorpholin-3-one and (5S, 6R)-5,6-bis(4-bromophenyl)-4-methylmorpholin-3-one (90 mg, 682 µmol, Example 1, Step B) in THF (5 mL) at −78° C. The bright yellow solution was stirred for 20 minutes at −78° C., after which a solution of 1-(bromomethyl)benzene (89 µL, 750 µmol) in THF (0.5 mL) was added. The reaction mixture was stirred at −78° C. for 30 minutes, the cooling bath was removed, and the mixture was allowed to warm to room temperature and stirred for an additional 30 minutes. The solution was diluted with ethyl acetate, extracted, washed with brine, dried over $MgSO_4$ and concentrated. The purification of the residue by flash chromatography on silica gel (eluent: 40% ethyl acetate/hexanes) provided the title compounds as a white solid.

1H NMR (500 MHz, $CDCl_3$, δ ppm): 7.36-7.24 (m, 9H), 6.80 (d, J=10.0 Hz, 2H), 6.72 (d, J=5.0 Hz, 2H), 5.22 (d, J=5.0 Hz, 1H), 4.80-4.90 (m, 1H), 4.34 (d, J=5.0 Hz, 1H), 3.43-3.34 (m, 2H), 2.96 (s, 3H); HRMS calcd for $C_{24}H_{21}Br_2NO_2$, 514.0012; found, 514.0009.

Example 2

(2S,5R,6S)-2-Benzyl-5,6-bis(4-bromophenyl)-4-methylmorpholin-3-one

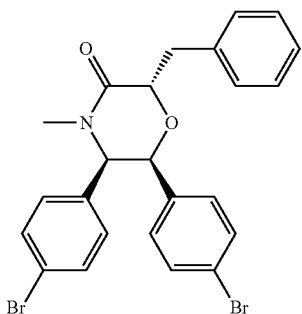 [SMILES: CN1C(=O)[C@H](Cc2ccccc2)O[C@@H](c2ccc(Br)cc2)[C@H]1c1ccc(Br)cc1]

The enantiomers (2S, 5R, 6S)-2-benzyl-5,6-bis(4-bromophenyl)-4-methylmorpholin-3-one and (2R, 5S, 6R)-2-benzyl-5,6-bis(4-bromophenyl)-4-methylmorpholin-3-one (150 mg, Example 1, Step C) were separated by chiral HPLC (OD-H column, flow rate: 18 mL/min on a Chiralcel® OD-H 30 mm I.D.×250 mm, 5 μm column (Daicel Inc., Fort Lee, N.J.), eluent: 10% IPA in hexanes) to give the title compound as the first (faster) eluting isomer, $[\alpha]_D^{23}$ +160.2° (c 0.65, DCM).

$^1$H NMR (500 MHz, CDCl$_3$, δ ppm): 7.36-7.24 (m, 9H), 6.80 (d, J=10.0 Hz, 2H), 6.72 (d, J=5.0 Hz, 2H), 5.22 (d, J=5.0 Hz, 1H), 4.80-4.90 (m, 1H), 4.34 (d, J=5.0 Hz, 1H), 3.43-3.34 (m, 2H), 2.96 (s, 3H); HRMS calcd for C$_{24}$H$_{21}$Br$_2$NO$_2$, 514.0012; found, 514.0009.

Example 3

(2R,5S,6R)-2-Benzyl-5,6-bis(4-bromophenyl)-4-methylmorpholin-3-one

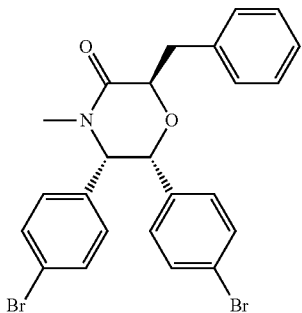

Further elution from Example 2 provided the title compound as the second (slower) eluting isomer, $[\alpha]_D^{23}$ -154.7° (c 1.0, DCM).

1H NMR (500 MHz, CDCl$_3$, δ ppm): 7.36-7.24 (m, 9H), 6.80 (d, J=10.0 Hz, 2H), 6.72 (d, J=5.0 Hz, 2H), 5.22 (d, J=5.0 Hz, 1H), 4.80-4.90 (m, 1H), 4.34 (d, J=5.0 Hz, 1H), 3.43-3.34 (m, 2H), 2.96 (s, 3H); HRMS calcd for C$_{24}$H$_{21}$Br$_2$NO$_2$, 514.0012; found, 514.0009.

Example 4

(2S,5R,6S)-2-Benzyl-5,6-bis(4-chlorophenyl)-4-methylmorpholin-3-one and (2R,5S,6R)-2-benzyl-5,6-bis(4-chlorophenyl)-4-methylmorpholin-3-one

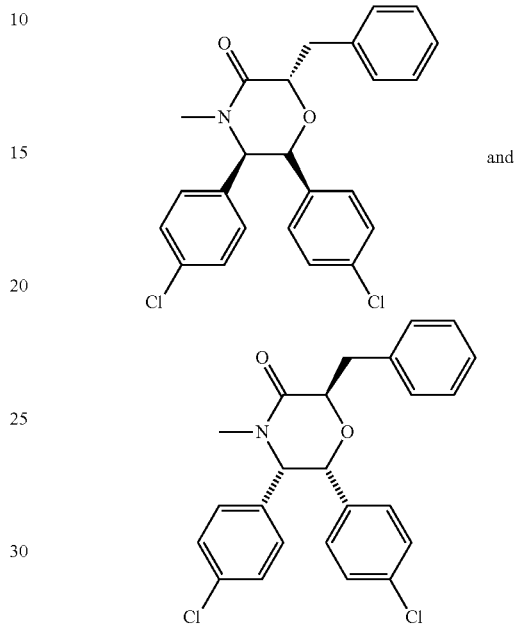

Step A. (R)-2-((tert-Butoxycarbonyl)amino)-2-(4-chlorophenyl)acetic acid and (S)-2-((tert-butoxycarbonyl)amino)-2-(4-chlorophenyl)acetic acid

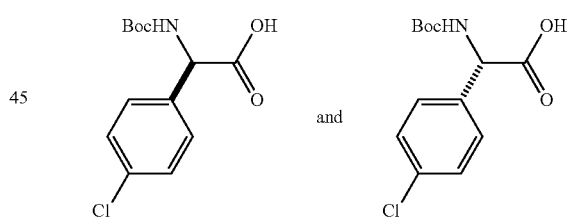

A 1 N sodium hydroxide solution (100 mL, 100 mmol) was added to a stirring solution of 2-amino-2-(4-chlorophenyl)acetic acid (20 g, 108 mmol) in dioxane:water (200 mL:100 mL) at 0° C. After 5 minutes di-tert-butyl dicarbonate (35 g, 162 mmol) and sodium hydrogen carbonate (4.2 mL, 108 mmol) were added in one portion. After stirring at room temperature for 24 hours, the reaction was evaporated under a vacuum and then acidified to pH 4 with KHSO$_4$. The separated organic layer was extracted with ethyl acetate, and the separated organic layer was dried over MgSO$_4$, filtered and evaporated under a vacuum to give the title compounds as a clear oil.

$^1$H NMR (500 MHz, DMSO-d$_6$, δ ppm): 12.91 (s, 1H), 7.66 (d, J=5.0 Hz, 1H), 7.43 (brs, 4H), 5.14 (d, J=5.0 Hz, 1H), 1.39 (s, 9H).

Step B. (R)-tert-Butyl 1-(4-chlorophenyl)-2-(methoxy(methyl)amino)-2-oxoethylcarbamate and (S)-tert-butyl 1-(4-chlorophenyl)-2-(methoxy(methyl)amino)-2-oxoethylcarbamate

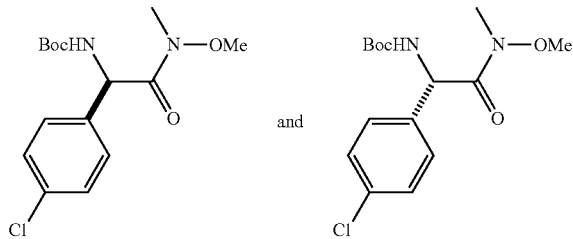

A solution of N,O-dimethylhydroxylamine hydrochloride (4.8 g, 49 mmol) and Hünig's base (8.5 mL, 49 mmol) in DCM (40 mL) was added dropwise over 10 minutes to a stirring solution of (R)-2-((tert-butoxycarbonyl)amino)-2-(4-chlorophenyl)acetic acid and (S)-2-((tert-butoxycarbonyl)amino)-2-(4-chlorophenyl)acetic acid (14 g, 49 mmol, Example 4, Step A), HTBU (19 g, 49 mmol), HOBT (7.5 g, 49 mmol) and Hünig's base (8.5 mL, 49 mmol) at 0° C. in DCM (200 mL). The reaction was allowed to warm to room temperature overnight. After the solvent was removed under a vacuum, the resulting oil was dissolved in ethyl acetate (400 mL) and washed with saturated aqueous NH$_4$Cl. The separated, organic layer was washed with NaCl (saturated solution, 100 mL). The organic layer was dried over MgSO$_4$, filtered and the solvent was removed under a vacuum. Flash column chromatography (SiO$_2$, gradient elution of 0% to 50% ethyl acetate in hexanes) afforded the title compounds as a white solid.

$^1$H NMR (400 MHz, CDCl$_3$, δ ppm): 7.35 (s, 4H), 5.80-5.88 (m, 1H), 5.65-5.73 (m, 1H), 3.52 (s, 3H), 3.20 (s, 3H), 1.43 (s, 9H).

Step C. (R)-tert-Butyl 1,2-bis(4-chlorophenyl)-2-oxoethylcarbamate and (S)-tert-butyl 1,2-bis(4-chlorophenyl)-2-oxoethylcarbamate

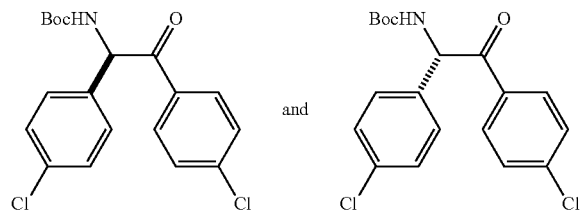

4-Chlorophenylmagnesium bromide (30 mL, 30 mmol) was added dropwise over 5 minutes to a stirring solution of (R)-tert-butyl 1-(4-chlorophenyl)-2-(methoxy(methyl)amino)-2-oxoethylcarbamate and (S)-tert-butyl 1-(4-chlorophenyl)-2-(methoxy(methyl)amino)-2-oxoethylcarbamate (4 g, 12 mmol, Example 4, Step B) in anhydrous THF (50 mL) at 0° C. The reaction was allowed to warm to rt over a period of 3 h and then treated with ethyl acetate (250 mL) and water (100 mL). The separated organic layer was washed with sat'd. NaCl solution (50 mL), dried over MgSO$_4$, filtered and evaporated under reduced pressure. Flash column chromatography (SiO$_2$, gradient elution with 0 to 25% ethyl acetate in hexanes) gave the title compounds as a white solid.

$^1$H NMR (400 MHz, CDCl$_3$, δ ppm): 7.86 (d, J=8.6 Hz, 2H), 7.34 (d, J=8.6 Hz, 2H), 7.20-7.26 (m, 4H), 6.22 (d, J=7.0 Hz, 1H), 6.12 (d, J=7.0 Hz, 1H), 1.41 (s, 9H).

Step D. tert-Butyl ((1R,2S)-1,2-bis(4-chlorophenyl)-2-hydroxyethyl)carbamate and tert-butyl ((1S,2R)-1,2-bis(4-chlorophenyl)-2-hydroxyethyl)carbamate

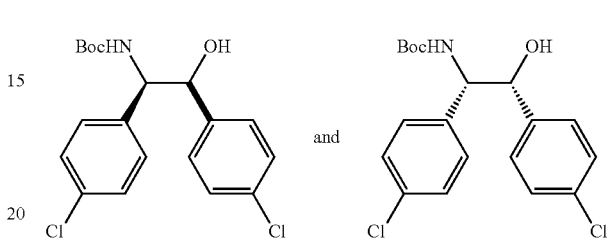

A solution of sodium borohydride (0.10 g, 3 mmol) in THF (10 mL) was added dropwise to a stirring solution of (R)-tert-butyl 1,2-bis(4-chlorophenyl)-2-oxoethylcarbamate and (S)-tert-butyl 1,2-bis(4-chlorophenyl)-2-oxoethylcarbamate (1 g, 3 mmol, Example 4, Step C) in anhydrous THF (30 mL). After the reaction was stirred at room temperature for 2 hours, it was treated with ethyl acetate (200 mL) and saturated aqueous Na$_2$CO$_3$ (10 mL) and water (40 mL). The separated organic layer was washed with brine (40 mL), dried over MgSO$_4$, filtered, and evaporated under reduced pressure to give the title compounds as a white solid.

$^1$H NMR (400 MHz, DMSO-d$_6$, δ ppm): 7.39-7.25 (m, 8H), 5.48 (d, J=4.0 Hz, 1H), 4.75-4.83 (m, 1H), 3.95 (d, J=4.0 Hz, 1H), 1.43 (s, 9H).

Step E. (1S,2R)-2-Amino-1,2-bis(4-chlorophenyl)ethanol and (1R,2S)-2-amino-1,2-bis(4-chlorophenyl)ethanol

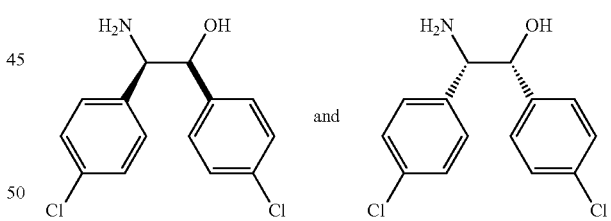

TFA (3 mL) was added dropwise over 5 minutes to a stirring solution of tert-butyl ((1R,2S)-1,2-bis(4-chlorophenyl)-2-hydroxyethyl)carbamate and tert-butyl ((1S,2R)-1,2-bis(4-chlorophenyl)-2-hydroxyethyl)carbamate (700 mg, 1831 µmol, Example 4, Step D) in CH$_2$Cl$_2$ (10 mL) at 0° C. After stirring at room temperature for 1.5 hours, the reaction was evaporated under a vacuum, dissolved in DCM (50 mL) and basified with aqueous NaOH until pH 14. The organic layer was dried over MgSO$_4$, filtered and evaporated under a vacuum. Flash column chromatography (SiO$_2$, eluent: DCM:MeOH 9:1) provided the title compounds as a white solid.

$^1$H NMR (400 MHz, DMSO-d$_6$, δ ppm): 7.30-7.13 (m, 8H), 5.42 (d, J=8.1 Hz, 1H), 4.66-4.70 (m, 1H), 4.60-4.65 (m, 1H).

Step F. (5R,6S)-5,6-Bis(4-chlorophenyl)morpholin-3-one and (5S,6R)-5,6-bis(4-chlorophenyl)morpholin-3-one

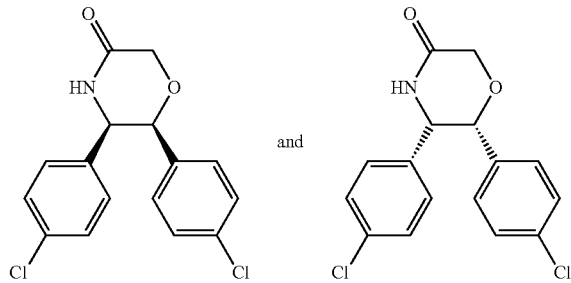

Triethylamine (0.70 mL, 5.1 mmol) was added a stirring solution of (1S,2R)-2-amino-1,2-bis(4-chlorophenyl)ethanol and (1R,2S)-2-amino-1,2-bis(4-chlorophenyl)ethanol (0.95 g, 3.4 mmol, Example 4, Step E) in anhydrous THF (20 mL) at 0° C. The reaction was stirred for 5 minutes and then 2-chloroacetyl chloride (0.27 mL, 3.4 mmol) was added dropwise over 3 minutes. After stirring at room temperature for 1 hour, the reaction was quenched with aqueous $NH_4Cl$ and diluted with ethyl acetate. The separated organic layer was dried over $MgSO_4$, filtered and evaporated under a vacuum to give a residue. The crude residue (400 mg, 1115 µmol) was diluted in anhydrous THF (20 mL), and sodium hydride (58.9 mg, 2454 µmol, 60% suspension in oil) was added portionwise at room temperature over 3 minutes under a $N_2$ atmosphere. After stirring at room temperature for 3 hours, the reaction was quenched with saturated $NH_4Cl$ solution and extracted with ethyl acetate (2×). The combined organic layers were washed with saturated aqueous NaCl solution, dried over $Na_2SO_4$, and filtered. The filtrate was concentrated under reduced pressure. Flash column chromatography ($SiO_2$, eluent: 5% MeOH in DCM) gave the title compounds as a white solid.

$^1$H NMR (400 MHz, DMSO-$d_6$, δ ppm): 8.75 (s, 1H), 7.26-7.20 (m, 4H), 7.05 (d, J=8.4 Hz, 2H), 6.91 (d, J=8.6 Hz, 2H), 5.35 (d, J=3.3 Hz, 1H), 4.75 (s, 1H), 4.48 (d, J=12.0 Hz, 1H), 4.37 (d, J=3.1 Hz, 1H).

Step G. (5R,6S)-5,6-Bis(4-chlorophenyl)-4-methylmorpholin-3-one and (5S,6R)-5,6-bis(4-chlorophenyl)-4-methylmorpholin-3-one

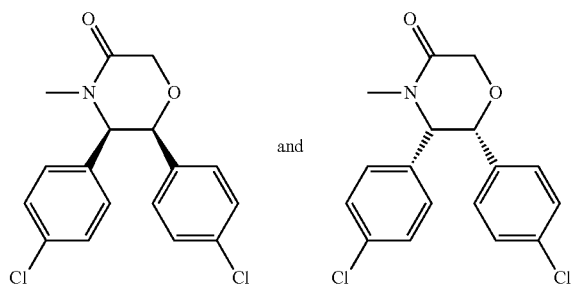

Sodium hydride (9.7 mg, 403 µmol, 60% suspension in oil) was added portionwise over 2 minutes to a stirring solution of (5R,6S)-5,6-bis(4-chlorophenyl)morpholin-3-one and (5S,6R)-5,6-bis(4-chlorophenyl)morpholin-3-one (100 mg, 310 µmol, Example 4, Step F) in DMF (3 mL) at 0° C. After 10 minutes at this temperature, iodomethane (25 µL, 403 µmol) was added dropwise over 1 minute. The reaction was allowed to warm to room temperature over 4 hours. The reaction was then treated with ethyl acetate and water. The separated organic layer was washed with brine, dried, filtered and evaporated under a vacuum. Flash column chromatography ($SiO_2$, gradient elution of 0% to 75% ethyl acetate in hexanes) gave the title compounds.

$^1$H NMR (400 MHz, $CDCl_3$, δ ppm): 7.09 (d, J=8.2 Hz, 4H), 6.78 (d, J=8.6 Hz, 2H), 6.69 (d, J=8.6 Hz, 2H), 5.09 (d, J=3.1 Hz, 1H), 4.56 (d, J=12.0 Hz, 1H), 4.42 (d, J=12.0 Hz, 1H), 4.28 (d, J=3.1 Hz, 1H), 2.82 (s, 3H); HRMS calcd for $C_{17}H_{15}C_{12}NO_2$, 336.0553; found, 336.0564.

Step H. (2S,5R,6S)-2-Benzyl-5,6-bis(4-chlorophenyl)-4-methylmorpholin-3-one and (2R,5S,6R)-2-benzyl-5,6-bis(4-chlorophenyl)-4-methylmorpholin-3-one

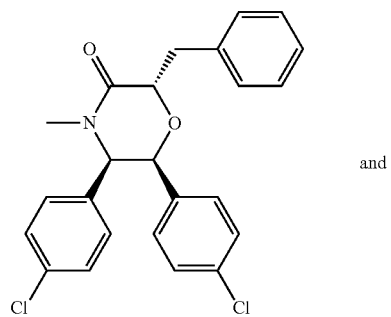

and

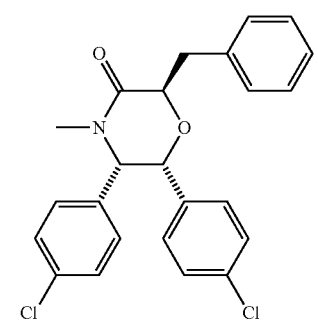

The title compounds were prepared from (5R,6S)-5,6-bis(4-chlorophenyl)-4-methylmorpholin-3-one and (5S,6R)-5,6-bis(4-chlorophenyl)-4-methylmorpholin-3-one (Example 4, Step G) as described for Example 1, Step C.

$^1$H NMR (400 MHz, $CDCl_3$, δ ppm): 7.09-6.93 (m, 9H), 6.63 (d, J=8.2 Hz, 2H), 6.55 (d, J=8.6 Hz, 2H), 5.01 (d, J=2.7 Hz, 1H), 4.67 (dd, J=8.2, 3.9 Hz, 1H), 4.13 (d, J=3.1 Hz, 1H), 3.22-3.11 (m, 2H), 2.74 (s, 3H); MS (ESI) 426.1 $[M+H]^+$.

Examples 5 to 9 were prepared from (5R,6S)-5,6-bis(4-bromophenyl)-4-methylmorpholin-3-one and (5S, 6R)-5,6-bis(4-bromophenyl)-4-methylmorpholin-3-one (Example 1, Step B) as described in Example 1, Step C substituting 1-(bromomethyl)benzene in Example 1, Step C with an equivalent amount of the appropriate alkyl bromide.

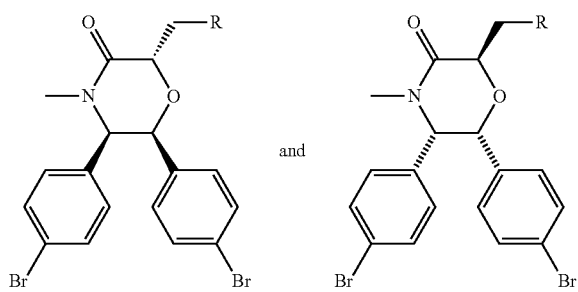

| Example | R | Reagent used |
|---|---|---|
| 5 | ⁓-C6H4-Br (para) | 1-bromo-4-(bromomethyl)benzene |
| 6 | ⁓-C6H4-F (para) | 1-(bromomethyl)-4-fluorobenzene |
| 7 | ⁓-C6H4-OMe (para) | 1-(bromomethyl)-4-methoxybenzene |
| 8 | ⁓-C6H4-OCF3 (para) | 1-(bromomethyl)-4-(trifluoromethoxy)benzene |
| 9 | ⁓-C6H4-OMe (meta) | 1-(bromomethyl)-3-methoxybenzene |

Example 5

(2S,5R,6S)-2-(4-Bromobenzyl)-5,6-bis(4-bromophenyl)-4-methylmorpholin-3-one and (2R,5S,6R)-2-(4-bromobenzyl)-5,6-bis(4-bromophenyl)-4-methylmorpholin-3-one $^1$H NMR (500 MHz, CDCl$_3$, δ ppm): 7.38-7.24 (m, 8H), 7.02 (d, J=5.0 Hz, 2H), 6.94 (d, J=5.0 Hz, 2H), 5.15 (d, J=2.5 Hz, 1H), 4.73-4.81 (m, 1H), 4.29 (d, J=2.5 Hz, 1H), 3.40-3.25 (m, 2H), 3.03 (s, 3H).

Example 6

(2S,5R,6S)-5,6-Bis(4-bromophenyl)-2-(4-fluorobenzyl)-4-methylmorpholin-3-one and (2R,5S,6R)-5,6-bis(4-bromophenyl)-2-(4-fluorobenzyl)-4-methylmorpholin-3-one $^1$H NMR (500 MHz, CDCl$_3$, δ ppm): 7.33-7.28 (m, 4H), 7.14-7.19 (m, 2H), 6.80-6.95 (m, 2H), 6.76 (d, J=5.0 Hz, 2H), 6.66 (d, J=5.0 Hz, 2H), 5.15 (d, J=2.5 Hz, 1H), 4.75-4.84 (m, 1H), 4.29 (d, J=2.5 Hz, 1H), 3.40-3.25 (m, 2H), 2.92 (s, 3H), HRMS calcd for C$_{24}$H$_{20}$Br$_2$FNO$_2$, 531.9918; found, 531.9928.

Example 7

(2S,5R,6S)-5,6-Bis(4-bromophenyl)-2-(4-methoxybenzyl)-4-methylmorpholin-3-one and (2R,5S,6R)-5,6-bis(4-bromophenyl)-2-(4-methoxybenzyl)-4-methylmorpholin-3-one $^1$H NMR (500 MHz, CDCl$_3$, δ ppm): 7.34-7.28 (m, 4H), 7.13 (d, J=10.0 Hz, 2H), 6.75-6.80 (m, 4H), 6.69 (d, J=10.0 Hz, 2H), 5.19 (d, J=5.0 Hz, 1H), 4.77-4.83 (m, 1H), 4.30 (d, J=5.0 Hz, 1H), 3.79 (s, 3H), 3.36-3.24 (m, 2H), 2.93 (s, 3H); MS (ESI) 546.0 [M+H]$^+$.

Example 8

(2S,5R,6S)-5,6-Bis(4-bromophenyl)-4-methyl-2-(4-(trifluoromethoxy)benzyl)morpholin-3-one and (2R,5S,6R)-5,6-bis(4-bromophenyl)-4-methyl-2-(4-(trifluoromethoxy)benzyl)morpholin-3-one $^1$H NMR (500 MHz, CDCl$_3$, δ ppm): 77.41-7.28 (m, 6H), 6.90-6.76 (m, 6H), 4.55-4.65 (m, 1H), 4.47 (d, J=10.0 Hz, 1H), 4.21 (d, J=10.0 Hz, 1H), 3.30-3.40 (m, 1H), 3.17-3.23 (m, 1H), 2.61 (s, 3H); MS (ESI) 600.0 [M+H]$^+$.

Example 9

(2S,5R,6S)-5,6-Bis(4-bromophenyl)-2-(3-methoxybenzyl)-4-methylmorpholin-3-one and (2R,5S,6R)-5,6-bis(4-bromophenyl)-2-(3-methoxybenzyl)-4-methylmorpholin-3-one $^1$H NMR (500 MHz, CDCl$_3$, δ ppm): 7.31-7.28 (m, 4H), 7.13-7.16 (m, 1H), 6.79-6.75 (m, 5H), 6.68 (d, J=5.0 Hz, 2H), 5.15 (d, J=5.0 Hz, 1H), 4.83-4.86 (m, 1H), 4.29 (d, J=5.0 Hz, 1H), 3.63 (s, 3H), 3.35 (dd, J=15.0, 10.0 Hz, 1H), 3.28 (dd, J=15.0, 10.0 Hz, 1H), 2.92 (s, 3H); MS (ESI) 546.0 [M+H]$^+$.

Example 10

(R)-2-((2S,5R,6S)-2-(4-Fluorobenzyl)-5,6-bis(4-chlorophenyl)-3-oxomorpholino)pentanoic acid

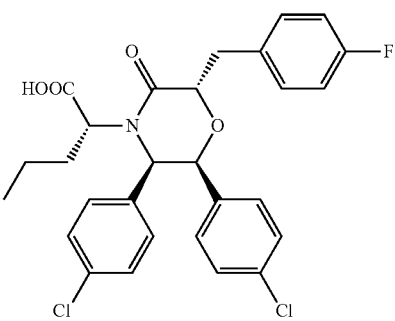

Step A. (R)-Ethyl 2-((2S,3R)-2,3-bis(4-chlorophenyl)-5-oxomorpholino)pentanoate and (S)-ethyl 2-((2R,3S)-2,3-bis(4-chlorophenyl)-5-oxomorpholino)pentanoate

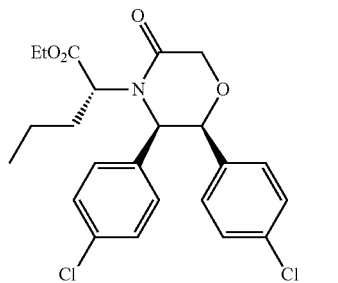

and

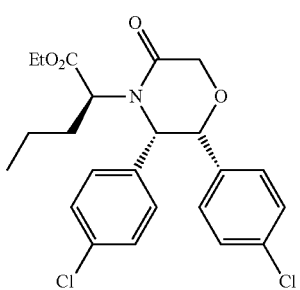

Sodium hydride (436 mg, 10913 µmol, 60% in mineral oil) was added to a solution of (5R,6S)-5,6-bis(4-chlorophenyl)morpholin-3-one and (5S,6R)-5,6-bis(4-chlorophenyl)morpholin-3-one (2930 mg, 9094 µmol, Example 4, Step F) in DMF (23 mL) at 0° C. After stirring for 20 minutes, ethyl 2-bromovalerate (2326 µL, 13641 µmol) was added in portions at 0° C., and the resulting solution was stirred at 25° C. for 16 hours. The reaction was quenched with saturated NH₄Cl solution, extracted with ethyl acetate (3×) and washed with brine (3×). The combined organic layers were dried over Na₂SO₄ and concentrated under the reduced pressure. Purification of the residue by flash chromatography (SiO₂, gradient elution of 30% to 50% MTBE in hexanes) provided (R)-ethyl 2-((2S,3R)-2,3-bis(4-chlorophenyl)-5-oxomorpholino)pentanoate and (S)-ethyl 2-((2R,3S)-2,3-bis(4-chlorophenyl)-5-oxomorpholino)pentanoate as the less polar products.

¹H NMR (400 MHz, CDCl₃, δ ppm): 7.17-7.14 (m, 4H), 6.85-6.81 (m, 4H), 5.24 (s, 1H), 4.90-4.97 (m, 1H), 4.71 (d, J=17.2 Hz, 1H), 4.60 (s, 1H), 4.59 (d, J=17.2 Hz, 1H), 4.08-4.14 (m, 2H), 1.70-1.81 (m, 1H), 1.32-1.45 (m, 1H), 1.33 (t, J=7.6, 3H), 1.20-1.26 (m, 1H), 1.00-1.10 (m, 1H), 0.62 (t, J=7.2 Hz, 3H); MS (ESI) 422.0 [M+H].

Step B. (R)-Ethyl 2-((2S,3R)-2,3-bis(4-chlorophenyl)-5-oxomorpholino)pentanoate

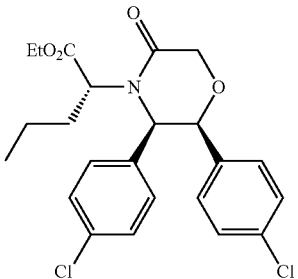

(R)-Ethyl 2-((2S,3R)-2,3-bis(4-chlorophenyl)-5-oxomorpholino)pentanoate and (S)-ethyl 2-((2R,3S)-2,3-bis(4-chlorophenyl)-5-oxomorpholino)pentanoate (Example 10, Step A) were separated by chiral HPLC OD-H column (flow rate: 18 mL/min on a Chiralcel® OD-H 30 mm I.D.×250 µm, 5 µm column (Daicel Inc., Fort Lee, N.J.) eluting with 5% IPA in hexanes) to give the title compound as the first (faster) eluting isomer.

¹H NMR (400 MHz, CDCl₃, δ ppm): 7.17-7.14 (m, 4H), 6.85-6.81 (m, 4H), 5.24 (s, 1H), 4.90-4.97 (m, 1H), 4.71 (d, J=17.2 Hz, 1H), 4.60 (s, 1H), 4.59 (d, J=17.2 Hz, 1H), 4.08-4.14 (m, 2H), 1.70-1.81 (m, 1H), 1.32-1.45 (m, 1H), 1.33 (t, J=7.6, 3H), 1.20-1.26 (m, 1H), 1.00-1.10 (m, 1H), 0.62 (t, J=7.2 Hz, 3H); MS (ESI) 422.0 [M+H].

Step C. (R)-Ethyl 2-((2S,5R,6S)-2-(4-fluorobenzyl)-5,6-bis(4-chlorophenyl)-3-oxomorpholino)pentanoate

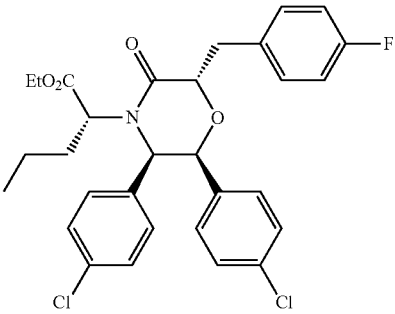 [SMILES: CCC[C@H](C(=O)O)N1C(=O)[C@H](Cc2ccc(F)cc2)O[C@@H](c2ccc(Cl)cc2)[C@H]1c1ccc(Cl)cc1]

Lithium bis(trimethylsilyl)amide (2.7 mL, 2.70 mmol, 1.0 M in THF) was added dropwise to a solution of (R)-ethyl 2-((2S,3R)-2,3-bis(4-chlorophenyl)-5-oxomorpholino)pentanoate (1.15 g, 2.45 mmol, Example 10, Step B) and 1-(bromomethyl)-4-fluorobenzene (464 µL, 3.68 mmol) in THF (8.2 mL, 0.3 M) at −78° C. After stirring at −78° C. for 2 hours, the reaction was quenched with saturated NH₄Cl solution, extracted with ethyl acetate (2×) and washed with brine. The combined organic layers were dried over Na₂SO₄ and concentrated under the reduced pressure. Purification of the residue by flash chromatography (SiO₂, gradient elution of 10% to 15% ethyl acetate in hexanes) provided the title compound as a colorless film.

¹H NMR (400 MHz, CDCl₃, δ ppm): 7.16-7.13 (m, 6H), 6.80-6.70 (m, 6H), 5.08 (s, 1H), 5.00-4.82 (m, 2H), 4.47 (s, 1H), 4.10-4.25 (m, 2H), 3.39-3.20 (m, 2H), 1.63-1.75 (m, 1H), 1.25-1.38 (m, 1H), 1.31 (t, J=7.0 Hz, 3H), 1.10-1.20 (m, 1H), 0.90-1.05 (m, 1H), 0.65 (t, J=8.0 Hz, 3H); MS (ESI) 558.1 [M+H]+.

Step D. (R)-2-((2S,5R,6S)-2-(4-Fluorobenzyl)-5,6-bis(4-chlorophenyl)-3-oxomorpholino)pentanoic acid

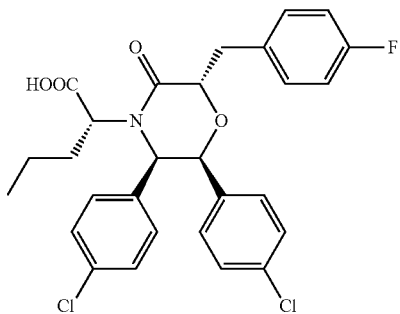 [SMILES: CCC[C@H](C(=O)O)N1C(=O)[C@H](Cc2ccc(F)cc2)O[C@@H](c2ccc(Cl)cc2)[C@H]1c1ccc(Cl)cc1]

A solution of 2 M lithium hydroxide in H$_2$O (202 μL, 405 μmol) was added to a solution of (R)-ethyl 2-((2S,5R,6S)-2-(4-fluorobenzyl)-5,6-bis(4-chlorophenyl)-3-oxomorpholino)pentanoate (113 mg, 202 μmol, Example 10, Step C) in MeOH/THF/H$_2$O (1/1/1, 2 mL, 0.1 M). After stirring at 25° C. for 4 hours, the reaction was concentrated under reduced pressure and acidified with 1 N aqueous HCl. The product was extracted with DCM (3×) and washed with brine. The combined organic layers were dried over Na$_2$SO$_4$ and concentrated under reduced pressure to provide the title compound as a white solid.

$^1$H NMR (400 MHz, CDCl$_3$, δ ppm): 7.20-7.10 (m, 6H), 6.80-6.90 (m, 2H), 6.80-6.70 (m, 4H), 5.02 (s, 1H), 4.85-4.91 (m, 1H), 4.60-4.70 (m, 1H), 4.40 (s, 1H), 3.30-3.38 (m, 1H), 3.15-3.23 (m, 1H), 1.75-1.85 (m, 1H), 1.40-1.55 (m, 1H), 1.10-1.25 (m, 1H), 0.90-1.15 (m, 1H), 0.68 (t, J=7.2 Hz, 3H); HRMS calcd for C$_{28}$H$_{26}$C$_{12}$FNO$_4$, 530.1296; found, 530.1316.

Example 11

(5R,6S)-6-(3-Chlorophenyl)-5-(4-chlorophenyl)-4-methylmorpholin-3-one and (5S,6R)-6-(3-chlorophenyl)-5-(4-chlorophenyl)-4-methylmorpholin-3-one

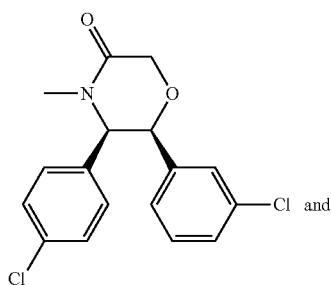

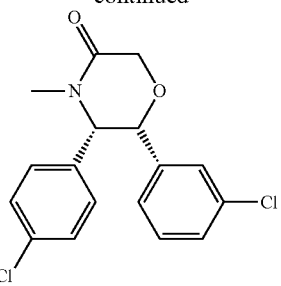

Step A. tert-Butyl (R)-2-(3-chlorophenyl)-1-(4-chlorophenyl)-2-oxoethylcarbamate and tert-butyl (S)-2-(3-chlorophenyl)-1-(4-chlorophenyl)-2-oxoethylcarbamate

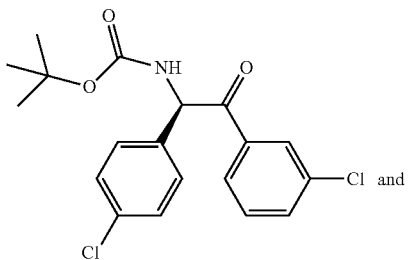

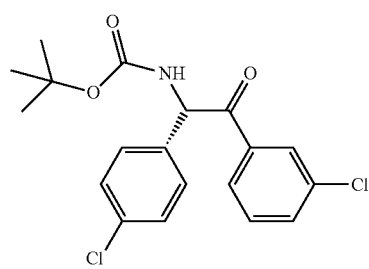

3-Chlorophenylmagnesium bromide (200 mL, 99 mmol, 0.5 M in THF) was slowly added to a solution of (R)-tert-Butyl 1-(4-chlorophenyl)-2-(methoxy(methyl)amino)-2-oxoethylcarbamate and (S)-tert-butyl 1-(4-chlorophenyl)-2-(methoxy(methyl)amino)-2-oxoethylcarbamate (13.00 g, 40 mmol, Example 4, Step B) in THF (180 mL) at 0° C. After stirring at 25° C. overnight, the mixture was quenched with saturated NH$_4$Cl solution (500 mL) and extracted with ethyl acetate. The organic layer was washed with brine, dried over MgSO$_4$ and concentrated under reduced pressure. Flash column chromatography (SiO$_2$, gradient elution of 5% to 20% ethyl acetate in hexanes) gave the title compounds.

$^1$H NMR (400 MHz, CDCl$_3$, δ ppm): 7.93 (s, 1H), 7.78 (d, J=7.8 Hz, 1H), 7.51 (d, J=9.0 Hz, 1H), 7.26-7.38 (m, 5H), 6.20 (d, J=7.4 Hz, 1H), 6.00 (d, J=7.0 Hz, 1H), 1.45 (s, 9H).

Step B. tert-Butyl ((1R,2S)-2-(3-chlorophenyl)-1-(4-chlorophenyl)-2-hydroxyethyl)carbamate and tert-butyl ((1S,2R)-2-(3-chlorophenyl)-1-(4-chlorophenyl)-2-hydroxyethyl)carbamate

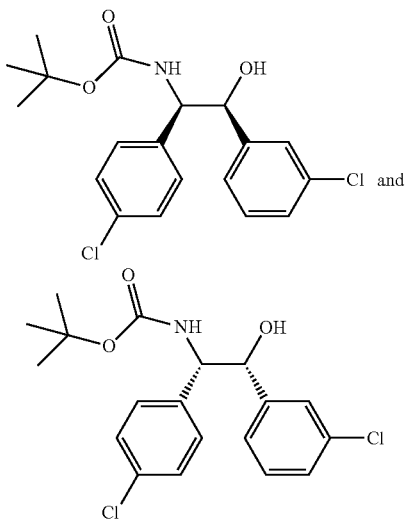

Sodium borohydride (0.7 g, 18 mmol) in THF (20 mL) was added dropwise over 3 minutes to a stirring solution of tert-butyl (R)-2-(3-chlorophenyl)-1-(4-chlorophenyl)-2-oxoethylcarbamate and tert-butyl (S)-2-(3-chlorophenyl)-1-(4-chlorophenyl)-2-oxoethylcarbamate (7 g, 18 mmol, Example 11, Step A) in THF (100 mL) at 0° C. The reaction was stirred while warming to 25° C. for 3 hours. After this time the reaction was treated with ethyl acetate and saturated sodium carbonate solution. The separated organic layer was washed with brine, dried over MgSO₄ and concentrated under reduced pressure to give the title compounds as a white solid.

$^1$H NMR (400 MHz, DMSO-d$_6$, δ ppm): 7.20-7.38 (m, 8H), 5.50 (d, J=5.1 Hz, 1H), 4.61 (dd, J=8.4, 5.3 Hz, 1H), 4.53 (d, J=9.4 Hz, 1H), 1.21 (s, 9H).

Step C. (1S,2R)-2-Amino-1-(3-chlorophenyl)-2-(4-chlorophenyl)ethanol and (1R,2S)-2-amino-1-(3-chlorophenyl)-2-(4-chlorophenyl)ethanol

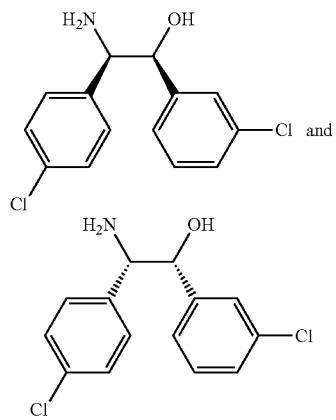

Trifluoroacetic acid (20 mL, 260 mmol) was added slowly over 20 minutes to a solution of tert-butyl ((1R,2S)-2-(3-chlorophenyl)-1-(4-chlorophenyl)-2-hydroxyethyl)carbamate and tert-butyl ((1S,2R)-2-(3-chlorophenyl)-1-(4-chlorophenyl)-2-hydroxyethyl)carbamate (6.2 g, 16 mmol, Example 11, Step B) in DCM (30 mL) at 0° C. After stirring at 25° C. for 3 hours, the reaction mixture was quenched with 4 M NaOH (pH 14), extracted with DCM (3×), washed with brine, dried over MgSO₄ and concentrated under reduced pressure. Flash column chromatography (SiO₂, eluent: 5% MeOH in DCM) gave the title compounds.

$^1$H NMR (400 MHz, MeOH-d$_4$, δ ppm): 6.95-7.21 (m, 8H), 4.72 (d, J=5.48 Hz, 1H), 3.94 (d, J=5.28 Hz, 1H).

Step D. (5R,6S)-6-(3-Chlorophenyl)-5-(4-chlorophenyl)morpholin-3-one and (5S,6R)-6-(3-chlorophenyl)-5-(4-chlorophenyl)morpholin-3-one

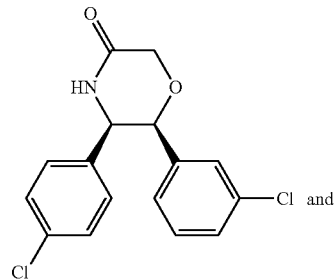

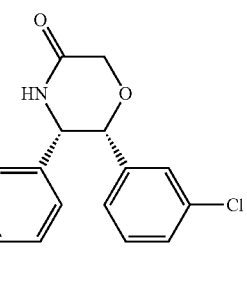

The title compounds were prepared from (1S,2R)-2-amino-1-(3-chlorophenyl)-2-(4-chlorophenyl)ethanol and (1R,2S)-2-amino-1-(3-chlorophenyl)-2-(4-chlorophenyl) ethanol (Example 11, Step C) using the procedure described in Example 4, Step F.

$^1$H NMR (400 MHz, CDCl$_3$, δ ppm): 7.02-7.19 (m, 4H), 6.88-7.00 (m, 1H), 6.73-6.88 (m, 3H), 5.07 (d, J=3.33 Hz, 1H), 4.51-4.66 (m, 2H), 4.40 (d, J=16.82 Hz, 1H); MS (ESI) 322.0 [M+H]⁺.

Step E. (5R,6S)-6-(3-Chlorophenyl)-5-(4-chlorophenyl)-4-methylmorpholin-3-one and (5S,6R)-6-(3-chlorophenyl)-5-(4-chlorophenyl)-4-methylmorpholin-3-one

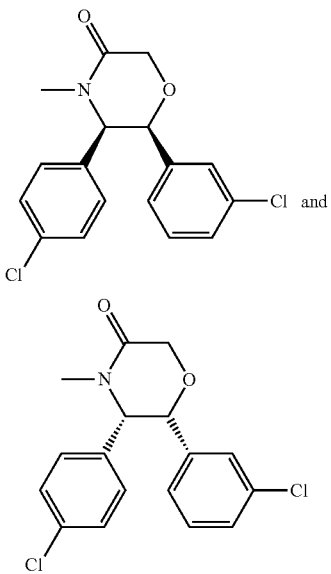

The title compounds were prepared from (5R,6S)-6-(3-chlorophenyl)-5-(4-chlorophenyl)morpholin-3-one and (5R,6S)-6-(3-chlorophenyl)-5-(4-chlorophenyl)morpholin-3-one (Example 11, Step D) using the procedure described in Example 4, Step G.

$^1$H NMR (400 MHz, CDCl$_3$, δ ppm): 7.06-7.22 (m, 4H), 6.96 (t, J=1.96 Hz, 1H), 6.72-6.87 (m, 3H), 5.16 (d, J=3.13 Hz, 1H), 4.65 (d, J=16.82 Hz, 1H), 4.49 (d, J=16.82 Hz, 1H), 4.38 (d, J=3.13 Hz, 1H), 2.87-2.97 (s, 3H); MS (ESI) 336.1 [M+H]$^+$.

Example 12

(5R,6S)-6-(3-Chlorophenyl)-5-(4-chlorophenyl)-4-(cyclopropylmethyl)morpholin-3-one and (5S,6R)-6-(3-chlorophenyl)-5-(4-chlorophenyl)-4-(cyclopropylmethyl)morpholin-3-one

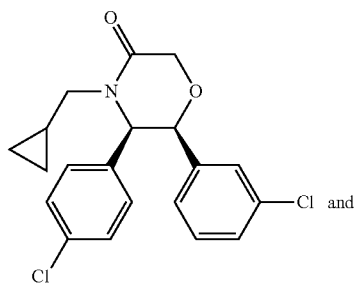

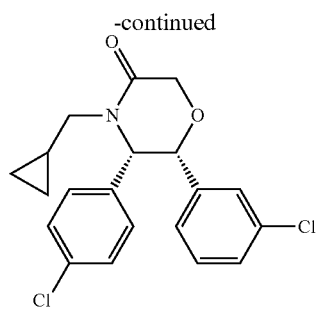

Sodium hydride (0.2 g, 6 mmol, 60% suspension in oil) was added portionwise over 2 minutes to a stirring solution of (5R,6S)-6-(3-chlorophenyl)-5-(4-chlorophenyl)morpholin-3-one and (5S,6R)-6-(3-chlorophenyl)-5-(4-chlorophenyl)morpholin-3-one (1.6 g, 5 mmol, Example 11, Step D) in DMF (6 mL) at 0° C. The reaction was stirred at this temperature for 20 minutes and treated with cyclopropylmethyl bromide (0.8 mL, 6 mmol). After stirring at 25° C. for 4 hours, the reaction mixture was diluted with ethyl acetate and saturated NH$_4$Cl solution. The separated organic layer was dried, filtered and evaporated under a vacuum. Flash column chromatography (SiO$_2$, gradient elution of 0% to 60% ethyl acetate in hexanes) gave the title compounds.

$^1$H NMR (400 MHz, CDCl$_3$, δ ppm): 7.02-7.20 (m, 4H), 6.87-7.00 (m, 1H), 6.68-6.87 (m, 3H), 5.13 (d, J=3.13 Hz, 1H), 4.56-4.71 (m, 2H), 4.41-4.52 (m, 1H), 3.82 (dd, J=14.28, 6.46 Hz, 1H), 2.54 (dd, J=14.18, 7.73 Hz, 1H), 0.79-0.97 (m, 1H), 0.44-0.57 (m, 1H), 0.31-0.44 (m, 1H), 0.11-0.21 (m, 1H), −0.01-0.11 (m, 1H); HRMS calcd for C$_{20}$H$_{19}$C$_{12}$NO$_2$, 376.0868; found, 376.0868.

Example 13

(2S,5R,6S)-2-Benzyl-6-(3-chlorophenyl)-5-(4-chlorophenyl)-4-methylmorpholin-3-one and (2R,5S,6R)-2-benzyl-6-(3-chlorophenyl)-5-(4-chlorophenyl)-4-methylmorpholin-3-one

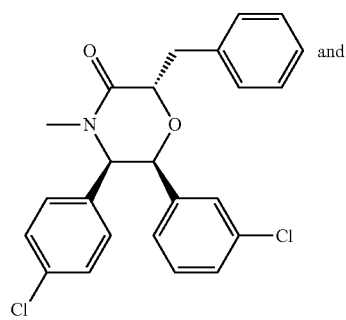

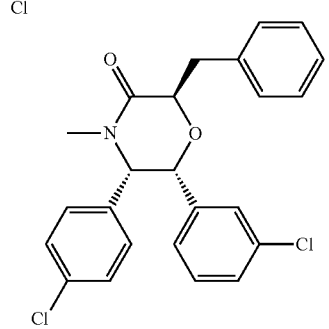

A solution of sodium bis(trimethylsilyl)amide (803 μL, 803 μmol, 1.0 M in THF) in THF (1.5 mL) was added dropwise via syringe to a solution of (5R,6S)-6-(3-chlorophenyl)-5-(4-chlorophenyl)-4-methylmorpholin-3-one and (5S,6R)-6-(3-chlorophenyl)-5-(4-chlorophenyl)-4-methylmorpholin-3-one (180 mg, 535 μmol, Example 11, Step E) in THF (2.0 mL) over 4 minutes at −78° C. The reaction was stirred for 20 minutes at this temperature and then 1-(bromomethyl)benzene (95 μL, 803 μmol) was added. After stirring at −78° C. for 2 hours, the reaction was quenched with saturated NH$_4$Cl solution and ethyl acetate. The separated organic layer was washed with brine, dried, filtered and evaporated under a vacuum. Flash column chromatography (SiO$_2$, gradient elution of 0% to 50% ethyl acetate in hexanes) gave the title compounds.

$^1$H NMR (400 MHz, CDCl$_3$, δ ppm): 7.09-6.93 (m, 9H), 6.63 (d, J=8.2 Hz, 2H), 6.55 (d, J=8.6 Hz, 2H), 5.01 (d, J=2.7 Hz, 1H), 4.67 (dd, J=8.2, 3.9 Hz, 1H), 4.13 (d, J=3.1 Hz, 1H), 3.22-3.11 (m, 2H), 2.74 (s, 3H); MS (ESI) 426.1 [M+H]$^+$.

Example 14

(2S,5R,6S)-6-(3-Chlorophenyl)-5-(4-chlorophenyl)-4-(cyclopropylmethyl)-2-((S)-2,3-dihydroxypropyl)morpholin-3-one and (2S,5R,6S)-6-(3-chlorophenyl)-5-(4-chlorophenyl)-4-(cyclopropylmethyl)-2-((R)-2,3-dihydroxypropyl)morpholin-3-one and (2S,5S,6R)-6-(3-chlorophenyl)-5-(4-chlorophenyl)-4-(cyclopropylmethyl)-2-((S)-2,3-dihydroxypropyl)morpholin-3-one and (2S,5S,6R)-6-(3-chlorophenyl)-5-(4-chlorophenyl)-4-(cyclopropylmethyl)-2-((R)-2,3-dihydroxypropyl)morpholin-3-one

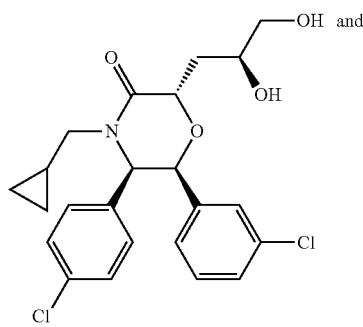

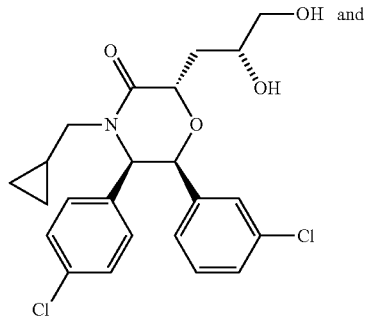

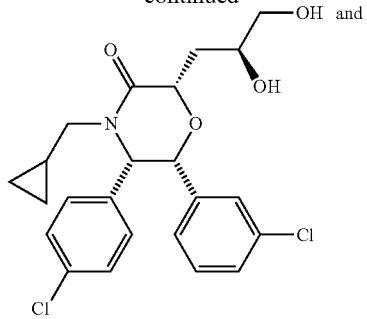

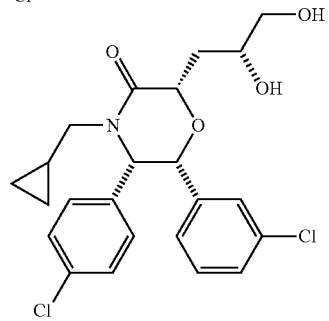

Step A. (2S,5R,6S)-2-Allyl-6-(3-chlorophenyl)-5-(4-chlorophenyl)-4-(cyclopropylmethyl)morpholin-3-one and (2R,5S,6R)-2-allyl-6-(3-chlorophenyl)-5-(4-chlorophenyl)-4-(cyclopropylmethyl)morpholin-3-one

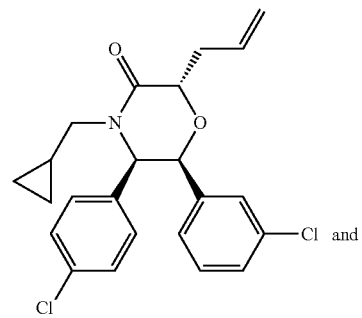

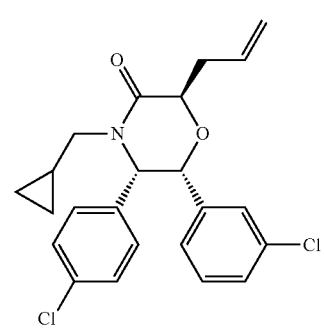

A solution of (5R,6S)-6-(3-chlorophenyl)-5-(4-chlorophenyl)-4-(cyclopropylmethyl)morpholin-3-one and (5S,6R)-6-(3-chlorophenyl)-5-(4-chlorophenyl)-4-(cyclopropylmethyl)morpholin-3-one (330 mg, 877 µmol, Example 12) in THF (2.5 mL) was added dropwise over 4 minutes to a stirring solution of sodium bis(trimethylsilyl)amide (965 µL, 965 µmol, 1.0 M in THF) in THF (1.0 mL) at −78° C. The reaction was stirred at this temperature for 25 minutes, and then treated with allyl bromide (83 µL, 965 µmol). After stirring at −78° C. for 4 hours, the reaction was quenched with saturated NH$_4$Cl solution and ethyl acetate. The separated organic layer was washed with brine, dried, filtered and evaporated under a vacuum. Flash column chromatography (SiO$_2$, gradient elution of 0% to 30% ethyl acetate in hexanes) gave the title compounds.

$^1$H NMR (400 MHz, CDCl$_3$, δ ppm): 7.05-7.23 (m, 4H), 6.93-7.05 (m, 1H), 6.83 (dt, J=7.63, 1.76 Hz, 1H), 6.68-6.80 (m, 2H), 5.91 (ddt, J=17.09, 10.15, 7.02, 7.02 Hz, 1H), 5.37 (d, J=3.13 Hz, 1H), 5.04-5.20 (m, 2H), 4.60-4.76 (m, 2H), 3.83 (dd, J=14.09, 6.46 Hz, 1H), 2.74-2.92 (m, 2H), 2.59 (dd, J=14.28, 7.63 Hz, 1H), 0.78-0.94 (m, 1H), 0.46-0.60 (m, 1H), 0.14-0.27 (m, 1H), 0.33-0.46 (m, 1H), −0.01-0.14 (m, 1H); MS (ESI) 416.0 [M+H]$^+$.

Step B. (2S,5R,6S)-6-(3-Chlorophenyl)-5-(4-chlorophenyl)-4-(cyclopropylmethyl)-2-((S)-2,3-dihydroxypropyl)morpholin-3-one and (2S,5R,6S)-6-(3-chlorophenyl)-5-(4-chlorophenyl)-4-(cyclopropylmethyl)-2-((R)-2,3-dihydroxypropyl)morpholin-3-one and (2S,5S,6R)-6-(3-chlorophenyl)-5-(4-chlorophenyl)-4-(cyclopropylmethyl)-2-((S)-2,3-dihydroxypropyl)morpholin-3-one and (2S,5S,6R)-6-(3-chlorophenyl)-5-(4-chlorophenyl)-4-(cyclopropylmethyl)-2-((R)-2,3-dihydroxypropyl)morpholin-3-one Potassium osmate(VI) dihydrate (10.6 mg, 28.8 µmol) and a solution of (2S,5R,6S)-2-allyl-6-(3-chlorophenyl)-5-(4-chlorophenyl)-4-(cyclopropylmethyl)morpholin-3-one and (2R,5S,6R)-2-allyl-6-(3-chlorophenyl)-5-(4-chlorophenyl)-4-(cyclopropylmethyl)morpholin-3-one (240 mg, 576 µmol, Example 14, Step A) in acetone (1 mL) were added to a stirring solution of 4-methylmorpholine N-oxide (540 mg, 4612 µmol) in tert-BuOH (3 mL) and water (3 mL). After stirring at 25° C. overnight, the reaction was quenched with saturated NH$_4$Cl solution, extracted with DCM, dried, and filtered. The solvent was removed under a vacuum and flash column chromatography (SiO$_2$, gradient elution of 0% to 67% ethyl acetate in hexanes) gave the title compounds.

$^1$H NMR (400 MHz, CDCl$_3$, δ ppm): 7.10-7.21 (m, 4H), 6.96 (d, J=1.8 Hz, 1H), 6.72-6.83 (m, 1H), 5.28 (d, J=2.9 Hz, 1H), 4.87-4.95 (m, 1H), 4.65 (d, J=2.8 Hz, 1H), 4.01-4.19 (m, 1H), 3.83 (dd, J=14.2, 6.4 Hz, 1H), 3.31-3.67 (m, 1H), 2.58-2.66 (m, 1H), 2.21-2.40 (m, 2H), 2.00-2.07 (m, 1H), 0.86-0.99 (m, 1H), 0.51-0.58 (m, 1H), 0.39-0.46 (m, 1H), 0.17-0.23 (m, 1H), 0.06-0.13 (m, 1H); MS (ESI) 450.1 [M+H]$^+$.

Example 15

(2-((2S,5R,6S)-6-(3-Chlorophenyl)-5-(4-chlorophenyl)-4-(cyclopropylmethyl)-3-oxomorpholin-2-yl)acetaldehydeacetaldehyde and (2-((2R,5S,6R)-6-(3-chlorophenyl)-5-(4-chlorophenyl)-4-(cyclopropylmethyl)-3-oxomorpholin-2-yl)acetaldehydeacetaldehyde

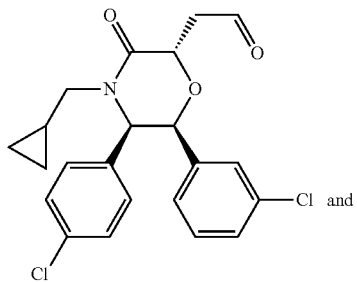

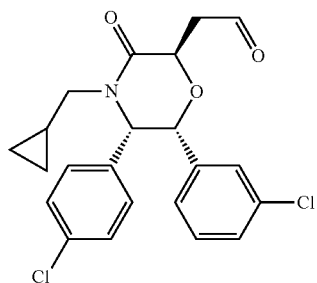

Sodium periodate (47 mg, 222 µmol) and aqueous pH 7 buffer (0.5 mL) was added to a stirring solution of (2S,5R,6S)-6-(3-chlorophenyl)-5-(4-chlorophenyl)-4-(cyclopropylmethyl)-2-((S)-2,3-dihydroxypropyl)morpholin-3-one and (2S,5R,6S)-6-(3-chlorophenyl)-5-(4-chlorophenyl)-4-(cyclopropylmethyl)-2-((R)-2,3-dihydroxypropyl)morpholin-3-one and (2S,5S,6R)-6-(3-chlorophenyl)-5-(4-chlorophenyl)-4-(cyclopropylmethyl)-2-((S)-2,3-dihydroxypropyl)morpholin-3-one and (2S,5S,6R)-6-(3-chlorophenyl)-5-(4-chlorophenyl)-4-(cyclopropylmethyl)-2-((R)-2,3-dihydroxypropyl)morpholin-3-one (20 mg, 44 µmol, Example 14, Step B) in THF (1.0 mL). The reaction was stirred at 25° C. for 4 hours and then diluted with DCM. The separated aqueous layer was extracted with DCM and the combined organic layers were dried, filtered and evaporated under a vacuum to give the title compounds.

$^1$H NMR (400 MHz, CDCl$_3$, δ ppm): 9.83 (t, J=1.66 Hz, 1H), 7.05-7.24 (m, 4H), 6.89-7.01 (m, 1H), 6.64-6.84 (m, 3H), 5.21-5.40 (m, 2H), 4.59-4.72 (m, 1H), 3.71-3.86 (m, 1H), 3.07-3.30 (m, 2H), 2.69 (dd, J=14.09, 7.83 Hz, 1H), 0.83-0.97 (m, 1H), 0.49-0.59 (m, 1H), 0.38-0.46 (m, 1H), 0.13-0.27 (m, 1H), 0.02-0.13 (m, 1H).

Example 16

(2S,5R,6S)-6-(3-Chlorophenyl)-5-(4-chlorophenyl)-4-(cyclopropylmethyl)-2-(2-hydroxyethyl)morpholin-3-one and (2R,5S,6R)-6-(3-chlorophenyl)-5-(4-chlorophenyl)-4-(cyclopropylmethyl)-2-(2-hydroxyethyl)morpholin-3-one

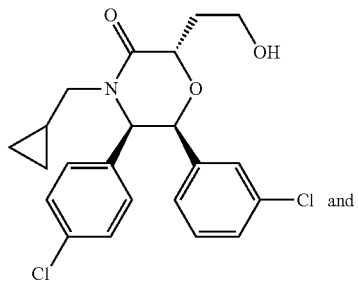

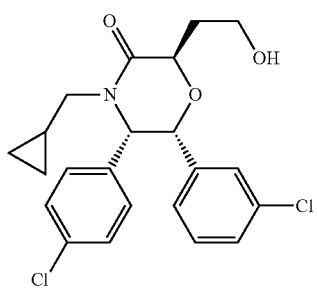

Sodium borohydride (1.8 mg, 48 µmol) was added to a stirring solution of (2-((2S,5R,6S)-6-(3-chlorophenyl)-5-(4-chlorophenyl)-4-(cyclopropylmethyl)-3-oxomorpholin-2-yl)acetaldehydeacetaldehyde and (2-((2R,5S,6R)-6-(3-chlorophenyl)-5-(4-chlorophenyl)-4-(cyclopropylmethyl)-3-oxomorpholin-2-yl)acetaldehydeacetaldehyde (20 mg, 48 µmol, Example 15) in THF. After stirring at 25° C. for 3 hours, the reaction was quenched with saturated NH$_4$Cl solution and ethyl acetate. The separated organic layer was washed with brine, dried, filtered and evaporated under a vacuum. Flash column chromatography (SiO$_2$, gradient eluent of 0% to 70% ethyl acetate in hexanes) gave the title compounds.

1H NMR (400 MHz, CDCl$_3$, δ ppm): 7.06-7.22 (m, 4H), 6.95-7.01 (m, 1H), 6.82 (dt, J=7.63, 1.76 Hz, 1H), 6.72-6.78 (m, 2H), 5.33 (d, J=3.13 Hz, 1H), 4.81-4.87 (m, 1H), 4.65 (d, J=2.93 Hz, 1H), 3.78-3.92 (m, 3H), 2.62 (dd, J=14.18, 7.73 Hz, 1H), 2.30-2.46 (m, 1H), 2.16-2.25 (m, 1H), 0.85-0.96 (m, 1H), 0.50-0.58 (m, 1H), 0.38-0.46 (m, 1H), 0.20 (dq, J=9.76, 4.83 Hz, 1H), 0.05-0.13 (m, 1H); HRMS calcd for C$_{22}$H$_{23}$Cl$_2$NO$_3$, 420.1128; found, 420.1132.

Example 17

(2-((2S,5R,6S)-6-(3-Chlorophenyl)-5-(4-chlorophenyl)-4-(cyclopropylmethyl)-3-oxomorpholin-2-yl)acetic acid and (2-((2R,5S,6R)-6-(3-chlorophenyl)-5-(4-chlorophenyl)-4-(cyclopropylmethyl)-3-oxomorpholin-2-yl)acetic acid

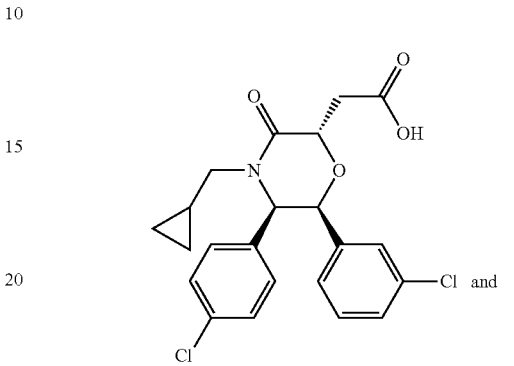

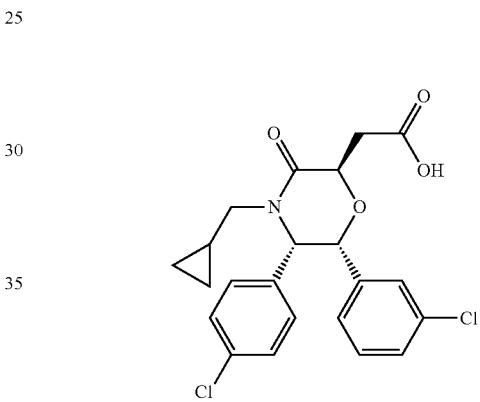

An aqueous solution of sodium chlorite (30 mg, 330 µmol) and monosodium dihydrogen phosphate (34 mg, 287 µmol) was added to a stirring solution of (2-((2S,5R,6S)-6-(3-chlorophenyl)-5-(4-chlorophenyl)-4-(cyclopropylmethyl)-3-oxomorpholin-2-yl)acetaldehydeacetaldehyde and (2-((2R,5S,6R)-6-(3-chlorophenyl)-5-(4-chlorophenyl)-4-(cyclopropylmethyl)-3-oxomorpholin-2-yl)acetaldehydeacetaldehyde (60 mg, 143 µmol, Example 15) in tert-BuOH (2.5 mL) and 2-methyl-2-butene (1.5 mL) at 0° C. The reaction was stirred in the dark while warming to 25° C. for 4 hours. After this time the reaction was diluted with ethyl acetate and water. The separated aqueous layer was extracted with ethyl acetate and the combined organic layers were washed with brine, dried, filtered and evaporated under a vacuum. Flash column chromatography (SiO$_2$, gradient elution of 0% to 70% ethyl acetate in hexanes) gave the title compounds as a white solid.

$^1$H NMR (400 MHz, CDCl$_3$, δ ppm): 7.08-7.20 (m, 4H), 6.95-6.98 (m, 1H), 6.81 (dt, J=7.63, 1.56 Hz, 1H), 6.72-6.77 (m, 2H), 5.29-5.36 (m, 1H), 5.15-5.20 (m, 1H), 4.66 (d, J=3.13 Hz, 1H), 3.78 (dd, J=14.09, 6.46 Hz, 1H), 3.22 (dd, J=16.24, 5.09 Hz, 1H), 3.02 (dd, J=16.24, 7.83 Hz, 1H), 2.71 (dd, J=14.09, 7.63 Hz, 1H), 0.84-0.97 (m, 1H), 0.50-0.58 (m, 1H), 0.38-0.46 (m, 1H), 0.20 (dq, J=9.76, 4.77 Hz, 1H), 0.05-0.13 (m, 1H); MS (ESI) 434.0 [M+H]$^+$.

Example 18

(2S,5R,6S)-6-(3-Chlorophenyl)-5-(4-chlorophenyl)-4-(cyclopropylmethyl)-2-(2-(methylamino)ethyl)morpholin-3-one and (2R,5S,6R)-6-(3-chlorophenyl)-5-(4-chlorophenyl)-4-(cyclopropylmethyl)-2-(2-(methylamino)ethyl)morpholin-3-one

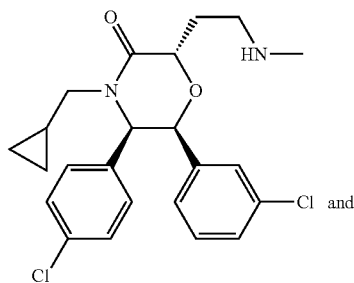

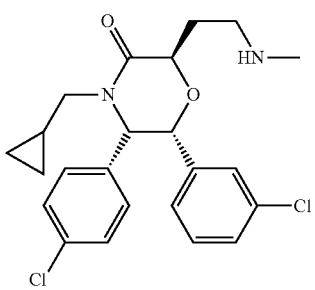

Methylamine (251 µL, 502 µmol) and methylamine hydrochloride (23 mg, 335 µmol) were added to a stirring solution of (2-((2S,5R,6S)-6-(3-chlorophenyl)-5-(4-chlorophenyl)-4-(cyclopropylmethyl)-3-oxomorpholin-2-yl)acetaldehydeacetaldehyde and (2-((2R,5S,6R)-6-(3-chlorophenyl)-5-(4-chlorophenyl)-4-(cyclopropylmethyl)-3-oxomorpholin-2-yl)acetaldehydeacetaldehyde (70 mg, 167 µmol, Example 15) in MeOH (2 mL). The reaction was stirred for 1 hour, cooled to 0° C., and treated with sodium cyanoborohydride (13 µL, 251 µmol) in MeOH (1.0 mL). The reaction was stirred for 2 hours and the solvent was evaporated under a vacuum. Flash column chromatography (SiO$_2$, eluent: 5% MeOH in DCM) gave the title compounds.

$^1$H NMR (400 MHz, CDCl$_3$, δ ppm): 7.10-7.21 (m, 4H), 6.90-6.99 (m, 2H), 6.71-6.80 (m, 2H), 5.48 (d, J=3.13 Hz, 1H), 4.68-4.83 (m, 2H), 3.68 (dd, J=14.08, 6.46 Hz, 1H), 3.15-3.35 (m, 2H), 2.66-2.90 (m, 5H), 2.27-2.44 (m, 1H), 0.84-0.95 (m, 1H), 0.51-0.59 (m, 1H), 0.38-0.46 (m, 1H), 0.11-0.18 (m, 1H), −0.03-0.07 (m, 1H); MS (ESI) 433.1 [M+H]$^+$.

Example 19

(2S,5R,6S)-6-(3-Chlorophenyl)-5-(4-chlorophenyl)-4-(cyclopropylmethyl)-2-(3-hydroxypropyl)morpholin-3-one and (2R,5S,6R)-6-(3-chlorophenyl)-5-(4-chlorophenyl)-4-(cyclopropylmethyl)-2-(3-hydroxypropyl)morpholin-3-one

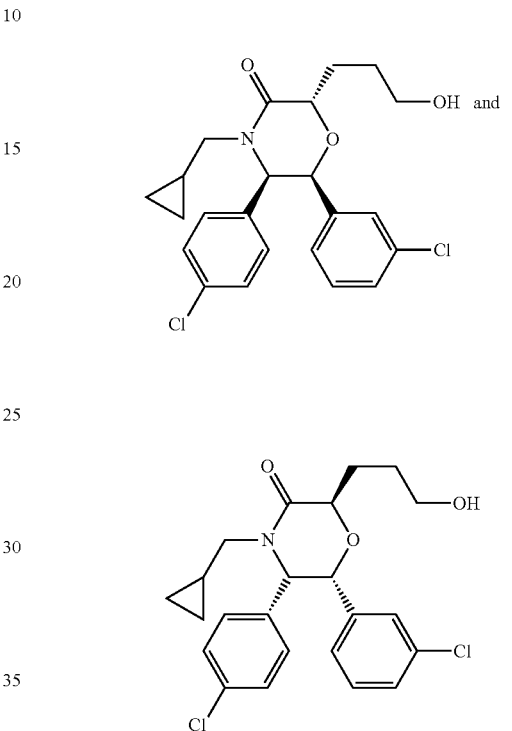

9-Borabicyclo(3.3.1)nonane (1441 µL, 721 µmol, 0.5 M in THF) was added dropwise over 2 minutes to a stirring solution of (2S,5R,6S)-2-allyl-6-(3-chlorophenyl)-5-(4-chlorophenyl)-4-(cyclopropylmethyl)morpholin-3-one and (2R,5S,6R)-2-allyl-6-(3-chlorophenyl)-5-(4-chlorophenyl)-4-(cyclopropylmethyl)morpholin-3-one (100 mg, 240 µmol, Example 14, Step A) in THF at 0° C. The reaction was stirred at this temperature for 3 hours, treated with additional 9-borabicyclo(3.3.1)nonane (1441 µL, 721 µmol) and warmed to 25° C. After 2 hours hydrogen peroxide (44 µL, 1441 µmol) and 3 M aqueous NaOH (0.5 mL) were added. After 2 hours 25° C., the reaction was quenched with aqueous Na$_2$S$_2$O$_3$ and diluted with ether. The separated organic layer was washed with brine, dried, filtered and evaporated under a vacuum. Reverse phase preparative HPLC (Gemini™ Prep C18 5 µm column, Phenomenex, Torrance, Calif., using a gradient elution of 0% to 100% acetonitrile, both eluents containing 0.1% TFA, 45 minutes) gave the title compounds.

1H NMR (400 MHz, CDCl$_3$, δ ppm): 7.07-7.22 (m, 4H), 6.99 (t, J=1.96 Hz, 1H), 6.83 (dt, J=7.63, 1.76 Hz, 1H), 6.71-6.79 (m, 2H), 5.31 (d, J=3.13 Hz, 1H), 4.61-4.71 (m, 2H), 3.84 (dd, J=14.18, 6.36 Hz, 1H), 3.65-3.76 (m, 2H), 2.56 (dd, J=14.18, 7.73 Hz, 1H), 2.18-2.28 (m, 1H), 1.95-2.15 (m, 1H), 1.71-1.87 (m, 2H), 0.84-0.97 (m, 1H), 0.49-0.58 (m, 1H), 0.37-0.46 (m, 1H), 0.15-0.23 (m, 1H), 0.05-0.13 (m, 1H).

Example 20

3-((2S,5R,6S)-6-(3-Chlorophenyl)-5-(4-chlorophenyl)-4-(cyclopropylmethyl)-3-oxomorpholin-2-yl)propanoic acid and 3-((2R,5S,6R)-6-(3-chlorophenyl)-5-(4-chlorophenyl)-4-(cyclopropylmethyl)-3-oxomorpholin-2-yl)propanoic acid

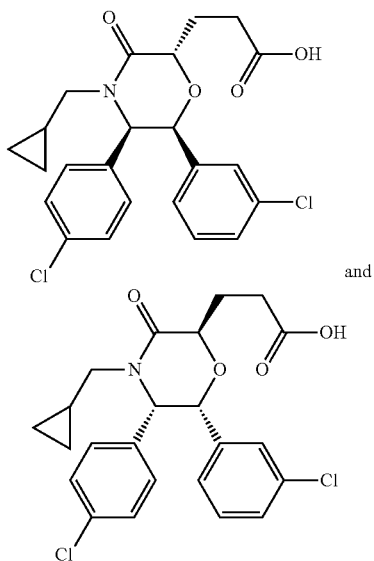

Step A. (3-((2S,5R,6S)-6-(3-Chlorophenyl)-5-(4-chlorophenyl)-4-(cyclopropylmethyl)-3-oxomorpholin-2-yl)propanal and (3-((2R,5S,6R)-6-(3-chlorophenyl)-5-(4-chlorophenyl)-4-(cyclopropylmethyl)-3-oxomorpholin-2-yl)propanal

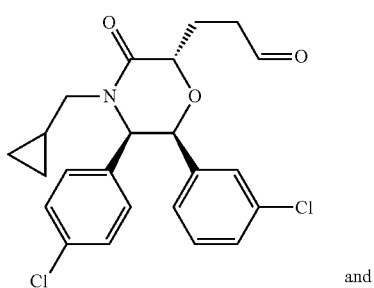

and

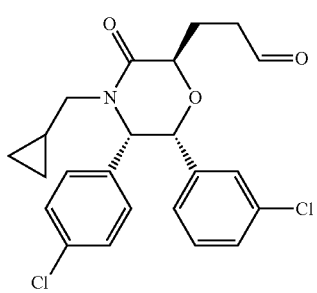

Sodium hydrogen carbonate (17 mg, 207 μmol) and Dess-Martin periodinane (26 mg, 62 μmol) were added to a stirring solution of (2S,5R,6S)-6-(3-chlorophenyl)-5-(4-chlorophenyl)-4-(cyclopropylmethyl)-2-(3-hydroxypropyl)morpholin-3-one and (2R,5S,6R)-6-(3-chlorophenyl)-5-(4-chlorophenyl)-4-(cyclopropylmethyl)-2-(3-hydroxypropyl)morpholin-3-one (18 mg, 41 μmol, Example 19) in DCM (4.0 mL). The reaction was stirred at room temperature for 3 hours, then treated with additional Dess-Martin reagent (26 mg, 62 μmol). After stirring at 25° C. for 1 hour, the reaction was diluted with ethyl acetate and treated with aqueous $Na_2S_2O_3$ and $NaHCO_3$. The mixture was stirred for 30 minutes, and then the separated organic layer was dried, filtered and evaporated under a vacuum to give the title compounds.

$^1$H NMR (400 MHz, $CDCl_3$, δ ppm): 9.74 (t, J=1.27 Hz, 1H), 7.08-7.23 (m, 4H), 6.91-6.99 (m, 1H), 6.82 (dt, J=7.63, 1.76 Hz, 1H), 6.65-6.76 (m, 2H), 5.28 (d, J=3.13 Hz, 1H), 4.58-4.70 (m, 2H), 3.84 (dd, J=14.09, 6.46 Hz, 1H), 2.63-2.74 (m, 2H), 2.57 (dd, J=14.08, 7.63 Hz, 1H), 2.32-2.51 (m, 2H), 0.84-0.96 (m, 1H), 0.50-0.59 (m, 1H), 0.38-0.47 (m, 1H), 0.15-0.23 (m, 1H), 0.05-0.13 (m, 1H).

Step B. (3-((2S,5R,6S)-6-(3-Chlorophenyl)-5-(4-chlorophenyl)-4-(cyclopropylmethyl)-3-oxomorpholin-2-yl)propanoic acid and (3-((2R,5S,6R)-6-(3-chlorophenyl)-5-(4-chlorophenyl)-4-(cyclopropylmethyl)-3-oxomorpholin-2-yl)propanoic acid An aqueous solution of sodium chlorite (5 mg, 52 μmol) and monosodium dihydrogen phosphate (6 mg, 52 μmol) was added to a stirring solution of (3-((2S,5R,6S)-6-(3-chlorophenyl)-5-(4-chlorophenyl)-4-(cyclopropylmethyl)-3-oxomorpholin-2-yl)propanal and (3-((2R,5S,6R)-6-(3-chlorophenyl)-5-(4-chlorophenyl)-4-(cyclopropylmethyl)-3-oxomorpholin-2-yl)propanal (9 mg, 21 μmol, Example 20, Step A) in tert-BuOH (2.5 mL) and 2-methyl-2-butene (1.5 mL) at 0° C. The reaction was stirred in the dark for 4 hours while warming slowly to 25° C. The reaction was diluted with ethyl acetate and water. The separated aqueous layer was extracted with ethyl acetate and the combined organic layers were washed with brine, dried, filtered and evaporated under a vacuum. Preparative reverse phase HPLC (Gemini™ Prep C18 5 μm column, Phenomenex, Torrance, Calif., using a gradient elution of 10% to 90% acetonitrile in water, where both solvents contain 0.1% TFA, 45 minutes) gave the title compounds as a white solid.

$^1$H NMR (400 MHz, $CDCl_3$, δ ppm): 7.02-7.19 (m, 4H), 6.96 (t, J=1.96 Hz, 1H), 6.80 (dt, J=7.48, 1.74 Hz, 1H), 6.69-6.76 (m, 2H), 5.28 (d, J=3.13 Hz, 1H), 4.60-4.66 (m, 2H), 3.83 (dd, J=14.18, 6.36 Hz, 1H), 2.32-2.61 (m, 5H), 0.84-0.96 (m, 1H), 0.50-0.58 (m, 1H), 0.38-0.46 (m, 1H), 0.15-0.23 (m, 1H), 0.05-0.12 (m, 1H); HRMS calcd for $C_{23}H_{23}Cl_2NO_4$, 448.1077; found, 448.1081.

Example 21

2-((2S,5R,6S)-6-(3-Chlorophenyl)-5-(4-chlorophenyl)-4-(cyclopropylmethyl)-3-oxomorpholin-2-yl)acetic acid

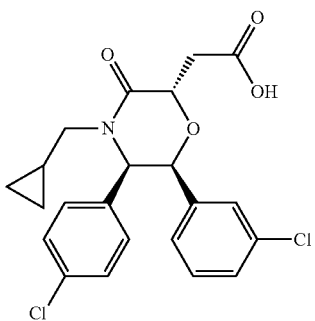 [SMILES: O=C(O)C[C@@H]1O[C@@H](c2cccc(Cl)c2)[C@@H](c2ccc(Cl)cc2)N(CC2CC2)C1=O]

The enantiomers from (2-((2S,5R,6S)-6-(3-chlorophenyl)-5-(4-chlorophenyl)-4-(cyclopropylmethyl)-3-oxomorpholin-2-yl)acetic acid and (2-((2R,5S,6R)-6-(3-chlorophenyl)-5-(4-chlorophenyl)-4-(cyclopropylmethyl)-3-oxomorpholin-2-yl)acetic acid (Example 17) were separated by chiral HPLC (flow rate: 18 mL/min, Chiralcel® OD-H 30 mm I.D.×250 mm, 5 µm column (Daicel Inc., Fort Lee, N.J.), eluent: 40% isopropyl alcohol in hexanes) to give the title compound as the first (faster) eluting isomer ($t_R$=8.2 minutes, $[\alpha]_D^{23}$+158° (c 1.12, MeOH).

$^1$H NMR (400 MHz, CDCl$_3$, δ ppm): 7.08-7.20 (m, 4H), 6.95-6.98 (m, 1H), 6.81 (dt, J=7.63, 1.56 Hz, 1H), 6.72-6.77 (m, 2H), 5.29-5.36 (m, 1H), 5.15-5.20 (m, 1H), 4.66 (d, J=3.13 Hz, 1H), 3.78 (dd, J=14.09, 6.46 Hz, 1H), 3.22 (dd, J=16.24, 5.09 Hz, 1H), 3.02 (dd, J=16.24, 7.83 Hz, 1H), 2.71 (dd, J=14.09, 7.63 Hz, 1H), 0.84-0.97 (m, 1H), 0.50-0.58 (m, 1H), 0.38-0.46 (m, 1H), 0.20 (dq, J=9.76, 4.77 Hz, 1H), 0.05-0.13 (m, 1H); MS (ESI) 434.0 [M+H]$^+$.

Example 22

2-((2R,5S,6R)-6-(3-chlorphenyl)-5-(4-chlorophenyl)-4-(cyclopropylmethyl)-3-oxomorpholin-2-yl)acetic acid

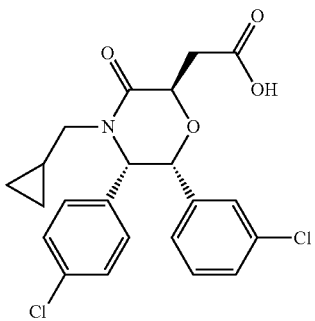 [SMILES: O=C(O)C[C@H]1O[C@H](c2cccc(Cl)c2)[C@H](c2ccc(Cl)cc2)N(CC2CC2)C1=O]

Further elution from Example 21 provided the title compound as the second (slower) eluting isomer ($t_R$=12.4 minutes, $[\alpha]_D^{23}$-156° (c 1.13, MeOH).

$^1$H NMR (400 MHz, CDCl$_3$, δ ppm): 7.08-7.20 (m, 4H), 6.95-6.98 (m, 1H), 6.81 (dt, J=7.63, 1.56 Hz, 1H), 6.72-6.77 (m, 2H), 5.29-5.36 (m, 1H), 5.15-5.20 (m, 1H), 4.66 (d, J=3.13 Hz, 1H), 3.78 (dd, J=14.09, 6.46 Hz, 1H), 3.22 (dd, J=16.24, 5.09 Hz, 1H), 3.02 (dd, J=16.24, 7.83 Hz, 1H), 2.71 (dd, J=14.09, 7.63 Hz, 1H), 0.84-0.97 (m, 1H), 0.50-0.58 (m, 1H), 0.38-0.46 (m, 1H), 0.20 (dq, J=9.76, 4.77 Hz, 1H), 0.05-0.13 (m, 1H); MS (ESI) 434.0 [M+H]$^+$.

Example 23

2-((2S,5R,6S)-6-(3-Chlorophenyl)-5-(4-chlorophenyl)-4-(cyclobutylmethyl)-3-oxomorpholin-2-yl)acetic acid and 2-((2R,5S,6R)-6-(3-chlorophenyl)-5-(4-chlorophenyl)-4-(cyclobutylmethyl)-3-oxomorpholin-2-yl)acetic acid

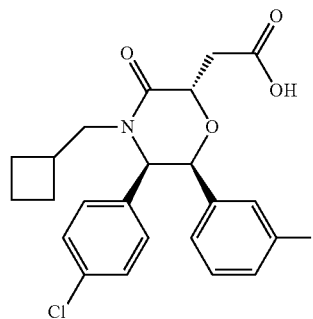

and

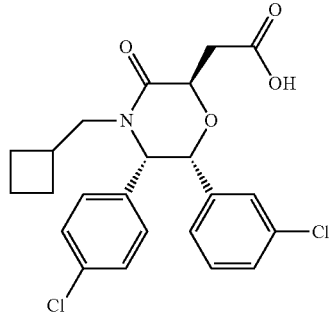

Step A. (5R,6S)-6-(3-Chlorophenyl)-5-(4-chlorophenyl)-4-(cyclobutylmethyl)morpholin-3-one and (5S,6R)-6-(3-chlorophenyl)-5-(4-chlorophenyl)-4-(cyclobutylmethyl)morpholin-3-one

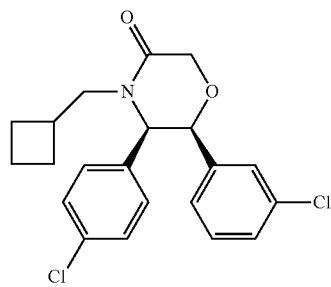

and

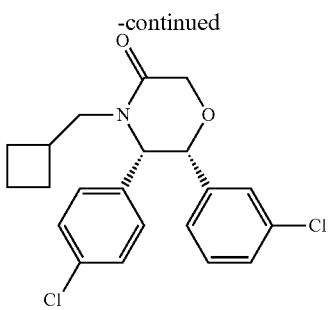

The title compounds were prepared from (5R,6S)-6-(3-chlorophenyl)-5-(4-chlorophenyl)morpholin-3-one and (5S,6R)-6-(3-chlorophenyl)-5-(4-chlorophenyl)morpholin-3-one (Example 11, Step D) using the method described in Example 12, substituting cyclobutylmethyl bromide for cyclopropylmethyl bromide.

$^1$H NMR (400 MHz, CDCl$_3$, δ ppm): 7.18-7.07 (m, 5H), 6.92 (s, 1H), 6.80-6.73 (m, 2H), 5.08 (d, J=4.0 Hz, 1H), 4.63 (d, J=16.0 Hz, 1H), 4.48 (d, J=16.0 Hz, 1H), 4.39 (d, J=4.0 Hz, 1 Hz, 1H), 3.85-3.95 (m, 1H), 2.75-2.80 (m, 1H), 2.53-2.65 (m, 1H), 2.04-1.60 (m, 6H); MS (ESI) 390.7 [M+H]$^+$.

Step B. (2S,5R,6S)-2-Allyl-6-(3-chlorophenyl)-5-(4-chlorophenyl)-4-(cyclobutylmethyl)morpholin-3-one and (2R,5S,6R)-2-Allyl-6-(3-chlorophenyl)-5-(4-chlorophenyl)-4-(cyclobutylmethyl)morpholin-3-one

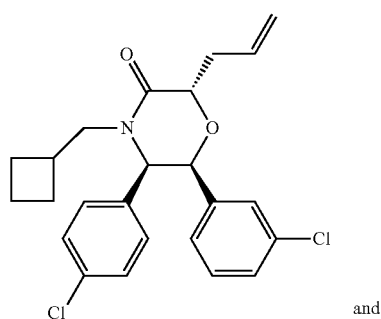
and
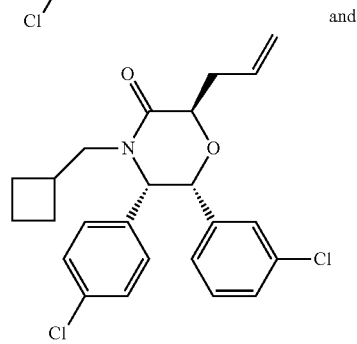

The title compounds were prepared from (2S,5R,6S)-2-allyl-6-(3-chlorophenyl)-5-(4-chlorophenyl)-4-(cyclobutylmethyl)morpholin-3-one and (2R,5S,6R)-2-allyl-6-(3-chlorophenyl)-5-(4-chlorophenyl)-4-(cyclobutylmethyl)morpholin-3-one (Example 23, Step A) using the method described in Example 14, Step A.

$^1$H NMR (400 MHz, CDCl$_3$, δ ppm): 7.20-7.07 (m, 4H), 6.95 (s, 1H), 6.75-6.85 (m, 1H), 6.72 (d, J=12.0 Hz, 2H), 5.80-6.00 (m, 1H), 5.31 (s, 1H), 5.17-5.08 (m, 2H), 4.65-4.73 (m, 1H), 4.38 (s, 1H), 3.90-4.00 (m, 1H), 2.85-2.56 (m, 3H), 2.50-2.60 (m, 1H), 2.09-1.66 (m, 4H), 1.65-1.75 (m, 2H); MS (ESI) 430.1 [M+H]$^+$.

Step C. 2-((2S,5R,6S)-6-(3-Chlorophenyl)-5-(4-chlorophenyl)-4-(cyclobutylmethyl)-3-oxomorpholin-2-yl)acetic acid and 2-((2R,5S,6R)-6-(3-chlorophenyl)-5-(4-chlorophenyl)-4-(cyclobutylmethyl)-3-oxomorpholin-2-yl)acetic acid

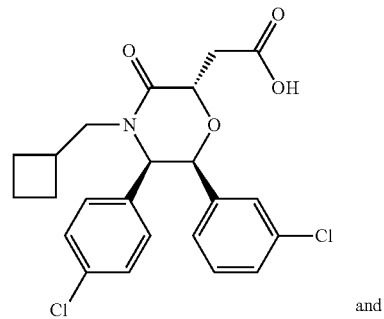
and
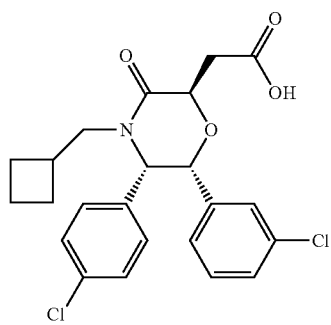

Sodium periodate (60 mg, 279 μmol) and ruthenium trichloride hydrate (0.8 mg, 3.6 μmol) were added to a stirring solution of (2S,5R,6S)-2-allyl-6-(3-chlorophenyl)-5-(4-chlorophenyl)-4-(cyclobutylmethyl)morpholin-3-one and (2R,5S,6R)-2-allyl-6-(3-chlorophenyl)-5-(4-chlorophenyl)-4-(cyclobutylmethyl)morpholin-3-one (30 mg, 70 umol, Example 23, Step B) in CCl$_4$:acetonitrile:water (1 mL:1 mL:2 mL). The reaction was stirred at room temperature for 4 hours, treated with ethyl acetate, and acidified to pH 2 with 1 M HCl. The separated aqueous layer was extracted with ethyl acetate and the combined organic layers were dried, filtered and evaporated under a vacuum. The residue was purified by preparative reverse phase HPLC (Gemini™ Prep C18 5 μm column, Phenomenex, Torrance, Calif., gradient elution of 0% to 100% acetonitrile, both eluents containing 0.1% TFA, 45 minutes) to give the title compounds.

$^1$H NMR (400 MHz, CDCl$_3$, δ ppm): 1.61-1.75 (m, 2H), 1.77-1.96 (m, 3H), 1.96-2.05 (m, 1H), 2.48-2.59 (m, 1H), 2.87-3.03 (m, 2H), 3.17 (dd, J=16.14, 5.38 Hz, 1H), 3.83 (dd, J=13.79, 7.53 Hz, 1H), 4.40 (d, J=2.93 Hz, 1H), 5.12-5.17 (m, 1H), 5.23-5.28 (m, 1H), 6.66-6.75 (m, 2H), 6.75-6.81 (m, 1H), 6.90-6.95 (m, 1H), 7.05-7.13 (m, 1H), 7.13-7.22 (m, 3H). MS (ESI) 448.1 [M+H]$^+$.

Example 24

(2S,5R,6S)-6-(3-Chlorophenyl)-5-(4-chlorophenyl)-4-isobutyl-3-oxomorpholin-2-yl)acetic acid and (2R,5S,6R)-6-(3-chlorophenyl)-5-(4-chlorophenyl)-4-isobutyl-3-oxomorpholin-2-yl)acetic acid

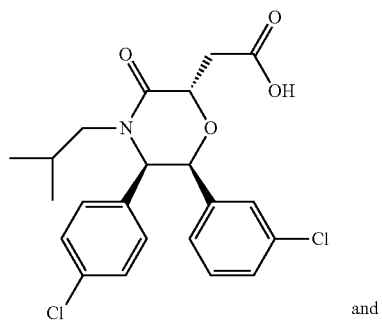

and

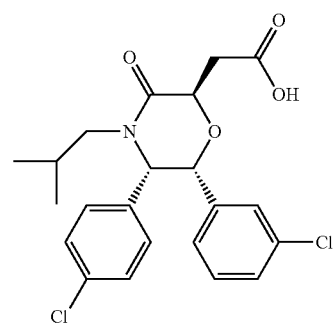

The title compounds were prepared from (5R,6S)-6-(3-chlorophenyl)-5-(4-chlorophenyl)morpholin-3-one and (5S,6R)-6-(3-chlorophenyl)-5-(4-chlorophenyl)morpholin-3-one (Example 11, Step D) using the methods described in Example 23, Steps A to C, substituting isobutyl bromide for cyclopropylmethyl bromide in Step A.

$^1$H NMR (400 MHz, CDCl$_3$, δ ppm): 0.89-1.00 (m, 6H), 1.97-2.08 (m, 1H), 2.42 (dd, J=13.60, 6.94 Hz, 1H), 3.05 (dd, J=16.33, 7.73 Hz, 1H), 3.20 (dd, J=16.33, 4.99 Hz, 1H), 3.80 (dd, J=13.50, 8.41 Hz, 1H), 4.44 (d, J=2.93 Hz, 1H), 5.14 (dd, J=7.73, 4.99 Hz, 1H), 5.29-5.36 (m, 1H), 6.70-6.76 (m, 2H), 6.81 (dt, J=7.63, 1.66 Hz, 1H), 6.96 (t, J=1.96 Hz, 1H), 7.08-7.21 (m, 4H); MS (ESI) 436.1 [M+H]$^+$.

Example 25

2-((2S,5R,6S)-6-(3-Chlorophenyl)-5-(4-chlorophenyl)-4-(cyclohexylmethyl)-3-oxomorpholin-2-yl)acetic acid and 2-((2R,5S,6R)-6-(3-chlorophenyl)-5-(4-chlorophenyl)-4-(cyclohexylmethyl)-3-oxomorpholin-2-yl)acetic acid

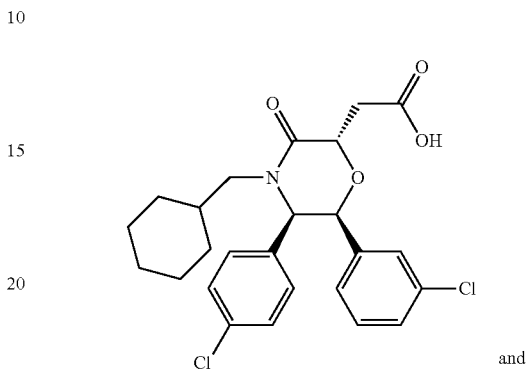

and

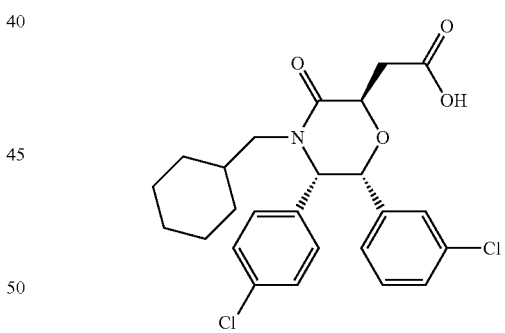

The title compounds were prepared from (5R,6S)-6-(3-chlorophenyl)-5-(4-chlorophenyl)morpholin-3-one and (5S,6R)-6-(3-chlorophenyl)-5-(4-chlorophenyl)morpholin-3-one (Example 11, Step D) using the methods described in Example 23, Steps A to C, substituting cyclohexylmethyl-bromide for cyclopropylmethyl bromide in Step A.

$^1$H NMR (400 MHz, MeOH-d$_4$, δ ppm): 0.89-1.07 (m, 2H), 1.13-1.22 (m, 2H), 1.58-1.80 (m, 6H), 2.60 (dd, J=13.69, 6.85 Hz, 1H), 2.96-3.12 (m, 2H), 3.64 (dd, J=13.69, 7.63 Hz, 1H), 4.68 (d, J=3.13 Hz, 1H), 4.80-4.90 (m, 1H), 5.18 (dd, J=9.10, 4.01 Hz, 1H), 5.55 (d, J=3.13 Hz, 1H), 6.86-6.94 (m, 2H), 6.96-7.04 (m, 2H), 7.13-7.23 (m, 4H). MS (ESI) 476.2 [M+H]$^+$.

Example 26

2-((2S,5R,6S)-4-Benzyl-6-(3-chlorophenyl)-5-(4-chlorophenyl)-3-oxomorpholin-2-yl)acetic acid and 2-((2R,5S,6R)-4-benzyl-6-(3-chlorophenyl)-5-(4-chlorophenyl)-3-oxomorpholin-2-yl)acetic acid

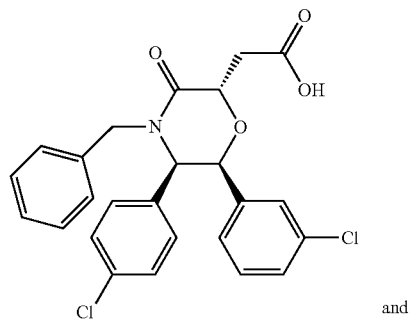

and

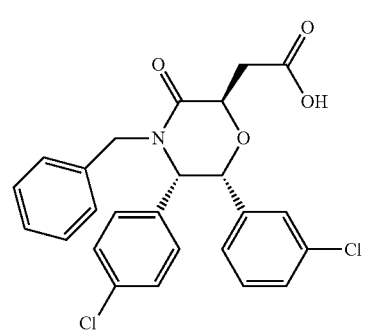

The title compounds were prepared from (5R,6S)-6-(3-chlorophenyl)-5-(4-chlorophenyl)morpholin-3-one and (5S,6R)-6-(3-chlorophenyl)-5-(4-chlorophenyl)morpholin-3-one (Example 11, Step D) using the methods described in Example 23, Steps A to C, substituting benzylbromide for cyclopropylmethyl bromide in Step A.

$^1$H NMR (400 MHz, CDCl$_3$, δ ppm): 3.00-3.25 (m, 2H), 3.51 (d, J=14.48 Hz, 1H), 4.28-4.35 (m, 1H), 5.22 (dd, J=2.35, 0.59 Hz, 1H), 5.25-5.34 (m, 1H), 5.45-5.59 (m, 1H), 6.66-6.79 (m, 3H), 6.81-6.88 (m, 1H), 7.01-7.09 (m, 1H), 7.09-7.25 (m, 5H), 7.33-7.45 (m, 3H). MS (ESI) 470.0 [M+H]$^+$.

Example 27

(R)-2-((2S,3R,6S)-2,3-Bis(4-chlorophenyl)-6-(4-fluorobenzyl)-5-oxomorpholino)-N-(methylsulfonyl)pentanamide and (S)-2-((2R,3S,6R)-2,3-bis(4-chlorophenyl)-6-(4-fluorobenzyl)-5-oxomorpholino)-N-(methylsulfonyl)pentanamide

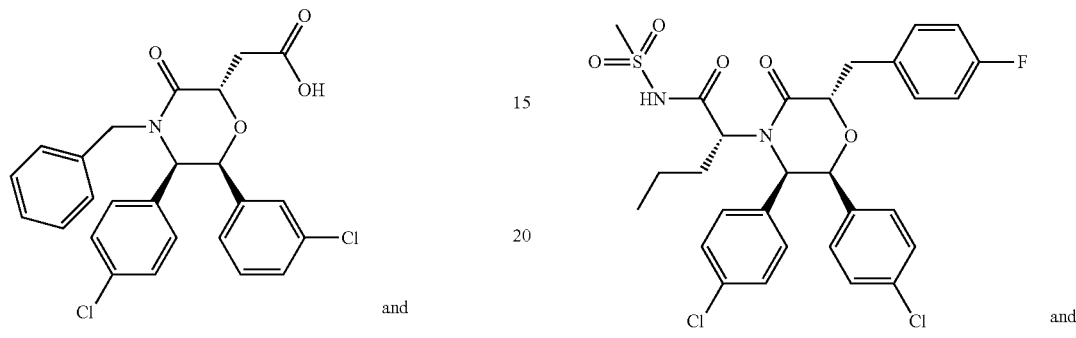

and

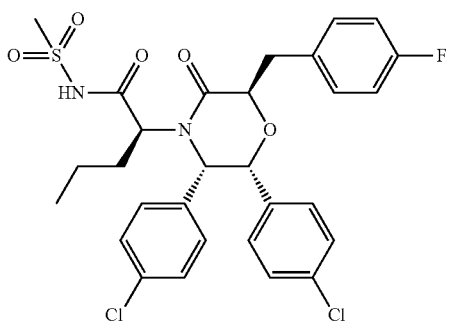

Step A. (R)-2-((2S,5R,6S)-2-(4-fluorobenzyl)-5,6-bis(4-chlorophenyl)-3-oxomorpholino)pentanoic acid and (S)-2-((2R,5S,6R)-2-(4-fluorobenzyl)-5,6-bis(4-chlorophenyl)-3-oxomorpholino)pentanoic acid

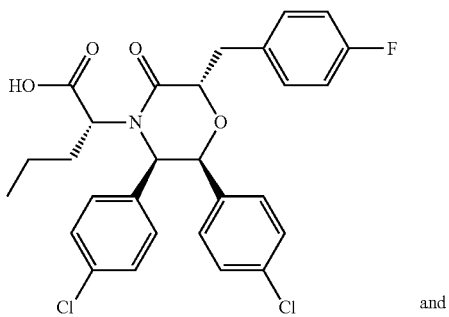

and

-continued

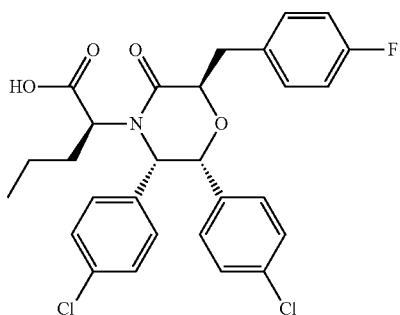

The title compounds were prepared from (R)-ethyl 2-((2S,3R)-2,3-bis(4-chlorophenyl)-5-oxomorpholino)pentanoate and (S)-ethyl 2-((2R,3S)-2,3-bis(4-chlorophenyl)-5-oxomorpholino)pentanoate (Example 10, Step A) using the methods described in Example 10, Steps C and D.

Step B. (R)-2-((2S,3R,6S)-2,3-Bis(4-chlorophenyl)-6-(4-fluorobenzyl)-5-oxomorpholino)-N-(methylsulfonyl)pentanamide and (S)-2-((2R,3S,6R)-2,3-bis(4-chlorophenyl)-6-(4-fluorobenzyl)-5-oxomorpholino)-N-(methylsulfonyl)pentanamide Methanesulfonamide (65 mg, 679 µmol) was added to a solution of 1,1'-carbonyldiimidazole (110 mg, 679 µmol), N-ethyl-N-isopropylpropan-2-amine (151 µL, 848 µmol) and (R)-2-((2S,5R,6S)-2-(4-fluorobenzyl)-5,6-bis(4-chlorophenyl)-3-oxomorpholino)pentanoic acid and (S)-2-((2R,5S,6R)-2-(4-fluorobenzyl)-5,6-bis(4-chlorophenyl)-3-oxomorpholino)pentanoic acid (90 mg, 0.17 mmol, Example 27, Step A) in THF (2 mL). The reaction was stirred at reflux for 12 hours, quenched with saturated NH$_4$Cl solution, and extracted with ethyl acetate. The organic layer was dried over MgSO$_4$ and concentrated under reduced pressure. The residue was purified by preparative reverse phase HPLC (Gemini™ Prep C18 5 µm column (Phenomenex, Torrance, Calif.), (40 minutes, elution gradient of 50% to 90% acetonitrile in water, where both solvents contain 0.1% TFA) to give the title compounds as a white solid.

$^1$H NMR (400 MHz, DMSO-d$_6$, δ ppm): 7.26-7.18 (m, 6H), 7.05-6.95 (m, 4H), 6.88 (d, J=8.0 Hz, 2H), 5.30 (d, J=4.0 Hz, 1H), 5.06 (m, 1H), 5.0 (d, J=4.0 Hz, 1H), 4.93 (m, 1H), 3.32 (s, 3H), 3.29 (m, 1H), 3.15-3.25 (m, 1H), 1.50-1.65 (m, 1H), 1.40-1.45 (m, 1H), 0.95-1.10 (m, 1H), 0.65-0.80 (m, 1H), 0.41 (t, J=8.0 Hz, 3H); MS (ESI) 607.2 [M+H]$^+$.

Example 28

1-((R)-2-((2S,3R,6S)-2,3-Bis(4-chlorophenyl)-6-(4-fluorobenzyl)-5-oxomorpholino)pentanoyl)azetidine-3-carboxylic acid and 1-((S)-2-((2R,3S,6R)-2,3-bis(4-chlorophenyl)-6-(4-fluorobenzyl)-5-oxomorpholino)pentanoyl)azetidine-3-carboxylic acid

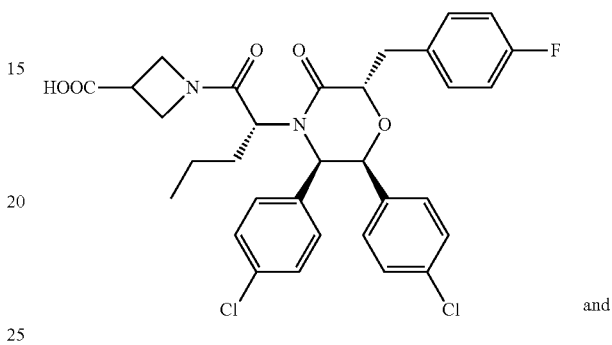

and

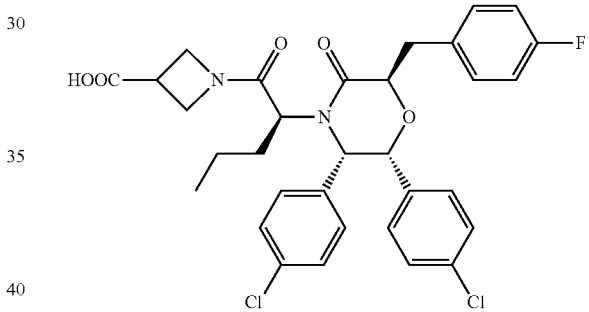

Step A. Methyl 1-((R)-2-((2S,3R,6S)-2,3-bis(4-chlorophenyl)-6-(4-fluorobenzyl)-5-oxomorpholino)pentanoyl)azetidine-3-carboxylate and methyl 1-((S)-2-((2R,3S,6R)-2,3-bis(4-chlorophenyl)-6-(4-fluorobenzyl)-5-oxomorpholino)pentanoyl)azetidine-3-carboxylate

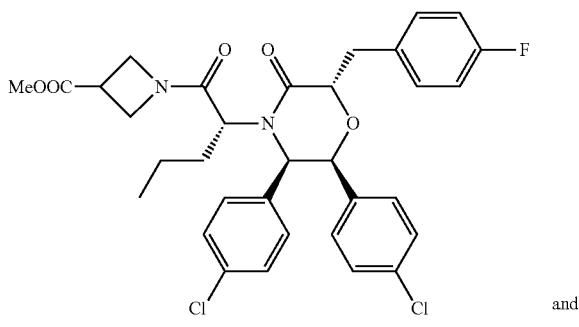

and

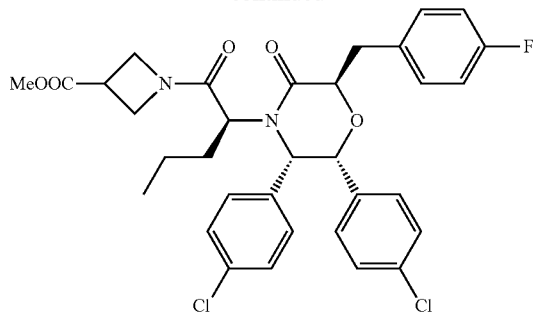

N-Ethyl-N'-(3-dimethylaminopropyl)carbodiimide hydrochloride (30 mg, 0.158 mmol), HOAt (22 mg, 0.158 mmol) and sodium bicarbonate (22 mg, 0.264 mmol) were successively added to a solution of (R)-2-((2S,5R,6S)-2-(4-fluorobenzyl)-5,6-bis(4-chlorophenyl)-3-oxomorpholino)pentanoic acid and (S)-2-((2R,5S,6R)-2-(4-fluorobenzyl)-5,6-bis(4-chlorophenyl)-3-oxomorpholino)pentanoic acid (70 mg, 0.132 mmol, Example 27, Step A) and methyl azetidine-3-carboxylate (18 mg, 0.158 mmol) in DMF (1.5 mL). After stirring at room temperature for 18 hours, the reaction was diluted with ethyl acetate and washed with brine. The organic layer was dried over $MgSO_4$ and concentrated. Purification of the residue by flash chromatography ($SiO_2$, eluent 50% ethyl acetate/hexanes) provided the title compounds.

$^1$H NMR (400 MHz, $CDCl_3$, δ ppm): 7.16-7.06 (m, 6H), 6.85-6.95 (m, 2H), 6.80-6.85 (m, 2H), 6.68-6.75 (m, 2H), 5.23 (s, 1H), 5.06 (s, 1H), 5.05 (s, 1H), 4.83-4.93 (m, 1H), 4.62-4.75 (m, 1H), 4.40-4.20 (m, 3H), 3.01 (s, 3H), 3.52-3.22 (m, 3H), 1.35-1.50 (m, 1H), 1.15-1.25 (m, 3H), 0.60 (t, J=8.0 Hz, 3H); MS (ESI) 627.1 [M+H]$^-$.

Step B. 1-((R)-2-((2S,3R,6S)-2,3-Bis(4-chlorophenyl)-6-(4-fluorobenzyl)-5-oxomorpholino)pentanoyl)azetidine-3-carboxylic acid and 1-((S)-2-((2R,3S,6R)-2,3-bis(4-chlorophenyl)-6-(4-fluorobenzyl)-5-oxomorpholino)pentanoyl)azetidine-3-carboxylic acid The title compounds were prepared from methyl 1-((R)-2-((2S,3R,6S)-2,3-bis(4-chlorophenyl)-6-(4-fluorobenzyl)-5-oxomorpholino)pentanoyl)azetidine-3-carboxylate and methyl 1-((S)-2-((2R,3S,6R)-2,3-bis(4-chlorophenyl)-6-(4-fluorobenzyl)-5-oxomorpholino)pentanoyl)azetidine-3-carboxylate (Example 28, Step A) using the method described in Example 10, Step D.

$^1$H NMR (400 MHz, $CDCl_3$, δ ppm): 7.16-7.30 (m, 6H), 7.00-7.10 (m, 2H), 6.75-6.95 (m, 4H), 4.85-5.50 (m, 4H), 3.90-4.60 (m, 5H), 3.20-3.60 (m, 3H), 1.25-1.40 (m, 1H), 0.95-1.10 (m, 1H), 0.80-0.95 (m, 1H), 0.50 (t, J=8.0 Hz, 3H); MS (ESI) 613.2 [M+H]$^+$.

Example 29

(R)-2-((2S,3R,6S)-2-(4-Chloro-3-fluorophenyl)-3-(4-chlorophenyl)-6-(4-fluorobenzyl)-5-oxomorpholino)pentanoic acid and (S)-2-((2R,3S,6R)-2-(4-chloro-3-fluorophenyl)-3-(4-chlorophenyl)-6-(4-fluorobenzyl)-5-oxomorpholino)pentanoic acid or (S)-2-((2S,3R,6S)-2-(4-chloro-3-fluorophenyl)-3-(4-chlorophenyl)-6-(4-fluorobenzyl)-5-oxomorpholino)pentanoic acid and (R)-2-((2R,3S,6R)-2-(4-chloro-3-fluorophenyl)-3-(4-chlorophenyl)-6-(4-fluorobenzyl)-5-oxomorpholino)pentanoic acid

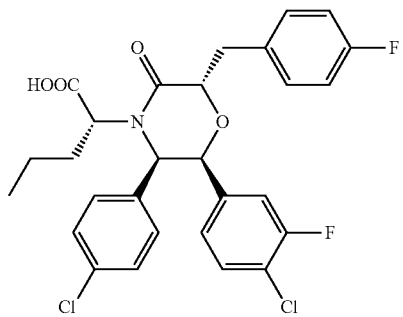

and

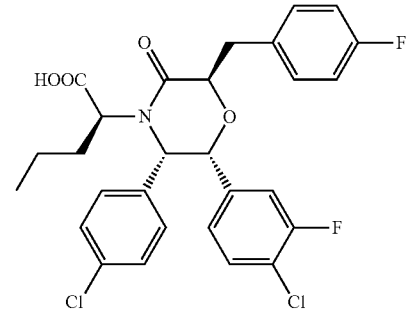

or

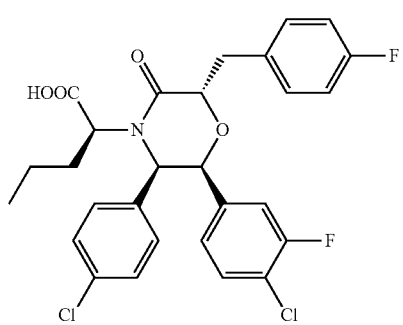

and

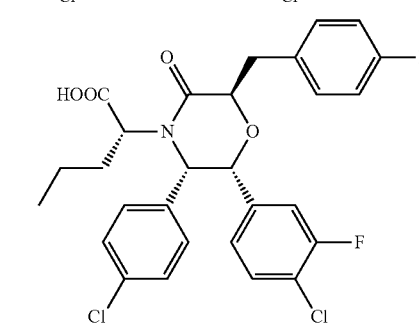

Step A. (5R,6S)-6-(4-Chloro-3-fluorophenyl)-5-(4-chlorophenyl)morpholin-3-one and (5S,6R)-6-(4-chloro-3-fluorophenyl)-5-(4-chlorophenyl)morpholin-3-one

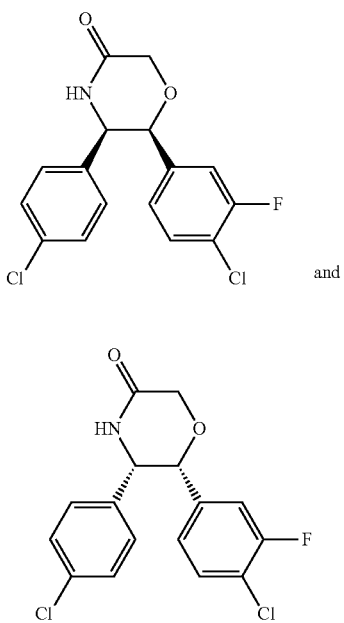

and

The title compounds were prepared as described in Example 4, Steps A to F, substituting 3-fluoro-4-chlorophenylmagnesium bromide for 4-chlorophenylmagnesium bromide in Step C.

1H NMR (400 MHz, DMSO-$d_6$, δ ppm): 8.77 (d, J=4.0 Hz, 1H), 7.35-7.45 (m, 1H), 7.24 (d, J=4.0 Hz, 2H), 7.05 (d, J=4.0 Hz, 1H), 6.95-6.80 (m, 3H), 5.28 (d, J=4.0 Hz, 1H), 4.81 (d, J=4.0 Hz, 1H), 4.49 (d, J=12.0 Hz, 1H), 4.38 (d, J=12.0 Hz, 1H); MS (ESI) 340.0 [M+H]$^+$.

Step B. (R)-2-((2S,3R,6S)-2-(4-Chloro-3-fluorophenyl)-3-(4-chlorophenyl)-6-(4-fluorobenzyl)-5-oxomorpholino)pentanoic acid and (S)-2-((2R,3S,6R)-2-(4-Chloro-3-fluorophenyl)-3-(4-chlorophenyl)-6-(4-fluorobenzyl)-5-oxomorpholino)pentanoic acid or (S)-2-((2S,3R,6S)-2-(4-chloro-3-fluorophenyl)-3-(4-chlorophenyl)-6-(4-fluorobenzyl)-5-oxomorpholino)pentanoic acid and (R)-2-((2R,3S,6R)-2-(4-chloro-3-fluorophenyl)-3-(4-chlorophenyl)-6-(4-fluorobenzyl)-5-oxomorpholino)pentanoic acid The title compounds were prepared from (5R,6S)-6-(4-chloro-3-fluorophenyl)-5-(4-chlorophenyl)morpholin-3-one and (5S,6R)-6-(4-chloro-3-fluorophenyl)-5-(4-chlorophenyl)morpholin-3-one (Example 29, Step A) by the methods described in Example 10, Steps A, C and D.

$^1$H NMR (400 MHz, CDCl$_3$, δ ppm): 7.15-7.04 (m, 5H), 6.75-6.85 (m, 2H), 6.65-6.75 (m, 2H), 6.56-6.49 (m, 2H), 4.91 (s, 1H), 4.85 (s, 1H), 4.45-4.65 (m, 1H), 4.40 (s, 1H), 3.10-3.30 (m, 2H), 1.75-1.90 (m, 1H), 1.35-1.55 (m, 1H), 1.10-1.20 (m, 1H), 0.90-1.10 (m, 1H), 0.60 (s, 3H); MS (ESI) 548.0 [M+H]$^+$.

Example 30

(R)-2-((2S,3R,6S)-2-(4-Chloro-2-methylphenyl)-3-(4-chlorophenyl)-6-(4-fluorobenzyl)-5-oxomorpholino)pentanoic acid and (S)-2-((2R,3S,6R)-2-(4-chloro-2-methylphenyl)-3-(4-chlorophenyl)-6-(4-fluorobenzyl)-5-oxomorpholino)pentanoic acid or (S)-2-((2S,3R,6S)-2-(4-chloro-2-methylphenyl)-3-(4-chlorophenyl)-6-(4-fluorobenzyl)-5-oxomorpholino)pentanoic acid and (R)-2-((2R,3S,6R)-2-(4-chloro-2-methylphenyl)-3-(4-chlorophenyl)-6-(4-fluorobenzyl)-5-oxomorpholino)pentanoic acid

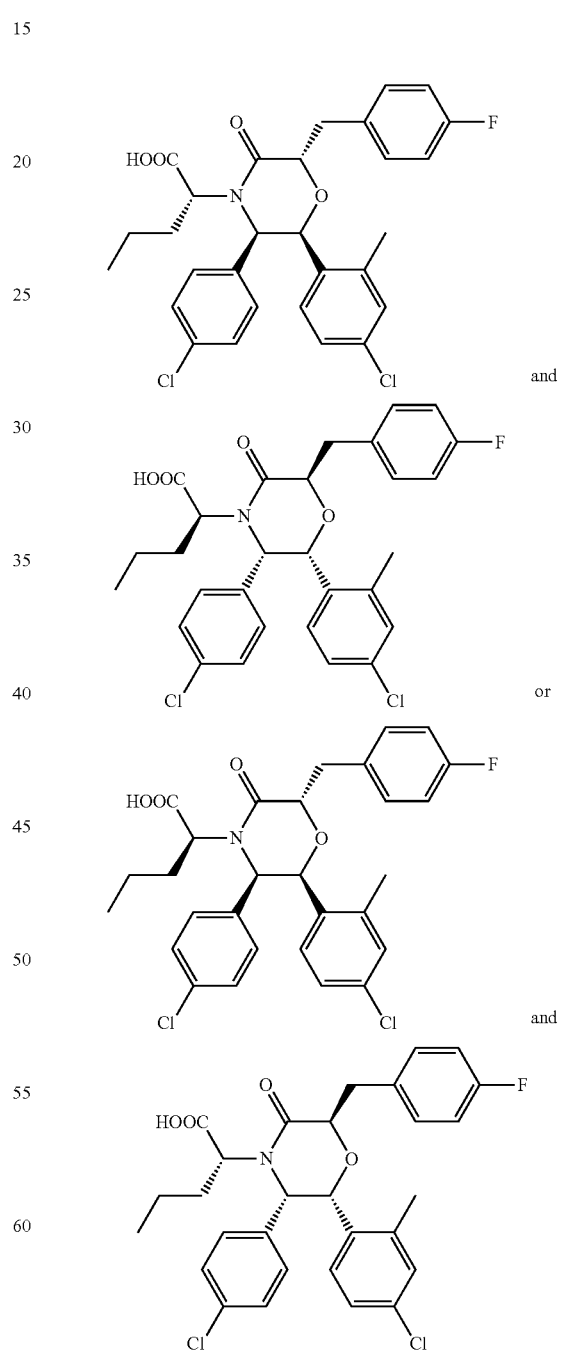

121

Step A. (5R,6S)-6-(4-Chloro-2-methylphenyl)-5-(4-chlorophenyl)morpholin-3-one and (5S,6R)-6-(4-chloro-2-methylphenyl)-5-(4-chlorophenyl)morpholin-3-one

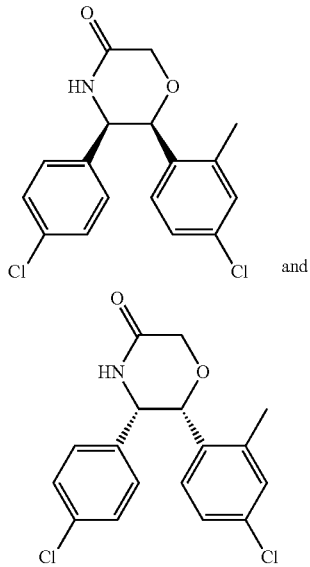

and

The title compounds were prepared as described in Example 4, Steps A to F, substituting 4-chloro-2-methylphenylmagnesium bromide for 4-chlorophenylmagnesium bromide in Step C.

1H NMR (400 MHz, DMSO-$d_6$, δ ppm): 8.70 (s, 1H), 7.20-7.25 (m, 3H), 6.80-6.90 (m, 3H), 6.43 (d, J=8.0 Hz, 1H), 5.33 (d, J=4.0 Hz, 1H), 4.65-4.75 (m, 1H), 4.30-4.50 (m, 2H), 2.42 (s, 3H).

Step B. (R)-2-((2S,3R,6S)-2-(4-Chloro-2-methylphenyl)-3-(4-chlorophenyl)-6-(4-fluorobenzyl)-5-oxomorpholino)pentanoic acid and (S)-2-((2R,3S,6R)-2-(4-chloro-2-methylphenyl)-3-(4-chlorophenyl)-6-(4-fluorobenzyl)-5-oxomorpholino)pentanoic acid or (S)-2-((2S,3R,6S)-2-(4-chloro-2-methylphenyl)-3-(4-chlorophenyl)-6-(4-fluorobenzyl)-5-oxomorpholino)pentanoic acid and (R)-2-((2R,3S,6R)-2-(4-chloro-2-methylphenyl)-3-(4-chlorophenyl)-6-(4-fluorobenzyl)-5-oxomorpholino)pentanoic acid The title compounds were prepared from (5R,6S)-6-(4-chloro-2-methylphenyl)-5-(4-chlorophenyl)morpholin-3-one and (5S,6R)-6-(4-chloro-2-methylphenyl)-5-(4-chlorophenyl)morpholin-3-one (Example 30, Step A) by the methods described in Example 10, Steps A, C and D.

$^1$H NMR (400 MHz, CDCl$_3$, δ ppm): 7.32-7.24 (m, 5H), 7.10-7.07 (m, 2H), 6.80-7.01 (m, 3H), 6.55 (d J=4.0 Hz, 1H), 5.19 (d, J=4.0 Hz, 1H), 5.11 (s, 1H), 4.75-4.90 (m, 1H), 4.57 (s, 1H), 3.65-3.75 (m, 1H), 3.30-3.45 (m, 1H), 2.27 (s, 3H), 1.95-2.10 (m, 1H), 1.70-1.85 (m, 1H), 1.45-1.55 (m, 1H), 1.20-1.35 (m, 1H), 0.60 (t, J=8.0 Hz, 3H); MS (ESI) 542.0 [M–H]$^+$.

Example 31

(R)-4-((2S,3R,6S)-2,3-Bis(4-chlorophenyl)-6-(4-fluorobenzyl)-5-oxomorpholino)heptanoic acid and (S)-4-((2R,3S,6R)-2,3-bis(4-chlorophenyl)-6-(4-fluorobenzyl)-5-oxomorpholino)heptanoic acid

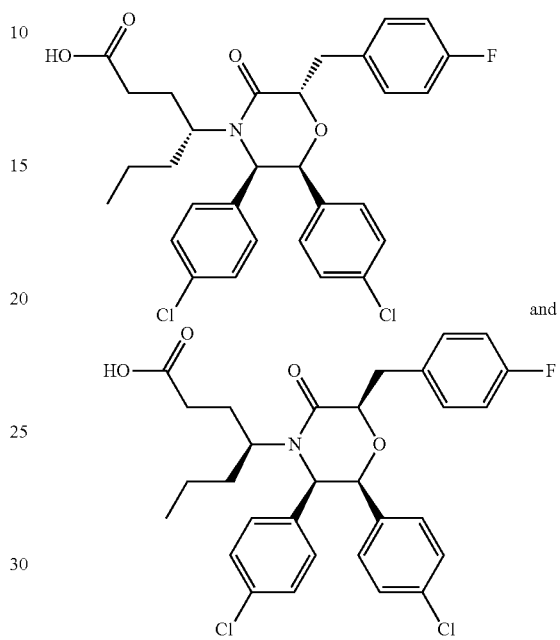

and

Step A. (R)-Ethyl 2-((2S,5R,6S)-2-(4-fluorobenzyl)-5,6-bis(4-chlorophenyl)-3-oxomorpholino)pentanoate and (S)-ethyl 2-((2R,5S,6R)-2-(4-fluorobenzyl)-5,6-bis(4-chlorophenyl)-3-oxomorpholino)pentanoate

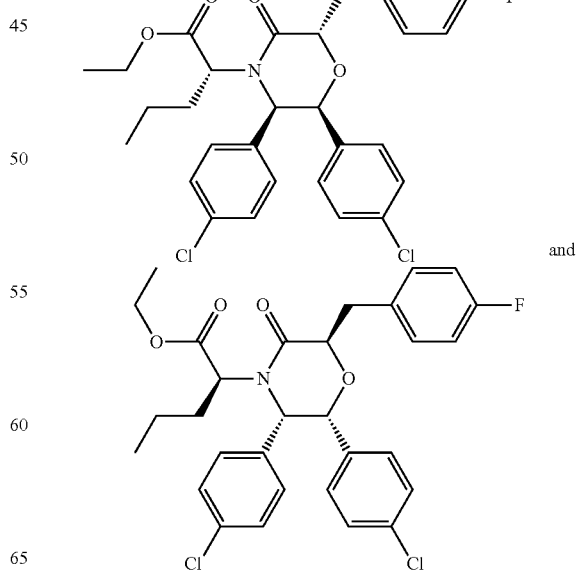

and

The title compounds were prepared from (R)-ethyl 2-((2S,3R)-2,3-bis(4-chlorophenyl)-5-oxomorpholino)pentanoate and (S)-ethyl 2-((2S,3R)-2,3-bis(4-chlorophenyl)-5-oxomorpholino)pentanoate (Example 10, Step A) by the method described in Example 10, Step C.

Step B. (2S,5R,6S)-5,6-Bis(4-chlorophenyl)-2-(4-fluorobenzyl)-4-((R)-1-hydroxypentan-2-yl)morpholin-3-one and (2R,5S,6R)-5,6-bis(4-chlorophenyl)-2-(4-fluorobenzyl)-4-((R)-1-hydroxypentan-2-yl)morpholin-3-one

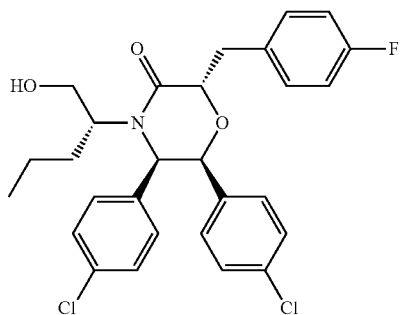

and

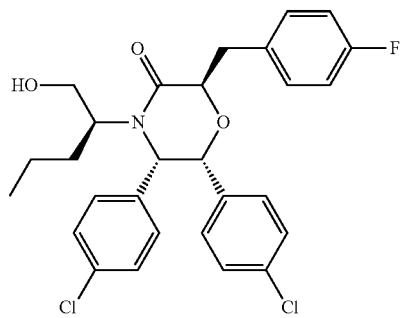

Sodium borohydride (81.3 mg, 2149 µmol) was added to a solution of (R)-ethyl 2-((2S,5R,6S)-2-(4-fluorobenzyl)-5,6-bis(4-chlorophenyl)-3-oxomorpholino)pentanoate and (S)-ethyl 2-((2R,5S,6R)-2-(4-fluorobenzyl)-5,6-bis(4-chlorophenyl)-3-oxomorpholino)pentanoate (400 mg, 716 µmol, Example 31, Step A) in DME/MeOH (5:1, 15 mL) at 0° C. After stirring at room temperature for 16 hours, the reaction was quenched with saturated NH₄Cl, extracted with ethyl acetate, and washed with 1 N NaOH and brine. The organic layer was dried over MgSO₄ and concentrated to give the title compounds as a white solid.

¹H NMR (400 MHz, CDCl₃, δ ppm): 7.20-7.12 (m, 6H), 6.90-7.00 (m, 2H), 6.75-6.72 (m, 4H), 4.89 (d, J=4.0 Hz, 1H), 4.85-4.90 (m, 1H), 4.26 (d, J=4.0 Hz, 1H), 3.75-3.85 (m, 1H), 3.70-3.60 (m, 2H), 3.45-3.60 (m, 1H), 3.35-3.45 (m, 1H), 3.20-3.30 (m, 1H), 1.70-1.59 (m, 2H), 1.40-1.10 (m, 2H), 0.89 (t, J=8.0 Hz, 3H).

Step C. (R)-2-((2S,3R,6S)-2,3-Bis(4-chlorophenyl)-6-(4-fluorobenzyl)-5-oxomorpholino)pentanal and (S)-2-((2R,3S,6R)-2,3-bis(4-chlorophenyl)-6-(4-fluorobenzyl)-5-oxomorpholino)pentanal

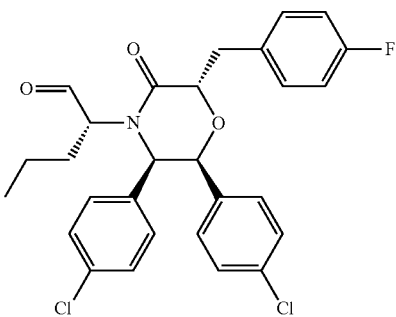

and

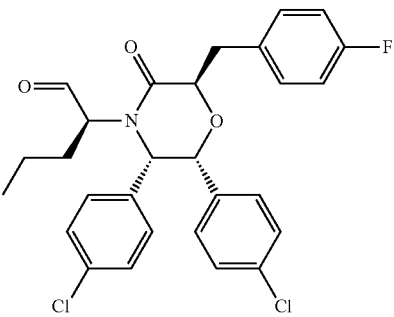

Dimethylsulfoxide (45 µL, 639 µmol) in DCM (1 mL) was added to a solution of oxalyl dichloride (28 µL, 320 µmol) in DCM (1 mL) at −60 OC under N₂. The mixture was stirred at −60° C. for 2 minutes, and a solution of (2S,5R,6S)-2-(4-fluorobenzyl)-5,6-bis(4-chlorophenyl)-4-((R)-1-hydroxypentan-2-yl)morpholin-3-one and (2R,5S,6R)-2-(4-fluorobenzyl)-5,6-bis(4-chlorophenyl)-4-((R)-1-hydroxypentan-2-yl)morpholin-3-one (150 mg, 290 µmol, Example 31, Step B) in DCM (1 mL) was added. The resulting solution was stirred for 15 minutes and triethylamine (203 µL, 1452 µmol) was added. After stirring at −60 OC for 5 minutes, the reaction was allowed to warm to room temperature, then 5 mL of water was added. The solution was extracted with DCM and washed with brine. The organic layer was dried over MgSO₄ and concentrated to give the title compounds as a white solid.

¹H NMR (400 MHz, CDCl₃, δ ppm): 9.46 (s, 1H), 7.20-7.12 (m, 6H), 6.90-7.00 (m, 2H), 6.81-6.75 (m, 4H), 5.04 (d, J=4.0 Hz, 1H), 4.90-4.95 (m, 1H), 4.24 (d, J=4.0 Hz, 1H), 3.75-3.85 (m, 1H), 3.35-3.48 (m, 1H), 3.20-3.30 (m, 1H), 1.90-2.10 (m, 1H), 1.70-1.85 (m, 1H), 1.40-1.26 (m, 2H), 0.89 (t, J=8.0 Hz, 3H); MS (ESI) 514.2 [M+H]⁻.

Step D. (R)-Ethyl 4-((2S,3R,6S)-2,3-bis(4-chloro-phenyl)-6-(4-fluorobenzyl)-5-oxomorpholino)hept-2-enoate and (S)-ethyl 4-((2R,3S,6R)-2,3-bis(4-chlorophenyl)-6-(4-fluorobenzyl)-5-oxomorpholino)hept-2-enoate

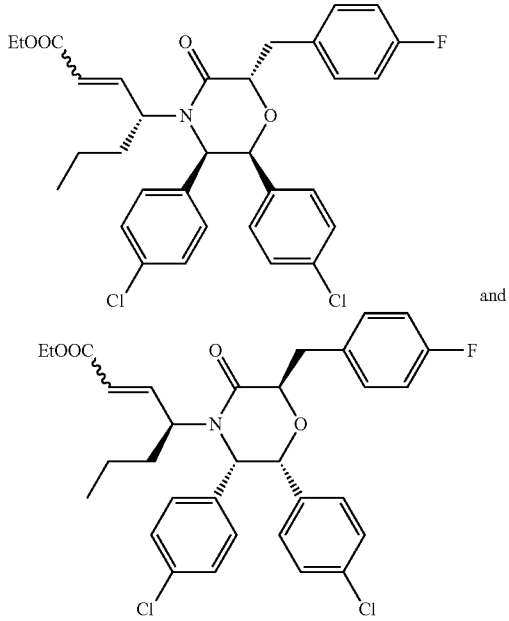

and

A solution of ethyl 2-(diethoxyphosphoryl)acetate (62 μL, 303 μmol) and DMPU (0.3 mL) in THF (1 mL) was added to a well stirred suspension of sodium hydride (11 mg, 278 μmol, 60% dispersion in mineral oil) in THF (1 mL) at 0° C. The mixture was stirred for 30 minutes, and treated with a solution of (R)-2-((2S,5R,6S)-2-(4-fluorobenzyl)-5,6-bis(4-chlorophenyl)-3-oxomorpholino)pentanal and (S)-2-((2R,5S,6R)-2-(4-fluorobenzyl)-5,6-bis(4-chlorophenyl)-3-oxomorpholino)pentanal (130 mg, 253 μmol, Example 31, Step C) in THF (1 mL). After stirring for 12 hours, the reaction was quenched with water, extracted with ethyl acetate, and washed with brine. The organic layer was dried over MgSO$_4$ and concentrated to give the title compounds.

Step E. (R)-Ethyl 4-((2S,3R,6S)-2,3-bis(4-chloro-phenyl)-6-(4-fluorobenzyl)-5-oxomorpholino)hep-tanoate and (S)-ethyl 4-((2R,3S,6R)-2,3-bis(4-chlorophenyl)-6-(4-fluorobenzyl)-5-oxomorpholino) heptanoate

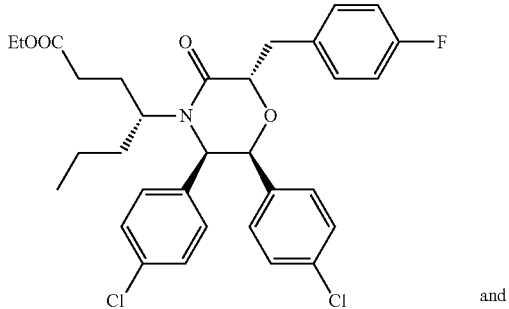

and

-continued

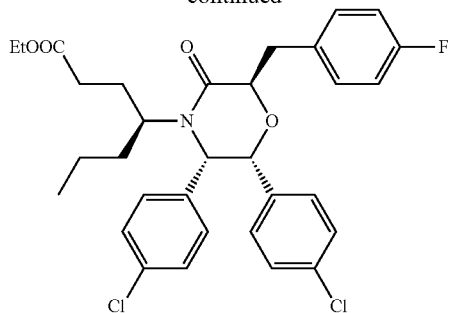

10% Palladium on carbon (15 mg, 14 μmol) was added to a solution of (R)-ethyl 4-((2S,3R,6S)-2,3-bis(4-chlorophenyl)-6-(4-fluorobenzyl)-5-oxomorpholino)hept-2-enoate and (S)-ethyl 4-((2R,3S,6R)-2,3-bis(4-chlorophenyl)-6-(4-fluorobenzyl)-5-oxomorpholino)hept-2-enoate (80 mg, 137 μmol, Example 31, Step D) in EtOH (4.4 mL) at room temperature. The reaction mixture was hydrogenated under atmospheric pressure at room temperature. After stirring at room temperature for 1 hour, the mixture was filtered through a short plug of silica gel, and the solid was washed with ethyl acetate. The filtrate was concentrated to give the title compounds.

1H NMR (400 MHz, CDCl$_3$, δ ppm): 7.15-7.05 (m, 6H), 6.75-6.85 (m, 2H), 6.70-6.65 (m, 4H), 4.80-4.85 (m, 1H), 4.67-4.68 (m, 1H), 4.20-4.35 (m, 1H), 4.10-4.20 (m, 1H), 4.00-4.08 (m, 2H), 3.25-3.35 (m, 1H), 3.10-3.20 (m, 1H), 2.10-2.20 (m, 1H), 1.90-2.05 (m, 1H), 1.80-1.90 (m, 2H), 1.25-0.75 (m, 7H), 0.56 (t, J=8.0 Hz, 3H).

Step F. (2S,5R,6S)-5,6-Bis(4-chlorophenyl)-2-(4-fluorobenzyl)-4-((R)-1-hydroxypentan-2-yl)morpho-lin-3-one and (2R,5S,6R)-5,6-bis(4-chlorophenyl)-2-(4-fluorobenzyl)-4-((R)-1-hydroxypentan-2-yl) morpholin-3-one

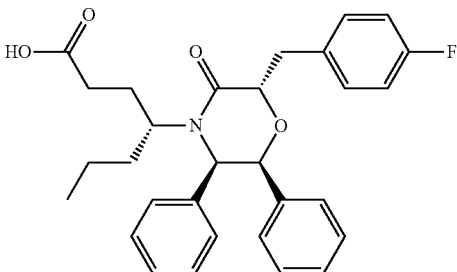

and

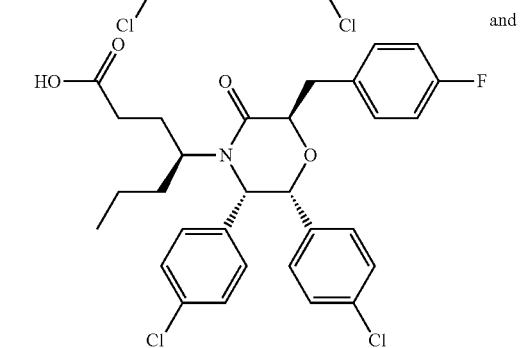

The title compounds were prepared from (R)-ethyl 4-((2S,3R,6S)-2,3-bis(4-chlorophenyl)-6-(4-fluorobenzyl)-5-oxomorpholino)heptanoate and (S)-ethyl 4-((2R,3S,6R)-2,3-bis(4-chlorophenyl)-6-(4-fluorobenzyl)-5-oxomorpholino)heptanoate (Example 31, Step E) by the method described in Example 10, Step D.

$^1$H NMR (400 MHz, DMSO-$d_6$, δ ppm): 7.24-7.15 (m, 6H), 7.10-7.00 (m, 4H), 7.00-6.90 (m, 2H), 5.29 (s, 1H), 4.88-4.98 (m, 1H), 4.65 (s, 1H), 3.30-3.40 (m, 1H), 3.15-3.25 (m, 1H), 2.50-2.65 (m, 1H), 2.10-2.20 (m, 1H), 1.95-2.05 (m, 1H), 1.75-1.85 (m, 1H), 1.10-0.60 (m, 5H), 0.49 (t, J=8.0 Hz, 3H); MS (ESI) 558.1 [M+H]$^-$.

Example 32

4-((R)-2-((2S,3R,6S)-2,3-Bis(4-chlorophenyl)-6-(4-cyanobenzyl)-5-oxomorpholino)pentanamido)butanoic acid

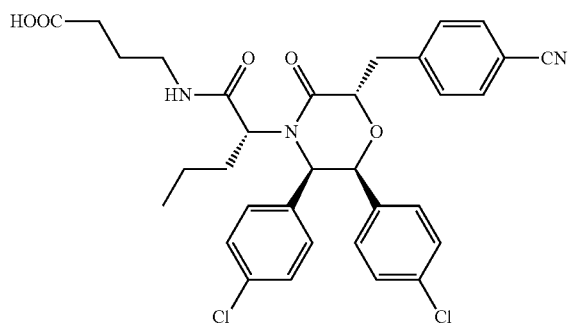 [SMILES: CCC[C@H](C(=O)NCCCC(=O)O)N1C(=O)[C@H](Cc2ccc(C#N)cc2)O[C@@H](c2ccc(Cl)cc2)[C@H]1c1ccc(Cl)cc1]

Step A. (R)-Ethyl 2-((2S,3R,6S)-2,3-bis(4-chlorophenyl)-6-(4-iodobenzyl)-5-oxomorpholino)pentanoate

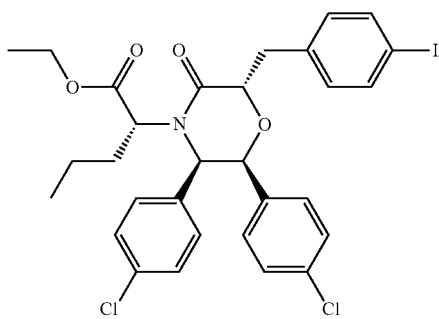 [SMILES: CCC[C@H](C(=O)OCC)N1C(=O)[C@H](Cc2ccc(I)cc2)O[C@@H](c2ccc(Cl)cc2)[C@H]1c1ccc(Cl)cc1]

The title compound was prepared from (R)-ethyl 2-((2S,3R)-2,3-bis(4-chlorophenyl)-5-oxomorpholino)pentanoate (Example 10, Step B) by the method described in Example 10, Step C, substituting 4-iodobenzyl bromide for 4-fluorobenzyl bromide.

Step B. (R)-2-((2S,3R,6S)-2,3-Bis(4-chlorophenyl)-6-(4-iodobenzyl)-5-oxomorpholino)pentanoic acid

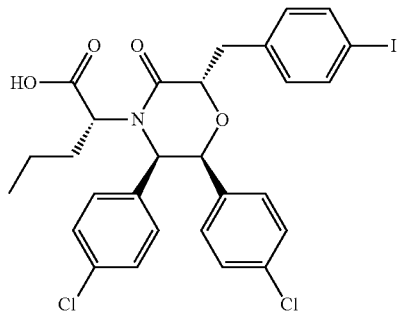 [SMILES: CCC[C@H](C(=O)O)N1C(=O)[C@H](Cc2ccc(I)cc2)O[C@@H](c2ccc(Cl)cc2)[C@H]1c1ccc(Cl)cc1]

The title compound was prepared from (R)-ethyl 2-((2S,3R,6S)-2,3-bis(4-chlorophenyl)-6-(4-iodobenzyl)-5-oxomorpholino)pentanoate (Example 32, Step A) by the method described in Example 10, Step D.

Step C. Ethyl 4-((R)-2-((2S,3R,6S)-2,3-bis(4-chlorophenyl)-6-(4-iodobenzyl)-5-oxomorpholino)pentanamido)butanoate

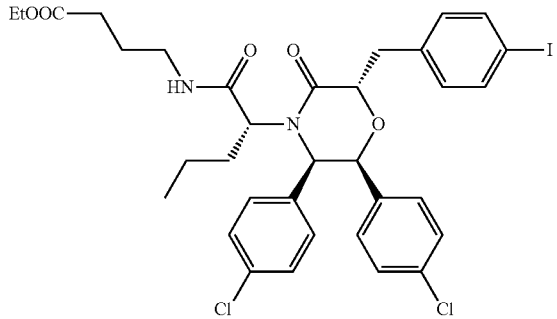 [SMILES: CCC[C@H](C(=O)NCCCC(=O)OCC)N1C(=O)[C@H](Cc2ccc(I)cc2)O[C@@H](c2ccc(Cl)cc2)[C@H]1c1ccc(Cl)cc1]

A solution of (R)-2-((2S,5R,6S)-2-(4-iodobenzyl)-5,6-bis(4-chlorophenyl)-3-oxomorpholino)pentanoic acid (2.00 g, 3.13 mmol, Example 32, Step B) and ethyl 4-aminobutanoate hydrochloride (1.58 g, 9.40 mmol) in DMF (12.0 mL) was treated, successively, with N-ethyl-N'-(3-dimethylaminopropyl)carbodiimide hydrochloride (1.80 g, 9.40 mmol), HOAt (1.28 g, 9.40 mmol) and sodium bicarbonate (1.58 g, 18.8 mmol). After stirring at 25° C. for 12 hours, the reaction was diluted with water, extracted with ethyl acetate (2×) and washed with saturated NaHCO$_3$ and brine (2×). The combined organic layers were dried over Na$_2$SO$_4$ and concentrated under the reduced pressure to give the title compounds as a white solid.

Step D. Ethyl 4-((R)-2-((2S,3R,6S)-2,3-bis(4-chlorophenyl)-6-(4-cyanobenzyl)-5-oxomorpholino)pentanamido)butanoate

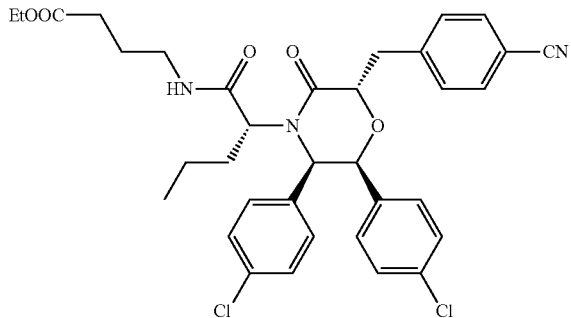 [SMILES: CCC[C@H](C(=O)NCCCC(=O)O)N1C(=O)[C@H](Cc2ccc(C#N)cc2)O[C@@H](c2ccc(Cl)cc2)[C@H]1c1ccc(Cl)cc1]

A solution of ethyl 4-((R)-2-((2S,5R,6S)-2-(4-iodobenzyl)-5,6-bis(4-chlorophenyl)-3-oxomorpholino)pentanamido)butanoate (1.250 g, 1.66 mmol, Example 32, Step C), dppf (0.0461 g, 0.0832 mmol), tris(dibenzylideneacetone)dipalladium(0) (0.0381 g, 0.0416 mmol), and zinc cyanide (0.195 g, 1.66 mmol) in DMF (5.0 mL) was charged with argon and stirred at 120° C. overnight. The reaction was quenched with saturated NH$_4$Cl solution, extracted with ethyl acetate (2×), and washed with brine. The combined organic layers were dried over Na$_2$SO$_4$ and concentrated under reduced pressure to give the title compound as a brown oil.

Step E. 4-((R)-2-((2S,3R,6S)-2,3-Bis(4-chlorophenyl)-6-(4-iodobenzyl)-5-oxomorpholino)pentanamido)butanoic acid

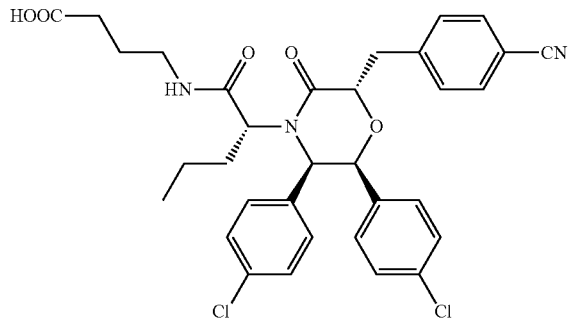 [SMILES: CCC[C@H](C(=O)NCCCC(=O)O)N1C(=O)[C@H](Cc2ccc(C#N)cc2)O[C@@H](c2ccc(Cl)cc2)[C@H]1c1ccc(Cl)cc1]

Trimethyltin hydroxide (0.945 g, 5.23 mmol) was added to a solution of ethyl 4-((R)-2-((2S,5R,6S)-2-(4-cyanobenzyl)-5,6-bis(4-chlorophenyl)-3-oxomorpholino)pentanamido)butanoate (0.850 g, 1.31 mmol, Example 32, Step D) in DCE (6.0 mL). After stirring at 80° C. for 18 hours, the reaction was concentrated. The residue was diluted with ethyl acetate and washed with 1N aqueous HCl (2×) and brine.

The separated organic layer was dried over Na$_2$SO$_4$ and concentrated under the reduced pressure. The residue was purified by preparative reverse phase HPLC (Gemini™ Prep C18 5 µm column (Phenomenex, Torrance, Calif.), 45 minutes, gradient elution of 10% to 90% acetonitrile in water, where both solvents contain 0.1% TFA) to provide the title compound as a white solid.

$^1$H NMR (400 MHz, CDCl$_3$, δ ppm): 7.53 (m, J=8.22 Hz, 2H), 7.32 (m, J=8.22 Hz, 2H), 7.11-7.21 (m, 4H), 6.65-6.75 (m, J=8.02 Hz, 3H), 6.67 (d, J=8.00 Hz, 2H), 5.04 (d, J=2.35 Hz, 1H), 4.97 (dd, J=7.82, 4.30 Hz, 1H), 4.79 (dd, J=9.39, 5.48 Hz, 1H), 4.43 (d, J=2.74 Hz, 1H), 3.35-3.48 (m, 2H), 1.81-1.95 (m, 1H), 1.53 (td, J=9.49, 4.50 Hz, 1H), 0.86-0.91 (m, 2H), 1.23-1.33 (m, 4H), 0.71 (t, J=7.43 Hz, 3H); MS (ESI) 620.0[M–H]$^-$.

Example 33

3-((R)-2-((2S,3R,6S)-2,3-Bis(4-chlorophenyl)-6-(4-cyanobenzyl)-5-oxomorpholino)pentanamido)propanoic acid

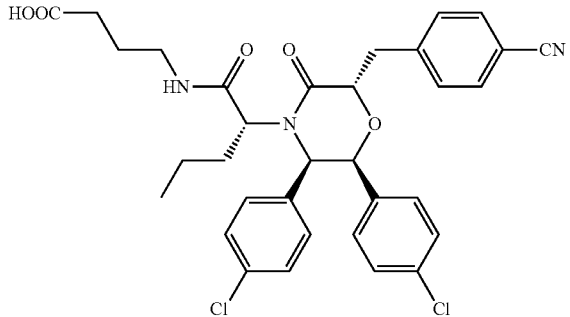

Step A. (R)-2-((2S,3R,6S)-2,3-Bis(4-chlorophenyl)-6-(4-cyanobenzyl)-5-oxomorpholino)pentanoic acid

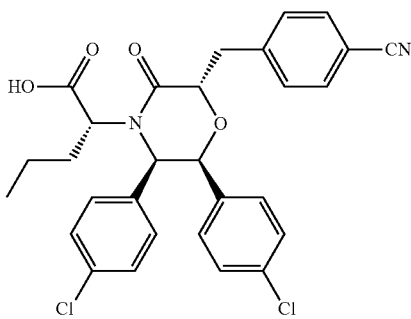 [SMILES: CCC[C@H](C(=O)O)N1C(=O)[C@H](Cc2ccc(C#N)cc2)O[C@@H](c2ccc(Cl)cc2)[C@H]1c1ccc(Cl)cc1]

A solution of (R)-ethyl 2-((2S,5R,6S)-2-(4-iodobenzyl)-5,6-bis(4-chlorophenyl)-3-oxomorpholino)pentanoate (539 mg, 809 µmol, Example 32, Step A), zinc cyanide (104 mg, 890 µmol), tris(dibenzylideneacetone)dipalladium(0) (37.0 mg, 40.4 µmol) and 1,1'-bis(diphenylphosphino)ferrocene (22.4 mg, 40.4 µmol) in DMF (1.35 mL, 0.6 M) was charged with argon and stirred at 120° C. for 6 hours. The reaction was diluted with H$_2$O, extracted with ethyl acetate (2×), and washed with brine. The combined organic layer was dried over Na$_2$SO$_4$ and concentrated under reduced pressure. The residue was purified by flash column chromatography (SiO$_2$, gradient elution of 20% to 25% ethyl acetate in hexanes) to give (R)-ethyl 2-((2S,5R,6S)-2-(4-cyanobenzyl)-5,6-bis(4-chlorophenyl)-3-oxomorpholino)pentanoate as a yellowish solid. The solid was dissolved in DCE (5 mL) and trimethyltin hydroxide (276 mg, 1528 µmol) was added. The mixture was warmed to 80° C. After stirring at 80° C. for 16 hours, the reaction was diluted with DCM, washed with 1N aqueous HCl (3×) and brine. The separated organic layer was dried over Na$_2$SO$_4$ and concentrated under the reduced pressure. Separation by preparative reverse phase HPLC (Gemini™ Prep C18 5 µm column (Phenomenex, Torrance, Calif.), 45 minutes, gradient elution 65% to 90% acetonitrile in water, where both solvents contain 0.1% TFA) provided the title compound as a white foam.

$^1$H NMR (400 MHz, CDCl$_3$, δ ppm): 7.52 (d, J=8.2 Hz, 2H), 7.33 (d, J=8.2 Hz, 2H), 7.15 (dd, J=8.6, 7.0 Hz, 4H), 6.75 (dd, J=15.1, 8.4 Hz, 4H), 4.94-5.12 (m, 2H), 4.79 (dd, J=9.4, 5.1 Hz, 1H), 4.43 (d, J=2.7 Hz, 1H), 3.23-3.60 (m, 2H), 1.81-1.98 (m, 1H), 1.49-1.61 (m, 1H), 1.25-1.35 (m, 1H), 1.03-1.16 (m, 1H), 0.71 (t, J=7.2 Hz, 3H). MS (ESI) 537.1[M+H]$^+$.

Step B. 3-((R)-2-((2S,3R,6S)-2,3-Bis(4-chlorophenyl)-6-(4-cyanobenzyl)-5-oxomorpholino)pentanamido)propanoic acid A solution of (R)-2-((2S,5R,6S)-2-(4-cyanobenzyl)-5,6-bis(4-chlorophenyl)-3-oxomorpholino)pentanoic acid (114 mg, 212 µmol) and β-alanine ethyl ester hydrochloride (48.9 mg, 318 µmol, Example 33, Step A) in DMF (0.53 mL, 0.4 M) at 0° C. was successively treated with N-ethyl-N'-(3-dimethylaminopropyl)carbodiimide hydrochloride (81.3 mg, 424 µmol), 3H-[1,2,3]triazolo[4,5-b]pyridin-3-ol (57.7 mg, 424 µmol), and sodium bicarbonate (53.5 mg, 636 µmol). After stirring at 25° C. for 14 hours, the reaction was diluted with water, extracted with ethyl acetate (2×), and washed with aqueous 1 N HCl, saturated NaHCO$_3$, and brine. The combined organic layers were dried over Na$_2$SO$_4$ and concentrated under reduced pressure. The residue was dissolved in DCE (2 mL, 0.1 M), and trimethyltin hydroxide (115 mg, 636 µmol) was added. The mixture was stirred at 90° C. for 6 hours and cooled to room temperature. The reaction was diluted with DCM and washed with 1N aqueous HCl (3×) and brine. The separated organic layer was dried over Na$_2$SO$_4$ and concentrated under reduced pressure. Separation by preparative reverse phase HPLC (Gemini™ Prep C18 5 µm column (Phenomenex, Torrance, Calif.), 25 minutes, gradient elution of 65% to 90% acetonitrile in water, where both solvents contain 0.1% TFA) provided the title compound as a white foam.

$^1$H NMR (400 MHz, CDCl$_3$, δ ppm): 7.44-7.58 (m, 3H), 7.25 (d, J=8.2 Hz, 2H), 7.16 (d, J=8.6 Hz, 2H), 7.12 (d, J=8.6 Hz, 2H), 6.78 (d, J=8.2 Hz, 2H), 6.69 (d, J=8.6 Hz, 2H), 5.21 (d, J=2.7 Hz, 1H), 5.05 (dd, J=8.8, 6.1 Hz, 1H), 4.96 (d, J=2.7 Hz, 1H), 4.88 (t, J=6.1 Hz, 1H), 3.71 (ddd, J=10.4, 7.0, 3.3 Hz, 1H), 3.49-3.59 (m, 1H), 3.29-3.37 (m, 2H), 2.67 (ddd, J=11.7, 7.4, 3.9 Hz, 2H), 1.50-1.63 (m, 1H), 1.07-1.18 (m, 2H), 0.92-1.04 (m, 1H), 0.70 (t, J=7.2 Hz, 3H). MS (ESI) 607.8[M+H]$^+$.

Example 34

(R)—N-(2-Amino-2-oxoethyl)-2-((2S,3R,6S)-2,3-bis(4-chlorophenyl)-6-(4-cyanobenzyl)-5-oxomorpholino)pentanamide and (S)—N-(2-amino-2-oxoethyl)-2-((2R,3S,6R)-2,3-bis(4-chlorophenyl)-6-(4-cyanobenzyl)-5-oxomorpholino)pentanamide

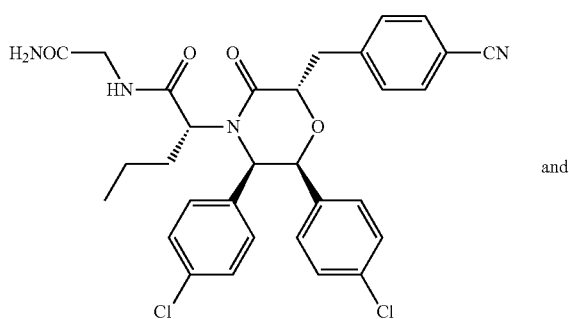

and

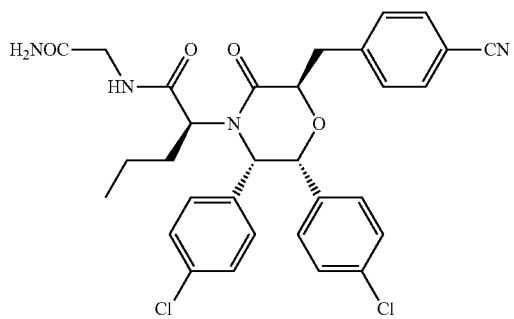

Step A. (R)-2-((2S,5R,6S)-2-(4-Cyanobenzyl)-5,6-bis(4-chlorophenyl)-3-oxomorpholino)pentanoic acid and (S)-2-((2R,5S,6R)-2-(4-cyanobenzyl)-5,6-bis(4-chlorophenyl)-3-oxomorpholino)pentanoic acid

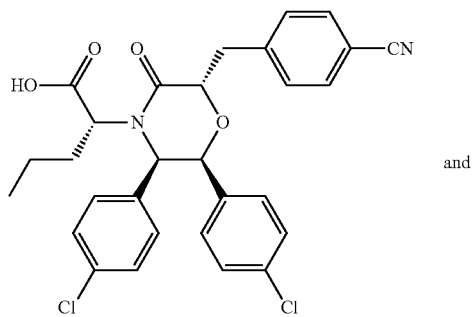

and

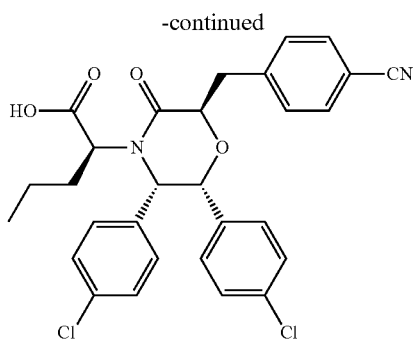

The title compound was prepared from (R)-ethyl 2-((2S, 3R)-2,3-bis(4-chlorophenyl)-5-oxomorpholino)pentanoate and (S)-ethyl 2-((2S,3R)-2,3-bis(4-chlorophenyl)-5-oxomorpholino)pentanoate (Example 10, Step A) as described in Example 32, Steps A, D, and E.

Step B. (R)—N-(2-Amino-2-oxoethyl)-2-((2S,3R,6S)-2,3-bis(4-chlorophenyl)-6-(4-cyanobenzyl)-5-oxomorpholino)pentanamide and (S)—N-(2-amino-2-oxoethyl)-2-((2R,3S,6R)-2,3-bis(4-chlorophenyl)-6-(4-cyanobenzyl)-5-oxomorpholino)pentanamide

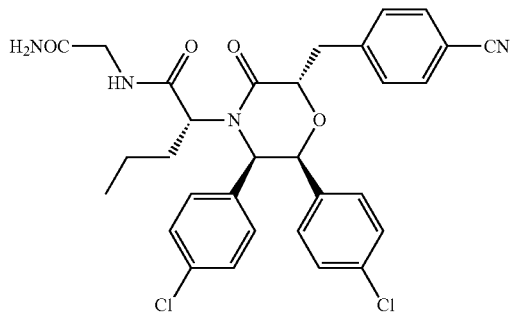

and

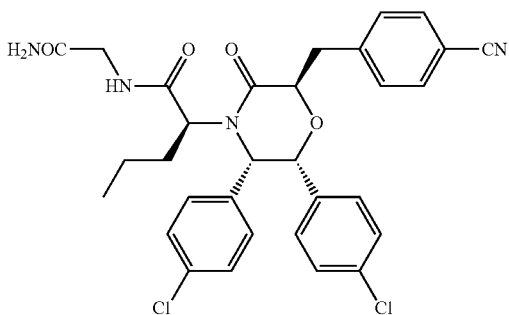

A solution of (R)-2-((2S,5R,6S)-2-(4-cyanobenzyl)-5,6-bis(4-chlorophenyl)-3-oxomorpholino)pentanoic acid and (S)-2-((2R,5S,6R)-2-(4-cyanobenzyl)-5,6-bis(4-chlorophenyl)-3-oxomorpholino)pentanoic acid (0.030 g, 0.056 mmol, Example 34, Step A) in DMF (0.5 mL, 0.1 M) at 50° C. was treated with sodium bicarbonate (0.04 g, 0.17 mmol), N-ethyl-N'-(3-dimethylaminopropyl)carbodiimide hydrochloride (0.016 g, 0.084 mmol), 3H-[1,2,3]triazolo[4,5-b]pyridin-3-ol (0.011 g, 0.084 mmol) and glycinamide hydrochloride (0.019 g, 0.17 mmol) were successively added. After stirring at 50° C. for 12 hours, the reaction was diluted with water, extracted with ethyl acetate (2×), and washed with saturated NaHCO₃ and brine (2×). The combined organic layers were dried over Na₂SO₄ and concentrated under reduced pressure. The residue was purified by preparative reverse phase HPLC (Gemini™ Prep C18 5 μm column (Phenomenex, Torrance, Calif.), 45 minutes, gradient elution of 10% to 90% acetonitrile in water, where both solvents contain 0.1% TFA) to give the title compounds as a white solid.

$^1$H NMR (400 MHz, CDCl$_3$, δ ppm): 7.51 (d, J=8.2 Hz, 2H), 7.49 (br s, 1H), 7.25 (d, J=8.2 Hz, 2H), 7.16 (2d, J=8.6 Hz, 2H), 7.12 (d, J=8.6 Hz, 2H), 6.78 (d, J=8.2 Hz, 2H), 6.69 (d, J=8.6 Hz, 2H), 5.21 (d, J=2.3 Hz, 1H), 5.05 (dd, J=8.6, 5.9 Hz, 1H), 4.96 (d, J=2.0 Hz, 1H), 4.88 (t, J=6.1 Hz, 1H), 3.65-3.77 (m, 1H), 3.48-3.58 (m, 1H), 3.29-3.36 (m, 2H), 2.58-2.78 (m, 2H), 1.51-1.63 (m, 1H), 1.04-1.20 (m, 2H), 0.89-1.04 (m, 1H), 0.62 (t, J=7.0 Hz, 3H).

Example 35

4-(((2S,5R,6S)-4-((R)-1-(1H-Tetrazol-5-yl)butyl)-5,6-bis(4-chlorophenyl)-3-oxomorpholin-2-yl)methyl)-2-fluorobenzonitrile

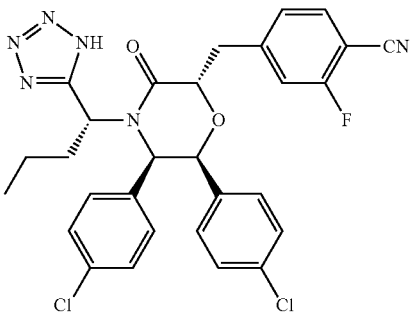 [SMILES: CCC[C@H](c1nnn[nH]1)N1C(=O)[C@H](Cc2ccc(C#N)c(F)c2)O[C@@H](c2ccc(Cl)cc2)[C@H]1c1ccc(Cl)cc1]

Step A. (R)-Ethyl 2-((2S,3R,6S)-2,3-bis(4-chlorophenyl)-6-(3-fluoro-4-iodobenzyl)-5-oxomorpholino)pentanoate

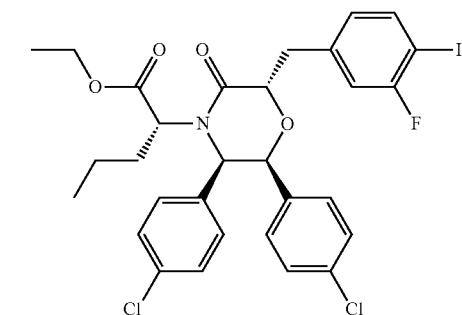 [SMILES: CCC[C@H](C(=O)OCC)N1C(=O)[C@H](Cc2ccc(I)c(F)c2)O[C@@H](c2ccc(Cl)cc2)[C@H]1c1ccc(Cl)cc1]

The title compound was prepared from (R)-ethyl 2-((2S, 3R)-2,3-bis(4-chlorophenyl)-5-oxomorpholino)pentanoate (Example 10, Step B) using the method described in Example 10, Step C, substituting 3-fluoro-4-iodobenzyl bromide for 4-fluorobenzyl bromide.

Step B. (R)-2-((2S,3R,6S)-2,3-Bis(4-chlorophenyl)-6-(3-fluoro-4-iodobenzyl)-5-oxomorpholino)pentanamide

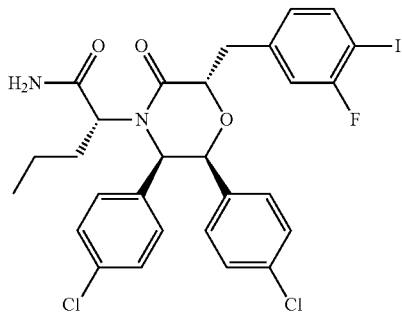 [SMILES: CCC[C@H](C(N)=O)N1C(=O)[C@H](Cc2ccc(I)c(F)c2)O[C@@H](c2ccc(Cl)cc2)[C@H]1c1ccc(Cl)cc1]

In a sealed tube, (R)-ethyl 2-((2S,5R,6S)-2-(3-fluoro-4-iodobenzyl)-5,6-bis(4-chlorophenyl)-3-oxomorpholino)pentanoate (0.30 g, 0.44 mmol, Example 35, Step A) was treated with ammonia (15 mL, 7 N in MeOH). The tube was sealed and stirred at 25° C. for 7 days. $NH_3$ and MeOH were removed under reduced pressure to give the title compound as a colorless oil.

Step C. (R)-2-((2S,3R,6S)-2,3-Bis(4-chlorophenyl)-6-(3-fluoro-4-iodobenzyl)-5-oxomorpholino)pentanenitrile

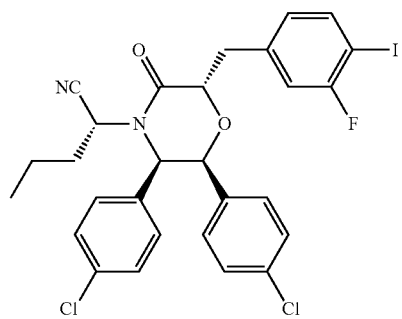 [SMILES: CCC[C@H](C#N)N1C(=O)[C@H](Cc2ccc(I)c(F)c2)O[C@@H](c2ccc(Cl)cc2)[C@H]1c1ccc(Cl)cc1]

A solution of (R)-2-((2S,5R,6S)-2-(3-fluoro-4-iodobenzyl)-5,6-bis(4-chlorophenyl)-3-oxomorpholino)pentanamide (0.140 g, 0.21 mmol, Example 35, Step B) and triethylamine (0.15 mL, 1.1 mmol) in THF (3 mL, 0.05 M) was treated with trifluoroacetic acid anhydride (0.075 mL, 0.53 mmol) at 0° C. After stirring at 0° C. for 3 hours, the reaction was quenched with 10% citric acid, extracted with ethyl acetate (2×) and washed with brine. The combined organic layers were dried over $Na_2SO_4$ and concentrated under reduced pressure. Purification of the residue by flash chromatography ($SiO_2$, gradient elution of 15% to 20% ethyl acetate in hexanes) provided the title compound.

$^1$H NMR (400 MHz, $CDCl_3$, δ ppm): 7.65-7.69 (m, 1H), 7.27-7.24 (m, 4H), 7.09 (d, J=8.0 Hz, 1H), 6.98-6.92 (m, 4H), 6.84 (d, J=4.0 Hz, 1H), 5.58 (d, J=4.0 Hz, 1H), 5.05 (d, J=4.0 Hz, 1H), 4.90 (d, J=4.0 Hz, 1H), 4.35-4.48 (m, 1H), 3.30-3.40 (m, 1H), 3.10-3.25 (m, 1H), 1.75-1.95 (m, 2H), 1.41-1.25 (m, 2H), 0.87 (t, J=8.0 Hz, 3H).

Step D. (2S,5R,6S)-4-((R)-1-(1H-Tetrazol-5-yl)butyl)-5,6-bis(4-chlorophenyl)-2-(3-fluoro-4-iodobenzyl)morpholin-3-one

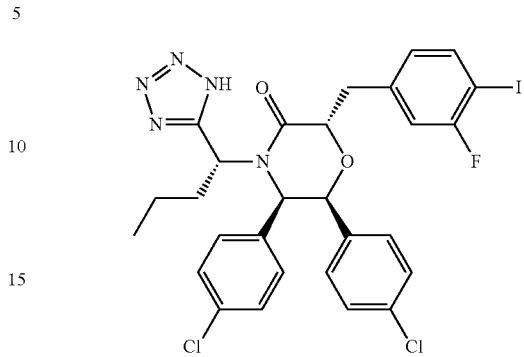

Sodium azide (15 mg, 0.23 mmol) and ammonium chloride (12.9 mg, 241 μmol) were added to a solution of (R)-2-((2S,5R,6S)-2-(3-fluoro-4-iodobenzyl)-5,6-bis(4-chlorophenyl)-3-oxomorpholino)pentanenitrile (0.115 g, 0.18 mmol, Example 35, Step C) in DMF (0.5 mL, 0.4 M). The resulting mixture was stirred at 90° C. for 16 hours. Additional sodium azide (16 mg) and ammonium chloride (13 mg) were added. After stirring at 90° C. for another 8 hours, the reaction was acidified with aqueous 10% citric acid solution, extracted with ethyl acetate (2×), and washed with brine. The combined organic layers were dried over $Na_2SO_4$ and concentrated under reduced pressure to give the title compound. MS (ESI) 678.1[M−H]$^-$.

Step E. 4-(((2S,5R,6S)-4-((R)-1-(1H-Tetrazol-5-yl)butyl)-5,6-bis(4-chlorophenyl)-3-oxomorpholin-2-yl)methyl)-2-fluorobenzonitrile

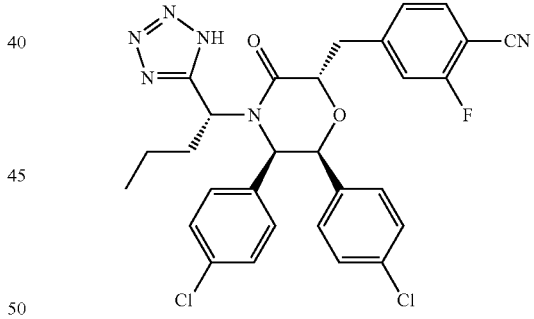

A solution of (2S,5R,6S)-4-((R)-1-(1H-tetrazol-5-yl)butyl)-5,6-bis(4-chlorophenyl)-2-(3-fluoro-4-iodobenzyl)morpholin-3-one (0.094 g, 0.14 mmol, Example 35, Step D), dppf (0.0015 g, 0.0028 mmol), zinc cyanide (0.016 g, 0.14 mmol), and tris(dibenzylideneacetone)dipalladium(0) (0.0013 g, 0.0014 mmol) in DMF (0.5 mL, 0.3 M) was charged with argon and stirred at 120° C. overnight. The reaction was acidified with aqueous 10% citric acid, extracted with ethyl acetate (2×), and washed with brine. The combined organic layers were dried over $Na_2SO_4$ and concentrated under reduced pressure. The residue was purified by preparative reverse phase HPLC (Gemini™ Prep C18 5 μm column (Phenomenex, Torrance, Calif.), 45 minutes, gradient elution of 10% to 90% acetonitrile in water, where both solvents contain 0.1% TFA) to give the title compound as a white solid.

$^1$H NMR (400 MHz, CDCl$_3$, δ ppm): 7.25-7.45 (m, 1H), 7.00-7.15 (m, 4H), 6.87 (d, J=8.0 Hz, 2H), 6.65-6.68 (m, 4H), 5.75-5.85 (m, 1H), 4.85-4.90 (m, 2H), 4.82 (s, 1H), 3.30-3.24 (m, 2H), 1.75-1.90 (m, 1H), 1.50-1.60 (m, 1H), 0.90-1.10 (m, 2H), 0.63 (t, J=8.0 Hz, 3H); MS (ESI) 577.2[M−H]$^-$.

Example 36

(2S,5R,6S)-4-((R)-1-(1H-Tetrazol-5-yl)butyl)-5,6-bis(4-chlorophenyl)-2-(4-iodobenzyl)morpholin-3-one and (2R,5S,6R)-4-((S)-1-(1H-tetrazol-5-yl)butyl)-5,6-bis(4-chlorophenyl)-2-(4-iodobenzyl)morpholin-3-one

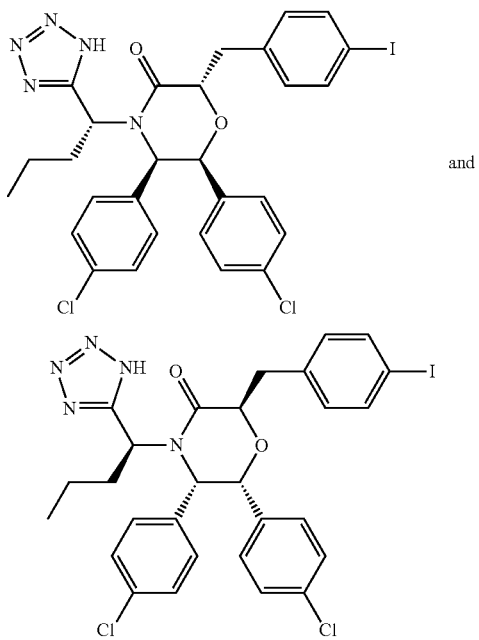

and

Step A. (R)-2-((2S,3R,6S)-2,3-Bis(4-chlorophenyl)-6-(4-iodobenzyl)-5-oxomorpholino)pentanoic acid and (S)-2-((2R,3S,6R)-2,3-bis(4-chlorophenyl)-6-(4-iodobenzyl)-5-oxomorpholino)pentanoic acid

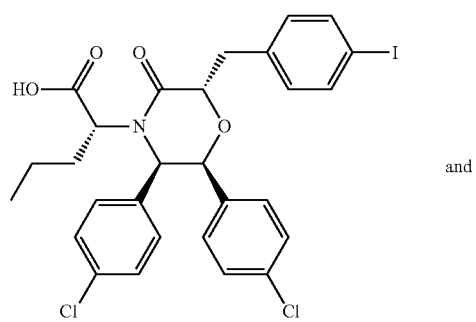

and

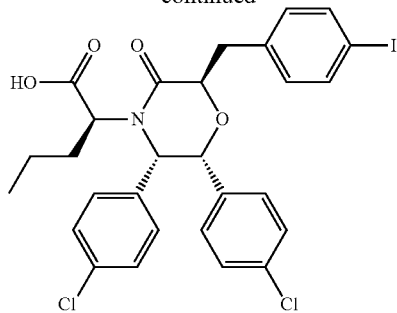

The title compound was prepared from (R)-ethyl 2-((2S,3R)-2,3-bis(4-chlorophenyl)-5-oxomorpholino)pentanoate and (S)-ethyl 2-((2S,3R)-2,3-bis(4-chlorophenyl)-5-oxomorpholino)pentanoate (Example 10, Step A) as described in Example 32, Steps A and B.

Step B. (2S,5R,6S)-4-((R)-1-(1H-Tetrazol-5-yl)butyl)-5,6-bis(4-chlorophenyl)-2-(4-iodobenzyl)morpholin-3-one and (2R,5S,6R)-4-((S)-1-(1H-tetrazol-5-yl)butyl)-5,6-bis(4-chlorophenyl)-2-(4-iodobenzyl)morpholin-3-one The title compounds were prepared from (R)-ethyl 2-((2S,3R,6S)-2,3-bis(4-chlorophenyl)-6-(4-iodobenzyl)-5-oxomorpholino)pentanoate and (S)-ethyl 2-((2R,3S,6R)-2,3-bis(4-chlorophenyl)-6-(4-iodobenzyl)-5-oxomorpholino)pentanoate (Example 36, Step A) as described in Example 35, Steps A through E.

$^1$H NMR (400 MHz, CDCl$_3$, δ ppm): 7.54 (d, J=8.2 Hz, 2H), 7.16 (d, J=8.6 Hz, 2H), 7.09 (d, J=8.6 Hz, 2H), 6.90 (d, J=8.2 Hz, 2H), 6.74 (d, J=8.6 Hz, 2H), 6.64 (d, J=8.2 Hz, 2H), 5.31-5.53 (m, 1H), 4.90 (dd, J=7.2, 4.9 Hz, 1H), 4.81-4.88 (m, 1H), 4.72 (d, J=2.7 Hz, 1H), 3.17-3.33 (m, 2H), 1.97-2.18 (m, 2H), 1.03-1.27 (m, 2H), 0.81 (t, J=7.2 Hz, 3H). MS (ESI) 661.7 [M+H]$^-$.

Example 37

(R)-2-((2S,3R)-2,3-Bis(4-chlorophenyl)-5-oxomorpholino)pentanoic acid

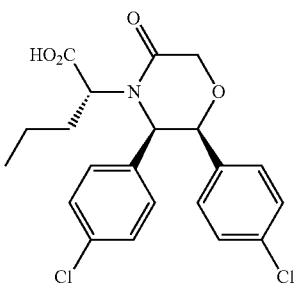 [SMILES: CCC[C@H](C(=O)O)N1C(=O)CO[C@@H](c2ccc(Cl)cc2)[C@H]1c1ccc(Cl)cc1]

An aqueous solution of NaOH (1 M, 0.250 mL, 0.250 mmol) was added to a solution of (R)-ethyl 2-((2S,3R)-2,3-bis(4-chlorophenyl)-5-oxomorpholino)pentanoate (584 mg, 2.793 mmol, Example 10, Step B) in THF (0.7 mL). The mixture was stirred at room temperature overnight. The mixture was acidified with 2 N HCl and extracted with DCM. The organic layer was dried over Na$_2$SO$_4$ and concentrated. The residue was purified by flash chromatography on silica gel (gradient elution of 1% to 10% MeOH in DCM) to give the title compound.

¹H NMR (400 MHz, CDCl₃, δ ppm): 7.16 (d, J=8.6 Hz, 4H), 6.80-6.87 (m, 4H), 5.23 (dd, J=2.5, 0.4 Hz, 1H), 4.69-4.83 (m, 2H), 4.57-4.66 (m, 1H), 4.54 (d, J=0.4 Hz, 1H), 1.80-1.94 (m, 1H), 1.52 (dtd, J=14.3, 9.6, 4.9 Hz, 1H), 1.24-1.34 (m, 1H), 1.07-1.18 (m, 1H), 0.83-0.92 (m, 1H), 0.69 (t, J=7.3 Hz, 3H). Spectrum (ESI) m/z=422 [M+1].

Example 38 (Reserved)

Example 39

(5S,6R,Z)-5,6-Bis(4-chlorophenyl)-4-methyl-2-(pyridin-3-ylmethylene)morpholin-3-one and (5R,6S,Z)-5,6-bis(4-chlorophenyl)-4-methyl-2-(pyridin-3-ylmethylene)morpholin-3-one

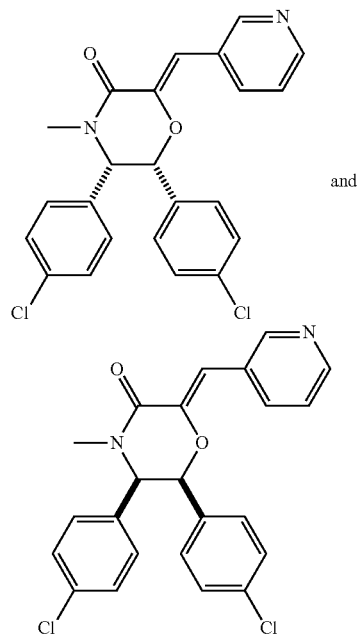

and

Sodium hydride (12 mg, 0.518 mmol, 60% dispersion in mineral oil) was added to a solution of (5R,6S)-5,6-bis(4-chlorophenyl)-4-methylmorpholin-3-one and (5S,6R)-5,6-bis(4-chlorophenyl)-4-methylmorpholin-3-one (29 mg, 0.086 mmol; Example 4, Step G) and nicotinaldehyde (14 mg, 0.129 mmol) in THF (1.0 mL) at room temperature. The mixture was heated to 70° C. overnight, cooled, and quenched with saturated NH₄Cl solution. The residue was purified by flash chromatography on silica gel (gradient elution of 50% to 100% ethyl acetate in hexanes) to give the title compounds.

¹H NMR (400 MHz, CDCl₃, δ ppm): 8.88 (dd, J=1.8, 0.6 Hz, 1H), 8.45 (dd, J=4.8, 1.7 Hz, 1H), 7.97-8.06 (m, 1H), 7.24-7.30 (m, 2H), 7.15-7.24 (m, 3H), 7.08 (s, 1H), 6.95-7.03 (m, 2H), 6.71-6.80 (m, 2H), 5.64 (d, J=3.3 Hz, 1H), 4.50 (d, J=3.1 Hz, 1H), 3.06 (s, 3H). Spectrum (ESI) m/z=425 [M+1].

Example 40

(2R,5S,6R)-5,6-Bis(4-chlorophenyl)-4-methyl-2-(2-morpholinoethyl)morpholin-3-one and (2S,5R,6S)-5,6-bis(4-chlorophenyl)-4-methyl-2-(2-morpholinoethyl)morpholin-3-one

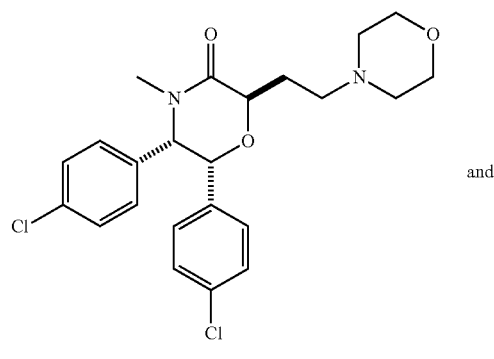

and

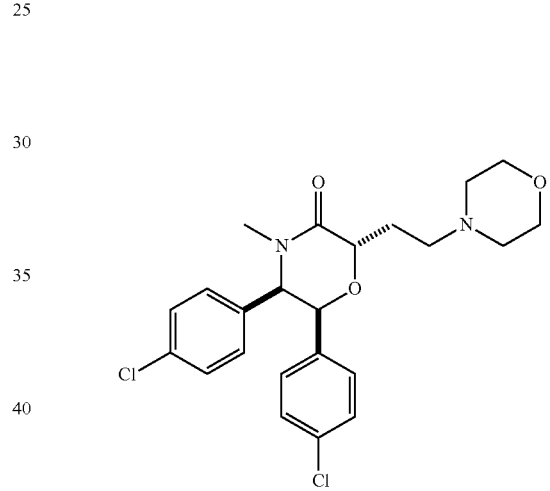

Step A. (2R,5S,6R)-2-Allyl-5,6-bis(4-chlorophenyl)-4-methylmorpholin-3-one and (2S,5R,6S)-2-allyl-5,6-bis(4-chlorophenyl)-4-methylmorpholin-3-one

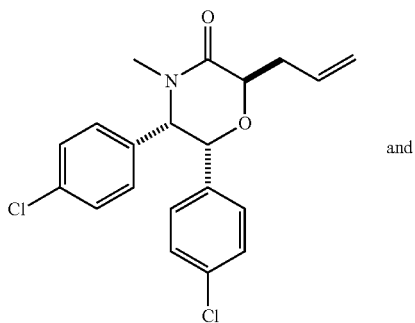

and

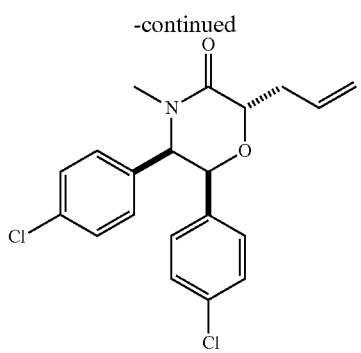

Sodium bis(trimethylsilyl)amide (1.285 mL, 1.285 mmol, 1 M in THF) was added to a solution of (5S,6R)-5,6-bis(4-chlorophenyl)-4-methylmorpholin-3-one and (5R,6S)-5,6-bis(4-chlorophenyl)-4-methylmorpholin-3-one (360 mg, 1.07 mmol, Example 4, Step G) in THF (1 mL) at −78° C. After stirring at −78° C. for 20 minutes, allyl bromide (0.130 mL, 1.50 mmol) was added. The mixture was stirred at −78° C. for 90 minutes. The mixture was quenched with saturated NH$_4$Cl solution and extracted with ethyl acetate (2×). The combined organic layers were washed with brine, dried over MgSO$_4$ and concentrated. The residue was purified by flash chromatography on silica gel (gradient elution of 30% to 90% ethyl acetate in hexanes) to give the title compounds.

Step B. 2-((2R,5S,6R)-5,6-Bis(4-chlorophenyl)-4-methyl-3-oxomorpholin-2-yl)acetaldehyde and 2-((2S,5R,6S)-5,6-Bis(4-chlorophenyl)-4-methyl-3-oxomorpholin-2-yl)acetaldehyde

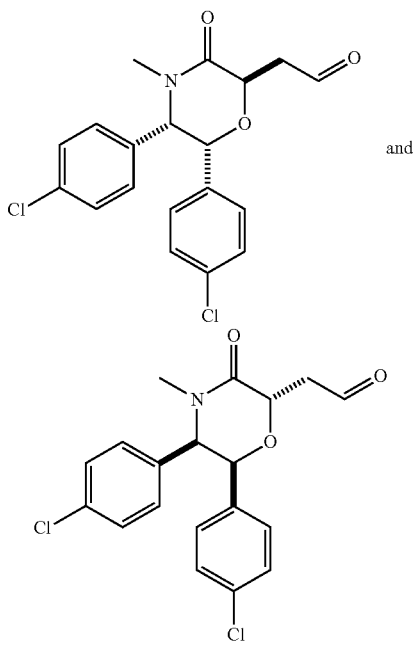

4-Methylmorpholine-N-oxide (230 mg, 1.967 mmol) and potassium osmate (7.3 mg, 0.020 mmol) were added to a slurried solution of (2R,5S,6R)-2-allyl-5,6-bis(4-chlorophenyl)-4-methylmorpholin-3-one and (2S,5R,6S)-2-allyl-5,6-bis(4-chlorophenyl)-4-methylmorpholin-3-one (148 mg, 0.393 mmol, Example 40, Step A) in tert-BuOH (1 mL), water (1 mL) and acetone (2 mL) under N$_2$ (g) at room temperature. The mixture was stirred at room temperature overnight and quenched with saturated Na$_2$S$_2$O$_3$. After stirring at room temperature for 10 minutes, the mixture was extracted with DCM (2). The combined organic layers were washed with brine, dried over MgSO$_4$ and concentrated. The residue was diluted with THF (2 mL) and potassium phosphate monobasic/sodium hydroxide buffer (1 mL, pH 7.00 Buffer Concentrate). Then sodium periodate (136 mg, 0.634 mmol) was added and the mixture was stirred at room temperature for 1 hour. The mixture was quenched with saturated NaHCO$_3$. Saturated Na$_2$S$_2$O$_3$ was added and the mixture was stirred at room temperature for 20 minutes. The mixture was extracted with DCM. The organic layer was washed with brine, dried over MgSO$_4$ and concentrated to give the title compounds.

Step C. (2R,5S,6R)-5,6-Bis(4-chlorophenyl)-4-methyl-2-(2-morpholinoethyl)morpholin-3-one and (2S,5R,6S)-5,6-bis(4-chlorophenyl)-4-methyl-2-(2-morpholinoethyl)morpholin-3-one

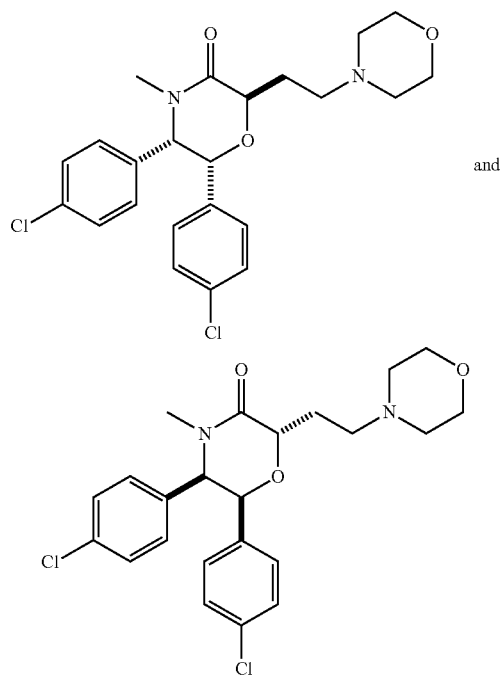

Morpholine (13 mg, 0.147 mmol) and sodium triacetoxyborohydride (42 mg, 0.198 mmol) were added to a solution of 2-((2R,5S,6R)-5,6-bis(4-chlorophenyl)-4-methyl-3-oxomorpholin-2-yl)acetaldehyde and 2-((2S,5R,6S)-5,6-bis(4-chlorophenyl)-4-methyl-3-oxomorpholin-2-yl)acetaldehyde (50 mg, 0.132 mmol, Example 40, Step B) in THF (1.5 mL). The mixture was stirred at room temperature overnight. The mixture was quenched with saturated NaHCO$_3$ and diluted with ethyl acetate. The organic layer was dried over MgSO$_4$ and concentrated. The residue was purified by flash chromatography on silica gel (gradient elution of 2% to 5% MeOH in DCM) to give the title compounds.

$^1$H NMR (400 MHz, CDCl$_3$, δ ppm): 7.11-7.19 (m, 4H), 6.84-6.90 (m, 2H), 6.71-6.78 (m, 2H), 5.32 (d, J=3.1 Hz, 1H), 4.75 (dd, J=10.3, 3.2 Hz, 1H), 4.33 (d, J=3.1 Hz, 1H), 3.69 (t, J=4.7 Hz, 4H), 2.88 (s, 3H), 2.40-2.55 (m, 6H), 2.25-2.36 (m, 1H), 2.01-2.14 (m, 1H). Spectrum (ESI) m/z=449.

Example 41

(2R,5S,6R)-5,6-Bis(4-chlorophenyl)-4-methyl-2-(pyridin-4-ylmethyl)morpholin-3-one and (2S,5R,6S)-5,6-bis(4-chlorophenyl)-4-methyl-2-(pyridin-4-ylmethyl)morpholin-3-one

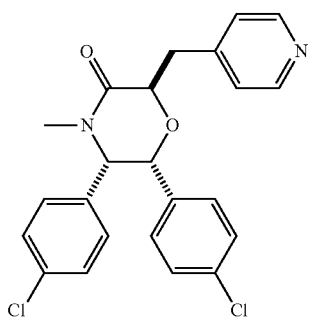

and

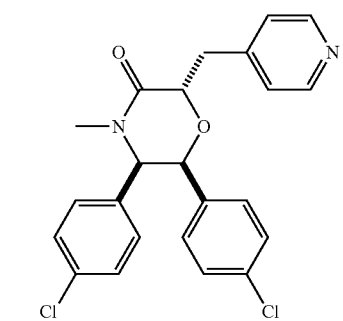

Step A. (2R,5S,6R)-5,6-Bis(4-chlorophenyl)-2-((S)-hydroxy(pyridin-4-yl)methyl)-4-methylmorpholin-3-one and (2S,5R,6S)-5,6-bis(4-chlorophenyl)-2-((R)-hydroxy(pyridin-4-yl)methyl)-4-methylmorpholin-3-one

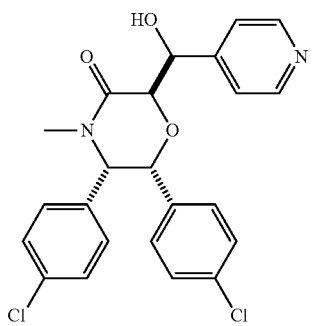

and

-continued

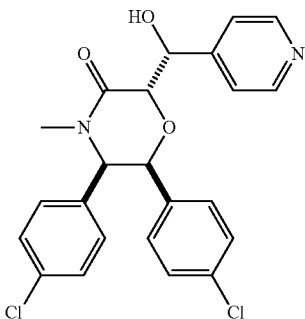

LiHMDS (1.0 M in THF, 0.326 mL, 0.326 mmol) was added to a solution (5S,6R)-5,6-bis(4-chlorophenyl)-4-methylmorpholin-3-one and (5R,6S)-5,6-bis(4-chlorophenyl)-4-methylmorpholin-3-one (73 mg, 0.217 mmol, Example 4, Step G) in THF (1 mL) at −78° C. The mixture was stirred at −78° C. for 15 minutes and then 4-pyridinecarboxaldehyde (0.037 mL, 0.391 mmol) was added. The color of the mixture turned from yellow to colorless after the addition of 4-pyridinecarboxaldehyde. The mixture was stirred at −78° C. for 30 minutes, quenched with saturated NH$_4$Cl solution, and extracted with ethyl acetate. The organic layer was washed with brine, dried over MgSO$_4$, and concentrated.

The residue was purified by flash chromatography on silica gel (gradient elution of 50% to 100% ethyl acetate in hexanes, and then 3% Et$_3$N in ethyl acetate) to give the title compounds.

Step B. (S)-((2R,5S,6R)-5,6-Bis(4-chlorophenyl)-4-methyl-3-oxomorpholin-2-yl)(pyridin-4-yl)methyl acetate and (R)-((2S,5R,6S)-5,6-bis(4-chlorophenyl)-4-methyl-3-oxomorpholin-2-yl)(pyridin-4-yl)methyl acetate

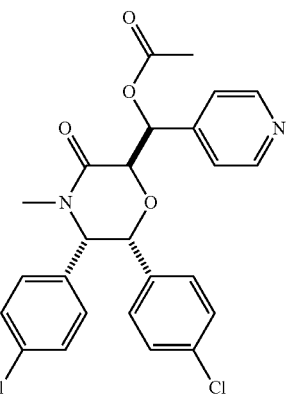

and

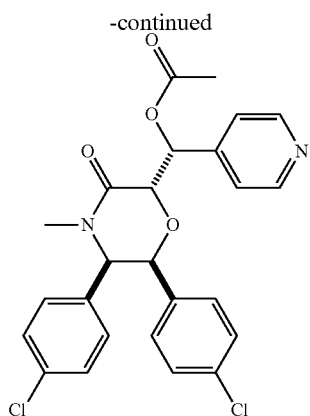

Acetic anhydride (0.035 mL, 0.372 mmol) was added to a solution of (2R,5S,6R)-5,6-bis(4-chlorophenyl)-2-((S)-hydroxy(pyridin-4-yl)methyl)-4-methylmorpholin-3-one and (2S,5R,6S)-5,6-bis(4-chlorophenyl)-2-((R)-hydroxy(pyridin-4-yl)methyl)-4-methylmorpholin-3-one (55 mg, 0.124 mmol, Example 41, Step A) in pyridine (0.7 mL). The mixture was stirred at room temperature overnight, quenched with water, and extracted with DCM (3×). The combined organic layers were washed with brine, dried over MgSO₄ and concentrated. The residue was purified by flash chromatography on silica gel (gradient elution of 0% to 3% Et₃N in ethyl acetate) to give the title compounds.

Step C. (2R,5S,6R)-5,6-Bis(4-chlorophenyl)-4-methyl-2-(pyridin-4-ylmethyl)morpholin-3-one and (2S,5R,6S)-5,6-bis(4-chlorophenyl)-4-methyl-2-(pyridin-4-ylmethyl)morpholin-3-one

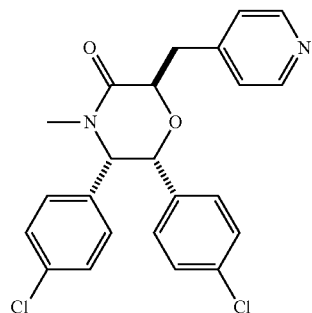

and

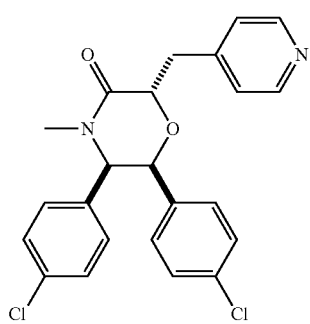

Samarium (II) iodide (0.1 M in THF, 6.3 mL, 0.63 mmol) and tert-BuOH (0.030 mL, 0.315 mmol) were added to (S)-((2R,5S,6R)-5,6-bis(4-chlorophenyl)-4-methyl-3-oxomorpholin-2-yl)(pyridin-4-yl)methyl acetate and (R)-((2S,5R,6S)-5,6-bis(4-chlorophenyl)-4-methyl-3-oxomorpholin-2-yl)(pyridin-4-yl)methyl acetate (102 mg, 0.210 mmol, Example 41, Step B) at room temperature. The color of the samarium (II) iodide solution turned from blue to yellow upon addition. The mixture was stirred at room temperature for 10 minutes, quenched with water, and diluted with saturated NaHCO₃ and ethyl acetate. The organic layer was washed with brine, dried over MgSO₄ and concentrated. The residue was purified by flash chromatography on silica gel (gradient elution of 1% to 2% MeOH in DCM). The residue was further purified by reverse phase preparative HPLC (gradient elution of 45% to 80% acetonitrile in water, where both solvents contain 0.1% TFA, 25 minutes) to give the title compounds.

$^1$H NMR (500 MHz, CDCl₃, δ ppm): 8.37-8.61 (m, 2H), 7.19-7.24 (m, 2H), 7.11-7.19 (m, 4H), 6.62-6.68 (m, 2H), 6.48-6.54 (m, 2H), 4.51 (dd, J=5.1, 1.0 Hz, 1H), 3.38-3.49 (m, 2H), 3.08-3.16 (m, 1H), 2.98 (dd, J=13.7, 10.5 Hz, 1H), 2.88 (s, 3H). Spectrum (ESI) m/z=427.

Example 42

(S)-2-((2R,3S,6R)-2,3-Bis(4-chlorophenyl)-5-oxo-6-(pyridin-4-ylmethyl)morpholino)pentanoic acid and (R)-2-((2S,3R,6S)-2,3-bis(4-chlorophenyl)-5-oxo-6-(pyridin-4-ylmethyl)morpholino)pentanoic acid

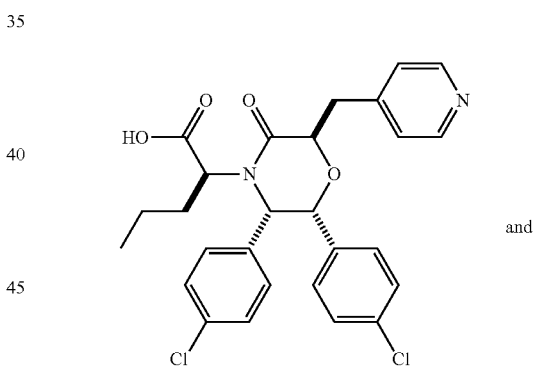

and

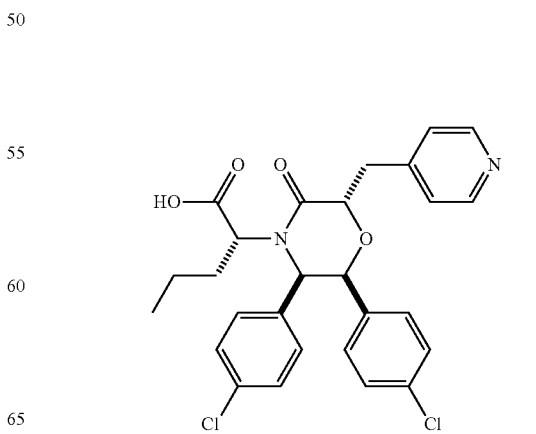

Step A. (S)-Ethyl 2-((2R,3S,6R)-2,3-bis(4-chlorophenyl)-6-((S)-hydroxy(pyridin-4-yl)methyl)-5-oxomorpholino)pentanoate and (R)-ethyl 2-((2S,3R,6S)-2,3-bis(4-chlorophenyl)-6-((R)-hydroxy(pyridin-4-yl)methyl)-5-oxomorpholino)pentanoate

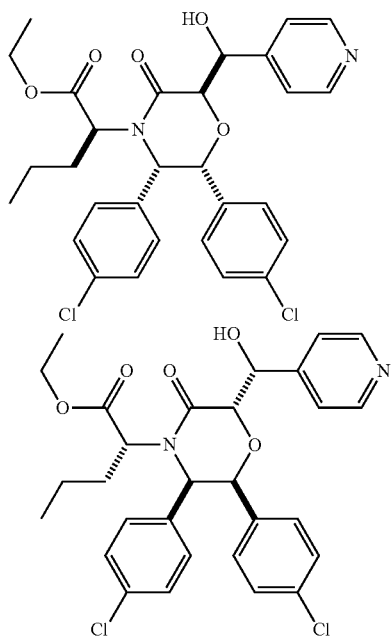
and

The title compounds were prepared from (S)-ethyl 2-((2R,3S)-2,3-bis(4-chlorophenyl)-5-oxomorpholino)pentanoate and (R)-ethyl 2-((2R,3S)-2,3-bis(4-chlorophenyl)-5-oxomorpholino)pentanoate (Example 10, Step A) by a procedure similar to the one described in (Example 41, Step A). The residue was purified by flash chromatography on silica gel (eluent: 25% ethyl acetate in hexanes, then 10% MeOH in DCM) to provide the title compounds.

Step B. (S)-Ethyl 2-((2R,5S,6R)-2-((S)-acetoxy(pyridin-4-yl)methyl)-5,6-bis(4-chlorophenyl)-3-oxomorpholino)pentanoate and (S)-ethyl 2-((2R,5S,6R)-2-((S)-acetoxy(pyridin-4-yl)methyl)-5,6-bis(4-chlorophenyl)-3-oxomorpholino)pentanoate

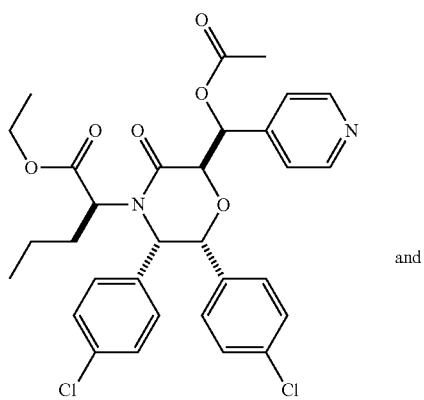
and

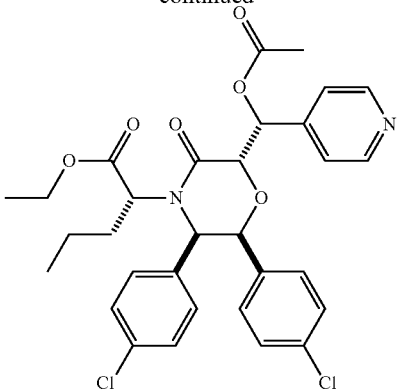

The title compounds were prepared from (S)-ethyl 2-((2R,3S,6R)-2,3-bis(4-chlorophenyl)-6-((S)-hydroxy(pyridin-4-yl)methyl)-5-oxomorpholino)pentanoate and (R)-ethyl 2-((2S,3R,6S)-2,3-bis(4-chlorophenyl)-6-((R)-hydroxy(pyridin-4-yl)methyl)-5-oxomorpholino)pentanoate (Example 42, Step B) by a procedure similar to the one described in (Example 41, Step B). The residue was purified by flash chromatography on silica gel (gradient elution of 50% to 100% ethyl acetate in hexanes) to provide the title compounds.

Step C. (S)-Ethyl 2-((2R,3S,6R)-2,3-bis(4-chlorophenyl)-5-oxo-6-(pyridin-4-ylmethyl)morpholino)pentanoate and (R)-ethyl 2-((2S,3R,6S)-2,3-bis(4-chlorophenyl)-5-oxo-6-(pyridin-4-ylmethyl)morpholino)pentanoate

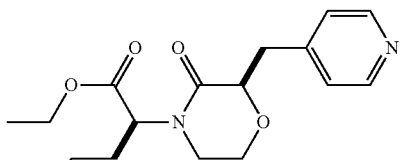
and

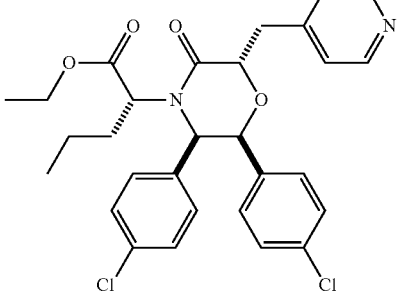

The title compounds were prepared from (S)-ethyl 2-((2R,5S,6R)-2-((S)-acetoxy(pyridin-4-yl)methyl)-5,6-bis(4-chlorophenyl)-3-oxomorpholino)pentanoate and (R)-ethyl 2-((2S,5R,6S)-2-((R)-acetoxy(pyridin-4-yl)methyl)-5,6-bis(4-chlorophenyl)-3-oxomorpholino)pentanoate (Example 42, Step B) by a procedure similar to the one described in (Example 41, Step C). The residue was purified by flash chromatography on silica gel (gradient elution of 50% to 100% ethyl acetate in hexanes) to provide the title compounds.

Step D. (S)-2-((2R,3S,6R)-2,3-Bis(4-chlorophenyl)-5-oxo-6-(pyridin-4-ylmethyl)morpholino)pentanoic acid and (R)-2-((2S,3R,6S)-2,3-bis(4-chlorophenyl)-5-oxo-6-(pyridin-4-ylmethyl)morpholino)pentanoic acid

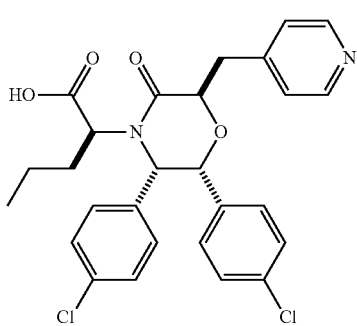

and

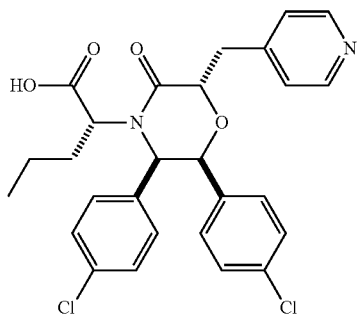

The title compounds were prepared from (S)-ethyl 2-((2R, 3S,6R)-2,3-bis(4-chlorophenyl)-5-oxo-6-(pyridin-4-ylmethyl)morpholino)pentanoate and (R)-ethyl 2-((2S,3R,6S)-2,3-bis(4-chlorophenyl)-5-oxo-6-(pyridin-4-ylmethyl) morpholino)pentanoate (Example 42, Step C) by a procedure similar to the one described in (Example 10, Step D). The residue was purified by flash chromatography on silica gel (eluent: 10% MeOH in DCM with 2.5% Et$_3$N) to provide the title compounds.

$^1$H NMR (400 MHz, CDCl$_3$, δ ppm): 8.35-8.49 (m, 2H), 7.15-7.20 (m, 2H), 7.10-7.16 (m, 2H), 7.08 (d, J=8.6 Hz, 2H), 6.80 (d, J=8.6 Hz, 2H), 6.75 (d, J=8.6 Hz, 2H), 5.33 (br s, 1H), 5.15 (dd, J=10.0, 4.3 Hz, 1H), 4.93 (d, J=4.3 Hz, 1H), 4.76 (dd, J=2.3, 0.4 Hz, 1H), 3.31-3.43 (m, 2H), 1.73-1.86 (m, 1H), 1.21 (s, 2H), 0.84-0.97 (m, 1H), 0.49 (t, J=7.2 Hz, 3H). Spectrum (ESI) m/z=513.

Example 43

(R)-2-((2S,3R)-2-(4-Chlorophenyl)-3-(1H-indol-2-yl)-5-oxomorpholino)pentanoic acid and (S)-2-((2R, 3S)-2-(4-Chlorophenyl)-3-(1H-indol-2-yl)-5-oxomorpholino)pentanoic acid

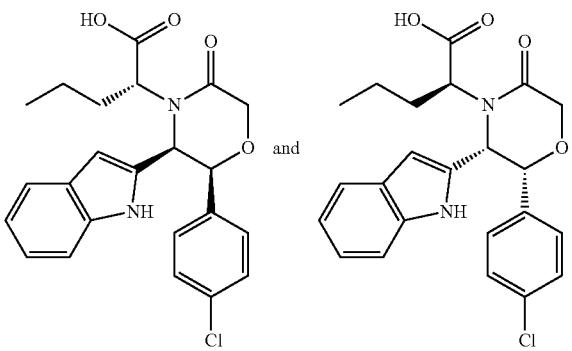 [SMILES: CCC[C@H](C(=O)O)N1C(=O)CO[C@@H](c2ccc(Cl)cc2)[C@H]1c1cc2ccccc2[nH]1 ; CCC[C@@H](C(=O)O)N1C(=O)CO[C@H](c2ccc(Cl)cc2)[C@@H]1c1cc2ccccc2[nH]1]

Step A. (1R,2R)-1-(4-Chlorophenyl)-1-(methoxymethoxy)-4-(triisopropylsilyl)but-3-yn-2-ol and (1S,2S)-1-(4-chlorophenyl)-1-(methoxymethoxy)-4-(triisopropylsilyl)but-3-yn-2-ol

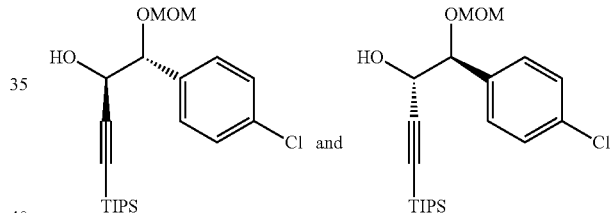

n-Butyllithium (32.6 mL, 82 mmol, 1.6 M solution in hexanes) was added dropwise over 15 minutes from an addition funnel to a solution of (triisopropylsilyl)acetylene (17.15 mL, 76 mmol) in anhydrous ether (100 mL) at −78° C. under argon. In a separate flask 1,2-dibromoethane (17.57 mL, 204 mmol) was added slowly to a mixture of magnesium (4.95 g, 204 mmol) in anhydrous ether (100 mL) at room temperature at a rate that maintained a gentle reflux. Once the MgBr$_2$ solution had cooled to room temperature, it was added via cannula to the solution containing the lithiated acetylene at −78° C. under argon. A large amount of solid white material formed. The solution was warmed to 0° C. The solid dissolved providing a greenish-gray solution. In a separate flask, DIBAL (40.8 mL, 61.2 mmol, 1.5 M solution in toluene) was added dropwise over 35 minutes from an addition funnel to a solution of methoxymethyl 2-(4-chlorophenyl)-2-(methoxymethoxy)acetate (14.00 g, 51.0 mmol) (Haddad, M.; Imogai, H.; Larcheveque, M. The First Enantioselective Synthesis of the cis-2-carboxy-5-phenylpyrrolidine. J. Org. Chem. 1998, 63, 5680-5683) in anhydrous ether (200 mL) at −78° C. under argon. After 1.5 hours the Grignard solution was added to the DIBAL solution via cannula over 15 minutes. During the addition, a large amount of white precipitate formed. Once the addition was complete, the reaction mixture was removed from the dry-ice bath and allowed to warm to room temperature. After 8 hours the reaction mixture was cooled to −20° C. and quenched with 10% HCl (200 mL) and diluted with water (300 mL). The layers were separated and the organic layer was washed with brine, dried over MgSO₄, filtered and concentrated under a vacuum to provide a pale yellow liquid. Flash column chromatography (750 g SiO₂, gradient elution with 0% to 35% ethyl acetate/hexanes) provided a colorless oil.

Step B. (1R,2R)-1-(4-Chlorophenyl)-1-(methoxymethoxy)-4-(triisopropylsilyl)but-3-yn-2-yl methanesulfonate and (1S,2S)-1-(4-chlorophenyl)-1-(methoxymethoxy)-4-(triisopropylsilyl)but-3-yn-2-yl methanesulfonate

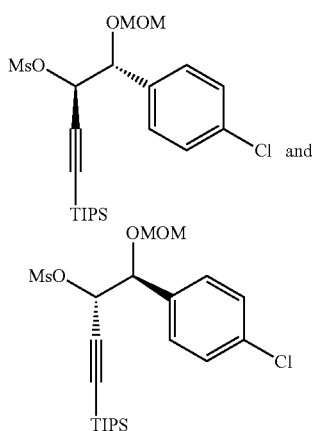

Triethylamine (4.81 mL, 34.5 mmol) was added to a solution of (1R,2R)-1-(4-chlorophenyl)-1-(methoxymethoxy)-4-(triisopropylsilyl)but-3-yn-2-ol and (1S,2S)-1-(4-chlorophenyl)-1-(methoxymethoxy)-4-(triisopropylsilyl)but-3-yn-2-ol (9.14 g, 23.02 mmol, Example 43, Step A) and methanesulfonyl chloride (1.973 mL, 25.3 mmol) in anhydrous DCM (230 mL) at 0° C. After the addition was complete, the ice bath was removed. After two hours the reaction mixture was washed with saturated aqueous NaHCO₃, brine, dried over MgSO₄, filtered and concentrated under a vacuum to provide a pale yellow oil.

Step C. ((3S,4R)-3-Azido-4-(4-chlorophenyl)-4-(methoxymethoxy)but-1-yn-1-yl)triisopropylsilane and ((3R,4S)-3-azido-4-(4-chlorophenyl)-4-(methoxymethoxy)but-1-yn-1-yl)triisopropylsilane

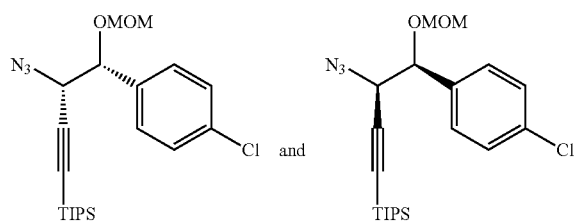

Sodium azide (1.647 g, 25.3 mmol) was added to a solution of (1R,2R)-1-(4-chlorophenyl)-1-(methoxymethoxy)-4-(triisopropylsilyl)but-3-yn-2-yl methanesulfonate and (1S,2S)-1-(4-chlorophenyl)-1-(methoxymethoxy)-4-(triisopropylsilyl)but-3-yn-2-yl methanesulfonate (10.94 g, 23.02 mmol, Example 43, Step B) in anhydrous DMF (230 mL) at room temperature. The reaction mixture was stirred at room temperature for 6 hours and then heated to 60° C. for 12 hours. The reaction mixture was cooled to room temperature, diluted with ethyl acetate (200 mL) and water (400 mL) and the layers were separated. The aqueous layer was extracted with ethyl acetate (2×), and the organics were pooled, washed with brine, dried over MgSO₄, filtered and concentrated under a vacuum to provide a colorless liquid. The liquid was adsorbed onto SiO₂ and purified by flash column chromatography (330 g SiO₂, gradient elution with 0% to 25% ethyl acetate in hexanes) to provide a colorless oil.

Step D. (1R,2S)-1-(4-Chlorophenyl)-1-(methoxymethoxy)-4-(triisopropylsilyl)but-3-yn-2-amine and (1S,2R)-1-(4-chlorophenyl)-1-(methoxymethoxy)-4-(triisopropylsilyl)but-3-yn-2-amine

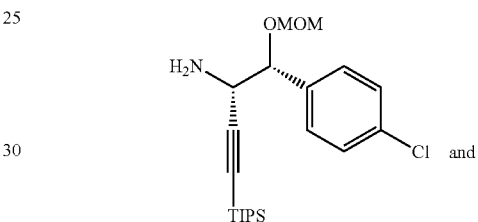

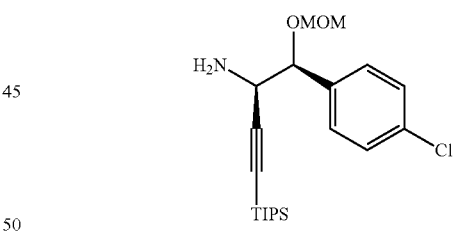

Lithium aluminum hydride (10.66 mL, 21.33 mmol, 2 M in THF) was added dropwise to a solution of ((3S,4R)-3-azido-4-(4-chlorophenyl)-4-(methoxymethoxy)but-1-ynyl)triisopropylsilane and ((3R,4S)-3-azido-4-(4-chlorophenyl)-4-(methoxymethoxy)but-1-ynyl)triisopropylsilane (6.00 g, 14.22 mmol, Example 43, Step C) in anhydrous THF (142 mL) at 0° C. under nitrogen. The reaction mixture stirred at 0° C. for 1 hour 40 minutes and was quenched by the sequential addition of water (0.9 mL), 15% NaOH (0.9 mL) and water (2.7 mL). The ice-bath was removed and the mixture stirred vigorously at room temperature for 30 minutes, filtered under a vacuum and concentrated under a vacuum to provide an orange oil. Flash column chromatography (330 g SiO₂, gradient elution with 0% to 5% MeOH/CH₂Cl₂) provided a yellow oil.

Step E. (1R,2S)-2-Amino-1-(4-chlorophenyl)-4-(triisopropylsilyl)but-3-yn-1-ol and (1S,2R)-2-Amino-1l-(4-chlorophenyl)-4-(triisopropylsilyl)but-3-yn-1-ol

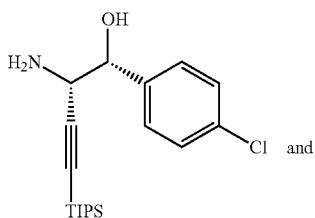

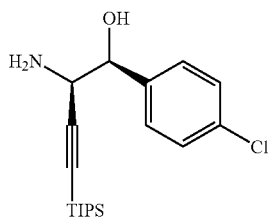

Hydrochloric acid (10% in MeOH) was added to a solution of (1R,2S)-1-(4-chlorophenyl)-1-(methoxymethoxy)-4-(triisopropylsilyl)but-3-yn-2-amine and (1S,2R)-1-(4-chlorophenyl)-1-(methoxymethoxy)-4-(triisopropylsilyl)but-3-yn-2-amine (4.32 g, 10.9 mmol, Example 1, Step D) in MeOH (25 mL) at room temperature. The reaction mixture was heated at 50° C. for 22 hours and then concentrated under a vacuum to provide a beige solid. The solid was taken up in DCM and saturated aqueous NaHCO₃, and the layers were separated. The aqueous layer was extracted with DCM (2×), and the organics were pooled, washed with brine, dried over MgSO₄, filtered and concentrated under a vacuum to provide a beige solid.

Step F. 2-Chloro-N-((1R,2S)-1-(4-chlorophenyl)-1-hydroxy-4-(triisopropylsilyl)but-3-yn-2-yl)acetamide and 2-chloro-N-((1S,2R)-1-(4-chlorophenyl)-1-hydroxy-4-(triisopropylsilyl)but-3-yn-2-yl)acetamide

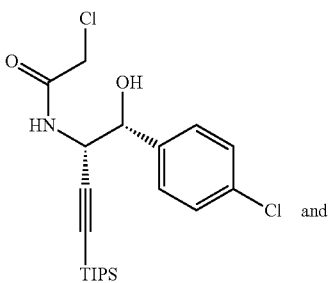

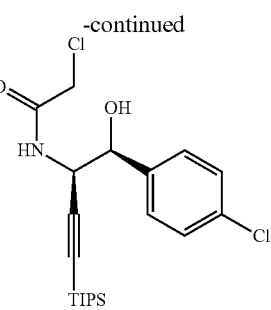

Chloroacetyl chloride (0.616 mL, 7.69 mmol) was added to a solution of (1S,2R)-2-amino-1-(4-chlorophenyl)-4-(triisopropylsilyl)but-3-yn-1-ol and (1R,2S)-2-amino-1-(4-chlorophenyl)-4-(triisopropylsilyl)but-3-yn-1-ol (2.46 g, 6.98 mmol, Example 43, Step E) and triethylamine (1.461 mL, 10.48 mmol) in anhydrous THF (69.9 mL) at 0° C. under nitrogen. After 2 hours the reaction was quenched with saturated aqueous NH₄Cl and the layers were separated. The aqueous layer was extracted with ethyl acetate (2×) and the organics were pooled, washed with brine, dried over MgSO₄, filtered and concentrated under a vacuum to provide a beige solid. Flash column chromatography (330 g SiO₂, gradient elution with 5% to 35% ethyl acetate in hexanes provided an off-white solid.

Step G. (5S,6R)-6-(4-Chlorophenyl)-5-((triisopropylsilyl)ethynyl)morpholin-3-one and (5R,6S)-6-(4-chlorophenyl)-5-((triisopropylsilyl)ethynyl)morpholin-3-one

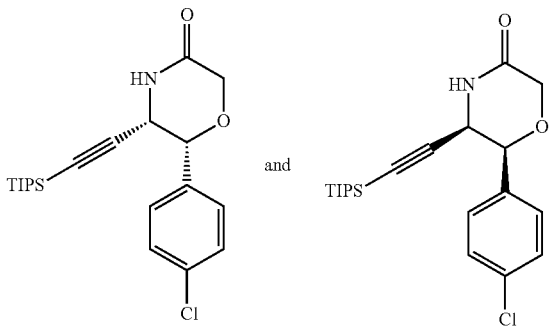

Sodium hydride (0.829 g, 20.73 mmol, 60% dispersion in mineral oil) was added to a solution of 2-chloro-N-((1S,2R)-1-(4-chlorophenyl)-1-hydroxy-4-(triisopropylsilyl)but-3-yn-2-yl)acetamide and 2-chloro-N-((1R,2S)-1-(4-chlorophenyl)-1-hydroxy-4-(triisopropylsilyl)but-3-yn-2-yl)acetamide (2.22 g, 5.18 mmol, Example 43, Step F) in anhydrous THF (51.8 mL) under nitrogen at 0° C. The ice bath was removed after the addition was complete. After 17 hours at room temperature, the reaction was quenched by the addition of ice cold water (50 mL) and saturated aqueous NH₄Cl (50 mL). The layers were separated and the aqueous layer was extracted with ethyl acetate (2×). The organics were pooled, washed with brine, dried over MgSO₄, filtered and concentrated under a vacuum to provide a yellow oil. Flash column chromatography (120 g SiO₂, gradient elution with 30% to 70% ethyl acetate in hexanes) provided an off-white solid.

Step H. (S)-Ethyl 2-((2R,3S)-2-(4-chlorophenyl)-5-oxo-3-((triisopropylsilyl)ethynyl)morpholino)pentanoate and (R)-ethyl 2-((2S,3R)-2-(4-chlorophenyl)-5-oxo-3-((triisopropylsilyl)ethynyl)morpholino)pentanoate

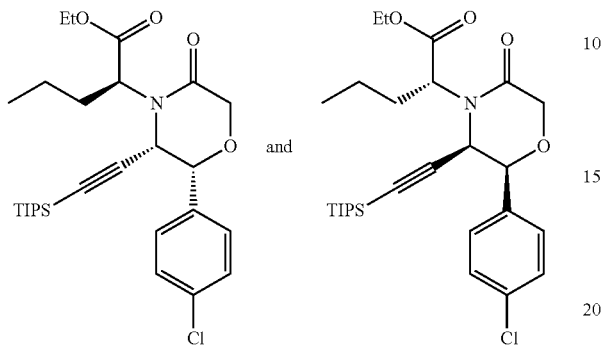

Sodium hydride (0.117 g, 2.92 mmol, 60% dispersion in mineral oil) was added to a solution of (5R,6S)-6-(4-chlorophenyl)-5-((triisopropylsilyl)ethynyl)morpholin-3-one and (5S,6R)-6-(4-chlorophenyl)-5-((triisopropylsilyl)ethynyl)morpholin-3-one (0.764 g, 1.95 mmol, Example 43, Step G) in anhydrous DMF (19.49 mL) at 0° C. under nitrogen. After 30 minutes, ethyl 2-bromovalerate (0.668 mL, 3.90 mmol) was added, and the reaction mixture was stirred at 0° C. for 2 hours before the reaction was quenched by the addition of saturated aqueous NH$_4$Cl and extracted with ethyl acetate (3×). The organics were pooled, washed with brine, dried over MgSO$_4$, filtered and concentrated under a vacuum to provide a pale yellow oil. Purification by flash column chromatography (80 g SiO$_2$, eluent: 30% MTBE in hexanes) provided separation of the desired isomer (title compound shown above) from its diastereomer with the propyl group syn to the alkyne.

The desired product eluted first to provide a colorless oil and the diastereomer eluted second to provide a white solid.

Step I. (S)-Ethyl 2-((2R,3S)-2-(4-chlorophenyl)-3-ethynyl-5-oxomorpholino)pentanoate and (R)-Ethyl 2-((2S,3R)-2-(4-chlorophenyl)-3-ethynyl-5-oxomorpholino)pentanoate

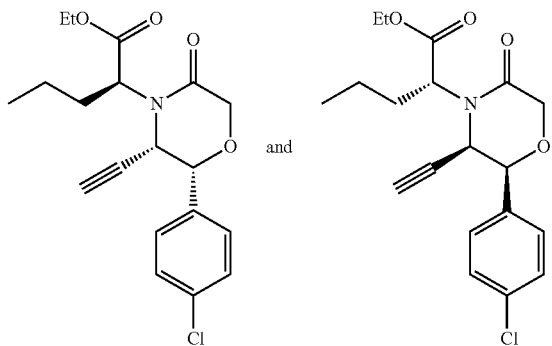 [SMILES: C#C[C@H]1[C@@H](c2ccc(Cl)cc2)OCC(=O)N1[C@@H](CCC)C(=O)OCC ; C#C[C@@H]1[C@H](c2ccc(Cl)cc2)OCC(=O)N1[C@H](CCC)C(=O)OCC]

Tetra-n-butylammonium fluoride (0.414 mL, 0.414 mmol) was added to a solution of (R)-ethyl 2-((2S,3R)-2-(4-chlorophenyl)-5-oxo-3-((triisopropylsilyl)ethynyl)morpholino)pentanoate and (S)-ethyl 2-((2R,3S)-2-(4-chlorophenyl)-5-oxo-3-((triisopropylsilyl)ethynyl)morpholino)pentanoate (0.196 g, 0.376 mmol, Example 43, Step H) in anhydrous THF (3.77 mL) at 0° C. under argon. After 15 minutes the reaction mixture was quenched with NH$_4$Cl and the layers were separated. The aqueous layer was extracted with ethyl acetate (2×) and the organic layers were pooled, washed with brine, dried over MgSO$_4$, filtered and concentrated under a vacuum to provide a colorless oil. Purification by flash column chromatography (12 g SiO$_2$, gradient elution with 0% to 30% ethyl acetate in hexanes provided a colorless oil.

Step J. (S)-Ethyl 2-((2R,3S)-3-((2-acetamidophenyl)ethynyl)-2-(4-chlorophenyl)-5-oxomorpholino)pentanoate and (R)-ethyl 2-((2S,3R)-3-((2-acetamidophenyl)ethynyl)-2-(4-chlorophenyl)-5-oxomorpholino)pentanoate

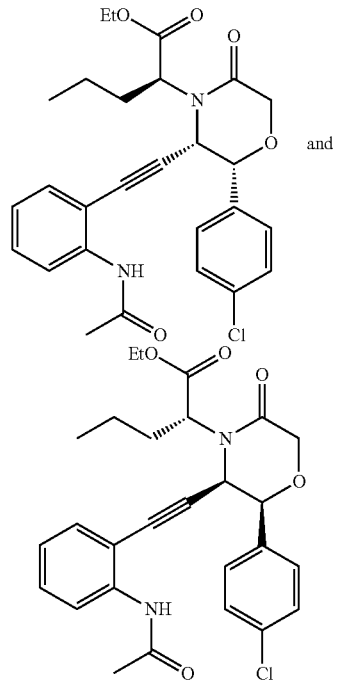

A solution of (R)-ethyl 2-((2S,3R)-2-(4-chlorophenyl)-3-ethynyl-5-oxomorpholino)pentanoate and (S)-ethyl 2-((2R,3S)-2-(4-chlorophenyl)-3-ethynyl-5-oxomorpholino)pentanoate (0.222 g, 0.610 mmol, Example 43, Step I) in anhydrous THF (6.10 mL) was degassed by bubbling argon through the solution for 10 minutes. Triethylamine (0.255 mL, 1.830 mmol), N-(2-iodophenyl)acetamide (0.159 g, 0.610 mmol), bis(triphenylphosphine)palladium(II) chloride (0.021 g, 0.031 mmol) and copper(I) iodide (5.81 mg, 0.031 mmol) were added and the solution was degassed for an additional 10 minutes. The reaction mixture was heated at 80° C. under argon for 12 hours. The reaction mixture was cooled to room temperature and diluted with water (20 mL). This solution was extracted with ethyl acetate (3×) and the organic layers were pooled, washed with brine, dried over MgSO$_4$, filtered and concentrated under a vacuum to provide a yellow oil. Purification by flash column chromatography (40 g SiO$_2$, gradient elution with 10% to 50% ethyl acetate in hexanes provided a colorless oil.

Step K. (R)-2-((2S,3R)-2-(4-Chlorophenyl)-3-(1H-indol-2-yl)-5-oxomorpholino)pentanoic acid and (S)-2-((2R,3S)-2-(4-chlorophenyl)-3-(1H-indol-2-yl)-5-oxomorpholino)pentanoic acid

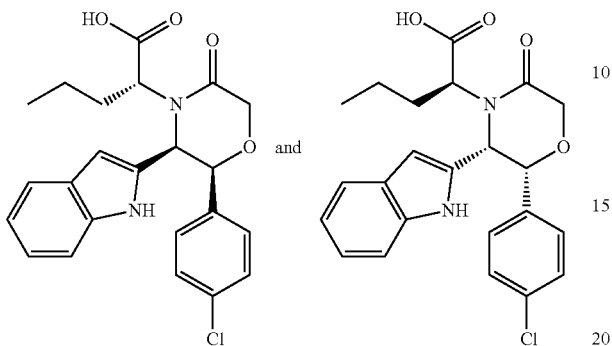

A solution of LiOH (100 mg) in water (1 mL) was added to a solution of (R)-ethyl 2-((2S,3R)-3-((2-acetamidophenyl)ethynyl)-2-(4-chlorophenyl)-5-oxomorpholino)pentanoate and (S)-ethyl 2-((2R,3S)-3-((2-acetamidophenyl)ethynyl)-2-(4-chlorophenyl)-5-oxomorpholino)pentanoate (0.046 g, 0.092 mmol, Example 43, Step J) in MeOH at room temperature. The reaction mixture was heated at 90° C. for 4 days. The reaction mixture was cooled, diluted with water (3 mL), and acidified (pH=4) by addition of 1 N HCl. This solution was extracted with ethyl acetate (3×) and the organic layers were pooled, washed with brine, dried over MgSO$_4$, filtered and concentrated under a vacuum to provide a brown oil. Purification by reverse phase preparative HPLC (C-18 column, gradient elution with 40% to 70% acetonitrile/water) provided the title compounds.

1H NMR (400 MHz, CDCl$_3$, δ ppm): 0.62 (t, J=7.4 Hz, 3H) 0.84-0.92 (m, 1H) 0.99-1.15 (m, 1H) 1.46 (m, 1H) 1.96-2.12 (m, 1H) 4.26 (d, J=17.0 Hz, 1H) 4.40 (d, J=17.0 Hz, 1H) 4.83 (d, J=6.5 Hz, 1H) 4.99 (d, J=6.3 Hz, 1H) 6.33 (s, 1H) 7.02-7.11 (m, 3H) 7.12-7.18 (m, 1H) 7.29 (m, 2H) 7.44-7.52 (m, 2H) 8.50 (br s, 1H).

Example 44

(R)-2-((2S,5R,6S)-2-Benzyl-5,6-bis(4-chlorophenyl)-3-oxomorpholino)pentanoic acid

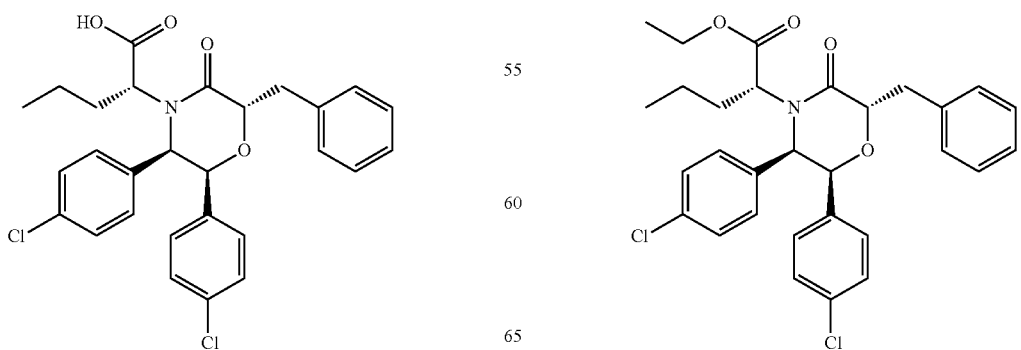

Step A. (R)-Ethyl 2-((2S,3R)-2,3-bis(4-chlorophenyl)-5-oxomorpholino)pentanoate

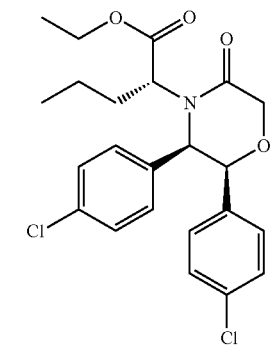 [SMILES: CCC[C@H](C(=O)OCC)N1C(=O)CO[C@@H](c2ccc(Cl)cc2)[C@H]1c1ccc(Cl)cc1]

Sodium hydride (3.73 g, 93.2 mmol, 60% dispersion in mineral oil) was added to a solution of (5R,6S)-5,6-bis(4-chlorophenyl)morpholin-3-one and (5S,6R)-5,6-bis(4-chlorophenyl)morpholin-3-one (20.0 g, 62.2 mmol, Example 4, Step F) in anhydrous DMF (150 mL) at 0° C. under nitrogen. After 1 hour, rac-ethyl 2-bromovalerate (21.2 mL, 124 mmol) was added. After 3 hours the reaction was quenched by the addition of saturated aqueous NH$_4$Cl and extracted with ethyl acetate (3×). The organic layers were pooled, washed with brine, dried over MgSO$_4$, filtered and concentrated under a vacuum to provide an orange oil. The compound was adsorbed onto SiO$_2$ (140 mL) and purified by flash column chromatography (3 stacked 330 g SiO$_2$ columns) to provide 11.38 g of the desired isomer. Further purification by chiral SFC (250×30 mm Chiralpak® IC and OD-H columns in series (Chiral Technologies, Inc., West Chester, Pa., USA) with 28 g/min MeOH+0.2% diethylamine+72 g/min CO$_2$ on a Thar 350 SFC (Thar Technologies, Inc., Pittsburgh, Pa.)) provided the title compound as the first eluting enantiomer (5.02 g), $[α]_D^{22}$=+196.1°.

Step B. (R)-Ethyl 2-((2S,5R,6S)-2-benzyl-5,6-bis(4-chlorophenyl)-3-oxomorpholino)pentanoate A 10 mL round-bottomed flask was charged with (R)-ethyl 2-((2S,3R)-2,3-bis(4-chlorophenyl)-5-oxomorpholino)pentanoate (0.165 g, 0.366 mmol, Example 44, Step A), anhydrous THF (2.443 mL) and benzyl bromide (0.048 mL, 0.403 mmol). This solution was degassed by bubbling argon through the solution for 10 minutes. The reaction mixture was cooled to −78° C. and LHMDS (0.403 mL, 0.403 mmol, 1 M in THF) was added dropwise. The reaction mixture was stirred at −78° C. under argon for three hours. The reaction mixture was quenched by the addition of saturated aqueous NH$_4$Cl. The layers were separated and the aqueous layer was extracted with ethyl acetate (2×). The organic layers were pooled, washed with brine, dried over MgSO$_4$, filtered and concentrated under a vacuum to provide a colorless glass. Purification by flash column chromatography (12 g SiO$_2$, eluent: 2.5% ethyl acetate in benzene provided a colorless oil.

Step C. (R)-2-((2S,5R,6S)-2-Benzyl-5,6-bis(4-chlorophenyl)-3-oxomorpholino)pentanoic acid

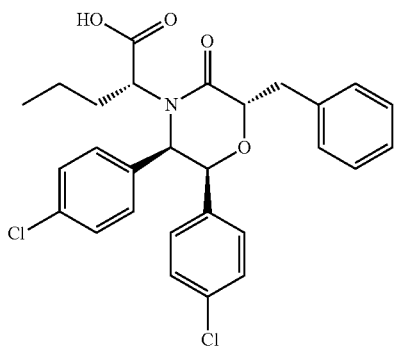 [SMILES: CCC[C@H](C(=O)O)N1C(=O)[C@H](Cc2ccccc2)O[C@@H](c2ccc(Cl)cc2)[C@H]1c1ccc(Cl)cc1]

Lithium hydroxide (100.0 mg, 4.18 mmol) in water (1 mL) was added to a solution of (R)-ethyl 2-((2S,5R,6S)-2-benzyl-5,6-bis(4-chlorophenyl)-3-oxomorpholino)pentanoate (0.082 g, 0.152 mmol, Example 44, Step B) in MeOH (3 mL) at room temperature. After 2 hours the pH was adjusted to 1 by addition of 1 N HCl and the mixture was stirred vigorously. The resulting precipitate was collected by vacuum filtration to provide the title compound as a white solid.

$^1$H NMR (400 MHz, CDCl$_3$, δ ppm): 7.22 (m, 5H), 7.12 (m, 4H), 6.78 (d, J=8.6 Hz, 2H), 6.73 (d, J=8.2 Hz, 2H), 5.02 (m, 1H), 4.96 (m, 1H), 4.60 m, 1H), 4.39 (d, J=2.4 Hz, 1H), 3.42 (dd, J=7.8 and 14.1 Hz, 1H), 3.31 (dd, J=3.9 and 14.1 Hz, 1H), 1.95-1.88 (m, 1H), 1.64-1.60 (m, 1H), 1.31-1.26 (m, 1H), 1.15-1.05 (m, 1H), 0.74 (t, J=7.0 Hz, 3H).

Example 45

(R)-2-((2S,3R,6S)-2,3-Bis(4-chlorophenyl)-6-(2-cyano-4-fluorobenzyl)-5-oxomorpholino)pentanoic acid

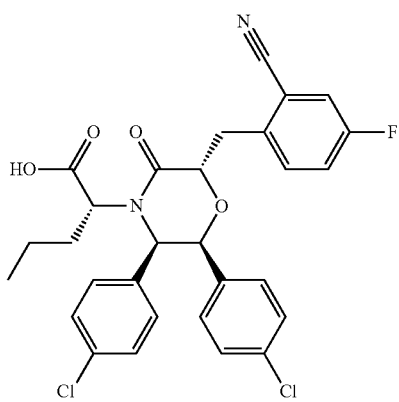 [SMILES: CCC[C@H](C(=O)O)N1C(=O)[C@H](Cc2ccc(F)cc2C#N)O[C@@H](c2ccc(Cl)cc2)[C@H]1c1ccc(Cl)cc1]

Step A. 2-(Bromomethyl)-5-fluorobenzonitrile

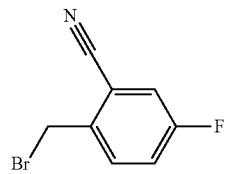

A solution of 5-fluoro-2-methylbenzonitrile (500 mg, 3700 μmol), NBS (659 mg, 3700 μmol), and AIBN (30.4 mg, 185 μmol) in carbon tetrachloride (37 mL) was heated at reflux for 3 hours. The mixture was quenched with water (10 mL) and cooled to room temperature. The mixture was extracted with DCM (2×, 100 mL). The combined organic layers were washed with brine, dried over Na$_2$SO$_4$ and concentrated. The residue was purified by flash chromatography on silica gel (eluent: 0% to 40% DCM in hexanes) to give the title compound.

Step B. (R)-Ethyl 2-((2S,3R,6S)-2,3-bis(4-chlorophenyl)-6-(2-cyano-4-fluorobenzyl)-5-oxomorpholino)pentanoate

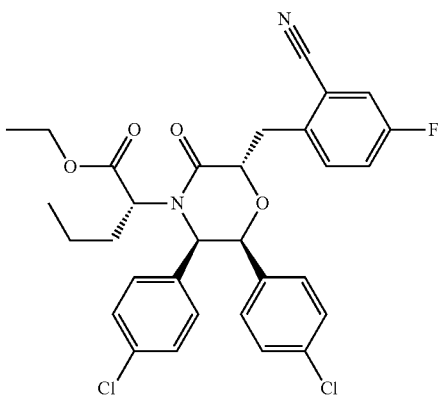 [SMILES: CCC[C@H](C(=O)OCC)N1C(=O)[C@H](Cc2ccc(F)cc2C#N)O[C@@H](c2ccc(Cl)cc2)[C@H]1c1ccc(Cl)cc1]

The title compound was prepared from (R)-ethyl 2-((2S,3R)-2,3-bis(4-chlorophenyl)-5-oxomorpholino)pentanoate (Example 44, Step A) and 2-(bromomethyl)-5-fluorobenzonitrile (Example 45, Step A) by a procedure similar to the that described in Example 10, Step C.

Step C. (R)-2-((2S,3R,6S)-2,3-Bis(4-chlorophenyl)-6-(2-cyano-4-fluorobenzyl)-5-oxomorpholino)pentanoic acid

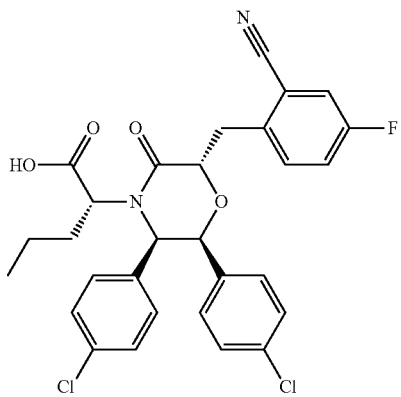 [SMILES: CCC[C@H](C(=O)O)N1C(=O)[C@H](Cc2ccc(F)cc2C#N)O[C@@H](c2ccc(Cl)cc2)[C@H]1c1ccc(Cl)cc1]

The title compound was prepared from (R)-ethyl 2-((2S,3R,6S)-2,3-bis(4-chlorophenyl)-6-(2-cyano-4-fluorobenzyl)-5-oxomorpholino)pentanoate (Example 45, Step B) by a procedure similar to the one described in (Example 10, Step D).

$^1$H NMR (500 MHz, CDCl$_3$, δ ppm): 7.40-7.46 (m, J=5.4 Hz, 1H), 7.19-7.26 (m, 2H), 7.13 (d, J=8.3 Hz, 4H), 6.71-6.81 (m, 4H), 5.39 (dd, J=2.2, 0.5 Hz, 1H), 4.89-4.97 (m, 1H), 4.80 (dd, J=9.3, 5.6 Hz, 1H), 4.53 (d, J=2.7 Hz, 1H), 3.61-3.69 (m, 1H), 3.54 (dd, J=14.5, 9.9 Hz, 1H), 1.85-1.96 (m, 1H), 1.52-1.59 (m, 1H), 1.24-1.36 (m, 1H), 1.08-1.20 (m, 1H), 0.71 (t, J=7.3 Hz, 3H). Spectrum (ESI) m/z=555 [M+1].

Examples 46 through 49 were also prepared from (R)-ethyl 2-((2S,3R)-2,3-bis(4-chlorophenyl)-5-oxomorpholino)pentanoate (Example 44, Step A) as described in (Example 10, Steps C and D) substituting 1-(bromomethyl) 4-fluorobenzene in Example 10, Step C with an equivalent amount of the appropriate alkyl bromide.

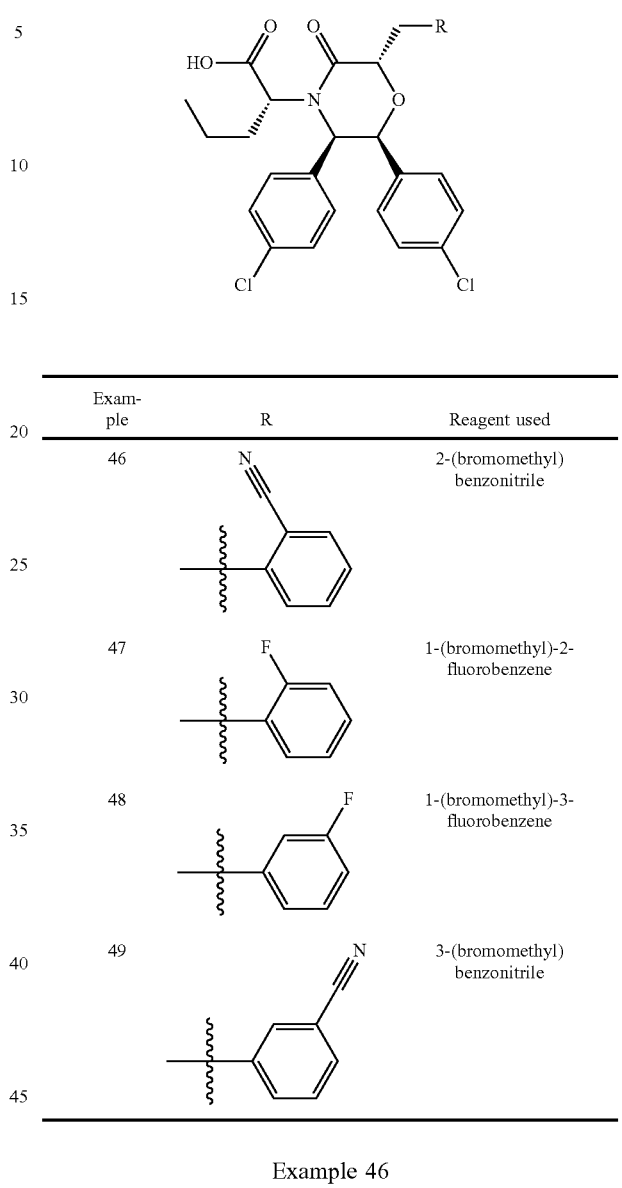

| Example | R | Reagent used |
|---|---|---|
| 46 | 2-cyanophenyl | 2-(bromomethyl)benzonitrile |
| 47 | 2-fluorophenyl | 1-(bromomethyl)-2-fluorobenzene |
| 48 | 3-fluorophenyl | 1-(bromomethyl)-3-fluorobenzene |
| 49 | 3-cyanophenyl | 3-(bromomethyl)benzonitrile |

Example 46

(R)-2-((2S,3R,6S)-2,3-Bis(4-chlorophenyl)-6-(2-cyanobenzyl)-5-oxomorpholino)pentanoic acid $^1$H NMR (400 MHz, CDCl$_3$, δ ppm): 7.48-7.55 (m, 2H), 7.42-7.47 (m, 1H), 7.28-7.34 (m, 1H), 7.07-7.15 (m, 4H), 6.73-6.81 (m, 4H), 5.46 (dd, J=2.0, 0.8 Hz, 1H), 4.96 (dd, J=9.9, 3.8 Hz, 1H), 4.79-4.87 (m, J=11.7 Hz, 1H), 4.57 (dd, J=2.2, 0.6 Hz, 1H), 3.65-3.71 (m, 1H), 3.52-3.61 (m, 1H), 1.81-1.98 (m, 1H), 1.45-1.59 (m, 1H), 1.25-1.35 (m, 1H), 1.04-1.17 (m, 1H), 0.64-0.72 (m, 3H). Spectrum (ESI) m/z=537 [M+1].

Example 47

(R)-2-((2S,3R,6S)-2,3-Bis(4-chlorophenyl)-6-(2-fluorobenzyl)-5-oxomorpholino)pentanoic acid $^1$H NMR (400 MHz, CDCl$_3$, δ ppm): 7.15-7.24 (m, 2H), 7.07-7.14 (m, 4H), 6.98-7.05 (m, 1H), 6.89-6.97 (m, 1H), 6.79 (dd, J=8.5, 1.9 Hz, 4H), 5.33-5.39 (m, 1H), 4.93 (dd, J=9.9, 3.8 Hz, 1H), 4.45-4.55 (m, 1H), 3.42-3.52 (m, 1H), 3.31-3.41 (m, 1H), 1.75-1.98 (m, 1H), 1.44-1.65 (m, 1H), 1.26 (d, J=4.5 Hz, 2H), 1.02-1.17 (m, 1H), 0.66-0.76 (m, 3H). Spectrum (ESI) m/z=530 [M+1].

Example 48

(R)-2-((2S,3R,6S)-2,3-Bis(4-chlorophenyl)-6-(3-fluorobenzyl)-5-oxomorpholino)pentanoic acid $^1$H NMR (400 MHz, CDCl$_3$, δ ppm): 7.08-7.21 (m, 5H), 6.88-6.98 (m, 3H), 6.72-6.81 (m, 4H), 5.04-5.11 (m, 1H), 4.94 (dd, J=7.8, 3.9 Hz, 1H), 4.62-4.74 (m, 1H), 4.44-4.51 (m, 1H), 3.25-3.43 (m, 2H), 1.80-1.97 (m, 1H), 1.47-1.62 (m, 1H), 1.24-1.33 (m, 1H), 1.00-1.15 (m, 1H), 0.64-0.73 (m, 3H). Spectrum (ESI) m/z=530 [M+1].

Example 49

(R)-2-((2S,3R,6S)-2,3-Bis(4-chlorophenyl)-6-(3-cyanobenzyl)-5-oxomorpholino)pentanoic acid $^1$H NMR (500 MHz, CDCl$_3$, δ ppm): 7.50-7.58 (m, 2H), 7.43 (dt, J=7.9, 1.5 Hz, 1H), 7.30-7.35 (m, 1H), 7.09-7.18 (m, 4H), 6.68-6.80 (m, 4H), 4.94-5.01 (m, 2H), 4.86 (dd, J=9.3, 5.4 Hz, 1H), 4.45 (d, J=2.7 Hz, 1H), 3.42-3.52 (m, 1H), 3.31-3.39 (m, 1H), 1.82-1.93 (m, 1H), 1.47-1.54 (m, 1H), 1.22-1.31 (m, 1H), 1.01-1.14 (m, 1H), 0.69 (t, J=7.3 Hz, 3H). Spectrum (ESI) m/z=537 [M+1].

Example 50

(R)-2-((2S,3R,6S)-2,3-Bis(4-chlorophenyl)-6-(3-(methylsulfonyl)benzyl)-5-oxomorpholino)pentanoic acid

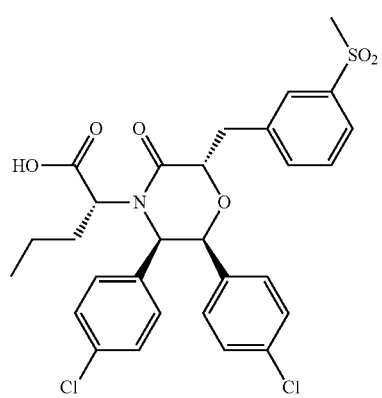 [SMILES: CCC[C@H](C(=O)O)N1C(=O)[C@H](Cc2cccc(S(C)(=O)=O)c2)O[C@@H](c2ccc(Cl)cc2)[C@H]1c1ccc(Cl)cc1]

Step A. (R)-Ethyl 2-((2S,3R,6S)-2,3-bis(4-chlorophenyl)-6-(3-iodobenzyl)-5-oxomorpholino)pentanoate

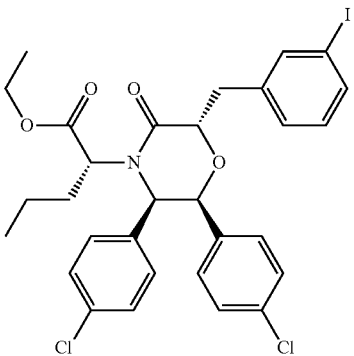 [SMILES: CCC[C@H](C(=O)OCC)N1C(=O)[C@H](Cc2cccc(I)c2)O[C@@H](c2ccc(Cl)cc2)[C@H]1c1ccc(Cl)cc1]

The title compound was prepared from (R)-ethyl 2-((2S,3R)-2,3-bis(4-chlorophenyl)-5-oxomorpholino)pentanoate (Example 44, Step A) and 1-(bromomethyl)-3-iodobenzene by a procedure similar to the one described in (Example 10, Step C).

Step B. (R)-Ethyl 2-((2S,3R,6S)-2,3-bis(4-chlorophenyl)-6-(3-(methylsulfonyl)benzyl)-5-oxomorpholino)pentanoate

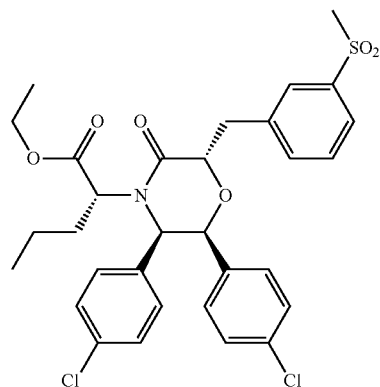 [SMILES: CCC[C@H](C(=O)OCC)N1C(=O)[C@H](Cc2cccc(S(C)(=O)=O)c2)O[C@@H](c2ccc(Cl)cc2)[C@H]1c1ccc(Cl)cc1]

A solution of (R)-ethyl 2-((2S,3R,6S)-2,3-bis(4-chlorophenyl)-6-(3-iodobenzyl)-5-oxomorpholino)pentanoate (81 mg, 0.122 mmol, Example 50, Step A), sodium methanesulfinate (49.6 mg, 486 μmol), and copper(I) iodide (34.7 mg, 182 μmol) in DMF (1216 μL) in a capped vial was stirred at 125° C. overnight. The mixture was diluted with ethyl acetate and filtered through diatomaceous earth. The filtrate was washed with saturated NaHCO$_3$ (3×, 50 mL). The organic layer was washed with brine, dried over Na$_2$SO$_4$, and concentrated. The crude residue was purified by preparative thin layer silica gel chromatography (eluent: 50% ethyl acetate/hexanes) to provide the title compound.

Step C. (R)-2-((2S,3R,6S)-2,3-Bis(4-chlorophenyl)-6-(3-(methylsulfonyl)benzyl)-5-oxomorpholino)pentanoic acid The title compound was prepared from (R)-ethyl 2-((2S, 3R,6S)-2,3-bis(4-chlorophenyl)-6-(3-(methylsulfonyl)benzyl)-5-oxomorpholino)pentanoate (Example 50, Step B) by a procedure similar to the one described in (Example 32, Step E).

<sup>1</sup>H NMR (400 MHz, CDCl<sub>3</sub>, δ ppm): 7.72-7.83 (m, 2H), 7.45-7.52 (m, 1H), 7.36-7.44 (m, 1H), 7.04-7.16 (m, 4H), 6.70-6.81 (m, 4H), 5.06-5.16 (m, 1H), 4.98 (td, J=8.2, 4.7 Hz, 2H), 4.55 (dd, J=2.1, 0.7 Hz, 1H), 3.46-3.56 (m, 1H), 3.39-3.46 (m, 1H), 2.83 (s, 3H), 1.76-1.90 (m, 1H), 1.32-

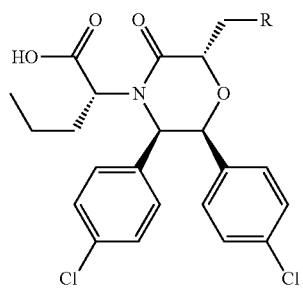

| Example | Alkyl Bromide | Reagent used | R (Final compound) |
|---|---|---|---|
| 51 | [structure: 1-iodo-2-(bromomethyl)benzene] | 1-(bromomethyl)-2-iodobenzene | [structure: 2-(methylsulfonyl)phenyl] |
| 52 | [structure: 2-iodo-4-fluoro-1-(bromomethyl)benzene] | 1-(bromomethyl)-4-fluoro-2-iodobenzene | [structure: 5-fluoro-2-(methylsulfonyl)phenyl] |
| 53 | [structure: 4-(bromomethyl)-2-fluoro-1-iodobenzene] | 4-(bromomethyl)-2-fluoro-1-iodobenzene | [structure: 3-fluoro-4-(methylsulfonyl)phenyl] |
| 54 | [structure: 1-(bromomethyl)-4-iodobenzene] | 1-(bromomethyl)-4-iodobenzene | [structure: 4-(methylsulfonyl)phenyl] |

1.46 (m, 1H), 1.15-1.30 (m, 1H), 0.95-1.10 (m, 1H), 0.57-0.65 (m, 3H). Spectrum (ESI) m/z=590 [M+1].

Examples 51 to 54 were also prepared from (R)-ethyl 2-((2S,3R)-2,3-bis(4-chlorophenyl)-5-oxomorpholino)pentanoate (Example 44, Step A) as described in (Example 50, Steps A through C) substituting 1-(bromomethyl)-3-iodobenzene in Example 50, Step A with an equivalent amount of the appropriate alkyl bromide. The required alkyl bromides are prepared as described in the individual examples.

Example 51

(R)-2-((2S,3R,6S)-2,3-Bis(4-chlorophenyl)-6-(2-(methylsulfonyl)benzyl)-5-oxomorpholino)pentanoic acid 1H NMR (400 MHz, CDCl<sub>3</sub>, δ ppm): 8.00 (dt, J=7.8, 0.8 Hz, 1H), 7.44-7.50 (m, 1H), 7.32-7.44 (m, 2H), 7.06-7.13 (m, 4H), 6.81 (dd, J=8.3, 3.4 Hz, 4H), 5.53 (br s, 1H), 5.07-5.17 (m, 1H), 4.78-4.87 (m, 1H), 4.61-4.68 (m, 1H), 3.94-4.04 (m, 1H), 3.74 (dd, J=14.7, 9.8 Hz, 1H), 3.02 (s, 3H), 1.80-1.96 (m, 1H), 1.48 (ddt, J=14.5, 9.7, 4.8 Hz, 1H), 1.20-1.34 (m, 1H), 1.02-1.15 (m, 1H), 0.61-0.70 (m, 3H). Spectrum (ESI) m/z=590 [M+1].

Example 52

(R)-2-((2S,3R,6S)-2,3-Bis(4-chlorophenyl)-6-(4-fluoro-2-(methylsulfonyl)benzyl)-5-oxomorpholino)pentanoic acid <sup>1</sup>H NMR (400 MHz, CDCl<sub>3</sub>, δ ppm): 7.79 (t, J=7.7 Hz, 1H), 7.07-7.21 (m, 6H), 6.70-6.82 (m, 4H), 5.10-5.19 (m, 1H), 4.90-5.04 (m, 2H), 4.46-4.55 (m, 1H), 3.43 (d, J=6.1 Hz, 2H), 3.19 (s, 3H), 1.74-1.87 (m, 1H), 1.34 (ddd, J=14.3, 9.7, 4.5 Hz, 1H), 1.14-1.25 (m, 1H), 0.93-1.05 (m, 1H), 0.55-0.62 (m, 3H). Spectrum (ESI) m/z=608 [M+1].

Synthesis of 1-(bromomethyl)-4-fluoro-2-iodobenzene

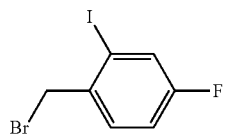

The title compound was prepared from 4-fluoro-2-iodotoluene by a procedure similar to the one described in Example 45, Step A.

Example 53

(R)-2-((2S,3R,6S)-2,3-Bis(4-chlorophenyl)-6-(3-fluoro-4-(methylsulfonyl)benzyl)-5-oxomorpholino)pentanoic acid ¹H NMR (400 MHz, CDCl₃, δ ppm): 7.71-7.85 (m, 1H), 7.10-7.22 (m, 6H), 6.70-6.81 (m, 4H), 4.89-5.07 (m, 3H), 4.40-4.46 (m, 1H), 3.46-3.58 (m, 1H), 3.35-3.46 (m, 1H), 3.20 (s, 3H), 1.77-1.94 (m, 1H), 1.44 (dq, J=9.6, 4.8 Hz, 1H), 1.18-1.25 (m, 1H), 0.95-1.14 (m, 1H), 0.65 (t, J=7.3 Hz, 3H).

Synthesis of 4-(bromomethyl)-2-fluoro-1-iodobenzene

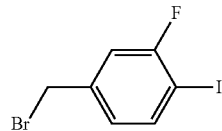

The title compound was prepared from 2-fluoro-4-iodotoluene (Alfa Aesar, Ward Hill, Mass.) by a procedure similar to the one described in (Example 45, Step A).

Example 54

(R)-2-((2S,3R,6S)-2,3-Bis(4-chlorophenyl)-6-(4-(methylsulfonyl)benzyl)-5-oxomorpholino)pentanoic acid ¹H NMR (500 MHz, CDCl₃, δ ppm): 7.79 (d, J=8.3 Hz, 2H), 7.41 (d, J=8.3 Hz, 2H), 7.13 (t, J=8.6 Hz, 4H), 6.74 (dd, J=17.0, 8.4 Hz, 4H), 4.94-5.05 (m, 2H), 4.80-4.91 (m, 1H), 4.41-4.52 (m, 1H), 3.45-3.57 (m, 1H), 3.35-3.45 (m, 1H), 2.98-3.09 (m, 3H), 1.77-1.94 (m, 1H), 1.45 (ddt, J=14.5, 9.7, 5.0 Hz, 1H), 1.18-1.31 (m, 1H), 0.98-1.12 (m, 1H), 0.65 (t, J=7.3 Hz, 3H). Spectrum (ESI) m/z=590 [M+1].

Example 55

(R)-2-((2S,3R,6S)-2,3-Bis(4-chlorophenyl)-6-(2-cyano-4-(methylsulfonyl)benzyl)-5-oxomorpholino)pentanoic acid

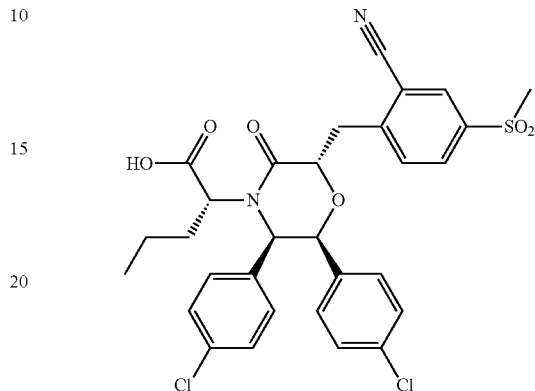

Step A. 2-methyl-5-(methylthio)benzonitrile

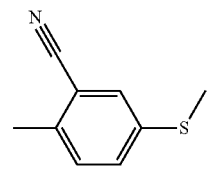

To a solution of 5-fluoro-2-methylbenzonitrile (3.770 g, 27.9 mmol) in DMF (279 mL) was added sodium thiomethoxide (7.82 g, 112 mmol) at room temperature. The mixture was heated to 100° C. and stirred at 100° C. for 2 hours. The mixture was cooled to room temperature and diluted with ether (2 L). The mixture was washed with saturated NaHCO₃ (3×, 300 mL) and brine. The organic layer was dried over Na₂SO₄ and concentrated to give the title compound.

Step B. 2-(Bromomethyl)-5-(methylthio)benzonitrile

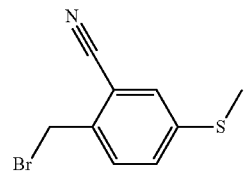

The title compound was prepared from 2-methyl-5-(methylthio)benzonitrile (Example 55, Step A) by a procedure similar to the one described in Example 45, Step A.

Step C. (R)-Ethyl 2-((2S,3R,6S)-2,3-bis(4-chlorophenyl)-6-(2-cyano-4-(methylthio)benzyl)-5-oxomorpholino)pentanoate

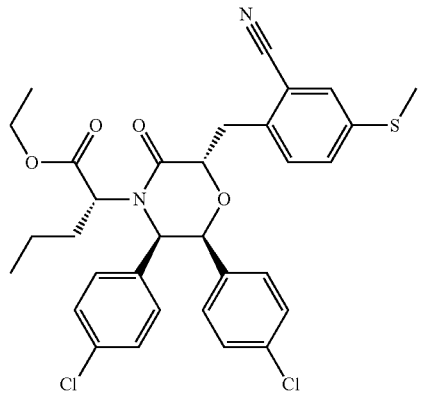 [SMILES: CCC[C@H](C(=O)OCC)N1C(=O)[C@H](Cc2ccc(SC)cc2C#N)O[C@@H](c2ccc(Cl)cc2)[C@H]1c1ccc(Cl)cc1]

The title compound was prepared from (R)-ethyl 2-((2S,3R)-2,3-bis(4-chlorophenyl)-5-oxomorpholino)pentanoate (Example 44, Step A) and 2-(bromomethyl)-5-(methylthio)benzonitrile (Example 55, Step B) by a procedure similar to the one described in Example 10, Step C.

Step D. (R)-Ethyl 2-((2S,3R,6S)-2,3-bis(4-chlorophenyl)-6-(2-cyano-4-(methylsulfonyl)benzyl)-5-oxomorpholino)pentanoate

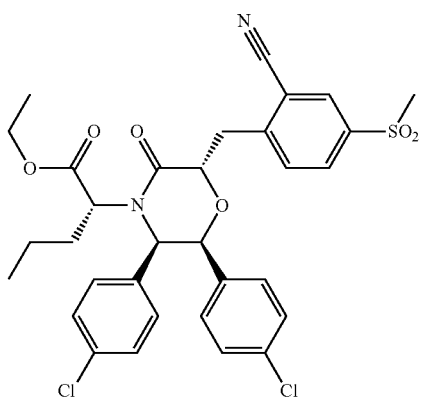 [SMILES: CCC[C@H](C(=O)OCC)N1C(=O)[C@H](Cc2ccc(S(C)(=O)=O)cc2C#N)O[C@@H](c2ccc(Cl)cc2)[C@H]1c1ccc(Cl)cc1]

4-Chlorobenzoperoxoic acid (127 mg, 0.736 mmol) was added to a solution of (R)-ethyl 2-((2S,3R,6S)-2,3-bis(4-chlorophenyl)-6-(2-cyano-4-(methylthio)benzyl)-5-oxomorpholino)pentanoate (125 mg, 0.204 mmol, Example 55, Step C) in DCM (2 mL) at room temperature. After stirring at room temperature overnight, the mixture was quenched with saturated aq. NaHCO₃ (50 mL) and diluted with DCM (150 mL). The layers were separated and the aqueous layer was back extracted with DCM (100 mL). The combined organic layers were washed with brine, dried over Na₂SO₄ and concentrated. The residue was purified by flash chromatography on silica gel (gradient elution with 0% to 3% MeOH in DCM) to give the title compound.

Step E. (R)-2-((2S,3R,6S)-2,3-Bis(4-chlorophenyl)-6-(2-cyano-4-(methylsulfonyl)benzyl)-5-oxomorpholino)pentanoic acid

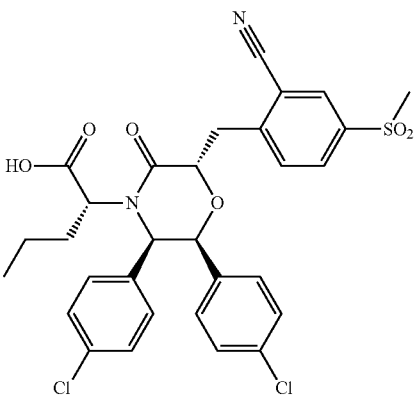 [SMILES: CCC[C@H](C(=O)O)N1C(=O)[C@H](Cc2ccc(S(C)(=O)=O)cc2C#N)O[C@@H](c2ccc(Cl)cc2)[C@H]1c1ccc(Cl)cc1]

The title compound was prepared from (R)-ethyl 2-((2S,3R,6S)-2,3-bis(4-chlorophenyl)-6-(2-cyano-4-(methylsulfonyl)benzyl)-5-oxomorpholino)pentanoate (Example 55, Step D) by a procedure similar to the one described in Example 32, Step E.

¹H NMR (500 MHz, CDCl₃, δ ppm): 8.03-8.12 (m, 2H), 7.71 (d, J=8.1 Hz, 1H), 7.08-7.15 (m, 4H), 6.76 (d, J=8.6 Hz, 4H), 5.37-5.47 (m, 1H), 5.00 (dd, J=9.9, 3.8 Hz, 1H), 4.89-4.97 (m, 1H), 4.53-4.60 (m, 1H), 3.79 (dd, J=14.3, 3.8 Hz, 1H), 3.64 (dd, J=14.3, 9.9 Hz, 1H), 3.06 (s, 3H), 1.78-1.94 (m, 1H), 1.36-1.51 (m, 1H), 1.18-1.31 (m, 1H), 0.97-1.12 (m, 1H), 0.60-0.66 (m, 3H). Spectrum (ESI) m/z=615 [M+1].

Example 56

(R)-2-((2S,3R,6S)-2,3-Bis(4-chlorophenyl)-5-oxo-6-(4-((trifluoromethyl)sulfonyl)benzyl)morpholino)pentanoic acid

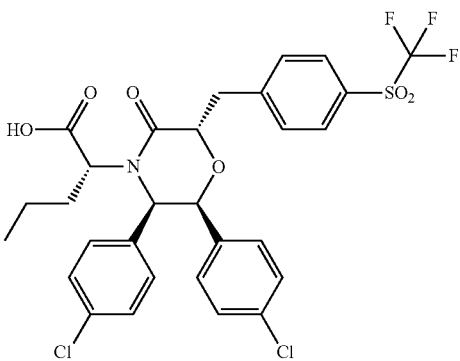 [SMILES: CCC[C@H](C(=O)O)N1C(=O)[C@H](Cc2ccc(S(=O)(=O)C(F)(F)F)cc2)O[C@@H](c2ccc(Cl)cc2)[C@H]1c1ccc(Cl)cc1]

Step A. (R)-Ethyl 2-((2S,3R,6S)-2,3-bis(4-chlorophenyl)-5-oxo-6-(4-((trifluoromethyl)thio)benzyl)morpholino)pentanoate

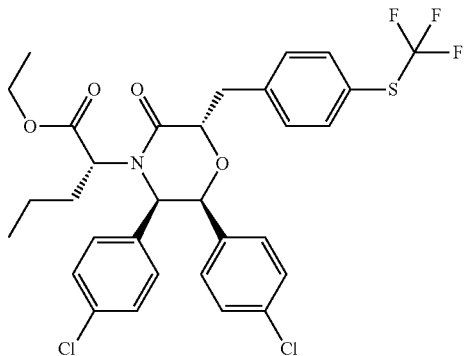 [SMILES: CCC[C@H](C(=O)OCC)N1C(=O)[C@H](Cc2ccc(SC(F)(F)F)cc2)O[C@@H](c2ccc(Cl)cc2)[C@H]1c1ccc(Cl)cc1]

The title compound was prepared from (R)-ethyl 2-((2S,3R)-2,3-bis(4-chlorophenyl)-5-oxomorpholino)pentanoate (Example 44, Step A) and 4-(trifluoromethylthiol)benzyl bromide by a procedure similar to the one described in Example 10, Step C.

Step B. (R)-Ethyl 2-((2S,3R,6S)-2,3-bis(4-chlorophenyl)-5-oxo-6-(4-((trifluoromethyl)sulfonyl)benzyl)morpholino)pentanoate

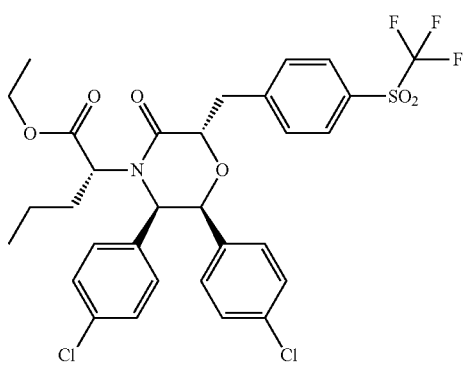 [SMILES: CCC[C@H](C(=O)OCC)N1C(=O)[C@H](Cc2ccc(S(=O)(=O)C(F)(F)F)cc2)O[C@@H](c2ccc(Cl)cc2)[C@H]1c1ccc(Cl)cc1]

The title compound was prepared from (R)-ethyl 2-((2S,3R,6S)-2,3-bis(4-chlorophenyl)-5-oxo-6-(4-((trifluoromethyl)thio)benzyl)morpholino)pentanoate (Example 56, Step A) by a procedure similar to the one described in Example 55, Step D.

Step C. (R)-2-((2S,3R,6S)-2,3-Bis(4-chlorophenyl)-5-oxo-6-(4-((trifluoromethyl)sulfonyl)benzyl)morpholino)pentanoic acid The title compound was prepared from (R)-ethyl 2-((2S,3R,6S)-2,3-bis(4-chlorophenyl)-5-oxo-6-(4-((trifluoromethyl)sulfonyl)benzyl)morpholino)pentanoate (Example 56, Step B) by a procedure similar to the one described in Example 32, Step E.
$^1$H NMR (500 MHz, CDCl$_3$, δ ppm): 7.88 (d, J=8.3 Hz, 2H), 7.47-7.55 (m, 2H), 7.08-7.18 (m, 4H), 6.64-6.80 (m, 4H), 4.99-5.06 (m, 1H), 4.91-4.99 (m, 1H), 4.67-4.82 (m, 1H), 4.45-4.51 (m, 1H), 3.51-3.58 (m, 1H), 3.41-3.47 (m, 1H), 1.79-1.93 (m, 1H), 1.47-1.60 (m, 1H), 1.25-1.34 (m, 1H), 1.00-1.12 (m, 1H), 0.65-0.72 (m, 3H). Spectrum (ESI) m/z=644 [M+1].

Example 57

(R)-2-((2S,3R,6S)-2,3-Bis(4-chlorophenyl)-6-(3-morpholinopropyl)-5-oxomorpholino)pentanoic acid

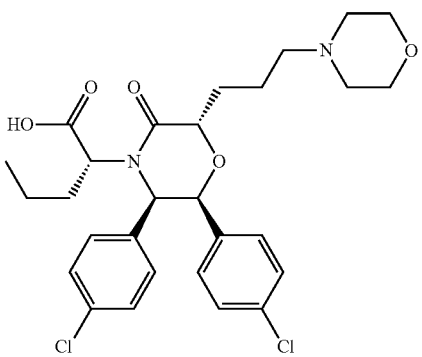 [SMILES: CCC[C@H](C(=O)O)N1C(=O)[C@H](CCCN2CCOCC2)O[C@@H](c2ccc(Cl)cc2)[C@H]1c1ccc(Cl)cc1]

Step A. (R)-Ethyl 2-((2S,5R,6S)-2-allyl-5,6-bis(4-chlorophenyl)-3-oxomorpholino)pentanoate

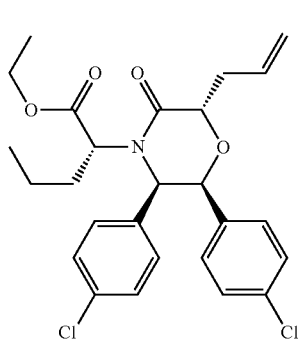 [SMILES: C=CC[C@@H]1O[C@@H](c2ccc(Cl)cc2)[C@@H](c2ccc(Cl)cc2)N([C@H](CCC)C(=O)OCC)C1=O]

In an oven-dried flask, (R)-Ethyl 2-((2S,3R)-2,3-bis(4-chlorophenyl)-5-oxomorpholino)pentanoate (1.0 g, 2.22 mmol, Example 44, Step A) and allyl bromide (0.376 mL, 4.44 mmol) were dissolved in THF (14.8 mL) and degassed by bubbling argon through the solution for 10 minutes. The mixture was cooled to −78° C. under argon. Then, LiHMDS (3.33 mL, 3.33 mmol, 1.0 M in THF) was added to the mixture and the mixture was stirred at −78° C. for 3 hours. The mixture was quenched with 50% saturated NH$_4$Cl solution and diluted with 50 mL of ethyl acetate. The mixture was warmed to room temperature and stirred overnight. The layers were separated and the aqueous layer was back-extracted with ethyl acetate (2×, 100 mL). The combined organic layers were washed with brine, dried over Na$_2$SO$_4$, and concentrated. The residue was purified by flash chromatography on silica gel (gradient elution with 50% to 100% DCM in hexanes) to give the title compound.

Step B. (R)-Ethyl 2-((2S,3R,6S)-2,3-bis(4-chlorophenyl)-6-(3-hydroxypropyl)-5-oxomorpholino)pentanoate

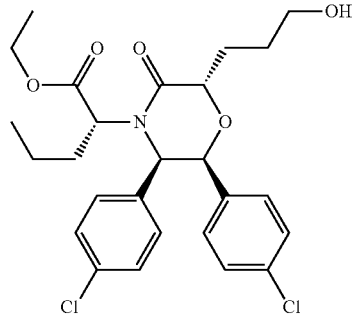 [SMILES: CCC[C@H](C(=O)OCC)N1C(=O)[C@H](CCCO)O[C@@H](c2ccc(Cl)cc2)[C@H]1c1ccc(Cl)cc1]

9-Borabicyclo[3.3.1]nonane (1622 μL, 0.811 mmol, 0.5 M in THF) was added dropwise to a solution of (R)-ethyl 2-((2S,5R,6S)-2-allyl-5,6-bis(4-chlorophenyl)-3-oxomorpholino)pentanoate (234 mg, 0.477 mmol, Example 57, Step A) in THF (795 μL, 0.477 mmol) at 0° C. under $N_2$ (g). The mixture was stirred at 0° C. for 5 minutes and then warmed to room temperature. The mixture was stirred at room temperature for 2 days.

Aqueous hydrogen peroxide (14.62 μL, 0.477 mmol, 30% solution) and pH 7 buffer were added to the solution and the reaction was allowed to stir at 60° C. for 3 hours. The mixture was diluted with water (10 mL) and ethyl acetate (100 mL). The layers were separated and the aqueous layer was back-extracted with ethyl acetate (100 mL). The combined organic layers were washed with brine, dried over $Na_2SO_4$ and concentrated. The residue was purified by flash chromatography on silica gel (gradient elution with 60% to 100% ethyl acetate in hexanes) to give the title compound.

Step C. (R)-Ethyl 2-((2S,3R,6S)-2,3-bis(4-chlorophenyl)-5-oxo-6-(3-oxopropyl)morpholino)pentanoate

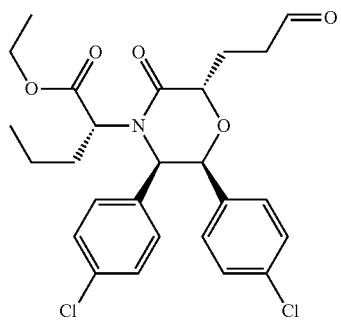 [SMILES: CCC[C@H](C(=O)OCC)N1C(=O)[C@H](CCC=O)O[C@@H](c2ccc(Cl)cc2)[C@H]1c1ccc(Cl)cc1]

Dess-Martin periodinane (222 mg, 0.523 mmol) was added to a stirring solution of (R)-ethyl 2-((2S,3R,6S)-2,3-bis(4-chlorophenyl)-6-(3-hydroxypropyl)-5-oxomorpholino)pentanoate (190 mg, 0.374 mmol, Example 57, Step B) in dichloromethane (3737 μL, 0.374 mmol) at room temperature. The mixture was stirred at room temperature for 4 hours. The mixture was diluted with water (10 mL) and DCM (100 mL). The layers were separated and the aqueous layer was back-extracted with 100 mL DCM. The combined organic layers were washed with brine, dried over $Na_2SO_4$ and concentrated. The crude residue was purified by preparative thin layer chromatography (eluent: 100% ethyl acetate) to provide the title compound.

Step D. (R)-Ethyl 2-((2S,3R,6S)-2,3-bis(4-chlorophenyl)-6-(3-morpholinopropyl)-5-oxomorpholino)pentanoate

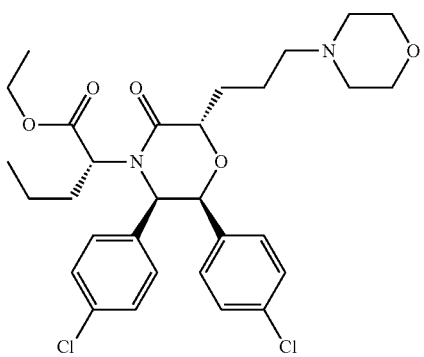 [SMILES: CCC[C@H](C(=O)OCC)N1C(=O)[C@H](CCCN2CCOCC2)O[C@@H](c2ccc(Cl)cc2)[C@H]1c1ccc(Cl)cc1]

Sodium triacetoxyborohydride (64.4 mg, 0.341 mmol) was added to a solution of (R)-ethyl 2-((2S,3R,6S)-2,3-bis(4-chlorophenyl)-5-oxo-6-(3-oxopropyl)morpholino)pentanoate (75 mg, 0.148 mmol; Example 57, Step C) and morpholine (25.6 μL, 0.296 mmol) in 1,2-dichloroethane (14.66 mg, 0.148 mmol). The mixture was stirred at room temperature overnight. The mixture was quenched with water (10 mL) and extracted with DCM (2×, 100 mL). The combined organic layers were washed with brine, dried over $Na_2SO_4$ and concentrated. The crude residue was purified by preparative thin layer chromatography (eluent: 2% MeOH in DCM) to provide the title compound.

Step E. (R)-2-((2S,3R,6S)-2,3-Bis(4-chlorophenyl)-6-(3-morpholinopropyl)-5-oxomorpholino)pentanoic acid

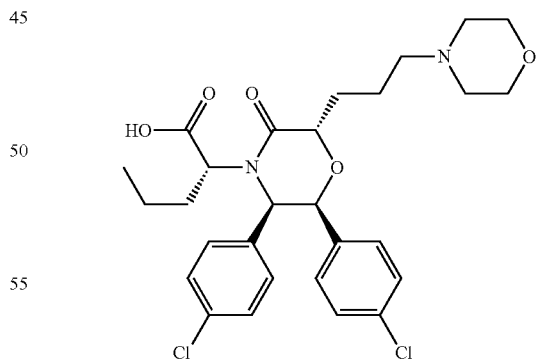

The title compound was prepared from (R)-ethyl 2-((2S,3R,6S)-2,3-bis(4-chlorophenyl)-6-(3-morpholinopropyl)-5-oxomorpholino)pentanoate (Example 57, Step D) by a procedure similar to the one described in (Example 10, Step D).

$^1$H NMR (400 MHz, MeOH-$d_4$, δ ppm): 7.08-7.23 (m, 4H), 6.95-7.07 (m, 2H), 6.85-6.98 (m, 2H), 5.52 (dd, J=2.2, 0.8 Hz, 1H), 5.04 (dd, J=10.5, 4.2 Hz, 1H), 4.82-4.84 (m, 1H), 4.77 (dd, J=9.1, 4.4 Hz, 1H), 3.76 (t, J=4.9 Hz, 4H), 2.80-2.92 (m, 6H), 2.08-2.19 (m, 2H), 1.82-1.92 (m, 1H), 1.70-1.81 (m, 1H), 1.04-1.25 (m, 2H), 0.83-0.95 (m, 2H), 0.46 (t, J=7.3 Hz, 3H). Spectrum (ESI) m/z=549 [M+1].

Example 58

(2S,5R,6S)-5,6-Bis(4-chlorophenyl)-4-(2-chloropyridin-4-yl)-2-(4-fluorobenzyl)morpholin-3-one and (2R,5S,6R)-5,6-bis(4-chlorophenyl)-4-(2-chloropyridin-4-yl)-2-(4-fluorobenzyl)morpholin-3-one

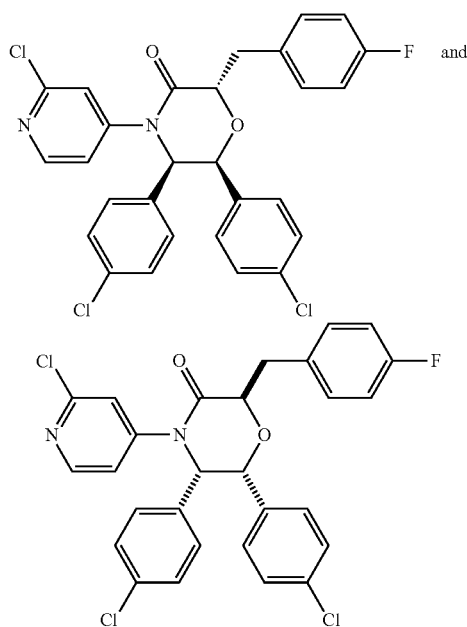

A solution of (2S,5R,6S)-5,6-bis(4-chlorophenyl)-2-(4-fluorobenzyl)morpholin-3-one and (2R,5S,6R)-5,6-bis(4-chlorophenyl)-2-(4-fluorobenzyl)morpholin-3-one (7 mg, 0.0065 mmol; Example 80, Step C), TMEDA (0.00098 mL, 0.0065 mmol), 2-chloro-4-iodopyridine (12 mg, 0.049 mmol), and potassium phosphate dibasic (11 mg, 0.065 mmol) in 1,4-dioxane (0.163 mL) was degassed by bubbling argon through the solution for 10 minutes. Copper(I) iodide (0.62 mg, 0.0033 mmol) was added, and the mixture was heated to 110° C. overnight. After cooling to room temperature, the crude residue was concentrated under a vacuum and purified by preparative thin layer chromatography (eluent: 100% ethyl acetate) to provide the title compounds.

1H NMR (400 MHz, CDCl$_3$, δ ppm): 8.25 (d, J=5.7 Hz, 1H), 7.35-7.49 (m, 1H), 7.08-7.22 (m, 6H), 6.94 (dd, J=5.5, 2.0 Hz, 1H), 6.82-6.91 (m, 4H), 5.99-6.16 (m, 2H), 5.36 (d, J=3.5 Hz, 1H), 4.77-4.85 (m, 2H), 3.60 (d, J=5.1 Hz, 1H), 3.40 (d, J=4.5 Hz, 1H). Spectrum (ESI) m/z=542, 544 [M+1].

Examples 59, 60 and 61 were also prepared from (2S,5R,6S)-5,6-bis(4-chlorophenyl)-2-(4-fluorobenzyl)morpholin-3-one and (2R,5S,6R)-5,6-bis(4-chlorophenyl)-2-(4-fluorobenzyl)morpholin-3-one (Example 80, Step C) as described in Example 58 substituting 2-chloro-4-iodopyridine in Example 58 with an equivalent amount of the appropriate iodide.

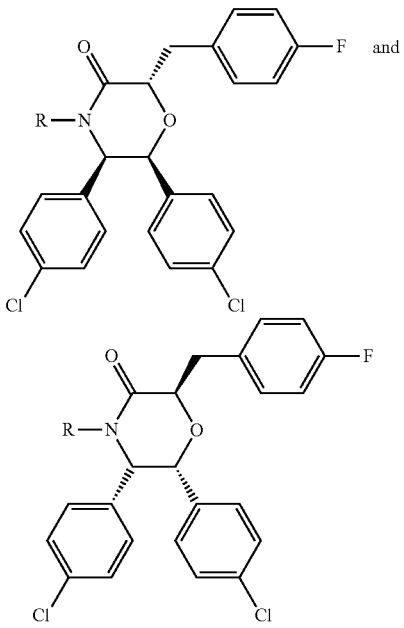

| Example | R | Reagent used |
|---|---|---|
| 59 | (3-pyridyl) | 3-iodopyridine |
| 60 | (1H-pyrazol-4-yl) | 4-iodo-1H-pyrazole |
| 61 | (4-pyridyl) | 4-iodopyridine |

Example 59

(2S,5R,6S)-5,6-Bis(4-chlorophenyl)-2-(4-fluorobenzyl)-4-phenylmorpholin-3-one and (2R,5S,6R)-5,6-bis(4-chlorophenyl)-2-(4-fluorobenzyl)-4-phenylmorpholin-3-one 1H NMR (400 MHz, CDCl$_3$, δ ppm): 8.43 (dd, J=4.6, 1.7 Hz, 1H), 8.33 (dd, J=2.5, 0.6 Hz, 1H), 7.43-7.50 (m, 2H), 7.25 (dd, J=2.5, 1.6 Hz, 1H), 7.11-7.23 (m, 5H), 6.79-6.89 (m, 4H), 6.02-6.09 (m, 2H), 5.44 (s, 1H), 4.85 (t, J=4.3 Hz, 1H), 4.73 (s, 1H), 3.60-3.69 (m, 1H), 3.31-3.41 (m, 1H). Spectrum (ESI) m/z=507 [M+1].

Example 60

(2S,5R,6S)-5,6-Bis(4-chlorophenyl)-2-(4-fluorobenzyl)-4-(1H-pyrazol-4-yl)morpholin-3-one and (2R, 5S,6R)-5,6-bis(4-chlorophenyl)-2-(4-fluorobenzyl)-4-(1H-pyrazol-4-yl)morpholin-3-one 1H NMR (500 MHz, CDCl$_3$, δ ppm): 7.08-7.20 (m, 6H), 6.89-7.00 (m, 2H), 6.79-6.87 (m, 2H), 6.72-6.79 (m, 2H), 6.55 (d, J=4.4 Hz, 2H), 5.12 (dd, J=2.9, 0.5 Hz, 1H), 4.84

(dd, J=8.6, 3.7 Hz, 1H), 4.54 (dd, J=4.4, 3.4 Hz, 1H), 3.40-3.53 (m, 1H), 3.31-3.40 (m, 1H), 3.19-3.29 (m, 1H).

Example 61

(2S,5R,6S)-5,6-Bis(4-chlorophenyl)-2-(4-fluorobenzyl)-4-(pyridin-4-yl)morpholin-3-one and (2R,5S,6R)-5,6-bis(4-chlorophenyl)-2-(4-fluorobenzyl)-4-(pyridin-4-yl)morpholin-3-one $^1$H NMR (400 MHz, CDCl$_3$, δ ppm): 8.33-8.60 (m, 2H), 7.38-7.49 (m, 2H), 7.09-7.23 (m, 4H), 6.98-7.07 (m, 2H), 6.76-6.91 (m, 4H), 5.98-6.11 (m, 2H), 5.38 (d, J=3.5 Hz, 1H), 4.79-4.94 (m, 2H), 3.64 (dd, J=14.2, 4.6 Hz, 1H), 3.37 (dd, J=14.2, 4.4 Hz, 1H). Spectrum (ESI) m/z=507 [M+1].

Example 62

(2S,5R,6S)-5,6-Bis(4-chlorophenyl)-2-(4-(methylsulfonyl)benzyl)-4-(pyridin-3-yl)morpholin-3-one and (2R,5S,6R)-5,6-bis(4-chlorophenyl)-2-(4-(methylsulfonyl)benzyl)-4-(pyridin-3-yl)morpholin-3-one

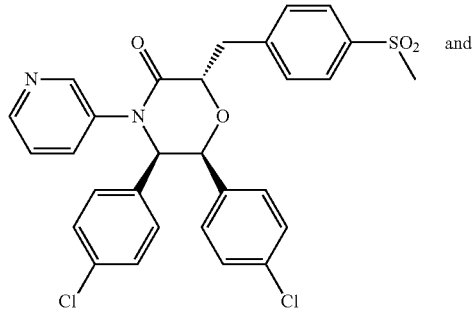

Step A. (2S,5R,6S)-5,6-Bbis(4-chlorophenyl)-2-(4-iodobenzyl)-4-(4-methoxybenzyl)morpholin-3-one and (2R,5S,6R)-5,6-Bis(4-chlorophenyl)-2-(4-iodobenzyl)-4-(4-methoxybenzyl)morpholin-3-one

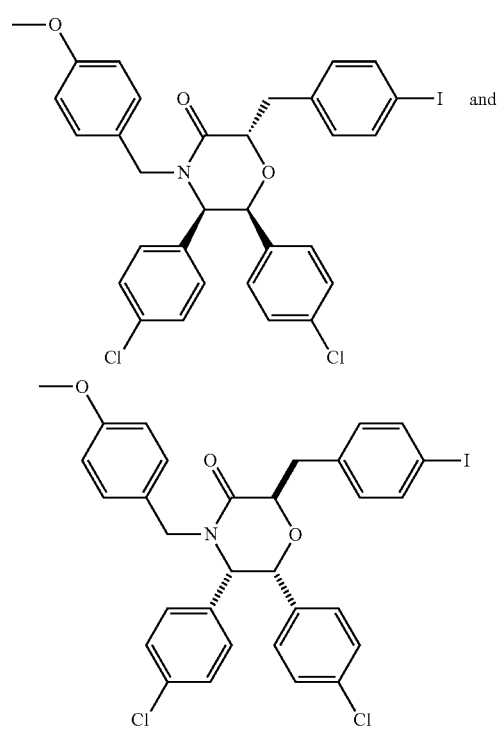

The title compounds were prepared from (5R,6S)-5,6-bis(4-chlorophenyl)-4-(4-methoxybenzyl)morpholin-3-one and (5S,6R)-5,6-bis(4-chlorophenyl)-4-(4-methoxybenzyl)morpholin-3-one (Example 80, Step A) and 1-(bromomethyl)-4-iodobenzene by a procedure similar to the one described in (Example 80, Step B).

Step B. (2S,5R,6S)-5,6-Bis(4-chlorophenyl)-2-(4-iodobenzyl)morpholin-3-one and (2R,5S,6R)-5,6-Bis(4-chlorophenyl)-2-(4-iodobenzyl)morpholin-3-one

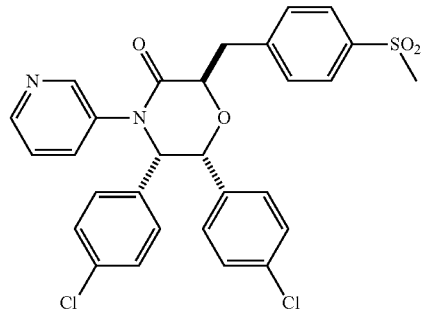

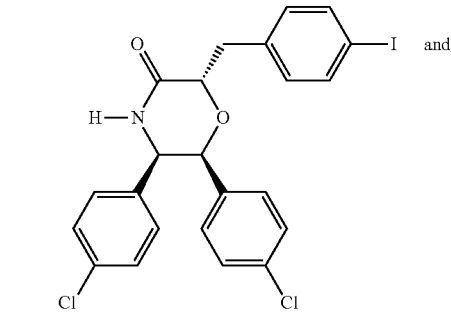

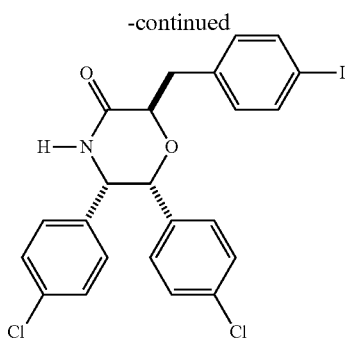

The title compounds were prepared from (2S,5R,6S)-5,6-bis(4-chlorophenyl)-2-(4-iodobenzyl)-4-(4-methoxybenzyl)morpholin-3-one and (2R,5S,6R)-5,6-bis(4-chlorophenyl)-2-(4-iodobenzyl)-4-(4-methoxybenzyl)morpholin-3-one (Example 62, Step A) by a procedure similar to the one described in (Example 80, Step C).

Step C. (2S,5R,6S)-5,6-Bis(4-chlorophenyl)-2-(4-iodobenzyl)-4-(pyridin-3-yl)morpholin-3-one and (2R,5S,6R)-5,6-bis(4-chlorophenyl)-2-(4-iodobenzyl)-4-(pyridin-3-yl)morpholin-3-one

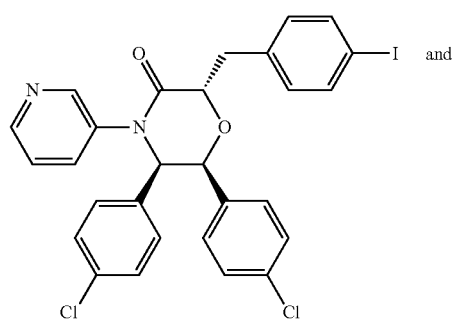

The title compounds were prepared from (2S,5R,6S)-5,6-bis(4-chlorophenyl)-2-(4-iodobenzyl)morpholin-3-one and (2R,5S,6R)-5,6-bis(4-chlorophenyl)-2-(4-iodobenzyl)morpholin-3-one (Example 62, Step B) by a procedure similar to the one described in Example 58.

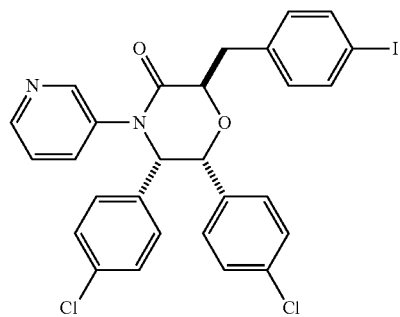

Step D. (2S,5R,6S)-5,6-Bis(4-chlorophenyl)-2-(4-(methylsulfonyl)benzyl)-4-(pyridin-3-yl)morpholin-3-one and (2R,5S,6R)-5,6-bis(4-chlorophenyl)-2-(4-(methylsulfonyl)benzyl)-4-(pyridin-3-yl)morpholin-3-one The title compounds were prepared from (2S,5R,6S)-5,6-bis(4-chlorophenyl)-2-(4-iodobenzyl)-4-(pyridin-3-yl)morpholin-3-one and (2R,5S,6R)-5,6-bis(4-chlorophenyl)-2-(4-iodobenzyl)-4-(pyridin-3-yl)morpholin-3-one (Example 62, Step C) by a procedure similar to the one described in Example 50, Step B.

$^1$H NMR (400 MHz, CDCl$_3$, δ ppm): 8.43-8.53 (m, 1H), 8.33-8.42 (m, 1H), 7.97-8.05 (m, 2H), 7.64-7.75 (m, 2H), 7.21-7.25 (m, 2H), 7.15-7.19 (m, 2H), 6.88-6.95 (m, 2H), 6.82-6.88 (m, 2H), 6.12-6.24 (m, 2H), 5.45 (d, J=3.5 Hz, 1H), 4.87-4.94 (m, 1H), 4.75 (d, J=3.5 Hz, 1H), 3.65-3.75 (m, 1H), 3.56 (dd, J=13.9, 4.3 Hz, 1H), 3.14 (s, 3H). Spectrum (ESI) m/z=567 [M+1].

Example 63

(2S,5R,6S)-5,6-Bis(4-chlorophenyl)-2-(2-fluoro-4-(methylsulfonyl)benzyl)-4-(pyridin-3-yl)morpholin-3-one and (2R,5S,6R)-5,6-bis(4-chlorophenyl)-2-(2-fluoro-4-(methylsulfonyl)benzyl)-4-(pyridin-3-yl)morpholin-3-one

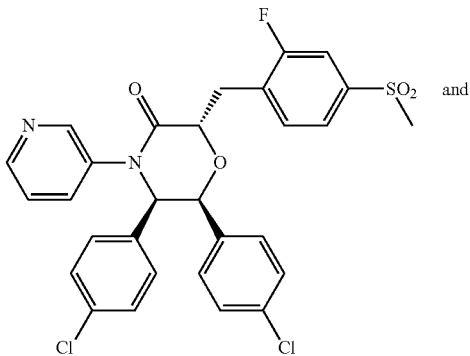

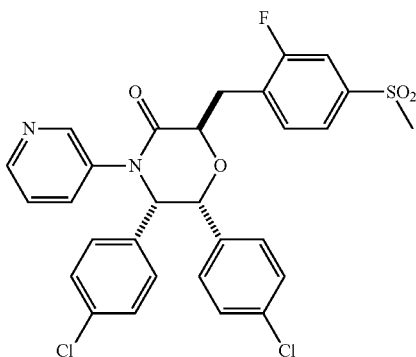

Step A. (2S,5R,6S)-5,6-Bis(4-chlorophenyl)-2-(2-fluoro-4-iodobenzyl)-4-(4-methoxybenzyl)morpholin-3-one and (2R,5S,6R)-5,6-bis(4-chlorophenyl)-2-(2-fluoro-4-iodobenzyl)-4-(4-methoxybenzyl)morpholin-3-one

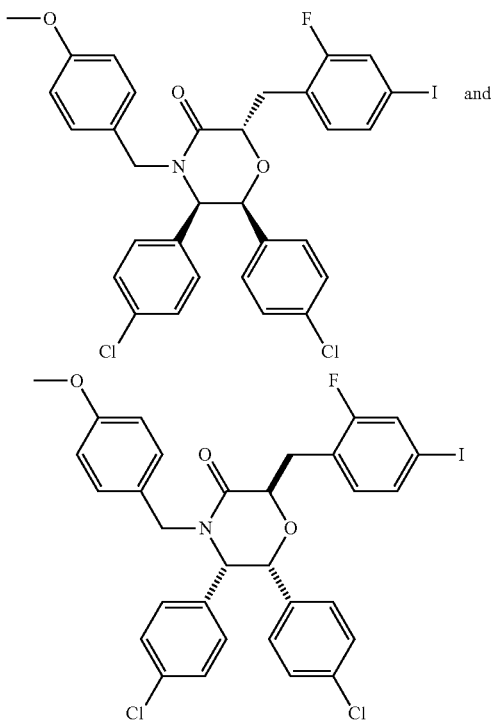

The title compounds were prepared from (5R,6S)-5,6-bis(4-chlorophenyl)-4-(4-methoxybenzyl)morpholin-3-one and (5S,6R)-5,6-bis(4-chlorophenyl)-4-(4-methoxybenzyl)morpholin-3-one (Example 80, Step A) and 1-(bromomethyl)-2-fluoro-4-iodobenzene (Example 53) by a procedure similar to the one described in Example 80, Step B.

Step B. (2S,5R,6S)-5,6-Bis(4-chlorophenyl)-2-(2-fluoro4-iodobenzyl)morpholin-3-one and (2R,5S,6R)-5,6-bis(4-chlorophenyl)-2-(2-fluoro-4-iodobenzyl)morpholin-3-one

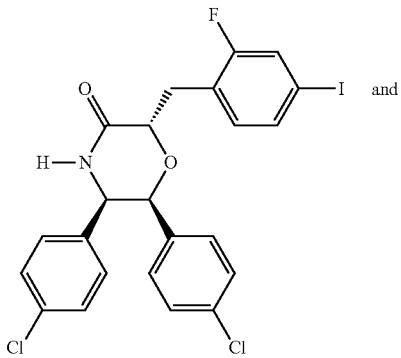

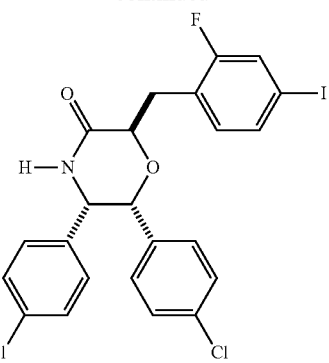

The title compounds were prepared from (2S,5R,6S)-5,6-bis(4-chlorophenyl)-2-(2-fluoro-4-iodobenzyl)-4-(4-methoxybenzyl)morpholin-3-one and (2R,5S,6R)-5,6-bis(4-chlorophenyl)-2-(2-fluoro-4-iodobenzyl)-4-(4-methoxybenzyl)morpholin-3-one (Example 63, Step A) by a procedure similar to the one described in Example 80, Step C.

Step C. (2S,5R,6S)-5,6-Bis(4-chlorophenyl)-2-(2-fluoro-4-iodobenzyl)-4-(pyridin-3-yl)morpholin-3-one and (2R,5S,6R)-5,6-bis(4-chlorophenyl)-2-(2-fluoro-4-iodobenzyl)-4-(pyridin-3-yl)morpholin-3-one

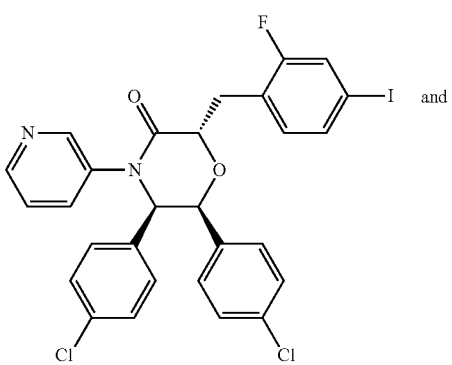

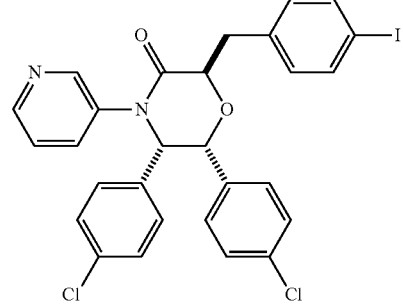

The title compounds were prepared from (2S,5R,6S)-5,6-bis(4-chlorophenyl)-2-(2-fluoro-4-iodobenzyl)morpholin-3-one and (2R,5S,6R)-5,6-bis(4-chlorophenyl)-2-(2-fluoro-4-iodobenzyl)morpholin-3-one (Example 63, Step B) by a procedure similar to the one described in Example 58.

Step D. (2S,5R,6S)-5,6-Bis(4-chlorophenyl)-2-(2-fluoro-4-(methylsulfonyl)benzyl)-4-(pyridin-3-yl)morpholin-3-one and (2R,5S,6R)-5,6-bis(4-chlorophenyl)-2-(2-fluoro-4-(methylsulfonyl)benzyl)-4-(pyridin-3-yl)morpholin-3-one The title compounds were prepared from (2S,5R,6S)-5,6-bis(4-chlorophenyl)-2-(2-fluoro-4-iodobenzyl)-4-(pyridin-3-yl)morpholin-3-one and (2R,5S,6R)-5,6-bis(4-chlorophenyl)-2-(2-fluoro-4-iodobenzyl)-4-(pyridin-3-yl)morpholin-3-one (Example 63, Step C) by a procedure similar to the one described in Example 50, Step B.

$^1$H NMR (500 MHz, CDCl$_3$, δ ppm): 8.38-8.57 (m, 2H), 7.64-7.83 (m, 3H), 7.36 (d, J=8.3 Hz, 1H), 7.11-7.20 (m, 3H), 7.00 (d, J=8.6 Hz, 2H), 6.82-6.90 (m, 2H), 6.37-6.45 (m, 2H), 5.43-5.54 (m, 1H), 4.87-4.95 (m, 1H), 4.73-4.83 (m, 1H), 3.75-3.83 (m, 1H), 3.52-3.60 (m, 1H), 3.12 (s, 3H). Spectrum (ESI) m/z=585 [M+1].

Example 64

(2S,5R,6S)-6-(3-Chlorophenyl)-5-(4-chlorophenyl)-4-(cyclopropylmethyl)-2-(2-(4-methylpiperazin-1-yl)-2-oxoethyl)morpholin-3-one and (2R,5S,6R)-6-(3-chlorophenyl)-5-(4-chlorophenyl)-4-(cyclopropylmethyl)-2-(2-(4-methylpiperazin-1-yl)-2-oxoethyl)morpholin-3-one

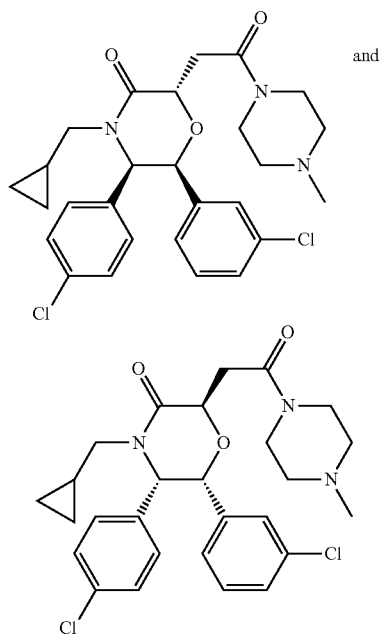

4-Methylpiperazine (28 mg, 0.28 mmol), HOAt (29 mg, 0.21 mmol), EDC (40 mg, 0.21 mmol), and NaHCO$_3$ (35 mg, 0.42 mmol) were added to a stirring solution of 2-((2S,5R,6S)-6-(3-chlorophenyl)-5-(4-chlorophenyl)-4-(cyclopropylmethyl)-3-oxomorpholin-2-yl)acetic acid and 2-((2R,5S,6R)-6-(3-chlorophenyl)-5-(4-chlorophenyl)-4-(cyclopropylmethyl)-3-oxomorpholin-2-yl)acetic acid (61 mg, 0.14 mmol, Example 17) in DMF (2.5 mL). The reaction was stirred at room temperature overnight. After this time the reaction was partitioned between ethyl acetate and water. The separated organic layer was washed with LiCl (1 M aqueous solution), dried over MgSO$_4$, filtered and evaporated under a vacuum. Purification by reverse phase preparative HPLC (Gemini™ Prep C18 5 μm column, Phenomenex, Torrance, Calif.; gradient elution with 10% to 90% acetonitrile in water, with both eluents containing 0.1% TFA) provided the title compounds.

$^1$H NMR (400 MHz, CDCl$_3$, δ ppm): 7.07-7.20 (m, 4H), 6.99 (s, 1H), 6.85 (d, J=7.6 Hz, 1H), 6.75 (d, J=8.4 Hz, 2H), 5.52 (d, J=2.7 Hz, 1H), 5.23 (dd, J=7.9, 3.0 Hz, 1H), 4.68 (d, J=2.9 Hz, 1H), 3.79 (dd, J=14.1, 6.3 Hz, 1H), 3.66 (br s, 2H), 3.51 (br s, 2H), 3.15 (dd, J=16.0, 8.0 Hz, 1H), 3.04 (dd, J=16.0, 3.1 Hz, 1H), 2.72 (dd, J=14.2, 7.7 Hz, 1H), 2.35 (br s, 4H), 2.27 (s, 3H), 0.82-0.95 (m, 1H), 0.53 (td, J=8.5, 4.6 Hz, 1H), 0.35-0.45 (m, 1H), 0.19 (dt, J=9.6, 4.8 Hz, 1H), 0.08 (td, J=9.8, 4.8 Hz, 1H). MS (ESI) 516.3 [M+H]$^+$.

Example 65

2-((2S,5R,6S)-4-((R)-1-Amino-1-oxopentan-2-yl)-6-(3-chlorophenyl)-5-(4-chlorophenyl)-3-oxomorpholin-2-yl)acetic acid and 2-((2R,5S,6R)-4-((S)-1-amino-1-oxopentan-2-yl)-6-(3-chlorophenyl)-5-(4-chlorophenyl)-3-oxomorpholin-2-yl)acetic acid or 2-((2S,5R,6S)-4-((S)-1-amino-1-oxopentan-2-yl)-6-(3-chlorophenyl)-5-(4-chlorophenyl)-3-oxomorpholin-2-yl)acetic acid and 2-((2R,5S,6R)-4-((R)-1-amino-1-oxopentan-2-yl)-6-(3-chlorophenyl)-5-(4-chlorophenyl)-3-oxomorpholin-2-yl)acetic acid

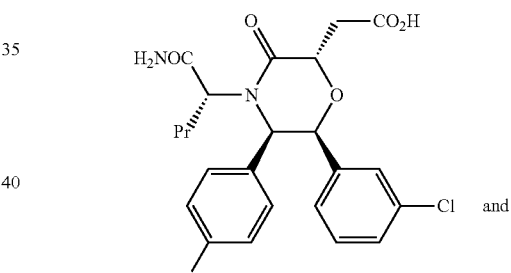

and

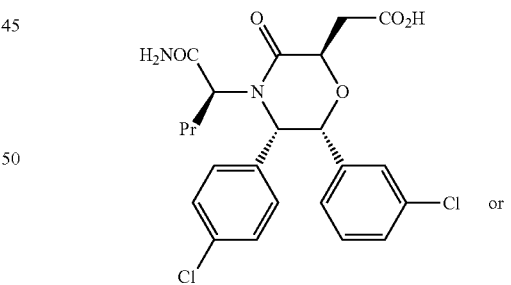

or

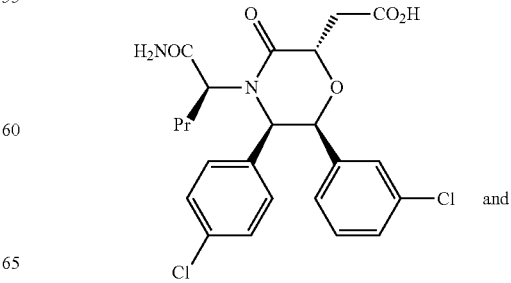

and

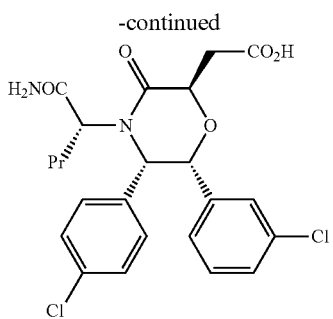

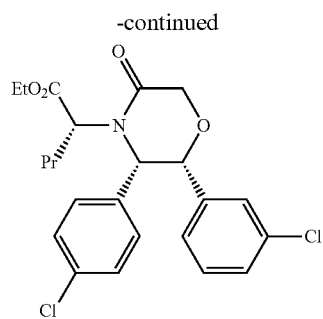

Step A. (R)-Ethyl 2-((2S,3R)-2-(3-chlorophenyl)-3-(4-chlorophenyl)-5-oxomorpholino)pentanoate and (S)-ethyl 2-((2R,3S)-2-(3-chlorophenyl)-3-(4-chlorophenyl)-5-oxomorpholino)pentanoate or (S)-ethyl 2-((2S,3R)-2-(3-chlorophenyl)-3-(4-chlorophenyl)-5-oxomorpholino)pentanoate and (R)-ethyl 2-((2R,3S)-2-(3-chlorophenyl)-3-(4-chlorophenyl)-5-oxomorpholino)pentanoate Sodium hydride (56 mg, 1.40 mmol, 60% dispersion in oil) was added portionwise over 1 minute to a stirring solution of (5R,6S)-6-(3-chlorophenyl)-5-(4-chlorophenyl)morpholin-3-one and (5S,6R)-6-(3-chlorophenyl)-5-(4-chlorophenyl)morpholin-3-one (450 mg, 1.40 mmol, Example 11, Step D) in DMF (10 mL) at 0° C. under a $N_2$ atmosphere. The reaction was stirred at this temperature for 15 minutes and ethyl-2-bromovalerate (292 µL, 1.40 mmol) was added in one portion. The reaction was stirred at room temperature for 4 hours and then quenched with saturated aqueous $NH_4Cl$ and diluted with ethyl acetate. The separated organic layer was washed with brine, dried over $MgSO_4$, filtered and evaporated under a vacuum. Flash column chromatography (12 g $SiO_2$, gradient elution of 1:0 to 1:1 hexanes:ethyl acetate) gave one pair of the title compounds as the first eluting product.

$^1$H NMR (400 MHz, $CDCl_3$, δ ppm): 7.04-7.19 (m, 4H), 6.92 (s, 1H), 6.70-6.86 (m, 3H), 5.23 (d, J=2.5 Hz, 1H), 4.91 (dd, J=9.5, 5.2 Hz, 1H), 4.67-4.75 (m, 1H), 4.60 (d, J=2.7 Hz, 1H), 4.52-4.59 (m, 1H), 4.18-4.27 (m, 2H), 1.70-1.84 (m, 1H), 1.39 (ddt, J=14.3, 9.5, 4.8, 4.8 Hz, 1H), 1.32 (t, J=7.1 Hz, 3H), 1.16-1.27 (m, 1H), 1.00-1.12 (m, 1H), 0.61 (t, J=7.3 Hz, 3H).

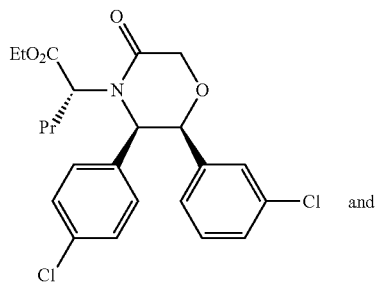
and

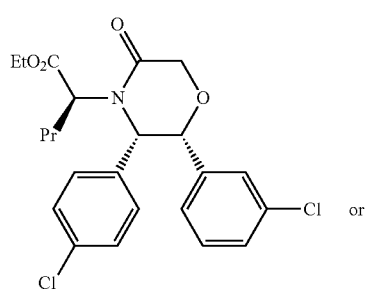
or

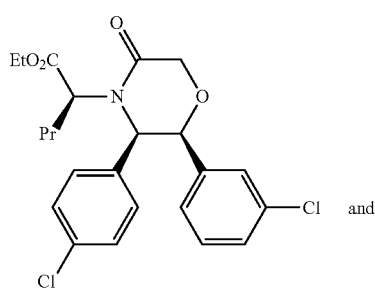
and

Step B. (R)-Ethyl 2-((2S,5R,6S)-2-allyl-6-(3-chlorophenyl)-5-(4-chlorophenyl)-3-oxomorpholino)pentanoate and (S)-ethyl 2-((2R,5S,6R)-2-allyl-6-(3-chlorophenyl)-5-(4-chlorophenyl)-3-oxomorpholino)pentanoate or (S)-ethyl 2-((2S,5R,6S)-2-allyl-6-(3-chlorophenyl)-5-(4-chlorophenyl)-3-oxomorpholino)pentanoate and (R)-ethyl 2-((2R,5S,6R)-2-allyl-6-(3-chlorophenyl)-5-(4-chlorophenyl)-3-oxomorpholino)pentanoate

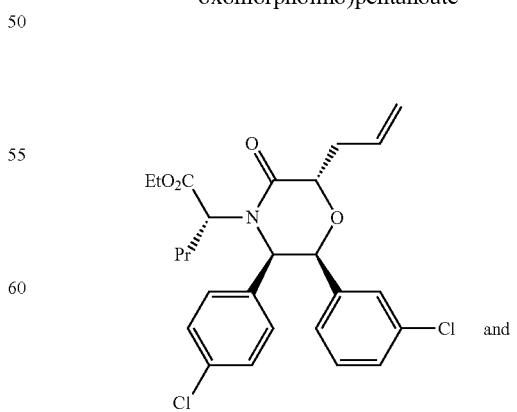
and

-continued

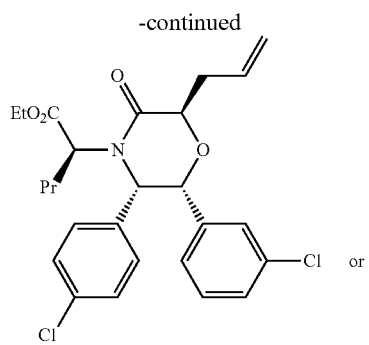

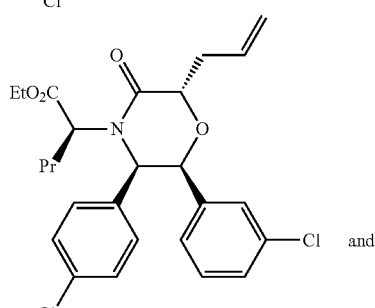

and

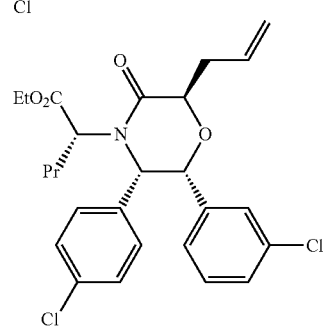

Lithium bis(trimethylsilyl)amide (179 μL, 179 μmol, 1.0 M solution in THF) was added dropwise over 1 minute to a stirring solution of (R)-ethyl 2-((2S,3R)-2-(3-chlorophenyl)-3-(4-chlorophenyl)-5-oxomorpholino)pentanoate and (S)-ethyl 2-((2R,3S)-2-(3-chlorophenyl)-3-(4-chlorophenyl)-5-oxomorpholino)pentanoate or (S)-ethyl 2-((2S,3R)-2-(3-chlorophenyl)-3-(4-chlorophenyl)-5-oxomorpholino) pentanoate and (R)-ethyl 2-((2R,3S)-2-(3-chlorophenyl)-3-(4-chlorophenyl)-5-oxomorpholino)pentanoate (70 mg, 155 μmol, first eluting isomers of Example 65, Step A) and allyl bromide (13 μL, 155 μmol) in THF (2.0 mL) at −78° C. under a N$_2$ atmosphere. The reaction was stirred at −78° C. for 2 hours. The reaction was treated with saturated aqueous NH$_4$Cl and ethyl acetate.

The separated aqueous layer was extracted with ethyl acetate, and the combined organic extracts were washed with brine, dried over MgSO$_4$, filtered and evaporated under a vacuum. Flash column chromatography (4 g SiO$_2$, gradient elution of 1:0 to 2:1 hexanes:ethyl acetate) gave the title compounds.

$^1$H NMR (400 MHz, CDCl$_3$, δ ppm): 7.07-7.19 (m, 4H), 6.92-6.97 (m, 1H), 6.77-6.85 (m, 3H), 5.93 (ddt, J=17.1, 10.1, 7.0, 7.0 Hz, 1H), 5.40-5.46 (m, 1H), 5.12-5.18 (m, 1H), 5.06-5.11 (m, 1H), 4.93 (dd, J=9.6, 5.3 Hz, 1H), 4.78 (t, J=6.4 Hz, 1H), 4.55 (d, J=2.9 Hz, 1H), 4.16-4.32 (m, 2H), 2.82 (tt, J=6.7, 0.8 Hz, 2H), 1.72-1.88 (m, 1H), 1.34-1.47 (m, 1H), 1.32 (t, J=7.1 Hz, 3H), 1.12-1.26 (m, 1H), 0.94-1.10 (m, 1H), 0.62 (t, J=7.3 Hz, 3H).

Step C. (R)-2-((2S,5R,6S)-2-Allyl-6-(3-chlorophenyl)-5-(4-chlorophenyl)-3-oxomorpholino)pentanamide and (S)-2-((2R,5S,6R)-2-allyl-6-(3-chlorophenyl)-5-(4-chlorophenyl)-3-oxomorpholino) pentanamide or (S)-2-((2S,5R,6S)-2-allyl-6-(3-chlorophenyl)-5-(4-chlorophenyl)-3-oxomorpholino) pentanamide and (R)-2-((2R,5S,6R)-2-allyl-6-(3-chlorophenyl)-5-(4-chlorophenyl)-3-oxomorpholino) pentanamide

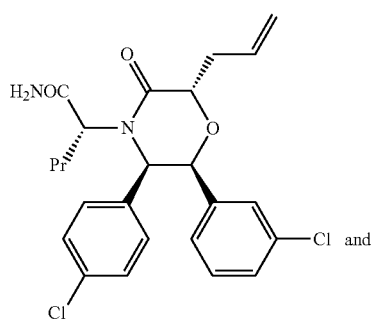

and

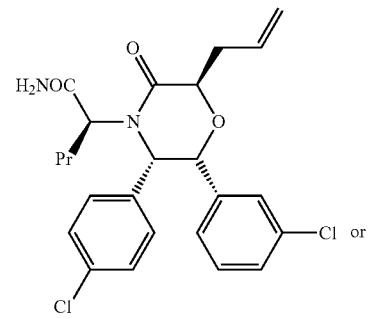

or

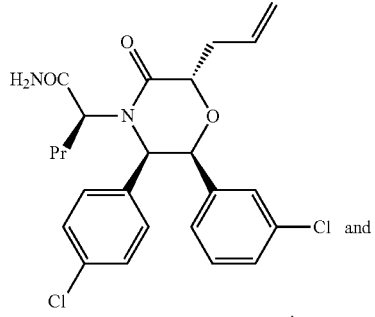

and

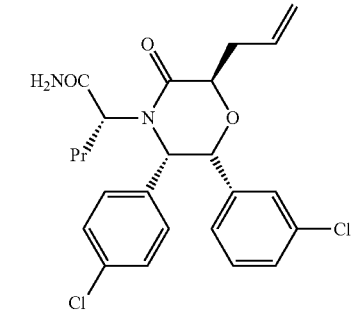

A solution of ammonia in methanol (3.1 mL, 183.5 mmol, 7 N) was added to (R)-ethyl 2-((2S,5R,6S)-2-allyl-6-(3-chlorophenyl)-5-(4-chlorophenyl)-3-oxomorpholino)pentanoate and (S)-ethyl 2-((2R,5S,6R)-2-allyl-6-(3-chlorophenyl)-5-(4-chlorophenyl)-3-oxomorpholino)pentanoate or (S)-ethyl 2-((2S,5R,6S)-2-allyl-6-(3-chlorophenyl)-5-(4- chlorophenyl)-3-oxomorpholino)pentanoate and (R)-ethyl 2-((2R,5S,6R)-2-allyl-6-(3-chlorophenyl)-5-(4-chlorophenyl)-3-oxomorpholino)pentanoate (30 mg, 61 µmol, Example 65, Step B), and the reaction was stirred at room temperature for 2 days. The solvent was evaporated under a vacuum and the product was purified by reverse phase preparative HPLC (Gemini™ Prep C18 5 µm column, Phenomenex, Torrance, Calif.; gradient elution with 10% to 90% acetonitrile in water, both eluents containing 0.1% TFA) to give the title compounds.

1H NMR (400 MHz, CDCl$_3$, δ ppm): 7.06-7.20 (m, 4H), 6.93 (s, 1H), 6.81 (d, J=7.6 Hz, 1H), 6.76 (d, J=8.4 Hz, 2H), 6.20 (br s, 1H), 5.90 (ddt, J=17.1, 10.1, 7.0, 7.0 Hz, 1H), 5.40 (br s, 1H), 5.22 (d, J=2.5 Hz, 1H), 5.15 (dd, J=17.0, 1.6 Hz, 1H), 5.09 (d, J=10.2 Hz, 1H), 5.01 (dd, J=8.7, 6.2 Hz, 1H), 4.83 (d, J=2.7 Hz, 1H), 4.79 (t, J=6.2 Hz, 1H), 2.80 (t, J=6.7 Hz, 2H), 1.57-1.76 (m, 1H), 0.97-1.22 (m, 3H), 0.66 (t, J=7.1 Hz, 3H).

Step D. 2-((2S,5R,6S)-4-((R)-1-Amino-1-oxopentan-2-yl)-6-(3-chlorophenyl)-5-(4-chlorophenyl)-3-oxomorpholin-2-yl)acetic acid and 2-((2R,5S,6R)-4-((S)-1-amino-1-oxopentan-2-yl)-6-(3-chlorophenyl)-5-(4-chlorophenyl)-3-oxomorpholin-2-yl)acetic acid or 2-((2S,5R,6S)-4-((S)-1-amino-1-oxopentan-2-yl)-6-(3-chlorophenyl)-5-(4-chlorophenyl)-3-oxomorpholin-2-yl)acetic acid and 2-((2R,5S,6R)-4-((R)-1-amino-1-oxopentan-2-yl)-6-(3-chlorophenyl)-5-(4-chlorophenyl)-3-oxomorpholin-2-yl)acetic acid

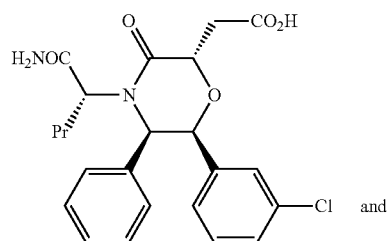 and

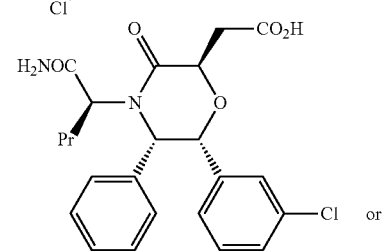 or

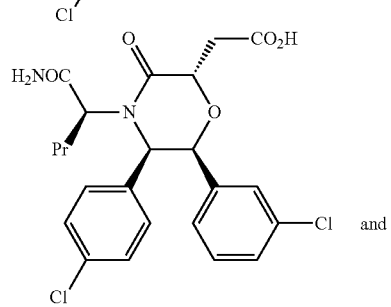 and

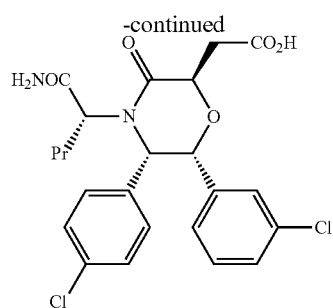

Sodium periodate (19 mg, 87 µmol), followed by ruthenium(III) chloride hydrate (0.5 mg, 2 µmol), was added to a rapidly stirring solution of (R)-2-((2S,5R,6S)-2-allyl-6-(3-chlorophenyl)-5-(4-chlorophenyl)-3-oxomorpholino)pentanamide and (S)-2-((2R,5S,6R)-2-allyl-6-(3-chlorophenyl)-5-(4-chlorophenyl)-3-oxomorpholino)pentanamide or (S)-2-((2S,5R,6S)-2-allyl-6-(3-chlorophenyl)-5-(4-chlorophenyl)-3-oxomorpholino)pentanamide and (R)-2-((2R,5S,6R)-2-allyl-6-(3-chlorophenyl)-5-(4-chlorophenyl)-3-oxomorpholino)pentanamide (10 mg, 22 µmol, Example 65, Step C) in a mixture of water (1 mL), acetonitrile (0.5 mL) and CCl$_4$ (0.5 mL). After stirring vigorously for 2 hours, the reaction was acidified with 10% citric acid and diluted with ethyl acetate. The separated organic layer was dried over MgSO$_4$, filtered, and evaporated under a vacuum. The residue was purified by reverse phase preparative HPLC (Gemini™ Prep C18 5 µm column, Phenomenex, Torrance, Calif.; gradient elution of 10% to 90% acetonitrile in water, with both eluents containing 0.1% TFA) to give the title compounds as a colorless film.

$^1$H NMR (400 MHz, CDCl$_3$, δ ppm): 7.11-7.21 (m, 4H), 6.93 (s, 1H), 6.88 (d, J=7.0 Hz, 1H), 6.70 (d, J=8.2 Hz, 2H), 5.70 (br s, 2H), 5.33 (br s, 1H), 4.93 (br s, 1H), 3.35 (dd, J=17.5, 3.2 Hz, 1H), 2.96 (d, J=16.6 Hz, 1H), 0.97-1.40 (m, 4H), 0.62-0.75 (m, 3H). MS (ESI) 479.1 [M+H]$^+$.

Example 66

2-((2S,5R,6S)-6-(3-Chlorophenyl)-5-(4-chlorophenyl)-4-((R)-1-cyanobutyl)-3-oxomorpholin-2-yl) acetic acid and 2-((2R,5S,6R)-6-(3-Chlorophenyl)-5-(4-chiorophenyl)-4-((S)-1-cyanobutyl)-3-oxomorpholin-2-yl)acetic acid or 2-((2S,5R,6S)-6-(3-chlorophenyl)-5-(4-chlorophenyl)-4-((S)-1-cyanobutyl)-3-oxomorpholin-2-yl)acetic acid and 2-((2R,5S,6R)-6-(3-chlorophenyl)-5-(4-chlorophenyl)-4-((R)-1-cyanobutyl)-3-oxomorpholin-2-yl) acetic acid

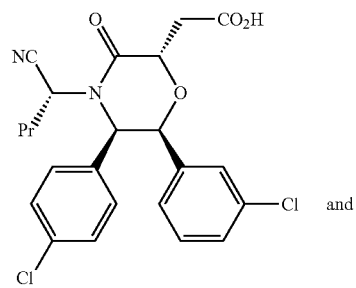 and

-continued

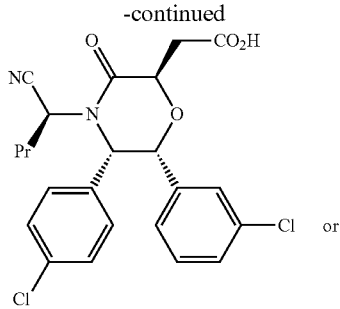

or

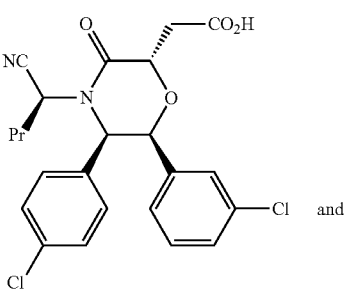

and

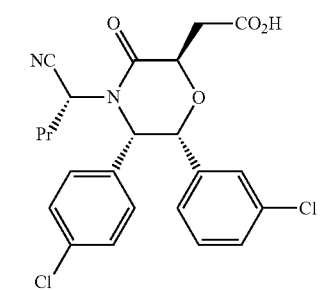

Step A. (R)-2-((2S,5R,6S)-2-Allyl-6-(3-chlorophenyl)-5-(4-chlorophenyl)-3-oxomorpholino)pentanenitrile and (S)-2-((2R,5S,6R)-2-allyl-6-(3-chlorophenyl)-5-(4-chlorophenyl)-3-oxomorpholino)pentanenitrile or (S)-2-((2S,5R,6S)-2-allyl-6-(3-chlorophenyl)-5-(4-chlorophenyl)-3-oxomorpholino)pentanenitrile and (R)-2-((2R,5S,6R)-2-allyl-6-(3-chlorophenyl)-5-(4-chlorophenyl)-3-oxomorpholino)pentanenitrile

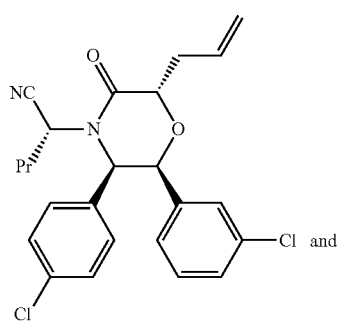

and

-continued

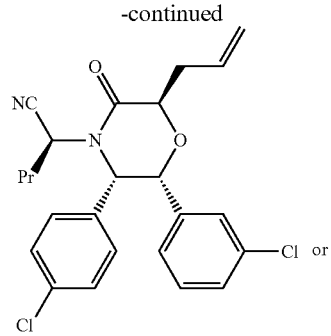

or

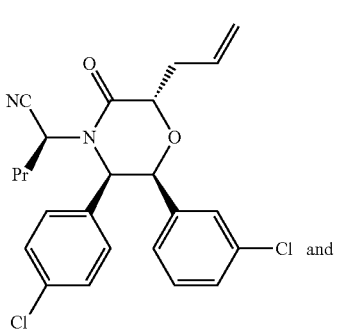

and

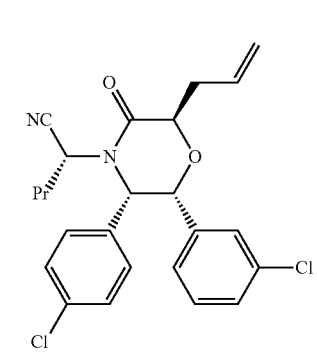

Trifluoroacetic acid anhydride (0.17 mL, 1.25 mmol) was added to a stirring solution of (R)-2-((2S,5R,6S)-2-allyl-6-(3-chlorophenyl)-5-(4-chlorophenyl)-3-oxomorpholino)pentanamide and (S)-2-((2R,5S,6R)-2-allyl-6-(3-chlorophenyl)-5-(4-chlorophenyl)-3-oxomorpholino)pentanamide or (S)-2-((2S,5R,6S)-2-allyl-6-(3-chlorophenyl)-5-(4-chlorophenyl)-3-oxomorpholino)pentanamide and (R)-2-((2R,5S,6R)-2-allyl-6-(3-chlorophenyl)-5-(4-chlorophenyl)-3-oxomorpholino)pentanamide (230 mg, 0.50 mmol, Example 65, Step C) and $Et_3N$ (0.35 mL, 2.49 mmol) in THF (5 mL) at 0° C. The reaction was stirred at 0° C. for 3 hours, and then it was partitioned between ethyl acetate and 10% aqueous citric acid. The separated aqueous layer was extracted with ethyl acetate (2×20 mL), and the combined organic extracts were washed with brine, dried over $MgSO_4$, filtered and concentrated under a vacuum to give the title compounds.

$^1$H NMR (400 MHz, $CDCl_3$, δ ppm): 7.06-7.21 (m, 4H), 6.93-6.98 (m, 1H), 6.78-6.88 (m, 3H), 5.90 (ddt, J=17.1, 10.1, 7.0, 7.0 Hz, 1H), 5.43-5.50 (m, 1H), 5.36 (d, J=2.9 Hz, 1H), 5.07-5.21 (m, 2H), 4.76-4.84 (m, 1H), 4.69-4.75 (m, 1H), 2.75-2.86 (m, 2H), 1.30-1.40 (m, 2H), 1.17-1.28 (m, 2H), 0.73-0.83 (m, 3H). MS (ESI) 443.1 [M+H]$^+$.

Step B. 2-((2S,5R,6S)-6-(3-Chlorophenyl)-5-(4-chlorophenyl)-4-((R)-1-cyanobutyl)-3-oxomorpholin-2-yl)acetic acid and 2-((2R,5S,6R)-6-(3-chlorophenyl)-5-(4-chlorophenyl)-4-((S)-1-cyanobutyl)-3-oxomorpholin-2-yl)acetic acid or 2-((2S,5R,6S)-6-(3-chlorophenyl)-5-(4-chlorophenyl)-4-((S)-1-cyanobutyl)-3-oxomorpholin-2-yl)acetic acid and 2-((2R,5S,6R)-6-(3-chlorophenyl)-5-(4-chlorophenyl)-4-((R)-1-cyanobutyl)-3-oxomorpholin-2-yl) acetic acid The title compound was prepared from (R)-2-((2S,5R,6S)-2-allyl-6-(3-chlorophenyl)-5-(4-chlorophenyl)-3-oxomorpholino)pentanenitrile and (S)-2-((2R,5S,6R)-2-allyl-6-(3-chlorophenyl)-5-(4-chlorophenyl)-3-oxomorpholino)pentanenitrile or (S)-2-((2S,5R,6S)-2-allyl-6-(3-chlorophenyl)-5-(4-chlorophenyl)-3-oxomorpholino)pentanenitrile and (R)-2-((2R,5S,6R)-2-allyl-6-(3-chlorophenyl)-5-(4-chlorophenyl)-3-oxomorpholino)pentanenitrile (Example 66, Step A) according to the procedure used for Example 65, Step D. The product was purified by reverse phase preparative HPLC (Gemini™ Prep C18 5 μm column, Phenomenex, Torrance, Calif.; gradient elution with 10% to 90% acetonitrile in water, both eluents containing 0.1% TFA) to give the title compounds.

$^1$H NMR (400 MHz, CDCl$_3$, δ ppm): 7.19 (d, J=8.4 Hz, 3H), 7.12 (t, J=7.8 Hz, 1H), 6.94 (s, 1H), 6.79-6.86 (m, 3H), 5.45-5.52 (m, 1H), 5.37 (d, J=2.5 Hz, 1H), 5.26 (dd, J=8.2, 4.1 Hz, 1H), 4.76 (d, J=2.7 Hz, 1H), 3.04-3.21 (m, 2H), 1.17-1.44 (m, 4H), 0.67-0.84 (m, 3H). MS (ESI) 461.0 [M+H]$^+$.

Example 67

2-((2S,5R,6S)-4-((R)-1-(1H-Tetrazol-5-yl)butyl)-6-(3-chlorophenyl)-5-(4-chlorophenyl)-3-oxomorpholin-2-yl)acetic acid and 2-((2R,5S,6R)-4-((S)-1-(1H-tetrazol-5-yl)butyl)-6-(3-chlorophenyl)-5-(4-chlorophenyl)-3-oxomorpholin-2-yl)acetic acid or 2-((2S,5R,6S)-4-((S)-1-(1H-tetrazol-5-yl)butyl)-6-(3-chlorophenyl)-5-(4-chlorophenyl)-3-oxomorpholin-2-yl)acetic acid and 2-((2R,5S,6R)-4-((R)-1-(1H-tetrazol-5-yl)butyl)-6-(3-chlorophenyl)-5-(4-chlorophenyl)-3-oxomorpholin-2-yl)acetic acid

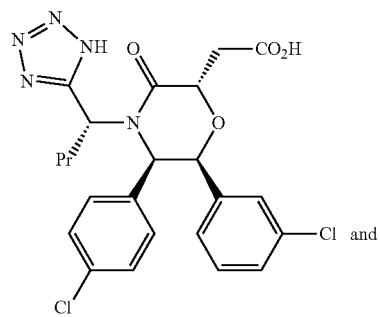 and

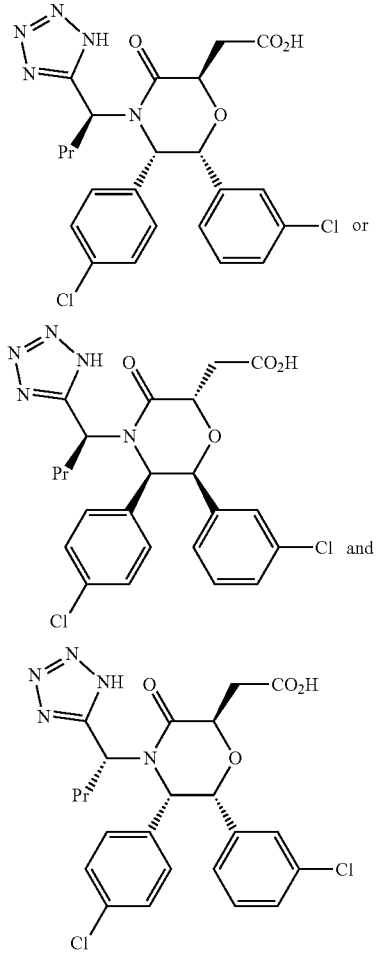

Step A. (2S,5R,6S)-4-((R)-1-(1H-Tetrazol-5-yl)butyl)-2-allyl-6-(3-chlorophenyl)-5-(4-chlorophenyl)morpholin-3-one and (2R,5S,6R)-4-((S)-1-(1H-tetrazol-5-yl)butyl)-2-allyl-6-(3-chlorophenyl)-5-(4-chlorophenyl)morpholin-3-one or (2S,5R,6S)-4-((S)-1-(1H-tetrazol-5-yl)butyl)-2-allyl-6-(3-chlorophenyl)-5-(4-chlorophenyl)morpholin-3-one and (2R,5S,6R)-4-((R)-1-(1H-tetrazol-5-yl)butyl)-2-allyl-6-(3-chlorophenyl)-5-(4-chlorophenyl)morpholin-3-one

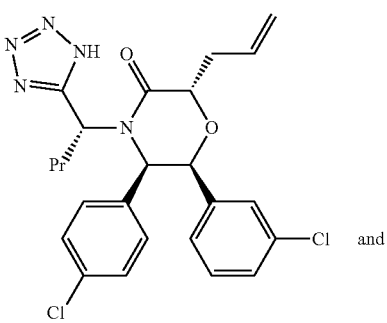 and

-continued

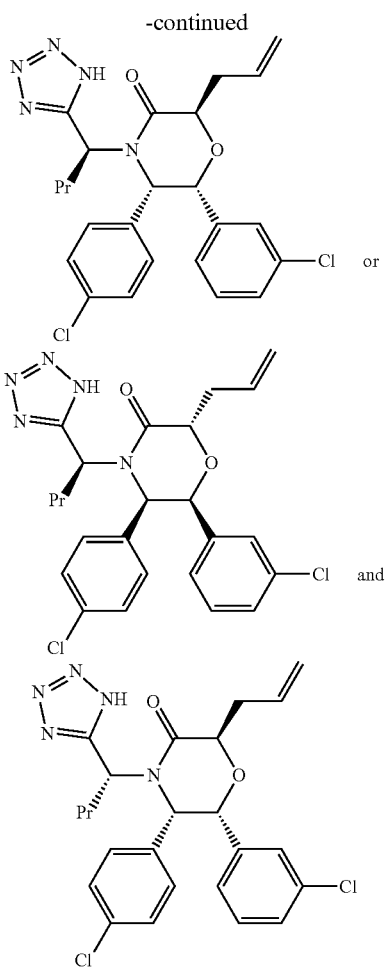

Sodium azide (17 mg, 0.26 mmol) and NH$_4$Cl (14 mg, 0.26 mmol) were added to a stirring solution of (R)-2-((2S,5R,6S)-2-allyl-6-(3-chlorophenyl)-5-(4-chlorophenyl)-3-oxomorpholino)pentanenitrile and (S)-2-((2R,5S,6R)-2-allyl-6-(3-chlorophenyl)-5-(4-chlorophenyl)-3-oxomorpholino)pentanenitrile or (S)-2-((2S,5R,6S)-2-allyl-6-(3-chlorophenyl)-5-(4-chlorophenyl)-3-oxomorpholino) pentanenitrile and (R)-2-((2R,5S,6R)-2-allyl-6-(3-chlorophenyl)-5-(4-chlorophenyl)-3-oxomorpholino) pentanenitrile (90 mg, 0.20 mmol, Example 66, Step A) in DMF (3 mL). The mixture was heated at 90° C. for 24 hours. The reaction was treated with an additional portion of sodium azide (17 mg, 0.26 mmol) and NH$_4$Cl (14 mg, 0.26 mmol) and heated at 95° C. for another 3 hours. An additional portion of sodium azide (85 mg, 1.3 mmol) was added and the reaction was stirred at 95° C. overnight. The reaction was allowed to cool to room temperature and partitioned between ethyl acetate and citric acid (0.1 M aqueous solution). The separated aqueous layer was extracted with ethyl acetate and the combined organic extracts were washed with brine, dried over MgSO$_4$, filtered and evaporated under a vacuum to give the title compounds.

$^1$H NMR (400 MHz, CDCl$_3$, δ ppm): 7.05-7.17 (m, 5H), 6.88 (s, 1H), 6.78 (d, J=8.4 Hz, 3H), 5.94 (t, J=7.5 Hz, 1H), 5.83 (ddt, J=17.1, 10.1, 6.9, 6.9 Hz, 1H), 5.20 (d, J=2.5 Hz, 1H), 5.00-5.15 (m, 2H), 4.84 (d, J=2.5 Hz, 1H), 4.79 (dd, J=7.6, 5.1 Hz, 1H), 2.69-2.78 (m, 2H), 1.81-1.93 (m, 1H), 1.51-1.65 (m, 1H), 1.19-1.29 (m, 1H), 1.02-1.17 (m, 1H), 0.60-0.70 (m, 3H). MS (ESI) 486.1 [M+H]$^+$.

Step B. 2-((2S,5R,6S)-4-((R)-1-(1H-Tetrazol-5-yl)butyl)-6-(3-chlorophenyl)-5-(4-chlorophenyl)-3-oxomorpholin-2-yl)acetic acid and 2-((2R,5S,6R)-4-((S)-1-(1H-tetrazol-5-yl)butyl)-6-(3-chlorophenyl)-5-(4-chlorophenyl)-3-oxomorpholin-2-yl)acetic acid or 2-((2S,5R,6S)-4-((S)-1-(1H-tetrazol-5-yl)butyl)-6-(3-chlorophenyl)-5-(4-chlorophenyl)-3-oxomorpholin-2-yl)acetic acid and 2-((2R,5S,6R)-4-((R)-1-(1H-tetrazol-5-yl)butyl)-6-(3-chlorophenyl)-5-(4-chlorophenyl)-3-oxomorpholin-2-yl)acetic acid The title compounds were prepared from (2S,5R,6S)-4-((R)-1-(1H-tetrazol-5-yl)butyl)-2-allyl-6-(3-chlorophenyl)-5-(4-chlorophenyl)morpholin-3-one and (2R,5S,6R)-4-((S)-1-(1H-tetrazol-5-yl)butyl)-2-allyl-6-(3-chlorophenyl)-5-(4-chlorophenyl)morpholin-3-one or (2S,5R,6S)-4-((S)-1-(1H-tetrazol-5-yl)butyl)-2-allyl-6-(3-chlorophenyl)-5-(4-chlorophenyl)morpholin-3-one and (2R,5S,6R)-4-((R)-1-(1H-tetrazol-5-yl)butyl)-2-allyl-6-(3-chlorophenyl)-5-(4-chlorophenyl)morpholin-3-one (Example 67, Step A) according to the procedure used for Example 2, Step D. The product was purified by reverse phase preparative HPLC (Gemini™ Prep C18 5 µm column, Phenomenex, Torrance, Calif.; gradient elution with 10% to 90% acetonitrile in water, both eluents containing 0.1% TFA) to give the title compounds.

$^1$H NMR (400 MHz, CDCl$_3$, δ ppm): 7.06-7.22 (m, 5H), 6.72-6.86 (m, 4H), 6.05 (br s, 1H), 5.51 (br s, 1H), 5.20 (t, J=4.5 Hz, 1H), 4.79 (br s, 1H), 3.37 (dd, J=17.4, 4.3 Hz, 1H), 3.11 (dd, J=17.5, 3.6 Hz, 1H), 1.98-2.11 (m, 1H), 1.54-1.70 (m, 1H), 0.89-1.21 (m, 2H), 0.65 (t, J=7.2 Hz, 3H). MS (ESI) 504.1 [M+H]$^+$.

Example 68

2-((2S,5R,6S)-6-(3-Chlorophenyl)-5-(4-chlorophenyl)-4-((R)-1-(5-methyl-1,3,4-oxadiazol-2-yl)butyl)-3-oxomorpholin-2-yl)acetic acid and 2-((2R,5S,6R)-6-(3-chlorophenyl)-5-(4-chlorophenyl)-4-((S)-1-(5-methyl-1,3,4-oxadiazol-2-yl)butyl)-3-oxomorpholin-2-yl)acetic acid or 2-((2S,5R,6S)-6-(3-chlorophenyl)-5-(4-chlorophenyl)-4-((S)-1-(5-methyl-1,3,4-oxadiazol-2-yl)butyl)-3-oxomorpholin-2-yl)acetic acid and 2-((2R,5S,6R)-6-(3-chlorophenyl)-5-(4-chlorophenyl)-4-((R)-1-(5-methyl-1,3,4-oxadiazol-2-yl)butyl)-3-oxomorpholin-2-yl)acetic acid

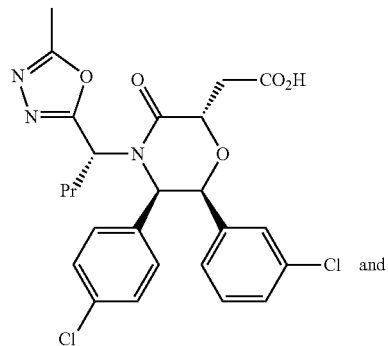

-continued

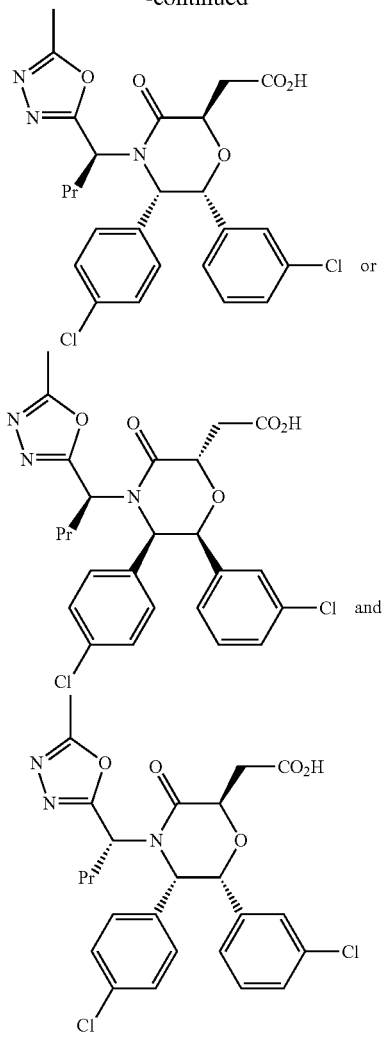

Step A. (R)-2-((2S,5R,6S)-2-Allyl-6-(3-chlorophenyl)-5-(4-chlorophenyl)-3-oxomorpholino)pentanoic acid and (S)-2-((2R,5S,6R)-2-allyl-6-(3-chlorophenyl)-5-(4-chlorophenyl)-3-oxomorpholino)pentanoic acid or (S)-2-((2S,5R,6S)-2-allyl-6-(3-chlorophenyl)-5-(4-chlorophenyl)-3-oxomorpholino)pentanoic acid and (R)-2-((2R,5S,6R)-2-allyl-6-(3-chlorophenyl)-5-(4-chlorophenyl)-3-oxomorpholino)pentanoic acid

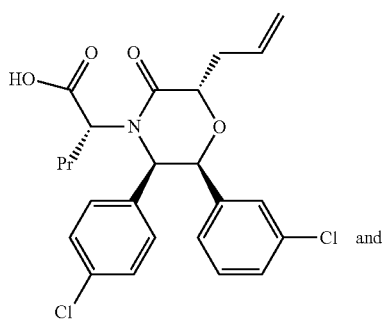

-continued

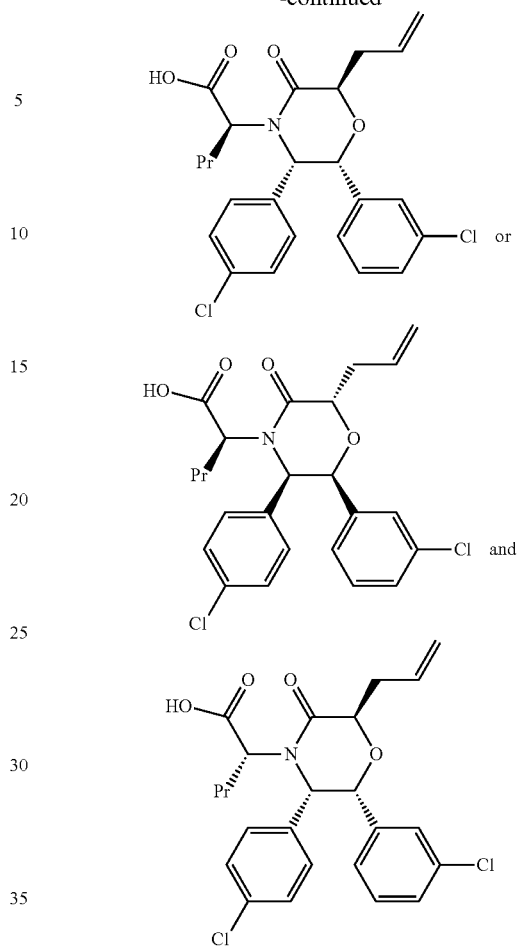

To a stirring solution of (R)-ethyl 2-((2S,5R,6S)-2-allyl-6-(3-chlorophenyl)-5-(4-chlorophenyl)-3-oxomorpholino)pentanoate and (S)-ethyl 2-((2R,5S,6R)-2-allyl-6-(3-chlorophenyl)-5-(4-chlorophenyl)-3-oxomorpholino)pentanoate or (S)-ethyl 2-((2S,5R,6S)-2-allyl-6-(3-chlorophenyl)-5-(4-chlorophenyl)-3-oxomorpholino)pentanoate and (R)-ethyl 2-((2R,5S,6R)-2-allyl-6-(3-chlorophenyl)-5-(4-chlorophenyl)-3-oxomorpholino)pentanoate (220 mg, 0.45 mmol, Example 65, Step B) in THF (2.0 mL) was added lithium hydroxide (10.7 mg, 0.45 mmol) and water (2 mL). The reaction was stirred at room temperature overnight. The reaction was treated with another portion of lithium hydroxide (10.7 mg, 0.45 mmol) and the mixture was stirred for 1 hour. Finally, the reaction was treated with an additional portion of lithium hydroxide (21.4 mg, 0.90 mmol) and the reaction was stirred for 3 hours. After this time the reaction was diluted with ethyl acetate and 0.1 M aqueous citric acid. The separated organic layer was washed with brine, dried over MgSO$_4$, filtered and evaporated under a vacuum to give the title compounds.

$^1$H NMR (400 MHz, CDCl$_3$, δ ppm): 9.66 (br s, 1H), 7.06-7.22 (m, 4H), 6.89-6.97 (m, 1H), 6.74-6.86 (m, 3H), 5.91 (ddt, J=17.1, 10.1, 7.0, 7.0 Hz, 1H), 5.42 (d, J=2.5 Hz, 1H), 5.03-5.20 (m, 2H), 4.74-4.94 (m, 2H), 4.49-4.57 (m, 1H), 2.81 (t, J=6.7 Hz, 2H), 1.81-1.93 (m, 1H), 1.49 (dtd, J=14.3, 9.6, 9.6, 4.8 Hz, 1H), 1.24-1.28 (m, 1H), 1.04-1.18 (m, 1H), 0.61-0.71 (m, 3H). MS (ESI) 462.1 [M+H]$^+$.

Step B. (R)—N'-Acetyl-2-((2S,5R,6S)-2-allyl-6-(3-chlorophenyl)-5-(4-chlorophenyl)-3-oxomorpholino)pentanehydrazide and (S)—N'-acetyl-2-((2R,5S,6R)-2-allyl-6-(3-chlorophenyl)-5-(4-chlorophenyl)-3-oxomorpholino)pentanehydrazide or (S)—N'-acetyl-2-((2S,5R,6S)-2-allyl-6-(3-chlorophenyl)-5-(4-chlorophenyl)-3-oxomorpholino)pentanehydrazide and (R)—N'-acetyl-2-((2R,5S,6R)-2-allyl-6-(3-chlorophenyl)-5-(4-chlorophenyl)-3-oxomorpholino)pentanehydrazide

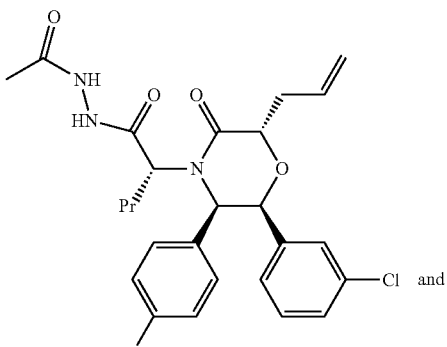 and

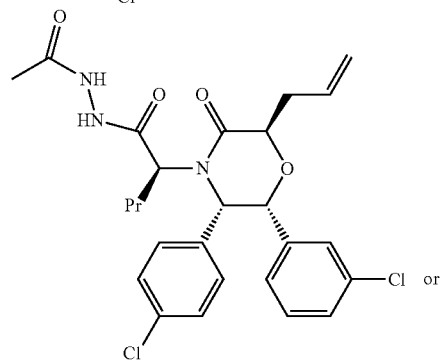 or

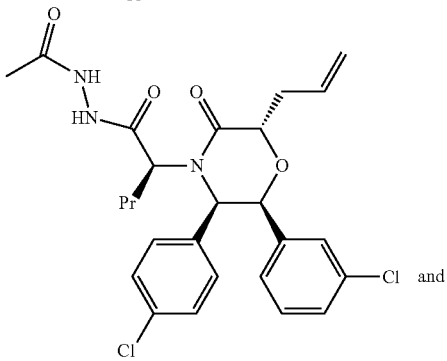 and

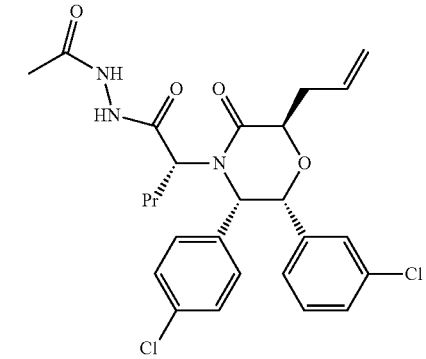

Acetohydrazide (38.5 mg, 0.52 mmol), NaHCO$_3$ (109 mg, 1.3 mmol), HOAt (88 mg, 0.65 mmol), and EDC (124 mg, 0.65 mmol) were added to a stirring solution of (R)-2-((2S,5R,6S)-2-allyl-6-(3-chlorophenyl)-5-(4-chlorophenyl)-3-oxomorpholino)pentanoic acid and (S)-2-((2R,5S,6R)-2-allyl-6-(3-chlorophenyl)-5-(4-chlorophenyl)-3-oxomorpholino)pentanoic acid or (S)-2-((2S,5R,6S)-2-allyl-6-(3-chlorophenyl)-5-(4-chlorophenyl)-3-oxomorpholino)pentanoic acid and (R)-2-((2R,5S,6R)-2-allyl-6-(3-chlorophenyl)-5-(4-chlorophenyl)-3-oxomorpholino)pentanoic acid (200 mg, 0.43 mmol, Example 68, Step A) in DMF (5 mL). The reaction was stirred at room temperature overnight, then diluted with ethyl acetate and water. The separated aqueous layer was extracted with ethyl acetate (2×50 mL) and the combined organic layers were washed with 1 M aqueous LiCl, dried over MgSO$_4$, filtered and evaporated under a vacuum. Purification by column chromatography (24 g SiO$_2$, gradient elution of 1:1 to 0:1 hexanes:ethyl acetate) gave the title compounds.

$^1$H NMR (400 MHz, CDCl$_3$, δ ppm): 8.38 (br s, 1H), 7.01-7.17 (m, 4H), 6.93 (s, 1H), 6.82 (d, J=7.4 Hz, 1H), 6.75 (d, J=8.4 Hz, 2H), 5.87 (ddt, J=17.1, 10.1, 6.9, 6.9 Hz, 1H), 5.50 (d, J=2.5 Hz, 1H), 5.17 (dd, J=8.5, 6.4 Hz, 1H), 5.10 (dd, J=17.1, 1.7 Hz, 1H), 5.02 (dd, J=10.2, 1.8 Hz, 1H), 4.75 (dd, J=8.8, 4.3 Hz, 1H), 4.71 (d, J=2.7 Hz, 1H), 2.71-2.84 (m, 2H), 2.07 (s, 3H), 1.48-1.64 (m, 1H), 0.88-1.16 (m, 3H), 0.44-0.62 (m, 3H). MS (ESI) 518.2 [M+H]$^+$.

Step C. (2S,5R,6S)-2-Allyl-6-(3-chlorophenyl)-5-(4-chlorophenyl)-4-((R)-1-(5-methyl-1,3,4-oxadiazol-2-yl)butyl)morpholin-3-one and (2R,5S,6R)-2-allyl-6-(3-chlorophenyl)-5-(4-chlorophenyl)-4-((S)-1-(5-methyl-1,3,4-oxadiazol-2-yl)butyl)morpholin-3-one or (2S,5R,6S)-2-allyl-6-(3-chlorophenyl)-5-(4-chlorophenyl)-4-((S)-1-(5-methyl-1,3,4-oxadiazol-2-yl)butyl)morpholin-3-one and (2R,5S,6R)-2-allyl-6-(3-chlorophenyl)-5-(4-chlorophenyl)-4-((R)-1-(5-methyl-1,3,4-oxadiazol-2-yl)butyl)morpholin-3-one

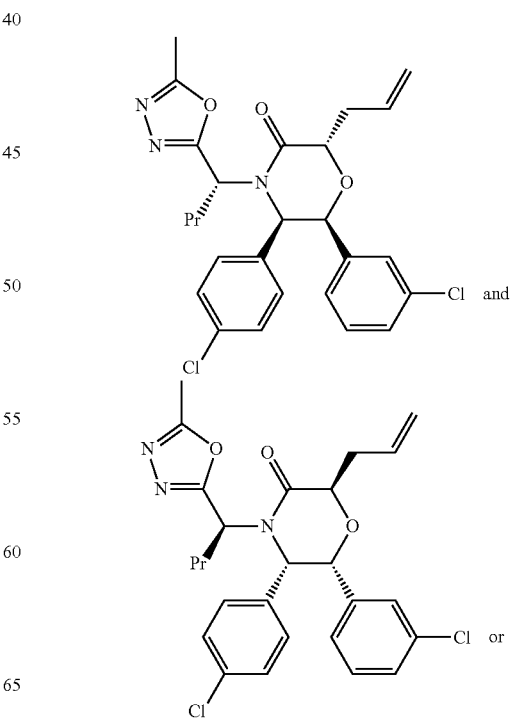

-continued

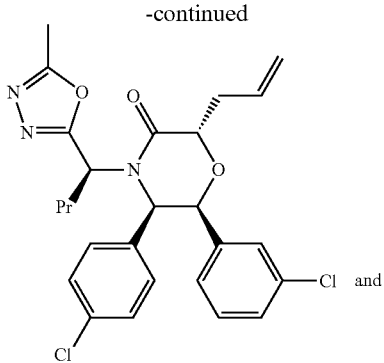

Burgess reagent (368 mg, 1.54 mmol) was added to a stirring solution of (R)—N'-acetyl-2-((2S,5R,6S)-2-allyl-6-(3-chlorophenyl)-5-(4-chlorophenyl)-3-oxomorpholino)pentanehydrazide and (S)—N'-acetyl-2-((2R,5S,6R)-2-allyl-6-(3-chlorophenyl)-5-(4-chlorophenyl)-3-oxomorpholino)pentanehydrazide or (S)—N'-acetyl-2-((2S,5R,6S)-2-allyl-6-(3-chlorophenyl)-5-(4-chlorophenyl)-3-oxomorpholino)pentanehydrazide and (R)—N'-acetyl-2-((2R,5S,6R)-2-allyl-6-(3-chlorophenyl)-5-(4-chlorophenyl)-3-oxomorpholino)pentanehydrazide (200 mg, 0.39 mmol, Example 68, Step B) in DCM (2 mL). The reaction was heated at 120° C. for 20 minutes in a microwave reactor, then diluted with DCM and saturated aqueous NaHCO$_3$.

The separated organic layer was washed with brine, dried over MgSO$_4$, filtered and evaporated under a vacuum. Column chromatography (12 g SiO$_2$, gradient elution of 1:0 to 1:2 hexanes:ethyl acetate) gave the title compounds.

$^1$H NMR (400 MHz, CDCl$_3$, δ ppm): 7.12-7.19 (m, 3H), 7.04-7.11 (m, 1H), 6.87-6.93 (m, 1H), 6.76-6.84 (m, 3H), 5.83-5.96 (m, 2H), 5.37 (dd, J=2.3, 0.6 Hz, 1H), 5.13 (dq, J=17.2, 1.6 Hz, 1H), 5.07 (dd, J=10.2, 1.8 Hz, 1H), 4.81 (t, J=6.4 Hz, 1H), 4.72 (d, J=2.7 Hz, 1H), 2.74-2.87 (m, 2H), 2.54-2.61 (m, 3H), 1.69-1.82 (m, 1H), 1.36-1.49 (m, 1H), 1.15-1.24 (m, 1H), 0.99-1.14 (m, 1H), 0.61 (t, J=7.3 Hz, 3H). MS (ESI) 500.0 [M+H]$^+$.

Step D. 2-((2S,5R,6S)-6-(3-Chlorophenyl)-5-(4-chlorophenyl)-4-((R)-1-(5-methyl-1,3,4-oxadiazol-2-yl)butyl)-3-oxomorpholin-2-yl)acetic acid and 2-((2R,5S,6R)-6-(3-chlorophenyl)-5-(4-chlorophenyl)-4-((S)-1-(5-methyl-1,3,4-oxadiazol-2-yl)butyl)-3-oxomorpholin-2-yl)acetic acid or 2-((2S,5R,6S)-6-(3-chlorophenyl)-5-(4-chlorophenyl)-4-((S)-1-(5-methyl-1,3,4-oxadiazol-2-yl)butyl)-3-oxomorpholin-2-yl)acetic acid and 2-((2R,5S,6R)-6-(3-chlorophenyl)-5-(4-chlorophenyl)-4-((R)-1-(5-methyl-1,3,4-oxadiazol-2-yl)butyl)-3-oxomorpholin-2-yl)acetic acid The title compounds were prepared from (2S,5R,6S)-2-allyl-6-(3-chlorophenyl)-5-(4-chlorophenyl)-4-((R)-1-(5-methyl-1,3,4-oxadiazol-2-yl)butyl)morpholin-3-one and (2R,5S,6R)-2-allyl-6-(3-chlorophenyl)-5-(4-chlorophenyl)-4-((S)-1-(5-methyl-1,3,4-oxadiazol-2-yl)butyl)morpholin-3-one or (2S,5R,6S)-2-allyl-6-(3-chlorophenyl)-5-(4-chlorophenyl)-4-((S)-1-(5-methyl-1,3,4-oxadiazol-2-yl)butyl)morpholin-3-one and (2R,5S,6R)-2-allyl-6-(3-chlorophenyl)-5-(4-chlorophenyl)-4-((R)-1-(5-methyl-1,3,4-oxadiazol-2-yl)butyl)morpholin-3-one (Example 68, Step C) by a procedure similar to the one described in Example 65, Step D. The product was purified by reverse phase preparative HPLC (Gemini™ Prep C18 5 μm column, Phenomenex, Torrance, Calif.; gradient elution of 10% to 90% acetonitrile in water, with both eluents containing 0.1% TFA) to give the title compounds.

$^1$H NMR (500 MHz, CDCl$_3$, δ ppm): 7.13-7.19 (m, 3H), 7.04-7.11 (m, 1H), 6.88 (s, 1H), 6.75-6.82 (m, 3H), 5.90 (t, J=7.3 Hz, 1H), 5.35-5.41 (m, 1H), 5.27 (dd, J=7.6, 4.6 Hz, 1H), 4.77 (d, J=2.2 Hz, 1H), 3.16 (dd, J=16.5, 4.5 Hz, 1H), 3.04 (dd, J=16.5, 7.7 Hz, 1H), 2.57 (s, 3H), 1.69-1.82 (m, 1H), 1.37-1.48 (m, 1H), 1.13-1.23 (m, 1H), 1.00-1.10 (m, 1H), 0.61 (t, J=7.3 Hz, 3H). MS (ESI) 518.2 [M+H]$^+$.

Example 69

2-((2S,5R,6S)-6-(3-Chlorophenyl)-5-(4-chlorophenyl)-4-((R)-cyclopropyl(5-methyl-1,3,4-oxadiazol-2-yl)methyl)-3-oxomorpholin-2-yl)acetic acid and 2-((2R,5S,6R)-6-(3-chlorophenyl)-5-(4-chlorophenyl)-4-((S)-cyclopropyl(5-methyl-1,3,4-oxadiazol-2-yl)methyl)-3-oxomorpholin-2-yl)acetic acid or 2-((2S,5R,6S)-6-(3-chlorophenyl)-5-(4-chlorophenyl)-4-((S)-cyclopropyl(5-methyl-1,3,4-oxadiazol-2-yl)methyl)-3-oxomorpholin-2-yl)acetic acid and 2-((2R,5S,6R)-6-(3-chlorophenyl)-5-(4-chlorophenyl)-4-((R)-cyclopropyl(5-methyl-1,3,4-oxadiazol-2-yl)methyl)-3-oxomorpholin-2-yl)acetic acid

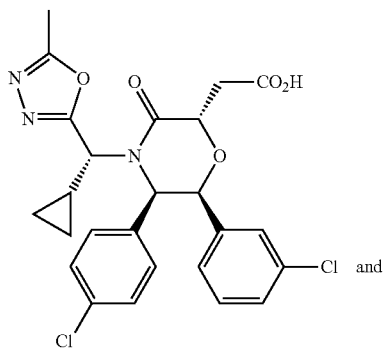

-continued

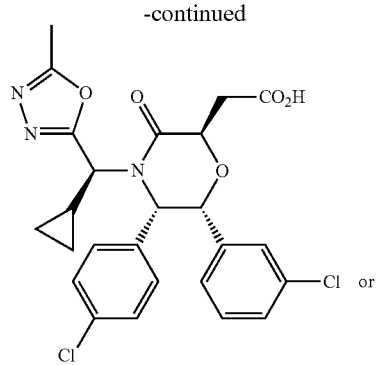

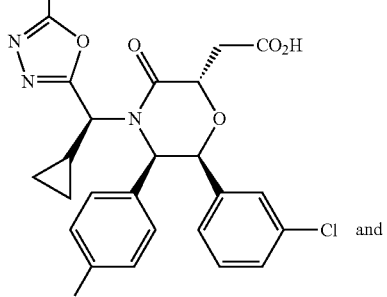

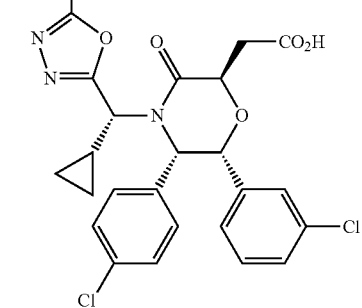

Step A. Ethyl 2-bromo-2-cyclopropylacetate

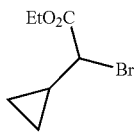

Methyl 2-cyclopropylacetate (4 g, 35 mmol) in THF (10 mL) was added dropwise over 5 minutes to a stirring solution of LDA (23 mL, 35 mmol, 1.8 M solution) in THF (80 mL) at −78° C. The reaction was stirred at this temperature for 20 minutes, and then trimethylchlorosilane (7 mL, 53 mmol) was added dropwise over 2 minutes. The reaction was stirred at −78° C. for 20 minutes, and a solution of NBS (14 g, 77 mmol) in THF (10 mL) was added dropwise over 3 minutes. The reaction was allowed to warm to room temperature overnight. The reaction was treated with ethyl acetate and water. The separated organic layer was washed with brine, dried over MgSO₄, filtered and evaporated under a vacuum. Flash column chromatography (80 g, SiO₂, gradient elution with 1:0 to 1:1 hexanes:ethyl acetate) gave the racemic title compound.

$^1$H NMR (400 MHz, CDCl₃, δ ppm): 4.26 (q, J=7.1 Hz, 2H), 3.45 (d, J=10.4 Hz, 1H), 1.54-1.66 (m, 1H), 1.24-1.36 (m, 3H), 0.79-0.89 (m, 2H), 0.50-0.60 (m, 1H), 0.39-0.49 (m, 1H).

Step B. (R)-Ethyl 2-((2S,3R)-2-(3-chlorophenyl)-3-(4-chlorophenyl)-5-oxomorpholino)-2-cyclopropylacetate and (S)-ethyl 2-((2R,3S)-2-(3-chlorophenyl)-3-(4-chlorophenyl)-5-oxomorpholino)-2-cyclopropylacetate or (S)-ethyl 2-((2S,3R)-2-(3-chlorophenyl)-3-(4-chlorophenyl)-5-oxomorpholino)-2-cyclopropylacetate and (R)-ethyl 2-((2R,3S)-2-(3-chlorophenyl)-3-(4-chlorophenyl)-5-oxomorpholino)-2-cyclopropylacetate

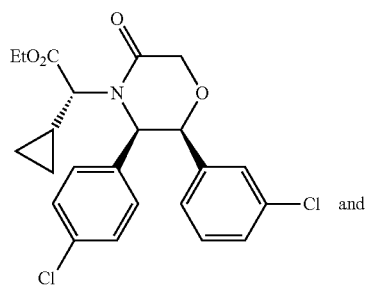

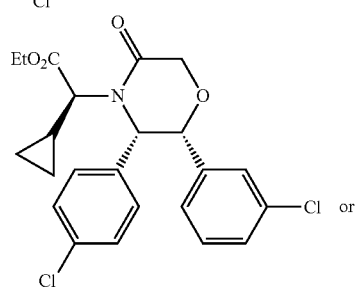

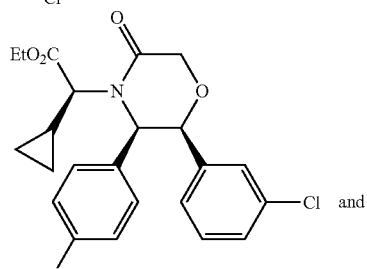

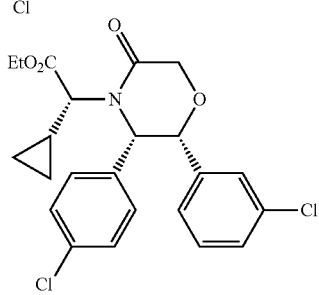

Sodium hydride (150 mg, 3.72 mmol, 60% dispersion in oil) was added to a stirring solution of (5R,6S)-6-(3-chlorophenyl)-5-(4-chlorophenyl)morpholin-3-one and (5S,6R)-6-(3-chlorophenyl)-5-(4-chlorophenyl)morpholin-3-one (1.0 g, 3.14 mmol, Example 11, Step D) in DMF (7.5 mL). The reaction was stirred for 10 minutes. at room temperature and treated with (+)-ethyl 2-bromo-2-cyclopropylacetate (707 mg, 3.41 mmol, Example 69, Step A). After 16 hours the reaction was treated with NH₄Cl (saturated aqueous solution) and ethyl acetate. The separated organic layer was washed with 1.0 M aqueous LiCl, dried over MgSO₄, filtered and evaporated under reduced pressure. Flash column chromatography (silica gel; gradient elution with 1:0 to 2:1 hexanes:ethyl acetate) gave one pair of the title compounds as the first eluting isomers.

¹H NMR (500 MHz, CDCl₃, δ ppm): 7.16-7.20 (m, 1H), 7.11 (dd, J=8.4, 7.0 Hz, 3H), 6.95 (t, J=2.0 Hz, 1H), 6.81 (dt, J=7.6, 1.7 Hz, 1H), 6.76 (d, J=8.3 Hz, 2H), 5.24-5.28 (m, 1H), 4.90 (d, J=2.7 Hz, 1H), 4.70 (d, J=17.4 Hz, 1H), 4.56 (d, J=17.4 Hz, 1H), 4.34 (d, J=10.5 Hz, 1H), 4.27 (q, J=7.1 Hz, 2H), 1.34 (t, J=7.2 Hz, 3H), 0.46-0.68 (m, 3H), −0.09-0.02 (m, 1H), −0.32--0.23 (m, 1H).

Step C. (R)-Ethyl 2-((2S,5R,6S)-2-allyl-6-(3-chlorophenyl)-5-(4-chlorophenyl)-3-oxomorpholino)-2-cyclopropylacetate and (S)-ethyl 2-((2R,5S,6R)-2-allyl-6-(3-chlorophenyl)-5-(4-chlorophenyl)-3-oxomorpholino)-2-cyclopropylacetate or (S)-ethyl 2-((2S,5R,6S)-2-allyl-6-(3-chlorophenyl)-5-(4-chlorophenyl)-3-oxomorpholino)-2-cyclopropylacetate and (R)-ethyl 2-((2R,5S,6R)-2-allyl-6-(3-chlorophenyl)-5-(4-chlorophenyl)-3-oxomorpholino)-2-cyclopropylacetate

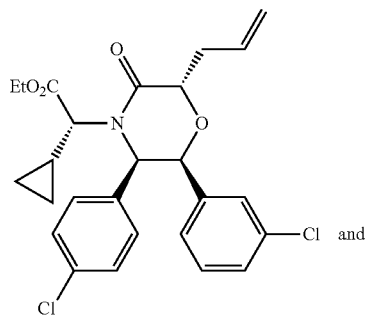
and

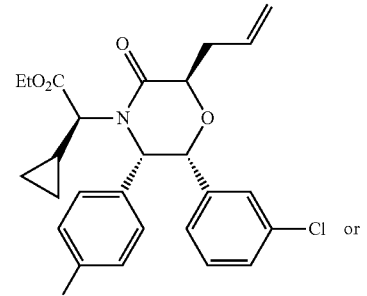
or

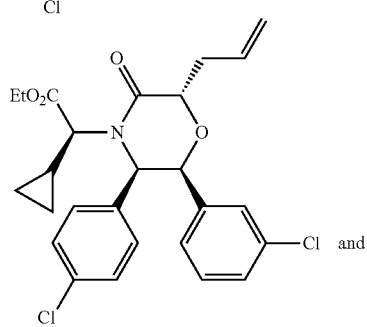
and

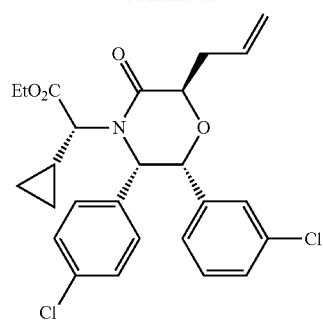

The title compounds were prepared from (R)-ethyl 2-((2S,3R)-2-(3-chlorophenyl)-3-(4-chlorophenyl)-5-oxomorpholino)-2-cyclopropylacetate and (S)-ethyl 2-((2R,3S)-2-(3-chlorophenyl)-3-(4-chlorophenyl)-5-oxomorpholino)-2-cyclopropylacetate or (S)-ethyl 2-((2S,3R)-2-(3-chlorophenyl)-3-(4-chlorophenyl)-5-oxomorpholino)-2-cyclopropylacetate and (R)-ethyl 2-((2R,3S)-2-(3-chlorophenyl)-3-(4-chlorophenyl)-5-oxomorpholino)-2-cyclopropylacetate (Example 69, Step B) by a procedure similar to the one described in Example 2, Step B. The product was purified by flash column chromatography (SiO₂, gradient elution of 1:0 to 1:1 hexanes:ethyl acetate).

¹H NMR (400 MHz, CDCl₃, δ ppm): 7.16-7.20 (m, 1H), 7.09-7.14 (m, 3H), 6.97 (t, J=2.0 Hz, 1H), 6.83 (dt, J=7.6, 1.8 Hz, 1H), 6.68-6.77 (m, 2H), 5.91 (ddt, J=17.1, 10.1, 6.9, 6.9 Hz, 1H), 5.44-5.49 (m, 1H), 5.14 (dq, J=17.2, 1.6 Hz, 1H), 5.04-5.10 (m, 1H), 4.85 (dd, J=2.5, 0.4 Hz, 1H), 4.76 (dd, J=7.8, 5.1 Hz, 1H), 4.32 (d, J=10.2 Hz, 1H), 4.23-4.30 (m, 2H), 2.72-2.88 (m, 2H), 1.35 (t, J=7.2 Hz, 3H), 0.45-0.72 (m, 3H), −0.10-0.02 (m, 1H), −0.37--0.20 (m, 1H).

Step D. (R)-2-((2S,5R,6S)-2-Allyl-6-(3-chlorophenyl)-5-(4-chlorophenyl)-3-oxomorpholino)-2-cyclopropylacetic acid and (S)-2-((2R,5S,6R)-2-allyl-6-(3-chlorophenyl)-5-(4-chlorophenyl)-3-oxomorpholino)-2-cyclopropylacetic acid or (S)-2-((2S,5R,6S)-2-allyl-6-(3-chlorophenyl)-5-(4-chlorophenyl)-3-oxomorpholino)-2-cyclopropylacetic acid and (R)-2-((2R,5S,6R)-2-allyl-6-(3-chlorophenyl)-5-(4-chlorophenyl)-3-oxomorpholino)-2-cyclopropylacetic acid

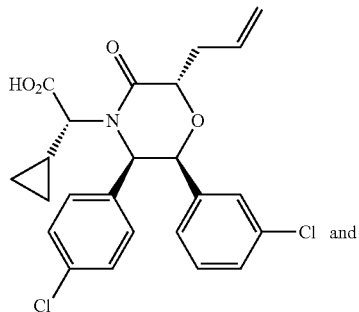
and

207
-continued

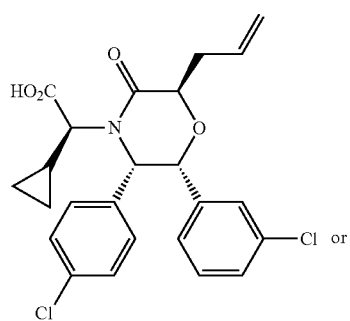
Cl or

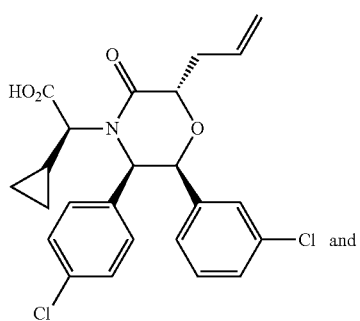
Cl and

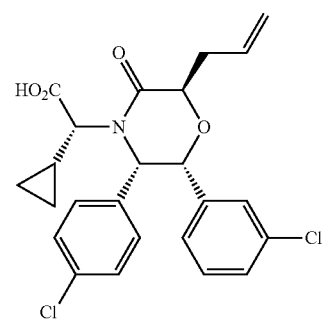
Cl

The title compounds were prepared from (R)-ethyl 2-((2S, 5R,6S)-2-allyl-6-(3-chlorophenyl)-5-(4-chlorophenyl)-3-oxomorpholino)-2-cyclopropylacetate and (S)-ethyl 2-((2R, 5S,6R)-2-allyl-6-(3-chlorophenyl)-5-(4-chlorophenyl)-3-oxomorpholino)-2-cyclopropylacetate or (S)-ethyl 2-((2S, 5R,6S)-2-allyl-6-(3-chlorophenyl)-5-(4-chlorophenyl)-3-oxomorpholino)-2-cyclopropylacetate and (R)-ethyl 2-((2R, 5S,6R)-2-allyl-6-(3-chlorophenyl)-5-(4-chlorophenyl)-3-oxomorpholino)-2-cyclopropylacetate (Example 69, Step C) by a procedure similar to the one described in Example 68, Step A. MS (ESI) 460.1 [M+H]+.

Step E. (R)—N'-Acetyl-2-((2S,5R,6S)-2-allyl-6-(3-chlorophenyl)-5-(4-chlorophenyl)-3-oxomorpholino)-2-cyclopropylacetohydrazide and (S)—N'-Acetyl-2-((2R,5S,6R)-2-allyl-6-(3-chlorophenyl)-5-(4-chlorophenyl)-3-oxomorpholino)-2-cyclopropylacetohydrazide or (S)—N'-Acetyl-2-((2S,5R,6S)-2-allyl-6-(3-chlorophenyl)-5-(4-chlorophenyl)-3-oxomorpholino)-2-cyclopropylacetohydrazide and (R)—N'-Acetyl-2-((2R,5S,6R)-2-allyl-6-(3-chlorophenyl)-5-(4-chlorophenyl)-3-oxomorpholino)-2-cyclopropylacetohydrazide

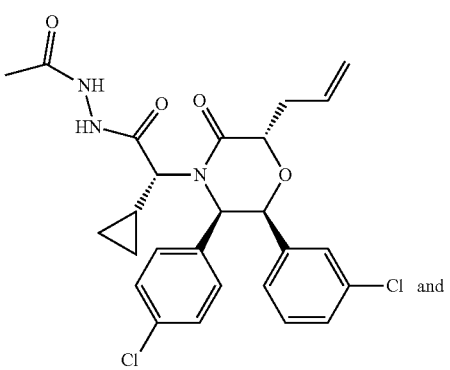
Cl and

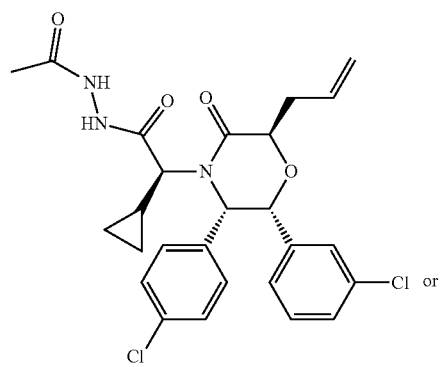
Cl or

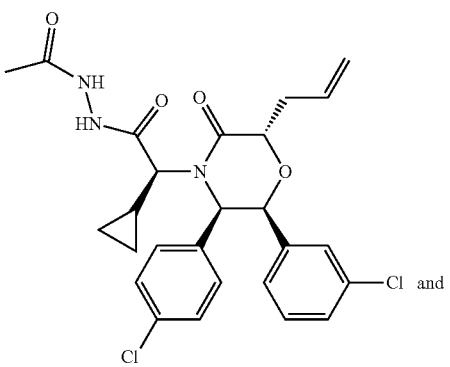
Cl and

-continued

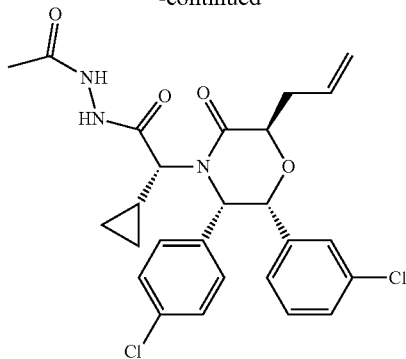

The title compounds were prepared from (R)-2-((2S,5R,6S)-2-allyl-6-(3-chlorophenyl)-5-(4-chlorophenyl)-3-oxomorpholino)-2-cyclopropylacetic acid and (S)-2-((2R,5S,6R)-2-allyl-6-(3-chlorophenyl)-5-(4-chlorophenyl)-3-oxomorpholino)-2-cyclopropylacetic acid or (S)-2-((2S,5R,6S)-2-allyl-6-(3-chlorophenyl)-5-(4-chlorophenyl)-3-oxomorpholino)-2-cyclopropylacetic acid and (R)-2-((2R,5S,6R)-2-allyl-6-(3-chlorophenyl)-5-(4-chlorophenyl)-3-oxomorpholino)-2-cyclopropylacetic acid (Example 69, Step D) by a procedure similar to the one described in Example 68, Step B.

$^1$H NMR (400 MHz, CDCl$_3$, δ ppm): 7.00-7.19 (m, 4H), 6.95 (s, 1H), 6.79-6.88 (m, 1H), 6.65-6.77 (m, 2H), 5.88 (ddt, J=17.1, 10.1, 7.0, 7.0 Hz, 1H), 5.49 (d, J=2.5 Hz, 1H), 4.98-5.18 (m, 2H), 4.80-4.88 (m, 1H), 4.74 (dd, J=8.9, 4.0 Hz, 1H), 4.39 (d, J=10.6 Hz, 1H), 2.66-2.84 (m, 2H), 2.08 (s, 3H), 0.69-0.88 (m, 1H), 0.49-0.62 (m, 1H), 0.33 (dq, J=9.8, 5.0 Hz, 1H), −0.10-0.10 (m, 1H), −0.44--0.25 (m, 1H).

Step F. (2S,5R,6S)-2-Allyl-6-(3-chlorophenyl)-5-(4-chlorophenyl)-4-((R)-cyclopropyl(5-methyl-1,3,4-oxadiazol-2-yl)methyl)morpholin-3-one and (2R,5S,6R)-2-allyl-6-(3-chlorophenyl)-5-(4-chlorophenyl)-4-((S)-cyclopropyl(5-methyl-1,3,4-oxadiazol-2-yl)methyl)morpholin-3-one or (2S,5R,6S)-2-allyl-6-(3-chlorophenyl)-5-(4-chlorophenyl)-4-((S)-cyclopropyl(5-methyl-1,3,4-oxadiazol-2-yl)methyl)morpholin-3-one and (2R,5S,6R)-2-allyl-6-(3-chlorophenyl)-5-(4-chlorophenyl)-4-((R)-cyclopropyl(5-methyl-1,3,4-oxadiazol-2-yl)methyl)morpholin-3-one

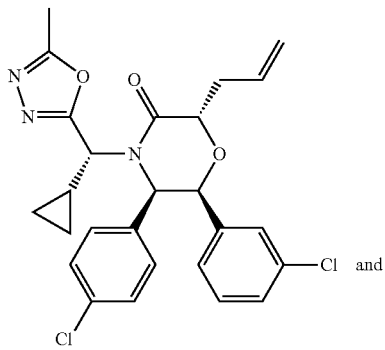

-continued

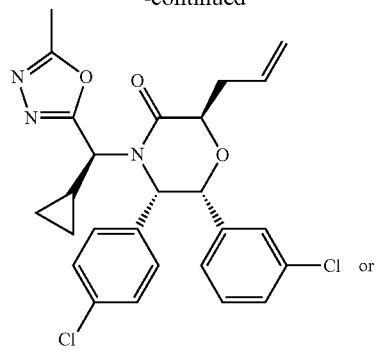

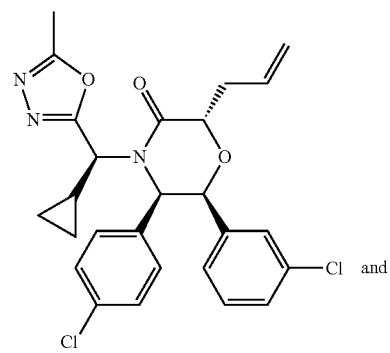

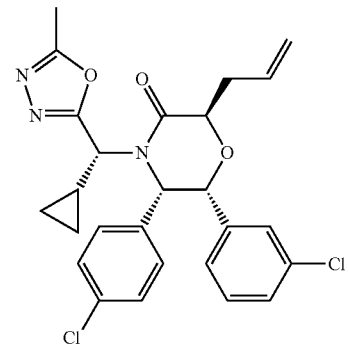

The title compounds were prepared from (R)—N'-acetyl-2-((2S,5R,6S)-2-allyl-6-(3-chlorophenyl)-5-(4-chlorophenyl)-3-oxomorpholino)-2-cyclopropylacetohydrazide and (S)—N'-acetyl-2-((2R,5S,6R)-2-allyl-6-(3-chlorophenyl)-5-(4-chlorophenyl)-3-oxomorpholino)-2-cyclopropylacetohydrazide or (S)—N'-acetyl-2-((2S,5R,6S)-2-allyl-6-(3-chlorophenyl)-5-(4-chlorophenyl)-3-oxomorpholino)-2-cyclopropylacetohydrazide and (R)—N'-acetyl-2-((2R,5S,6R)-2-allyl-6-(3-chlorophenyl)-5-(4-chlorophenyl)-3-oxomorpholino)-2-cyclopropylacetohydrazide (Example 69, Step E) by a procedure similar to the one described in Example 68, Step C.

$^1$H NMR (400 MHz, CDCl$_3$, δ ppm): 7.05-7.20 (m, 4H), 6.97 (s, 1H), 6.69-6.87 (m, 3H), 5.89 (ddt, J=17.1, 10.1, 7.0, 7.0 Hz, 1H), 5.43-5.50 (m, 1H), 5.21 (d, J=10.4 Hz, 1H), 5.13 (dd, J=17.1, 1.5 Hz, 1H), 5.07 (d, J=10.2 Hz, 1H), 4.98 (d, J=2.5 Hz, 1H), 4.77-4.82 (m, 1H), 2.73-2.84 (m, 2H), 2.59 (s, 3H), −0.21-0.77 (m, 5H).

Step G. 2-((2S,5R,6S)-6-(3-Chlorophenyl)-5-(4-chlorophenyl)-4-((R)-cyclopropyl(5-methyl-1,3,4-oxadiazol-2-yl)methyl)-3-oxomorpholin-2-yl)acetic acid and 2-((2R,5S,6R)-6-(3-chlorophenyl)-5-(4-chlorophenyl)-4-((S)-cyclopropyl(5-methyl-1,3,4-oxadiazol-2-yl)methyl)-3-oxomorpholin-2-yl)acetic acid or 2-((2S,5R,6S)-6-(3-chlorophenyl)-5-(4-chlorophenyl)-4-((S)-cyclopropyl(5-methyl-1,3,4-oxadiazol-2-yl)methyl)-3-oxomorpholin-2-yl)acetic acid and 2-((2R,5S,6R)-6-(3-chlorophenyl)-5-(4-chlorophenyl)-4-((R)-cyclopropyl(5-methyl-1,3,4-oxadiazol-2-yl)methyl)-3-oxomorpholin-2-yl)acetic acid

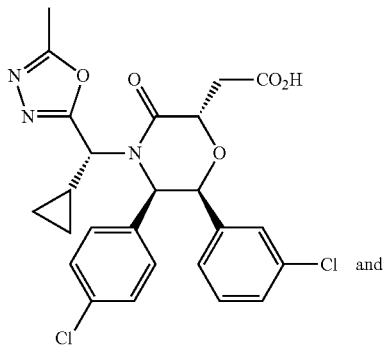 and

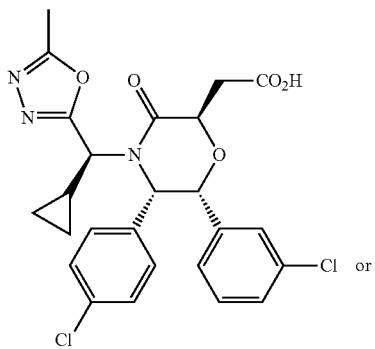 or

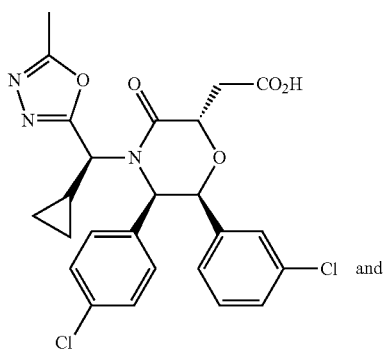 and

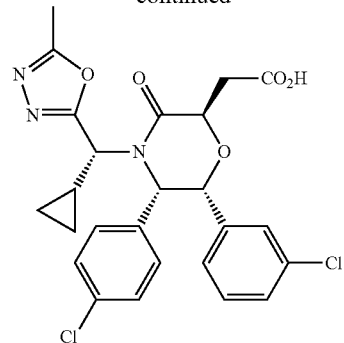

The title compounds were prepared from (2S,5R,6S)-2-allyl-6-(3-chlorophenyl)-5-(4-chlorophenyl)-4-((R)-cyclopropyl(5-methyl-1,3,4-oxadiazol-2-yl)methyl)morpholin-3-one and (2R,5S,6R)-2-allyl-6-(3-chlorophenyl)-5-(4-chlorophenyl)-4-((S)-cyclopropyl(5-methyl-1,3,4-oxadiazol-2-yl)methyl)morpholin-3-one or (2S,5R,6S)-2-allyl-6-(3-chlorophenyl)-5-(4-chlorophenyl)-4-((S)-cyclopropyl(5-methyl-1,3,4-oxadiazol-2-yl)methyl)morpholin-3-one and (2R,5S,6R)-2-allyl-6-(3-chlorophenyl)-5-(4-chlorophenyl)-4-((R)-cyclopropyl(5-methyl-1,3,4-oxadiazol-2-yl)methyl)morpholin-3-one (Example 69, Step F) by a procedure similar to the one described in Example 65, Step D. The product was purified by reverse phase preparative HPLC (Gemini™ Prep C18 5 μm column, Phenomenex, Torrance, Calif.; gradient elution with 10% to 90% acetonitrile in water, with both eluents containing 0.1% TFA) to give the title compounds.

$^1$H NMR (400 MHz, CDCl$_3$, δ ppm): 7.07-7.20 (m, 4H), 6.96 (s, 1H), 6.84 (d, J=7.6 Hz, 1H), 6.77 (d, J=8.2 Hz, 2H), 5.47 (br s, 1H), 5.28 (br s, 1H), 5.17 (d, J=9.4 Hz, 1H), 5.03 (br s, 1H), 3.17 (d, J=15.7 Hz, 1H), 3.03 (dd, J=16.0, 8.0 Hz, 1H), 2.46-2.65 (m, 3H), 0.92 (br s, 1H), 0.59 (d, J=5.1 Hz, 1H), 0.50 (d, J=4.5 Hz, 1H), 0.09-0.22 (m, 1H), −0.25-−0.12 (m, 1H).

Example 70

(S)-2-((2S,3R,6S)-2,3-Bis(4-chlorophenyl)-6-(4-cyanobenzyl)-5-oxomorpholino)-2-cyclopropylacetic acid and (R)-2-((2R,3S,6R)-2,3-bis(4-chlorophenyl)-6-(4-cyanobenzyl)-5-oxomorpholino)-2-cyclopropylacetic acid or (R)-2-((2S,3R,6S)-2,3-bis(4-chlorophenyl)-6-(4-cyanobenzyl)-5-oxomorpholino)-2-cyclopropylacetic acid and (S)-2-((2R,3S,6R)-2,3-bis(4-chlorophenyl)-6-(4-cyanobenzyl)-5-oxomorpholino)-2-cyclopropylacetic acid

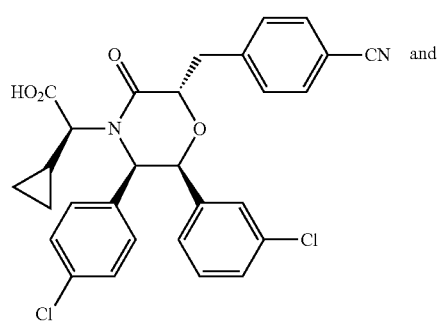 and

-continued

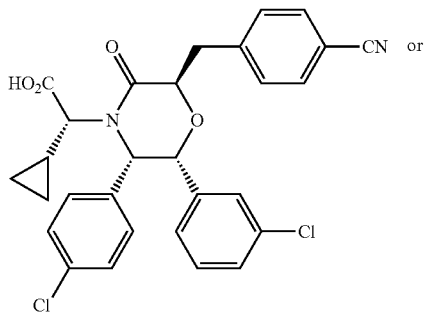

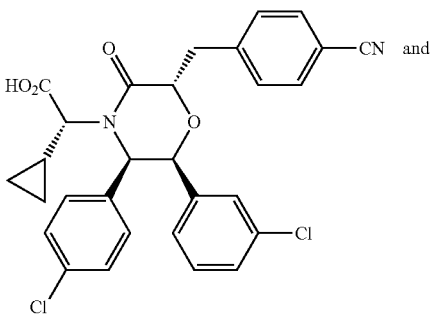

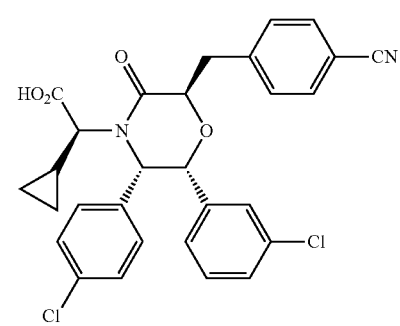

Step A. (R)-Ethyl 2-((2S,3R)-2,3-bis(4-chlorophenyl)-5-oxomorpholino)-2-cyclopropylacetate and (S)-ethyl 2-((2R,3S)-2,3-bis(4-chlorophenyl)-5-oxomorpholino)-2-cyclopropylacetate or (S)-ethyl 2-((2S,3R)-2,3-bis(4-chlorophenyl)-5-oxomorpholino)-2-cyclopropylacetate and (R)-ethyl 2-((2R,3S)-2,3-bis(4-chlorophenyl)-5-oxomorpholino)-2-cyclopropylacetate

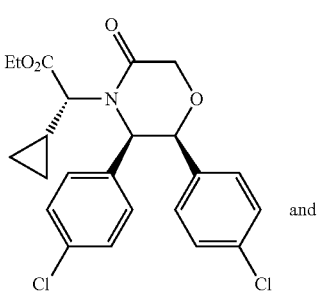

-continued

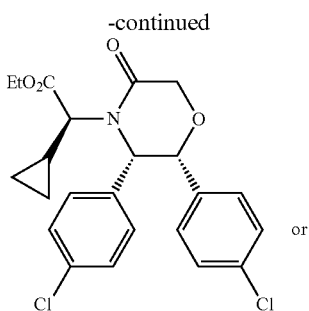

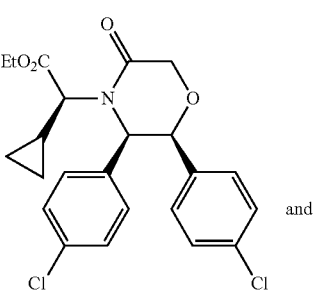

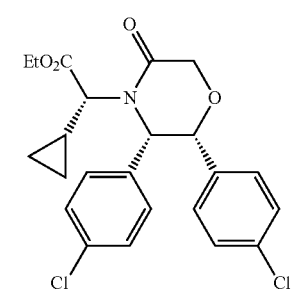

The title compounds were prepared from (5R,6S)-5,6-bis(4-chlorophenyl)morpholin-3-one and (5S,6R)-5,6-bis(4-chlorophenyl)morpholin-3-one (Example 4, Step F) by a procedure similar to the one described in Example 69, Step B, to give one pair of the title compounds as the first eluting isomers.

$^1$H NMR (400 MHz, CDCl$_3$, δ ppm): 7.15-7.20 (m, 2H), 7.09-7.14 (m, 2H), 6.83-6.89 (m, 2H), 6.72-6.77 (m, 2H), 5.26 (d, J=2.7 Hz, 1H), 4.88 (d, J=2.7 Hz, 1H), 4.70 (d, J=17.2 Hz, 1H), 4.57 (d, J=17.2 Hz, 1H), 4.34 (d, J=10.2 Hz, 1H), 4.26 (q, J=7.0 Hz, 2H), 1.30-1.39 (m, 3H), 0.44-0.69 (m, 3H), −0.08-0.01 (m, 1H), −0.33-−0.23 (m, 1H).

Step B. (R)-Ethyl 2-((2S,3R,6S)-2,3-bis(4-chlorophenyl)-6-(4-cyanobenzyl)-5-oxomorpholino)-2-cyclopropylacetate and (S)-ethyl 2-((2R,3S,6R)-2,3-bis(4-chlorophenyl)-6-(4-cyanobenzyl)-5-oxomorpholino)-2-cyclopropylacetate or (S)-ethyl 2-((2S,3R,6S)-2,3-bis(4-chlorophenyl)-6-(4-cyanobenzyl)-5-oxomorpholino)-2-cyclopropylacetate and (R)-ethyl 2-((2R,3S,6R)-2,3-bis(4-chlorophenyl)-6-(4-cyanobenzyl)-5-oxomorpholino)-2-cyclopropylacetate

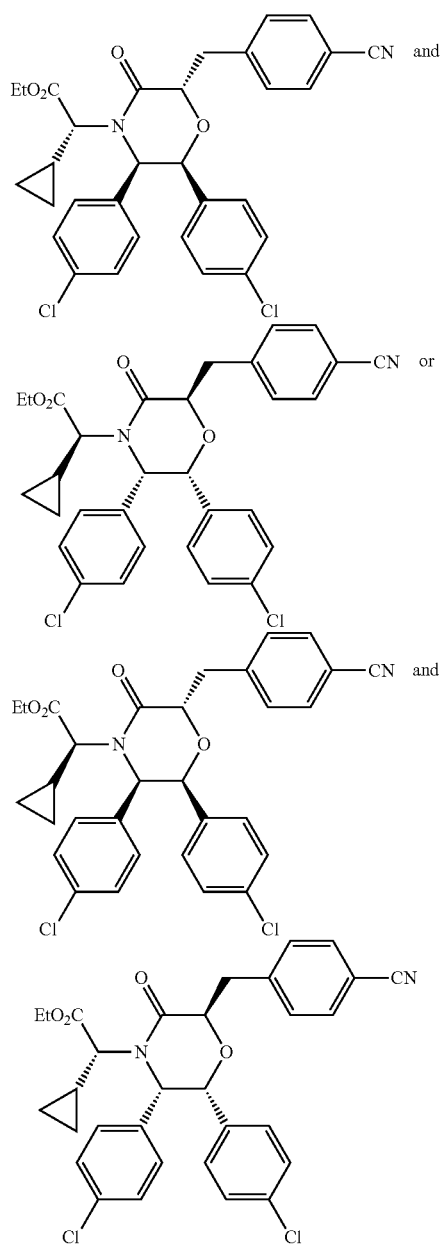

(R)-ethyl 2-((2S,3R)-2,3-bis(4-chlorophenyl)-5-oxomorpholino)-2-cyclopropylacetate and (S)-ethyl 2-((2R,3S)-2,3-bis(4-chlorophenyl)-5-oxomorpholino)-2-cyclopropylacetate or (S)-ethyl 2-((2S,3R)-2,3-bis(4-chlorophenyl)-5-oxomorpholino)-2-cyclopropylacetate and (R)-ethyl 2-((2R,3S)-2,3-bis(4-chlorophenyl)-5-oxomorpholino)-2-cyclopropylacetate (60 mg, 134 µmol, first eluting isomers, Example 70, Step A) in THF (1.5 mL) were added to a stirring solution of lithium bis(trimethylsilyl)amide (147 µL, 147 µmol, 1.0 M solution in tetrahydrofuran) in THF (1.5 mL) at −78° C. The reaction was stirred at −78° C. for 20 minutes and treated with a solution of 4-(iodomethyl)benzonitrile (39 mg, 161 µmol) in THF (1.0 mL). After stirring at −78° C. for 1 hour, the reaction was treated with saturated aqueous NH$_4$Cl and ethyl acetate. The separated aqueous layer was extracted with ethyl acetate, and the combined organic layers were washed with brine, dried over MgSO$_4$, filtered and evaporated under a vacuum. Flash column chromatography (12 g SiO$_2$, gradient elution of 1:0 to 2:1 hexanes:ethyl acetate) gave the title compounds.

$^1$H NMR (400 MHz, CDCl$_3$, δ ppm): 7.48-7.56 (m, 2H), 7.28-7.34 (m, 2H), 7.08-7.19 (m, 4H), 6.74-6.83 (m, 4H), 5.03-5.07 (m, 1H), 4.91-4.97 (m, 1H), 4.68 (d, J=2.9 Hz, 1H), 4.04 (dq, J=10.8, 7.1 Hz, 1H), 3.88 (dq, J=10.8, 7.1 Hz, 1H), 3.53 (d, J=10.4 Hz, 1H), 3.34-3.42 (m, 2H), 1.31-1.43 (m, 1H), 1.20 (t, J=7.1 Hz, 3H), 0.72 (tdd, J=8.6, 8.6, 6.1, 4.9 Hz, 1H), 0.47-0.55 (m, 1H), 0.37-0.46 (m, 1H), −0.10-0.00 (m, 1H). MS (ESI) 563.2 [M+H]$^+$.

Step C. (S)-2-((2S,3R,6S)-2,3-Bis(4-chlorophenyl)-6-(4-cyanobenzyl)-5-oxomorpholino)-2-cyclopropylacetic acid and (R)-2-((2R,3S,6R)-2,3-bis(4-chlorophenyl)-6-(4-cyanobenzyl)-5-oxomorpholino)-2-cyclopropylacetic acid or (R)-2-((2S,3R,6S)-2,3-bis(4-chlorophenyl)-6-(4-cyanobenzyl)-5-oxomorpholino)-2-cyclopropylacetic acid and (S)-2-((2R,3S,6R)-2,3-bis(4-chlorophenyl)-6-(4-cyanobenzyl)-5-oxomorpholino)-2-cyclopropylacetic acid Lithium hydroxide (53 µL, 106 µmol, 2 M aqueous solution) was added to a stirring solution of (R)-ethyl 2-((2S,3R,6S)-2,3-bis(4-chlorophenyl)-6-(4-cyanobenzyl)-5-oxomorpholino)-2-cyclopropylacetate and (S)-ethyl 2-((2R,3S,6R)-2,3-bis(4-chlorophenyl)-6-(4-cyanobenzyl)-5-oxomorpholino)-2-cyclopropylacetate or (S)-ethyl 2-((2S,3R,6S)-2,3-bis(4-chlorophenyl)-6-(4-cyanobenzyl)-5-oxomorpholino)-2-cyclopropylacetate and (R)-ethyl 2-((2R,3S,6R)-2,3-bis(4-chlorophenyl)-6-(4-cyanobenzyl)-5-oxomorpholino)-2-cyclopropylacetate (30 mg, 53 µmol, Example 70, Step B) in MeOH (0.7 mL), THF (0.7 mL) and water (0.7 mL). The reaction was stirred at room temperature overnight, then acidified with 1 M HCl and treated with ethyl acetate. The separated aqueous layer was extracted with ethyl acetate, and the combined organic layers were washed with brine, dried, filtered and evaporated under a vacuum. The product was purified by reverse phase preparative HPLC (Gemini™ Prep C18 5 µm column, Phenomenex, Torrance, Calif.; gradient elution of 10% to 90% acetonitrile in water, both eluents containing 0.1% TFA) to give one pair of the title compounds as the first eluting isomers.

$^1$H NMR (400 MHz, CDCl$_3$, δ ppm): 7.52-7.59 (m, 2H), 7.32 (d, J=8.2 Hz, 2H), 7.10-7.20 (m, 4H), 6.73-6.86 (m, 4H), 5.02-5.08 (m, 1H), 4.99 (dd, J=6.6, 5.6 Hz, 1H), 4.54-4.63 (m, 1H), 3.35-3.44 (m, 2H), 3.21-3.29 (m, 1H), 1.46-1.59 (m, 1H), 0.74 (d, J=0.6 Hz, 2H), 0.42-0.52 (m, 1H), 0.31-0.42 (m, 1H). MS (ESI) 535.2 [M+H]$^+$.

Example 71

(S)-2-((2S,3R,6S)-2,3-Bis(4-chlorophenyl)-6-(4-cyanobenzyl)-5-oxomorpholino)-2-cyclopropylacetic acid and (R)-2-((2R,3S,6R)-2,3-bis(4-chlorophenyl)-6-(4-cyanobenzyl)-5-oxomorpholino)-2-cyclopropylacetic acid or (R)-2-((2S,3R,6S)-2,3-bis(4-chlorophenyl)-6-(4-cyanobenzyl)-5-oxomorpholino)-2-cyclopropylacetic acid and (S)-2-((2R,3S,6R)-2,3-bis(4-chlorophenyl)-6-(4-cyanobenzyl)-5-oxomorpholino)-2-cyclopropylacetic acid

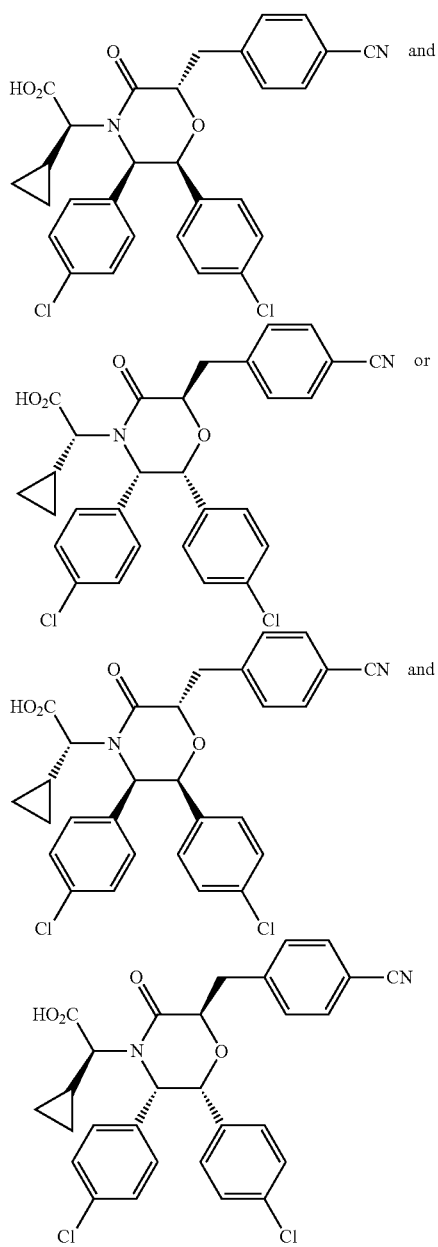

Further elution of Example 70 provided a pair of the title compounds as the second eluting set of isomers:

$^1$H NMR (400 MHz, CDCl$_3$, δ ppm): 7.52 (d, J=8.0 Hz, 2H), 7.31 (d, J=8.0 Hz, 2H), 7.18 (d, J=8.4 Hz, 2H), 7.12 (d, J=8.4 Hz, 2H), 6.78 (d, J=8.4 Hz, 2H), 6.70 (d, J=8.2 Hz, 2H), 5.10 (br s, 1H), 4.96 (dd, J=7.3, 3.6 Hz, 1H), 4.76 (br s, 1H), 4.26 (d, J=10.0 Hz, 1H), 3.30-3.51 (m, 2H), 0.77 (br s, 1H), 0.67 (br s, 1H), 0.58 (br s, 1H), −0.03 (br s, 1H), −0.18 (br s, 1H). MS (ESI) 535.2 [M+H]$^+$.

Example 72

(5R,6S)-6-(3-Chlorophenyl)-5-(4-chlorophenyl)-4-(cyclopropylmethyl)thiomorpholin-3-one

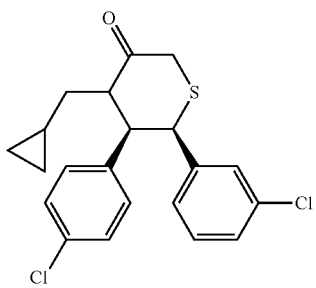 [SMILES: O=C1CS[C@@H](c2cccc(Cl)c2)[C@@H](c2ccc(Cl)cc2)C1CC1CC1]

Step A. 1-Chloro-4-(nitromethyl)benzene

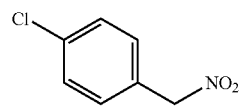 [SMILES: O=[N+]([O-])Cc1ccc(Cl)cc1]

A suspension of AgNO$_2$ (392 g) in diethyl ether (1.6 L) was cooled to 0° C., and a solution of 4-chlorobenzylbromide (395 g, 1.92 mol) in diethyl ether (1.6 L) was added dropwise over 1 hour (temperature maintained below 3° C. during addition). The reaction mixture was stirred for 16 hours at 0° C. in the dark. The mixture was filtered, the solids were washed with diethyl ether (3×), and the combined filtrates were concentrated under reduced pressure. The residue was purified by flash column chromatography on silica gel (gradient elution with 0% to 10% ethyl acetate in heptane) to give the title compound.

Step B. (1R,2R)-2-Amino-1-(3-chlorophenyl)-2-(4-chlorophenyl)ethanol hydrochloride and (1S,2S)-2-amino-1-(3-chlorophenyl)-2-(4-chlorophenyl)ethanol hydrochloride

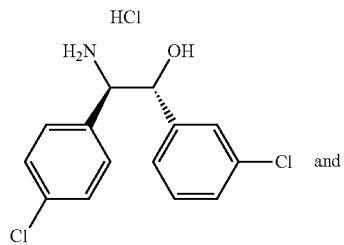

-continued

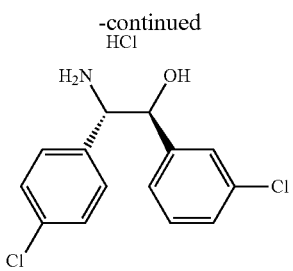

1-Chloro-4-(nitromethyl)-benzene (205 g, 1.19 mol, Example 72, step A), alumina (135 g), pyridine (96 mL, 1.19 mol) and chlorotriethylsilane (200 mL, 180 g, 1.19 mol) were added to a flask containing 3-chlorobenzaldehyde (135 mL, 168 g, 1.19 mol). The flask was covered in aluminium foil and spun for 16 hours on a rotary evaporator in the dark at room temperature. The thick paste was filtered and washed with isopropanol. The filtrate was divided into two equal batches which were processed in parallel. To each batch, hydrochloric acid (7 L, 7 mol, 1 M) was added, followed by zinc powder (800 g, 12.3 mol) in several portions. The reaction mixture was stirred for 90 minutes until the observed exothermic (to 35° C.) reaction was complete. The mixture was cooled to 0° C. and basified to pH 10 with 30% NaOH. The suspension was filtered through a pad of diatomaceous earth and washed with DCM. The aqueous layer was separated and extracted with DCM. The combined organic layers were dried over $Na_2SO_4$, filtered, and the filtrate was concentrated under reduced pressure. The residue was dissolved in MTBE (1.5 L) and cooled to 0° C. Then, HCl (375 mL, 1.5 mol, 4 N in dioxane) was added dropwise. The solid was collected by filtration and purified by crystallization from dioxane/ethanol to give the title compounds as a racemic mixture.

Step C. (1R,2R)-2-Amino-1-(3-chlorophenyl)-2-(4-chlorophenyl)ethanol and (1S,2S)-2-amino-1-(3-chlorophenyl)-2-(4-chlorophenyl)ethanol

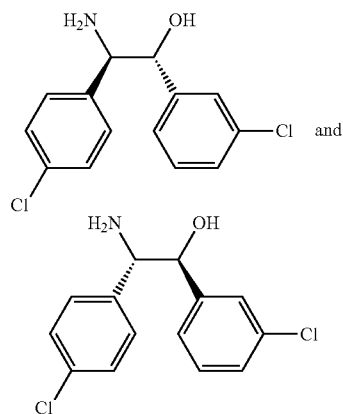

Aqueous sodium hydroxide (500 mL, 1 mol, 2 M) was added to a mixture of (1R,2R)-2-amino-1-(3-chlorophenyl)-2-(4-chlorophenyl)ethanol hydrochloride and (1S,2S)-2-amino-1-(3-chlorophenyl)-2-(4-chlorophenyl)ethanol hydrochloride (65.5 g, 0.205 mol, Example 72, Step B) in ethyl acetate (500 mL). The layers were separated, and the aqueous layer was extracted with ethyl acetate. The combined organic layers were washed with brine, dried over $Na_2SO_4$ and concentrated under a vacuum to give the racemic title compounds as a white solid.

Mass Spectrum (ESI) m/z=282.0 (M+H).

Step D. (1R,2R)-2-Amino-1-(3-chlorophenyl)-2-(4-chlorophenyl)ethanol

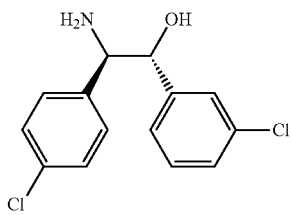 [SMILES: N[C@H](c1ccc(Cl)cc1)[C@H](O)c1cccc(Cl)c1]

A mixture of (1R,2R)-2-amino-1-(3-chlorophenyl)-2-(4-chlorophenyl)ethanol and (1S,2S)-2-amino-1-(3-chlorophenyl)-2-(4-chlorophenyl)ethanol (57 g, 0.2 mol; Example 72, Step C) was dissolved in ethanol (2.65 L) and (+)-di-p-toluoyl-D-tartaric acid (68.4 g, 0.169 mol) was added. The mixture was heated to reflux, and water (175 mL) was added until the solution became clear. The mixture was seeded with seeding crystals (e.e. 95%) and cooled to room temperature over a period of 16 hours. The mixture was filtered, and the solid was washed with ethanol and dried to give the salt, ee. 75%. This salt was recrystallized twice from 12.5:1 EtOH: water (36 mL/gram of salt) using seed crystals to initialize crystallization to provide the salt in 97.6% ee. The salt was dissolved in 1:1 ethyl acetate:aqueous NaOH (2 N). The layers were separated, and the aqueous layer was extracted with ethyl acetate. The combined organic layers were washed with brine, dried over $Na_2SO_4$, filtered, and the filtrate was concentrated under reduced pressure to give the title compound in 97.8% ee. Enantiomeric excess was determined by HPLC using an 250×46 mm Chiralpak® AD-H column (Chiral Technologies, Inc., West Chester, Pa., USA) and eluting with 5% IPA/hexanes at room temperature; $t_R$=21.7 minutes. $[\alpha]_D^{23.5}$+92.7° (c 0.385, MeOH). (1S,2S)-2-amino-1-(3-chlorophenyl)-2-(4-chlorophenyl) ethanol: room temperature; $t_R$=20.1 minutes.

Step E. (1R,2R)-1-(3-Chlorophenyl)-2-(4-chlorophenyl)-2-((cyclopropylmethyl)amino)ethanol

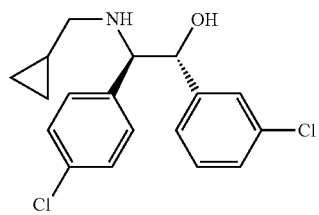 [SMILES: O[C@H](c1cccc(Cl)c1)[C@H](NCC1CC1)c1ccc(Cl)cc1]

Cyclopropanecarboxaldehyde (89 μL, 1.19 mmol) was added to a stirring solution of 335 mg (1.19 mmol) of (1R,2R)-2-amino-1-(3-chlorophenyl)-2-(4-chlorophenyl) ethanol (Example 72, Step D) in MeOH (3 mL), and the reaction was stirred at room temperature overnight under a $N_2$ atmosphere. An additional portion of sodium borohydride (79 mg, 2.078 mmol) was added and the reaction was stirred at room temperature. After 10 minutes, the reaction mixture was acidified to pH 2 with aqueous HCl (1 M) and concentrated under reduced pressure. The resulting residue was partitioned between DCM and aqueous NaHCO$_3$. The separated aqueous layer was extracted with DCM (2×) and the combined organic extracts were dried over MgSO$_4$, filtered and evaporated under reduced pressure to give the title compound.

$^1$H NMR (400 MHz, CDCl$_3$, δ ppm): 7.13-7.24 (m, 4H), 7.05-7.11 (m, 1H), 6.92-6.97 (m, 2H), 6.81 (dt, J=7.6, 1.6 Hz, 1H), 4.47 (d, J=8.6 Hz, 1H), 3.57 (d, J=8.6 Hz, 1H), 2.44 (dd, J=11.9, 6.5 Hz, 1H), 2.23 (dd, J=12.0, 7.3 Hz, 1H), −0.09-0.99 (m, 5H). MS (ESI) 336.1 [M+H]$^+$.

Step F. (4R,5R)-5-(3-Chlorophenyl)-4-(4-chlorophenyl)-3-(cyclopropylmethyl)-1,2,3-oxathiazolidine 2-oxide

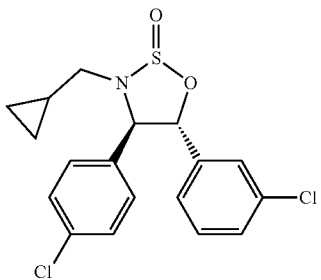 [SMILES: O=S1O[C@H](c2cccc(Cl)c2)[C@@H](c2ccc(Cl)cc2)N1CC1CC1]

Imidazole (323 mg, 4.75 mmol) and triethylamine (367 μL, 2.61 mmol) were added to a stirring solution of (1R,2R)-1-(3-chlorophenyl)-2-(4-chlorophenyl)-2-(cyclopropylmethylamino)ethanol (399 mg, 1.19 mmol, Example 72, Step E) in DCM (12 mL). The reaction was cooled to 0° C. and thionyl chloride (100 μL, 1.365 mmol) was added dropwise over 2 minutes. The reaction was stirred at 0° C. for 80 minutes and quenched with water. The separated organic layer was dried over MgSO$_4$, filtered and evaporated under a vacuum to give the title compound. The product was used immediately in the next step without further purification.

Step G. (4R,5R)-5-(3-Chlorophenyl)-4-(4-chlorophenyl)-3-(cyclopropylmethyl)-1,2,3-oxathiazolidine 2,2-dioxide

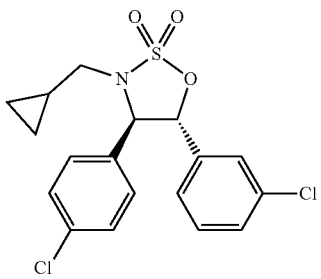 [SMILES: O=S1(=O)O[C@H](c2cccc(Cl)c2)[C@@H](c2ccc(Cl)cc2)N1CC1CC1]

Ruthenium(III) chloride hydrate (2.65 mg, 0.012 mmol), sodium periodate (302 mg, 1.412 mmol) and water (6 mL) were added to a stirring solution of (4R,5R)-5-(3-chlorophenyl)-4-(4-chlorophenyl)-3-(cyclopropylmethyl)-1,2,3-oxathiazolidine 2-oxide (450 mg, 1.177 mmol, Example 72, Step F) in acetonitrile (6 mL) at 0° C. The reaction mixture was warmed to room temperature, stirred for 3 hours, and partitioned between ethyl acetate and water. The separated aqueous layer was extracted with ethyl acetate and the combined organic extracts were washed with brine, dried over MgSO$_4$, filtered and evaporated under a vacuum. Column chromatography (12 g SiO$_2$, gradient elution of 1:0 to 2:1 hexanes:ethyl acetate) gave the title compound.

$^1$H NMR (400 MHz, CDCl$_3$, δ ppm): 7.28-7.33 (m, 3H), 7.11-7.24 (m, 4H), 6.94 (dt, J=7.7, 1.5 Hz, 1H), 5.26 (d, J=9.2 Hz, 1H), 4.44 (d, J=9.2 Hz, 1H), 2.98 (dd, J=14.1, 5.9 Hz, 1H), 2.67 (dd, J=14.1, 8.2 Hz, 1H), 0.92-1.04 (m, 1H), 0.45-0.53 (m, 1H), 0.32-0.44 (m, 1H), −0.15-0.06 (m, 2H).

Step H. Methyl 2-(((1S,2R)-1-(3-chlorophenyl)-2-(4-chlorophenyl)-2-((cyclopropylmethyl)amino)ethyl)thio)acetate

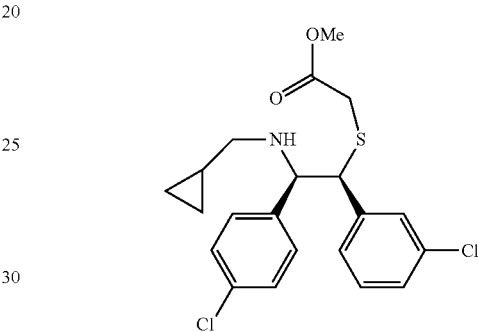

Methyl 2-mercaptoacetate (51.2 μL, 0.565 mmol) and cesium carbonate (184 mg, 0.565 mmol) were added to a stirring solution of (4R,5R)-5-(3-chlorophenyl)-4-(4-chlorophenyl)-3-(cyclopropylmethyl)-1,2,3-oxathiazolidine 2,2-dioxide (150 mg, 0.38 mmol, Example 72, Step G) in DMF (4 mL) and the reaction was stirred at room temperature overnight. The reaction mixture was partitioned between ethyl acetate and water. The separated organic layer was washed with 1 M aqueous LiCl, dried over MgSO$_4$, filtered and evaporated under reduced pressure to give the title compound. MS (ESI) 424.0 [M+H]$^+$.

Step I. (5R,6S)-6-(3-Chlorophenyl)-5-(4-chlorophenyl)-4-(cyclopropylmethyl)thiomorpholin-3-one Water (1.0 mL) and aqueous sodium hydroxide (0.121 g, 3.02 mmol, 1.0 mL water) were sequentially added to a stirring solution of methyl 2-(((1S,2R)-1-(3-chlorophenyl)-2-(4-chlorophenyl)-2-((cyclopropylmethyl)amino)ethyl)thio)acetate (0.16 g, 0.38 mmol, Example 72, Step H) in THF (2.0 mL) at room temperature. After three hours, the reaction was diluted with ethyl acetate and acidified to pH 2 with 1.0 M aqueous HCl. The separated organic layer was dried over MgSO$_4$, filtered and evaporated under a vacuum. The resulting intermediate was dissolved in DCM (35 mL) and cooled to 0° C. under a N$_2$ atmosphere. Oxalyl chloride (0.19 mL, 0.38 mmol) was added followed by DMF (2 drops) and the reaction was warmed to room temperature and stirred for 30 minutes. Additional oxalyl chloride (0.19 mL) and DMF (2 drops) were added, and the reaction was stirred at room temperature. After 2 hours the reaction mixture was partitioned between DCM (40 mL) and water (10 mL). The separated organic layer was dried over MgSO$_4$, filtered and evaporated under a vacuum. Flash column chromatography (12 g SiO$_2$, gradient elution of 1:0 to 7:3 hexanes:ethyl acetate) gave the title compound.

$^1$H NMR (500 MHz, CDCl$_3$, δ ppm): 7.21-7.25 (m, 1H), 7.14-7.18 (m, 2H), 7.07-7.13 (m, 1H), 6.86 (t, J=2.1 Hz, 1H), 6.75-6.82 (m, 2H), 6.60 (dt, J=7.8, 1.3 Hz, 1H), 4.97 (d, J=3.9 Hz, 1H), 4.65-4.73 (m, 1H), 3.86-3.95 (m, 2H), 3.44-3.55 (m, 1H), 2.36 (dd, J=14.2, 7.8 Hz, 1H), 1.20-1.35 (m, 1H), 0.48-0.56 (m, 1H), 0.36-0.45 (m, 1H), 0.11-0.20 (m, 1H), 0.00-0.09 (m, 1H). MS (ESI) 392.0 [M+H]$^+$.

Example 73

(5R,6S)-6-(3-Chlorophenyl)-5-(4-chlorophenyl)-4-(cyclopropylmethyl)-2,2-dimethylthiomorpholine-3-one 1,1-dioxide

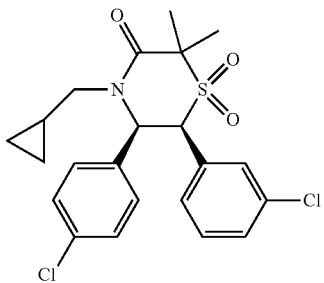 [SMILES: CC1(C)C(=O)N(CC2CC2)[C@H](c2ccc(Cl)cc2)[C@H](c2cccc(Cl)c2)S1(=O)=O]

Step A. (5R,6S)-6-(3-Chlorophenyl)-5-(4-chlorophenyl)-4-(cyclopropylmethyl)-2,2-dimethylthiomorpholine-3-one

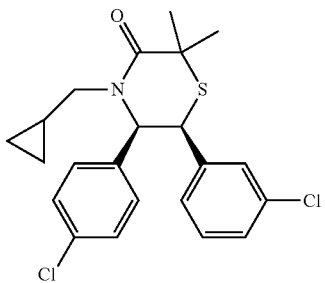 [SMILES: CC1(C)S[C@@H](c2cccc(Cl)c2)[C@@H](c2ccc(Cl)cc2)N(CC2CC2)C1=O]

Lithium bis(trimethylsilyl)amide (382 μL, 0.382 mmol, 1.0 M in THF) was added THF (0.5 mL) under a N$_2$ atmosphere, and the solution was cooled to. (5R,6S)-6-(3-Chlorophenyl)-5-(4-chlorophenyl)-4-(cyclopropylmethyl) thiomorpholin-3-one (50 mg, 0.127 mmol, Example 72, Step I) in THF (2.5 mL) was added dropwise via syringe over 5 minutes. After stirring for 15 minutes at −78° C., methyl iodide (19.92 μL, 0.319 mmol) in THF (0.3 mL) was added dropwise via syringe over 3 minutes. The reaction was stirred at −78° C. for 3 hours and at room temperature for 30 minutes. The reaction was quenched with saturated aqueous NH$_4$Cl and ethyl acetate. The separated organic layer was washed with MgSO$_4$, filtered and evaporated under a vacuum. Column chromatography (SiO$_2$, 4 g, gradient elution with 1:0 to 4:1 hexanes:ethyl acetate) gave the title compound.

$^1$H NMR (400 MHz, CDCl$_3$, δ ppm): 7.21-7.25 (m, 1H), 7.16 (d, J=8.6 Hz, 2H), 7.07-7.13 (m, 1H), 6.90 (t, J=1.9 Hz, 1H), 6.74 (d, J=8.2 Hz, 2H), 6.62 (d, J=7.6 Hz, 1H), 4.99 (d, J=4.1 Hz, 1H), 4.82 (d, J=3.9 Hz, 1H), 3.89 (dd, J=14.1, 6.1 Hz, 1H), 2.33 (dd, J=14.1, 7.4 Hz, 1H), 1.84 (s, 3H), 1.70 (s, 3H), 0.85-1.02 (m, 1H), 0.49-0.58 (m, 1H), 0.35-0.45 (m, 1H), 0.16 (dq, J=9.4, 4.8 Hz, 1H), 0.07 (td, J=9.7, 5.0 Hz, 1H). MS (ESI) 420.0 [M+H]$^+$.

Step B. (5R,6S)-6-(3-Chlorophenyl)-5-(4-chlorophenyl)-4-(cyclopropylmethyl)-2,2-dimethylthiomorpholine-3-one 1,1-dioxide Sodium periodate (8.95 mg, 0.042 mmol), ruthenium(III) chloride hydrate (0.429 mg, 1.903 μmol), and water (0.4 mL) were sequentially added to a stirring solution of (5R, 6S)-6-(3-chlorophenyl)-5-(4-chlorophenyl)-4-(cyclopropylmethyl)-2,2-dimethylthiomorpholin-3-one (8 mg, 0.019 mmol, Example 73, Step A) in acetonitrile (0.6 mL). After 1 hour at room temperature, the reaction was partitioned between ethyl acetate and water. The separated aqueous layer was extracted with ethyl acetate and the combined organics extracts were washed with water and brine, dried over MgSO$_4$, filtered and evaporated under a vacuum to give the title compound.

$^1$H NMR (400 MHz, CDCl$_3$, δ ppm): 7.34-7.40 (m, 1H), 7.14-7.23 (m, 4H), 6.97 (dt, J=7.9, 1.3 Hz, 1H), 6.70 (d, J=8.0 Hz, 2H), 5.09 (d, J=6.1 Hz, 1H), 4.93 (d, J=6.1 Hz, 1H), 4.04-4.11 (m, 1H), 2.30 (dd, J=14.3, 7.6 Hz, 1H), 1.89 (s, 3H), 1.82 (s, 3H), 0.89-0.98 (m, 1H), 0.52-0.61 (m, 1H), 0.41-0.52 (m, 1H), 0.05-0.17 (m, 2H). MS (ESI) 452.0 [M+H]$^+$.

Example 74

(5R,6S)-6-(3-Chlorophenyl)-5-(4-chlorophenyl)-4-isopropylthiomorpholin-3-one

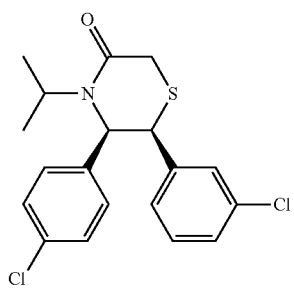 [SMILES: CC(C)N1C(=O)CS[C@@H](c2cccc(Cl)c2)[C@H]1c1ccc(Cl)cc1]

Step A. (1R,2R)-1-(3-Chlorophenyl)-2-(4-chlorophenyl)-2-(isopropylamino)ethanol

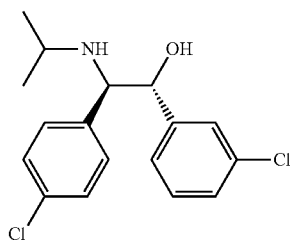 [SMILES: CC(C)N[C@H](c1ccc(Cl)cc1)[C@H](O)c1cccc(Cl)c1]

Acetone (78 µL, 1.063 mmol), acetic acid (154 µL, 2.69 mmol), and sodium cyanoborohydride (111 mg, 1.77 mmol) were sequentially added to a stirring solution of (1R,2R)-2-amino-1-(3-chlorophenyl)-2-(4-chlorophenyl)ethanol (200 mg, 0.71 mmol, Example 72, Step D) in methanol (7 mL). The reaction was heated at 65° C. for 14 hours. The reaction was then cooled to room temperature and evaporated under a vacuum. The resulting white solid was partitioned between ethyl acetate and saturated aqueous NaHCO₃. The separated aqueous layer was extracted with ethyl acetate, and the combined organic extracts were washed with brine, dried over MgSO₄ and filtered under reduced pressure to give the title compound.

¹H NMR (400 MHz, CDCl₃, δ ppm): 7.18-7.25 (m, 3H), 7.12-7.18 (m, 1H), 7.05-7.10 (m, 1H), 6.92-6.97 (m, 2H), 6.79 (dt, J=7.6, 1.5 Hz, 1H), 4.43 (d, J=8.8 Hz, 1H), 3.58 (d, J=9.0 Hz, 1H), 2.70 (dt, J=12.5, 6.2 Hz, 1H), 1.07 (d, J=6.1 Hz, 3H), 1.03 (d, J=6.5 Hz, 3H).

Step B. (4R,5R)-5-(3-Chlorophenyl)-4-(4-chlorophenyl)-3-isopropyl-1,2,3-oxathiazolidine 2-oxide

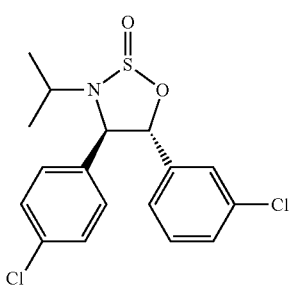 [SMILES: CC(C)N1[C@H](c2ccc(Cl)cc2)[C@@H](c2cccc(Cl)c2)OS1=O]

The title compound was prepared from (1R,2R)-1-(3-chlorophenyl)-2-(4-chlorophenyl)-2-(isopropylamino)ethanol (Example 74, Step A) by a procedure similar to the one described in Example 72, Step F. MS (ESI) 392.0 [M+Na]⁺.

Step C. (4R,5R)-5-(3-Chlorophenyl)-4-(4-chlorophenyl)-3-isopropyl-1,2,3-oxathiazolidine 2,2-dioxide

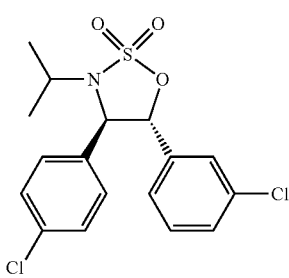 [SMILES: CC(C)N1[C@H](c2ccc(Cl)cc2)[C@@H](c2cccc(Cl)c2)OS1(=O)=O]

The title compound was prepared from (4R,5R)-5-(3-chlorophenyl)-4-(4-chlorophenyl)-3-isopropyl-1,2,3-oxathiazolidine 2-oxide (Example 74, Step B) by a procedure similar to the one described in Example 72, Step G.

¹H NMR (400 MHz, CDCl₃, δ ppm): 7.37-7.48 (m, 3H), 7.21-7.34 (m, 4H), 7.03 (dt, J=7.6, 1.6 Hz, 1H), 5.34 (d, J=8.8 Hz, 1H), 4.60 (d, J=9.0 Hz, 1H), 3.56 (quin, J=6.8 Hz, 1H), 1.45 (d, J=6.8 Hz, 3H), 1.17 (d, J=6.7 Hz, 3H).

Step D. Methyl 2-(((1S,2R)-1-(3-chlorophenyl)-2-(4-chlorophenyl)-2-(isopropylamino)ethyl)thio)acetate

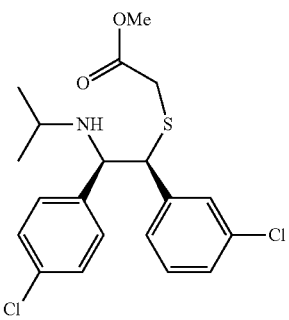 [SMILES: COC(=O)CS[C@@H](c1cccc(Cl)c1)[C@H](NC(C)C)c1ccc(Cl)cc1]

The title compound was prepared from (4R,5R)-5-(3-chlorophenyl)-4-(4-chlorophenyl)-3-isopropyl-1,2,3-oxathiazolidine 2,2-dioxide (Example 74, Step C) by a procedure similar to the one described in Example 72, Step H. MS (ESI) 412.0 [M+H]⁺.

Step E. (5R,6S)-6-(3-Chlorophenyl)-5-(4-chlorophenyl)-4-isopropylthiomorpholin-3-one

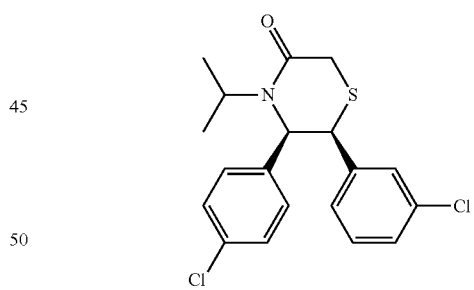

The title compound was prepared from methyl 2-(((1S,2R)-1-(3-chlorophenyl)-2-(4-chlorophenyl)-2-(isopropylamino)ethyl)thio)acetate (Example 74, Step D), by a procedure similar to the one described in Example 72, Step I.

¹H NMR (400 MHz, CDCl₃, δ ppm): 7.22-7.26 (m, 1H), 7.15-7.19 (m, 2H), 7.10-7.15 (m, 1H), 6.86 (t, J=1.9 Hz, 1H), 6.75-6.82 (m, 2H), 6.62 (d, J=7.8 Hz, 1H), 4.76 (d, J=3.5 Hz, 1H), 4.55 (d, J=3.5 Hz, 1H), 4.27-4.40 (m, 1H), 3.88 (d, J=17.8 Hz, 1H), 3.55 (d, J=17.6 Hz, 1H), 1.24 (d, J=6.7 Hz, 3H), 0.92 (d, J=7.0 Hz, 3H). MS (ESI) 380.0 [M+H]⁺.

Example 75

2-((2R,5R,6S)-6-(3-Chlorophenyl)-5-(4-chlorophenyl)-4-isopropyl-1,1-dioxido-3-oxothiomorpholin-2-yl)acetic acid and 2-((2S,5R,6S)-6-(3-chlorophenyl)-5-(4-chlorophenyl)-4-isopropyl-1,1-dioxido-3-oxothiomorpholin-2-yl)acetic acid

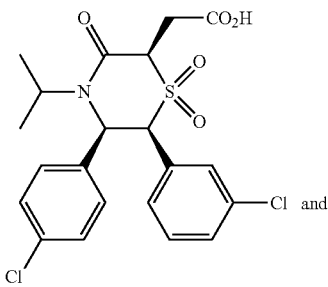

Step A. (2S,5R,6S)-2-Allyl-6-(3-chlorophenyl)-5-(4-chlorophenyl)-4-isopropylthiomorpholin-3-one

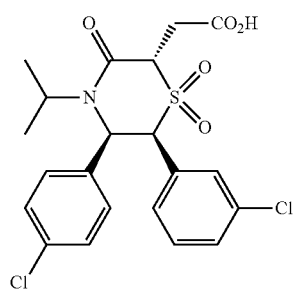

To a stirring solution of lithium bis(trimethylsilyl)amide (1 M solution in THF, 526 μL, 0.526 mmol) in THF (1.0 mL) at −78° C. under a N$_2$ atmosphere was added dropwise via syringe over 3 minutes a solution of 200 mg (0.526 mmol) of (5R,6S)-6-(3-chlorophenyl)-5-(4-chlorophenyl)-4-isopropylthiomorpholin-3-one (Example 74, Step E) in THF (1.5 mL). The reaction was stirred at this temperature for 10 minutes and then a solution of allyl bromide (45.5 μL, 0.526 mmol) in THF (0.5 mL) was added dropwise via syringe over 1 minute. The reaction was stirred at −78° C. for 40 minutes and then it was quenched by the addition of NH$_4$Cl (saturated aqueous solution). The mixture was allowed to warm to room temperature and then it was partitioned between ethyl acetate and water. The separated organic layer was dried over MgSO$_4$, filtered and evaporated under a vacuum. Column chromatography (12 g SiO$_2$, hexanes:ethyl acetate, 1:0 t o 8:2) gave the title compound.

$^1$H NMR (400 MHz, CDCl$_3$, δ ppm): 7.21-7.27 (m, 1H), 7.10-7.19 (m, 3H), 6.89-6.93 (m, 1H), 6.73-6.79 (m, 2H), 6.65 (dt, J=7.8, 1.5 Hz, 1H), 5.94 (ddt, J=17.1, 10.1, 7.0, 7.0 Hz, 1H), 5.10-5.27 (m, 2H), 4.77 (d, J=3.5 Hz, 1H), 4.59-4.67 (m, 1H), 4.43 (dt, J=13.7, 6.8 Hz, 1H), 3.71 (dd, J=8.0, 4.5 Hz, 1H), 2.79-3.00 (m, 2H), 1.19-1.34 (m, 3H), 0.85-0.96 (m, 3H). MS (ESI) 420.0 [M+H]$^+$.

Step B. 2-((2R,5R,6S)-6-(3-Chlorophenyl)-5-(4-chlorophenyl)-4-isopropyl-1,1-dioxido-3-oxothiomorpholin-2-yl)acetic acid and 2-((2S,5R,6S)-6-(3-Chlorophenyl)-5-(4-chlorophenyl)-4-isopropyl-1,1-dioxido-3-oxothiomorpholin-2-yl)acetic acid To a stirring solution of 70 mg (0.167 mmol) of (2S,5R,6S)-2-allyl-6-(3-chlorophenyl)-5-(4-chlorophenyl)-4-isopropylthiomorpholin-3-one (Example 75, Step B) in CCl$_4$:acetonitrile:water (0.6 mL:0.6 mL:1 mL) was added sodium periodate (178 mg, 0.833 mmol) and ruthenium(III) chloride hydrate (3.75 mg, 0.017 mmol). The reaction was stirred at room temperature for 2 hours. After this time the reaction was partitioned between ethyl acetate and water. The separated organic layer was dried over MgSO$_4$, filtered and evaporated under a vacuum. Purification by reverse phase preparative HPLC (Gemini™ Prep C18 5 μm column, Phenomenex, Torrance, Calif.; eluent 20 to 70% acetonitrile in water+0.1% TFA, gradient elution) provided the title compound as a 1:1 mixture of stereoisomers.

$^1$H NMR (500 MHz, CDCl$_3$, δ ppm): 7.35-7.44 (m, 1H), 7.24-7.31 (m, 2H), 7.14-7.22 (m, 2H), 7.02-7.09 (m, 1H), 6.78-6.91 (m, 2H), 4.75-5.04 (m, 2H), 4.45-4.60 (m, 1H), 3.82-4.38 (m, 1H), 3.31-3.53 (m, 1H), 3.17-3.25 (m, 1H), 0.97-1.32 (m, 6H). MS (ESI) 470.0 [M+H]$^+$.

Example 76

(3R,4S,8R)-4-(3-Chlorophenyl)-3-(4-chlorophenyl)-2-isopropyltetrahydropyrrolo[1,2-a]pyrazine-1,6(2H,7H)-dione

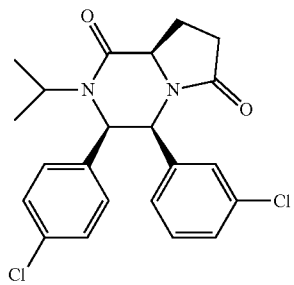 [SMILES: CC(C)N1C(=O)[C@H]2CCC(=O)N2[C@@H](c2cccc(Cl)c2)[C@H]1c1ccc(Cl)cc1]

Step A. (R)-Ethyl 1-((1S,2R)-1-(3-chlorophenyl)-2-(4-chlorophenyl)-2-(isopropylamino)ethyl)-5-oxopyrrolidine-2-carboxylate

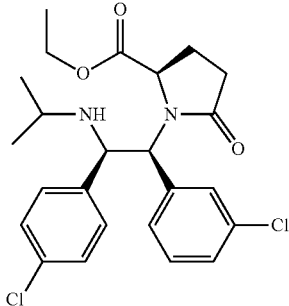 [SMILES: CCOC(=O)[C@H]1CCC(=O)N1[C@@H](c1cccc(Cl)c1)[C@H](NC(C)C)c1ccc(Cl)cc1]

Sodium hydride (36.4 mg, 0.835 mmol, 60% dispersion in oil) was added to a stirring solution of (4R,5R)-5-(3-chlorophenyl)-4-(4-chlorophenyl)-3-isopropyl-1,2,3-oxathiazolidine 2,2-dioxide (215 mg, 0.557 mmol, Example 74, Step C) and (R)-ethyl 5-oxopyrrolidine-2-carboxylate (87 mg, 0.557 mmol) in DMF (1.0 mL) under a $N_2$ atmosphere. After heating at 80° C. in an oil bath for 2 hours, the reaction was cooled to room temperature, treated with an additional portion of NaH (36.4 mg, 0.835 mmol, 60% dispersion in oil) and heated at 80° C. for 1 hour. The reaction was cooled and partitioned between ethyl acetate and 1.0 M LiCl. The separated organic layer was washed with 1.0 M aqueous LiCl and the combined organic extracts were dried over $MgSO_4$, filtered and evaporated under a vacuum to give the title compound. MS (ESI) 463.0 [M+H]$^+$.

Step B. (R)-1-((1S,2R)-1-(3-Chlorophenyl)-2-(4-chlorophenyl)-2-(isopropylamino)ethyl)-5-oxopyrrolidine-2-carboxylic acid

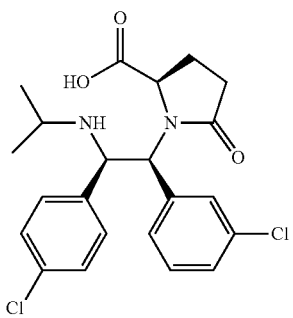 [SMILES: CC(C)N[C@H](c1ccc(Cl)cc1)[C@H](c1cccc(Cl)c1)N1C(=O)CC[C@@H]1C(=O)O]

Sodium hydroxide (216 mg, 5.39 mmol) in water (1.0 mL) was added to a stirring solution of (R)-ethyl 1-((1S,2R)-1-(3-chlorophenyl)-2-(4-chlorophenyl)-2-(isopropylamino)ethyl)-5-oxopyrrolidine-2-carboxylate (250 mg, 0.54 mmol, Example 76, Step A) in THF:water (1.0 mL:0.5 mL) at room temperature The reaction was stirred at room temperature for 1 hour then heated at reflux for 5 hours. The reaction was cooled to room temperature and partitioned between ethyl acetate and water. The separated aqueous layer was acidified to pH 2 with 1.0 M HCl and extracted with DCM (2×). The separated organic layer was dried over $MgSO_4$, filtered and evaporated under a vacuum to give the title compound. MS (ESI) 435.0 [M+H]$^+$.

Step C. (3R,4S,8R)-4-(3-Chlorophenyl)-3-(4-chlorophenyl)-2-isopropyltetrahydropyrrolo[1,2-a]pyrazine-1,6(2H,7H)-dione

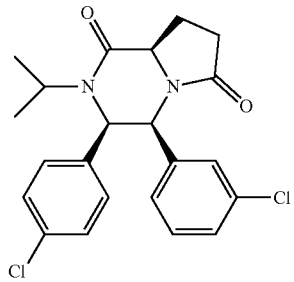 [SMILES: CC(C)N1C(=O)[C@H]2CCC(=O)N2[C@@H](c2cccc(Cl)c2)[C@H]1c1ccc(Cl)cc1]

Oxalyl chloride (0.053 mL, 0.107 mmol) and DMF (3 drops) were added to a stirring solution of (R)-1-((1S,2R)-1-(3-chlorophenyl)-2-(4-chlorophenyl)-2-(isopropylamino)ethyl)-5-oxopyrrolidine-2-carboxylic acid (31 mg, 0.071 mmol, Example 76, Step B) in DCM (7 mL) under a $N_2$ atmosphere. After stirring for 1 hour at room temperature, the reaction was partitioned between DCM and $NaHCO_3$. The separated organic layer was dried over $MgSO_4$, filtered and evaporated under a vacuum. Purification by reverse phase preparative HPLC (Gemini™ Prep C18 5 μm column, Phenomenex, Torrance, Calif.; gradient elution with 20% to 75% acetonitrile in water, both eluents containing 0.1% TFA) provided the title compound.

$^1$H NMR (400 MHz, CDCl$_3$, δ ppm): 7.21-7.27 (m, 3H), 7.04-7.12 (m, 1H), 6.80 (s, 1H), 6.65 (t, J=5.9 Hz, 3H), 4.78 (br s, 1H), 4.64 (br s, 1H), 4.35 (dd, J=10.1, 6.9 Hz, 1H), 3.93 (br s, 1H), 2.25-2.60 (m, 4H), 1.22-1.40 (d, J=6.5 Hz, 3H), 0.98 (d, J=6.5 Hz, 3H). MS (ESI) 417.1 [M+H]$^+$.

Example 77

(3R,4S,8S)-4-(3-Chlorophenyl)-3-(4-chlorophenyl)-2-isopropyltetrahydropyrrolo[1,2-a]pyrazine-1,6(2H,7H)-dione

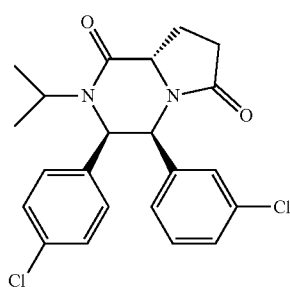 [SMILES: CC(C)N1C(=O)[C@@H]2CCC(=O)N2[C@@H](c2cccc(Cl)c2)[C@H]1c1ccc(Cl)cc1]

Step A. (S)-Methyl 1-((1S,2R)-1-(3-chlorophenyl)-2-(4-chlorophenyl)-2-(isopropylamino)ethyl)-5-oxopyrrolidine-2-carboxylate

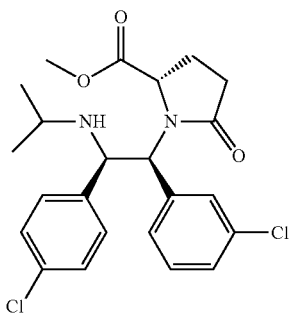 [SMILES: COC(=O)[C@@H]1CCC(=O)N1[C@@H](c1cccc(Cl)c1)[C@H](NC(C)C)c1ccc(Cl)cc1]

The title compound was prepared from (4R,5R)-5-(3-chlorophenyl)-4-(4-chlorophenyl)-3-isopropyl-1,2,3-oxathiazolidine 2,2-dioxide (Experiment 74, Step C) and (S)-methyl 5-oxopyrrolidine-2-carboxylate by a procedure similar to the one described in Example 76, Step A. MS (ESI) 449.0 [M+H]+.

Step B. (S)-1-((1S,2R)-1-(3-Chlorophenyl)-2-(4-chlorophenyl)-2-(isopropylamino)ethyl)-5-oxopyrrolidine-2-carboxylic acid

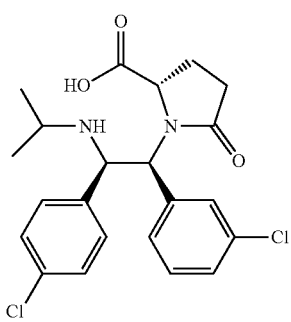 [SMILES: CC(C)N[C@H](c1ccc(Cl)cc1)[C@H](c1cccc(Cl)c1)N1C(=O)CC[C@H]1C(=O)O]

The title compound was prepared from (S)-methyl 1-((1S,2R)-1-(3-chlorophenyl)-2-(4-chlorophenyl)-2-(isopropylamino)ethyl)-5-oxopyrrolidine-2-carboxylate (Example 77, Step A), by a procedure similar to the one described in Example 76, Step B. MS (ESI) 435.1 [M+H]+.

Step C. (3R,4S,8S)-4-(3-Chlorophenyl)-3-(4-chlorophenyl)-2-isopropyltetrahydropyrrolo[1,2-a]pyrazine-1,6(2H,7H)-dione

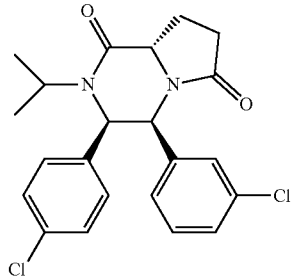 [SMILES: CC(C)N1C(=O)[C@@H]2CCC(=O)N2[C@@H](c2cccc(Cl)c2)[C@H]1c1ccc(Cl)cc1]

The title compound was prepared from (S)-1-((1S,2R)-1-(3-chlorophenyl)-2-(4-chlorophenyl)-2-(isopropylamino)ethyl)-5-oxopyrrolidine-2-carboxylic acid (Example 77, Step B) by a procedure similar to the one described in Example 76, Step C. Purification by reverse phase preparative HPLC (Gemini™ Prep C18 5 µm column, Phenomenex, Torrance, Calif.; gradient elution with 25% to 70% acetonitrile in water, both eluents containing 0.1% TFA) provided the title compound.

$^1$H NMR (400 MHz, CDCl$_3$, δ ppm): 7.23-7.28 (m, 1H), 7.15-7.22 (m, 1H), 7.07 (d, J=8.4 Hz, 2H), 6.97 (br s, 1H), 6.87 (d, J=7.4 Hz, 1H), 6.50 (d, J=8.4 Hz, 2H), 5.21 (d, J=6.5 Hz, 1H), 4.84-5.03 (m, 2H), 4.52-4.70 (m, 1H), 2.69-2.83 (m, 1H), 2.27-2.54 (m, 3H), 1.21-1.35 (d, J=6.8 Hz, 3H), 0.88 (d, J=6.8 Hz, 3H). MS (ESI) 417.1 [M+H]+.

Example 78

2-((2S,5R,6S)-6-(3-Chlorophenyl)-5-(4-chlorophenyl)-4-((S)-1-hydroxybutan-2-yl)-3-oxomorpholin-2-yl)acetic acid or 2-((2R,5R,6S)-6-(3-chlorophenyl)-5-(4-chlorophenyl)-4-((S)-1-hydroxybutan-2-yl)-3-oxomorpholin-2-yl)acetic acid

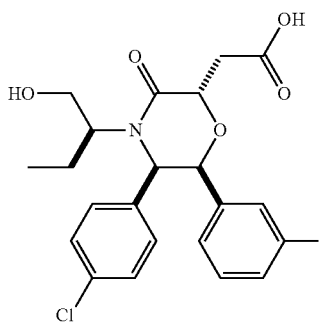

-continued

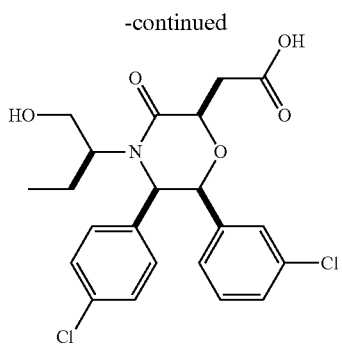

Step A. tert-Butyl ((1R,2S)-2-(3-chlorophenyl)-1-(4-chlorophenyl)-2-hydroxyethyl)carbamate

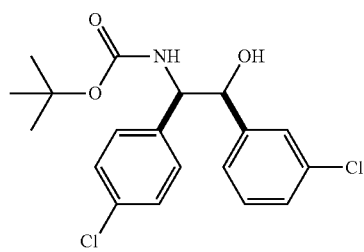 [SMILES: CC(C)(C)OC(=O)N[C@H](c1ccc(Cl)cc1)[C@@H](O)c1cccc(Cl)c1]

tert-Butyl ((1R,2S)-2-(3-chlorophenyl)-1-(4-chlorophenyl)-2-hydroxyethyl)carbamate and tert-butyl ((1S,2R)-2-(3-chlorophenyl)-1-(4-chlorophenyl)-2-hydroxyethyl)carbamate (Example 11, Step B) were separated by chiral SFC (150×50 mm Chiralpak® AD column (Chiral Technologies, Inc., West Chester, Pa., USA) with 50 g/min MeOH+20 mM NH$_3$+125 g/min CO$_2$ on a Thar 350 SFC (Thar Technologies, Inc., Pittsburgh, Pa.)) to give the title compound as the second (slower) eluting isomer.

Step B. (1S,2R)-2-Amino-1-(3-chlorophenyl)-2-(4-chlorophenyl)ethanol 2,2,2-trifluoroacetate

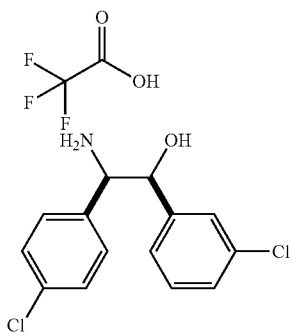

Trifluoroacetic acid (576 μL, 7.48 mmol) was added to a solution of tert-butyl ((1R,2S)-2-(3-chlorophenyl)-1-(4-chlorophenyl)-2-hydroxyethyl)carbamate (286 mg, 0.748 mmol, Example 78, Step A) in DCM (2.5 mL) at room temperature. The mixture was stirred at room temperature for 1 hour. The mixture was concentrated under a vacuum to give the title compound.

Step C. tert-Butyl 2-((2R,5R,6S)-6-(3-chlorophenyl)-5-(4-chlorophenyl)-3-oxomorpholin-2-yl)acetate and tert-butyl 2-((2S,5R,6S)-6-(3-chlorophenyl)-5-(4-chlorophenyl)-3-oxomorpholin-2-yl) acetate

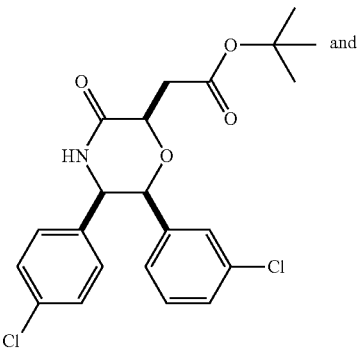

and

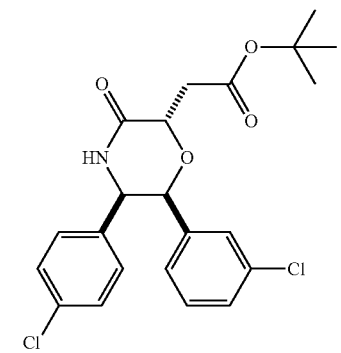

(E)-4-(tert-Butoxy)-4-oxobut-2-enoic acid (148 mg, 0.859 mmol; AMRI, Albany, N.Y.), N-ethyl-N-isopropylpropan-2-amine (390 μL, 2.241 mmol) and HATU (327 mg, 0.859 mmol) were added to a solution of (1S,2R)-2-amino-1-(3-chlorophenyl)-2-(4-chlorophenyl)ethanol 2,2,2-trifluoroacetate (296 mg, 0.747 mmol, Example 78, Step B) in DMF (7.5 mL) at room temperature. After 8 hours, the mixture was diluted with ethyl acetate and washed with 1 M LiCl, 1 M HCl, saturated NaHCO$_3$, and brine. The organic layer was dried over Na$_2$SO$_4$, filtered and the filtrate was concentrated under a vacuum. The residue was dissolved in THF (7.5 mL) and sodium hydride (44.8 mg, 1.121 mmol, 60% dispersion in mineral oil) was added. The mixture turned yellowish orange and gas evolution was observed. The mixture was stirred at room temperature for 2 hours and became cloudy. The reaction was quenched with saturated NH$_4$Cl and extracted with ethyl acetate. The organic layer was dried over Na$_2$SO$_4$, filtered and the filtrate was concentrated under a vacuum to give the title compounds as a mixture of diastereomers.

Step D. (R)-1-((3,4-Dimethoxybenzyl)oxy)butan-2-ol

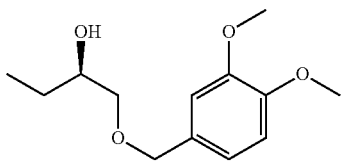 [SMILES: CC[C@@H](O)COCc1ccc(OC)c(OC)c1]

A solution of 3,4-dimethoxybenzyl alcohol (29.4 mL, 202 mmol) in DMF (100 mL) was added dropwise over 30 minutes to a suspension of sodium hydride (8.91 g, 223 mmol, 60% dispersion in mineral oil) in DMF (300 mL) at 60° C. The mixture was stirred at 60° C. for 0.5 hours until gas evolution ceased. The mixture was cooled to 45° C., and (R)-2-ethyloxirane (17.61 mL, 202 mmol) was added dropwise. After stirring at 45° C. overnight, the mixture was cooled to room temperature, diluted with saturated aqueous NaHCO$_3$ (300 mL) and extracted with diethyl ether (3×300 mL). The combined organic extracts were washed with water (3×), dried over MgSO$_4$, filtered, and the filtrate was concentrated under a vacuum. The residue was divided into 3 parts and purified by flash chromatography on silica gel (330 g column; gradient elution with 10% to 40% acetone in hexanes) to give the title compound as an off-white oil.

Step E. (R)-1-((3,4-Dimethoxybenzyl)oxy)butan-2-yl 4-bromobenzenesulfonate

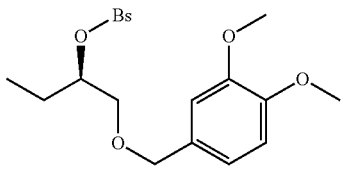

4-Bromobenzene-1-sulfonyl chloride (20.74 g, 81 mmol) was added to a solution of DMAP (14.54 g, 119 mmol) and (R)-1-((3,4-dimethoxybenzyl)oxy)butan-2-ol (13.0 g, 54.1 mmol, Example 78, Step D) in CH$_2$Cl$_2$ (180 mL). The mixture was stirred at room temperature overnight. The mixture was partitioned between ethyl acetate (50 mL) and saturated NaHCO$_3$ (100 mL). The layers were separated and the aqueous layer was extracted with ethyl acetate. The combined organic layers were washed with 0.1 M HCl (2×), brine, dried over MgSO$_4$, filtered and the filtrate was concentrated under a vacuum. The residue was divided into 2 parts and purified by flash chromatography on silica gel (330 g column; gradient elution of 10% to 30% acetone in hexanes) to give the title compound.

Step F. tert-Butyl 2-((2R,5R,6S)-6-(3-chlorophenyl)-5-(4-chlorophenyl)-4-((S)-1-((3,4-dimethoxybenzyl)oxy)butan-2-yl)-3-oxomorpholin-2-yl)acetate and tert-butyl 2-((2S,5R,6S)-6-(3-chlorophenyl)-5-(4-chlorophenyl)-4-((S)-1-((3,4-dimethoxybenzyl)oxy)butan-2-yl)-3-oxomorpholin-2-yl)acetate

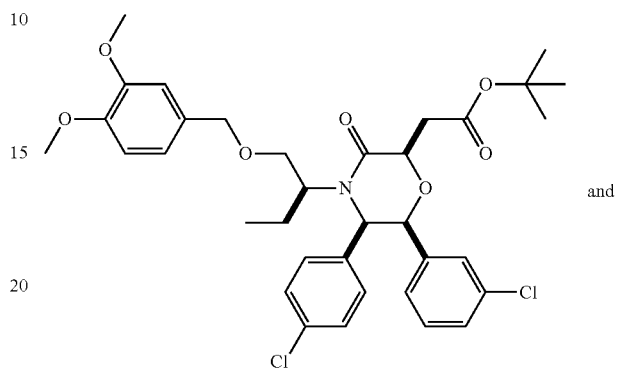

Sodium tert-butoxide (30.3 mg, 0.315 mmol) was added to a solution of tert-butyl 2-((2R,5R,6S)-6-(3-chlorophenyl)-5-(4-chlorophenyl)-3-oxomorpholin-2-yl)acetate and tert-butyl 2-((2S,5R,6S)-6-(3-chlorophenyl)-5-(4-chlorophenyl)-3-oxomorpholin-2-yl)acetate (125 mg, 0.286 mmol, Example 78, Step C) and (R)-1-((3,4-dimethoxybenzyl)oxy)butan-2-yl 4-bromobenzenesulfonate (145 mg, 0.315 mmol, Example 78, Step E) in dioxane (716 µL) at room temperature. The light orange slurry was stirred at 85° C. overnight, then cooled to room temperature and quenched with water. The mixture was extracted with ethyl acetate (3×). The combined organic layers were dried over Na$_2$SO$_4$, filtered and the filtrate was concentrated under a vacuum. The residue was purified by flash chromatography on silica gel (12 g column; gradient elution with 0% to 50% ethyl acetate in hexanes) to give the title compounds as a mixture of diastereomers.

Step G. tert-Butyl 2-((2S,5R,6S)-6-(3-chlorophenyl)-5-(4-chlorophenyl)-4-((S)-1-hydroxybutan-2-yl)-3-oxomorpholin-2-yl)acetate or tert-butyl 2-((2R,5R,6S)-6-(3-chlorophenyl)-5-(4-chlorophenyl)-4-((S)-1-hydroxybutan-2-yl)-3-oxomorpholin-2-yl)acetate

Step H. 2-((2S,5R,6S)-6-(3-Chlorophenyl)-5-(4-chlorophenyl)-4-((S)-1-hydroxybutan-2-yl)-3-oxomorpholin-2-yl)acetic acid or 2-((2R,5R,6S)-6-(3-chlorophenyl)-5-(4-chlorophenyl)-4-((S)-1-hydroxybutan-2-yl)-3-oxomorpholin-2-yl)acetic acid

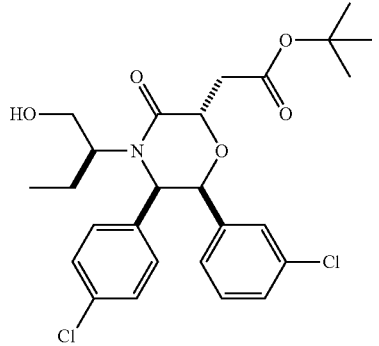

or

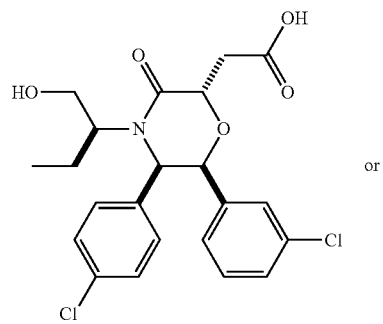

or

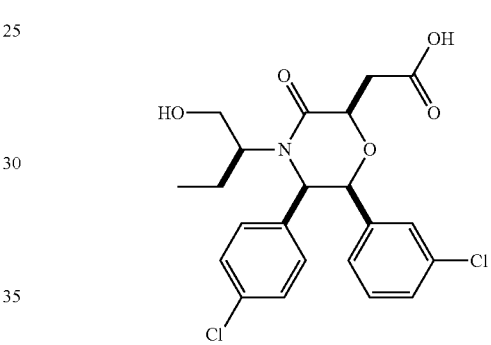

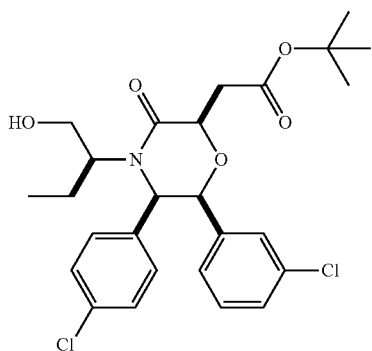

2,3-Dichloro-5,6-dicyano-1,4-benzoquinone (39.7 mg, 0.175 mmol) was added to a 0° C. solution of tert-butyl 2-((2S,5R,6S)-6-(3-chlorophenyl)-5-(4-chlorophenyl)-4-((S)-1-((3,4-dimethoxybenzyl)oxy)butan-2-yl)-3-oxomorpholin-2-yl)acetate and tert-butyl 2-((2S,5R,6S)-6-(3-chlorophenyl)-5-(4-chlorophenyl)-4-((S)-1-((3,4-dimethoxybenzyl)oxy)butan-2-yl)-3-oxomorpholin-2-yl)acetate (96 mg, 0.146 mmol, Example 78, Step F) in DCM (1385 µL) and water (72.9 µL). The dark green mixture was stirred at 0° C. for 2 hours, quenched with saturated NaHCO$_3$ solution, and extracted with DCM (3×). The combined organic layers were dried over Na$_2$SO$_4$, filtered and the filtrate was concentrated under a vacuum. The residue was purified by flash chromatography on silica gel (4 g column; gradient elution with 70% to 90% MTBE in hexanes) to give one of the title compounds as the first (faster) eluting isomer.

Trifluoroacetic acid (15 µL, 0.197 mmol) was added to a solution of tert-butyl 2-((2S,5R,6S)-6-(3-chlorophenyl)-5-(4-chlorophenyl)-4-((S)-1-hydroxybutan-2-yl)-3-oxomorpholin-2-yl)acetate or tert-butyl 2-((2R,5R,6S)-6-(3-chlorophenyl)-5-(4-chlorophenyl)-4-((S)-1-hydroxybutan-2-yl)-3-oxomorpholin-2-yl)acetate (10 mg, 0.020 mmol, Example 78, Step G) in DCM (197 µL) at room temperature. After stirring at room temperature for 4.5 hours, the mixture was concentrated, and the residue was dissolved in ethyl acetate (172 µL) and water (35 µL). Sodium bicarbonate (12 mg, 0.103 mmol) was added and the mixture was heated at 70° C. for 30 minutes. The mixture was cooled to room temperature and acetic acid (12 µL, 0.207 mmol) was slowly added. The mixture was partitioned between DCM and brine, and the aqueous layer was back extracted with DCM and ethyl acetate. The combined organic layers were dried over Na$_2$SO$_4$, filtered and the filtrate was concentrated under a vacuum. The residue was purified by reverse phase preparative HPLC (Gemini™ Prep C18 5 µm column (Phenomenex, Torrance, Calif.), gradient elution with 0% to 100% acetonitrile in water, both eluents containing 0.1% TFA, 20 minutes) to give the title compound.

$^1$H NMR (400 MHz, CDCl$_3$, δ ppm): 7.13-7.22 (m, 2H), 6.89-7.13 (m, 4H), 6.76-6.87 (m, 2H), 5.41 (dd, J=2.6, 0.5 Hz, 1H), 5.20 (t, J=5.7 Hz, 1H), 4.48 (d, J=3.1 Hz, 1H), 3.70-3.82 (m, 1H), 3.13-3.18 (m, 2H), 1.79-1.94 (m, 1H), 1.48-1.60 (m, 1H), 0.95 (d, J=6.7 Hz, 2H), 0.75 (t, J=7.5 Hz, 3H). Spectrum (ESI) m/z=452 [M+1].

Example 79

2-((2R,5R,6S)-6-(3-Chlorophenyl)-5-(4-chlorophenyl)-4-((S)-1-hydroxybutan-2-yl)-3-oxomorpholin-2-yl)acetic acid or 2-((2S,5R,6S)-6-(3-chlorophenyl)-5-(4-chlorophenyl)-4-((S)-1-hydroxybutan-2-yl)-3-oxomorpholin-2-yl)acetic acid

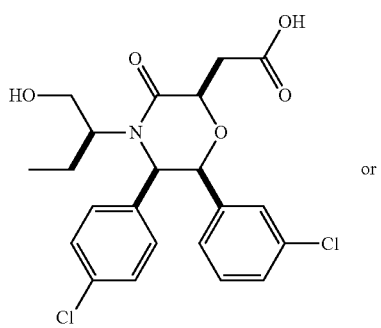

or

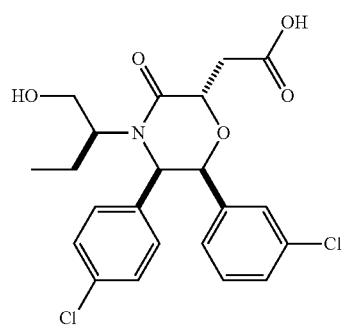

Step A. tert-Butyl 2-((2R,5R,6S)-6-(3-chlorophenyl)-5-(4-chlorophenyl)-4-((S)-1-hydroxybutan-2-yl)-3-oxomorpholin-2-yl)acetate or tert-butyl 2-((2S,5R,6S)-6-(3-chlorophenyl)-5-(4-chlorophenyl)-4-((S)-1-hydroxybutan-2-yl)-3-oxomorpholin-2-yl)acetate

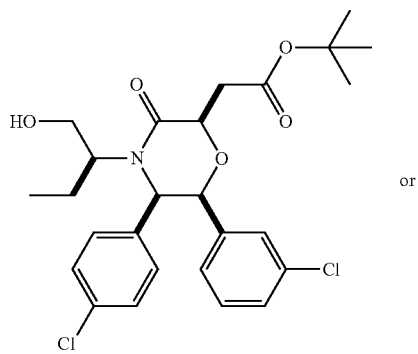

or

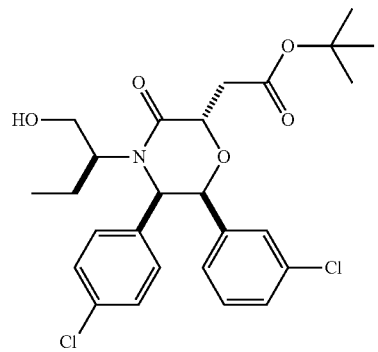

The title compound was isolated in Step G, Example 78 as the second (slower) eluting isomer.

Step B. 2-((2R,5R,6S)-6-(3-Chlorophenyl)-5-(4-chlorophenyl)-4-((S)-1-hydroxybutan-2-yl)-3-oxomorpholin-2-yl)acetic acid or 2-((2S,5R,6S)-6-(3-chlorophenyl)-5-(4-chlorophenyl)-4-((S)-1-hydroxybutan-2-yl)-3-oxomorpholin-2-yl)acetic acid The title compound was obtained by a procedure analogous to the one described in Example 78, Step H using tert-butyl 2-((2R,5R,6S)-6-(3-chlorophenyl)-5-(4-chlorophenyl)-4-((S)-1-hydroxybutan-2-yl)-3-oxomorpholin-2-yl)acetate or tert-butyl 2-((2S,5R,6S)-6-(3-chlorophenyl)-5-(4-chlorophenyl)-4-((S)-1-hydroxybutan-2-yl)-3-oxomorpholin-2-yl)acetate (Example 79, Step A) as the starting material.

$^1$H NMR (400 MHz, CD$_3$CN, δ ppm): 7.02-7.18 (m, 6H), 6.87-6.97 (m, 2H), 5.27-5.29 (m, 1H), 4.85-4.92 (m, 1H), 4.59 (d, J=3.5 Hz, 1H), 3.19-3.29 (m, 1H), 3.01-3.11 (m, 1H), 2.89-2.99 (m, 1H), 1.48-1.68 (m, 2H), 1.23-1.30 (m, 3H), 0.72 (t, J=7.6 Hz, 3H). Spectrum (ESI) m/z=452 [M+1].

Example 80

(2S,5R,6S)-5,6-Bis(4-chlorophenyl)-2-(4-fluorobenzyl)morpholin-3-one

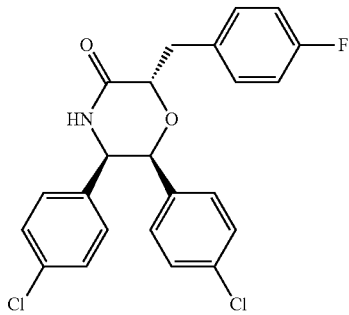 [SMILES: O=C1N[C@H](c2ccc(Cl)cc2)[C@H](c2ccc(Cl)cc2)O[C@H]1Cc1ccc(F)cc1]

241

Step A. (5R,6S)-5,6-Bis(4-chlorophenyl)-4-(4-methoxybenzyl)morpholin-3-one and (5S,6R)-5,6-Bis(4-chlorophenyl)-4-(4-methoxybenzyl)morpholin-3-one

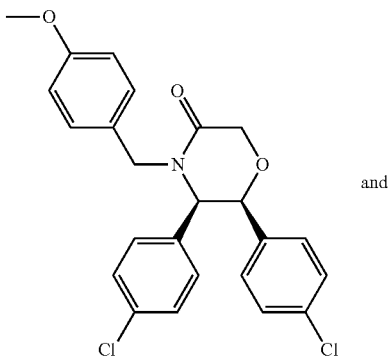

and

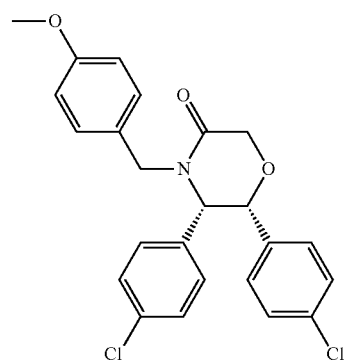

Sodium hydride (0.358 g, 14.90 mmol, 60% dispersion in mineral oil) was added to a solution of (5R,6S)-5,6-bis(4-chlorophenyl)morpholin-3-one and (5S,6R)-5,6-bis(4-chlorophenyl)morpholin-3-one (2.000 g, 6.21 mmol, Example 4, Step F) in DMF (24.83 mL, 12.42 mmol). After stirring at room temperature for 20 minutes, 1-(bromomethyl)-4-methoxybenzene (2.147 mL, 14.90 mmol) was added dropwise. The mixture was stirred at room temperature for 2 days. The mixture was diluted with saturated NaHCO$_3$ and ethyl acetate and the layers were separated. The organic layer was washed with saturated NaHCO$_3$ (2×). The combined aqueous layers were back extracted with ethyl acetate. The combined organic layers were washed with brine, dried over Na$_2$SO$_4$, filtered and the filtrate was concentrated under a vacuum. The residue was purified by flash chromatography on silica gel (40 g column; gradient elution with 0% to 30% ethyl acetate in hexanes) to give the title compounds as a racemic mixture.

242

Step B. (2S,5R,6S)-5,6-Bis(4-chlorophenyl)-2-(4-fluorobenzyl)-4-(4-methoxybenzyl)morpholin-3-one and (2R,5S,6R)-5,6-bis(4-chlorophenyl)-2-(4-fluorobenzyl)-4-(4-methoxybenzyl)morpholin-3-one

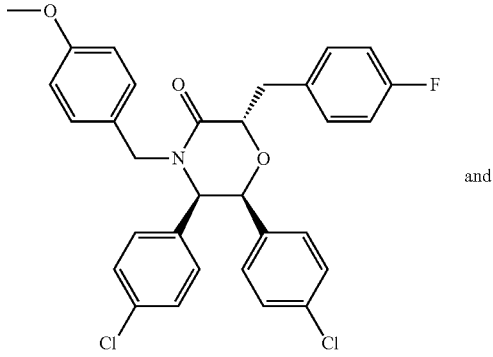

and

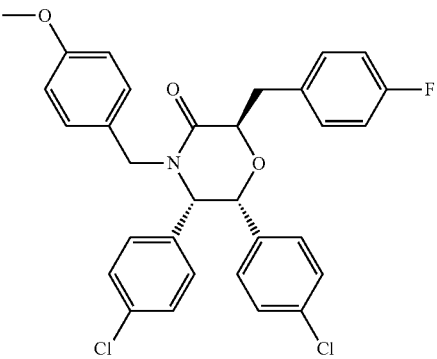

In an oven dried flask, a solution of (5R,6S)-5,6-bis(4-chlorophenyl)-4-(4-methoxybenzyl)morpholin-3-one and (5S,6R)-5,6-bis(4-chlorophenyl)-4-(4-methoxybenzyl)morpholin-3-one (1.000 g, 2.261 mmol, Example 80, Step A) in degassed THF (30.1 mL, 4.52 mmol) was cooled to −78° C. under N$_2$. 1-(Bromomethyl)-4-fluorobenzene (1.239 mL, 9.95 mmol) was added, and the mixture was stirred at −78° C. for 5 minutes. LiHMDS (6.78 mL, 6.78 mmol, 1.0 M in THF) was added and the mixture was stirred at −78° C. for 3 hours. The mixture was quenched with saturated NH$_4$Cl solution, diluted with ethyl acetate, and the layers were separated. The aqueous layer was extracted with ethyl acetate. The combined organic layers were washed with brine, dried over Na$_2$SO$_4$, filtered and the filtrate was concentrated under a vacuum. The residue was purified by flash chromatography on silica gel (40 g column; gradient elution with 0% to 30% ethyl acetate in hexanes) to give the title compounds as a racemic mixture.

Step C. (2S,5R,6S)-5,6-Bis(4-chlorophenyl)-2-(4-fluorobenzyl)morpholin-3-one

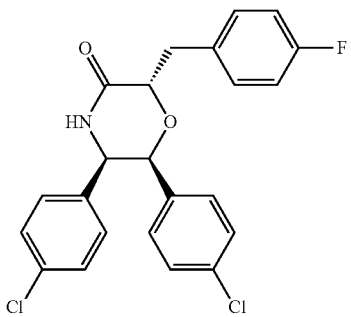 [SMILES: O=C1N[C@H](c2ccc(Cl)cc2)[C@H](c2ccc(Cl)cc2)O[C@H]1Cc1ccc(F)cc1]

Ammonium cerium(IV) nitrate (6573 mg, 11.99 mmol) was added to a solution of (2S,5R,6S)-5,6-bis(4-chlorophenyl)-2-(4-fluorobenzyl)-4-(4-methoxybenzyl)morpholin-3-one and (2R,5S,6R)-5,6-bis(4-chlorophenyl)-2-(4-fluorobenzyl)-4-(4-methoxybenzyl)morpholin-3-one (825 mg, 1.499 mmol, Example 80, Step B) in MeCN (50 mL) and water (10 mL) at 0° C. The mixture was warmed to room temperature and stirred for 16 hours. The mixture was quenched with water, diluted with ethyl acetate, and the layers were separated. The aqueous layer was extracted with ethyl acetate, and the combined organic layers were washed with brine, dried over Na$_2$SO$_4$, filtered, and the filtrate was concentrated under a vacuum. The residue was purified by flash chromatography on silica gel (40 g column; gradient elution with 50% to 70% ethyl acetate in hexanes). The product was further purified by chiral SFC (250×30 mm Chiralpak® AD column (Chiral Technologies, Inc., West Chester, Pa., USA) with 48 g/min MeOH+72 g/min CO$_2$ on a Thar 350 SFC (Thar Technologies, Inc., Pittsburgh, Pa.)) to give the title compound as the final (slowest) eluting isomer.

$^1$H NMR (400 MHz, CDCl$_3$, δ ppm): 7.10-7.21 (m, 6H), 6.93 (t, J=8.7 Hz, 2H), 6.82 (d, J=8.4 Hz, 2H), 6.77 (d, J=8.4 Hz, 2H), 6.36 (br. s, 1H), 5.08-5.16 (m, 1H), 4.85 (dd, J=8.5, 3.8 Hz, 1H), 4.54 (t, J=3.6 Hz, 1H), 3.31-3.41 (m, 1H), 3.21-3.29 (m, 1H). Mass Spectrum (ESI) m/z=430 [M+1].

Example 81

(2R,5S,6R)-5,6-Bis(4-chlorophenyl)-2-(4-fluorobenzyl)morpholin-3-one

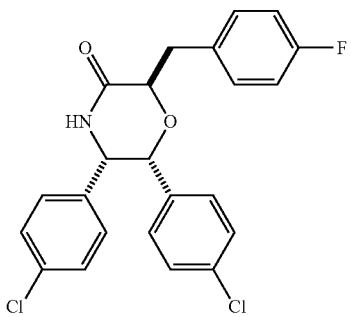 [SMILES: O=C1N[C@@H](c2ccc(Cl)cc2)[C@@H](c2ccc(Cl)cc2)O[C@@H]1Cc1ccc(F)cc1]

The fast eluting peak from Example 80, Step C was further purified by flash chromatography on silica gel (40 g column; gradient elution with 0% to 10% ethyl acetate in hexanes) to give the title compound.

$^1$H NMR (400 MHz, CDCl$_3$, δ ppm): 7.11-7.19 (m, 6H), 6.90-6.96 (m, 2H), 6.82 (d, J=8.6 Hz, 2H), 6.77 (d, J=8.4 Hz, 2H), 6.36 (br. s, 1H), 5.12 (d, J=3.3 Hz, 1H), 4.85 (dd, J=8.6, 3.5 Hz, 1H), 4.54 (t, J=3.7 Hz, 1H), 3.34 (d, J=8.6 Hz, 1H), 3.19-3.30 (m, 1H). Mass Spectrum (ESI) m/z=430 [M+1].

Example 82

2-((2S,5R,6S)-6-(3-Chlorophenyl)-5-(4-chlorophenyl)-4-(cyclopropylmethyl)-5-methyl-3-oxomorpholin-2-yl)acetic acid

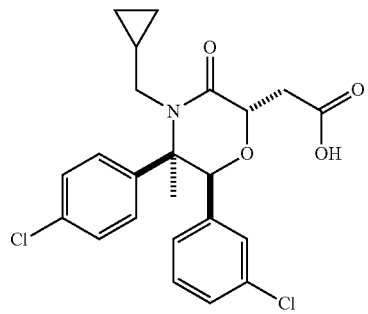

Step A. (R)-4-(4-Chlorophenyl)-4-methyloxazolidin-2-one

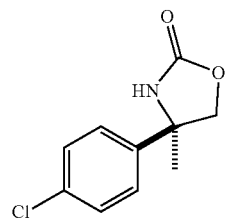

A solution of triphosgene (1.670 mL, 11.26 mmol) in DCM (20 mL) was added dropwise over 1 hour to a solution of (2R)-2-amino-2-(4-chlorophenyl))propan-1-ol HCl salt (5 g, 22.51 mmol, Net Chem, Brantford, Ontario, Canada) and triethylamine (9.4 mL, 67.5 mmol) in CH$_2$Cl$_2$ (45.0 mL) at 0° C. The mixture was stirred for 2 hours at 0° C. and at room temperature overnight. The mixture was quenched with saturated NaHCO$_3$ and stirred for 1 hour. The layers were separated. The aqueous layer was extracted with DCM (3×). The combined organic layers were dried over MgSO$_4$, filtered, and the filtrate was concentrated under a vacuum. The residue was purified by flash chromatography on silica gel (120 g column; gradient elution with 10% to 30% acetone in hexanes) to provide the title compound as a light-yellow oil.

Step B. (R)-tert-Butyl 4-(4-chlorophenyl)-4-methyl-2-oxooxazolidine-3-carboxylate

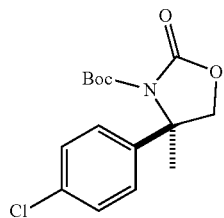

Di-tert-butyl dicarbonate (6.98 mL, 32.6 mmol) was added to a solution of (R)-4-(4-chlorophenyl)-4-methyloxazolidin-2-one (4.6 g, 21.73 mmol, Example 82, Step A), DMAP (0.266 g, 2.173 mmol) and triethylamine (4.53 mL, 32.6 mmol) in THF (43.5 mL) at 0° C. The mixture was stirred at room temperature overnight, then it was diluted with saturated NaHCO$_3$ (30 mL) and extracted with diethyl ether (x). The combined organic layers were dried over MgSO$_4$, filtered and the filtrate was concentrated under a vacuum. The residue was further purified by flash chromatography on silica gel (120 g column; gradient elution with 10% to 30% acetone in hexanes) to provide the title compound as a white solid.

Step C. (R)-tert-Butyl (2-(4-chlorophenyl)-1-hydroxypropan-2-yl)carbamate

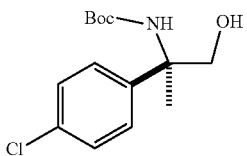

Potassium carbonate (2.76 g, 45.7 mmol) was added to a solution of (R)-tert-butyl 4-(4-chlorophenyl)-4-methyl-2-oxooxazolidine-3-carboxylate (5.7 g, 18.28 mmol, Example 82, Step B) in MeOH (73 mL). After stirring at room temperature overnight, the mixture was diluted with dichloromethane (80 mL) and washed with brine (3×30 mL). The organic extract was washed with water (30 mL) and dried over MgSO$_4$. The solution was filtered and concentrated under a vacuum. The residue was adsorbed onto a plug of silica gel and purified by flash chromatography on silica gel (120 g column; gradient elution of 5% to 35% acetone in hexanes) to provide the title compound as white solid.

Step D. (R)-tert-Butyl (2-(4-chlorophenyl)-1-oxopropan-2-yl)carbamate

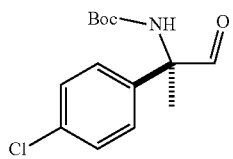

Dess-Martin periodinane (13.36 g, 31.5 mmol) was added to a suspension of (R)-tert-butyl (2-(4-chlorophenyl)-1-hydroxypropan-2-yl)carbamate (4.5 g, 15.75 mmol, Example 82, Step C) in DCM (3120 μL) and water (312 μL) at room temperature. After stirring at 25° C. for 2 hours, the mixture was diluted with ether (40 mL), and a solution of Na$_2$S$_2$O$_3$ (25 g, 158 mmol) in saturated aqueous NaHCO$_3$ (40 mL) was added. The mixture was stirred vigorously for 10 minutes and the layers were separated. The aqueous layer was extracted with ether, and the combined organic layers were dried over MgSO$_4$, filtered, and the filtrate was concentrated under a vacuum to give the title compound as an off-white solid.

Step E. tert-Butyl ((1S,2R)-1-(3-chlorophenyl)-2-(4-chlorophenyl)-1-hydroxypropan-2-yl)carbamate and tert-butyl ((1R,2R)-1-(3-chlorophenyl)-2-(4-chlorophenyl)-1-hydroxypropan-2-yl)carbamate

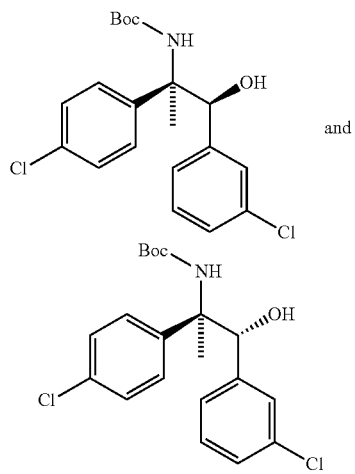

A solution of (3-chlorophenyl)magnesium bromide (40 mL, 40 mmol, 1.0 M in Et$_2$O) was added to a solution of (R)-tert-butyl (2-(4-chlorophenyl)-1-oxopropan-2-yl)carbamate (5.66 g, 19.95 mmol, Example 82, Step D) in Et$_2$O (20 mL) at room temperature. After stirring overnight, the mixture was quenched with saturated NH$_4$Cl and extracted with ethyl acetate (3×). The combined organic layers were dried over MgSO$_4$, filtered, and the filtrate was concentrated under a vacuum. The residue was purified by flash chromatography on silica gel (330 g column; gradient elution with 0% to 40% ethyl acetate in hexanes) to provide the title compounds as a 3:1 mixture of isomers.

Step F. ((1S,2R)-2-Amino-1-(3-chlorophenyl)-2-(4-chlorophenyl)propan-1-ol

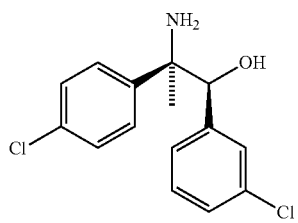 [SMILES: C[C@@](N)(c1ccc(Cl)cc1)[C@@H](O)c1cccc(Cl)c1]

Hydrochloric acid (34.1 mL, 136 mmol, 4.0 M in dioxane) was added to tert-butyl ((1S,2R)-1-(3-chlorophenyl)-2-(4-chlorophenyl)-1-hydroxypropan-2-yl)carbamate and tert-butyl ((1R,2R)-1-(3-chlorophenyl)-2-(4-chlorophenyl)-1-hydroxypropan-2-yl)carbamate (3.0 g, 7.57 mmol, Example 82, Step E). After stirring at room temperature for two hours, the mixture was basified with saturated NaHCO$_3$. The layers were separated, and the aqueous layer was extracted with DCM (3×). The combined organic layers were dried over MgSO$_4$, filtered, and the filtrate was concentrated under a vacuum.

The residue was adsorbed onto a plug of silica gel and purified by flash chromatography on silica gel (120 g column; eluent: 70:25:5 DCM:acetone:MeOH+0.1% triethylamine) to provide the title compound as the second (slower) eluting isomer.

Step G. (1S)-1-(3-Chlorophenyl)-2-(4-chlorophenyl)-2-((cyclopropylmethyl)amino)propan-1-ol

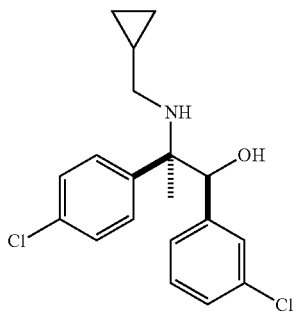

Acetic acid (143 μL, 2.496 mmol) and cyclopropanecarboxaldehyde (199 μL, 2.67 mmol) were added to a stirring solution of (1S, 2R)-2-amino-1-(3-chlorophenyl)-2-(4-chlorophenyl)propan-1-ol (264 mg, 0.891 mmol, Example 82, Step F) in MeOH (2971 μL) at room temperature. Then, sodium cyanoborohydride (140 mg, 2.228 mmol) was added, and evolution of gas was observed. The mixture was warmed to 60° C. and stirred overnight. The reaction was cooled to room temperature and acidified to pH 2 with 1 M HCl. The mixture was concentrated, and the residue was partitioned between DCM and saturated NaHCO$_3$. The separated aqueous layer was extracted with DCM (3×) and the combined organic extracts were dried over Na$_2$SO$_4$, filtered, and the filtrate was concentrated under a vacuum to provide the title compound.

Step H. Methyl 2-((1S, 2R)-1-(3-chlorophenyl)-2-(4-chlorophenyl)-2-((cyclopopylmethyl)amino)propoxy)acetate

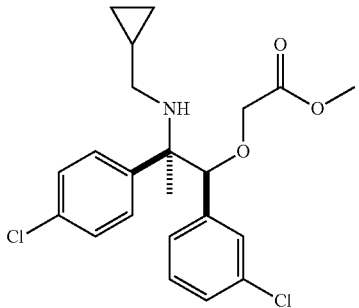

Sodium hydride (35.6 mg, 0.891 mmol, 60% dispersion in mineral oil) was added to a solution of (1S)-1-(3-chlorophenyl)-2-(4-chlorophenyl)-2-((cyclopropylmethyl)amino)propan-1-ol (312 mg, 0.891 mmol, Example 82, Step G) in THF (4454 μL) at room temperature. The light yellow/gray slurry was stirred at room temperature for 30 minutes, and methyl 2-bromoacetate (85 μL, 0.891 mmol) was added dropwise. After 4 hours at room temperature, sodium hydride (35.6 mg, 0.891 mmol, 60% dispersion in mineral oil) and methyl 2-bromoacetate (85 μL, 0.891 mmol) were added. The mixture was stirred at room temperature overnight, and additional sodium hydride (35.6 mg, 0.891 mmol, 60% dispersion in mineral oil) and methyl 2-bromoacetate (85 μL, 0.891 mmol) were added. The mixture was heated to 35° C. for 6.5 hours. The mixture was cooled to room temperature, quenched with saturated NH$_4$Cl and extracted with ethyl acetate (2×). The combined organic layers were dried over Na$_2$SO$_4$, filtered, and the filtrate was concentrated under a vacuum to provide the title compound.

Step I. (5R,6S)-6-(3-Chlorophenyl)-5-(4-chlorophenyl)-4-(cyclopropylmethyl)-5-methylmorpholin-3-one

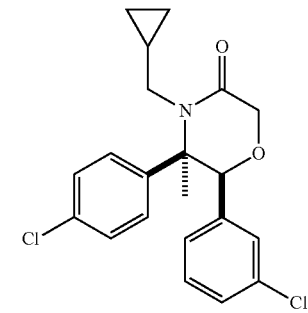

3 Å Molecular sieves were added to a solution of methyl 2-((1S)-1-(3-chlorophenyl)-2-(4-chlorophenyl)-2-((cyclopropylmethyl)amino)propoxy)acetate (376 mg, 0.890 mmol, Example 82, Step H) in distilled xylenes (18 mL) at room temperature. The mixture was heated at 135° C. for 2 days. The mixture was cooled to room temperature and filtered. The filtrate was concentrated. The residue was purified by flash chromatography on silica gel (12 g column; gradient elution with 0% to 50% ethyl acetate in hexanes) to give the title compound.

Step J. (2S,5R,6S)-2-Allyl-6-(3-chlorophenyl)-5-(4-chlorophenyl)-4-(cyclopropylmethyl)-5-methylmorpholin-3-one

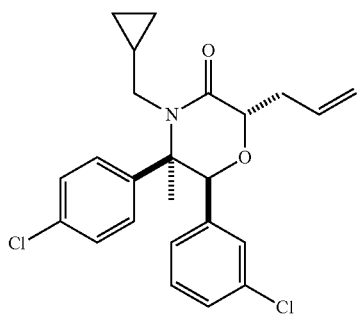

(5R,6S)-6-(3-chlorophenyl)-5-(4-chlorophenyl)-4-(cyclopropylmethyl)-5-methylmorpholin-3-one (64 mg, 0.164 mmol; Example 82, Step I) was dissolved in toluene and concentrated under a vacuum thrice. The resulting residue was dissolved in THF (1640 µL) and degassed by bubbling argon through the solution for 10 minutes. Then, the mixture was cooled to −78° C. under argon and lithium bis(trimethylsilyl)amide (590 µL, 0.590 mmol, 1.0 M in THF) was added dropwise. The mixture turned orange. Allyl bromide (51.1 µL, 0.590 mmol) was added and the mixture was stirred at −78° C. for 1 hour. The mixture was quenched with saturated NH$_4$Cl solution, warmed to room temperature, and extracted with ethyl acetate. The organic layer was dried over Na$_2$SO$_4$, filtered, and the filtrate was concentrated under a vacuum. The residue was purified by flash chromatography on silica gel (4 g column; gradient elution with 0% to 25% ethyl acetate in hexanes) to give the title compound.

Step K. 2-((2S,5R,6S)-6-(3-Chlorophenyl)-5-(4-chlorophenyl)-4-(cyclopropylmethyl)-5-methyl-3-oxomorpholin-2-yl)acetic acid

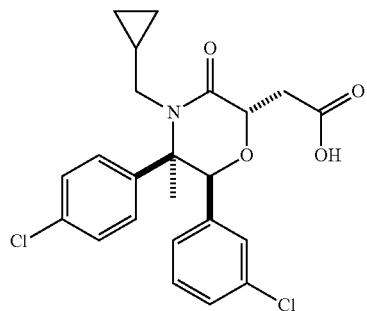

Sodium periodate (113 mg, 0.530 mmol) and ruthenium (III) chloride hydrate (0.438 mg, 1.943 µmol) were added to a solution of (2S,5R,6S)-2-allyl-6-(3-chlorophenyl)-5-(4-chlorophenyl)-4-(cyclopropylmethyl)-5-methylmorpholin-3-one (38 mg, 0.088 mmol, Example 82, Step J) in ethyl acetate (631 µL) and acetonitrile (631 µL) and water (946 µL) at room temperature. After stirring for 1 hour, the mixture was diluted with water and extracted with ethyl acetate (3×). The organic layer was dried over Na$_2$SO$_4$, filtered, and the filtrate was concentrated under a vacuum. The residue was purified by reverse phase preparative HPLC (Gemini™ Prep C18 5 µm column (Phenomenex, Torrance, Calif.), gradient elution of 0% to 100% acetonitrile, both eluents containing 0.1% TFA, 20 minutes) to give the title compound.

$^1$H NMR (400 MHz, CDCl$_3$, δ ppm): 7.17-7.25 (m, 3H), 7.06 (t, J=7.9 Hz, 1H), 6.76-6.83 (m, 2H), 6.64-6.71 (m, 1H), 6.58 (dt, J=7.8, 1.4 Hz, 1H), 5.16 (dd, J=8.2, 4.9 Hz, 1H), 4.85 (s, 1H), 3.37 (dd, J=14.3, 6.7 Hz, 1H), 3.12-3.22 (m, 1H), 2.94-3.06 (m, 2H), 1.72 (s, 3H), 0.83-0.98 (m, 1H), 0.36-0.49 (m, 2H), 0.15-0.28 (m, 2H). Spectrum (ESI) m/z=448 [M+1].

Biological Assays

Compounds of the present invention display inhibition of the interaction between HDM2 and p53 in the following assays.

Homogenous Time-Resolved Fluorescence Assay (HTRF1 Assay)

The standard assay conditions for the in vitro HTRF assay consisted of a 50 ul total reaction volume in black 384-well Costar polypropylene plates in 1×PBS buffer pH 7.4, 1 mM DTT, 0.1% BSA, 2.5 nM GST-hMDM2 (aa 1-188), 5 nM biotinylated-p53 (aa 1-83), 1.8 nM SA-XLent (Cisbio; Bedford, Mass.), 0.6 nM anti-GST cryptate monoclonal antibody (Cisbio; Bedford, Mass.) and 200 mM KF. Amino acid residues 1-188 of human MDM2 were expressed as an amino-terminal glutathione-S-transferase (GST) fusion protein (GST-hMDM2) in *Escherichia coli*. Residues 1-83 of human p53 were expressed as an amino-terminal AviTag™-TrxA-6×His fusion protein (biotinylated p53) in *E. coli*. Each protein was purified from cell paste by affinity chromatography.

Specifically, 10 uL of GST-hMDM2 was incubated with 10 ul of diluted compound (various concentrations, serially diluted) in 10% DMSO for 20 minutes at room temperature. 20 uL of biotinylated-p53 was added to the GST-hMDM2+ compound mixture, and then incubated at room temperature for 60 min. 10 uL of detection buffer consisting of SA-XLent, anti-GST cryptate antibody and KF was added to GST-hMDM2, biotinylated-p53 and compound reaction and left at room temperature to reach equilibrium for >4 hrs. The final concentration of DMSO in the reaction was 2%. Time-resolved fluorescence readings were measured on a microplate multilabel reader. Percentage of inhibition was calculated relative to nutlin-3.

HTRF2 Assay

As the potencies of the HDM2 inhibitors increased, an improved HTRF assay (HTRF2 assay) was developed. All assay conditions remained the same as described above, with the exception of the following changes in reagent concentrations: 0.2 nM GST-hMDM2 (1-188), 0.5 nM biotinylated-p53 (1-83), 0.18 nM SA-XLent, and 100 mM KF.

HTRF3 Assay

This assay was run using the same conditions as the HTRF1 assay except that 20 uL of GST-hMDM2 was incubated with 1.0 ul of diluted compound.

Results are provided in Table 1 below.

TABLE 1

| Example Number | HTRF1 IC$_{50}$ (µM) | HTRF2 IC$_{50}$ (µM) | HTRF3 IC$_{50}$ (µM) |
|---|---|---|---|
| 1, Step B | 5.41 | | 34.6 |
| 1, Step C | 1.96 | 15.8 | 21.9 |
| 2 | 1.03 | 4.58 | 6.04 |
| 3 | 17.2 | | >100 |
| 4 | 1.76 | 10 | 21.4 |
| 5 | 1.47 | | 44.5 |
| 6 | 1.75 | 10 | 9.83 |
| 7 | 1.89 | 100 | 8.45 |
| 8 | 5.35 | | >100 |
| 9 | 2.14 | | 36.4 |
| 10 | 0.0866 | 0.434 | 0.557 |
| 11 | 11.7 | | 41.2 |
| 12 | 1.8 | 8.2 | 10 |
| 13 | 4.11 | | 78.4 |
| 14, Step A | 1.34 | | 51 |
| 14, Step B | | 3.67 | 4.64 |
| 15 | | 3.32 | 3.96 |
| 16 | 0.876 | 2.6 | 3.97 |
| 17 | 0.299 | 1.46 | 1.16 |
| 18 | 9.95 | | 40.6 |
| 19 | | 7.23 | 6.91 |
| 20 | 1.27 | 4.57 | 6.38 |
| 21 | 0.217 | 17.1 | 26 |
| 22 | 0.104 | 0.408 | 0.738 |
| 23 | 0.233 | 1 | 1.1 |
| 24 | 0.492 | 2.15 | 2.38 |
| 25 | 0.886 | 4.22 | 3.51 |
| 26 | 0.591 | 2.78 | 3.06 |
| 27 | | 0.758 | |
| 28 | | 0.524 | |
| 29 | | 0.565 | 1.09 |
| 30 | | 0.677 | 0.726 |
| 31 | | 1.33 | |
| 32 | 0.0399 | 0.15 | |
| 33 | | 0.199 | 0.171 |
| 34 | | 0.745 | 0.486 |
| 35 | | 0.473 | 0.403 |
| 36 | | 0.712 | 0.514 |
| 37 | 2.13 | 8.87 | 11.1 |
| 39 | | 6.64 | 10.4 |
| 40 | | 6.59 | 19.1 |
| 41 | | 4.53 | 5.6 |
| 42 | | 0.947 | 0.539 |
| 43 | | 1.29 | |
| 44 | | 0.757 | |
| 45 | | 0.466 | |
| 46 | | 0.259 | |
| 47 | | 0.4 | |
| 48 | | 0.42 | |
| 49 | | 0.561 | |
| 50 | | 0.568 | |
| 51 | | 0.676 | |
| 52 | | 0.279 | |
| 53 | | 0.276 | |
| 54 | | 0.196 | |
| 55 | | 0.179 | |
| 56 | | 0.453 | |
| 57 | | 0.391 | |
| 58 | | 5 | |
| 59 | | 10 | |
| 60 | | 12.5 | |
| 61 | | 15.8 | |
| 62 | | 15.8 | |
| 63 | | 20 | |
| 64 | | 0.322 | 2.74 |
| 65 | | | 0.361 |
| 66 | | 0.697 | 0.718 |
| 67 | | 0.425 | 0.426 |
| 68 | | 0.659 | 0.488 |
| 69 | | 0.924 | 0.617 |
| 70 | | 8.8 | 6.99 |
| 71 | | 0.952 | 0.544 |
| 72 | 1.25 | 6.17 | |
| 73 | 0.466 | 2.74 | |
| 74 | 1.68 | | |
| 75 | 2.41 | | |
| 76 | 3.63 | | |
| 77 | 3.18 | | |
| 78 | 0.611 | | |
| 79 | 1 | | |
| 80 | 0.973 | 4.94 | |
| 81 | 2.34 | 8.75 | |
| 82 | 6.26 | | |

The following compounds were made using processes analogous to those of Examples 1 to 82 and have been tested in the various HTRF assays described above. The results are set forth below in Table 2.

TABLE 2

| Compound Name | HTRF1 IC$_{50}$ (µM) | HTRF2 IC$_{50}$ (µM) | HTRF3 IC$_{50}$ (µM) |
|---|---|---|---|
| 1,1-dimethylethyl (2R,3S)-2,3-bis(4-bromophenyl)-5-oxo-1-piperazinecarboxylate and 1,1-dimethylethyl (2S,3R)-2,3-bis(4-bromophenyl)-5-oxo-1-piperazinecarboxylate | >30.0 | | 40.8 |
| (2R,5S,6R)-5,6-bis(4-bromophenyl)-4-methyl-2-(2-propen-1-yl)-3-morpholinone and (2S,5R,6S)-5,6-bis(4-bromophenyl)-4-methyl-2-(2-propen-1-yl)-3-morpholinone | | 25 | 23.7 |
| (5R,6S)-5,6-bis(4-bromophenyl)-4-cyclopropyl-3-morpholinone and (5S,6R)-5,6-bis(4-bromophenyl)-4-cyclopropyl-3-morpholinone | | | 38.2 |
| (2S,5R,6S)-5,6-bis(4-bromophenyl)-2,4-dimethyl-3-morpholinone | | 22.7 | 23.2 |
| (2R,5R,6S)-5,6-bis(4-bromophenyl)-2,4-dimethyl-3-morpholinone | | | 46.8 |
| (2R,5S,6R)-5,6-bis(4-bromophenyl)-4-cyclopropyl-2-(phenylmethyl)-3-morpholinone and (2S,5R,6S)-5,6-bis(4-bromophenyl)-4-cyclopropyl-2-(phenylmethyl)-3-morpholinone | | | 51.8 |
| (2R)-2-((2S,3R,6S)-2,3-bis(4-chlorophenyl)-6-(4-(methylsulfonyl)benzyl)-5-oxo-4-morpholinyl)pentanoic acid and (2S)-2-((2R,3S,6R)-2,3-bis(4-chlorophenyl)-6-(4- | | 0.374 | |

TABLE 2-continued

| Compound Name | HTRF1 IC$_{50}$ (μM) | HTRF2 IC$_{50}$ (μM) | HTRF3 IC$_{50}$ (μM) |
|---|---|---|---|
| (methylsulfonyl)benzyl)-5-oxo-4-morpholinyl)pentanoic acid | | | |
| (2R,5S,6R)-5,6-bis(4-bromophenyl)-4-methyl-2-phenyl-3-morpholinone and (2S,5R,6S)-5,6-bis(4-bromophenyl)-4-methyl-2-phenyl-3-morpholinone | | 20 | 12.3 |
| N-((2R)-2-((2S,3R,6S)-2,3-bis(4-chlorophenyl)-6-(4-cyano-3-fluorobenzyl)-5-oxo-4-morpholinyl)pentanoyl)glycine | | 0.517 | 0.39 |
| (5R,6S)-5,6-bis(4-bromophenyl)-1-methyl-4-(phenylmethyl)-2-piperazinone and (5S,6R)-5,6-bis(4-bromophenyl)-1-methyl-4-(phenylmethyl)-2-piperazinone | | | 72.3 |
| (2R,5S,6R)-5,6-bis(4-bromophenyl)-4-methyl-2-(3-methyl-2-buten-1-yl)-3-morpholinone and (2S,5R,6S)-5,6-bis(4-bromophenyl)-4-methyl-2-(3-methyl-2-buten-1-yl)-3-morpholinone | | 25 | 13.2 |
| (2R)-2-((2S,3R,6S)-2,3-bis(4-chlorophenyl)-6-(4-cyano-3-fluorobenzyl)-5-oxo-4-morpholinyl)pentanoic acid | | 0.539 | 0.443 |
| (5R,6S)-5,6-bis(4-bromophenyl)-4-(phenylmethyl)-2-piperazinone and (5S,6R)-5,6-bis(4-bromophenyl)-4-(phenylmethyl)-2-piperazinone | | | 84.4 |
| (2R)-2-((2S,3R,6S)-2,3-bis(4-chlorophenyl)-6-(4-cyanobenzyl)-5-oxo-4-morpholinyl)pentanoic acid and (2S)-2-((2R,3S,6R)-2,3-bis(4-chlorophenyl)-6-(4-cyanobenzyl)-5-oxo-4-morpholinyl)pentanoic acid | | 0.465 | 0.596 |
| (5R,6S)-5,6-bis(4-chlorophenyl)-4-((1R)-2-hydroxy-1-phenylethyl)-3-morpholinone and (5R,6S)-5,6-bis(4-chlorophenyl)-4-((1S)-2-hydroxy-1-phenylethyl)-3-morpholinone and (5S,6R)-5,6-bis(4-chlorophenyl)-4-((1R)-2-hydroxy-1-phenylethyl)-3-morpholinone and (5S,6R)-5,6-bis(4-chlorophenyl)-4-((1S)-2-hydroxy-1-phenylethyl)-3-morpholinone | | | 38.2 |
| (2R)-2-((2S,3R)-2,3-bis(4-chlorophenyl)-5-oxo-4-morpholinyl)-3-phenylpropanoic acid and (2S)-2-((2R,3S)-2,3-bis(4-chlorophenyl)-5-oxo-4-morpholinyl)-3-phenylpropanoic acid or (2S)-2-((2S,3R)-2,3-bis(4-chlorophenyl)-5-oxo-4-morpholinyl)-3-phenylpropanoic acid and (2R)-2-((2R,3S)-2,3-bis(4-chlorophenyl)-5-oxo-4-morpholinyl)-3-phenylpropanoic acid | | | 69.1 |
| (5R,6S)-5,6-bis(4-chlorophenyl)-4-((1R)-1-(hydroxymethyl)butyl)-3-morpholinone and (5S,6R)-5,6-bis(4-chlorophenyl)-4-((1S)-1-(hydroxymethyl)butyl)-3-morpholinone or (5R,6S)-5,6-bis(4-chlorophenyl)-4-((1S)-1-(hydroxymethyl)butyl)-3-morpholinone and (5S,6R)-5,6-bis(4-chlorophenyl)-4-((1R)-1-(hydroxymethyl)butyl)-3-morpholinone | | 5.12 | 6.35 |
| (2R)-2-((2S,3R,6S)-2,3-bis(4-chlorophenyl)-6-(2-methoxybenzyl)-5-oxo-4-morpholinyl)pentanoic acid | | 0.496 | |
| (2R)-((2S,3R)-2,3-bis(4-chlorophenyl)-5-oxo-4-morpholinyl)(4-chlorophenyl)ethanoic acid and (2S)-((2R,3S)-2,3-bis(4-chlorophenyl)-5-oxo-4-morpholinyl)(4-chlorophenyl)ethanoic acid or (2S)-((2S,3R)-2,3-bis(4-chlorophenyl)-5-oxo-4-morpholinyl)(4-chlorophenyl)ethanoic acid and (2R)-((2R,3S)-2,3-bis(4-chlorophenyl)-5-oxo-4-morpholinyl)(4-chlorophenyl)ethanoic acid | | 16.8 | 19.8 |
| (2R)-2-((2R,3S)-2,3-bis(4-chlorophenyl)-5-oxo-4-morpholinyl)-3-phenylpropanoic acid and (2S)-2-((2S,3R)-2,3-bis(4-chlorophenyl)-5-oxo-4-morpholinyl)-3-phenylpropanoic acid or (2S)-2-((2R,3S)-2,3-bis(4-chlorophenyl)-5-oxo-4-morpholinyl)-3-phenylpropanoic acid and (2R)-2-((2S,3R)-2,3-bis(4-chlorophenyl)-5-oxo-4-morpholinyl)-3-phenylpropanoic acid | | | 61.3 |
| (2R,5S,6R)-5,6-bis(4-chlorophenyl)-2-(4-fluorobenzyl)-4-((1S)-1-(hydroxymethyl)butyl)-3-morpholinone and (2S,5R,6S)-5,6-bis(4- | | 2.07 | 1.28 |

TABLE 2-continued

| Compound Name | HTRF1 IC$_{50}$ (μM) | HTRF2 IC$_{50}$ (μM) | HTRF3 IC$_{50}$ (μM) |
|---|---|---|---|
| chlorophenyl)-2-(4-fluorobenzyl)-4-((1R)-1-(hydroxymethyl)butyl)-3-morpholinone or (2R,5S,6R)-5,6-bis(4-chlorophenyl)-2-(4-fluorobenzyl)-4-((1R)-1-(hydroxymethyl)butyl)-3-morpholinone and (2S,5R,6S)-5,6-bis(4-chlorophenyl)-2-(4-fluorobenzyl)-4-((1S)-1-(hydroxymethyl)butyl)-3-morpholinone | | | |
| (5R,6S)-5,6-bis(4-chlorophenyl)-4-((1R)-1-(4-chlorophenyl)-2-hydroxyethyl)-3-morpholinone and (5S,6R)-5,6-bis(4-chlorophenyl)-4-((1S)-1-(4-chlorophenyl)-2-hydroxyethyl)-3-morpholinone or (5R,6S)-5,6-bis(4-chlorophenyl)-4-((1S)-1-(4-chlorophenyl)-2-hydroxyethyl)-3-morpholinone and (5S,6R)-5,6-bis(4-chlorophenyl)-4-((1R)-1-(4-chlorophenyl)-2-hydroxyethyl)-3-morpholinone | | 5 | 7.88 |
| (5R,6S)-5,6-bis(4-chlorophenyl)-4-((1R)-1-(1-hydroxy-1-methylethyl)butyl)-3-morpholinone and (5S,6R)-5,6-bis(4-chlorophenyl)-4-((1S)-1-(1-hydroxy-1-methylethyl)butyl)-3-morpholinone or (5R,6S)-5,6-bis(4-chlorophenyl)-4-((1S)-1-(1-hydroxy-1-methylethyl)butyl)-3-morpholinone and (5S,6R)-5,6-bis(4-chlorophenyl)-4-((1R)-1-(1-hydroxy-1-methylethyl)butyl)-3-morpholinone | | 12.6 | 16.1 |
| (2R)-2-((2S,3R,6S)-2,3-bis(4-chlorophenyl)-6-(4-fluorobenzyl)-5-oxo-4-morpholinyl)pentanamide and (2S)-2-((2R,3S,6R)-2,3-bis(4-chlorophenyl)-6-(4-fluorobenzyl)-5-oxo-4-morpholinyl)pentanamide or (2S)-2-((2S,3R,6S)-2,3-bis(4-chlorophenyl)-6-(4-fluorobenzyl)-5-oxo-4-morpholinyl)pentanamide and (2R)-2-((2R,3S,6R)-2,3-bis(4-chlorophenyl)-6-(4-fluorobenzyl)-5-oxo-4-morpholinyl)pentanamide | s | 0.838 | 0.506 |
| (2R)-2-((2S,3R)-2,3-bis(4-chlorophenyl)-5-oxo-4-morpholinyl)pentanamide and (2S)-2-((2R,3S)-2,3-bis(4-chlorophenyl)-5-oxo-4-morpholinyl)pentanamide or (2S)-2-((2S,3R)-2,3-bis(4-chlorophenyl)-5-oxo-4-morpholinyl)pentanamide and (2R)-2-((2R,3S)-2,3-bis(4-chlorophenyl)-5-oxo-4-morpholinyl)pentanamide | | 4.29 | 3.19 |
| (2S,5R,6S)-5,6-bis(4-chlorophenyl)-2-(4-fluorobenzyl)-4-((1R)-1-(hydroxymethyl)butyl)-3-morpholinone or (2S,5R,6S)-5,6-bis(4-chlorophenyl)-2-(4-fluorobenzyl)-4-((1S)-1-(hydroxymethyl)butyl)-3-morpholinone | | 0.644 | 0.744 |
| (2R)-2-((2S,3R,6S)-2,3-bis(4-chlorophenyl)-6-(4-fluorobenzyl)-5-oxo-4-morpholinyl)pentanamide or (2S)-2-((2S,3R,6S)-2,3-bis(4-chlorophenyl)-6-(4-fluorobenzyl)-5-oxo-4-morpholinyl)pentanamide | | 0.623 | 0.507 |
| (2R)-2-((2S,3R)-2,3-bis(4-chlorophenyl)-5-oxo-4-morpholinyl)pentyl carbamate and (2S)-2-((2R,3S)-2,3-bis(4-chlorophenyl)-5-oxo-4-morpholinyl)pentyl carbamate or (2S)-2-((2S,3R)-2,3-bis(4-chlorophenyl)-5-oxo-4-morpholinyl)pentyl carbamate and (2R)-2-((2R,3S)-2,3-bis(4-chlorophenyl)-5-oxo-4-morpholinyl)pentyl carbamate | | 3.61 | 3.72 |
| (2R)-2-((2S,3R,6S)-3-(4-chlorophenyl)-2-(3,4-dichlorophenyl)-6-(4-fluorobenzyl)-5-oxo-4-morpholinyl)pentanoic acid and (2S)-2-((2R,3S,6R)-3-(4-chlorophenyl)-2-(3,4-dichlorophenyl)-6-(4-fluorobenzyl)-5-oxo-4-morpholinyl)pentanoic acid or (2S)-2-((2S,3R,6S)-3-(4-chlorophenyl)-2-(3,4-dichlorophenyl)-6-(4-fluorobenzyl)-5-oxo-4-morpholinyl)pentanoic acid and (2R)-2-((2R,3S,6R)-3-(4-chlorophenyl)-2-(3,4-dichlorophenyl)-6-(4-fluorobenzyl)-5-oxo-4-morpholinyl)pentanoic acid | | 3.69 | 3.58 |
| ((2R,5S,6R)-6-(3-chlorophenyl)-5-(4-chlorophenyl)-4-(cyclopropylmethyl)-3-oxo-2-morpholinyl)acetic acid and ((2S,5S,6R)-6-(3-chlorophenyl)-5-(4-chlorophenyl)-4-(cyclopropylmethyl)-3-oxo-2-morpholinyl)acetic | 0.66 | | |

TABLE 2-continued

| Compound Name | HTRF1 IC$_{50}$ (μM) | HTRF2 IC$_{50}$ (μM) | HTRF3 IC$_{50}$ (μM) |
|---|---|---|---|
| acid or ((2S,5R,6S)-6-(3-chlorophenyl)-5-(4-chlorophenyl)-4-(cyclopropylmethyl)-3-oxo-2-morpholinyl)acetic acid and ((2R,5R,6S)-6-(3-chlorophenyl)-5-(4-chlorophenyl)-4-(cyclopropylmethyl)-3-oxo-2-morpholinyl)acetic acid | | | |
| ((2R,5S,6R)-6-(3-chlorophenyl)-5-(4-chlorophenyl)-4-((1R)-1-methylbutyl)-3-oxo-2-morpholinyl)acetic acid and ((2S,5R,6S)-6-(3-chlorophenyl)-5-(4-chlorophenyl)-4-((1S)-1-methylbutyl)-3-oxo-2-morpholinyl)acetic acid or ((2R,5S,6R)-6-(3-chlorophenyl)-5-(4-chlorophenyl)-4-((1S)-1-methylbutyl)-3-oxo-2-morpholinyl)acetic acid and ((2S,5R,6S)-6-(3-chlorophenyl)-5-(4-chlorophenyl)-4-((1R)-1-methylbutyl)-3-oxo-2-morpholinyl)acetic acid | | 0.677 | 0.677 |
| (2R)-2-((2S,3R)-3-(4-chlorophenyl)-2-(3,4-dichlorophenyl)-5-oxo-4-morpholinyl)pentanamide and (2S)-2-((2R,3S)-3-(4-chlorophenyl)-2-(3,4-dichlorophenyl)-5-oxo-4-morpholinyl)pentanamide or (2S)-2-((2S,3R)-3-(4-chlorophenyl)-2-(3,4-dichlorophenyl)-5-oxo-4-morpholinyl)pentanamide and (2R)-2-((2R,3S)-3-(4-chlorophenyl)-2-(3,4-dichlorophenyl)-5-oxo-4-morpholinyl)pentanamide | | 9.16 | 15.7 |
| (2R)-((2S,3R,6S)-2,3-bis(4-chlorophenyl)-6-(4-fluorobenzyl)-5-oxo-4-morpholinyl)(4-chlorophenyl)ethanoic acid and (2S)-((2R,3S,6R)-2,3-bis(4-chlorophenyl)-6-(4-fluorobenzyl)-5-oxo-4-morpholinyl)(4-chlorophenyl)ethanoic acid or (2S)-((2S,3R,6S)-2,3-bis(4-chlorophenyl)-6-(4-fluorobenzyl)-5-oxo-4-morpholinyl)(4-chlorophenyl)ethanoic acid and (2R)-((2R,3S,6R)-2,3-bis(4-chlorophenyl)-6-(4-fluorobenzyl)-5-oxo-4-morpholinyl)(4-chlorophenyl)ethanoic acid | | 1.41 | 3.65 |
| (2R)-2-((2S,3R,6S)-2,3-bis(4-chlorophenyl)-6-(4-fluorobenzyl)-5-oxo-4-morpholinyl)-2-(4-chlorophenyl)ethanamide and (2S)-2-((2R,3S,6R)-2,3-bis(4-chlorophenyl)-6-(4-fluorobenzyl)-5-oxo-4-morpholinyl)-2-(4-chlorophenyl)ethanamide or (2S)-2-((2S,3R,6S)-2,3-bis(4-chlorophenyl)-6-(4-fluorobenzyl)-5-oxo-4-morpholinyl)-2-(4-chlorophenyl)ethanamide and (2R)-2-((2R,3S,6R)-2,3-bis(4-chlorophenyl)-6-(4-fluorobenzyl)-5-oxo-4-morpholinyl)-2-(4-chlorophenyl)ethanamide | | 5 | 11.3 |
| methyl 4-(((2R)-2-((2S,3R,6S)-2,3-bis(4-chlorophenyl)-6-(4-(methylsulfonyl)benzyl)-5-oxo-4-morpholinyl)pentanoyl)amino)butanoate | | 0.749 | |
| (2R)-2-((2S,3R,6S)-2-(3-chlorophenyl)-3-(4-chlorophenyl)-6-((2R)-2,3-dihydroxypropyl)-5-oxo-4-morpholinyl)pentanamide and (2S)-2-((2R,3S,6R)-2-(3-chlorophenyl)-3-(4-chlorophenyl)-6-((2S)-2,3-dihydroxypropyl)-5-oxo-4-morpholinyl)pentanamide or (2S)-2-((2S,3R,6S)-2-(3-chlorophenyl)-3-(4-chlorophenyl)-6-((2R)-2,3-dihydroxypropyl)-5-oxo-4-morpholinyl)pentanamide and (2R)-2-((2R,3S,6R)-2-(3-chlorophenyl)-3-(4-chlorophenyl)-6-((2S)-2,3-dihydroxypropyl)-5-oxo-4-morpholinyl)pentanamide or (2R)-2-((2S,3R,6S)-2-(3-chlorophenyl)-3-(4-chlorophenyl)-6-((2S)-2,3-dihydroxypropyl)-5-oxo-4-morpholinyl)pentanamide and (2S)-2-((2R,3S,6R)-2-(3-chlorophenyl)-3-(4-chlorophenyl)-6-((2R)-2,3-dihydroxypropyl)-5-oxo-4-morpholinyl)pentanamide or (2S)-2-((2S,3R,6S)-2-(3-chlorophenyl)-3-(4-chlorophenyl)-6-((2S)-2,3-dihydroxypropyl)-5-oxo-4-morpholinyl)pentanamide and (2R)-2-((2R,3S,6R)-2-(3-chlorophenyl)-3-(4-chlorophenyl)-6-((2R)-2,3-dihydroxypropyl)-5-oxo-4-morpholinyl)pentanamide | | 0.752 | 1.69 |

TABLE 2-continued

| Compound Name | HTRF1 IC$_{50}$ (μM) | HTRF2 IC$_{50}$ (μM) | HTRF3 IC$_{50}$ (μM) |
|---|---|---|---|
| (2R)-2-((2S,3R)-2,3-bis(4-chlorophenyl)-5-oxo-4-morpholinyl)-2-(4-chlorophenyl)ethanamide and (2S)-2-((2R,3S)-2,3-bis(4-chlorophenyl)-5-oxo-4-morpholinyl)-2-(4-chlorophenyl)ethanamide or (2S)-2-((2S,3R)-2,3-bis(4-chlorophenyl)-5-oxo-4-morpholinyl)-2-(4-chlorophenyl)ethanamide and (2R)-2-((2R,3S)-2,3-bis(4-chlorophenyl)-5-oxo-4-morpholinyl)-2-(4-chlorophenyl)ethanamide | | 7.44 | 13.7 |
| (2R)-2-((2S,3R,6S)-3-(4-chlorophenyl)-2-(3,4-dichlorophenyl)-6-(4-fluorobenzyl)-5-oxo-4-morpholinyl)pentanamide and (2S)-2-((2R,3S,6S)-3-(4-chlorophenyl)-2-(3,4-dichlorophenyl)-6-(4-fluorobenzyl)-5-oxo-4-morpholinyl)pentanamide or (2S)-2-((2S,3R,6S)-3-(4-chlorophenyl)-2-(3,4-dichlorophenyl)-6-(4-fluorobenzyl)-5-oxo-4-morpholinyl)pentanamide and (2R)-2-((2R,3S,6S)-3-(4-chlorophenyl)-2-(3,4-dichlorophenyl)-6-(4-fluorobenzyl)-5-oxo-4-morpholinyl)pentanamide | | 2.38 | 1.95 |
| (2R)-2-((2S,3R,6S)-2,3-bis(4-chlorophenyl)-6-(2-(4-methyl-1-piperazinyl)ethyl)-5-oxo-4-morpholinyl)pentanoic acid | | 0.79 | |
| (2R)-2-((2S,3R)-2,3-bis(4-chlorophenyl)-5-oxo-4-morpholinyl)-N-methylpentanamide and (2S)-2-((2R,3S)-2,3-bis(4-chlorophenyl)-5-oxo-4-morpholinyl)-N-methylpentanamide or (2S)-2-((2S,3R)-2,3-bis(4-chlorophenyl)-5-oxo-4-morpholinyl)-N-methylpentanamide and (2R)-2-((2R,3S)-2,3-bis(4-chlorophenyl)-5-oxo-4-morpholinyl)-N-methylpentanamide | | 2.87 | 4.45 |
| (2R)-2-((2S,3R)-2,3-bis(4-chlorophenyl)-5-oxo-4-morpholinyl)-N-(2-hydroxyethyl)pentanamide and (2S)-2-((2R,3S)-2,3-bis(4-chlorophenyl)-5-oxo-4-morpholinyl)-N-(2-hydroxyethyl)pentanamide or (2S)-2-((2S,3R)-2,3-bis(4-chlorophenyl)-5-oxo-4-morpholinyl)-N-(2-hydroxyethyl)pentanamide and (2R)-2-((2R,3S)-2,3-bis(4-chlorophenyl)-5-oxo-4-morpholinyl)-N-(2-hydroxyethyl)pentanamide | | 3.44 | 5.25 |
| (2R)-2-((2S,3R)-2,3-bis(4-chlorophenyl)-5-oxo-4-morpholinyl)-N,N-dimethylpentanamide and (2S)-2-((2R,3S)-2,3-bis(4-chlorophenyl)-5-oxo-4-morpholinyl)-N,N-dimethylpentanamide or (2S)-2-((2S,3R)-2,3-bis(4-chlorophenyl)-5-oxo-4-morpholinyl)-N,N-dimethylpentanamide and (2R)-2-((2R,3S)-2,3-bis(4-chlorophenyl)-5-oxo-4-morpholinyl)-N,N-dimethylpentanamide | | 4.16 | 5.09 |
| (2R)-2-((2S,3R)-2,3-bis(4-chlorophenyl)-5-oxo-4-morpholinyl)-N-(2-(4-morpholinyl)ethyl)pentanamide and (2S)-2-((2R,3S)-2,3-bis(4-chlorophenyl)-5-oxo-4-morpholinyl)-N-(2-(4-morpholinyl)ethyl)pentanamide or (2S)-2-((2S,3R)-2,3-bis(4-chlorophenyl)-5-oxo-4-morpholinyl)-N-(2-(4-morpholinyl)ethyl)pentanamide and (2R)-2-((2R,3S)-2,3-bis(4-chlorophenyl)-5-oxo-4-morpholinyl)-N-(2-(4-morpholinyl)ethyl)pentanamide | | 4.53 | 4.75 |
| (2R)-2-((2S,3R,6S)-2,3-bis(4-chlorophenyl)-6-(3-(1H-imidazol-1-yl)propyl)-5-oxo-4-morpholinyl)pentanoic acid | | 0.973 | |
| (2R)-2-((2S,3R)-2,3-bis(4-chlorophenyl)-5-oxo-4-morpholinyl)-N-propylpentanamide and (2S)-2-((2R,3S)-2,3-bis(4-chlorophenyl)-5-oxo-4-morpholinyl)-N-propylpentanamide or (2S)-2-((2S,3R)-2,3-bis(4-chlorophenyl)-5-oxo-4-morpholinyl)-N-propylpentanamide and (2R)-2-((2R,3S)-2,3-bis(4-chlorophenyl)-5-oxo-4-morpholinyl)-N-propylpentanamide | | 5 | 6.55 |
| (5R,6S)-4-((1R)-1-(aminomethyl)butyl)-5,6-bis(4-chlorophenyl)-3-morpholinone and (5S,6R)-4-((1S)-1-(aminomethyl)butyl)-5,6-bis(4-chlorophenyl)-3-morpholinone or (5R,6S)-4-((1S)-1-(aminomethyl)butyl)-5,6-bis(4-chlorophenyl)-3-morpholinone and (5S,6R)-4- | | 6.09 | 6.88 |

TABLE 2-continued

| Compound Name | HTRF1 IC$_{50}$ (μM) | HTRF2 IC$_{50}$ (μM) | HTRF3 IC$_{50}$ (μM) |
|---|---|---|---|
| ((1R)-1-(aminomethyl)butyl)-5,6-bis(4-chlorophenyl)-3-morpholinone | | | |
| (2R)-2-((2S,3R,6S)-2-(4-chloro-3-fluorophenyl)-3-(4-chlorophenyl)-6-(4-fluorobenzyl)-5-oxo-4-morpholinyl)pentanamide and (2S)-2-((2R,3S,6R)-2-(4-chloro-3-fluorophenyl)-3-(4-chlorophenyl)-6-(4-fluorobenzyl)-5-oxo-4-morpholinyl)pentanamide or (2S)-2-((2S,3R,6S)-2-(4-chloro-3-fluorophenyl)-3-(4-chlorophenyl)-6-(4-fluorobenzyl)-5-oxo-4-morpholinyl)pentanamide and (2R)-2-((2R,3S,6R)-2-(4-chloro-3-fluorophenyl)-3-(4-chlorophenyl)-6-(4-fluorobenzyl)-5-oxo-4-morpholinyl)pentanamide | | 2 | 1.21 |
| (2R)-2-((2S,3R,6S)-2,3-bis(4-chlorophenyl)-5-oxo-6-(2-propen-1-yl)-4-morpholinyl)pentanamide and (2S)-2-((2R,3S,6R)-2,3-bis(4-chlorophenyl)-5-oxo-6-(2-propen-1-yl)-4-morpholinyl)pentanamide or (2S)-2-((2S,3R,6S)-2,3-bis(4-chlorophenyl)-5-oxo-6-(2-propen-1-yl)-4-morpholinyl)pentanamide and (2R)-2-((2R,3S,6R)-2,3-bis(4-chlorophenyl)-5-oxo-6-(2-propen-1-yl)-4-morpholinyl)pentanamide | | 1.94 | 1.25 |
| (2R)-2-((2R,3S,6R)-2,3-bis(4-chlorophenyl)-6-(4-fluorobenzyl)-5-oxo-4-morpholinyl)pentanoic acid and (2R)-2-((2S,3R,6S)-2,3-bis(4-chlorophenyl)-6-(4-fluorobenzyl)-5-oxo-4-morpholinyl)pentanoic acid and (2S)-2-((2R,3S,6R)-2,3-bis(4-chlorophenyl)-6-(4-fluorobenzyl)-5-oxo-4-morpholinyl)pentanoic acid and (2S)-2-((2S,3R,6S)-2,3-bis(4-chlorophenyl)-6-(4-fluorobenzyl)-5-oxo-4-morpholinyl)pentanoic acid | | 1.3 | 1.05 |
| N-((2R)-2-((2S,3R)-2,3-bis(4-chlorophenyl)-5-oxo-4-morpholinyl)pentyl)-2-hydroxyacetamide and N-((2S)-2-((2R,3S)-2,3-bis(4-chlorophenyl)-5-oxo-4-morpholinyl)pentyl)-2-hydroxyacetamide or N-((2S)-2-((2S,3R)-2,3-bis(4-chlorophenyl)-5-oxo-4-morpholinyl)pentyl)-2-hydroxyacetamide and N-((2R)-2-((2R,3S)-2,3-bis(4-chlorophenyl)-5-oxo-4-morpholinyl)pentyl)-2-hydroxyacetamide | | 3.71 | 4.56 |
| (2R)-2-((2S,3R,6S)-2,3-bis(4-chlorophenyl)-6-(3-methoxybenzyl)-5-oxo-4-morpholinyl)pentanoic acid | | 1.11 | |
| (2R)-2-((2S,3R)-2-(4-chloro-2-methylphenyl)-3-(4-chlorophenyl)-5-oxo-4-morpholinyl)pentanoic acid and (2S)-2-((2R,3S)-2-(4-chloro-2-methylphenyl)-3-(4-chlorophenyl)-5-oxo-4-morpholinyl)pentanoic acid or (2S)-2-((2S,3R)-2-(4-chloro-2-methylphenyl)-3-(4-chlorophenyl)-5-oxo-4-morpholinyl)pentanoic acid and (2R)-2-((2R,3S)-2-(4-chloro-2-methylphenyl)-3-(4-chlorophenyl)-5-oxo-4-morpholinyl)pentanoic acid | | 7.67 | 8.53 |
| (3R)-3-((2R,3S,6R)-2-(3-chlorophenyl)-3-(4-chlorophenyl)-6-(4-fluorobenzyl)-5-oxo-4-morpholinyl)hexanoic acid | | 1.15 | |
| (2R)-2-((2S,3R,6S)-2,3-bis(4-chlorophenyl)-5-oxo-6-(2-propen-1-yl)-4-morpholinyl)pentanoic acid and (2S)-2-((2R,3S,6R)-2,3-bis(4-chlorophenyl)-5-oxo-6-(2-propen-1-yl)-4-morpholinyl)pentanoic acid | | 0.997 | 2.03 |
| (2R)-2-((2S,3R,6S)-2,3-bis(4-chlorophenyl)-6-((2S)-2,3-dihydroxypropyl)-5-oxo-4-morpholinyl)pentanamide and (2S)-2-((2R,3S,6R)-2,3-bis(4-chlorophenyl)-6-((2R)-2,3-dihydroxypropyl)-5-oxo-4-morpholinyl)pentanamide or (2R)-2-((2S,3R,6S)-2,3-bis(4-chlorophenyl)-6-((2R)-2,3-dihydroxypropyl)-5-oxo-4-morpholinyl)pentanamide and (2S)-2-((2R,3S,6R)-2,3-bis(4-chlorophenyl)-6-((2S)-2,3-dihydroxypropyl)-5-oxo-4-morpholinyl)pentanamide | | 1.76 | 2.4 |

TABLE 2-continued

| Compound Name | HTRF1 IC$_{50}$ (μM) | HTRF2 IC$_{50}$ (μM) | HTRF3 IC$_{50}$ (μM) |
|---|---|---|---|
| (2R)-2-((2S,3R,6S)-2,3-bis(4-chlorophenyl)-6-((2R)-2,3-dihydroxypropyl)-5-oxo-4-morpholinyl)pentanamide and (2S)-2-((2R,3S,6R)-2,3-bis(4-chlorophenyl)-6-((2S)-2,3-dihydroxypropyl)-5-oxo-4-morpholinyl)pentanamide or (2R)-2-((2S,3R,6S)-2,3-bis(4-chlorophenyl)-6-((2S)-2,3-dihydroxypropyl)-5-oxo-4-morpholinyl)pentanamide and (2S)-2-((2R,3S,6R)-2,3-bis(4-chlorophenyl)-6-((2R)-2,3-dihydroxypropyl)-5-oxo-4-morpholinyl)pentanamide | | 2.38 | 2.57 |
| (2R)-2-((2S,3R,6S)-2,3-bis(4-chlorophenyl)-6-((2R)-2,3-dihydroxypropyl)-5-oxo-4-morpholinyl)pentanoic acid and (2R)-2-((2S,3R,6S)-2,3-bis(4-chlorophenyl)-6-((2S)-2,3-dihydroxypropyl)-5-oxo-4-morpholinyl)pentanoic acid and (2S)-2-((2R,3S,6R)-2,3-bis(4-chlorophenyl)-6-((2R)-2,3-dihydroxypropyl)-5-oxo-4-morpholinyl)pentanoic acid and (2S)-2-((2R,3S,6R)-2,3-bis(4-chlorophenyl)-6-((2S)-2,3-dihydroxypropyl)-5-oxo-4-morpholinyl)pentanoic acid | | 3.52 | 8.22 |
| (2R)-2-((2S,5R,6S)-2-(2-amino-2-oxoethyl)-5,6-bis(4-chlorophenyl)-3-oxo-4-morpholinyl)pentanoic acid and (2S)-2-((2R,5S,6R)-2-(2-amino-2-oxoethyl)-5,6-bis(4-chlorophenyl)-3-oxo-4-morpholinyl)pentanoic acid | | 3.85 | 5.49 |
| ((2R,5S,6R)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid or ((2S,5R,6S)-6-(3-chlorophenyl)-5-(4-chlorophenyl)-4-((1R)-1-(((cyclopropylsulfonyl)(phenyl)amino)methyl)propyl)-3-oxo-2-morpholinyl)acetic acid or ((2S,5S,6R)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid or ((2R,5R,6S)-6-(3-chlorophenyl)-5-(4-chlorophenyl)-4-((1R)-1-(((cyclopropylsulfonyl)(phenyl)amino)methyl)propyl)-3-oxo-2-morpholinyl)acetic acid or ((2R,5S,6R)-6-(3-chlorophenyl)-5-(4-chlorophenyl)-4-((1R)-1-(((cyclopropylsulfonyl)(phenyl)amino)methyl)propyl)-3-oxo-2-morpholinyl)acetic acid or ((2S,5R,6S)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid or ((2S,5S,6R)-6-(3-chlorophenyl)-5-(4-chlorophenyl)-4-((1R)-1-(((cyclopropylsulfonyl)(phenyl)amino)methyl)propyl)-3-oxo-2-morpholinyl)acetic acid or ((2R,5R,6S)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid | 1.27 | | |
| ((2R,5S,6R)-4-((1S)-1-carbamoylbutyl)-5,6-bis(4-chlorophenyl)-3-oxo-2-morpholinyl)acetic acid and ((2S,5R,6S)-4-((1R)-1-carbamoylbutyl)-5,6-bis(4-chlorophenyl)-3-oxo-2-morpholinyl)acetic acid | | 7.82 | 13.5 |
| ((2R,5S,6R)-6-(3-chlorophenyl)-5-(4-chlorophenyl)-4-((1S)-1-(ethoxycarbonyl)butyl)-3-oxo-2-morpholinyl)acetic acid and ((2S,5R,6S)-6-(3-chlorophenyl)-5-(4-chlorophenyl)-4-((1R)-1-(ethoxycarbonyl)butyl)-3-oxo-2-morpholinyl)acetic acid or ((2R,5S,6R)-6-(3-chlorophenyl)-5-(4-chlorophenyl)-4-((1R)-1-(ethoxycarbonyl)butyl)-3-oxo-2-morpholinyl)acetic acid and ((2S,5R,6S)-6-(3-chlorophenyl)-5-(4-chlorophenyl)-4-((1S)-1- | | 2.31 | 1.3 |

TABLE 2-continued

| Compound Name | HTRF1 IC$_{50}$ (μM) | HTRF2 IC$_{50}$ (μM) | HTRF3 IC$_{50}$ (μM) |
|---|---|---|---|
| (ethoxycarbonyl)butyl)-3-oxo-2-morpholinyl)acetic acid | | | |
| (2R)-2-((2S,3R,6S)-2,3-bis(4-chlorophenyl)-6-(4-fluorobenzyl)-5-oxo-4-morpholinyl)-N-(2-(4-morpholinyl)ethyl)pentanamide and (2S)-2-((2R,3S,6R)-2,3-bis(4-chlorophenyl)-6-(4-fluorobenzyl)-5-oxo-4-morpholinyl)-N-(2-(4-morpholinyl)ethyl)pentanamide | | 0.691 | 0.706 |
| (5R,6S)-5,6-bis(4-chlorophenyl)-4-((1R)-1-(4-morpholinylmethyl)butyl)-3-morpholinone and (5S,6R)-5,6-bis(4-chlorophenyl)-4-((1S)-1-(4-morpholinylmethyl)butyl)-3-morpholinone | | 4 | 12.1 |
| ((2R,5R,6S)-6-(3-chlorophenyl)-5-(4-chlorophenyl)-4-(cyclopropylmethyl)-3-oxo-2-morpholinyl)acetic acid and ((2S,5R,6S)-6-(3-chlorophenyl)-5-(4-chlorophenyl)-4-(cyclopropylmethyl)-3-oxo-2-morpholinyl)acetic acid or ((2R,5S,6R)-6-(3-chlorophenyl)-5-(4-chlorophenyl)-4-(cyclopropylmethyl)-3-oxo-2-morpholinyl)acetic acid, ((2S,5S,6R)-6-(3-chlorophenyl)-5-(4-chlorophenyl)-4-(cyclopropylmethyl)-3-oxo-2-morpholinyl)acetic acid | 1.33 | | |
| N-((2R)-2-((2S,3R)-2,3-bis(4-chlorophenyl)-5-oxo-4-morpholinyl)pentyl)methanesulfonamide and N-((2S)-2-((2R,3S)-2,3-bis(4-chlorophenyl)-5-oxo-4-morpholinyl)pentyl)methanesulfonamide | | 5.12 | 7.15 |
| (2R,5S,6R)-5,6-bis(4-chlorophenyl)-2-(4-fluorobenzyl)-4-((1S)-1-((4-methyl-1-piperazinyl)carbonyl)butyl)-3-morpholinone and (2S,5R,6S)-5,6-bis(4-chlorophenyl)-2-(4-fluorobenzyl)-4-((1R)-1-((4-methyl-1-piperazinyl)carbonyl)butyl)-3-morpholinone | | 0.922 | 0.583 |
| (2R,5S,6R)-5,6-bis(4-chlorophenyl)-2-(4-fluorobenzyl)-4-((1S)-1-(4-morpholinylcarbonyl)butyl)-3-morpholinone and (2S,5R,6S)-5,6-bis(4-chlorophenyl)-2-(4-fluorobenzyl)-4-((1R)-1-(4-morpholinylcarbonyl)butyl)-3-morpholinone | | 1.05 | 1.27 |
| (2R,5S,6R)-4-((1S)-1-(aminomethyl)butyl)-5,6-bis(4-chlorophenyl)-2-(4-fluorobenzyl)-3-morpholinone and (2S,5R,6S)-4-((1R)-1-(aminomethyl)butyl)-5,6-bis(4-chlorophenyl)-2-(4-fluorobenzyl)-3-morpholinone | | 4.65 | 3.09 |
| (5R,6S)-2-benzyl-5,6-bis(4-chlorophenyl)-4-methyl-3-morpholinone or (5S,6R)-2-benzyl-5,6-bis(4-chlorophenyl)-4-methyl-3-morpholinone | 1.45 | 4.88 | 8.31 |
| ((2R,5S,6R)-6-(3-chlorophenyl)-5-(4-chlorophenyl)-4-(cyclopropylsulfonyl)-3-oxo-2-morpholinyl)acetic acid and ((2S,5R,6S)-6-(3-chlorophenyl)-5-(4-chlorophenyl)-4-(cyclopropylsulfonyl)-3-oxo-2-morpholinyl)acetic acid | | 4.21 | 1.47 |
| (2R,5S,6R)-5,6-bis(4-chlorophenyl)-2-(4-fluorobenzyl)-4-((1S)-1-(4-morpholinylmethyl)butyl)-3-morpholinone and (2S,5R,6S)-5,6-bis(4-chlorophenyl)-2-(4-fluorobenzyl)-4-((1R)-1-(4-morpholinylmethyl)butyl)-3-morpholinone | | | 55.1 |
| (2R)-2-((2S,3R,6S)-3-(4-chlorophenyl)-6-(4-fluorobenzyl)-5-oxo-2-phenyl-4-morpholinyl)pentanoic acid and (2S)-2-((2R,3S,6R)-3-(4-chlorophenyl)-6-(4-fluorobenzyl)-5-oxo-2-phenyl-4-morpholinyl)pentanoic acid or (2S)-2-((2S,3R,6S)-3-(4-chlorophenyl)-6-(4-fluorobenzyl)-5-oxo-2-phenyl-4-morpholinyl)pentanoic acid and (2R)-2-((2R,3S,6R)-3-(4-chlorophenyl)-6-(4-fluorobenzyl)-5-oxo-2-phenyl-4-morpholinyl)pentanoic acid | | 1.47 | |
| (2R)-2-((2S,3R,6S)-2,3-bis(4-chlorophenyl)-6-(2-(4-morpholinyl)ethyl)-5-oxo-4-morpholinyl)pentanoic acid | | 1.49 | |
| (2R)-((2S,3R,6S)-2,3-bis(4-chlorophenyl)-6-(4-fluorobenzyl)-5-oxo-4- | | 1.52 | |

TABLE 2-continued

| Compound Name | HTRF1 IC$_{50}$ (μM) | HTRF2 IC$_{50}$ (μM) | HTRF3 IC$_{50}$ (μM) |
|---|---|---|---|
| morpholinyl)(phenyl)ethanoic acid and (2S)-((2R,3S,6R)-2,3-bis(4-chlorophenyl)-6-(4-fluorobenzyl)-5-oxo-4-morpholinyl)(phenyl)ethanoic acid or (2S)-((2S,3R,6S)-2,3-bis(4-chlorophenyl)-6-(4-fluorobenzyl)-5-oxo-4-morpholinyl)(phenyl)ethanoic acid and (2R)-((2R,3S,6R)-2,3-bis(4-chlorophenyl)-6-(4-fluorobenzyl)-5-oxo-4-morpholinyl)(phenyl)ethanoic acid | | | |
| (2R)-2-((2S,3R)-2-(4-chlorophenyl)-3-(3,4-dichlorophenyl)-5-oxo-4-morpholinyl)pentanoic acid and (2S)-2-((2R,3S)-2-(4-chlorophenyl)-3-(3,4-dichlorophenyl)-5-oxo-4-morpholinyl)pentanoic acid or (2S)-2-((2S,3R)-2-(4-chlorophenyl)-3-(3,4-dichlorophenyl)-5-oxo-4-morpholinyl)pentanoic acid and (2R)-2-((2R,3S)-2-(4-chlorophenyl)-3-(3,4-dichlorophenyl)-5-oxo-4-morpholinyl)pentanoic acid | | | 48.9 |
| (5R,6S)-6-(3-chlorophenyl)-5-(4-chlorophenyl)-4-(1-methylethyl)-3-thiomorpholinone 1,1-dioxide | 1.56 | | |
| (2R)-2-((2S,3R,6S)-2-(3-chlorophenyl)-3-(4-chlorophenyl)-6-(2-(4-morpholinyl)-2-oxoethyl)-5-oxo-4-morpholinyl)pentanoic acid and (2S)-2-((2R,3S,6R)-2-(3-chlorophenyl)-3-(4-chlorophenyl)-6-(2-(4-morpholinyl)-2-oxoethyl)-5-oxo-4-morpholinyl)pentanoic acid or (2S)-2-((2S,3R,6S)-2-(3-chlorophenyl)-3-(4-chlorophenyl)-6-(2-(4-morpholinyl)-2-oxoethyl)-5-oxo-4-morpholinyl)pentanoic acid and (2R)-2-((2R,3S,6R)-2-(3-chlorophenyl)-3-(4-chlorophenyl)-6-(2-(4-morpholinyl)-2-oxoethyl)-5-oxo-4-morpholinyl)pentanoic acid | | 1.6 | 4.31 |
| (2R)-2-((2S,3R)-3-(4-bromophenyl)-2-(4-chlorophenyl)-5-oxo-4-morpholinyl)pentanoic acid and (2S)-2-((2R,3S)-3-(4-bromophenyl)-2-(4-chlorophenyl)-5-oxo-4-morpholinyl)pentanoic acid or (2S)-2-((2S,3R)-3-(4-bromophenyl)-2-(4-chlorophenyl)-5-oxo-4-morpholinyl)pentanoic acid and (2R)-2-((2R,3S)-3-(4-bromophenyl)-2-(4-chlorophenyl)-5-oxo-4-morpholinyl)pentanoic acid | | 2.69 | 11.6 |
| (2R)-2-((2S,3R,6S)-2,3-bis(4-chlorophenyl)-5-oxo-6-(2-(1-piperidinyl)ethyl)-4-morpholinyl)pentanoic acid | | 1.73 | |
| (2R)-2-((2S,3R)-2-(4-chlorophenyl)-3-(4-cyclopropylphenyl)-5-oxo-4-morpholinyl)pentanoic acid and (2S)-2-((2R,3S)-2-(4-chlorophenyl)-3-(4-cyclopropylphenyl)-5-oxo-4-morpholinyl)pentanoic acid or (2S)-2-((2S,3R)-2-(4-chlorophenyl)-3-(4-cyclopropylphenyl)-5-oxo-4-morpholinyl)pentanoic acid and (2R)-2-((2R,3S)-2-(4-chlorophenyl)-3-(4-cyclopropylphenyl)-5-oxo-4-morpholinyl)pentanoic acid | | | 64.9 |
| (2R)-2-((2S,3R,6S)-3-(4-bromophenyl)-2-(4-chlorophenyl)-6-(4-fluorobenzyl)-5-oxo-4-morpholinyl)pentanoic acid and (2S)-2-((2R,3S,6R)-3-(4-bromophenyl)-2-(4-chlorophenyl)-6-(4-fluorobenzyl)-5-oxo-4-morpholinyl)pentanoic acid or (2S)-2-((2S,3R,6S)-3-(4-bromophenyl)-2-(4-chlorophenyl)-6-(4-fluorobenzyl)-5-oxo-4-morpholinyl)pentanoic acid and (2R)-2-((2R,3S,6R)-3-(4-bromophenyl)-2-(4-chlorophenyl)-6-(4-fluorobenzyl)-5-oxo-4-morpholinyl)pentanoic acid | | 0.707 | 1.28 |
| 2-(((2R,5S,6R)-5,6-bis(4-chlorophenyl)-4-methyl-3-oxo-2-morpholinyl)methyl)benzonitrile and 2-(((2S,5R,6S)-5,6-bis(4-chlorophenyl)-4-methyl-3-oxo-2-morpholinyl)methyl)benzonitrile | | 1.77 | 8.03 |
| (2R)-2-((2S,3R,6S)-2-(3-chlorophenyl)-3-(4-chlorophenyl)-6-(4-fluorobenzyl)-5-oxo-4-morpholinyl)pentanamide and (2S)-2-((2R,3S,6R)-2-(3-chlorophenyl)-3-(4- | | 2.5 | 1.81 |

TABLE 2-continued

| Compound Name | HTRF1 IC$_{50}$ (μM) | HTRF2 IC$_{50}$ (μM) | HTRF3 IC$_{50}$ (μM) |
|---|---|---|---|
| chlorophenyl)-6-(4-fluorobenzyl)-5-oxo-4-morpholinyl)pentanamide or (2S)-2-((2S,3R,6S)-2-(3-chlorophenyl)-3-(4-chlorophenyl)-6-(4-fluorobenzyl)-5-oxo-4-morpholinyl)pentanamide and (2R)-2-((2R,3S,6R)-2-(3-chlorophenyl)-3-(4-chlorophenyl)-6-(4-fluorobenzyl)-5-oxo-4-morpholinyl)pentanamide | | | |
| (2R)-2-((2S,3R,6S)-2,3-bis(4-chlorophenyl)-6-(2-fluoro-4-(methylsulfonyl)benzyl)-5-oxo-4-morpholinyl)pentanoic acid and (2S)-2-((2R,3S,6R)-2,3-bis(4-chlorophenyl)-6-(2-fluoro-4-(methylsulfonyl)benzyl)-5-oxo-4-morpholinyl)pentanoic acid | | 1.82 | |
| (2R)-2-((2S,3R,6S)-2,3-bis(4-chlorophenyl)-6-(4-fluorobenzyl)-5-oxo-4-morpholinyl)hexanoic acid and (2S)-2-((2R,3S,6R)-2,3-bis(4-chlorophenyl)-6-(4-fluorobenzyl)-5-oxo-4-morpholinyl)hexanoic acid or (2S)-2-((2S,3R,6S)-2,3-bis(4-chlorophenyl)-6-(4-fluorobenzyl)-5-oxo-4-morpholinyl)hexanoic acid and (2R)-2-((2R,3S,6R)-2,3-bis(4-chlorophenyl)-6-(4-fluorobenzyl)-5-oxo-4-morpholinyl)hexanoic acid | | 2.13 | 1.86 |
| (2R,5S,6R)-5,6-bis(4-chlorophenyl)-2-(4-fluorobenzyl)-4-((1S)-1-(1H-tetrazol-5-yl)butyl)-3-morpholinone and (2S,5R,6S)-5,6-bis(4-chlorophenyl)-2-(4-fluorobenzyl)-4-((1R)-1-(1H-tetrazol-5-yl)butyl)-3-morpholinone | | 1.33 | 0.845 |
| N-((2R)-2-((2S,3R,6S)-2,3-bis(4-chlorophenyl)-6-(4-fluorobenzyl)-5-oxo-4-morpholinyl)pentanoyl)glycine and N-((2S)-2-((2R,3S,6R)-2,3-bis(4-chlorophenyl)-6-(4-fluorobenzyl)-5-oxo-4-morpholinyl)pentanoyl)glycine | | | 0.909 |
| (2R)-2-((2S,3R,6S)-3-(4-bromophenyl)-2-(4-chlorophenyl)-6-(4-cyanobenzyl)-5-oxo-4-morpholinyl)pentanoic acid and (2S)-2-((2R,3S,6R)-3-(4-bromophenyl)-2-(4-chlorophenyl)-6-(4-cyanobenzyl)-5-oxo-4-morpholinyl)pentanoic acid | | 0.358 | 0.584 |
| 3-((2R,5S,6R)-6-(3-chlorophenyl)-5-(4-chlorophenyl)-4-(cyclopropylmethyl)-3-oxo-2-morpholinyl)propanenitrile and 3-((2S,5R,6S)-6-(3-chlorophenyl)-5-(4-chlorophenyl)-4-(cyclopropylmethyl)-3-oxo-2-morpholinyl)propanenitrile | 2.01 | 6.3 | 16.3 |
| ((2S,5S,6R)-6-(3-chlorophenyl)-5-(4-chlorophenyl)-4-(cyclopropylmethyl)-3-oxo-2-morpholinyl)acetic acid or ((2R,5R,6S)-6-(3-chlorophenyl)-5-(4-chlorophenyl)-4-(cyclopropylmethyl)-3-oxo-2-morpholinyl)acetic acid or ((2R,5S,6R)-6-(3-chlorophenyl)-5-(4-chlorophenyl)-4-(cyclopropylmethyl)-3-oxo-2-morpholinyl)acetic acid or ((2S,5R,6S)-6-(3-chlorophenyl)-5-(4-chlorophenyl)-4-(cyclopropylmethyl)-3-oxo-2-morpholinyl)acetic acid | 2.04 | | |
| 2-((2R,5S,6R)-6-(3-chlorophenyl)-5-(4-chlorophenyl)-4-(cyclopropylmethyl)-3-oxo-2-morpholinyl)-N-(2-(4-morpholinyl)ethyl)acetamide and 2-((2S,5R,6S)-6-(3-chlorophenyl)-5-(4-chlorophenyl)-4-(cyclopropylmethyl)-3-oxo-2-morpholinyl)-N-(2-(4-morpholinyl)ethyl)acetamide | | 2.05 | 3.58 |
| (2R)-2-((2S,3R)-2-(3-chlorophenyl)-3-(4-chlorophenyl)-6-(4-fluorobenzyl)-5-oxo-4-morpholinyl)pentanoic acid and (2S)-2-((2R,3S)-2-(3-chlorophenyl)-3-(4-chlorophenyl)-6-(4-fluorobenzyl)-5-oxo-4-morpholinyl)pentanoic acid or (2S)-2-((2S,3R)-2-(3-chlorophenyl)-3-(4-chlorophenyl)-6-(4-fluorobenzyl)-5-oxo-4-morpholinyl)pentanoic acid and (2R)-2-((2R,3S)-2-(3-chlorophenyl)-3-(4-chlorophenyl)-6-(4-fluorobenzyl)-5-oxo-4-morpholinyl)pentanoic acid | | 3.92 | 2.09 |
| (S)-2-((2R,5S,6R)-6-(3-chlorophenyl)-5-(4-chlorophenyl)-4-(cyclopropylmethyl)-3- | | 2.09 | 2.56 |

TABLE 2-continued

| Compound Name | HTRF1 IC$_{50}$ (μM) | HTRF2 IC$_{50}$ (μM) | HTRF3 IC$_{50}$ (μM) |
|---|---|---|---|
| oxomorpholin-2-yl)-2-hydroxyacetic acid and (R)-2-((2S,5R,6S)-6-(3-chlorophenyl)-5-(4-chlorophenyl)-4-(cyclopropylmethyl)-3-oxomorpholin-2-yl)-2-hydroxyacetic acid or (R)-2-((2R,5S,6R)-6-(3-chlorophenyl)-5-(4-chlorophenyl)-4-(cyclopropylmethyl)-3-oxomorpholin-2-yl)-2-hydroxyacetic acid and (S)-2-((2S,5R,6S)-6-(3-chlorophenyl)-5-(4-chlorophenyl)-4-(cyclopropylmethyl)-3-oxomorpholin-2-yl)-2-hydroxyacetic acid | | | |
| (2R)-2-((2S,3R,6S)-2-(3-chlorophenyl)-3-(4-chlorophenyl)-6-((2S)-2,3-dihydroxypropyl)-5-oxo-4-morpholinyl)pentanamide and (2S)-2-((2R,3S,6R)-2-(3-chlorophenyl)-3-(4-chlorophenyl)-6-((2R)-2,3-dihydroxypropyl)-5-oxo-4-morpholinyl)pentanamide or (2S)-2-((2S,3R,6S)-2-(3-chlorophenyl)-3-(4-chlorophenyl)-6-((2S)-2,3-dihydroxypropyl)-5-oxo-4-morpholinyl)pentanamide and (2R)-2-((2R,3S,6R)-2-(3-chlorophenyl)-3-(4-chlorophenyl)-6-((2R)-2,3-dihydroxypropyl)-5-oxo-4-morpholinyl)pentanamide or (2R)-2-((2S,3R,6S)-2-(3-chlorophenyl)-3-(4-chlorophenyl)-6-((2R)-2,3-dihydroxypropyl)-5-oxo-4-morpholinyl)pentanamideand (2S)-2-((2R,3S,6R)-2-(3-chlorophenyl)-3-(4-chlorophenyl)-6-((2S)-2,3-dihydroxypropyl)-5-oxo-4-morpholinyl)pentanamide or (2S)-2-((2S,3R,6S)-2-(3-chlorophenyl)-3-(4-chlorophenyl)-6-((2R)-2,3-dihydroxypropyl)-5-oxo-4-morpholinyl)pentanamideand (2R)-2-((2R,3S,6R)-2-(3-chlorophenyl)-3-(4-chlorophenyl)-6-((2S)-2,3-dihydroxypropyl)-5-oxo-4-morpholinyl)pentanamide | | 2.1 | 2.25 |
| ((2R,5S,6R)-6-(3-chloro-2-fluorophenyl)-5-(4-chlorophenyl)-4-(cyclopropylmethyl)-3-oxo-2-morpholinyl)acetic acid and ((2S,5R,6S)-6-(3-chloro-2-fluorophenyl)-5-(4-chlorophenyl)-4-(cyclopropylmethyl)-3-oxo-2-morpholinyl)acetic acid | | | 32.6 |
| ((2R,5S,6R)-4-butyl-6-(3-chlorophenyl)-5-(4-chlorophenyl)-3-oxo-2-morpholinyl)acetic acid and ((2S,5R,6S)-4-butyl-6-(3-chlorophenyl)-5-(4-chlorophenyl)-3-oxo-2-morpholinyl)acetic acid | | 2.35 | 2.14 |
| (2R)-2-((2S,3R)-3-(4-chlorophenyl)-2-(2,4-dichlorophenyl)-5-oxo-4-morpholinyl)pentanoic acid, (2S)-2-((2R,3S)-3-(4-chlorophenyl)-2-(2,4-dichlorophenyl)-5-oxo-4-morpholinyl)pentanoic acid or (2S)-2-((2S,3R)-3-(4-chlorophenyl)-2-(2,4-dichlorophenyl)-5-oxo-4-morpholinyl)pentanoic acid, (2R)-2-((2R,3S)-3-(4-chlorophenyl)-2-(2,4-dichlorophenyl)-5-oxo-4-morpholinyl)pentanoic acid | | | 33.3 |
| N'-acetyl-2((2R,5S,6R)-6-(3-chlorophenyl)-5-(4-chlorophenyl)-4-(cyclopropylmethyl)-3-oxo-2-morpholinyl)acetohydrazide and N'-acetyl-2-((2S,5R,6S)-6-(3-chlorophenyl)-5-(4-chlorophenyl)-4-(cyclopropylmethyl)-3-oxo-2-morpholinyl)acetohydrazide | | 6.06 | 2.15 |
| (2R,5S,6R)-6-(3-chlorophenyl)-5-(4-chlorophenyl)-4-(cyclopropylmethyl)-2-(2-(4-morpholinyl)-2-oxoethyl)-3-morpholinone and (2S,5R,6S)-6-(3-chlorophenyl)-5-(4-chlorophenyl)-4-(cyclopropylmethyl)-2-(2-(4-morpholinyl)-2-oxoethyl)-3-morpholinone | | 2.92 | 2.18 |
| (2R)-2-((2S,3R)-2-(3-chlorophenyl)-3-(4-chlorophenyl)-5-oxo-4-morpholinyl)pentanamide and (2S)-2-((2R,3S)-2-(3-chlorophenyl)-3-(4-chlorophenyl)-5-oxo-4-morpholinyl)pentanamide or (2S)-2-((2S,3R)-2-(3-chlorophenyl)-3-(4-chlorophenyl)-5-oxo-4-morpholinyl)pentanamide and (2R)-2-((2R,3S)-2-(3-chlorophenyl)-3-(4-chlorophenyl)-5-oxo-4-morpholinyl)pentanamide | | 2.78 | 2.19 |
| 2-((2R,5S,6R)-6-(3-chlorophenyl)-5-(4-chlorophenyl)-4-(cyclopropylmethyl)-3-oxo-2-morpholinyl)ethyl carbamateand 2-((2S,5R,6S)-6- | | 2.25 | 4.46 |

TABLE 2-continued

| Compound Name | HTRF1 IC$_{50}$ (µM) | HTRF2 IC$_{50}$ (µM) | HTRF3 IC$_{50}$ (µM) |
|---|---|---|---|
| (3-chlorophenyl)-5-(4-chlorophenyl)-4-(cyclopropylmethyl)-3-oxo-2-morpholinyl)ethyl carbamate | | | |
| (2R)-((2S,3R,6S)-2,3-bis(4-chlorophenyl)-6-(4-fluorobenzyl)-5-oxo-4-morpholinyl)(3-chlorophenyl)ethanoic acid and (2S)-((2R,3S,6R)-2,3-bis(4-chlorophenyl)-6-(4-fluorobenzyl)-5-oxo-4-morpholinyl)(3-chlorophenyl)ethanoic acid or (2S)-((2S,3R,6S)-2,3-bis(4-chlorophenyl)-6-(4-fluorobenzyl)-5-oxo-4-morpholinyl)(3-chlorophenyl)ethanoic acid and (2R)-((2R,3S,6R)-2,3-bis(4-chlorophenyl)-6-(4-fluorobenzyl)-5-oxo-4-morpholinyl)(3-chlorophenyl)ethanoic acid | | 2.25 | |
| ((2S,5S,6R)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid or ((2R,5R,6S)-6-(3-chlorophenyl)-5-(4-chlorophenyl)-4-((1R)-1-(((cyclopropylsulfonyl)(phenyl)amino)methyl)propyl)-3-oxo-2-morpholinyl)acetic acid or ((2S,5S,6R)-6-(3-chlorophenyl)-5-(4-chlorophenyl)-4-((1R)-1-(((cyclopropylsulfonyl)(phenyl)amino)methyl)propyl)-3-oxo-2-morpholinyl)acetic acid or ((2R,5R,6S)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid or ((2R,5S,6R)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid or ((2S,5R,6S)-6-(3-chlorophenyl)-5-(4-chlorophenyl)-4-((1R)-1-(((cyclopropylsulfonyl)(phenyl)amino)methyl)propyl)-3-oxo-2-morpholinyl)acetic acid or ((2R,5S,6R)-6-(3-chlorophenyl)-5-(4-chlorophenyl)-4-((1R)-1-(((cyclopropylsulfonyl)(phenyl)amino)methyl)propyl)-3-oxo-2-morpholinyl)acetic acid or ((2S,5R,6S)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid | 2.32 | | |
| (2R)-2-((2S,3R,6S)-3-(4-chlorophenyl)-2-(2,4-dichlorophenyl)-6-(4-fluorobenzyl)-5-oxo-4-morpholinyl)pentanoic acid and (2S)-2-((2R,3S,6R)-3-(4-chlorophenyl)-2-(2,4-dichlorophenyl)-6-(4-fluorobenzyl)-5-oxo-4-morpholinyl)pentanoic acid or (2S)-2-((2S,3R,6S)-3-(4-chlorophenyl)-2-(2,4-dichlorophenyl)-6-(4-fluorobenzyl)-5-oxo-4-morpholinyl)pentanoic acid and (2R)-2-((2R,3S,6R)-3-(4-chlorophenyl)-2-(2,4-dichlorophenyl)-6-(4-fluorobenzyl)-5-oxo-4-morpholinyl)pentanoic acid | | 2.16 | 1.23 |
| 4-(((2R)-2-((2S,3R,6S)-2,3-bis(4-chlorophenyl)-6-(4-(methylsulfonyl)benzyl)-5-oxo-4-morpholinyl)pentanoyl)amino)butanoic acid | | 2.44 | |
| ((2R,5S,6R)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid and ((2S,5S,6R)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid or ((2S,5R,6S)-6-(3-chlorophenyl)-5-(4-chlorophenyl)-4-((1R)-1-(((cyclopropylsulfonyl)(phenyl)amino)methyl)propyl)-3-oxo-2-morpholinyl)acetic acid and ((2R,5R,6S)-6-(3-chlorophenyl)-5-(4-chlorophenyl)-4-((1R)-1-(((cyclopropylsulfonyl)(phenyl)amino)methyl) | 2.57 | | |

TABLE 2-continued

| Compound Name | HTRF1 IC$_{50}$ (µM) | HTRF2 IC$_{50}$ (µM) | HTRF3 IC$_{50}$ (µM) |
|---|---|---|---|
| propyl)-3-oxo-2-morpholinyl)acetic acid or ((2R,5S,6R)-6-(3-chlorophenyl)-5-(4-chlorophenyl)-4-((1R)-1-(((cyclopropylsulfonyl)(phenyl)amino)methyl)propyl)-3-oxo-2-morpholinyl)acetic acid and ((2S,5S,6R)-6-(3-chlorophenyl)-5-(4-chlorophenyl)-4-((1R)-1-(((cyclopropylsulfonyl)(phenyl)amino)methyl)propyl)-3-oxo-2-morpholinyl)acetic acid or ((2S,5R,6S)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid and ((2R,5R,6S)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid | | | |
| (S)-2-((2S,5R,6S)-6-(3-chlorophenyl)-5-(4-chlorophenyl)-4-(cyclopropylmethyl)-3-oxomorpholin-2-yl)-2-hydroxyacetic acid and (R)-2-((2R,5S,6R)-6-(3-chlorophenyl)-5-(4-chlorophenyl)-4-(cyclopropylmethyl)-3-oxomorpholin-2-yl)-2-hydroxyacetic acid or (R)-2-((2S,5R,6S)-6-(3-chlorophenyl)-5-(4-chlorophenyl)-4-(cyclopropylmethyl)-3-oxomorpholin-2-yl)-2-hydroxyacetic acid and (S)-2-((2R,5S,6R)-6-(3-chlorophenyl)-5-(4-chlorophenyl)-4-(cyclopropylmethyl)-3-oxomorpholin-2-yl)-2-hydroxyacetic acid | | 2.59 | 3.19 |
| 3-((2R,3S)-3-(4-chlorophenyl)-4-(cyclopropylmethyl)-5-oxo-2-morpholinyl)benzonitrile and 3-((2S,3R)-3-(4-chlorophenyl)-4-(cyclopropylmethyl)-5-oxo-2-morpholinyl)benzonitrile | | 19 | 29.8 |
| (2R)-2-((2R,3S,6R)-2-(3-chlorophenyl)-3-(4-chlorophenyl)-6-(4-fluorobenzyl)-5-oxo-4-morpholinyl)pentanoic acid and (2S)-2-((2S,3R,6S)-2-(3-chlorophenyl)-3-(4-chlorophenyl)-6-(4-fluorobenzyl)-5-oxo-4-morpholinyl)pentanoic acid or (2S)-2-((2R,3S,6R)-2-(3-chlorophenyl)-3-(4-chlorophenyl)-6-(4-fluorobenzyl)-5-oxo-4-morpholinyl)pentanoic acid and (2R)-2-((2S,3R,6S)-2-(3-chlorophenyl)-3-(4-chlorophenyl)-6-(4-fluorobenzyl)-5-oxo-4-morpholinyl)pentanoic acid | 2.66 | 12.7 | 7.21 |
| N-((2R)-2-((2S,3R,6S)-2,3-bis(4-chlorophenyl)-6-(4-cyanobenzyl)-5-oxo-4-morpholinyl)pentanoyl)glycine and N-((2S)-2-((2R,3S,6R)-2,3-bis(4-chlorophenyl)-6-(4-cyanobenzyl)-5-oxo-4-morpholinyl)pentanoyl)glycine | | 0.63 | 0.446 |
| N-((2R)-2-((2S,3R)-2,3-bis(4-chlorophenyl)-5-oxo-4-morpholinyl)pentanoyl)glycine and N-((2S)-2-((2R,3S)-2,3-bis(4-chlorophenyl)-5-oxo-4-morpholinyl)pentanoyl)glycine | | 5.05 | 7.64 |
| 2-((2R,5S,6R)-6-(3-chlorophenyl)-5-(4-chlorophenyl)-4-(cyclopropylmethyl)-3-oxo-2-morpholinyl)-N,N-dimethylacetamide and 2-((2S,5R,6S)-6-(3-chlorophenyl)-5-(4-chlorophenyl)-4-(cyclopropylmethyl)-3-oxo-2-morpholinyl)-N,N-dimethylacetamide | | 7.56 | 2.78 |
| ethyl (2R)-2-((2S,3R,6S)-2,3-bis(4-chlorophenyl)-6-(3-(4-chlorophenyl)propyl)-5-oxo-4-morpholinyl)pentanoate | | 2.79 | |
| (2R)-2-((2S,3R)-3-(4-chlorophenyl)-2-(4-cyanophenyl)-5-oxo-4-morpholinyl)pentanoic acid and (2S)-2-((2R,3S)-3-(4-chlorophenyl)-2-(4-cyanophenyl)-5-oxo-4-morpholinyl)pentanoic acid or (2S)-2-((2S,3R)-3-(4-chlorophenyl)-2-(4-cyanophenyl)-5-oxo-4-morpholinyl)pentanoic acid and (2R)-2-((2R,3S)-3-(4-chlorophenyl)-2-(4-cyanophenyl)-5-oxo-4-morpholinyl)pentanoic acid | | | 66.4 |

TABLE 2-continued

| Compound Name | HTRF1 IC$_{50}$ (μM) | HTRF2 IC$_{50}$ (μM) | HTRF3 IC$_{50}$ (μM) |
|---|---|---|---|
| (2R)-2-((2S,3R,6S)-2,3-bis(4-chlorophenyl)-6-(3-hydroxypropyl)-5-oxo-4-morpholinyl)pentanoic acid | | 3.01 | |
| (2R)-2-((2S,3R,6S)-2,3-bis(4-chlorophenyl)-6-(4-iodobenzyl)-5-oxo-4-morpholinyl)pentanamide and (2S)-2-((2R,3S,6R)-2,3-bis(4-chlorophenyl)-6-(4-iodobenzyl)-5-oxo-4-morpholinyl)pentanamide | | 0.912 | 1.16 |
| (2R)-2-((2S,3R,6S)-2,3-bis(4-chlorophenyl)-6-(4-fluorobenzyl)-5-oxo-4-morpholinyl)-4-pentenoic acid and (2S)-((2R,3S,6R)-2,3-bis(4-chlorophenyl)-6-(4-fluorobenzyl)-5-oxo-4-morpholinyl)-4-pentenoic acid or (2S)-2-((2S,3R,6S)-2,3-bis(4-chlorophenyl)-6-(4-fluorobenzyl)-5-oxo-4-morpholinyl)-4-pentenoic acid and (2R)-2-((2R,3S,6R)-2,3-bis(4-chlorophenyl)-6-(4-fluorobenzyl)-5-oxo-4-morpholinyl)-4-pentenoic acid | | 2.82 | 2.62 |
| (2R)-2-((2S,3R,6S)-2,3-bis(4-chlorophenyl)-6-(4-iodobenzyl)-5-oxo-4-morpholinyl)pentanenitrile and (2S)-2-((2R,3S,6R)-2,3-bis(4-chlorophenyl)-6-(4-iodobenzyl)-5-oxo-4-morpholinyl)pentanenitrile | | | 58.5 |
| 4-(((2R,5S,6R)-5,6-bis(4-chlorophenyl)-3-oxo-4-((1S)-1-(1H-tetrazol-5-yl)butyl)-2-morpholinyl)methyl)benzonitrile and 4-(((2S,5R,6S)-5,6-bis(4-chlorophenyl)-3-oxo-4-((1R)-1-(1H-tetrazol-5-yl)butyl)-2-morpholinyl)methyl)benzonitrile | | 0.415 | 0.391 |
| (5R,6S)-6-(3-chlorophenyl)-5-(4-chlorophenyl)-4-cyclopropylmethyl)-3-morpholinone or (5S,6R)-6-(3-chlorophenyl)-5-(4-chlorophenyl)-4-cyclopropylmethyl)-3-morpholinone | | 3.52 | 6.96 |
| (5R,6S)-6-(3-chlorophenyl)-5-(4-chlorophenyl)-4-(((1R,2R)-2-methylcyclopropyl)methyl)-3-morpholinone and (5R,6S)-6-(3-chlorophenyl)-5-(4-chlorophenyl)-4-(((1S,2S)-2-methylcyclopropyl)methyl)-3-morpholinone and (5S,6R)-6-(3-chlorophenyl)-5-(4-chlorophenyl)-4-(((1R,2R)-2-methylcyclopropyl)methyl)-3-morpholinone and (5S,6R)-6-(3-chlorophenyl)-5-(4-chlorophenyl)-4-(((1S,2S)-2-methylcyclopropyl)methyl)-3-morpholinone | | | 70.5 |
| N-((2R)-2-((2S,3R,6S)-2,3-bis(4-chlorophenyl)-6-(4-cyanobenzyl)-5-oxo-4-morpholinyl)pentanoyl)-beta-alanine and N-((2S)-2-((2R,3S,6R)-2,3-bis(4-chlorophenyl)-6-(4-cyanobenzyl)-5-oxo-4-morpholinyl)pentanoyl)-beta-alanine or N-((2S)-2-((2S,3R,6S)-2,3-bis(4-chlorophenyl)-6-(4-cyanobenzyl)-5-oxo-4-morpholinyl)pentanoyl)-beta-alanine and N-((2R)-2-((2R,3S,6R)-2,3-bis(4-chlorophenyl)-6-(4-cyanobenzyl)-5-oxo-4-morpholinyl)pentanoyl)-beta-alanine | | 0.428 | 0.263 |
| N-((2R)-2-((2R,3S,6R)-2,3-bis(4-chlorophenyl)-6-(4-cyanobenzyl)-5-oxo-4-morpholinyl)pentanoyl)-beta-alanine and N-((2S)-2-((2S,3R,6S)-2,3-bis(4-chlorophenyl)-6-(4-cyanobenzyl)-5-oxo-4-morpholinyl)pentanoyl)-beta-alanine or N-((2R)-2-((2R,3S,6R)-2,3-bis(4-chlorophenyl)-6-(4-cyanobenzyl)-5-oxo-4-morpholinyl)pentanoyl)-beta-alanine and N-((2S)-2-((2S,3R,6S)-2,3-bis(4-chlorophenyl)-6-(4-cyanobenzyl)-5-oxo-4-morpholinyl)pentanoyl)-beta-alanine | | 2.66 | 8.53 |
| N-((2R)-2-((2S,3R)-2,3-bis(4-chlorophenyl)-5-oxo-4-morpholinyl)pentanoyl)-beta-alanine and N-((2S)-2-((2R,3S)-2,3-bis(4-chlorophenyl)-5-oxo-4-morpholinyl)pentanoyl)-beta-alanine or N-((2S)-2-((2S,3R)-2,3-bis(4-chlorophenyl)-5-oxo-4-morpholinyl)pentanoyl)-beta-alanine and N-((2R)-2-((2R,3S)-2,3-bis(4-chlorophenyl)-5-oxo-4-morpholinyl)pentanoyl)-beta-alanine | | 3.05 | 3.78 |
| (5R,6S)-6-(3-chlorophenyl)-5-(4-chlorophenyl)-4-(cyclopropylsulfonyl)-3-morpholinone and | | 7.9 | 3.66 |

TABLE 2-continued

| Compound Name | HTRF1 IC$_{50}$ (μM) | HTRF2 IC$_{50}$ (μM) | HTRF3 IC$_{50}$ (μM) |
|---|---|---|---|
| (5S,6R)-6-(3-chlorophenyl)-5-(4-chlorophenyl)-4-(cyclopropylsulfonyl)-3-morpholinone | | | |
| 4-(((2R,5S,6R)-5,6-bis(4-chlorophenyl)-4-methyl-3-oxo-2-morpholinyl)methyl)benzamide and 4-(((2S,5R,6S)-5,6-bis(4-chlorophenyl)-4-methyl-3-oxo-2-morpholinyl)methyl)benzamide | | 3.66 | 5.8 |
| (3R)-3-((2S,3R,6S)-2-(3-chlorophenyl)-3-(4-chlorophenyl)-6-(4-fluorobenzyl)-5-oxo-4-morpholinyl)hexanoic acid | | 3.66 | |
| (((2R)-2-((2S,3R)-2,3-bis(4-chlorophenyl)-5-oxo-4-morpholinyl)pentyl)oxy)acetic acid and (((2S)-2-((2R,3S)-2,3-bis(4-chlorophenyl)-5-oxo-4-morpholinyl)pentyl)oxy)acetic acid | | 6.58 | 7.22 |
| (2R)-2-((2R,3S,6R)-2,3-bis(4-chlorophenyl)-6-(4-(methylsulfonyl)benzyl)-5-oxo-4-morpholinyl)pentanoic acid and (2S)-2-((2S,3R,6S)-2,3-bis(4-chlorophenyl)-6-(4-(methylsulfonyl)benzyl)-5-oxo-4-morpholinyl)pentanoic acid | | 3.75 | |
| 4-(((2R,5S,6R)-5,6-bis(4-chlorophenyl)-4-methyl-3-oxo-2-morpholinyl)methyl)-2-fluorobenzonitrile and 4-(((2S,5R,6S)-5,6-bis(4-chlorophenyl)-4-methyl-3-oxo-2-morpholinyl)methyl)-2-fluorobenzonitrile | | 6.3 | 3.8 |
| (2R,5S,6R)-5,6-bis(4-chlorophenyl)-2-(4-fluorobenzyl)-4-(4-pyridinyl)-3-morpholinone and (2S,5R,6S)-5,6-bis(4-chlorophenyl)-2-(4-fluorobenzyl)-4-(4-pyridinyl)-3-morpholinone | | 3.86 | |
| (2R,5S,6R)-6-(3-chlorophenyl)-5-(4-chlorophenyl)-4-(cyclopropylmethyl)-2-((5-methyl-1,3,4-oxadiazol-2-yl)methyl)-3-morpholinone and (2S,5R,6S)-6-(3-chlorophenyl)-5-(4-chlorophenyl)-4-(cyclopropylmethyl)-2-((5-methyl-1,3,4-oxadiazol-2-yl)methyl)-3-morpholinone | | 4.96 | 3.87 |
| (2R)-2-((2S,3R,6S)-2,3-bis(4-chlorophenyl)-6-(4-cyano-2-fluorobenzyl)-5-oxo-4-morpholinyl)pentanoic acid and (2S)-2-((2R,3S,6R)-2,3-bis(4-chlorophenyl)-6-(4-cyano-2-fluorobenzyl)-5-oxo-4-morpholinyl)pentanoic acid | | 1.12 | 0.927 |
| 3-(((2R)-2-((2S,3R)-2,3-bis(4-chlorophenyl)-5-oxo-4-morpholinyl)pentyl)amino)-3-oxopropanoic acid and 3-(((2S)-2-((2R,3S)-2,3-bis(4-chlorophenyl)-5-oxo-4-morpholinyl)pentyl)amino)-3-oxopropanoic acid | | 5.5 | 6.99 |
| N-((2R)-2-((2S,3R)-2,3-bis(4-chlorophenyl)-5-oxo-4-morpholinyl)pentyl)glycine and N-((2S)-2-((2R,3S)-2,3-bis(4-chlorophenyl)-5-oxo-4-morpholinyl)pentyl)glycine | | 7.12 | 10 |
| ((2R,5S,6R)-6-(3-chloro-4-fluorophenyl)-5-(4-chlorophenyl)-4-(cyclopropylmethyl)-3-oxo-2-morpholinyl)acetic acid and ((2S,5R,6S)-6-(3-chloro-4-fluorophenyl)-5-(4-chlorophenyl)-4-(cyclopropylmethyl)-3-oxo-2-morpholinyl)acetic acid | | 4.22 | 6.24 |
| (2R,5S,6R)-5,6-bis(4-chlorophenyl)-4-methyl-2-(4-(methylsulfonyl)benzyl)-3-morpholinone and (2S,5R,6S)-5,6-bis(4-chlorophenyl)-4-methyl-2-(4-(methylsulfonyl)benzyl)-3-morpholinone | | 4.33 | 7.97 |
| (2R)-2-((2S,3R,6S)-2,3-bis(4-chlorophenyl)-6-(4-cyanobenzyl)-5-oxo-4-morpholinyl)-N-(1H-tetrazol-5-ylmethyl)pentanamide and (2S)-2-((2R,3S,6R)-2,3-bis(4-chlorophenyl)-6-(4-cyanobenzyl)-5-oxo-4-morpholinyl)-N-(1H-tetrazol-5-ylmethyl)pentanamide | | 0.61 | 0.484 |
| ((2R,5S,6R)-6-(3-chlorophenyl)-5-(4-chlorophenyl)-4-(cyclopropylcarbonyl)-3-oxo-2-morpholinyl)acetic acid and ((2S,5R,6S)-6-(3-chlorophenyl)-5-(4-chlorophenyl)-4-(cyclopropylcarbonyl)-3-oxo-2-morpholinyl)acetic acid | | 10.8 | 4.65 |
| (5R,6S)-6-(3-chlorophenyl)-5-(4-chlorophenyl)-4-(cyclopropylmethyl)-3-thiomorpholinone 1,1-dioxide | | 4.76 | 22.4 |

TABLE 2-continued

| Compound Name | HTRF1 IC$_{50}$ (μM) | HTRF2 IC$_{50}$ (μM) | HTRF3 IC$_{50}$ (μM) |
| --- | --- | --- | --- |
| 2-((2R,5S,6R)-6-(3-chlorophenyl)-5-(4-chlorophenyl)-4-(cyclopropylmethyl)-3-oxo-2-morpholinyl)ethyl methanesulfonate and 2-((2S,5R,6S)-6-(3-chlorophenyl)-5-(4-chlorophenyl)-4-(cyclopropylmethyl)-3-oxo-2-morpholinyl)ethyl methanesulfonate | | 4.81 | 6.86 |
| (2R)-2-((2S,3R,6S)-2,3-bis(4-chlorophenyl)-6-(4-cyanobenzyl)-5-oxo-4-morpholinyl)-N-(2-(1H-tetrazol-5-yl)ethyl)pentanamide and (2S)-2-((2R,3S,6R)-2,3-bis(4-chlorophenyl)-6-(4-cyanobenzyl)-5-oxo-4-morpholinyl)-N-(2-(1H-tetrazol-5-yl)ethyl)pentanamide | | 2.03 | 0.425 |
| N-((2R)-2-((2S,3R)-2,3-bis(4-chlorophenyl)-5-oxo-4-morpholinyl)pentyl)-2-(1H-tetrazol-5-yl)acetamide and N-((2S)-2-((2R,3S)-2,3-bis(4-chlorophenyl)-5-oxo-4-morpholinyl)pentyl)-2-(1H-tetrazol-5-yl)acetamide | | 10.9 | 8.12 |
| 4-(((2R)-2-((2S,3R,6S)-2,3-bis(4-chlorophenyl)-6-(4-cyanobenzyl)-5-oxo-4-morpholinyl)pentanoyl)amino)butanoic acid and 4-(((2S)-2-((2R,3S,6R)-2,3-bis(4-chlorophenyl)-6-(4-cyanobenzyl)-5-oxo-4-morpholinyl)pentanoyl)amino)butanoic acid | | 0.452 | 0.339 |
| (2R)-2-((2S,3R,6S)-2,3-bis(4-chlorophenyl)-6-(4-cyanobenzyl)-5-oxo-4-morpholinyl)pentanoic acid | | 0.393 | 0.297 |
| (5R,6S)-5,6-bis(4-chlorophenyl)-4-(2-(methylsulfanyl)-4-pyrimidinyl)-3-morpholinone and (5S,6R)-5,6-bis(4-chlorophenyl)-4-(2-(methylsulfanyl)-4-pyrimidinyl)-3-morpholinone | | 5 | |
| 1-((2R)-2-((2S,3R)-2,3-bis(4-chlorophenyl)-5-oxo-4-morpholinyl)pentanoyl)-4-piperidinecarboxylic acid and 1-((2S)-2-((2R,3S)-2,3-bis(4-chlorophenyl)-5-oxo-4-morpholinyl)pentanoyl)-4-piperidinecarboxylic acid | | 3.36 | 5.5 |
| (4-((2R)-2-((2S,3R)-2,3-bis(4-chlorophenyl)-5-oxo-4-morpholinyl)pentanoyl)-1-piperazinyl)acetic acid and (4-((2S)-2-((2R,3S)-2,3-bis(4-chlorophenyl)-5-oxo-4-morpholinyl)pentanoyl)-1-piperazinyl)acetic acid | | 4.82 | 6.61 |
| (2S)-4-(((2R)-2-((2S,3R,6S)-2,3-bis(4-chlorophenyl)-6-(4-cyanobenzyl)-5-oxo-4-morpholinyl)pentanoyl)amino)-2-hydroxybutanoic acid and (2S)-4-(((2S)-2-((2R,3S,6R)-2,3-bis(4-chlorophenyl)-6-(4-cyanobenzyl)-5-oxo-4-morpholinyl)pentanoyl)amino)-2-hydroxybutanoic acid | | 0.459 | 0.294 |
| (3R)-4-(((2R)-2-((2S,3R,6S)-2,3-bis(4-chlorophenyl)-6-(4-cyanobenzyl)-5-oxo-4-morpholinyl)pentanoyl)amino)-3-hydroxybutanoic acid and (3R)-4-(((2S)-2-((2R,3S,6R)-2,3-bis(4-chlorophenyl)-6-(4-cyanobenzyl)-5-oxo-4-morpholinyl)pentanoyl)amino)-3-hydroxybutanoic acid and (3S)-4-(((2R)-2-((2S,3R,6S)-2,3-bis(4-chlorophenyl)-6-(4-cyanobenzyl)-5-oxo-4-morpholinyl)pentanoyl)amino)-3-hydroxybutanoic acid and (3S)-4-(((2S)-2-((2R,3S,6R)-2,3-bis(4-chlorophenyl)-6-(4-cyanobenzyl)-5-oxo-4-morpholinyl)pentanoyl)amino)-3-hydroxybutanoic acid | | 0.428 | 0.328 |
| (2R)-3-(((2R)-2-((2S,3R,6S)-2,3-bis(4-chlorophenyl)-6-(4-cyanobenzyl)-5-oxo-4-morpholinyl)pentanoyl)amino)-2-methylpropanoic acid and (2R)-3-(((2S)-2-((2R,3S,6R)-2,3-bis(4-chlorophenyl)-6-(4-cyanobenzyl)-5-oxo-4-morpholinyl)pentanoyl)amino)-2-methylpropanoic acid and (2S)-3-(((2R)-2-((2S,3R,6S)-2,3-bis(4-chlorophenyl)-6-(4-cyanobenzyl)-5-oxo-4-morpholinyl)pentanoyl)amino)-2- | | 0.386 | 0.358 |

TABLE 2-continued

| Compound Name | HTRF1 IC$_{50}$ (µM) | HTRF2 IC$_{50}$ (µM) | HTRF3 IC$_{50}$ (µM) |
|---|---|---|---|
| methylpropanoic acid and (2S)-3-(((2S)-2-((2R,3S,6R)-2,3-bis(4-chlorophenyl)-6-(4-cyanobenzyl)-5-oxo-4-morpholinyl)pentanoyl)amino)-2-methylpropanoic acid | | | |
| N-((2R)-2-((2S,3R,6S)-2,3-bis(4-chlorophenyl)-6-(4-cyanobenzyl)-5-oxo-4-morpholinyl)pentanoyl)-L-alanine and N-((2S)-2-((2R,3S,6R)-2,3-bis(4-chlorophenyl)-6-(4-cyanobenzyl)-5-oxo-4-morpholinyl)pentanoyl)-D-alanine | | 0.419 | 0.365 |
| (2R)-2-((2R,3S)-2-(4-chlorophenyl)-3-(1H-indol-2-yl)-5-oxo-4-morpholinyl)pentanoic acid and (2S)-2-((2S,3R)-2-(4-chlorophenyl)-3-(1H-indol-2-yl)-5-oxo-4-morpholinyl)pentanoic acid | | 5.9 | |
| N-((2R)-2-((2S,3R,6S)-2,3-bis(4-chlorophenyl)-6-(4-cyanobenzyl)-5-oxo-4-morpholinyl)pentanoyl)-D-alanine and N-((2S)-2-((2R,3S,6R)-2,3-bis(4-chlorophenyl)-6-(4-cyanobenzyl)-5-oxo-4-morpholinyl)pentanoyl)-L-alanine | | 0.44 | 0.537 |
| methyl 4-(((2R,5S,6R)-5,6-bis(4-chlorophenyl)-4-methyl-3-oxo-2-morpholinyl)methyl)benzoate and methyl 4-(((2S,5R,6S)-5,6-bis(4-chlorophenyl)-4-methyl-3-oxo-2-morpholinyl)methyl)benzoate | | 6.14 | 8.6 |
| 3-(((2R)-2-((2S,3R,6S)-2,3-bis(4-chlorophenyl)-6-(4-cyanobenzyl)-5-oxo-4-morpholinyl)pentanoyl)amino)-N-(tert-butoxycarbonyl)-D-alanine and 3-(((2S)-2-((2R,3S,6R)-2,3-bis(4-chlorophenyl)-6-(4-cyanobenzyl)-5-oxo-4-morpholinyl)pentanoyl)amino)-N-(tert-butoxycarbonyl)-D-alanine | | 0.66 | 0.795 |
| (5R,6S)-6-(3-chlorophenyl)-5-(4-chlorophenyl)-4-(cyclobutylmethyl)-3-morpholinone and (5S,6R)-6-(3-chlorophenyl)-5-(4-chlorophenyl)-4-(cyclobutylmethyl)-3-morpholinone | | 6.25 | 18.2 |
| 4-(((2R,5S,6R)-5,6-bis(4-chlorophenyl)-4-methyl-3-oxo-2-morpholinyl)methyl)benzonitrile and 4-(((2S,5R,6S)-5,6-bis(4-chlorophenyl)-4-methyl-3-oxo-2-morpholinyl)methyl)benzonitrile | | 6.3 | 7 |
| (4-((2R)-2-((2S,3R,6S)-2,3-bis(4-chlorophenyl)-6-(4-cyanobenzyl)-5-oxo-4-morpholinyl)pentanoyl)-1-piperazinyl)acetic acid and (4-((2S)-2-((2R,3S,6R)-2,3-bis(4-chlorophenyl)-6-(4-cyanobenzyl)-5-oxo-4-morpholinyl)pentanoyl)-1-piperazinyl)acetic acid | | 0.674 | 0.441 |
| 3-(((2R)-2-((2S,3R,6S)-2,3-bis(4-chlorophenyl)-6-(4-cyanobenzyl)-5-oxo-4-morpholinyl)pentanoyl)amino)-2,2-dimethylpropanoic acid and 3-(((2S)-2-((2R,3S,6R)-2,3-bis(4-chlorophenyl)-6-(4-cyanobenzyl)-5-oxo-4-morpholinyl)pentanoyl)amino)-2,2-dimethylpropanoic acid | | 0.633 | 0.345 |
| (5R,6S)-5,6-bis(4-chlorophenyl)-4-(2-chloro-4-pyridinyl)-3-morpholinone and (5S,6R)-5,6-bis(4-chlorophenyl)-4-(2-chloro-4-pyridinyl)-3-morpholinone | | 7.18 | |
| 3-(((2R,5S,6R)-5,6-bis(4-chlorophenyl)-4-methyl-3-oxo-2-morpholinyl)methyl)benzamide and 3-(((2S,5R,6S)-5,6-bis(4-chlorophenyl)-4-methyl-3-oxo-2-morpholinyl)methyl)benzamide | | 7.39 | 12.4 |
| 3-(((2R)-2-((2S,3R,6S)-2,3-bis(4-chlorophenyl)-6-(4-cyanobenzyl)-5-oxo-4-morpholinyl)pentanoyl)amino)-D-alanine and 3-(((2S)-2-((2R,3S,6R)-2,3-bis(4-chlorophenyl)-6-(4-cyanobenzyl)-5-oxo-4-morpholinyl)pentanoyl)amino)-D-alanine | | 0.95 | 0.542 |
| (2R)-2-((2S,3R,6S)-2,3-bis(4-chlorophenyl)-6-(4-methoxybenzyl)-5-oxo-4-morpholinyl)pentanoic acid and (2S)-2-((2R,3S,6R)-2,3-bis(4-chlorophenyl)-6-(4-methoxybenzyl)-5-oxo-4-morpholinyl)pentanoic acid | | 1.34 | 1.93 |

TABLE 2-continued

| Compound Name | HTRF1 IC$_{50}$ (μM) | HTRF2 IC$_{50}$ (μM) | HTRF3 IC$_{50}$ (μM) |
|---|---|---|---|
| (2R)-2-((2S,3R)-2-(3-chlorophenyl)-3-(4-chlorophenyl)-5-oxo-4-morpholinyl)pentanoic acid and (2S)-2-((2R,3S)-2-(3-chlorophenyl)-3-(4-chlorophenyl)-5-oxo-4-morpholinyl)pentanoic acid | | 7.81 | 19 |
| 3-(4-((2R)-2-((2S,3R)-2,3-bis(4-chlorophenyl)-5-oxo-4-morpholinyl)pentanoyl)-1-piperazinyl)propanoic acid and 3-(4-((2S)-2-((2R,3S)-2,3-bis(4-chlorophenyl)-5-oxo-4-morpholinyl)pentanoyl)-1-piperazinyl)propanoic acid | | 3.6 | 4.59 |
| (2R)-((2S,3R,6S)-2-(3-chlorophenyl)-3-(4-chlorophenyl)-6-(4-fluorobenzyl)-5-oxo-4-morpholinyl)(cyclopropyl)ethanoic acid and (2S)-((2R,3S,6R)-2-(3-chlorophenyl)-3-(4-chlorophenyl)-6-(4-fluorobenzyl)-5-oxo-4-morpholinyl)(cyclopropyl)ethanoic acid or (2S)-((2S,3R,6S)-2-(3-chlorophenyl)-3-(4-chlorophenyl)-6-(4-fluorobenzyl)-5-oxo-4-morpholinyl)(cyclopropyl)ethanoic acid and (2R)-((2R,3S,6R)-2-(3-chlorophenyl)-3-(4-chlorophenyl)-6-(4-fluorobenzyl)-5-oxo-4-morpholinyl)(cyclopropypethanoic acid | | 7.85 | 8.35 |
| (2R,5S,6R)-5,6-bis(4-chlorophenyl)-2-(4-fluorobenzyl)-4-(1-methyl-1H-imidazol-4-yl)-3-morpholinone and (2S,5R,6S)-5,6-bis(4-chlorophenyl)-2-(4-fluorobenzyl)-4-(1-methyl-1H-imidazol-4-yl)-3-morpholinone | | 7.9 | |
| 4-(((2R,5S,6R)-5,6-bis(4-chlorophenyl)-4-methyl-3-oxo-2-morpholinyl)methyl)benzoic acid and 4-(((2S,5R,6S)-5,6-bis(4-chlorophenyl)-4-methyl-3-oxo-2-morpholinyl)methyl)benzoic acid | | 7.99 | 13.3 |
| (5R,6S)-6-(3-chlorophenyl)-5-(4-chlorophenyl)-4-(2-methylpropyl)-3-morpholinone and (5S,6R)-6-(3-chlorophenyl)-5-(4-chlorophenyl)-4-(2-methylpropyl)-3-morpholinone | | 8.75 | 20.2 |
| 1-((2R)-2-((2S,3R,6S)-2,3-bis(4-chlorophenyl)-6-(4-fluorobenzyl)-5-oxo-4-morpholinyl)pentanoyl)-D-proline and 1-((2S)-2-((2R,3S,6R)-2,3-bis(4-chlorophenyl)-6-(4-fluorobenzyl)-5-oxo-4-morpholinyl)pentanoyl)-D-proline | | 1.05 | 1.01 |
| (5R,6S)-5,6-bis(4-chlorophenyl)-4-(2-pyrazinyl)-3-morpholinone and (5S,6R)-5,6-bis(4-chlorophenyl)-4-(2-pyrazinyl)-3-morpholinone | | 9.3 | |
| (2R,5S,6R)-5,6-bis(4-chlorophenyl)-4-(cyclopropylmethyl)-2-((2R)-2,3-dihydroxypropyl)-3-morpholinone and (2R,5S,6R)-5,6-bis(4-chlorophenyl)-4-(cyclopropylmethyl)-2-((2S)-2,3-dihydroxypropyl)-3-morpholinone and (2S,5R,6S)-5,6-bis(4-chlorophenyl)-4-(cyclopropylmethyl)-2-((2R)-2,3-dihydroxypropyl)-3-morpholinone and (2S,5R,6S)-5,6-bis(4-chlorophenyl)-4-(cyclopropylmethyl)-2-((2S)-2,3-dihydroxypropyl)-3-morpholinone | | 9.94 | 18.2 |
| (5R,6S)-6-(3-chlorophenyl)-5-(4-chlorophenyl)-4-cyclopentyl-3-morpholinone and (5S,6R)-6-(3-chlorophenyl)-5-(4-chlorophenyl)-4-cyclopentyl-3-morpholinone | | 10 | 16.6 |
| methyl 1-((2R)-2-((2S,3R,6S)-2,3-bis(4-chlorophenyl)-6-(4-fluorobenzyl)-5-oxo-4-morpholinyl)pentanoyl)-L-prolinate and methyl 1-((2S)-2-((2R,3S,6R)-2,3-bis(4-chlorophenyl)-6-(4-fluorobenzyl)-5-oxo-4-morpholinyl)pentanoyl)-L-prolinate | | 1.39 | 1.83 |
| (5R,6S)-5,6-bis(4-chlorophenyl)-4-methyl-3-morpholinone | 11.8 | | 38.6 |
| 1-((2R)-2-((2S,3R,6S)-2,3-bis(4-chlorophenyl)-6-(4-iodobenzyl)-5-oxo-4-morpholinyl)pentanoyl)-4-piperidinecarboxylic acid and 1-((2S)-2-((2R,3S,6R)-2,3-bis(4-chlorophenyl)-6-(4-iodobenzyl)-5-oxo-4-morpholinyl)pentanoyl)-4-piperidinecarboxylic acid | | 0.892 | 0.583 |

TABLE 2-continued

| Compound Name | HTRF1 IC$_{50}$ (μM) | HTRF2 IC$_{50}$ (μM) | HTRF3 IC$_{50}$ (μM) |
|---|---|---|---|
| (2R)-2-((2S,5R,6S)-2-(4-chlorobenzyl)-5,6-bis(4-chlorophenyl)-3-oxo-4-morpholinyl)pentanoic acid and (2S)-2-((2R,5S,6R)-2-(4-chlorobenzyl)-5,6-bis(4-chlorophenyl)-3-oxo-4-morpholinyl)pentanoic acid | | 1.26 | 1.19 |
| (2R,5S,6R)-2-(4-(aminomethyl)benzyl)-5,6-bis(4-chlorophenyl)-4-methyl-3-morpholinone and (2S,5R,6S)-2-(4-(aminomethyl)benzyl)-5,6-bis(4-chlorophenyl)-4-methyl-3-morpholinone | | 12.7 | 15.9 |
| 3-(((2R)-2-((2S,3R,6S)-2,3-bis(4-chlorophenyl)-6-(4-iodobenzyl)-5-oxo-4-morpholinyl)pentyl)amino)-3-oxopropanoic acid and 3-(((2S)-2-((2R,3S,6R)-2,3-bis(4-chlorophenyl)-6-(4-iodobenzyl)-5-oxo-4-morpholinyl)pentyl)amino)-3-oxopropanoic acid | | 18.4 | 17.7 |
| (5R,6S)-6-(3-chlorophenyl)-5-(4-chlorophenyl)-4-(1,3-thiazol-4-ylmethyl)-3-morpholinone and (5S,6R)-6-(3-chlorophenyl)-5-(4-chlorophenyl)-4-(1,3-thiazol-4-ylmethyl)-3-morpholinone | | 13.7 | 17.7 |
| (5R,6S)-6-(3-chlorophenyl)-5-(4-chlorophenyl)-4-(2-hydroxy-2-methylpropyl)-3-morpholinone and (5S,6R)-6-(3-chlorophenyl)-5-(4-chlorophenyl)-4-(2-hydroxy-2-methylpropyl)-3-morpholinone | | 14.5 | 15.9 |
| (5S,6R)-2-benzyl-5,6-bis(4-chlorophenyl)-4-methyl-3-morpholinone | 15.6 | | >100 [3] |
| ((2R,5S,6R)-6-(3-chlorophenyl)-5-(4-chlorophenyl)-4-((1-cyanocyclopropyl)methyl)-3-oxo-2-morpholinyl)acetic acid and ((2S,5R,6S)-6-(3-chlorophenyl)-5-(4-chlorophenyl)-4-((1-cyanocyclopropyl)methyl)-3-oxo-2-morpholinyl)acetic acid | | 16.1 | 28.3 |
| 1-(((((2R)-2-((2S,3R,6S)-2,3-bis(4-chlorophenyl)-6-(4-cyanobenzyl)-5-oxo-4-morpholinyl)pentanoyl)amino)methyl)cyclopentanecarboxylic acid and 1-(((((2S)-2-((2R,3S,6R)-2,3-bis(4-chlorophenyl)-6-(4-cyanobenzyl)-5-oxo-4-morpholinyl)pentanoyl)amino)methyl)cyclopentanecarboxylic acid | | 0.646 | 0.56 |
| (3S)-3-((2R,3S,6R)-2-(3-chlorophenyl)-3-(4-chlorophenyl)-6-(4-fluorobenzyl)-5-oxo-4-morpholinyl)hexanoic acid and (3S)-3-((2S,3R,6S)-2-(3-chlorophenyl)-3-(4-chlorophenyl)-6-(4-fluorobenzyl)-5-oxo-4-morpholinyl)hexanoic acid | | 16.4 | |
| (2R)-2-((2R,3S)-2-(3-chlorophenyl)-3-(4-chlorophenyl)-5-oxo-4-morpholinyl)pentanoic acid and (2R)-2-((2S,3R)-2-(3-chlorophenyl)-3-(4-chlorophenyl)-5-oxo-4-morpholinyl)pentanoic acid and (2S)-2-((2R,3S)-2-(3-chlorophenyl)-3-(4-chlorophenyl)-5-oxo-4-morpholinyl)pentanoic acid and (2S)-2-((2S,3R)-2-(3-chlorophenyl)-3-(4-chlorophenyl)-5-oxo-4-morpholinyl)pentanoic acid | | 16.8 | 19.5 |
| (2R)-2-((2S,3R,6S)-2,3-bis(4-chlorophenyl)-6-(4-iodobenzyl)-5-oxo-4-morpholinyl)pentanoic acid and (2S)-2-((2R,3S,6R)-2,3-bis(4-chlorophenyl)-6-(4-iodobenzyl)-5-oxo-4-morpholinyl)pentanoic acid | | 0.789 | |
| (5R,6S)-5,6-bis(4-chlorophenyl)-4-(4-pyridinyl)-3-morpholinone and (5S,6R)-5,6-bis(4-chlorophenyl)-4-(4-pyridinyl)-3-morpholinone | | 16.8 | 24.2 |
| (2R)-((2R,3S)-2-(3-chlorophenyl)-3-(4-chlorophenyl)-5-oxo-4-morpholinyl)(cyclopropyl)ethanoic acid and (2R)-((2S,3R)-2-(3-chlorophenyl)-3-(4-chlorophenyl)-5-oxo-4-morpholinyl)(cyclopropyl)ethanoic acid and (2S)-((2R,3S)-2-(3-chlorophenyl)-3-(4-chlorophenyl)-5-oxo-4-morpholinyl)(cyclopropyl)ethanoic acid and (2S)-((2S,3R)-2-(3-chlorophenyl)-3-(4-chlorophenyl)-5-oxo-4-morpholinyl)(cyclopropyl)ethanoic acid | | 16.9 | 17 |
| (2R)-2-((2R,3S)-2,3-bis(4-chlorophenyl)-5-oxo-4-morpholinyl)pentanoic acid and (2R)-2-((2S,3R)-2,3-bis(4-chlorophenyl)-5-oxo-4- | | 18.1 | 17.2 |

TABLE 2-continued

| Compound Name | HTRF1 IC$_{50}$ (μM) | HTRF2 IC$_{50}$ (μM) | HTRF3 IC$_{50}$ (μM) |
|---|---|---|---|
| morpholinyl)pentanoic acid and (2S)-2-((2R,3S)-2,3-bis(4-chlorophenyl)-5-oxo-4-morpholinyl)pentanoic acid and (2S)-2-((2S,3R)-2,3-bis(4-chlorophenyl)-5-oxo-4-morpholinyl)pentanoic acid | | | |
| (2R)-2-((2S,5R,6S)-2-(4-biphenylylmethyl)-5,6-bis(4-chlorophenyl)-3-oxo-4-morpholinyl)pentanoic acid and (2S)-2-((2R,5S,6R)-2-(4-biphenylylmethyl)-5,6-bis(4-chlorophenyl)-3-oxo-4-morpholinyl)pentanoic acid | | 1.44 | |
| ethyl (2R)-2-((2S,3R,6S)-2,3-bis(4-chlorophenyl)-6-(4-cyano-2-fluorobenzyl)-5-oxo-4-morpholinyl)pentanoate and ethyl (2S)-2-((2R,3S,6R)-2,3-bis(4-chlorophenyl)-6-(4-cyano-2-fluorobenzyl)-5-oxo-4-morpholinyl)pentanoate | | 17.4 | |
| (2R,5S,6R)-5,6-bis(4-chlorophenyl)-2-(4-((dimethylamino)methyl)benzyl)-4-methyl-3-morpholinone and (2S,5R,6S)-5,6-bis(4-chlorophenyl)-2-(4-((dimethylamino)methyl)benzyl)-4-methyl-3-morpholinone | | 17.5 | 22.5 |
| (5R,6S)-5,6-bis(4-chlorophenyl)-6-methyl-3-morpholinone and (5S,6R)-5,6-bis(4-chlorophenyl)-6-methyl-3-morpholinone | | 100 | |
| (2R)-2-((2S,5R,6S)-2-(4-carbamoylbenzyl)-5,6-bis(4-chlorophenyl)-3-oxo-4-morpholinyl)pentanoic acid and (2S)-2-((2R,5S,6R)-2-(4-carbamoylbenzyl)-5,6-bis(4-chlorophenyl)-3-oxo-4-morpholinyl)pentanoic acid | | 0.816 | |
| (2R)-2-((2S,3R,6S)-2,3-bis(4-chlorophenyl)-5-oxo-6-(4-(1H-pyrazol-1-yl)benzyl)-4-morpholinyl)pentanoic acid and (2S)-2-((2R,3S,6R)-2,3-bis(4-chlorophenyl)-5-oxo-6-(4-(1H-pyrazol-1-yl)benzyl)-4-morpholinyl)pentanoic acid | | 1.01 | |
| (2R)-2-((2S,3R,6S)-2,3-bis(4-chlorophenyl)-5-oxo-6-(4-(1H-pyrrol-1-yl)benzyl)-4-morpholinyl)pentanoic acid and (2S)-2-((2R,3S,6R)-2,3-bis(4-chlorophenyl)-5-oxo-6-(4-(1H-pyrrol-1-yl)benzyl)-4-morpholinyl)pentanoic acid | | 1.3 | |
| (2R)-2-((2S,3R)-2,3-bis(4-chlorophenyl)-5-oxo-4-morpholinyl)hexanoic acid and (2S)-2-((2R,3S)-2,3-bis(4-chlorophenyl)-5-oxo-4-morpholinyl)hexanoic acid or (2S)-2-((2S,3R)-2,3-bis(4-chlorophenyl)-5-oxo-4-morpholinyl)hexanoic acid and (2R)-2-((2R,3S)-2,3-bis(4-chlorophenyl)-5-oxo-4-morpholinyl)hexanoic acid | | 23.4 | 27.5 |
| (2R)-2-((2S,3R)-2,3-bis(4-chlorophenyl)-2-methyl-5-oxo-4-morpholinyl)pentanoic acid and (2S)-2-((2R,3S)-2,3-bis(4-chlorophenyl)-2-methyl-5-oxo-4-morpholinyl)pentanoic acid or (2S)-2-((2S,3R)-2,3-bis(4-chlorophenyl)-2-methyl-5-oxo-4-morpholinyl)pentanoic acid and (2R)-2-((2R,3S)-2,3-bis(4-chlorophenyl)-2-methyl-5-oxo-4-morpholinyl)pentanoic acid | | 5.04 | |
| (5R,6S)-5,6-bis(4-chlorophenyl)-4-(3-pyridinyl)-3-morpholinone and (5S,6R)-5,6-bis(4-chlorophenyl)-4-(3-pyridinyl)-3-morpholinone | | 29.6 | 23.9 |
| (5S,6R)-5,6-bis(4-bromophenyl)-4-(1-methylethyl)-3-morpholinone and (5R,6S)-5,6-bis(4-bromophenyl)-4-(1-methylethyl)-3-morpholinone | | >100 | 24.6 |
| (2R)-2-((2R,3S)-2,3-bis(4-chlorophenyl)-2-methyl-5-oxo-4-morpholinyl)pentanoic acid and (2S)-2-((2S,3R)-2,3-bis(4-chlorophenyl)-2-methyl-5-oxo-4-morpholinyl)pentanoic acid or (2S)-2-((2R,3S)-2,3-bis(4-chlorophenyl)-2-methyl-5-oxo-4-morpholinyl)pentanoic acid and (2R)-2-((2S,3R)-2,3-bis(4-chlorophenyl)-2-methyl-5-oxo-4-morpholinyl)pentanoic acid | | 16.1 | |
| (5R,6S)-6-(3-chlorophenyl)-5-(4-chlorophenyl)-4-(2-methoxyethyl)-3-morpholinone and (5S,6R)- | | 27.1 | 26.2 |

TABLE 2-continued

| Compound Name | HTRF1 IC$_{50}$ (μM) | HTRF2 IC$_{50}$ (μM) | HTRF3 IC$_{50}$ (μM) |
|---|---|---|---|
| 6-(3-chlorophenyl)-5-(4-chlorophenyl)-4-(2-methoxyethyl)-3-morpholinone | | | |
| (2R)-((2S,3R)-2,3-bis(4-chlorophenyl)-5-oxo-4-morpholinyl)(phenyl)ethanoic acid and (2S)-((2R,3S)-2,3-bis(4-chlorophenyl)-5-oxo-4-morpholinyl)(phenyl)ethanoic acid or (2S)-((2S,3R)-2,3-bis(4-chlorophenyl)-5-oxo-4-morpholinyl)(phenyl)ethanoic acid and (2R)-((2R,3S)-2,3-bis(4-chlorophenyl)-5-oxo-4-morpholinyl)(phenyl)ethanoic acid | | 26.6 | 27.8 |
| (2R)-((2S,3R)-2-(3-chlorophenyl)-3-(4-chlorophenyl)-5-oxo-4-morpholinyl)(cyclopropyl)ethanoic acid and (2S)-((2R,3S)-2-(3-chlorophenyl)-3-(4-chlorophenyl)-5-oxo-4-morpholinyl)(cyclopropyl)ethanoic acid or (2S)-((2S,3R)-2-(3-chlorophenyl)-3-(4-chlorophenyl)-5-oxo-4-morpholinyl)(cyclopropyl)ethanoic acid and (2R)-((2R,3S)-2-(3-chlorophenyl)-3-(4-chlorophenyl)-5-oxo-4-morpholinyl)(cyclopropyl)ethanoic acid | | 28.9 | 27.9 |
| (2R)-2-((2R,3S,6R)-2,3-bis(4-chlorophenyl)-6-(2-fluoro-4-(methylsulfonyl)benzyl)-5-oxo-4-morpholinyl)pentanoic acid and (2S)-2-((2S,3R,6S)-2,3-bis(4-chlorophenyl)-6-(2-fluoro-4-(methylsulfonyl)benzyl)-5-oxo-4-morpholinyl)pentanoic acid | | 29.6 | |
| ((2R,5S,6R)-5,6-bis(4-chlorophenyl)-4-methyl-3-oxo-2-morpholinyl)acetonitrile and ((2S,5R,6S)-5,6-bis(4-chlorophenyl)-4-methyl-3-oxo-2-morpholinyl)acetonitrile | | | 30.6 |
| (5R,6S)-5,6-bis(4-chlorophenyl)-4-phenyl-3-morpholinone and (5S,6R)-5,6-bis(4-chlorophenyl)-4-phenyl-3-morpholinone | | 31.6 | >100 [2] |
| (2R)-2-((2S,3R,6S)-2,3-bis(4-chlorophenyl)-5-oxo-6-(4-(1H-1,2,4-triazol-1-yl)benzyl)-4-morpholinyl)pentanoic acid and (2S)-2-((2R,3S,6R)-2,3-bis(4-chlorophenyl)-5-oxo-6-(4-(1H-1,2,4-triazol-1-yl)benzyl)-4-morpholinyl)pentanoic acid | | 1.15 | |
| (2R)-2-((2S,3R,6S)-2,3-bis(4-chlorophenyl)-6-(4-fluorobenzyl)-2-methyl-5-oxo-4-morpholinyl)pentanoic acid and (2S)-2-((2R,3S,6R)-2,3-bis(4-chlorophenyl)-6-(4-fluorobenzyl)-2-methyl-5-oxo-4-morpholinyl)pentanoic acid or (2S)-2-((2S,3R,6S)-2,3-bis(4-chlorophenyl)-6-(4-fluorobenzyl)-2-methyl-5-oxo-4-morpholinyl)pentanoic acid and (2R)-2-((2R,3S,6R)-2,3-bis(4-chlorophenyl)-6-(4-fluorobenzyl)-2-methyl-5-oxo-4-morpholinyl)pentanoic acid | | 17.9 | |
| (2R,5S,6R)-5,6-bis(4-chlorophenyl)-4-methyl-2-(1H-tetrazol-5-ylmethyl)-3-morpholinone and (2S,5R,6S)-5,6-bis(4-chlorophenyl)-4-methyl-2-(1H-tetrazol-5-ylmethyl)-3-morpholinone | | | 32.6 |
| (2R)-2-((2R,3S)-2,3-bis(4-chlorophenyl)-5-oxo-4-morpholinyl)hexanoic acid and (2R)-2-((2S,3R)-2,3-bis(4-chlorophenyl)-5-oxo-4-morpholinyl)hexanoic acid and (2S)-2-((2R,3S)-2,3-bis(4-chlorophenyl)-5-oxo-4-morpholinyl)hexanoic acid and (2S)-2-((2S,3R)-2,3-bis(4-chlorophenyl)-5-oxo-4-morpholinyl)hexanoic acid | | | 33.1 |
| (2R)-2-((2S,3R)-2-(3-chlorophenyl)-3-(4-chlorophenyl)-2-methyl-5-oxo-4-morpholinyl)pentanoic acid and (2S)-2-((2R,3S)-2-(3-chlorophenyl)-3-(4-chlorophenyl)-2-methyl-5-oxo-4-morpholinyl)pentanoic acid or (2S)-2-((2S,3R)-2-(3-chlorophenyl)-3-(4-chlorophenyl)-2-methyl-5-oxo-4-morpholinyl)pentanoic acid and (2R)-2-((2R,3S)-2-(3-chlorophenyl)-3-(4-chlorophenyl)-2-methyl-5-oxo-4-morpholinyl)pentanoic acid | | 20 | |
| (2R)-2-((2S,3R)-2,3-bis(4-chlorophenyl)-5-oxo-4-morpholinyl)-4-methylpentanoic acid and (2S)-2-((2R,3S)-2,3-bis(4-chlorophenyl)-5-oxo-4- | | | 34.5 |

TABLE 2-continued

| Compound Name | HTRF1 IC$_{50}$ (μM) | HTRF2 IC$_{50}$ (μM) | HTRF3 IC$_{50}$ (μM) |
|---|---|---|---|
| morpholinyl)-4-methylpentanoic acid or (2S)-2-((2S,3R)-2,3-bis(4-chlorophenyl)-5-oxo-4-morpholinyl)-4-methylpentanoic acid and (2R)-2-((2R,3S)-2,3-bis(4-chlorophenyl)-5-oxo-4-morpholinyl)-4-methylpentanoic acid | | | |
| 4-(((2R)-2-((2S,3R,6S)-2,3-bis(4-chlorophenyl)-6-(4-iodobenzyl)-5-oxo-4-morpholinyl)pentanoyl)amino)butanoic acid | | 0.388 | |
| ((2R,5S,6R)-6-(3-chlorophenyl)-5-(4-chlorophenyl)-4-(cyclopropylmethyl)-6-methyl-3-oxo-2-morpholinyl)acetic acid and ((2S,5R,6S)-6-(3-chlorophenyl)-5-(4-chlorophenyl)-4-(cyclopropylmethyl)-6-methyl-3-oxo-2-morpholinyl)acetic acid | | 35.9 | |
| (4R)-4-((2R,3S)-2,3-bis(4-chlorophenyl)-5-oxo-4-morpholinyl)heptanoic acid and (4S)-4-((2S,3R)-2,3-bis(4-chlorophenyl)-5-oxo-4-morpholinyl)heptanoic acid | | 4.14 | |
| (4R)-4-((2S,3R)-2,3-bis(4-chlorophenyl)-5-oxo-4-morpholinyl)heptanoic acid and (4S)-4-((2R,3S)-2,3-bis(4-chlorophenyl)-5-oxo-4-morpholinyl)heptanoic acid | | 24.7 | |
| (2R)-2-((2R,3S)-2,3-bis(4-chlorophenyl)-5-oxo-4-morpholinyl)butanoic acid and (2R)-2-((2S,3R)-2,3-bis(4-chlorophenyl)-5-oxo-4-morpholinyl)butanoic acid and (2S)-2-((2R,3S)-2,3-bis(4-chlorophenyl)-5-oxo-4-morpholinyl)butanoic acid and (2S)-2-((2S,3R)-2,3-bis(4-chlorophenyl)-5-oxo-4-morpholinyl)butanoic acid | | | 40.2 |
| (5R,6S)-5,6-bis(4-chlorophenyl)-4-(cyclopropylmethyl)-3-morpholinone and (5S,6R)-5,6-bis(4-chlorophenyl)-4-(cyclopropylmethyl)-3-morpholinone | | | 41.8 |
| (5S,6R)-5,6-bis(4-bromophenyl)-4-ethyl-3-morpholinone and (5R,6S)-5,6-bis(4-bromophenyl)-4-ethyl-3-morpholinone | | | 42.4 |
| 2-((2R,5S,6R)-5,6-bis(4-chlorophenyl)-4-methyl-3-oxo-2-morpholinyl)acetamide and 2-((2S,5R,6S)-5,6-bis(4-chlorophenyl)-4-methyl-3-oxo-2-morpholinyl)acetamide | | | 43.9 |
| (2R)-2-((2R,3S,6R)-2-(3-chlorophenyl)-3-(4-chlorophenyl)-6-(4-fluorobenzyl)-5-oxo-4-morpholinyl)-2-(4-fluorobenzyl)pentanoic acid and (2S)-2-((2S,3R,6S)-2-(3-chlorophenyl)-3-(4-chlorophenyl)-6-(4-fluorobenzyl)-5-oxo-4-morpholinyl)-2-(4-fluorobenzyl)pentanoic acid or (2S)-2-((2R,3S,6R)-2-(3-chlorophenyl)-3-(4-chlorophenyl)-6-(4-fluorobenzyl)-5-oxo-4-morpholinyl)-2-(4-fluorobenzyl)pentanoic acid and (2R)-2-((2S,3R,6S)-2-(3-chlorophenyl)-3-(4-chlorophenyl)-6-(4-fluorobenzyl)-5-oxo-4-morpholinyl)-2-(4-fluorobenzyl)pentanoic acid | | | 44.8 |
| (2R,5S,6R)-5,6-bis(4-chlorophenyl)-2-(2-hydroxyethyl)-4-methyl-3-morpholinone and (2S,5R,6S)-5,6-bis(4-chlorophenyl)-2-(2-hydroxyethyl)-4-methyl-3-morpholinone | | | 45.4 |
| (2R,5S,6R)-5,6-bis(4-chlorophenyl)-2-((2R)-2,3-dihydroxypropyl)-4-methyl-3-morpholinone and (2R,5S,6R)-5,6-bis(4-chlorophenyl)-2-((2S)-2,3-dihydroxypropyl)-4-methyl-3-morpholinone and (2S,5R,6S)-5,6-bis(4-chlorophenyl)-24(2R)-2,3-dihydroxypropyl)-4-methyl-3-morpholinone and (2S,5R,6S)-5,6-bis(4-chlorophenyl)-24(2S)-2,3-dihydroxypropyl)-4-methyl-3-morpholinone | | | 46.5 |
| 1-((2R)-2-((2S,3R,6S)-2,3-bis(4-chlorophenyl)-6-(4-fluorobenzyl)-5-oxo-4-morpholinyl)pentyl)-4-piperidinecarboxylic acid and 1-((2S)-2-((2R,3S,6R)-2,3-bis(4-chlorophenyl)-6-(4-fluorobenzyl)-5-oxo-4-morpholinyl)pentyl)-4-piperidinecarboxylic acid | | 2.12 | |
| N-((2R)-2-((2S,3R,6S)-2,3-bis(4-chlorophenyl)-6-(4-fluorobenzyl)-5-oxo-4-morpholinyl)pentanoyl)-N-methylglycine and N-((2S)-2-((2R,3S,6R)-2,3-bis(4-chlorophenyl)-6- | | 6.15 | |

TABLE 2-continued

| Compound Name | HTRF1 IC$_{50}$ (μM) | HTRF2 IC$_{50}$ (μM) | HTRF3 IC$_{50}$ (μM) |
|---|---|---|---|
| (4-fluorobenzyl)-5-oxo-4-morpholinyl)pentanoyl)-N-methylglycine | | | |
| (3R,5R,6S)-5,6-bis(4-chlorophenyl)-3-propyl-2,5,6,8-tetrahydro-3H-imidazo[2,1-c][1,4]oxazine and (3S,5S,6R)-5,6-bis(4-chlorophenyl)-3-propyl-2,5,6,8-tetrahydro-3H-imidazo[2,1-c][1,4]oxazine | | 11 | |
| (2R)-2-((2S,3R,6S)-2,3-bis(4-chlorophenyl)-6-(2-(dimethylamino)ethyl)-5-oxo-4-morpholinyl)pentanoic acid and (2S)-2-((2R,3S,6R)-2,3-bis(4-chlorophenyl)-6-(2-(dimethylamino)ethyl)-5-oxo-4-morpholinyl)pentanoic acid | | | 56.1 |
| N-((2R)-2-((2S,3R,6S)-2,3-bis(4-chlorophenyl)-6-(4-fluorobenzyl)-5-oxo-4-morpholinyl)pentanoyl)-N-methyl-beta-alanine and N-((2S)-2-((2R,3S,6R)-2,3-bis(4-chlorophenyl)-6-(4-fluorobenzyl)-5-oxo-4-morpholinyl)pentanoyl)-N-methyl-beta-alanine | | 0.498 | |
| 4-(((2S,5R,6S)-5-(4-chlorophenyl)-4-methyl-6-(2-methylpropyl)-3-oxo-2-morpholinyl)methyl)-2-fluorobenzonitrile or 4-(((2R,5S,6R)-5-(4-chlorophenyl)-4-methyl-6-(2-methylpropyl)-3-oxo-2-morpholinyl)methyl)-2-fluorobenzonitrile | | | 59.3 |
| (2R)-2-((2R,3S)-2,3-bis(4-chlorophenyl)-5-oxo-4-morpholinyl)propanoic acid and (2R)-2-((2S,3R)-2,3-bis(4-chlorophenyl)-5-oxo-4-morpholinyl)propanoic acid and (2S)-2-((2R,3S)-2,3-bis(4-chlorophenyl)-5-oxo-4-morpholinyl)propanoic acid and (2S)-2-((2S,3R)-2,3-bis(4-chlorophenyl)-5-oxo-4-morpholinyl)propanoic acid | | | 61.7 |
| (5R,6S)-5,6-bis(4-chlorophenyl)-4-(2,6-dichloro-4-pyridinyl)-3-morpholinone and (5S,6R)-5,6-bis(4-chlorophenyl)-4-(2,6-dichloro-4-pyridinyl)-3-morpholinone | | 63 | |
| (2R)-2-((2S,3R,6S)-2,3-bis(4-chlorophenyl)-6-(4-iodobenzyl)-5-oxo-4-morpholinyl)-N-hydroxypentanamide and (2S)-2-((2R,3S,6R)-2,3-bis(4-chlorophenyl)-6-(4-iodobenzyl)-5-oxo-4-morpholinyl)-N-hydroxypentanamide | | 1.66 | |
| (2R)-2-((2S,3R,6S)-2,3-bis(4-chlorophenyl)-6-(4-fluorobenzyl)-5-oxo-4-morpholinyl)-N-(cyclopropylsulfonyl)pentanamide and (2S)-2-((2R,3S,6R)-2,3-bis(4-chlorophenyl)-6-(4-fluorobenzyl)-5-oxo-4-morpholinyl)-N-(cyclopropylsulfonyl)pentanamide | | 1.21 | |
| (2R)-2-((2R,3S)-2,3-bis(4-chlorophenyl)-5-oxo-4-morpholinyl)-3-methylbutanoic acid and (2R)-2-((2S,3R)-2,3-bis(4-chlorophenyl)-5-oxo-4-morpholinyl)-3-methylbutanoic acid and (2S)-2-((2R,3S)-2,3-bis(4-chlorophenyl)-5-oxo-4-morpholinyl)-3-methylbutanoic acid and (2S)-2-((2S,3R)-2,3-bis(4-chlorophenyl)-5-oxo-4-morpholinyl)-3-methylbutanoic acid | | | 66.9 |
| (2R,5R,6S)-5,6-bis(4-chlorophenyl)-2-hydroxy-4-methyl-3-morpholinone and (2S,5S,6R)-5,6-bis(4-chlorophenyl)-2-hydroxy-4-methyl-3-morpholinone | | | 67.5 |
| (2R,5S,6R)-5,6-bis(4-chlorophenyl)-4-((1S)-1-((4-(cyclopropylmethyl)-1-piperazinyl)carbonyl)butyl)-2-(4-iodobenzyl)-3-morpholinone and (2S,5R,6S)-5,6-bis(4-chlorophenyl)-4-((1R)-1-((4-(cyclopropylmethyl)-1-piperazinyl)carbonyl)butyl)-2-(4-iodobenzyl)-3-morpholinone | | 1.53 | |
| (3R,5S,6R)-5,6-bis(4-chlorophenyl)-3-propyl-2,5,6,8-tetrahydro-3H-imidazo[2,1-c][1,4]oxazine and (3S,5R,6S)-5,6-bis(4-chlorophenyl)-3-propyl-2,5,6,8-tetrahydro-3H-imidazo[2,1-c][1,4]oxazine | | 39.9 | |
| 1-((2R)-2-((2S,3R,6S)-2,3-bis(4-chlorophenyl)-6-(4-cyanobenzyl)-5-oxo-4-morpholinyl)pentanoyl)-3-azetidinecarboxylic acid and 1-((2S)-2-((2R,3S,6R)-2,3-bis(4-chlorophenyl)-6-(4-cyanobenzyl)-5-oxo-4-morpholinyl)pentanoyl)-3-azetidinecarboxylic acid | | 0.479 | |

TABLE 2-continued

| Compound Name | HTRF1 IC$_{50}$ (μM) | HTRF2 IC$_{50}$ (μM) | HTRF3 IC$_{50}$ (μM) |
|---|---|---|---|
| 3-(((2R,5S,6R)-5,6-bis(4-chlorophenyl)-4-methyl-3-oxo-2-morpholinyl)methyl)benzoic acid and 3-(((2S,5R,6S)-5,6-bis(4-chlorophenyl)-4-methyl-3-oxo-2-morpholinyl)methyl)benzoic acid | | | 76.4 |
| (2R,5R,6S)-5,6-bis(4-chlorophenyl)-2-(4-fluorobenzyl)-4-(3-pyridinyl)-3-morpholinone and (2S,5S,6R)-5,6-bis(4-chlorophenyl)-2-(4-fluorobenzyl)-4-(3-pyridinyl)-3-morpholinone | | 79 | |
| 4-(((2R,5S,6R)-5,6-bis(4-chlorophenyl)-4-((1S)-1-((4-(cyclopropylmethyl)-1-piperazinyl)carbonyl)butyl)-3-oxo-2-morpholinyl)methyl)benzonitrile and 4-(((2S,5R,6S)-5,6-bis(4-chlorophenyl)-4-((1R)-1-((4-(cyclopropylmethyl)-1-piperazinyl)carbonyl)butyl)-3-oxo-2-morpholinyl)methyl)benzonitrile | | 1.38 | |
| 3-(((2R,5S,6R)-5,6-bis(4-chlorophenyl)-4-methyl-3-oxo-2-morpholinyl)methyl)benzonitrile and 3-(((2S,5R,6S)-5,6-bis(4-chlorophenyl)-4-methyl-3-oxo-2-morpholinyl)methyl)benzonitrile | | | 93.5 |
| (2R)-2-((2S,3R,6S)-2,3-bis(4-chlorophenyl)-6-(4-cyanobenzyl)-5-oxo-4-morpholinyl)-N-(methylsulfonyl)pentanamide and (2S)-2-((2R,3S,6R)-2,3-bis(4-chlorophenyl)-6-(4-cyanobenzyl)-5-oxo-4-morpholinyl)-N-(methylsulfonyl)pentanamide | | 0.305 | |

Pharmaceutical Formulation of Example 21

2-((2S,5R,6S)-6-(3-Chlorophenyl)-5-(4-chlorophenyl)-4-(cyclopropylmethyl)-3-oxomorpholin-2-yl)acetic acid (Example 21)

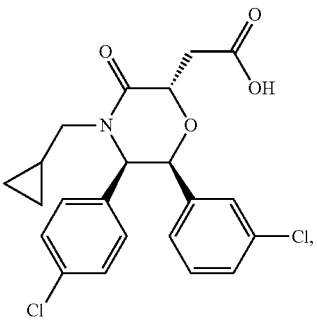 [SMILES: O=C(O)C[C@@H]1O[C@@H](c2cccc(Cl)c2)[C@@H](c2ccc(Cl)cc2)N(CC2CC2)C1=O]

e.g., in the amount of 30 mg, 100 mg, and 300 mg, may be formulated in 20% v/v Capmul PG-8, 5% v/v Tween 80 and 75% v/v H$_2$O.

What is claimed is:

1. A compound of Formula I, or a pharmaceutically acceptable salt thereof,

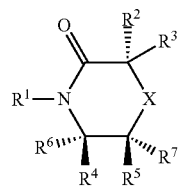

I wherein,

X is O or —S(═O)$_2$—;

R$^1$ is hydrogen, C$_{1-6}$alkyl, —(CR$^e$R$^e$)$_n$C$_{6-8}$aryl, —(CR$^e$R$^e$)$_n$C$_{3-8}$cycloalkyl, —(CR$^e$R$^e$)$_n$3-8membered heterocycloalkyl, —S(═O)$_2$C$_{3-8}$cycloalkyl, —C(═O)C$_{3-8}$cycloalkyl, or

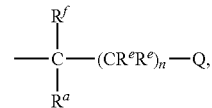

wherein any heteroaryl or heterocycloalkyl group has one or more heteroatoms independently selected from O, N or S, and wherein any cycloalkyl, heterocycloalkyl, heteroaryl or aryl group can be unsubstituted or substituted with from 1 to 3 substituents independently selected from C$_{1-6}$alkyl, halo, —CN, —CF$_3$, —SR$^e$, —S(═O)$_2$R$^e$, —CHF$_2$, —CH$_2$F, —NR$^e$R$^e$, —OCF$_3$, —OCHF$_2$, —OCH$_2$F, or —OR$^e$;

Q is —(CR$^e$R$^e$)$_n$C$_{6-8}$aryl, —(CR$^e$R$^e$)$_n$C$_{3-8}$membered heterocycloalkyl, —(CR$^e$R$^e$)$_n$5-8membered heteroaryl, —(CR$^e$R$^e$)$_n$C$_{3-8}$cycloalkyl, —CN, —(CR$^e$R$^e$)$_n$OH, —C(═O)OH, —NR$^e$R$^e$, —(CR$^e$R$^e$)$_n$OR$^e$, —C(═O)N(R$^e$)S(═O)$_2$R$^e$, —C(═O)NR$^e$R$^e$, —C(═O)NR$^e$(CR$^e$R$^e$)$_n$C(═O)OR$^e$, —C(═O)NR$^e$(CR$^e$R$^e$)$_n$C(═O)NR$^e$R$^e$, —N(R$^e$)(CR$^e$R$^e$)$_n$C(═O)OR$^e$, —OC(═O)NR$^e$R$^e$, —S(═O)$_2$C$_{3-8}$cycloalkyl, —C(═O)N(R$^e$)(CR$^e$R$^e$)$_n$OH, —C(═O)N(R$^e$)(CR$^e$R$^e$)$_n$3-8membered heterocycloalkyl, —N(R$^e$)C(═O)(CR$^e$R$^e$)$_n$OH, —N(R$^e$)S(═O)$_2$R$^e$, —N(R$^e$)C(═O)(CR$^e$R$^e$)$_n$C(═O)OR$^e$, —C(═O)3-8membered heterocycloalkyl, —S(═O)$_2$3-8membered heterocycloalkyl, —C(═O)N(R$^e$)S(═O)$_2$C$_{3-8}$cycloalkyl, —O(CR$^e$R$^e$)$_n$C(═O)R$^e$, —C(═O)N(R$^e$)(CR$^e$R$^e$)$_n$5-8membered heteroaryl, —N(R$^e$)C(═O)(CR$^e$R$^e$)$_n$5-8membered heteroaryl, —C(═O)3-8membered heterocycloalkyl(CR$^e$R$^e$)$_n$ C(=O)OR$^e$, or —C(=O)(CR$^e$R$^e$)$_n$C(=O)OR$^e$, wherein any heteroaryl or heterocycloalkyl group has one or more heteroatoms independently selected from O, N or S, and wherein any cycloalkyl, heterocycloalkyl, heteroaryl or aryl group can be unsubstituted or substituted with from 1 to 3 substituents independently selected from C$_{1-6}$alkyl, halo, —CN, —C(=O)OR$^e$, —CF$_3$, —S(=O)$_2$R$^e$, —CHF$_2$, —CH$_2$F, —NR$^e$R$^e$, —OCF$_3$, —OCHF$_2$, —OCH$_2$F, or —OR$^e$;

R$^2$ is hydrogen, C$_{1-6}$alkyl, —(CR$^e$R$^e$)$_n$C(=O)OR$^e$, —(CR$^e$R$^e$)$_n$NR$^e$R$^e$, —(CR$^e$R$^e$)$_n$C(=O)NR$^e$R$^e$, —(CR$^e$R$^e$)$_n$OH, —(CR$^e$R$^e$)$_n$C(=O)H, —(CR$^e$R$^e$)$_n$C$_{6-8}$aryl, —(CR$^e$R$^e$)$_n$3-8membered heterocycloalkyl, —(CR$^e$R$^e$)$_n$5-8membered heteroaryl, —(CR$^e$R$^e$)$_n$CN, —(CR$^e$R$^e$)$_n$C(=O)5-8membered heterocycloalkyl, —(CR$^e$R$^e$)$_n$C(=O)N(R$^e$)(CR$^e$R$^e$)$_n$3-8membered heterocycloalkyl, —(CR$^e$R$^e$)$_n$—CH(OH)CH$_2$OH, —CH=CH$_5$-8membered heteroaryl, —(CR$^e$R$^e$)$_n$CH=CR$^e$R$^e$, —(CR$^e$R$^e$)$_n$OS(=O)$_2$C$_{1-6}$alkyl, —(CR$^e$R$^e$)$_n$OS(=O)OR$^e$, or —(CR$^e$R$^e$)$_n$OC(=O)NR$^e$R$^e$, wherein any heteroaryl or heterocycloalkyl group has one or two heteroatoms independently selected from 0, N or S, and wherein any cycloalkyl, heterocycloalkyl, heteroaryl or aryl group can be unsubstituted or substituted with from 1 to 3 substituents independently selected from C1-6alkyl, halo, —(CR$^e$R$^e$)$_n$halo, —OCF$_3$, —OCF$_2$H, —OCFH$_2$, —CN, —S(=O)$_2$CF$_3$, —C(=O)NR$^e$R$^e$, —C(=O)OR$^e$, C$_{6-8}$aryl, 5-8membered heteroaryl, —CF$_3$, —SR$^e$, —S(=O)$_2$R$^e$, —CHF$_2$, —CH$_2$F, —NR$^e$R$^e$, or —OR$^e$;

R$^3$ is hydrogen or C1-6alkyl;

R$^4$ is C$_{6-8}$aryl or 5-9membered heteroaryl, wherein any heteroaryl group has one or more heteroatom independently selected from O, N or S, and wherein the aryl or heteroaryl group is substituted with from 1 to 3 substituents independently selected from C$_{1-6}$alkyl, halo, —CF$_3$, —CN, C$_{3-8}$cycloalkyl, —SR$^e$, —S(=O)$_2$R$^e$, —CHF$_2$, —CH$_2$F, —OCF$_3$, —OCHF$_2$, —OCH$_2$F, or —OR$^e$;

R$^5$ is C6-8aryl or 5-9membered heteroaryl, wherein any heteroaryl group has one or more heteroatom independently selected from O, N or S, and wherein the aryl or heteroaryl group is substituted with from 1 to 3 substituents independently selected from C$_{1-6}$alkyl, halo, —CF$_3$, —CN, C$_{3-8}$cycloalkyl, —S—S, —S(=O)$_2$R$^e$, —CHF$_2$, —CH$_2$F, —OCF$_3$, —OCHF$_2$, —OCH$_2$F, or —OR$^e$;

R$^6$ is hydrogen or C$_{1-6}$alkyl;

R$^7$ is hydrogen or C$_{1-6}$alkyl;

each R$^a$ is independently hydrogen, C$_{1-6}$alkyl, C$_{2-6}$alkenyl, —(CR$^e$R$^e$)$_n$C$_{3-8}$cycloalkyl, or —(CR$^e$R$^e$)$_n$C$_{6-8}$aryl, wherein any cycloalkyl or aryl group can be unsubstituted or substituted with from 1 to 3 substituents independently selected from C1-6alkyl, halo, —CN, —SR$^e$, —C(=O)OR$^e$—CF$_3$, —S(=O)$_2$R$^e$, —CHF$_2$, —CH$_2$F, —OCF$_3$, —OCHF$_2$, —OCH$_2$F, or —OR$^e$;

each R$^e$ is independently hydrogen, C1-6alkyl, or —OH;
each R$^f$ is independently hydrogen, C1-6alkyl, or —OH;
each n is independently 0, 1, 2, 3 or 4; and
each m is independently 0, 1, 2, 3 or 4,
provided that R$^2$ and R$^3$ are not both hydrogen.

2. The compound of claim 1 wherein X is O.

3. The compound of claim 1 wherein X is S(=O)$_2$—.

4. The compound of claim 1 wherein R$^3$ is hydrogen.

5. The compound of claim 1 wherein R$^3$ is C$_{1-6}$alkyl.

6. The compound of claim 1 wherein R$^3$ is methyl.

7. The compound of claim 1 wherein R$^6$ is hydrogen.

8. The compound of claim 1 wherein R$^6$ is methyl.

9. The compound of claim 1 wherein R$^7$ is hydrogen.

10. The compound of claim 1 wherein R$^7$ is methyl.

11. The compound of claim 1 wherein R$^4$ is substituted C$_{6-8}$aryl.

12. The compound of claim 1 wherein R$^4$ is substituted phenyl.

13. The compound of claim 1 wherein R$^4$ is phenyl substituted with from 1 to 3 halo groups.

14. The compound of claim 1 wherein R$^4$ is phenyl substituted with a fluorine.

15. The compound of claim 1 wherein R$^4$ is phenyl substituted with a bromine.

16. The compound of claim 1 wherein R$^4$ is 4-chlorophenyl or 4-bromophenyl.

17. The compound of claim 1 wherein R$^5$ is substituted C$_{6-8}$aryl.

18. The compound of claim 1 wherein R$^5$ is substituted phenyl.

19. The compound of claim 1 wherein R$^5$ is phenyl substituted with from 1 to 3 halo groups.

20. The compound of claim 1 wherein R$^5$ is phenyl substituted with a fluorine.

21. The compound of claim 1 wherein R$^5$ is phenyl substituted with a bromine.

22. The compound of claim 1 wherein R$^5$ is 4-chlorophenyl or 4-bromophenyl.

23. The compound of claim 1 wherein R$^5$ is 3-chlorophenyl or 3-bromophenyl.

24. The compound of claim 1 wherein R$^2$ is hydrogen.

25. The compound of claim 1 wherein R$^e$ is C$_{1-6}$alkyl.

26. The compound of claim 1 wherein R$^2$ is —CH$_2$C(=O)OH.

27. The compound of claim 1 wherein R$^2$ is —CH$_2$phenyl.

28. The compound of claim 1 wherein R$^2$ is —CH$_2$phenyl substituted with from 1 to 3 substituents independently selected from C$_{1-6}$alkyl, halo, —(CR$^e$R$^e$)$_n$halo, —OC$_{1-6}$alkyl, —OCF$_3$, —OCF$_2$H, —OCFH$_2$, —CN, —S(=O)$_2$CF$_3$, —C(=O)NR$^e$R$^e$, —C(=O)OR$^e$, C$_{6-8}$aryl, —CF$_3$, —S(=O)$_2$R$^e$, —CHF$_2$, —CH$_2$F, or —OR$^e$.

29. The compound of claim 1 wherein R$^2$ is —CH$_2$phenyl substituted with from 1 to 3 substituents independently selected from C$_{1-6}$alkyl, halo, —OC$_{1-6}$alkyl, —OCF$_3$, —OCF$_2$H, —OCFH$_2$, —CN, —CF$_3$, —SR$^e$, —S(=O)2R$^e$, —CHF$_2$, —CH$_2$F, —NR$^e$R$^e$, or —OR$^e$.

30. The compound of claim 1 wherein R$^e$ is —CH$_2$pyridyl.

31. The compound of claim 1 wherein R$^2$ is —CH$_2$pyridyl substituted with from 1 to 3 substituents independently selected from C$_{1-6}$alkyl, halo, —OC$_{1-6}$alkyl, —OCF$_3$, —OCF$_2$H, —OCFH$_2$, —CN, —CF$_3$, —SR$^e$, —S(=O)$_2$R$^e$, —CHF$_2$, —CH$_2$F, —NR$^e$R$^e$, or —OR$^e$.

32. The compound of claim 1 wherein R$^1$ is C$_{1-6}$alkyl.

33. The compound of claim 1 wherein R$^1$ is methyl.

34. The compound of claim 1 wherein R$^1$ is —(CR$^e$R$^e$)$_n$C$_{3-8}$cycloalkyl.

35. The compound of claim 1 wherein R$^1$ is —CH$_2$cyclopropyl, —CH$_2$cyclobutyl or —CH$_2$cyclohexyl.

36. The compound of claim 1 wherein $R^1$ is

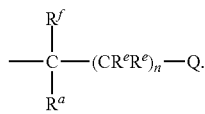

37. The compound of claim 1 wherein $R^1$ is

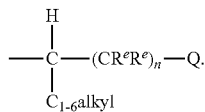

38. The compound of claim 1 wherein $R^1$ is

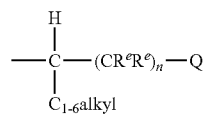

and
Q is —C(=O)NR$^e$(CR$^e$R$^e$)$_n$C(=O)OR$^e$ or 5-8membered heteroaryl.

39. The compound of claim 1 wherein $R^1$ is 5-8membered heteroaryl.

40. The compound of claim 1 wherein:
X is O;
$R^3$ is hydrogen or methyl;
$R^4$ is phenyl substituted with from 1 to 3 halo groups;
$R^5$ is phenyl substituted with from 1 to 3 halo groups;
$R^6$ is hydrogen or methyl; and
$R^7$ is hydrogen or methyl.

41. The compound of claim 40 wherein:
$R^2$ is —CH$_2$C(=O)OH.

42. The compound of claim 40 wherein:
$R^e$ is —CH$_2$phenyl substituted with from 1 to 3 substituents independently selected from C$_{1-6}$alkyl, halo, —OC$_{1-6}$alkyl, —OCF$_3$, —OCF$_2$H, —OCFH$_2$, —CN, —CF$_3$, —SR$^e$, —S(=O)$_2$R$^e$, —CHF$_2$, —CH$_2$F, —NR$^e$R$^e$, or —OR$^e$.

43. A compound, or a pharmaceutically acceptable salt thereof, selected from:
(2S,5R,6S)-2-benzyl-5,6-bis(4-bromophenyl)-4-methylmorpholin-3-one;
(2R,5S,6R)-2-benzyl-5,6-bis(4-bromophenyl)-4-methylmorpholin-3-one;
(2S,5R,6S)-2-benzyl-5,6-bis(4-chlorophenyl)-4-methylmorpholin-3-one;
(2R,5S,6R)-2-benzyl-5,6-bis(4-chlorophenyl)-4-methylmorpholin-3-one;
(2S,5R,6S)-2-(4-bromobenzyl)-5,6-bis(4-bromophenyl)-4-methylmorpholin-3-one;
(2R,5S,6R)-2-(4-bromobenzyl)-5,6-bis(4-bromophenyl)-4-methylmorpholin-3-one;
(2S,5R,6S)-5,6-bis(4-bromophenyl)-2-(4-fluorobenzyl)-4-methylmorpholin-3-one;
(2R,5S,6R)-5,6-bis(4-bromophenyl)-2-(4-fluorobenzyl)-4-methylmorpholin-3-one;
(2S,5R,6S)-5,6-bis(4-bromophenyl)-2-(4-methoxybenzyl)-4-methylmorpholin-3-one;
(2R,5S,6R)-5,6-bis(4-bromophenyl)-2-(4-methoxybenzyl)-4-methylmorpholin-3-one;
(2S,5R,6S)-5,6-bis(4-bromophenyl)-4-methyl-2-(4-(trifluoromethoxy)benzyl)morpholin-3-one;
(2R,5S,6R)-5,6-bis(4-bromophenyl)-4-methyl-2-(4-(trifluoromethoxy)benzyl)morpholin-3-one;
(2S,5R,6S)-5,6-bis(4-bromophenyl)-2-(3-methoxybenzyl)-4-methylmorpholin-3-one;
(2R,5S,6R)-5,6-bis(4-bromophenyl)-2-(3-methoxybenzyl)-4-methylmorpholin-3-one;
(R)-2-((2S,5R,6S)-2-(4-fluorobenzyl)-5,6-bis(4-chlorophenyl)-3-oxomorpholino)pentanoic acid;
(5R,6S)-6-(3-chlorophenyl)-5-(4-chlorophenyl)-4-methylmorpholin-3-one;
(5S,6R)-6-(3-chlorophenyl)-5-(4-chlorophenyl)-4-methylmorpholin-3-one;
(5R,6S)-6-(3-chlorophenyl)-5-(4-chlorophenyl)-4-(cyclopropylmethyl)morpholin-3-one;
(5S,6R)-6-(3-chlorophenyl)-5-(4-chlorophenyl)-4-(cyclopropylmethyl)morpholin-3-one;
(2S,5R,6S)-2-benzyl-6-(3-chlorophenyl)-5-(4-chlorophenyl)-4-methylmorpholin-3-one;
(2R,5S,6R)-2-benzyl-6-(3-chlorophenyl)-5-(4-chlorophenyl)-4-methylmorpholin-3-one;
(2S,5R,6S)-6-(3-chlorophenyl)-5-(4-chlorophenyl)-4-(cyclopropylmethyl)-2-((S)-2,3-dihydroxypropyl)morpholin-3-one;
(2S,5R,6S)-6-(3-chlorophenyl)-5-(4-chlorophenyl)-4-(cyclopropylmethyl)-2-((R)-2,3-dihydroxypropyl)morpholin-3-one;
(2S,5S,6R)-6-(3-chlorophenyl)-5-(4-chlorophenyl)-4-(cyclopropylmethyl)-2-((S)-2,3-dihydroxypropyl)morpholin-3-one;
(2S,5S,6R)-6-(3-chlorophenyl)-5-(4-chlorophenyl)-4-(cyclopropylmethyl)-2-((R)-2,3-dihydroxypropyl)morpholin-3-one;
(2-((2S,5R,6S)-6-(3-chlorophenyl)-5-(4-chlorophenyl)-4-(cyclopropylmethyl)-3-oxomorpholin-2-yl)acetaldehydeacetaldehyde;
(2-((2R,5S,6R)-6-(3-chlorophenyl)-5-(4-chlorophenyl)-4-(cyclopropylmethyl)-3-oxomorpholin-2-yl)acetaldehydeacetaldehyde;
(2S,5R,6S)-6-(3-chlorophenyl)-5-(4-chlorophenyl)-4-(cyclopropylmethyl)-2-(2-hydroxyethyl)morpholin-3-one;
(2R,5S,6R)-6-(3-chlorophenyl)-5-(4-chlorophenyl)-4-(cyclopropylmethyl)-2-(2-hydroxyethyl)morpholin-3-one;
(2-((2S,5R,6S)-6-(3-chlorophenyl)-5-(4-chlorophenyl)-4-(cyclopropylmethyl)-3-oxomorpholin-2-yl)acetic acid;
(2-((2R,5S,6R)-6-(3-chlorophenyl)-5-(4-chlorophenyl)-4-(cyclopropylmethyl)-3-oxomorpholin-2-yl)acetic acid;
(2S,5R,6S)-6-(3-chlorophenyl)-5-(4-chlorophenyl)-4-(cyclopropylmethyl)-2-(2-(methylamino)ethyl)morpholin-3-one;
(2R,5S,6R)-6-(3-chlorophenyl)-5-(4-chlorophenyl)-4-(cyclopropylmethyl)-2-(2-(methylamino)ethyl)morpholin-3-one;
(2S,5R,6S)-6-(3-chlorophenyl)-5-(4-chlorophenyl)-4-(cyclopropylmethyl)-2-(3-hydroxypropyl)morpholin-3-one;
(2R,5S,6R)-6-(3-chlorophenyl)-5-(4-chlorophenyl)-4-(cyclopropylmethyl)-2-(3-hydroxypropyl)morpholin-3-one;

3-((2S,5R,6S)-6-(3-chlorophenyl)-5-(4-chlorophenyl)-4-(cyclopropylmethyl)-3-oxomorpholin-2-yl)propanoic acid;
3-((2R,5S,6R)-6-(3-chlorophenyl)-5-(4-chlorophenyl)-4-(cyclopropylmethyl)-3-oxomorpholin-2-yl)propanoic acid;
2-((2R,5S,6R)-6-(3-chlorophenyl)-5-(4-chlorophenyl)-4-(cyclopropylmethyl)-3-oxomorpholin-2-yl)acetic acid;
2-((2S,5R,6S)-6-(3-chlorophenyl)-5-(4-chlorophenyl)-4-(cyclobutylmethyl)-3-oxomorpholin-2-yl)acetic acid;
2-((2R,5S,6R)-6-(3-chlorophenyl)-5-(4-chlorophenyl)-4-(cyclobutylmethyl)-3-oxomorpholin-2-yl)acetic acid;
(2S,5R,6S)-6-(3-chlorophenyl)-5-(4-chlorophenyl)-4-isobutyl-3-oxomorpholin-2-yl)acetic acid;
(2R,5S,6R)-6-(3-chlorophenyl)-5-(4-chlorophenyl)-4-isobutyl-3-oxomorpholin-2-yl)acetic acid;
2-((2S,5R,6S)-6-(3-chlorophenyl)-5-(4-chlorophenyl)-4-(cyclohexylmethyl)-3-oxomorpholin-2-yl)acetic acid;
2-((2R,5S,6R)-6-(3-chlorophenyl)-5-(4-chlorophenyl)-4-(cyclohexylmethyl)-3-oxomorpholin-2-yl)acetic acid;
2-((2S,5R,6S)-4-benzyl-6-(3-chlorophenyl)-5-(4-chlorophenyl)-3-oxomorpholin-2-yl)acetic acid;
2-((2R,5S,6R)-4-benzyl-6-(3-chlorophenyl)-5-(4-chlorophenyl)-3-oxomorpholin-2-yl)acetic acid;
(R)-2-((2S,3R,6S)-2,3-bis(4-chlorophenyl)-6-(4-fluorobenzyl)-5-oxomorpholino)-N-(methylsulfonyl)pentanamide;
(S)-2-((2R,3S,6R)-2,3-bis(4-chlorophenyl)-6-(4-fluorobenzyl)-5-oxomorpholino)-N-(methylsulfonyl)pentanamide;
1-((R)-2-((2S,3R,6S)-2,3-bis(4-chlorophenyl)-6-(4-fluorobenzyl)-5-oxomorpholino)pentanoyl)azetidine-3-carboxylic acid;
1-((S)-2-((2R,3S,6R)-2,3-bis(4-chlorophenyl)-6-(4-fluorobenzyl)-5-oxomorpholino)pentanoyl)azetidine-3-carboxylic acid;
(R)-2-((2S,3R,6S)-2-(4-chloro-3-fluorophenyl)-3-(4-chlorophenyl)-6-(4-fluorobenzyl)-5-oxomorpholino)pentanoic acid;
(S)-2-((2R,3S,6R)-2-(4-chloro-3-fluorophenyl)-3-(4-chlorophenyl)-6-(4-fluorobenzyl)-5-oxomorpholino)pentanoic acid;
(S)-2-((2S,3R,6S)-2-(4-chloro-3-fluorophenyl)-3-(4-chlorophenyl)-6-(4-fluorobenzyl)-5-oxomorpholino)pentanoic acid;
(R)-2-((2R,3S,6R)-2-(4-chloro-3-fluorophenyl)-3-(4-chlorophenyl)-6-(4-fluorobenzyl)-5-oxomorpholino)pentanoic acid;
(R)-2-((2S,3R,6S)-2-(4-chloro-2-methylphenyl)-3-(4-chlorophenyl)-6-(4-fluorobenzyl)-5-oxomorpholino)pentanoic acid;
(S)-2-((2R,3S,6R)-2-(4-chloro-2-methylphenyl)-3-(4-chlorophenyl)-6-(4-fluorobenzyl)-5-oxomorpholino)pentanoic acid;
(S)-2-((2S,3R,6S)-2-(4-chloro-2-methylphenyl)-3-(4-chlorophenyl)-6-(4-fluorobenzyl)-5-oxomorpholino)pentanoic acid;
(R)-2-((2R,3S,6R)-2-(4-chloro-2-methylphenyl)-3-(4-chlorophenyl)-6-(4-fluorobenzyl)-5-oxomorpholino)pentanoic acid;
(R)-4-((2S,3R,6S)-2,3-bis(4-chlorophenyl)-6-(4-fluorobenzyl)-5-oxomorpholino)heptanoic acid;
(S)-4-((2R,3S,6R)-2,3-bis(4-chlorophenyl)-6-(4-fluorobenzyl)-5-oxomorpholino)heptanoic acid;
4-((R)-2-((2S,3R,6S)-2,3-bis(4-chlorophenyl)-6-(4-cyanobenzyl)-5-oxomorpholino)pentanamido)butanoic acid;
3-((R)-2-((2S,3R,6S)-2,3-Bis(4-chlorophenyl)-6-(4-cyanobenzyl)-5-oxomorpholino)pentanamido)propanoic acid;
(R)—N-(2-amino-2-oxoethyl)-2-((2S,3R,6S)-2,3-bis(4-chlorophenyl)-6-(4-cyanobenzyl)-5-oxomorpholino) pentanamide;
(S)—N-(2-amino-2-oxoethyl)-2-((2R,3S,6R)-2,3-bis(4-chlorophenyl)-6-(4-cyanobenzyl)-5-oxomorpholino) pentanamide;
4-(((2S,5R,6S)-4-((R)-1-(1H-tetrazol-5-yl)butyl)-5,6-bis(4-chlorophenyl)-3-oxomorpholin-2-yl)methyl)-2-fluorobenzonitrile;
(2S,5R,6S)-4-((R)-1-(1H-tetrazol-5-yl)butyl)-5,6-bis(4-chlorophenyl)-2-(4-iodobenzyl)morpholin-3-one;
(2R,5S,6R)-4-((S)-1-(1H-tetrazol-5-yl)butyl)-5,6-bis(4-chlorophenyl)-2-(4-iodobenzyl)morpholin-3-one;
(R)-2-((2S,3R)-2,3-bis(4-chlorophenyl)-5-oxomorpholino)pentanoic acid;
(S)-2-((2R,3S,6R)-2,3-bis(4-chlorophenyl)-6-(4-fluorobenzyl)-5-oxomorpholino)pentanoic acid;
(2R,5S,6R)-5,6-bis(4-chlorophenyl)-4-methyl-2-(2-morpholinoethyl)morpholin-3-one;
(2S,5R,6S)-5,6-bis(4-chlorophenyl)-4-methyl-2-(2-morpholinoethyl)morpholin-3-one;
(2R,5S,6R)-5,6-bis(4-chlorophenyl)-4-methyl-2-(pyridin-4-ylmethyl)morpholin-3-one;
(2S,5R,6S)-5,6-bis(4-chlorophenyl)-4-methyl-2-(pyridin-4-ylmethyl)morpholin-3-one;
(S)-2-((2R,3S,6R)-2,3-bis(4-chlorophenyl)-5-oxo-6-(pyridin-4-ylmethyl)morpholino)pentanoic acid;
(R)-2-((2S,3R,6S)-2,3-bis(4-chlorophenyl)-5-oxo-6-(pyridin-4-ylmethyl)morpholino)pentanoic acid;
(R)-2-((2S,3R)-2-(4-chlorophenyl)-3-(1H-indol-2-yl)-5-oxomorpholino)pentanoic acid;
(S)-2-((2R,3S)-2-(4-Chlorophenyl)-3-(1H-indol-2-yl)-5-oxomorpholino)pentanoic acid;
(R)-2-((2S,5R,6S)-2-benzyl-5,6-bis(4-chlorophenyl)-3-oxomorpholino)pentanoic acid;
(R)-2-((2S,3R,6S)-2,3-bis(4-chlorophenyl)-6-(2-cyano-4-fluorobenzyl)-5-oxomorpholino)pentanoic acid;
(R)-2-((2S,3R,6S)-2,3-bis(4-chlorophenyl)-6-(2-cyanobenzyl)-5-oxomorpholino)pentanoic acid;
(R)-2-((2S,3R,6S)-2,3-bis(4-chlorophenyl)-6-(2-fluorobenzyl)-5-oxomorpholino)pentanoic acid;
(R)-2-((2S,3R,6S)-2,3-bis(4-chlorophenyl)-6-(3-fluorobenzyl)-5-oxomorpholino)pentanoic acid;
(R)-2-((2S,3R,6S)-2,3-bis(4-chlorophenyl)-6-(3-cyanobenzyl)-5-oxomorpholino)pentanoic acid;
(R)-2-((2S,3R,6S)-2,3-bis(4-chlorophenyl)-6-(3-(methylsulfonyl)benzyl)-5-oxomorpholino)pentanoic acid;
(R)-2-((2S,3R,6S)-2,3-bis(4-chlorophenyl)-6-(2-(methylsulfonyl)benzyl)-5-oxomorpholino)pentanoic acid;
(R)-2-((2S,3R,6S)-2,3-bis(4-chlorophenyl)-6-(4-fluoro-2-(methylsulfonyl)benzyl)-5-oxomorpholino)pentanoic acid;
(R)-2-((2S,3R,6S)-2,3-bis(4-chlorophenyl)-6-(3-fluoro-4-(methylsulfonyl)benzyl)-5-oxomorpholino)pentanoic acid;
(R)-2-((2S,3R,6S)-2,3-bis(4-chlorophenyl)-6-(4-(methylsulfonyl)benzyl)-5-oxomorpholino)pentanoic acid;
(R)-2-((2S,3R,6S)-2,3-bis(4-chlorophenyl)-5-oxo-6-(4-((trifluoromethyl)sulfonyl)benzyl)morpholino)pentanoic acid;
(R)-2-((2S,3R,6S)-2,3-bis(4-chlorophenyl)-6-(3-morpholinopropyl)-5-oxomorpholino)pentanoic acid;
(2S, 5R,6S)-5,6-bis(4-chlorophenyl)-4-(2-chloropyridin-4-yl)-2-(4-fluorobenzyl)morpholin-3-one;

(2R,5S,6R)-5,6-bis(4-chlorophenyl)-4-(2-chloropyridin-4-yl)-2-(4-fluorobenzyl)morpholin-3-one;
(2S, 5R,6S)-5,6-bis(4-chlorophenyl)-2-(4-fluorobenzyl)-4-phenylmorpholin-3-one;
(2R,5S,6R)-5,6-bis(4-chlorophenyl)-2-(4-fluorobenzyl)-4-phenylmorpholin-3-one;
(2S, 5R,6S)-5,6-bis(4-chlorophenyl)-2-(4-fluorobenzyl)-4-(1H-pyrazol-4-yl)morpholin-3-one;
(2R,5S,6R)-5,6-bis(4-chlorophenyl)-2-(4-fluorobenzyl)-4-(1H-pyrazol-4-yl)morpholin-3-one;
(2S, 5R,6S)-5,6-bis(4-chlorophenyl)-2-(4-fluorobenzyl)-4-(pyridin-4-yl)morpholin-3-one;
(2R,5S,6R)-5,6-bis(4-chlorophenyl)-2-(4-fluorobenzyl)-4-(pyridin-4-yl)morpholin-3-one;
(2S, 5R,6S)-5,6-bis(4-chlorophenyl)-2-(4-(methylsulfonyl)benzyl)-4-(pyridin-3-yl)morpholin-3-one;
(2R,5S,6R)-5,6-bis(4-chlorophenyl)-2-(4-(methylsulfonyl)benzyl)-4-(pyridin-3-yl)morpholin-3-one;
(2S, 5R,6S)-5,6-bis(4-chlorophenyl)-2-(2-fluoro-4-(methylsulfonyl)benzyl)-4-(pyridin-3-yl)morpholin-3-one;
(2R,5S,6R)-5,6-bis(4-chlorophenyl)-2-(2-fluoro-4-(methylsulfonyl)benzyl)-4-(pyridin-3-yl)morpholin-3-one;
(2S, 5R,6S)-6-(3-chlorophenyl)-5-(4-chlorophenyl)-4-(cyclopropylmethyl)-2-(2-(4-methylpiperazin-1-yl)-2-oxoethyl)morpholin-3-one;
(2R,5S,6R)-6-(3-chlorophenyl)-5-(4-chlorophenyl)-4-(cyclopropylmethyl)-2-(2-(4-methylpiperazin-1-yl)-2-oxoethyl)morpholin-3-one;
2-((2S, 5R,6S)-4-((R)-1-amino-1-oxopentan-2-yl)-6-(3-chlorophenyl)-5-(4-chlorophenyl)-3-oxomorpholin-2-yl)acetic acid;
2-((2R,5S, 6R)-4-((S)-1-amino-1-oxopentan-2-yl)-6-(3-chlorophenyl)-5-(4-chlorophenyl)-3-oxomorpholin-2-yl)acetic acid;
2-((2S, 5R,6S)-4-((S)-1-amino-1-oxopentan-2-yl)-6-(3-chlorophenyl)-5-(4-chlorophenyl)-3-oxomorpholin-2-yl)acetic acid;
2-((2R,5S,6R)-4-((R)-1-amino-1-oxopentan-2-yl)-6-(3-chlorophenyl)-5-(4-chlorophenyl)-3-oxomorpholin-2-yl)acetic acid;
2-((2S,5R,6S)-6-(3-chlorophenyl)-5-(4-chlorophenyl)-4-((R)-1-cyanobutyl)-3-oxomorpholin-2-yl)acetic acid;
2-((2R,5S,6R)-6-(3-chlorophenyl)-5-(4-chlorophenyl)-4-((S)-1-cyanobutyl)-3-oxomorpholin-2-yl)acetic acid;
2-((2S,5R,6S)-6-(3-chlorophenyl)-5-(4-chlorophenyl)-4-((S)-1-cyanobutyl)-3-oxomorpholin-2-yl)acetic acid;
2-((2R,5S,6R)-6-(3-chlorophenyl)-5-(4-chlorophenyl)-4-((R)-1-cyanobutyl)-3-oxomorpholin-2-yl)acetic acid;
2-((2S,5R,6S)-4-((R)-1-(1H-tetrazol-5-yl)butyl)-6-(3-chlorophenyl)-5-(4-chlorophenyl)-3-oxomorpholin-2-yl)acetic acid;
2-((2R,5S,6R)-4-((S)-1-(1H-tetrazol-5-yl)butyl)-6-(3-chlorophenyl)-5-(4-chlorophenyl)-3-oxomorpholin-2-yl)acetic acid;
2-((2S,5R,6S)-4-((S)-1-(1H-tetrazol-5-yl)butyl)-6-(3-chlorophenyl)-5-(4-chlorophenyl)-3-oxomorpholin-2-yl)acetic acid;
2-((2R,5S,6R)-4-((R)-1-(1H-tetrazol-5-yl)butyl)-6-(3-chlorophenyl)-5-(4-chlorophenyl)-3-oxomorpholin-2-yl)acetic acid;
2-((2S,5R,6S)-6-(3-chlorophenyl)-5-(4-chlorophenyl)-4-((R)-1-(5-methyl-1,3,4-oxadiazol-2-yl)butyl)-3-oxomorpholin-2-yl)acetic acid;
2-((2R,5S,6R)-6-(3-chlorophenyl)-5-(4-chlorophenyl)-4-((S)-1-(5-methyl-1,3,4-oxadiazol-2-yl)butyl)-3-oxomorpholin-2-yl)acetic acid;
2-((2S,5R,6S)-6-(3-chlorophenyl)-5-(4-chlorophenyl)-4-((S)-1-(5-methyl-1,3,4-oxadiazol-2-yl)butyl)-3-oxomorpholin-2-yl)acetic acid;
2-((2R,5S,6R)-6-(3-chlorophenyl)-5-(4-chlorophenyl)-4-((R)-1-(5-methyl-1,3,4-oxadiazol-2-yl)butyl)-3-oxomorpholin-2-yl)acetic acid;
2-((2S,5R,6S)-6-(3-chlorophenyl)-5-(4-chlorophenyl)-4-((R)-cyclopropyl(5-methyl-1,3,4-oxadiazol-2-yl)methyl)-3-oxomorpholin-2-yl)acetic acid;
2-((2R,5S,6R)-6-(3-chlorophenyl)-5-(4-chlorophenyl)-4-((S)-cyclopropyl(5-methyl-1,3,4-oxadiazol-2-yl)methyl)-3-oxomorpholin-2-yl)acetic acid;
2-((2S,5R,6S)-6-(3-chlorophenyl)-5-(4-chlorophenyl)-4-((S)-cyclopropyl(5-methyl-1,3,4-oxadiazol-2-yl)methyl)-3-oxomorpholin-2-yl)acetic acid;
2-((2R,5S,6R)-6-(3-chlorophenyl)-5-(4-chlorophenyl)-4-((R)-cyclopropyl(5-methyl-1,3,4-oxadiazol-2-yl)methyl)-3-oxomorpholin-2-yl)acetic acid;
(S)-2-((2S,3R,6S)-2,3-bis(4-chlorophenyl)-6-(4-cyanobenzyl)-5-oxomorpholino)-2-cyclopropylacetic acid;
(R)-2-((2R,3S,6R)-2,3-bis(4-chlorophenyl)-6-(4-cyanobenzyl)-5-oxomorpholino)-2-cyclopropylacetic acid;
(R)-2-((2S,3R,6S)-2,3-bis(4-chlorophenyl)-6-(4-cyanobenzyl)-5-oxomorpholino)-2-cyclopropylacetic acid;
(S)-2-((2R,3S,6R)-2,3-bis(4-chlorophenyl)-6-(4-cyanobenzyl)-5-oxomorpholino)-2-cyclopropylacetic acid;
(5R,6S)-6-(3-chlorophenyl)-5-(4-chlorophenyl)-4-(cyclopropylmethyl)thiomorpholin-3-one;
(5R,6S)-6-(3-chlorophenyl)-5-(4-chlorophenyl)-4-(cyclopropylmethyl)-2,2-dimethylthiomorpholin-3-one 1,1-dioxide;
(5R,6S)-6-(3-chlorophenyl)-5-(4-chlorophenyl)-4-isopropylthiomorpholin-3-one;
2-((2R,5R,6S)-6-(3-chlorophenyl)-5-(4-chlorophenyl)-4-isopropyl-1,1-dioxido-3-oxothiomorpholin-2-yl)acetic acid;
2-((2S,5R,6S)-6-(3-chlorophenyl)-5-(4-chlorophenyl)-4-isopropyl-1,1-dioxido-3-oxothiomorpholin-2-yl)acetic acid;
2-((2S,5R,6S)-6-(3-chlorophenyl)-5-(4-chlorophenyl)-4-((S)-1-hydroxybutan-2-yl)-3-oxomorpholin-2-yl)acetic acid;
2-((2R,5R,6S)-6-(3-chlorophenyl)-5-(4-chlorophenyl)-4-((S)-1-hydroxybutan-2-yl)-3-oxomorpholin-2-yl)acetic acid;
(2S,5R,6S)-5,6-bis(4-chlorophenyl)-2-(4-fluorobenzyl)morpholin-3-one;
(2R,5S,6R)-5,6-bis(4-chlorophenyl)-2-(4-fluorobenzyl)morpholin-3-one; or
2-((2S,5R,6S)-6-(3-chlorophenyl)-5-(4-chlorophenyl)-4-(cyclopropylmethyl)-5-methyl-3-oxomorpholin-2-yl)acetic acid.

44. A compound, or a pharmaceutically acceptable salt thereof, selected from:
1,1-dimethylethyl (2R,3S)-2,3-bis(4-bromophenyl)-5-oxo-1-piperazinecarboxylate;
1,1-dimethylethyl (2S,3R)-2,3-bis(4-bromophenyl)-5-oxo-1-piperazinecarboxylate;
(2R,5S,6R)-5,6-bis(4-bromophenyl)-4-methyl-2-(2-propen-1-yl)-3-morpholinone;
(2S, 5R,6S)-5,6-bis(4-bromophenyl)-4-methyl-2-(2-propen-1-yl)-3-morpholinone;
(5R,6S)-5,6-bis(4-bromophenyl)-4-cyclopropyl-3-morpholinone;

(5S,6R)-5,6-bis(4-bromophenyl)-4-cyclopropyl-3-morpholinone;
(2S, 5R,6S)-5,6-bis(4-bromophenyl)-2,4-dimethyl-3-morpholinone;
(2R,5R,6S)-5,6-bis(4-bromophenyl)-2,4-dimethyl-3-morpholinone;
(2R,5S,6R)-5,6-bis(4-bromophenyl)-4-cyclopropyl-2-(phenylmethyl)-3-morpholinone;
(2S,5R,6S)-5,6-bis(4-bromophenyl)-4-cyclopropyl-2-(phenylmethyl)-3-morpholinone;
(2R)-2-((2S,3R,6S)-2,3-bis(4-chlorophenyl)-6-(4-(methylsulfonyl)benzyl)-5-oxo-4-morpholinyl)pentanoic acid;
(2S)-2-((2R,3S,6R)-2,3-bis(4-chlorophenyl)-6-(4-(methylsulfonyl)benzyl)-5-oxo-4-morpholinyl)pentanoic acid;
(2R,5S,6R)-5,6-bis(4-bromophenyl)-4-methyl-2-phenyl-3-morpholinone;
(2S,5R,6S)-5,6-bis(4-bromophenyl)-4-methyl-2-phenyl-3-morpholinone;
N-((2R)-2-((2S,3R,6S)-2,3-bis(4-chlorophenyl)-6-(4-cyano-3-fluorobenzyl)-5-oxo-4-morpholinyl)pentanoyl)glycine;
(5R,6S)-5,6-bis(4-bromophenyl)-1-methyl-4-(phenylmethyl)-2-piperazinone;
(5S,6R)-5,6-bis(4-bromophenyl)-1-methyl-4-(phenylmethyl)-2-piperazinone;
(2R)-2-((2S,3R,6S)-2,3-bis(4-chlorophenyl)-6-(3-fluorobenzyl)-5-oxo-4-morpholinyl)pentanoic acid;
(2R,5S,6R)-5,6-bis(4-bromophenyl)-4-methyl-2-(3-methyl-2-buten-1-yl)-3-morpholinone;
(2S,5R,6S)-5,6-bis(4-bromophenyl)-4-methyl-2-(3-methyl-2-buten-1-yl)-3-morpholinone;
(2R)-2-((2S,3R,6S)-2,3-bis(4-chlorophenyl)-6-(4-cyano-3-fluorobenzyl)-5-oxo-4-morpholinyl)pentanoic acid;
(5R,6S)-5,6-bis(4-bromophenyl)-4-(phenylmethyl)-2-piperazinone;
(5S,6R)-5,6-bis(4-bromophenyl)-4-(phenylmethyl)-2-piperazinone;
(2R)-2-((2S,3R,6S)-2,3-bis(4-chlorophenyl)-6-(4-cyanobenzyl)-5-oxo-4-morpholinyl)pentanoic acid;
(2S)-2-((2R,3S,6R)-2,3-bis(4-chlorophenyl)-6-(4-cyanobenzyl)-5-oxo-4-morpholinyl)pentanoic acid;
(5R,6S)-5,6-bis(4-chlorophenyl)-4-((1R)-2-hydroxy-1-phenylethyl)-3-morpholinone;
(5R,6S)-5,6-bis(4-chlorophenyl)-4-((1S)-2-hydroxy-1-phenylethyl)-3-morpholinone;
(5S,6R)-5,6-bis(4-chlorophenyl)-4-((1R)-2-hydroxy-1-phenylethyl)-3-morpholinone;
(5S,6R)-5,6-bis(4-chlorophenyl)-4-((1S)-2-hydroxy-1-phenylethyl)-3-morpholinone;
(2R)-2-((2S,3R)-2,3-bis(4-chlorophenyl)-5-oxo-4-morpholinyl)-3-phenylpropanoic acid;
(2S)-2-((2S,3R)-2,3-bis(4-chlorophenyl)-5-oxo-4-morpholinyl)-3-phenylpropanoic acid;
(2R)-2-((2R,3S)-2,3-bis(4-chlorophenyl)-5-oxo-4-morpholinyl)-3-phenylpropanoic acid;
(5R,6S)-5,6-bis(4-chlorophenyl)-4-((1R)-1-(hydroxymethyl)butyl)-3-morpholinone;
(5S,6R)-5,6-bis(4-chlorophenyl)-4-((1S)-1-(hydroxymethyl)butyl)-3-morpholinone;
(5R,6S)-5,6-bis(4-chlorophenyl)-4-((1S)-1-(hydroxymethyl)butyl)-3-morpholinone;
(5S,6R)-5,6-bis(4-chlorophenyl)-4-((1R)-1-(hydroxymethyl)butyl)-3-morpholinone;
(2R)-2-((2S,3R,6S)-2,3-bis(4-chlorophenyl)-6-(2-methoxybenzyl)-5-oxo-4-morpholinyl)pentanoic acid;
(2R)-((2S,3R)-2,3-bis(4-chlorophenyl)-5-oxo-4-morpholinyl)(4-chlorophenyl)ethanoic acid;
(2S)-((2R,3S)-2,3-bis(4-chlorophenyl)-5-oxo-4-morpholinyl)(4-chlorophenyl)ethanoic acid;
(2S)-((2S,3R)-2,3-bis(4-chlorophenyl)-5-oxo-4-morpholinyl)(4-chlorophenyl)ethanoic acid;
(2R)-((2R,3S)-2,3-bis(4-chlorophenyl)-5-oxo-4-morpholinyl)(4-chlorophenyl)ethanoic acid;
(2R,5S,6R)-5,6-bis(4-chlorophenyl)-2-(4-fluorobenzyl)-4-((1S)-1-(hydroxymethyl)butyl)-3-morpholinone;
(2S, 5R,6S)-5,6-bis(4-chlorophenyl)-2-(4-fluorobenzyl)-4-((1R)-1-(hydroxymethyl)butyl)-3-morpholinone;
(2R,5S,6R)-5,6-bis(4-chlorophenyl)-2-(4-fluorobenzyl)-4-((1R)-1-(hydroxymethyl)butyl)-3-morpholinone;
(2S, 5R,6S)-5,6-bis(4-chlorophenyl)-2-(4-fluorobenzyl)-4-((1S)-1-(hydroxymethyl)butyl)-3-morpholinone;
(5R,6S)-5,6-bis(4-chlorophenyl)-4-((1R)-1-(4-chlorophenyl)-2-hydroxyethyl)-3-morpholinone;
(5S,6R)-5,6-bis(4-chlorophenyl)-4-((1S)-1-(4-chlorophenyl)-2-hydroxyethyl)-3-morpholinone;
(5R,6S)-5,6-bis(4-chlorophenyl)-4-((1S)-1-(4-chlorophenyl)-2-hydroxyethyl)-3-morpholinone;
(5S,6R)-5,6-bis(4-chlorophenyl)-4-((1R)-1-(4-chlorophenyl)-2-hydroxyethyl)-3-morpholinone;
(5R,6S)-5,6-bis(4-chlorophenyl)-4-((1R)-1-(1-hydroxy-1-methylethyl)butyl)-3-morpholinone;
(5S,6R)-5,6-bis(4-chlorophenyl)-4-((1S)-1-(1-hydroxy-1-methylethyl)butyl)-3-morpholinone;
(5R,6S)-5,6-bis(4-chlorophenyl)-4-((1S)-1-(1-hydroxy-1-methylethyl)butyl)-3-morpholinone;
(5S,6R)-5,6-bis(4-chlorophenyl)-4-((1R)-1-(1-hydroxy-1-methylethyl)butyl)-3-morpholinone;
(2R)-2-((2S,3R,6S)-2,3-bis(4-chlorophenyl)-6-(4-fluorobenzyl)-5-oxo-4-morpholinyl)pentanamide;
(2S)-2-((2R,3S,6R)-2,3-bis(4-chlorophenyl)-6-(4-fluorobenzyl)-5-oxo-4-morpholinyl)pentanamide;
(2S)-2-((2S,3R,6S)-2,3-bis(4-chlorophenyl)-6-(4-fluorobenzyl)-5-oxo-4-morpholinyl)pentanamide;
(2R)-2-((2R,3S,6R)-2,3-bis(4-chlorophenyl)-6-(4-fluorobenzyl)-5-oxo-4-morpholinyl)pentanamide;
(2R)-2-((2S,3R)-2,3-bis(4-chlorophenyl)-5-oxo-4-morpholinyl)pentanamide;
(2S)-2-((2R,3S)-2,3-bis(4-chlorophenyl)-5-oxo-4-morpholinyl)pentanamide;
(2S)-2-((2S,3R)-2,3-bis(4-chlorophenyl)-5-oxo-4-morpholinyl)pentanamide;
(2R)-2-((2R,3S)-2,3-bis(4-chlorophenyl)-5-oxo-4-morpholinyl)pentanamide;
(2R)-2-((2S,3R)-2,3-bis(4-chlorophenyl)-5-oxo-4-morpholinyl)pentyl carbamate;
(2S)-2-((2R,3S)-2,3-bis(4-chlorophenyl)-5-oxo-4-morpholinyl)pentyl carbamate;
(2S)-2-((2S,3R)-2,3-bis(4-chlorophenyl)-5-oxo-4-morpholinyl)pentyl carbamate;
(2R)-2-((2R,3S)-2,3-bis(4-chlorophenyl)-5-oxo-4-morpholinyl)pentyl carbamate;
(2R)-2-((2S,3R,6S)-3-(4-chlorophenyl)-2-(3,4-dichlorophenyl)-6-(4-fluorobenzyl)-5-oxo-4-morpholinyl)pentanoic acid;
(2S)-2-((2R,3S,6R)-3-(4-chlorophenyl)-2-(3,4-dichlorophenyl)-6-(4-fluorobenzyl)-5-oxo-4-morpholinyl)pentanoic acid;
(2S)-2-((2S,3R,6S)-3-(4-chlorophenyl)-2-(3,4-dichlorophenyl)-6-(4-fluorobenzyl)-5-oxo-4-morpholinyl)pentanoic acid;

(2R)-2-((2R,3S,6R)-3-(4-chlorophenyl)-2-(3,4-dichlorophenyl)-6-(4-fluorobenzyl)-5-oxo-4-morpholinyl)pentanoic acid;
((2R,5S,6R)-6-(3-chlorophenyl)-5-(4-chlorophenyl)-4-(cyclopropylmethyl)-3-oxo-2-morpholinyl)acetic acid;
((2S,5S,6R)-6-(3-chlorophenyl)-5-(4-chlorophenyl)-4-(cyclopropylmethyl)-3-oxo-2-morpholinyl)acetic acid;
((2S,5R,6S)-6-(3-chlorophenyl)-5-(4-chlorophenyl)-4-(cyclopropylmethyl)-3-oxo-2-morpholinyl)acetic acid;
((2R,5R,6S)-6-(3-chlorophenyl)-5-(4-chlorophenyl)-4-(cyclopropylmethyl)-3-oxo-2-morpholinyl)acetic acid;
((2R,5S,6R)-6-(3-chlorophenyl)-5-(4-chlorophenyl)-4-((1R)-1-methylbutyl)-3-oxo-2-morpholinyl)acetic acid;
((2S,5R,6S)-6-(3-chlorophenyl)-5-(4-chlorophenyl)-4-((1S)-1-methylbutyl)-3-oxo-2-morpholinyl)acetic acid;
((2R,5S,6R)-6-(3-chlorophenyl)-5-(4-chlorophenyl)-4-((1S)-1-methylbutyl)-3-oxo-2-morpholinyl)acetic acid;
((2S,5R,6S)-6-(3-chlorophenyl)-5-(4-chlorophenyl)-4-((1R)-1-methylbutyl)-3-oxo-2-morpholinyl)acetic acid;
(2R)-2-((2S,3R)-3-(4-chlorophenyl)-2-(3,4-dichlorophenyl)-5-oxo-4-morpholinyl)pentanamide;
(2S)-2-((2R,3S)-3-(4-chlorophenyl)-2-(3,4-dichlorophenyl)-5-oxo-4-morpholinyl)pentanamide;
(2S)-2-((2S,3R)-3-(4-chlorophenyl)-2-(3,4-dichlorophenyl)-5-oxo-4-morpholinyl)pentanamide;
(2R)-2-((2R,3S)-3-(4-chlorophenyl)-2-(3,4-dichlorophenyl)-5-oxo-4-morpholinyl)pentanamide;
(2R)-((2S,3R,6S)-2,3-bis(4-chlorophenyl)-6-(4-fluorobenzyl)-5-oxo-4-morpholinyl)(4-chlorophenyl)ethanoic acid;
(2S)-((2R,3S,6R)-2,3-bis(4-chlorophenyl)-6-(4-fluorobenzyl)-5-oxo-4-morpholinyl)(4-chlorophenyl)ethanoic acid;
(2S)-((2R,3S,6S)-2,3-bis(4-chlorophenyl)-6-(4-fluorobenzyl)-5-oxo-4-morpholinyl)(4-chlorophenyl)ethanoic acid;
(2R)-((2R,3S,6R)-2,3-bis(4-chlorophenyl)-6-(4-fluorobenzyl)-5-oxo-4-morpholinyl)(4-chlorophenyl)ethanoic acid;
(2R)-2-((2S,3R,6S)-2,3-bis(4-chlorophenyl)-6-(4-fluorobenzyl)-5-oxo-4-morpholinyl)-2-(4-chlorophenyl)ethanamide;
(2S)-2-((2R,3S,6R)-2,3-bis(4-chlorophenyl)-6-(4-fluorobenzyl)-5-oxo-4-morpholinyl)-2-(4-chlorophenyl)ethanamide;
(2S)-2-((2S,3R,6S)-2,3-bis(4-chlorophenyl)-6-(4-fluorobenzyl)-5-oxo-4-morpholinyl)-2-(4-chlorophenyl)ethanamide;
(2R)-2-((2R,3S,6R)-2,3-bis(4-chlorophenyl)-6-(4-fluorobenzyl)-5-oxo-4-morpholinyl)-2-(4-chlorophenyl)ethanamide;
methyl 4-(((2R)-2-((2S,3R,6S)-2,3-bis(4-chlorophenyl)-6-(4-(methylsulfonyl)benzyl)-5-oxo-4-morpholinyl)pentanoyl)amino)butanoate;
(2R)-2-((2S,3R,6S)-2-(3-chlorophenyl)-3-(4-chlorophenyl)-6-((2R)-2,3-dihydroxypropyl)-5-oxo-4-morpholinyl)pentanamide;
(2S)-2-((2R,3S,6R)-2-(3-chlorophenyl)-3-(4-chlorophenyl)-6-((2S)-2,3-dihydroxypropyl)-5-oxo-4-morpholinyl)pentanamide;
(2S)-2-((2S,3R,6S)-2-(3-chlorophenyl)-3-(4-chlorophenyl)-6-((2R)-2,3-dihydroxypropyl)-5-oxo-4-morpholinyl)pentanamide;
(2R)-2-((2R,3S,6R)-2-(3-chlorophenyl)-3-(4-chlorophenyl)-6-((2S)-2,3-dihydroxypropyl)-5-oxo-4-morpholinyl)pentanamide;
(2R)-2-((2S,3R,6S)-2-(3-chlorophenyl)-3-(4-chlorophenyl)-6-((2S)-2,3-dihydroxypropyl)-5-oxo-4-morpholinyl)pentanamide;
(2S)-2-((2R,3S,6R)-2-(3-chlorophenyl)-3-(4-chlorophenyl)-6-((2R)-2,3-dihydroxypropyl)-5-oxo-4-morpholinyl)pentanamide;
(2S)-2-((2S,3R,6S)-2-(3-chlorophenyl)-3-(4-chlorophenyl)-6-((2S)-2,3-dihydroxypropyl)-5-oxo-4-morpholinyl)pentanamide;
(2R)-2-((2R,3S,6R)-2-(3-chlorophenyl)-3-(4-chlorophenyl)-6-((2R)-2,3-dihydroxypropyl)-5-oxo-4-morpholinyl)pentanamide;
(2R)-2-((2S,3R)-2,3-bis(4-chlorophenyl)-5-oxo-4-morpholinyl)-2-(4-chlorophenyl)ethanamide;
(2S)-2-((2R,3S)-2,3-bis(4-chlorophenyl)-5-oxo-4-morpholinyl)-2-(4-chlorophenyl)ethanamide;
(2S)-2-((2S,3R)-2,3-bis(4-chlorophenyl)-5-oxo-4-morpholinyl)-2-(4-chlorophenyl)ethanamide;
(2R)-2-((2R,3S)-2,3-bis(4-chlorophenyl)-5-oxo-4-morpholinyl)-2-(4-chlorophenyl)ethanamide;
(2R)-2-((2S,3R,6S)-3-(4-chlorophenyl)-2-(3,4-dichlorophenyl)-6-(4-fluorobenzyl)-5-oxo-4-morpholinyl)pentanamide;
(2S)-2-((2R,3S,6S)-3-(4-chlorophenyl)-2-(3,4-dichlorophenyl)-6-(4-fluorobenzyl)-5-oxo-4-morpholinyl)pentanamide;
(2S)-2-((2S,3R,6S)-3-(4-chlorophenyl)-2-(3,4-dichlorophenyl)-6-(4-fluorobenzyl)-5-oxo-4-morpholinyl)pentanamide;
(2R)-2-((2R,3S,6S)-3-(4-chlorophenyl)-2-(3,4-dichlorophenyl)-6-(4-fluorobenzyl)-5-oxo-4-morpholinyl)pentanamide;
(2R)-2-((2S,3R,6S)-2,3-bis(4-chlorophenyl)-6-(2-(4-methyl-1-piperazinyl)ethyl)-5-oxo-4-morpholinyl)pentanoic acid;
(2R)-2-((2S,3R)-2,3-bis(4-chlorophenyl)-5-oxo-4-morpholinyl)-N-methylpentanamide;
(2S)-2-((2R,3S)-2,3-bis(4-chlorophenyl)-5-oxo-4-morpholinyl)-N-methylpentanamide;
(2S)-2-((2S,3R)-2,3-bis(4-chlorophenyl)-5-oxo-4-morpholinyl)-N-methylpentanamide;
(2R)-2-((2R,3S)-2,3-bis(4-chlorophenyl)-5-oxo-4-morpholinyl)-N-methylpentanamide;
(2R)-2-((2S,3R)-2,3-bis(4-chlorophenyl)-5-oxo-4-morpholinyl)-N-(2-hydroxyethyl)pentanamide;
(2S)-2-((2R,3S)-2,3-bis(4-chlorophenyl)-5-oxo-4-morpholinyl)-N-(2-hydroxyethyl)pentanamide;
(2S)-2-((2S,3R)-2,3-bis(4-chlorophenyl)-5-oxo-4-morpholinyl)-N-(2-hydroxyethyl)pentanamide;
(2R)-2-((2R,3S)-2,3-bis(4-chlorophenyl)-5-oxo-4-morpholinyl)-N-(2-hydroxyethyl)pentanamide;
(2R)-2-((2S,3R)-2,3-bis(4-chlorophenyl)-5-oxo-4-morpholinyl)-N,N-dimethylpentanamide;
(2S)-2-((2R,3S)-2,3-bis(4-chlorophenyl)-5-oxo-4-morpholinyl)-N,N-dimethylpentanamide;
(2S)-2-((2S,3R)-2,3-bis(4-chlorophenyl)-5-oxo-4-morpholinyl)-N,N-dimethylpentanamide;
(2R)-2-((2R,3S)-2,3-bis(4-chlorophenyl)-5-oxo-4-morpholinyl)-N,N-dimethylpentanamide;
(2R)-2-((2S,3R)-2,3-bis(4-chlorophenyl)-5-oxo-4-morpholinyl)-N-(2-(4-morpholinyl)ethyl)pentanamide;
(2S)-2-((2R,3S)-2,3-bis(4-chlorophenyl)-5-oxo-4-morpholinyl)-N-(2-(4-morpholinyl)ethyl)pentanamide;

(2S)-2-((2S,3R)-2,3-bis(4-chlorophenyl)-5-oxo-4-morpholinyl)-N-(2-(4-morpholinyl)ethyl)pentanamide;
(2R)-2-((2R,3S)-2,3-bis(4-chlorophenyl)-5-oxo-4-morpholinyl)-N-(2-(4-morpholinyl)ethyl)pentanamide;
(2R)-2-((2S,3R,6S)-2,3-bis(4-chlorophenyl)-6-(3-(1H-imidazol-1-yl)propyl)-5-oxo-4-morpholinyl)pentanoic acid;
(2R)-2-((2S,3R)-2,3-bis(4-chlorophenyl)-5-oxo-4-morpholinyl)-N-propylpentanamide;
(2S)-2-((2R,3S)-2,3-bis(4-chlorophenyl)-5-oxo-4-morpholinyl)-N-propylpentanamide;
(2S)-2-((2S,3R)-2,3-bis(4-chlorophenyl)-5-oxo-4-morpholinyl)-N-propylpentanamide;
(2R)-2-((2R,3S)-2,3-bis(4-chlorophenyl)-5-oxo-4-morpholinyl)-N-propylpentanamide;
(5R,6S)-4-((1R)-1-(aminomethyl)butyl)-5,6-bis(4-chlorophenyl)-3-morpholinone;
(5S,6R)-4-((1S)-1-(aminomethyl)butyl)-5,6-bis(4-chlorophenyl)-3-morpholinone;
(5R,6S)-4-((1S)-1-(aminomethyl)butyl)-5,6-bis(4-chlorophenyl)-3-morpholinone;
(5S,6R)-4-((1R)-1-(aminomethyl)butyl)-5,6-bis(4-chlorophenyl)-3-morpholinone;
(2R)-2-((2S,3R,6S)-2-(4-chloro-3-fluorophenyl)-3-(4-chlorophenyl)-6-(4-fluorobenzyl)-5-oxo-4-morpholinyl)pentanamide;
(2S)-2-((2R,3S,6R)-2-(4-chloro-3-fluorophenyl)-3-(4-chlorophenyl)-6-(4-fluorobenzyl)-5-oxo-4-morpholinyl)pentanamide;
(2S)-2-((2S,3R,6S)-2-(4-chloro-3-fluorophenyl)-3-(4-chlorophenyl)-6-(4-fluorobenzyl)-5-oxo-4-morpholinyl)pentanamide;
(2R)-2-((2R,3S,6R)-2-(4-chloro-3-fluorophenyl)-3-(4-chlorophenyl)-6-(4-fluorobenzyl)-5-oxo-4-morpholinyl)pentanamide;
(2R)-2-((2S,3R,6S)-2,3-bis(4-chlorophenyl)-5-oxo-6-(2-propen-1-yl)-4-morpholinyl)pentanamide;
(2S)-2-((2R,3S,6R)-2,3-bis(4-chlorophenyl)-5-oxo-6-(2-propen-1-yl)-4-morpholinyl)pentanamide;
(2S)-2-((2S,3R,6S)-2,3-bis(4-chlorophenyl)-5-oxo-6-(2-propen-1-yl)-4-morpholinyl)pentanamide;
(2R)-2-((2R,3S,6R)-2,3-bis(4-chlorophenyl)-5-oxo-6-(2-propen-1-yl)-4-morpholinyl)pentanamide;
(2R)-2-((2R,3S,6R)-2,3-bis(4-chlorophenyl)-6-(4-fluorobenzyl)-5-oxo-4-morpholinyl)pentanoic acid;
(2R)-2-((2S,3R,6S)-2,3-bis(4-chlorophenyl)-6-(4-fluorobenzyl)-5-oxo-4-morpholinyl)pentanoic acid;
(2S)-2-((2R,3S,6R)-2,3-bis(4-chlorophenyl)-6-(4-fluorobenzyl)-5-oxo-4-morpholinyl)pentanoic acid;
(2S)-2-((2S,3R,6S)-2,3-bis(4-chlorophenyl)-6-(4-fluorobenzyl)-5-oxo-4-morpholinyl)pentanoic acid;
N-((2R)-2-((2S,3R)-2,3-bis(4-chlorophenyl)-5-oxo-4-morpholinyl)pentyl)-2-hydroxyacetamide;
N-((2S)-2-((2R,3S)-2,3-bis(4-chlorophenyl)-5-oxo-4-morpholinyl)pentyl)-2-hydroxyacetamide;
N-((2S)-2-((2S,3R)-2,3-bis(4-chlorophenyl)-5-oxo-4-morpholinyl)pentyl)-2-hydroxyacetamide;
N-((2R)-2-((2R,3S)-2,3-bis(4-chlorophenyl)-5-oxo-4-morpholinyl)pentyl)-2-hydroxyacetamide;
(2R)-2-((2S,3R,6S)-2,3-bis(4-chlorophenyl)-6-(3-methoxybenzyl)-5-oxo-4-morpholinyl)pentanoic acid;
(2R)-2-((2S,3R)-2-(4-chloro-2-methylphenyl)-3-(4-chlorophenyl)-5-oxo-4-morpholinyl)pentanoic acid;
(2S)-2-((2R,3S)-2-(4-chloro-2-methylphenyl)-3-(4-chlorophenyl)-5-oxo-4-morpholinyl)pentanoic acid;
(2S)-2-((2S,3R)-2-(4-chloro-2-methylphenyl)-3-(4-chlorophenyl)-5-oxo-4-morpholinyl)pentanoic acid;
(2R)-2-((2R,3S)-2-(4-chloro-2-methylphenyl)-3-(4-chlorophenyl)-5-oxo-4-morpholinyl)pentanoic acid;
(3R)-3-((2R,3S,6R)-2-(3-chlorophenyl)-3-(4-chlorophenyl)-6-(4-fluorobenzyl)-5-oxo-4-morpholinyl)hexanoic acid;
(2R)-2-((2S,3R,6S)-2,3-bis(4-chlorophenyl)-5-oxo-6-(2-propen-1-yl)-4-morpholinyl)pentanoic acid;
(2S)-2-((2R,3S,6R)-2,3-bis(4-chlorophenyl)-5-oxo-6-(2-propen-1-yl)-4-morpholinyl)pentanoic acid;
(2R)-2-((2S,3R,6S)-2,3-bis(4-chlorophenyl)-6-((2S)-2,3-dihydroxypropyl)-5-oxo-4-morpholinyl)pentanamide;
(2S)-2-((2R,3S,6R)-2,3-bis(4-chlorophenyl)-6-((2R)-2,3-dihydroxypropyl)-5-oxo-4-morpholinyl)pentanamide;
(2R)-2-((2S,3R,6S)-2,3-bis(4-chlorophenyl)-6-((2R)-2,3-dihydroxypropyl)-5-oxo-4-morpholinyl)pentanamide;
(2S)-2-((2R,3S,6R)-2,3-bis(4-chlorophenyl)-6-((2S)-2,3-dihydroxypropyl)-5-oxo-4-morpholinyl)pentanamide;
(2R)-2-((2S,3R,6S)-2,3-bis(4-chlorophenyl)-6-((2R)-2,3-dihydroxypropyl)-5-oxo-4-morpholinyl)pentanoic acid;
(2R)-2-((2S,3R,6S)-2,3-bis(4-chlorophenyl)-6-((2S)-2,3-dihydroxypropyl)-5-oxo-4-morpholinyl)pentanoic acid;
(2S)-2-((2R,3S,6R)-2,3-bis(4-chlorophenyl)-6-((2R)-2,3-dihydroxypropyl)-5-oxo-4-morpholinyl)pentanoic acid;
(2S)-2-((2R,3S,6R)-2,3-bis(4-chlorophenyl)-6-((2S)-2,3-dihydroxypropyl)-5-oxo-4-morpholinyl)pentanoic acid;
(2R)-2-((2S,5R,6S)-2-(2-amino-2-oxoethyl)-5,6-bis(4-chlorophenyl)-3-oxo-4-morpholinyl)pentanoic acid;
(2S)-2-((2R,5S,6R)-2-(2-amino-2-oxoethyl)-5,6-bis(4-chlorophenyl)-3-oxo-4-morpholinyl)pentanoic acid;
((2R,5S,6R)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid;
((2S,5R,6S)-6-(3-chlorophenyl)-5-(4-chlorophenyl)-4-((1R)-1-(((cyclopropylsulfonyl)(phenyl)amino)methyl)propyl)-3-oxo-2-morpholinyl)acetic acid;
((2S,5S,6R)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid;
((2R,5R,6S)-6-(3-chlorophenyl)-5-(4-chlorophenyl)-4-((1R)-1-(((cyclopropylsulfonyl)(phenyl)amino)methyl)propyl)-3-oxo-2-morpholinyl)acetic acid;
((2R,5S,6R)-6-(3-chlorophenyl)-5-(4-chlorophenyl)-4-((1R)-1-(((cyclopropylsulfonyl)(phenyl)amino)methyl)propyl)-3-oxo-2-morpholinyl)acetic acid;
((2S,5R,6S)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid;
((2S,5S,6R)-6-(3-chlorophenyl)-5-(4-chlorophenyl)-4-((1R)-1-(((cyclopropylsulfonyl)(phenyl)amino)methyl)propyl)-3-oxo-2-morpholinyl)acetic acid;
((2R,5R,6S)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid;
((2R,5S,6R)-4-((1S)-1-carbamoylbutyl)-5,6-bis(4-chlorophenyl)-3-oxo-2-morpholinyl)acetic acid;
((2S,5R,6S)-4-((1R)-1-carbamoylbutyl)-5,6-bis(4-chlorophenyl)-3-oxo-2-morpholinyl)acetic acid;
((2R,5S,6R)-6-(3-chlorophenyl)-5-(4-chlorophenyl)-4-((1S)-1-(ethoxycarbonyl)butyl)-3-oxo-2-morpholinyl)acetic acid;
((2S,5R,6S)-6-(3-chlorophenyl)-5-(4-chlorophenyl)-4-((1R)-1-(ethoxycarbonyl)butyl)-3-oxo-2-morpholinyl)acetic acid;

((2R,5S,6R)-6-(3-chlorophenyl)-5-(4-chlorophenyl)-4-((1R)-1-(ethoxycarbonyl)butyl)-3-oxo-2-morpholinyl)acetic acid;

((2S, 5R,6S)-6-(3-chlorophenyl)-5-(4-chlorophenyl)-4-((1S)-1-(ethoxycarbonyl)butyl)-3-oxo-2-morpholinyl)acetic acid;

(2R)-2-((2S,3R,6S)-2,3-bis(4-chlorophenyl)-6-(4-fluorobenzyl)-5-oxo-4-morpholinyl)-N-(2-(4-morpholinyl)ethyl)pentanamide;

(2S)-2-((2R,3S,6R)-2,3-bis(4-chlorophenyl)-6-(4-fluorobenzyl)-5-oxo-4-morpholinyl)-N-(2-(4-morpholinyl)ethyl)pentanamide;

(5R,6S)-5,6-bis(4-chlorophenyl)-4-((1R)-1-(4-morpholinylmethyl)butyl)-3-morpholinone;

(5S,6R)-5,6-bis(4-chlorophenyl)-4-((1S)-1-(4-morpholinylmethyl)butyl)-3-morpholinone;

N-((2R)-2-((2S,3R)-2,3-bis(4-chlorophenyl)-5-oxo-4-morpholinyl)pentyl)methanesulfonamide;

N-((2S)-2-((2R,3S)-2,3-bis(4-chlorophenyl)-5-oxo-4-morpholinyl)pentyl)methanesulfonamide;

(2R,5S,6R)-5,6-bis(4-chlorophenyl)-2-(4-fluorobenzyl)-4-((1S)-1-((4-methyl-1-piperazinyl)carbonyl)butyl)-3-morpholinone;

(2S, 5R,6S)-5,6-bis(4-chlorophenyl)-2-(4-fluorobenzyl)-4-((1R)-1-((4-methyl-1-piperazinyl)carbonyl)butyl)-3-morpholinone;

(2R,5S,6R)-5,6-bis(4-chlorophenyl)-2-(4-fluorobenzyl)-4-((1S)-1-(4-morpholinylcarbonyl)butyl)-3-morpholinone;

(2S, 5R,6S)-5,6-bis(4-chlorophenyl)-2-(4-fluorobenzyl)-4-((1R)-1-(4-morpholinylcarbonyl)butyl)-3-morpholinone;

(2R,5S,6R)-4-((1S)-1-(aminomethyl)butyl)-5,6-bis(4-chlorophenyl)-2-(4-fluorobenzyl)-3-morpholinone;

(2S, 5R,6S)-4-((1R)-1-(aminomethyl)butyl)-5,6-bis(4-chlorophenyl)-2-(4-fluorobenzyl)-3-morpholinone;

(5R,6S)-2-benzyl-5,6-bis(4-chlorophenyl)-4-methyl-3-morpholinone;

(5S,6R)-2-benzyl-5,6-bis(4-chlorophenyl)-4-methyl-3-morpholinone;

((2R,5S,6R)-6-(3-chlorophenyl)-5-(4-chlorophenyl)-4-(cyclopropylsulfonyl)-3-oxo-2-morpholinyl)acetic acid;

((2S,5R,6S)-6-(3-chlorophenyl)-5-(4-chlorophenyl)-4-(cyclopropylsulfonyl)-3-oxo-2-morpholinyl)acetic acid;

(2R,5S,6R)-5,6-bis(4-chlorophenyl)-2-(4-fluorobenzyl)-4-((1S)-1-(4-morpholinylmethyl)butyl)-3-morpholinone;

(2S,5R,6S)-5,6-bis(4-chlorophenyl)-2-(4-fluorobenzyl)-4-((1R)-1-(4-morpholinylmethyl)butyl)-3-morpholinone;

(2R)-2-((2S,3R,6S)-3-(4-chlorophenyl)-6-(4-fluorobenzyl)-5-oxo-2-phenyl-4-morpholinyl)pentanoic acid;

(2S)-2-((2R,3S,6R)-3-(4-chlorophenyl)-6-(4-fluorobenzyl)-5-oxo-2-phenyl-4-morpholinyl)pentanoic acid;

(2S)-2-((2S,3R,6S)-3-(4-chlorophenyl)-6-(4-fluorobenzyl)-5-oxo-2-phenyl-4-morpholinyl)pentanoic acid;

(2R)-2-((2R,3S,6R)-3-(4-chlorophenyl)-6-(4-fluorobenzyl)-5-oxo-2-phenyl-4-morpholinyl)pentanoic acid;

(2R)-2-((2S,3R,6S)-2,3-bis(4-chlorophenyl)-6-(2-(4-morpholinyl)ethyl)-5-oxo-4-morpholinyl)pentanoic acid;

(2R)-((2S,3R,6S)-2,3-bis(4-chlorophenyl)-6-(4-fluorobenzyl)-5-oxo-4-morpholinyl)(phenyl)ethanoic acid;

(2S)-((2R,3S,6R)-2,3-bis(4-chlorophenyl)-6-(4-fluorobenzyl)-5-oxo-4-morpholinyl)(phenyl)ethanoic acid;

(2S)-((2S,3R,6S)-2,3-bis(4-chlorophenyl)-6-(4-fluorobenzyl)-5-oxo-4-morpholinyl)(phenyl)ethanoic acid;

(2R)-((2R,3S,6R)-2,3-bis(4-chlorophenyl)-6-(4-fluorobenzyl)-5-oxo-4-morpholinyl)(phenyl)ethanoic acid;

(2R)-2-((2S,3R)-2-(4-chlorophenyl)-3-(3,4-dichlorophenyl)-5-oxo-4-morpholinyl)pentanoic acid;

(2S)-2-((2R,3S)-2-(4-chlorophenyl)-3-(3,4-dichlorophenyl)-5-oxo-4-morpholinyl)pentanoic acid;

(2S)-2-((2S,3R)-2-(4-chlorophenyl)-3-(3,4-dichlorophenyl)-5-oxo-4-morpholinyl)pentanoic acid;

(2R)-2-((2R,3S)-2-(4-chlorophenyl)-3-(3,4-dichlorophenyl)-5-oxo-4-morpholinyl)pentanoic acid;

(5R,6S)-6-(3-chlorophenyl)-5-(4-chlorophenyl)-4-(1-methylethyl)-3-thiomorpholinone 1,1-dioxide;

(2R)-2-((2S,3R,6S)-2-(3-chlorophenyl)-3-(4-chlorophenyl)-6-(2-(4-morpholinyl)-2-oxoethyl)-5-oxo-4-morpholinyl)pentanoic acid;

(2S)-2-((2R,3S,6R)-2-(3-chlorophenyl)-3-(4-chlorophenyl)-6-(2-(4-morpholinyl)-2-oxoethyl)-5-oxo-4-morpholinyl)pentanoic acid;

(2S)-2-((2S,3R,6S)-2-(3-chlorophenyl)-3-(4-chlorophenyl)-6-(2-(4-morpholinyl)-2-oxoethyl)-5-oxo-4-morpholinyl)pentanoic acid;

(2R)-2-((2R,3S,6R)-2-(3-chlorophenyl)-3-(4-chlorophenyl)-6-(2-(4-morpholinyl)-2-oxoethyl)-5-oxo-4-morpholinyl)pentanoic acid;

(2R)-2-((2S,3R)-3-(4-bromophenyl)-2-(4-chlorophenyl)-5-oxo-4-morpholinyl)pentanoic acid;

(2S)-2-((2R,3S)-3-(4-bromophenyl)-2-(4-chlorophenyl)-5-oxo-4-morpholinyl)pentanoic acid;

(2S)-2-((2S,3R)-3-(4-bromophenyl)-2-(4-chlorophenyl)-5-oxo-4-morpholinyl)pentanoic acid;

(2R)-2-((2R,3S)-3-(4-bromophenyl)-2-(4-chlorophenyl)-5-oxo-4-morpholinyl)pentanoic acid;

(2R)-2-((2S,3R,6S)-2,3-bis(4-chlorophenyl)-5-oxo-6-(2-(1-piperidinyl)ethyl)-4-morpholinyl)pentanoic acid;

(2R)-2-((2S,3R)-2-(4-chlorophenyl)-3-(4-cyclopropylphenyl)-5-oxo-4-morpholinyl)pentanoic acid;

(2S)-2-((2R,3S)-2-(4-chlorophenyl)-3-(4-cyclopropylphenyl)-5-oxo-4-morpholinyl)pentanoic acid;

(2S)-2-((2S,3R)-2-(4-chlorophenyl)-3-(4-cyclopropylphenyl)-5-oxo-4-morpholinyl)pentanoic acid;

(2R)-2-((2R,3S)-2-(4-chlorophenyl)-3-(4-cyclopropylphenyl)-5-oxo-4-morpholinyl)pentanoic acid;

(2R)-2-((2S,3R,6S)-3-(4-bromophenyl)-2-(4-chlorophenyl)-6-(4-fluorobenzyl)-5-oxo-4-morpholinyl)pentanoic acid;

(2S)-2-((2R,3S,6R)-3-(4-bromophenyl)-2-(4-chlorophenyl)-6-(4-fluorobenzyl)-5-oxo-4-morpholinyl)pentanoic acid;

(2S)-2-((2S,3R,6S)-3-(4-bromophenyl)-2-(4-chlorophenyl)-6-(4-fluorobenzyl)-5-oxo-4-morpholinyl)pentanoic acid;

(2R)-2-((2R,3S,6R)-3-(4-bromophenyl)-2-(4-chlorophenyl)-6-(4-fluorobenzyl)-5-oxo-4-morpholinyl)pentanoic acid;

2-(((2R,5S,6R)-5,6-bis(4-chlorophenyl)-4-methyl-3-oxo-2-morpholinyl)methyl)benzonitrile;

2-(((2S,5R,6S)-5,6-bis(4-chlorophenyl)-4-methyl-3-oxo-2-morpholinyl)methyl)benzonitrile;

(2R)-2-((2S,3R,6S)-2-(3-chlorophenyl)-3-(4-chlorophenyl)-6-(4-fluorobenzyl)-5-oxo-4-morpholinyl)pentanamide;

(2S)-2-((2R,3S,6R)-2-(3-chlorophenyl)-3-(4-chlorophenyl)-6-(4-fluorobenzyl)-5-oxo-4-morpholinyl)pentanamide;

(2S)-2-((2S,3R,6S)-2-(3-chlorophenyl)-3-(4-chlorophenyl)-6-(4-fluorobenzyl)-5-oxo-4-morpholinyl)pentanamide;
(2R)-2-((2R,3S,6R)-2-(3-chlorophenyl)-3-(4-chlorophenyl)-6-(4-fluorobenzyl)-5-oxo-4-morpholinyl)pentanamide;
(2R)-2-((2S,3R,6S)-2,3-bis(4-chlorophenyl)-6-(2-fluoro-4-(methylsulfonyl)benzyl)-5-oxo-4-morpholinyl)pentanoic acid;
(2S)-2-((2R,3S,6R)-2,3-bis(4-chlorophenyl)-6-(2-fluoro-4-(methylsulfonyl)benzyl)-5-oxo-4-morpholinyl)pentanoic acid;
(2R)-2-((2S,3R,6S)-2,3-bis(4-chlorophenyl)-6-(4-fluorobenzyl)-5-oxo-4-morpholinyl)hexanoic acid;
(2S)-2-((2R,3S,6R)-2,3-bis(4-chlorophenyl)-6-(4-fluorobenzyl)-5-oxo-4-morpholinyl)hexanoic acid;
(2S)-2-((2S,3R,6S)-2,3-bis(4-chlorophenyl)-6-(4-fluorobenzyl)-5-oxo-4-morpholinyl)hexanoic acid;
(2R)-2-((2R,3S,6R)-2,3-bis(4-chlorophenyl)-6-(4-fluorobenzyl)-5-oxo-4-morpholinyl)hexanoic acid;
(2R,5S,6R)-5,6-bis(4-chlorophenyl)-2-(4-fluorobenzyl)-4-((1S)-1-(1H-tetrazol-5-yl)butyl)-3-morpholinone;
(2S, 5R,6S)-5,6-bis(4-chlorophenyl)-2-(4-fluorobenzyl)-4-((1R)-1-(1H-tetrazol-5-yl)butyl)-3-morpholinone;
N-((2R)-2-((2S,3R,6S)-2,3-bis(4-chlorophenyl)-6-(4-fluorobenzyl)-5-oxo-4-morpholinyl)pentanoyl)glycine;
N-((2S)-2-((2R,3S,6R)-2,3-bis(4-chlorophenyl)-6-(4-fluorobenzyl)-5-oxo-4-morpholinyl)pentanoyl)glycine;
(2R)-2-((2S,3R,6S)-3-(4-bromophenyl)-2-(4-chlorophenyl)-6-(4-cyanobenzyl)-5-oxo-4-morpholinyl)pentanoic acid;
(2S)-2-((2R,3S,6R)-3-(4-bromophenyl)-2-(4-chlorophenyl)-6-(4-cyanobenzyl)-5-oxo-4-morpholinyl)pentanoic acid;
3-((2R,5S,6R)-6-(3-chlorophenyl)-5-(4-chlorophenyl)-4-(cyclopropylmethyl)-3-oxo-2-morpholinyl)propanenitrile;
3-((2S,5R,6S)-6-(3-chlorophenyl)-5-(4-chlorophenyl)-4-(cyclopropylmethyl)-3-oxo-2-morpholinyl)propanenitrile;
2-((2R,5S,6R)-6-(3-chlorophenyl)-5-(4-chlorophenyl)-4-(cyclopropylmethyl)-3-oxo-2-morpholinyl)-N-(2-(4-morpholinyl)ethyl)acetamide;
2-((2S,5R,6S)-6-(3-chlorophenyl)-5-(4-chlorophenyl)-4-(cyclopropylmethyl)-3-oxo-2-morpholinyl)-N-(2-(4-morpholinyl)ethyl)acetamide;
(2R)-2-((2S,3R)-2-(3-chlorophenyl)-3-(4-chlorophenyl)-6-(4-fluorobenzyl)-5-oxo-4-morpholinyl)pentanoic acid;
(2S)-2-((2R,3S)-2-(3-chlorophenyl)-3-(4-chlorophenyl)-6-(4-fluorobenzyl)-5-oxo-4-morpholinyl)pentanoic acid;
(2S)-2-((2S,3R)-2-(3-chlorophenyl)-3-(4-chlorophenyl)-6-(4-fluorobenzyl)-5-oxo-4-morpholinyl)pentanoic acid;
(2R)-2-((2R,3S)-2-(3-chlorophenyl)-3-(4-chlorophenyl)-6-(4-fluorobenzyl)-5-oxo-4-morpholinyl)pentanoic acid;
(S)-2-((2R,5S,6R)-6-(3-chlorophenyl)-5-(4-chlorophenyl)-4-(cyclopropylmethyl)-3-oxomorpholin-2-yl)-2-hydroxyacetic acid;
(R)-2-((2S,5R,6S)-6-(3-chlorophenyl)-5-(4-chlorophenyl)-4-(cyclopropylmethyl)-3-oxomorpholin-2-yl)-2-hydroxyacetic acid;
(R)-2-((2R,5S,6R)-6-(3-chlorophenyl)-5-(4-chlorophenyl)-4-(cyclopropylmethyl)-3-oxomorpholin-2-yl)-2-hydroxyacetic acid;
(S)-2-((2S,5R,6S)-6-(3-chlorophenyl)-5-(4-chlorophenyl)-4-(cyclopropylmethyl)-3-oxomorpholin-2-yl)-2-hydroxyacetic acid;
((2R,5S,6R)-6-(3-chloro-2-fluorophenyl)-5-(4-chlorophenyl)-4-(cyclopropylmethyl)-3-oxo-2-morpholinyl)acetic acid;
((2S,5R,6S)-6-(3-chloro-2-fluorophenyl)-5-(4-chlorophenyl)-4-(cyclopropylmethyl)-3-oxo-2-morpholinyl)acetic acid;
((2R,5S,6R)-4-butyl-6-(3-chlorophenyl)-5-(4-chlorophenyl)-3-oxo-2-morpholinyl)acetic acid;
((2S,5R,6S)-4-butyl-6-(3-chlorophenyl)-5-(4-chlorophenyl)-3-oxo-2-morpholinyl)acetic acid;
(2R)-2-((2S,3R)-3-(4-chlorophenyl)-2-(2,4-dichlorophenyl)-5-oxo-4-morpholinyl)pentanoic acid;
(2S)-2-((2R,3S)-3-(4-chlorophenyl)-2-(2,4-dichlorophenyl)-5-oxo-4-morpholinyl)pentanoic acid;
(2S)-2-((2S,3R)-3-(4-chlorophenyl)-2-(2,4-dichlorophenyl)-5-oxo-4-morpholinyl)pentanoic acid;
(2R)-2-((2R,3S)-3-(4-chlorophenyl)-2-(2,4-dichlorophenyl)-5-oxo-4-morpholinyl)pentanoic acid;
N'-acetyl-2-((2R,5S,6R)-6-(3-chlorophenyl)-5-(4-chlorophenyl)-4-(cyclopropylmethyl)-3-oxo-2-morpholinyl)acetohydrazide;
N'-acetyl-2-((2S,5R,6S)-6-(3-chlorophenyl)-5-(4-chlorophenyl)-4-(cyclopropylmethyl)-3-oxo-2-morpholinyl)acetohydrazide;
(2R,5S,6R)-6-(3-chlorophenyl)-5-(4-chlorophenyl)-4-(cyclopropylmethyl)-2-(2-(4-morpholinyl)-2-oxoethyl)-3-morpholinone;
(2S,5R,6S)-6-(3-chlorophenyl)-5-(4-chlorophenyl)-4-(cyclopropylmethyl)-2-(2-(4-morpholinyl)-2-oxoethyl)-3-morpholinone;
(2R)-2-((2S,3R)-2-(3-chlorophenyl)-3-(4-chlorophenyl)-5-oxo-4-morpholinyl)pentanamide;
(2S)-2-((2R,3S)-2-(3-chlorophenyl)-3-(4-chlorophenyl)-5-oxo-4-morpholinyl)pentanamide;
(2S)-2-((2S,3R)-2-(3-chlorophenyl)-3-(4-chlorophenyl)-5-oxo-4-morpholinyl)pentanamide;
(2R)-2-((2R,3S)-2-(3-chlorophenyl)-3-(4-chlorophenyl)-5-oxo-4-morpholinyl)pentanamide;
2-((2R,5S,6R)-6-(3-chlorophenyl)-5-(4-chlorophenyl)-4-(cyclopropylmethyl)-3-oxo-2-morpholinyl)ethyl carbamate;
2-((2S,5R,6S)-6-(3-chlorophenyl)-5-(4-chlorophenyl)-4-(cyclopropylmethyl)-3-oxo-2-morpholinyl)ethyl carbamate;
(2R)-((2S,3R,6S)-2,3-bis(4-chlorophenyl)-6-(4-fluorobenzyl)-5-oxo-4-morpholinyl)(3-chlorophenyl)ethanoic acid;
(2S)-((2R,3S,6R)-2,3-bis(4-chlorophenyl)-6-(4-fluorobenzyl)-5-oxo-4-morpholinyl)(3-chlorophenyl)ethanoic acid;
(2S)-((2S,3R,6S)-2,3-bis(4-chlorophenyl)-6-(4-fluorobenzyl)-5-oxo-4-morpholinyl)(3-chlorophenyl)ethanoic acid;
(2R)-((2R,3S,6R)-2,3-bis(4-chlorophenyl)-6-(4-fluorobenzyl)-5-oxo-4-morpholinyl)(3-chlorophenyl)ethanoic acid;
(2R)-2-((2S,3R,6S)-3-(4-chlorophenyl)-2-(2,4-dichlorophenyl)-6-(4-fluorobenzyl)-5-oxo-4-morpholinyl)pentanoic acid;
(2S)-2-((2R,3S,6R)-3-(4-chlorophenyl)-2-(2,4-dichlorophenyl)-6-(4-fluorobenzyl)-5-oxo-4-morpholinyl)pentanoic acid;

(2S)-2-((2S,3R,6S)-3-(4-chlorophenyl)-2-(2,4-dichlorophenyl)-6-(4-fluorobenzyl)-5-oxo-4-morpholinyl)pentanoic acid;
(2R)-2-((2R,3S,6R)-3-(4-chlorophenyl)-2-(2,4-dichlorophenyl)-6-(4-fluorobenzyl)-5-oxo-4-morpholinyl)pentanoic acid;
4-(((2R)-2-((2S,3R,6S)-2,3-bis(4-chlorophenyl)-6-(4-(methylsulfonyl)benzyl)-5-oxo-4-morpholinyl)pentanoyl)amino)butanoic acid;
((2R,5S,6R)-6-(3-chlorophenyl)-5-(4-chlorophenyl)-4-((1R)-1-(((cyclopropylsulfonyl)(phenyl)amino)methyl)propyl)-3-oxo-2-morpholinyl)acetic acid;
3-((2R,3S)-3-(4-chlorophenyl)-4-(cyclopropylmethyl)-5-oxo-2-morpholinyl)benzonitrile;
3-((2S,3R)-3-(4-chlorophenyl)-4-(cyclopropylmethyl)-5-oxo-2-morpholinyl)benzonitrile;
(2R)-2-((2R,3S,6R)-2-(3-chlorophenyl)-3-(4-chlorophenyl)-6-(4-fluorobenzyl)-5-oxo-4-morpholinyl)pentanoic acid;
(2S)-2-((2S,3R,6S)-2-(3-chlorophenyl)-3-(4-chlorophenyl)-6-(4-fluorobenzyl)-5-oxo-4-morpholinyl)pentanoic acid;
(2S)-2-((2R,3S,6R)-2-(3-chlorophenyl)-3-(4-chlorophenyl)-6-(4-fluorobenzyl)-5-oxo-4-morpholinyl)pentanoic acid;
(2R)-2-((2S,3R,6S)-2-(3-chlorophenyl)-3-(4-chlorophenyl)-6-(4-fluorobenzyl)-5-oxo-4-morpholinyl)pentanoic acid;
N-((2R)-2-((2S,3R,6S)-2,3-bis(4-chlorophenyl)-6-(4-cyanobenzyl)-5-oxo-4-morpholinyl)pentanoyl)glycine;
N-((2S)-2-((2R,3S,6R)-2,3-bis(4-chlorophenyl)-6-(4-cyanobenzyl)-5-oxo-4-morpholinyl)pentanoyl)glycine;
N-((2R)-2-((2S,3R)-2,3-bis(4-chlorophenyl)-5-oxo-4-morpholinyl)pentanoyl)glycine;
N-((2S)-2-((2R,3S)-2,3-bis(4-chlorophenyl)-5-oxo-4-morpholinyl)pentanoyl)glycine;
2-((2R,5S,6R)-6-(3-chlorophenyl)-5-(4-chlorophenyl)-4-(cyclopropylmethyl)-3-oxo-2-morpholinyl)-N,N-dimethylacetamide;
2-((2S,5R,6S)-6-(3-chlorophenyl)-5-(4-chlorophenyl)-4-(cyclopropylmethyl)-3-oxo-2-morpholinyl)-N,N-dimethylacetamide;
ethyl (2R)-2-((2S,3R,6S)-2,3-bis(4-chlorophenyl)-6-(3-(4-morpholinyl)propyl)-5-oxo-4-morpholinyl)pentanoate;
(2R)-2-((2S,3R)-3-(4-chlorophenyl)-2-(4-cyanophenyl)-5-oxo-4-morpholinyl)pentanoic acid;
(2S)-2-((2R,3S)-3-(4-chlorophenyl)-2-(4-cyanophenyl)-5-oxo-4-morpholinyl)pentanoic acid;
(2S)-2-((2S,3R)-3-(4-chlorophenyl)-2-(4-cyanophenyl)-5-oxo-4-morpholinyl)pentanoic acid;
(2R)-2-((2R,3S)-3-(4-chlorophenyl)-2-(4-cyanophenyl)-5-oxo-4-morpholinyl)pentanoic acid;
(2R)-2-((2S,3R,6S)-2,3-bis(4-chlorophenyl)-6-(3-hydroxypropyl)-5-oxo-4-morpholinyl)pentanoic acid;
(2R)-2-((2S,3R,6S)-2,3-bis(4-chlorophenyl)-6-(4-iodobenzyl)-5-oxo-4-morpholinyl)pentanamide;
(2S)-2-((2R,3S,6R)-2,3-bis(4-chlorophenyl)-6-(4-iodobenzyl)-5-oxo-4-morpholinyl)pentanamide;
(2R)-2-((2S,3R,6S)-2,3-bis(4-chlorophenyl)-6-(4-fluorobenzyl)-5-oxo-4-morpholinyl)-4-pentenoic acid;
(2S)-2-((2R,3S,6R)-2,3-bis(4-chlorophenyl)-6-(4-fluorobenzyl)-5-oxo-4-morpholinyl)-4-pentenoic acid;
(2S)-2-((2S,3R,6S)-2,3-bis(4-chlorophenyl)-6-(4-fluorobenzyl)-5-oxo-4-morpholinyl)-4-pentenoic acid;
(2R)-2-((2R,3S,6R)-2,3-bis(4-chlorophenyl)-6-(4-fluorobenzyl)-5-oxo-4-morpholinyl)-4-pentenoic acid;
(2R)-2-((2S,3R,6S)-2,3-bis(4-chlorophenyl)-6-(4-iodobenzyl)-5-oxo-4-morpholinyl)pentanenitrile;
(2S)-2-((2R,3S,6R)-2,3-bis(4-chlorophenyl)-6-(4-iodobenzyl)-5-oxo-4-morpholinyl)pentanenitrile;
4-(((2R,5S,6R)-5,6-bis(4-chlorophenyl)-3-oxo-4-((1S)-1-(1H-tetrazol-5-yl)butyl)-2-morpholinyl)methyl)benzonitrile;
4-(((2S,5R,6S)-5,6-bis(4-chlorophenyl)-3-oxo-4-((1R)-1-(1H-tetrazol-5-yl)butyl)-2-morpholinyl)methyl)benzonitrile;
(5R,6S)-6-(3-chlorophenyl)-5-(4-chlorophenyl)-4-(cyclopropylmethyl)-3-morpholinone;
(5S,6R)-6-(3-chlorophenyl)-5-(4-chlorophenyl)-4-(cyclopropylmethyl)-3-morpholinone;
(5R,6S)-6-(3-chlorophenyl)-5-(4-chlorophenyl)-4-((1R,2R)-2-methylcyclopropyl)methyl)-3-morpholinone;
(5R,6S)-6-(3-chlorophenyl)-5-(4-chlorophenyl)-4-(((1S,2S)-2-methylcyclopropyl)methyl)-3-morpholinone;
(5S,6R)-6-(3-chlorophenyl)-5-(4-chlorophenyl)-4-(((1R,2R)-2-methylcyclopropyl)methyl)-3-morpholinone;
(5S,6R)-6-(3-chlorophenyl)-5-(4-chlorophenyl)-4-(((1S,2S)-2-methylcyclopropyl)methyl)-3-morpholinone;
N-((2R)-2-((2S,3R,6S)-2,3-bis(4-chlorophenyl)-6-(4-cyanobenzyl)-5-oxo-4-morpholinyl)pentanoyl)-beta-alanine;
N-((2S)-2-((2R,3S,6R)-2,3-bis(4-chlorophenyl)-6-(4-cyanobenzyl)-5-oxo-4-morpholinyl)pentanoyl)-beta-alanine;
N-((2S)-2-((2S,3R,6S)-2,3-bis(4-chlorophenyl)-6-(4-cyanobenzyl)-5-oxo-4-morpholinyl)pentanoyl)-beta-alanine;
N-((2R)-2-((2R,3S,6R)-2,3-bis(4-chlorophenyl)-6-(4-cyanobenzyl)-5-oxo-4-morpholinyl)pentanoyl)-beta-alanine;
N-((2R)-2-((2S,3R)-2,3-bis(4-chlorophenyl)-5-oxo-4-morpholinyl)pentanoyl)-beta-alanine;
N-((2S)-2-((2R,3S)-2,3-bis(4-chlorophenyl)-5-oxo-4-morpholinyl)pentanoyl)-beta-alanine;
N-((2S)-2-((2S,3R)-2,3-bis(4-chlorophenyl)-5-oxo-4-morpholinyl)pentanoyl)-beta-alanine;
N-((2R)-2-((2R,3S)-2,3-bis(4-chlorophenyl)-5-oxo-4-morpholinyl)pentanoyl)-beta-alanine;
(5R,6S)-6-(3-chlorophenyl)-5-(4-chlorophenyl)-4-(cyclopropylsulfonyl)-3-morpholinone;
(5S,6R)-6-(3-chlorophenyl)-5-(4-chlorophenyl)-4-(cyclopropylsulfonyl)-3-morpholinone;
4-(((2R,5S,6R)-5,6-bis(4-chlorophenyl)-4-methyl-3-oxo-2-morpholinyl)methyl)benzamide;
4-(((2S,5R,6S)-5,6-bis(4-chlorophenyl)-4-methyl-3-oxo-2-morpholinyl)methyl)benzamide;
(3R)-3-((2S,3R,6S)-2-(3-chlorophenyl)-3-(4-chlorophenyl)-6-(4-fluorobenzyl)-5-oxo-4-morpholinyl) hexanoic acid;
(((2R)-2-((2S,3R)-2,3-bis(4-chlorophenyl)-5-oxo-4-morpholinyl)pentyl)oxy)acetic acid;
(((2S)-2-((2R,3S)-2,3-bis(4-chlorophenyl)-5-oxo-4-morpholinyl)pentyl)oxy)acetic acid;
(2R)-2-((2R,3S,6R)-2,3-bis(4-chlorophenyl)-6-(4-(methylsulfonyl)benzyl)-5-oxo-4-morpholinyl)pentanoic acid;
(2S)-2-((2S,3R,6S)-2,3-bis(4-chlorophenyl)-6-(4-(methylsulfonyl)benzyl)-5-oxo-4-morpholinyl)pentanoic acid;
4-(((2R,5S,6R)-5,6-bis(4-chlorophenyl)-4-methyl-3-oxo-2-morpholinyl)methyl)-2-fluorobenzonitrile;
4-(((2S,5R,6S)-5,6-bis(4-chlorophenyl)-4-methyl-3-oxo-2-morpholinyl)methyl)-2-fluorobenzonitrile;

(2R,5S,6R)-5,6-bis(4-chlorophenyl)-2-(4-fluorobenzyl)-4-(4-pyridinyl)-3-morpholinone;
(2S,5R,6S)-5,6-bis(4-chlorophenyl)-2-(4-fluorobenzyl)-4-(4-pyridinyl)-3-morpholinone;
(2R,5S,6R)-6-(3-chlorophenyl)-5-(4-chlorophenyl)-4-(cyclopropylmethyl)-2-((5-methyl-1,3,4-oxadiazol-2-yl)methyl)-3-morpholinone;
(2S,5R,6S)-6-(3-chlorophenyl)-5-(4-chlorophenyl)-4-(cyclopropylmethyl)-2-((5-methyl-1,3,4-oxadiazol-2-yl)methyl)-3-morpholinone;
(2R)-2-((2S,3R,6S)-2,3-bis(4-chlorophenyl)-6-(4-cyano-2-fluorobenzyl)-5-oxo-4-morpholinyl)pentanoic acid;
(2S)-2-((2R,3S,6R)-2,3-bis(4-chlorophenyl)-6-(4-cyano-2-fluorobenzyl)-5-oxo-4-morpholinyl)pentanoic acid;
(5R,6R)-6-(3-chlorophenyl)-5-(4-chlorophenyl)-2,2,6-trimethyl-4-(1-methylethyl)-3-thiomorpholinone 1,1-dioxide;
(5S,6S)-6-(3-chlorophenyl)-5-(4-chlorophenyl)-2,2,6-trimethyl-4-(1-methylethyl)-3-thiomorpholinone 1,1-dioxide;
(5R,6S)-6-(3-chlorophenyl)-5-(4-chlorophenyl)-2,2,6-trimethyl-4-(1-methylethyl)-3-thiomorpholinone 1,1-dioxide;
(5S,6R)-6-(3-chlorophenyl)-5-(4-chlorophenyl)-2,2,6-trimethyl-4-(1-methylethyl)-3-thiomorpholinone 1,1-dioxide;
3-(((2R)-2-((2S,3R)-2,3-bis(4-chlorophenyl)-5-oxo-4-morpholinyl)pentyl)amino)-3-oxopropanoic acid;
3-(((2S)-2-((2R,3S)-2,3-bis(4-chlorophenyl)-5-oxo-4-morpholinyl)pentyl)amino)-3-oxopropanoic acid;
N-((2R)-2-((2S,3R)-2,3-bis(4-chlorophenyl)-5-oxo-4-morpholinyl)pentyl)glycine;
N-((2S)-2-((2R,3S)-2,3-bis(4-chlorophenyl)-5-oxo-4-morpholinyl)pentyl)glycine;
((2R,5S,6R)-6-(3-chloro-4-fluorophenyl)-5-(4-chlorophenyl)-4-(cyclopropylmethyl)-3-oxo-2-morpholinyl)acetic acid;
((2S,5R,6S)-6-(3-chloro-4-fluorophenyl)-5-(4-chlorophenyl)-4-(cyclopropylmethyl)-3-oxo-2-morpholinyl)acetic acid;
(2R,5S,6R)-5,6-bis(4-chlorophenyl)-4-methyl-2-(4-(methylsulfonyl)benzyl)-3-morpholinone;
(2S,5R,6S)-5,6-bis(4-chlorophenyl)-4-methyl-2-(4-(methylsulfonyl)benzyl)-3-morpholinone;
(2R)-2-((2S,3R,6S)-2,3-bis(4-chlorophenyl)-6-(4-cyanobenzyl)-5-oxo-4-morpholinyl)-N-(1H-tetrazol-5-ylmethyl)pentanamide;
(2S)-2-((2R,3S,6R)-2,3-bis(4-chlorophenyl)-6-(4-cyanobenzyl)-5-oxo-4-morpholinyl)-N-(1H-tetrazol-5-ylmethyl)pentanamide;
((2R,5S,6R)-6-(3-chlorophenyl)-5-(4-chlorophenyl)-4-(cyclopropylcarbonyl)-3-oxo-2-morpholinyl)acetic acid;
((2S,5R,6S)-6-(3-chlorophenyl)-5-(4-chlorophenyl)-4-(cyclopropylcarbonyl)-3-oxo-2-morpholinyl)acetic acid;
(5R,6S)-6-(3-chlorophenyl)-5-(4-chlorophenyl)-4-(cyclopropylmethyl)-3-thiomorpholinone 1,1-dioxide;
2-((2R,5S,6R)-6-(3-chlorophenyl)-5-(4-chlorophenyl)-4-(cyclopropylmethyl)-3-oxo-2-morpholinyl)ethyl methanesulfonate;
2-((2S,5R,6S)-6-(3-chlorophenyl)-5-(4-chlorophenyl)-4-(cyclopropylmethyl)-3-oxo-2-morpholinyl)ethyl methanesulfonate;
(2R)-2-((2S,3R,6S)-2,3-bis(4-chlorophenyl)-6-(4-cyanobenzyl)-5-oxo-4-morpholinyl)-N-(2-(1H-tetrazol-5-yl)ethyl)pentanamide;
(2S)-2-((2R,3S,6R)-2,3-bis(4-chlorophenyl)-6-(4-cyanobenzyl)-5-oxo-4-morpholinyl)-N-(2-(1H-tetrazol-5-yl)ethyl)pentanamide;
N-((2R)-2-((2S,3R)-2,3-bis(4-chlorophenyl)-5-oxo-4-morpholinyl)pentyl)-2-(1H-tetrazol-5-yl)acetamide;
N-((2S)-2-((2R,3S)-2,3-bis(4-chlorophenyl)-5-oxo-4-morpholinyl)pentyl)-2-(1H-tetrazol-5-yl)acetamide;
4-(((2R)-2-((2S,3R,6S)-2,3-bis(4-chlorophenyl)-6-(4-cyanobenzyl)-5-oxo-4-morpholinyl)pentanoyl)amino)butanoic acid;
4-(((2S)-2-((2R,3S,6R)-2,3-bis(4-chlorophenyl)-6-(4-cyanobenzyl)-5-oxo-4-morpholinyl)pentanoyl)amino)butanoic acid;
(5R,6S)-5,6-bis(4-chlorophenyl)-4-(2-(methylsulfanyl)-4-pyrimidinyl)-3-morpholinone;
(5S,6R)-5,6-bis(4-chlorophenyl)-4-(2-(methylsulfanyl)-4-pyrimidinyl)-3-morpholinone;
1-((2R)-2-((2S,3R)-2,3-bis(4-chlorophenyl)-5-oxo-4-morpholinyl)pentanoyl)-4-piperidinecarboxylic acid;
1-((2S)-2-((2R,3S)-2,3-bis(4-chlorophenyl)-5-oxo-4-morpholinyl)pentanoyl)-4-piperidinecarboxylic acid;
(4-((2R)-2-((2S,3R)-2,3-bis(4-chlorophenyl)-5-oxo-4-morpholinyl)pentanoyl)-1-piperazinyl)acetic acid;
(4-((2S)-2-((2R,3S)-2,3-bis(4-chlorophenyl)-5-oxo-4-morpholinyl)pentanoyl)-1-piperazinyl)acetic acid;
(2S)-4-(((2R)-2-((2S,3R,6S)-2,3-bis(4-chlorophenyl)-6-(4-cyanobenzyl)-5-oxo-4-morpholinyl)pentanoyl)amino)-2-hydroxybutanoic acid;
(2S)-4-(((2S)-2-((2R,3S,6R)-2,3-bis(4-chlorophenyl)-6-(4-cyanobenzyl)-5-oxo-4-morpholinyl)pentanoyl)amino)-2-hydroxybutanoic acid;
(3R)-4-(((2R)-2-((2S,3R,6S)-2,3-bis(4-chlorophenyl)-6-(4-cyanobenzyl)-5-oxo-4-morpholinyl)pentanoyl)amino)-3-hydroxybutanoic acid;
(3R)-4-(((2S)-2-((2R,3S,6R)-2,3-bis(4-chlorophenyl)-6-(4-cyanobenzyl)-5-oxo-4-morpholinyl)pentanoyl)amino)-3-hydroxybutanoic acid;
(3S)-4-(((2R)-2-((2S,3R,6S)-2,3-bis(4-chlorophenyl)-6-(4-cyanobenzyl)-5-oxo-4-morpholinyl)pentanoyl)amino)-3-hydroxybutanoic acid;
(3S)-4-(((2S)-2-((2R,3S,6R)-2,3-bis(4-chlorophenyl)-6-(4-cyanobenzyl)-5-oxo-4-morpholinyl)pentanoyl)amino)-3-hydroxybutanoic acid;
(2R)-3-(((2R)-2-((2S,3R,6S)-2,3-bis(4-chlorophenyl)-6-(4-cyanobenzyl)-5-oxo-4-morpholinyl)pentanoyl)amino)-2-methylpropanoic acid;
(2R)-3-(((2S)-2-((2R,3S,6R)-2,3-bis(4-chlorophenyl)-6-(4-cyanobenzyl)-5-oxo-4-morpholinyl)pentanoyl)amino)-2-methylpropanoic acid;
(2S)-3-(((2R)-2-((2S,3R,6S)-2,3-bis(4-chlorophenyl)-6-(4-cyanobenzyl)-5-oxo-4-morpholinyl)pentanoyl)amino)-2-methylpropanoic acid;
(2S)-3-(((2S)-2-((2R,3S,6R)-2,3-bis(4-chlorophenyl)-6-(4-cyanobenzyl)-5-oxo-4-morpholinyl)pentanoyl)amino)-2-methylpropanoic acid;
N-((2R)-2-((2S,3R,6S)-2,3-bis(4-chlorophenyl)-6-(4-cyanobenzyl)-5-oxo-4-morpholinyl)pentanoyl)-L-alanine;
N-((2S)-2-((2R,3S,6R)-2,3-bis(4-chlorophenyl)-6-(4-cyanobenzyl)-5-oxo-4-morpholinyl)pentanoyl)-D-alanine;
(2R)-2-((2R,3S)-2-(4-chlorophenyl)-3-(1H-indol-2-yl)-5-oxo-4-morpholinyl)pentanoic acid;
(2S)-2-((2S,3R)-2-(4-chlorophenyl)-3-(1H-indol-2-yl)-5-oxo-4-morpholinyl)pentanoic acid;

N-((2R)-2-((2S,3R,6S)-2,3-bis(4-chlorophenyl)-6-(4-cyanobenzyl)-5-oxo-4-morpholinyl)pentanoyl)-D-alanine;
N-((2S)-2-((2R,3S,6R)-2,3-bis(4-chlorophenyl)-6-(4-cyanobenzyl)-5-oxo-4-morpholinyl)pentanoyl)-L-alanine;
methyl 4-(((2R,5S,6R)-5,6-bis(4-chlorophenyl)-4-methyl-3-oxo-2-morpholinyl)methyl)benzoate;
methyl 4-(((2S,5R,6S)-5,6-bis(4-chlorophenyl)-4-methyl-3-oxo-2-morpholinyl)methyl)benzoate;
3-(((2R)-2-((2S,3R,6S)-2,3-bis(4-chlorophenyl)-6-(4-cyanobenzyl)-5-oxo-4-morpholinyl)pentanoyl)amino)-N-(tert-butoxycarbonyl)-D-alanine;
3-(((2S)-2-((2R,3S,6R)-2,3-bis(4-chlorophenyl)-6-(4-cyanobenzyl)-5-oxo-4-morpholinyl)pentanoyl)amino)-N-(tert-butoxycarbonyl)-D-alanine;
(5R,6S)-6-(3-chlorophenyl)-5-(4-chlorophenyl)-4-(cyclobutylmethyl)-3-morpholinone;
(5S,6R)-6-(3-chlorophenyl)-5-(4-chlorophenyl)-4-(cyclobutylmethyl)-3-morpholinone;
4-(((2R,5S,6R)-5,6-bis(4-chlorophenyl)-4-methyl-3-oxo-2-morpholinyl)methyl)benzonitrile;
4-(((2S,5R,6S)-5,6-bis(4-chlorophenyl)-4-methyl-3-oxo-2-morpholinyl)methyl)benzonitrile;
(4-((2R)-2-((2S,3R,6S)-2,3-bis(4-chlorophenyl)-6-(4-cyanobenzyl)-5-oxo-4-morpholinyl)pentanoyl)-1-piperazinyl)acetic acid;
(4-((2S)-2-((2R,3S,6R)-2,3-bis(4-chlorophenyl)-6-(4-cyanobenzyl)-5-oxo-4-morpholinyl)pentanoyl)-1-piperazinyl)acetic acid;
3-(((2R)-2-((2S,3R,6S)-2,3-bis(4-chlorophenyl)-6-(4-cyanobenzyl)-5-oxo-4-morpholinyl)pentanoyl)amino)-2,2-dimethylpropanoic acid;
3-(((2S)-2-((2R,3S,6R)-2,3-bis(4-chlorophenyl)-6-(4-cyanobenzyl)-5-oxo-4-morpholinyl)pentanoyl)amino)-2,2-dimethylpropanoic acid;
(5R,6S)-5,6-bis(4-chlorophenyl)-4-(2-chloro-4-pyridinyl)-3-morpholinone;
(5S,6R)-5,6-bis(4-chlorophenyl)-4-(2-chloro-4-pyridinyl)-3-morpholinone;
3-(((2R,5S,6R)-5,6-bis(4-chlorophenyl)-4-methyl-3-oxo-2-morpholinyl)methyl)benzamide;
3-(((2S,5R,6S)-5,6-bis(4-chlorophenyl)-4-methyl-3-oxo-2-morpholinyl)methyl)benzamide;
3-(((2R)-2-((2S,3R,6S)-2,3-bis(4-chlorophenyl)-6-(4-cyanobenzyl)-5-oxo-4-morpholinyl)pentanoyl)amino)-D-alanine;
3-(((2S)-2-((2R,3S,6R)-2,3-bis(4-chlorophenyl)-6-(4-cyanobenzyl)-5-oxo-4-morpholinyl)pentanoyl)amino)-D-alanine;
(2R)-2-((2S,3R,6S)-2,3-bis(4-chlorophenyl)-6-(4-methoxybenzyl)-5-oxo-4-morpholinyl)pentanoic acid;
(2S)-2-((2R,3S,6R)-2,3-bis(4-chlorophenyl)-6-(4-methoxybenzyl)-5-oxo-4-morpholinyl)pentanoic acid;
(2R)-2-((2S,3R)-2-(3-chlorophenyl)-3-(4-chlorophenyl)-5-oxo-4-morpholinyl)pentanoic acid;
(2S)-2-((2R,3S)-2-(3-chlorophenyl)-3-(4-chlorophenyl)-5-oxo-4-morpholinyl)pentanoic acid;
3-(4-((2R)-2-((2S,3R)-2,3-bis(4-chlorophenyl)-5-oxo-4-morpholinyl)pentanoyl)-1-piperazinyl)propanoic acid;
3-(4-((2S)-2-((2R,3S)-2,3-bis(4-chlorophenyl)-5-oxo-4-morpholinyl)pentanoyl)-1-piperazinyl)propanoic acid;
(2R)-((2S,3R,6S)-2-(3-chlorophenyl)-3-(4-chlorophenyl)-6-(4-fluorobenzyl)-5-oxo-4-morpholinyl)(cyclopropyl)ethanoic acid;
(2S)-((2R,3S,6R)-2-(3-chlorophenyl)-3-(4-chlorophenyl)-6-(4-fluorobenzyl)-5-oxo-4-morpholinyl)(cyclopropyl)ethanoic acid;
(2S)-((2S,3R,6S)-2-(3-chlorophenyl)-3-(4-chlorophenyl)-6-(4-fluorobenzyl)-5-oxo-4-morpholinyl)(cyclopropyl)ethanoic acid;
(2R)-((2R,3S,6R)-2-(3-chlorophenyl)-3-(4-chlorophenyl)-6-(4-fluorobenzyl)-5-oxo-4-morpholinyl)(cyclopropyl)ethanoic acid;
(2R,5S,6R)-5,6-bis(4-chlorophenyl)-2-(4-fluorobenzyl)-4-(1-methyl-1H-imidazol-4-yl)-3-morpholinone;
(2S,5R,6S)-5,6-bis(4-chlorophenyl)-2-(4-fluorobenzyl)-4-(1-methyl-1H-imidazol-4-yl)-3-morpholinone;
4-(((2R,5S,6R)-5,6-bis(4-chlorophenyl)-4-methyl-3-oxo-2-morpholinyl)methyl)benzoic acid;
4-(((2S,5R,6S)-5,6-bis(4-chlorophenyl)-4-methyl-3-oxo-2-morpholinyl)methyl)benzoic acid;
(5R,6S)-6-(3-chlorophenyl)-5-(4-chlorophenyl)-4-(2-methylpropyl)-3-morpholinone;
(5S,6R)-6-(3-chlorophenyl)-5-(4-chlorophenyl)-4-(2-methylpropyl)-3-morpholinone;
1-((2R)-2-((2S,3R,6S)-2,3-bis(4-chlorophenyl)-6-(4-fluorobenzyl)-5-oxo-4-morpholinyl)pentanoyl)-D-proline;
1-((2S)-2-((2R,3S,6R)-2,3-bis(4-chlorophenyl)-6-(4-fluorobenzyl)-5-oxo-4-morpholinyl)pentanoyl)-D-proline;
(5R,6S)-5,6-bis(4-chlorophenyl)-4-(2-pyrazinyl)-3-morpholinone;
(5S,6R)-5,6-bis(4-chlorophenyl)-4-(2-pyrazinyl)-3-morpholinone;
(2R,5S,6R)-5,6-bis(4-chlorophenyl)-4-(cyclopropylmethyl)-2-((2R)-2,3-dihydroxypropyl)-3-morpholinone;
(2R,5S,6R)-5,6-bis(4-chlorophenyl)-4-(cyclopropylmethyl)-2-((2S)-2,3-dihydroxypropyl)-3-morpholinone;
(2S,5R,6S)-5,6-bis(4-chlorophenyl)-4-(cyclopropylmethyl)-2-((2R)-2,3-dihydroxypropyl)-3-morpholinone;
(2S,5R,6S)-5,6-bis(4-chlorophenyl)-4-(cyclopropylmethyl)-2-((2S)-2,3-dihydroxypropyl)-3-morpholinone;
(5R,6S)-6-(3-chlorophenyl)-5-(4-chlorophenyl)-4-cyclopentyl-3-morpholinone;
(5S,6R)-6-(3-chlorophenyl)-5-(4-chlorophenyl)-4-cyclopentyl-3-morpholinone;
methyl 1-((2R)-2-((2S,3R,6S)-2,3-bis(4-chlorophenyl)-6-(4-fluorobenzyl)-5-oxo-4-morpholinyl)pentanoyl)-L-prolinate;
methyl 1-((2S)-2-((2R,3S,6R)-2,3-bis(4-chlorophenyl)-6-(4-fluorobenzyl)-5-oxo-4-morpholinyl)pentanoyl)-L-prolinate;
1-((2R)-2-((2S,3R,6S)-2,3-bis(4-chlorophenyl)-6-(4-iodobenzyl)-5-oxo-4-morpholinyl)pentanoyl)-4-piperidinecarboxylic acid;
1-((2S)-2-((2R,3S,6R)-2,3-bis(4-chlorophenyl)-6-(4-iodobenzyl)-5-oxo-4-morpholinyl)pentanoyl)-4-piperidinecarboxylic acid;
(2R)-2-((2S,5R,6S)-2-(4-chlorobenzyl)-5,6-bis(4-chlorophenyl)-3-oxo-4-morpholinyl)pentanoic acid;
(2S)-2-((2R,5S,6R)-2-(4-chlorobenzyl)-5,6-bis(4-chlorophenyl)-3-oxo-4-morpholinyl)pentanoic acid;
(2R,5S,6R)-2-(4-(aminomethyl)benzyl)-5,6-bis(4-chlorophenyl)-4-methyl-3-morpholinone;
(2S,5R,6S)-2-(4-(aminomethyl)benzyl)-5,6-bis(4-chlorophenyl)-4-methyl-3-morpholinone;
3-(((2R)-2-((2S,3R,6S)-2,3-bis(4-chlorophenyl)-6-(4-iodobenzyl)-5-oxo-4-morpholinyl)pentyl)amino)-3-oxopropanoic acid;

3-(((2S)-2-((2R,3S,6R)-2,3-bis(4-chlorophenyl)-6-(4-iodobenzyl)-5-oxo-4-morpholinyl)pentyl)amino)-3-oxopropanoic acid;
(5R,6S)-6-(3-chlorophenyl)-5-(4-chlorophenyl)-4-(1,3-thiazol-4-ylmethyl)-3-morpholinone;
(5S,6R)-6-(3-chlorophenyl)-5-(4-chlorophenyl)-4-(1,3-thiazol-4-ylmethyl)-3-morpholinone;
(5R,6S)-6-(3-chlorophenyl)-5-(4-chlorophenyl)-4-(2-hydroxy-2-methylpropyl)-3-morpholinone;
(5S,6R)-6-(3-chlorophenyl)-5-(4-chlorophenyl)-4-(2-hydroxy-2-methylpropyl)-3-morpholinone;
((2R,5S,6R)-6-(3-chlorophenyl)-5-(4-chlorophenyl)-4-((1-cyanocyclopropyl)methyl)-3-oxo-2-morpholinyl)acetic acid;
((2S,5R,6S)-6-(3-chlorophenyl)-5-(4-chlorophenyl)-4-((1-cyanocyclopropyl)methyl)-3-oxo-2-morpholinyl)acetic acid;
1-((((2R)-2-((2S,3R,6S)-2,3-bis(4-chlorophenyl)-6-(4-cyanobenzyl)-5-oxo-4-morpholinyl)pentanoyl)amino)methyl)cyclopentanecarboxylic acid;
1-((((2S)-2-((2R,3S,6R)-2,3-bis(4-chlorophenyl)-6-(4-cyanobenzyl)-5-oxo-4-morpholinyl)pentanoyl)amino)methyl)cyclopentanecarboxylic acid;
(3S)-3-((2R,3S,6R)-2-(3-chlorophenyl)-3-(4-chlorophenyl)-6-(4-fluorobenzyl)-5-oxo-4-morpholinyl)hexanoic acid;
(3S)-3-((2S,3R,6S)-2-(3-chlorophenyl)-3-(4-chlorophenyl)-6-(4-fluorobenzyl)-5-oxo-4-morpholinyl)hexanoic acid;
(2R)-2-((2R,3S)-2-(3-chlorophenyl)-3-(4-chlorophenyl)-5-oxo-4-morpholinyl)pentanoic acid;
(2S)-2-((2S,3R)-2-(3-chlorophenyl)-3-(4-chlorophenyl)-5-oxo-4-morpholinyl)pentanoic acid;
(2R)-2-((2S,3R,6S)-2,3-bis(4-chlorophenyl)-6-(4-iodobenzyl)-5-oxo-4-morpholinyl)pentanoic acid;
(2S)-2-((2R,3S,6R)-2,3-bis(4-chlorophenyl)-6-(4-iodobenzyl)-5-oxo-4-morpholinyl)pentanoic acid;
(5R,6S)-5,6-bis(4-chlorophenyl)-4-(4-pyridinyl)-3-morpholinone;
(5S,6R)-5,6-bis(4-chlorophenyl)-4-(4-pyridinyl)-3-morpholinone;
(2R)-((2R,3S)-2-(3-chlorophenyl)-3-(4-chlorophenyl)-5-oxo-4-morpholinyl)(cyclopropyl)ethanoic acid;
(2R)-((2R,3R)-2-(3-chlorophenyl)-3-(4-chlorophenyl)-5-oxo-4-morpholinyl)(cyclopropyl)ethanoic acid;
(2S)-((2R,3S)-2-(3-chlorophenyl)-3-(4-chlorophenyl)-5-oxo-4-morpholinyl)(cyclopropyl)ethanoic acid;
(2S)-((2S,3R)-2-(3-chlorophenyl)-3-(4-chlorophenyl)-5-oxo-4-morpholinyl)(cyclopropyl)ethanoic acid;
(2R)-2-((2R,3S)-2,3-bis(4-chlorophenyl)-5-oxo-4-morpholinyl)pentanoic acid;
(2R)-2-((2S,3R)-2,3-bis(4-chlorophenyl)-5-oxo-4-morpholinyl)pentanoic acid;
(2S)-2-((2R,3S)-2,3-bis(4-chlorophenyl)-5-oxo-4-morpholinyl)pentanoic acid;
(2S)-2-((2S,3R)-2,3-bis(4-chlorophenyl)-5-oxo-4-morpholinyl)pentanoic acid;
(2R)-2-((2S,5R,6S)-2-(4-biphenylylmethyl)-5,6-bis(4-chlorophenyl)-3-oxo-4-morpholinyl)pentanoic acid;
(2S)-2-((2R,5S,6R)-2-(4-biphenylylmethyl)-5,6-bis(4-chlorophenyl)-3-oxo-4-morpholinyl)pentanoic acid;
ethyl (2R)-2-((2S,3R,6S)-2,3-bis(4-chlorophenyl)-6-(4-cyano-2-fluorobenzyl)-5-oxo-4-morpholinyl)pentanoate;
ethyl (2S)-2-((2R,3S,6R)-2,3-bis(4-chlorophenyl)-6-(4-cyano-2-fluorobenzyl)-5-oxo-4-morpholinyl)pentanoate;
(2R,5S,6R)-5,6-bis(4-chlorophenyl)-2-(4-((dimethylamino)methyl)benzyl)-4-methyl-3-morpholinone;
(2S,5R,6S)-5,6-bis(4-chlorophenyl)-2-(4-((dimethylamino)methyl)benzyl)-4-methyl-3-morpholinone;
(5R,6S)-5,6-bis(4-chlorophenyl)-6-methyl-3-morpholinone;
(5S,6R)-5,6-bis(4-chlorophenyl)-6-methyl-3-morpholinone;
(2R)-2-((2S,5R,6S)-2-(4-carbamoylbenzyl)-5,6-bis(4-chlorophenyl)-3-oxo-4-morpholinyl)pentanoic acid;
(2S)-2-((2R,5S,6R)-2-(4-carbamoylbenzyl)-5,6-bis(4-chlorophenyl)-3-oxo-4-morpholinyl)pentanoic acid;
(2R)-2-((2S,3R,6S)-2,3-bis(4-chlorophenyl)-5-oxo-6-(4-(1H-pyrazol-1-yl)benzyl)-4-morpholinyl)pentanoic acid;
(2S)-2-((2R,3S,6R)-2,3-bis(4-chlorophenyl)-5-oxo-6-(4-(1H-pyrazol-1-yl)benzyl)-4-morpholinyl)pentanoic acid;
(2R)-2-((2S,3R,6S)-2,3-bis(4-chlorophenyl)-5-oxo-6-(4-(1H-pyrrol-1-yl)benzyl)-4-morpholinyl)pentanoic acid;
(2S)-2-((2R,3S,6R)-2,3-bis(4-chlorophenyl)-5-oxo-6-(4-(1H-pyrrol-1-yl)benzyl)-4-morpholinyl)pentanoic acid;
(2R)-2-((2S,3R)-2,3-bis(4-chlorophenyl)-5-oxo-4-morpholinyl)hexanoic acid;
(2S)-2-((2R,3S)-2,3-bis(4-chlorophenyl)-5-oxo-4-morpholinyl)hexanoic acid;
(2S)-2-((2S,3R)-2,3-bis(4-chlorophenyl)-5-oxo-4-morpholinyl)hexanoic acid;
(2R)-2-((2R,3S)-2,3-bis(4-chlorophenyl)-5-oxo-4-morpholinyl)hexanoic acid;
(2R)-2-((2S,3R)-2,3-bis(4-chlorophenyl)-2-methyl-5-oxo-4-morpholinyl)pentanoic acid;
(2S)-2-((2R,3S)-2,3-bis(4-chlorophenyl)-2-methyl-5-oxo-4-morpholinyl)pentanoic acid;
(2S)-2-((2S,3R)-2,3-bis(4-chlorophenyl)-2-methyl-5-oxo-4-morpholinyl)pentanoic acid;
(2R)-2-((2R,3S)-2,3-bis(4-chlorophenyl)-2-methyl-5-oxo-4-morpholinyl)pentanoic acid;
(5R,6S)-5,6-bis(4-chlorophenyl)-4-(3-pyridinyl)-3-morpholinone;
(5S,6R)-5,6-bis(4-chlorophenyl)-4-(3-pyridinyl)-3-morpholinone;
(5S,6R)-5,6-bis(4-bromophenyl)-4-(1-methylethyl)-3-morpholinone;
(5R,6S)-5,6-bis(4-bromophenyl)-4-(1-methylethyl)-3-morpholinone;
(5R,6S)-6-(3-chlorophenyl)-5-(4-chlorophenyl)-4-(2-methoxyethyl)-3-morpholinone;
(5S,6R)-6-(3-chlorophenyl)-5-(4-chlorophenyl)-4-(2-methoxyethyl)-3-morpholinone;
(2R)-((2S,3R)-2,3-bis(4-chlorophenyl)-5-oxo-4-morpholinyl)(phenyl)ethanoic acid;
(2S)-((2R,3S)-2,3-bis(4-chlorophenyl)-5-oxo-4-morpholinyl)(phenyl)ethanoic acid;
(2S)-((2S,3R)-2,3-bis(4-chlorophenyl)-5-oxo-4-morpholinyl)(phenyl)ethanoic acid;
(2R)-((2R,3S)-2,3-bis(4-chlorophenyl)-5-oxo-4-morpholinyl)(phenyl)ethanoic acid;
(2R)-2-((2R,3S,6R)-2,3-bis(4-chlorophenyl)-6-(2-fluoro-4-(methylsulfonyl)benzyl)-5-oxo-4-morpholinyl)pentanoic acid;
(2S)-2-((2S,3R,6S)-2,3-bis(4-chlorophenyl)-6-(2-fluoro-4-(methylsulfonyl)benzyl)-5-oxo-4-morpholinyl)pentanoic acid;

((2R,5S,6R)-5,6-bis(4-chlorophenyl)-4-methyl-3-oxo-2-morpholinyl)acetonitrile;
((2S,5R,6S)-5,6-bis(4-chlorophenyl)-4-methyl-3-oxo-2-morpholinyl)acetonitrile;
(5R,6S)-5,6-bis(4-chlorophenyl)-4-phenyl-3-morpholinone;
(5S,6R)-5,6-bis(4-chlorophenyl)-4-phenyl-3-morpholinone;
(2R)-2-((2S,3R,6S)-2,3-bis(4-chlorophenyl)-5-oxo-6-(4-(1H-1,2,4-triazol-1-yl)benzyl)-4-morpholinyl)pentanoic acid;
(2S)-2-((2R,3S,6R)-2,3-bis(4-chlorophenyl)-5-oxo-6-(4-(1H-1,2,4-triazol-1-yl)benzyl)-4-morpholinyl)pentanoic acid;
(2R)-2-((2S,3R,6S)-2,3-bis(4-chlorophenyl)-6-(4-fluorobenzyl)-2-methyl-5-oxo-4-morpholinyl)pentanoic acid;
(2S)-2-((2R,3S,6R)-2,3-bis(4-chlorophenyl)-6-(4-fluorobenzyl)-2-methyl-5-oxo-4-morpholinyl)pentanoic acid;
(2S)-2-((2S,3R,6S)-2,3-bis(4-chlorophenyl)-6-(4-fluorobenzyl)-2-methyl-5-oxo-4-morpholinyl)pentanoic acid;
(2R)-2-((2R,3S,6R)-2,3-bis(4-chlorophenyl)-6-(4-fluorobenzyl)-2-methyl-5-oxo-4-morpholinyl)pentanoic acid;
(2R,5S,6R)-5,6-bis(4-chlorophenyl)-4-methyl-2-(1H-tetrazol-5-ylmethyl)-3-morpholinone;
(2S,5R,6S)-5,6-bis(4-chlorophenyl)-4-methyl-2-(1H-tetrazol-5-ylmethyl)-3-morpholinone;
(2R)-2-((2S,3R)-2-(3-chlorophenyl)-3-(4-chlorophenyl)-2-methyl-5-oxo-4-morpholinyl)pentanoic acid;
(2S)-2-((2R,3S)-2-(3-chlorophenyl)-3-(4-chlorophenyl)-2-methyl-5-oxo-4-morpholinyl)pentanoic acid;
(2S)-2-((2S,3R)-2-(3-chlorophenyl)-3-(4-chlorophenyl)-2-methyl-5-oxo-4-morpholinyl)pentanoic acid;
(2R)-2-((2R,3S)-2-(3-chlorophenyl)-3-(4-chlorophenyl)-2-methyl-5-oxo-4-morpholinyl)pentanoic acid;
(2R)-2-((2S,3R)-2,3-bis(4-chlorophenyl)-5-oxo-4-morpholinyl)-4-methylpentanoic acid;
(2S)-2-((2R,3S)-2,3-bis(4-chlorophenyl)-5-oxo-4-morpholinyl)-4-methylpentanoic acid;
(2S)-2-((2S,3R)-2,3-bis(4-chlorophenyl)-5-oxo-4-morpholinyl)-4-methylpentanoic acid;
(2R)-2-((2R,3S)-2,3-bis(4-chlorophenyl)-5-oxo-4-morpholinyl)-4-methylpentanoic acid;
4-(((2R)-2-((2S,3R,6S)-2,3-bis(4-chlorophenyl)-6-(4-iodobenzyl)-5-oxo-4-morpholinyl)pentanoyl)amino)butanoic acid;
((2R,5S,6R)-6-(3-chlorophenyl)-5-(4-chlorophenyl)-4-(cyclopropylmethyl)-6-methyl-3-oxo-2-morpholinyl)acetic acid;
((2S,5R,6S)-6-(3-chlorophenyl)-5-(4-chlorophenyl)-4-(cyclopropylmethyl)-6-methyl-3-oxo-2-morpholinyl)acetic acid;
(4R)-4-((2R,3S)-2,3-bis(4-chlorophenyl)-5-oxo-4-morpholinyl)heptanoic acid;
(4S)-4-((2S,3R)-2,3-bis(4-chlorophenyl)-5-oxo-4-morpholinyl)heptanoic acid;
(4R)-4-((2S,3R)-2,3-bis(4-chlorophenyl)-5-oxo-4-morpholinyl)heptanoic acid;
(4S)-4-((2R,3S)-2,3-bis(4-chlorophenyl)-5-oxo-4-morpholinyl)heptanoic acid;
(2R)-2-((2R,3S)-2,3-bis(4-chlorophenyl)-5-oxo-4-morpholinyl)butanoic acid;
(2R)-2-((2S,3R)-2,3-bis(4-chlorophenyl)-5-oxo-4-morpholinyl)butanoic acid;
(2S)-2-((2R,3S)-2,3-bis(4-chlorophenyl)-5-oxo-4-morpholinyl)butanoic acid;
(2S)-2-((2S,3R)-2,3-bis(4-chlorophenyl)-5-oxo-4-morpholinyl)butanoic acid;
(5R,6S)-5,6-bis(4-chlorophenyl)-4-(cyclopropylmethyl)-3-morpholinone;
(5S,6R)-5,6-bis(4-chlorophenyl)-4-(cyclopropylmethyl)-3-morpholinone;
(5S,6R)-5,6-bis(4-bromophenyl)-4-ethyl-3-morpholinone;
(5R,6S)-5,6-bis(4-bromophenyl)-4-ethyl-3-morpholinone;
2-((2R,5S,6R)-5,6-bis(4-chlorophenyl)-4-methyl-3-oxo-2-morpholinyl)acetamide;
2-((2S,5R,6S)-5,6-bis(4-chlorophenyl)-4-methyl-3-oxo-2-morpholinyl)acetamide;
(2R)-2-((2R,3S,6R)-2-(3-chlorophenyl)-3-(4-chlorophenyl)-6-(4-fluorobenzyl)-5-oxo-4-morpholinyl)-2-(4-fluorobenzyl)pentanoic acid;
(2S)-2-((2S,3R,6S)-2-(3-chlorophenyl)-3-(4-chlorophenyl)-6-(4-fluorobenzyl)-5-oxo-4-morpholinyl)-2-(4-fluorobenzyl)pentanoic acid;
(2S)-2-((2R,3S,6R)-2-(3-chlorophenyl)-3-(4-chlorophenyl)-6-(4-fluorobenzyl)-5-oxo-4-morpholinyl)-2-(4-fluorobenzyl)pentanoic acid;
(2R)-2-((2S,3R,6S)-2-(3-chlorophenyl)-3-(4-chlorophenyl)-6-(4-fluorobenzyl)-5-oxo-4-morpholinyl)-2-(4-fluorobenzyl)pentanoic acid;
(2R,5S,6R)-5,6-bis(4-chlorophenyl)-2-(2-hydroxyethyl)-4-methyl-3-morpholinone;
(2S,5R,6S)-5,6-bis(4-chlorophenyl)-2-(2-hydroxyethyl)-4-methyl-3-morpholinone;
(2R,5S,6R)-5,6-bis(4-chlorophenyl)-2-((2R)-2,3-dihydroxypropyl)-4-methyl-3-morpholinone;
(2R,5S,6R)-5,6-bis(4-chlorophenyl)-2-((2S)-2,3-dihydroxypropyl)-4-methyl-3-morpholinone;
(2S,5R,6S)-5,6-bis(4-chlorophenyl)-2-((2R)-2,3-dihydroxypropyl)-4-methyl-3-morpholinone;
(2S,5R,6S)-5,6-bis(4-chlorophenyl)-2-((2S)-2,3-dihydroxypropyl)-4-methyl-3-morpholinone;
1-((2R)-2-((2S,3R,6S)-2,3-bis(4-chlorophenyl)-6-(4-fluorobenzyl)-5-oxo-4-morpholinyl)pentyl)-4-piperidinecarboxylic acid;
1-((2S)-2-((2R,3S,6R)-2,3-bis(4-chlorophenyl)-6-(4-fluorobenzyl)-5-oxo-4-morpholinyl)pentyl)-4-piperidinecarboxylic acid;
N-((2R)-2-((2S,3R,6S)-2,3-bis(4-chlorophenyl)-6-(4-fluorobenzyl)-5-oxo-4-morpholinyl)pentanoyl)-N-methylglycine;
N-((2S)-2-((2R,3S,6R)-2,3-bis(4-chlorophenyl)-6-(4-fluorobenzyl)-5-oxo-4-morpholinyl)pentanoyl)-N-methylglycine;
(3R,5R,6S)-5,6-bis(4-chlorophenyl)-3-propyl-2,5,6,8-tetrahydro-3H-imidazo[2,1-c][1,4]oxazine;
(3S,5S,6R)-5,6-bis(4-chlorophenyl)-3-propyl-2,5,6,8-tetrahydro-3H-imidazo[2,1-c][1,4]oxazine;
(2R)-2-((2S,3R,6S)-2,3-bis(4-chlorophenyl)-6-(2-(dimethylamino)ethyl)-5-oxo-4-morpholinyl)pentanoic acid;
(2S)-2-((2R,3S,6R)-2,3-bis(4-chlorophenyl)-6-(2-(dimethylamino)ethyl)-5-oxo-4-morpholinyl)pentanoic acid;
N-((2R)-2-((2S,3R,6S)-2,3-bis(4-chlorophenyl)-6-(4-fluorobenzyl)-5-oxo-4-morpholinyl)pentanoyl)-N-methyl-beta-alanine;

N-((2S)-2-((2R,3S,6R)-2,3-bis(4-chlorophenyl)-6-(4-fluorobenzyl)-5-oxo-4-morpholinyl)pentanoyl)-N-methyl-beta-alanine;
4-(((2S,5R,6S)-5-(4-chlorophenyl)-4-methyl-6-(2-methylpropyl)-3-oxo-2-morpholinyl)methyl)-2-fluorobenzonitrile;
4-(((2R,5S,6R)-5-(4-chlorophenyl)-4-methyl-6-(2-methylpropyl)-3-oxo-2-morpholinyl)methyl)-2-fluorobenzonitrile;
(2R)-2-((2R,3S)-2,3-bis(4-chlorophenyl)-5-oxo-4-morpholinyl)propanoic acid;
(2R)-2-((2S,3R)-2,3-bis(4-chlorophenyl)-5-oxo-4-morpholinyl)propanoic acid;
(2S)-2-((2R,3S)-2,3-bis(4-chlorophenyl)-5-oxo-4-morpholinyl)propanoic acid;
(2S)-2-((2S,3R)-2,3-bis(4-chlorophenyl)-5-oxo-4-morpholinyl)propanoic acid;
(5R,6S)-5,6-bis(4-chlorophenyl)-4-(2,6-dichloro-4-pyridinyl)-3-morpholinone;
(5S,6R)-5,6-bis(4-chlorophenyl)-4-(2,6-dichloro-4-pyridinyl)-3-morpholinone;
(2R)-2-((2S,3R,6S)-2,3-bis(4-chlorophenyl)-6-(4-iodobenzyl)-5-oxo-4-morpholinyl)-N-hydroxypentanamide;
(2S)-2-((2R,3S,6R)-2,3-bis(4-chlorophenyl)-6-(4-iodobenzyl)-5-oxo-4-morpholinyl)-N-hydroxypentanamide;
(2R)-2-((2S,3R,6S)-2,3-bis(4-chlorophenyl)-6-(4-fluorobenzyl)-5-oxo-4-morpholinyl)-N-(cyclopropylsulfonyl)pentanamide;
(2S)-2-((2R,3S,6R)-2,3-bis(4-chlorophenyl)-6-(4-fluorobenzyl)-5-oxo-4-morpholinyl)-N-(cyclopropylsulfonyl)pentanamide;
(2R)-2-((2R,3S)-2,3-bis(4-chlorophenyl)-5-oxo-4-morpholinyl)-3-methylbutanoic acid;
(2R)-2-((2S,3R)-2,3-bis(4-chlorophenyl)-5-oxo-4-morpholinyl)-3-methylbutanoic acid;
(2S)-2-((2R,3S)-2,3-bis(4-chlorophenyl)-5-oxo-4-morpholinyl)-3-methylbutanoic acid;
(2S)-2-((2S,3R)-2,3-bis(4-chlorophenyl)-5-oxo-4-morpholinyl)-3-methylbutanoic acid;
(2R,5R,6S)-5,6-bis(4-chlorophenyl)-2-hydroxy-4-methyl-3-morpholinone;
(2S,5S,6R)-5,6-bis(4-chlorophenyl)-2-hydroxy-4-methyl-3-morpholinone;
(2R,5S,6R)-5,6-bis(4-chlorophenyl)-4-((1S)-1-((4-(cyclopropylmethyl)-1-piperazinyl)carbonyl)butyl)-2-(4-iodobenzyl)-3-morpholinone;
(2S,5R,6S)-5,6-bis(4-chlorophenyl)-4-((1R)-1-((4-(cyclopropylmethyl)-1-piperazinyl)carbonyl)butyl)-2-(4-iodobenzyl)-3-morpholinone;
(3R,5S,6R)-5,6-bis(4-chlorophenyl)-3-propyl-2,5,6,8-tetrahydro-3H-imidazo[2,1-c][1,4]oxazine;
(3S,5R,6S)-5,6-bis(4-chlorophenyl)-3-propyl-2,5,6,8-tetrahydro-3H-imidazo[2,1-c][1,4]oxazine;
1-((2R)-2-((2S,3R,6S)-2,3-bis(4-chlorophenyl)-6-(4-cyanobenzyl)-5-oxo-4-morpholinyl)pentanoyl)-3-azetidinecarboxylic acid;
1-((2S)-2-((2R,3S,6R)-2,3-bis(4-chlorophenyl)-6-(4-cyanobenzyl)-5-oxo-4-morpholinyl)pentanoyl)-3-azetidinecarboxylic acid;
3-(((2R,5S,6R)-5,6-bis(4-chlorophenyl)-4-methyl-3-oxo-2-morpholinyl)methyl)benzoic acid;
3-(((2S,5R,6S)-5,6-bis(4-chlorophenyl)-4-methyl-3-oxo-2-morpholinyl)methyl)benzoic acid;
(2R,5R,6S)-5,6-bis(4-chlorophenyl)-2-(4-fluorobenzyl)-4-(3-pyridinyl)-3-morpholinone;
(2S,5S,6R)-5,6-bis(4-chlorophenyl)-2-(4-fluorobenzyl)-4-(3-pyridinyl)-3-morpholinone;
4-(((2R,5S,6R)-5,6-bis(4-chlorophenyl)-4-((1S)-1-((4-(cyclopropylmethyl)-1-piperazinyl)carbonyl)butyl)-3-oxo-2-morpholinyl)methyl)benzonitrile;
4-(((2S,5R,6S)-5,6-bis(4-chlorophenyl)-4-((1R)-1-((4-(cyclopropylmethyl)-1-piperazinyl)carbonyl)butyl)-3-oxo-2-morpholinyl)methyl)benzonitrile;
3-(((2R,5S,6R)-5,6-bis(4-chlorophenyl)-4-methyl-3-oxo-2-morpholinyl)methyl)benzonitrile;
3-(((2S,5R,6S)-5,6-bis(4-chlorophenyl)-4-methyl-3-oxo-2-morpholinyl)methyl)benzonitrile;
(2R)-2-((2S,3R,6S)-2,3-bis(4-chlorophenyl)-6-(4-cyanobenzyl)-5-oxo-4-morpholinyl)-N-(methylsulfonyl)pentanamide; or
(2S)-2-((2R,3S,6R)-2,3-bis(4-chlorophenyl)-6-(4-cyanobenzyl)-5-oxo-4-morpholinyl)-N-(methylsulfonyl)pentanamide.

45. A compound, or a pharmaceutically acceptable salt thereof, selected from:
(5S,6R,Z)-5,6-bis(4-chlorophenyl)-4-methyl-2-(pyridin-3-ylmethylene)morpholin-3-one;
(5R,6S,Z)-5,6-bis(4-chlorophenyl)-4-methyl-2-(pyridin-3-ylmethylene)morpholin-3-one;
(3R,4S,8R)-4-(3-chlorophenyl)-3-(4-chlorophenyl)-2-isopropyltetrahydropyrrolo[1,2-a]pyrazine-1,6(2H,7H)-dione;
(3R,4S,8S)-4-(3-chlorophenyl)-3-(4-chlorophenyl)-2-isopropyltetrahydropyrrolo[1,2-a]pyrazine-1,6(2H,7H)-dione;
((2R,5S,6R)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid;
((2S,5S,6R)-6-(3-chlorophenyl)-5-(4-chlorophenyl)-4-((1S)-1-(((cyclopropylsulfonyl)(phenyl)amino)methyl)propyl)-3-oxo-2-morpholinyl)acetic acid;
(2R)-2-((2R,3S)-2-(4-chlorophenyl)-3-(1H-indol-2-yl)-5-oxo-4-morpholinyl)pentanoic acid;
(2S)-2-((2S,3R)-2-(4-chlorophenyl)-3-(1H-indol-2-yl)-5-oxo-4-morpholinyl)pentanoic acid;
3-(((2R)-2-((2S,3R,6S)-2,3-bis(4-chlorophenyl)-6-(4-cyanobenzyl)-5-oxo-4-morpholinyl)pentanoyl)amino)-N-(tert-butoxycarbonyl)-D-alanine;
3-(((2S)-2-((2R,3S,6R)-2,3-bis(4-chlorophenyl)-6-(4-cyanobenzyl)-5-oxo-4-morpholinyl)pentanoyl)amino)-N-(tert-butoxycarbonyl)-D-alanine;
1-((((2R)-2-((2S,3R,6S)-2,3-bis(4-chlorophenyl)-6-(4-cyanobenzyl)-5-oxo-4-morpholinyl)pentanoyl)amino)methyl)cyclopentanecarboxylic acid;
1-((((2S)-2-((2R,3S,6R)-2,3-bis(4-chlorophenyl)-6-(4-cyanobenzyl)-5-oxo-4-morpholinyl)pentanoyl)amino)methyl)cyclopentanecarboxylic acid;
(2R,3R)-3-(4-chlorophenyl)-4-(cyclopropylmethyl)-N-(2-hydroxyphenyl)-5-oxo-2-morpholinecarboxamide;
(3R,5R,6S)-5,6-bis(4-chlorophenyl)-3-propyl-2,5,6,8-tetrahydro-3H-imidazo[2,1-c][1,4]oxazine;
(3S,5S,6R)-5,6-bis(4-chlorophenyl)-3-propyl-2,5,6,8-tetrahydro-3H-imidazo[2,1-c][1,4]oxazine;
4-(((2S,5R,6S)-5-(4-chlorophenyl)-4-methyl-6-(2-methylpropyl)-3-oxo-2-morpholinyl)methyl)-2-fluorobenzonitrile;
(2R)-2-((2S,3R,6S)-2,3-bis(4-chlorophenyl)-6-(4-iodobenzyl)-5-oxo-4-morpholinyl)-N-hydroxypentanamide;
(2S)-2-((2R,3S,6R)-2,3-bis(4-chlorophenyl)-6-(4-iodobenzyl)-5-oxo-4-morpholinyl)-N-hydroxypentanamide;

(2R,5S,6R)-5,6-bis(4-chlorophenyl)-4-((1S)-1-((4-(cyclopropylmethyl)-1-piperazinyl)carbonyl)butyl)-2-(4-iodobenzyl)-3-morpholinone;

(2S,5R,6S)-5,6-bis(4-chlorophenyl)-4-((1R)-1-((4-(cyclopropylmethyl)-1-piperazinyl)carbonyl)butyl)-2-(4-iodobenzyl)-3-morpholinone;

(3R,5S,6R)-5,6-bis(4-chlorophenyl)-3-propyl-2,5,6,8-tetrahydro-3H-imidazo[2,1-c][1,4]oxazine;

(3S,5R,6S)-5,6-bis(4-chlorophenyl)-3-propyl-2,5,6,8-tetrahydro-3H-imidazo[2,1-c][1,4]oxazine;

4-(((2R,5S,6R)-5,6-bis(4-chlorophenyl)-4-((1S)-1-((4-(cyclopropylmethyl)-1-piperazinyl)carbonyl)butyl)-3-oxo-2-morpholinyl)methyl)benzonitrile; or 4-(((2S,5R,6S)-5,6-bis(4-chlorophenyl)-4-((1R)-1-((4-(cyclopropylmethyl)-1-piperazinyl)carbonyl)butyl)-3-oxo-2-morpholinyl)methyl)benzonitrile.

46. A pharmaceutical composition comprising a compound of claim 1, or a pharmaceutically acceptable salt thereof, and a pharmaceutically acceptable excipient.

* * * * *